(12) United States Patent
Reinmüller

(10) Patent No.: US 11,591,289 B2
(45) Date of Patent: Feb. 28, 2023

(54) AROMATIC COMPOUNDS

(71) Applicant: XENIOPRO GMBH, Kelkheim (DE)

(72) Inventor: Viktoria Reinmüller, Allschwil (CH)

(73) Assignee: Xeniopro GmbH, Kelkheim (DE)

( * ) Notice: Subject to any disclaimer, the term of this patent is extended or adjusted under 35 U.S.C. 154(b) by 78 days.

(21) Appl. No.: 16/488,458

(22) PCT Filed: Feb. 26, 2018

(86) PCT No.: PCT/EP2018/054686
§ 371 (c)(1),
(2) Date: Aug. 23, 2019

(87) PCT Pub. No.: WO2018/154118
PCT Pub. Date: Aug. 30, 2018

(65) Prior Publication Data
US 2020/0031763 A1 Jan. 30, 2020
US 2021/0107863 A2 Apr. 15, 2021
US 2022/0348535 A2 Nov. 3, 2022

Related U.S. Application Data

(60) Provisional application No. 62/463,212, filed on Feb. 24, 2017.

(30) Foreign Application Priority Data

Mar. 10, 2017 (EP) .................... 17160326
Dec. 7, 2017 (EP) .................... 17205950

(51) Int. Cl.
*C07C 233/65* (2006.01)
*C07C 65/24* (2006.01)
*C07C 69/94* (2006.01)
*C07D 213/80* (2006.01)
*A61K 31/44* (2006.01)

(52) U.S. Cl.
CPC ............ *C07C 233/65* (2013.01); *C07C 65/24* (2013.01); *C07C 69/94* (2013.01); *C07D 213/80* (2013.01); *A61K 31/44* (2013.01)

(58) Field of Classification Search
CPC .................................................... A61K 31/44
See application file for complete search history.

(56) References Cited

U.S. PATENT DOCUMENTS

| 2,754,286 A | 7/1956 | Elmore |
| 3,113,849 A | 12/1963 | McCoy |
| 3,940,403 A | 2/1976 | Ryozo et al. |
| 9,296,682 B2 * | 3/2016 | Radtke ............... A61K 31/09 |
| 10,772,876 B2 * | 9/2020 | Reinmueller ......... A61P 35/00 |

FOREIGN PATENT DOCUMENTS

| EP | 1145718 A1 | 10/2001 |
| EP | 1710233 A1 | 10/2006 |
| GB | 2380193 A | 4/2003 |
| JP | 2011001294 A | 1/2011 |
| WO | 9303012 A1 | 2/1993 |
| WO | 9324442 A1 | 12/1993 |
| WO | 2007022371 A2 | 2/2007 |
| WO | 2009032249 A1 | 3/2009 |
| WO | 2013093885 A1 | 6/2013 |
| WO | 2017158190 A1 | 9/2017 |
| WO | 2018096510 A1 | 5/2018 |

OTHER PUBLICATIONS

Li et al: "Synthesis of Diaryl Ethers, Diaryl Sulfides, Heteroaryl Ethers and Heteroaryl Sulfides under Microwave Dielectric Heating", Synthesis, Georg Thieme Verlag, Stuttgart, DE, No. 8, Apr. 19, 2005 (Apr. 19, 2005), pp. 1305-1313, XP002435109.

Koden et al: "Effect of Chain Length on Mesomorphism of Steroid Esters of 4-(4-Alkylphenyl-X)benzoic Acids with X=Co, O, S, and CH2", Journal of Physical Chemistry, Jan. 1, 1973 (Jan. 1, 1973), pp. 4730-4737, XP055470685.

Ito et al : "Notiz uber einige neue Diphenylather-aldehyde und deren Thiosemicarbazone.", Pharmaceutical Bulletin, vol. 5, No. 6, Jan. 1, 1957 (Jan. 1, 1957), pp. 619-621, XP055486381.

Guan et al : "Design, Synthesis, and Structure-Activity Relationship of New Pyrimidinamine Derivatives Containing an Aryloxy Pyridine Moiety", Journal of Agricultural and Food Chemistry, vol. 65, No. 6, Feb. 6, 2017 (Feb. 6, 2017), pp. 1272-1280, XP055485673.

Hergenrother et al : "Synthesis and thermal reaction of 2-[4-(4-ethynylphenoxy)phenylene]-3-phenylquinoxaline",Journal of Heterocyclic Chemistry,vol. 13, No. 5,Oct. 1, 1976 (Oct. 1, 1976), pp. 993-999, XP055485851.

Hou et al: "Evaluation of Novel N-(piperidine-4-yl)benzamide Derivatives as Potential Cell Cycle Inhibitors in HepG2 Cells", Chemical Biology & Drug Design., vol. 86, No. 2, Aug. 1, 2015 (Aug. 1, 2015), pp. 223-231, XP055485858.

Buck et al: "Ullmann diaryl ether synthesis: rate acceleration by 2,2,6,6-tetramethylheptane-3,5-dione", Organic Letters , 14(23), 6012-6015 CODEN: ORLEF7; ISSN: 1523-7052, vol. 4, No. 9, Jan. 1, 2002 (Jan. 1, 2002), pp. 1623-1626, XP002403679.

Database Registry [Online] Chemical Abstracts Service, Columbus, Ohio, US; May 15, 2008 (May 15, 2008), XP002782250,accession No. 1020936-29-1 Database accession No. 1020936-29-1 RN 1020936-29-1.

Database Registry [Online] Chemical Abstracts Service, Columbus, Ohio, US; Jul. 27, 2008 (Jul. 27, 2008), XP002782251,accession No. 1036524-79-4 Database accession No. 1036524-79-4 RN 1036524-79-4.

Database Registry [Online] Chemical Abstracts Service, Columbus, Ohio, US; Jul. 28, 2008 (Jul. 28, 2008 ), XP002782252,accession No. 1036598-46-5 Database accession No. 1036598-46-5 RN 1036598-46-5.

(Continued)

*Primary Examiner* — Kevin E Weddington
(74) *Attorney, Agent, or Firm* — Rothwell, Figg, Ernst & Manbeck, P.C.

(57) ABSTRACT

The present invention comprises novel aromatic molecules, which can be used in the treatment of pathological conditions, such as cancer, skin diseases, muscle disorders, and immune system-related disorders such as disorders of the hematopoietic system including the hematologic system in human and veterinary medicine.

30 Claims, No Drawings

(56) References Cited

OTHER PUBLICATIONS

Database Registry [Online] Chemical Abstracts Service, Columbus, Ohio, US; Aug. 17, 2008 (Aug. 17, 2008), XP002782253,accession No. 1041517-52-5 Database accession No. 1041517-52-5 RN 1041517-52-5.
Database Registry [Online] Chemical Abstracts Service, Columbus, Ohio, US; Nov. 25, 2013 (Nov. 25, 2013), XP002782254,accession No. 1480752-41-7 Database accession No. 1480752-41-7 RN 1480752-41-7.
Database Registry [Online] Chemical Abstracts Service, Columbus, Ohio, US; Feb. 1, 2009 (Feb. 1, 2009), XP002782255,accession No. 1099130-61-6 Database accession No. 1099130-61-6 RN 1099130-61-6.
Database Registry [Online] Chemical Abstracts Service, Columbus, Ohio, US; Feb. 20, 2014 (Feb. 20, 2014), XP002782256,accession No. 1550449-98-3 Database accession No. 1550449-98-3 RN 1550449-98-3.
Database Registry [Online] Chemical Abstracts Service, Columbus, Ohio, US; Dec. 5, 2012 (Dec. 5, 2012), XP002782257,accession No. 1411168-77-8 Database accession No. 1411168-77-8 RN 1411168-77-8.
Database Registry [Online] Chemical Abstracts Service, Columbus, Ohio, US; Jun. 22, 2016 (Jun. 22, 2016), XP002782258,accession No. 1937165-19-9 Database accession No. 1937165-19-9 RN 1937165-19-9.
Database Registry [Online] Chemical Abstracts Service, Columbus, Ohio, US; Nov. 15, 2007 (Nov. 15, 2007), XP002782259,accession No. 953720-22-4 Database accession No. 953720-22-4 RN 953720-22-4.
Database Registry [Online] Chemical Abstracts Service, Columbus, Ohio, US; Nov. 19, 2007 (Nov. 19, 2007), XP002782260,accession No. 954564-77-3 Database accession No. 954564-77-3 RN 954564-77-3.
Database Registry [Online] Chemical Abstracts Service, Columbus, Ohio, US; Feb. 1, 2009 (Feb. 1, 2009), XP002782261,accession No. 1098368-66-1 Database accession No. 1098368-66-1 RN 1098368-66-1.
Database Registry [Online] Chemical Abstracts Service, Columbus, Ohio, US; Nov. 4, 2013 (Nov. 4, 2013), XP002782262,accession No. 1468989-97-0 Database accession No. 1468989-97-0 RN 1468989-97-0.
Database Registry [Online] Chemical Abstracts Service, Columbus, Ohio, US; Dec. 29, 2013 (Dec. 29, 2013), XP002782264,accession No. 1506498-75-4 Database accession No. 1506498-75-4 RN 1506498-75-4.
Database Registry [Online] Chemical Abstracts Service, Columbus, Ohio, US; Feb. 20, 2014 (Feb. 20, 2014), XP002782265,accession No. 1550451-20-1 Database accession No. 1550451-20-1 RN 1550451-20-1.
Database Registry [Online] Chemical Abstracts Service, Columbus, Ohio, US; May 25, 2016 (May 25, 2016), XP002782266,accession No. 1917642-56-8 Database accession No. 1917642-56-8 RN 1917642-56-8.
Database Registry [Online] Chemical Abstracts Service, Columbus, Ohio, US; Jul. 3, 2016 (Jul. 3, 2016), XP002782267,accession No. 1944481-23-5 Database accession No. 1944481-23-5 RN 1944481-23-5.
Database Registry [Online] Chemical Abstracts Service, Columbus, Ohio, US; Jul. 25, 2016 (Jul. 25, 2016), XP002782268,accession No. 1958884-22-4 Database accession No. 1958884-22-4 RN 1958884-22-4.
Database Registry [Online] Chemical Abstracts Service, Columbus, Ohio, US; Jul. 29, 2016 (Jul. 29, 2016), XP002782269,accession No. 1962787-08-1 Database accession No. 1962787-08-1 RN 1962787-08-1.
Yabunaka et al: "Hybrid ubiquinone: novel inhibitor of mitochondrial complex I", Biochimica et Biophysica Acta. Bioenerget, Amsterdam, NL, vol. 1556, No. 2-3, Dec. 2, 2002 (Dec. 2, 2002), pp. 106-112, XP004396758.
Carrasco et al: "Probing the aurone scaffold against Plasmodium falciparum: Design, synthesis and antimalarial activity", European Journal of Medicinal Chemistry, vol. 80, Jun. 1, 2014 (Jun. 1, 2014), pp. 523-534, XP055513880.
Carrasco et al: "Probing the Azaaurone Scaffold against the Hepatic and Erythrocytic Stages of Malaria Parasites", ChemMedChem, vol. 11, No. 19, Aug. 19, 2016 (Aug. 19, 2016), pp. 2194-2204, XP055513882.
International Search Report cited in PCT/EP2018/054686 dated Oct. 23, 2018, 14 pgs.
Partial International Search Report dated Jul. 11, 2018, cited in PCT/EP2018/054686, 31 pages.
Notification Concerning Transmittal of International Preliminary Report on Patentability (Chapter I) cited in PCT/EP2018/054686 dated Aug. 27, 2019, 23 pages.
Koden et al: "Effect of Chain Length on Mesomorphism of Steroid Esters of 4-(4-Alkylphenyl-X)benzoic Acids with X=Co, O, S, and CH2", Journal of Physical Chemistry, Jan. 1, 1983 (Jan. 1, 1983), pp. 4730-4737, XP055470685.

* cited by examiner

AROMATIC COMPOUNDS

CROSS REFERENCE TO RELATED APPLICATION

This application is a 35 U.S.C. 371 National Phase Entry Application from PCT/EP2018/054686, filed Feb. 26, 2018, which claims the benefit of U.S. Patent Application No. 62/463,212 filed on Feb. 24, 2017, European Patent Application No. 17160326.9 filed Mar. 10, 2017 and European Patent Application No. 17205950.3 filed on Dec. 7, 2017, the disclosures of which are incorporated herein by reference in their entirety.

The present invention relates to novel aromatic compounds and their use as therapeutic agents, which can be used in the treatment of pathological conditions, such as cancer, skin disorders, muscle disorders, and immune system-related disorders such as disorders of the hematopoietic system including the hematologic system in human and veterinary medicine.

BACKGROUND

Notch signaling is a fundamental cell-to-cell communication pathway that regulates central processes in embryonic development as well as in the maintenance of adult tissues. The effect of a Notch signal is highly dependent on the signal strength, duration, and most importantly on the cellular context. In this regard, Notch activity leads to numerous cell-type specific responses, which implicate for example cell fate decisions, the induction or inhibition of differentiation, and the regulation of cell proliferation.

If a signaling event is not correctly controlled, a consequent loss of balance in according cellular processes may drive abnormal cellular changes and finally end in diverse disease situations, such as cancer.

Initially, Notch signaling was discovered as an oncogenic pathway. Corresponding pathological conditions are linked to abnormally augmented signaling levels. In these particular cases, the use of Notch inhibiting agents represents a promising strategy for therapeutic intervention and numerous corresponding drugs are currently in development.

Conversely, there is increasing evidence for tumor-suppressor functions of the Notch pathway in other cellular contexts (Lobry et al., *J. Exp. Med.* 2011, 208, 1931-1935; South et al., *Semin. Cell Dev. Biol.* 2012, 23, 458-464), most notably concerning organs, in which Notch negatively impacts proliferation or triggers differentiation, such as in the skin or in the neuroendocrine system (Dotto, *Oncogene* 2008, 27, 5115-5123; Kunnimalaiyaan et al., *The Oncologist* 2007, 12, 535-542). This finding is not only based on observations that certain tumors display impairments in Notch activity. Additionally, various successful demonstrations confirmed that the artificial activation of Notch signaling has a beneficial impact on according malignant degenerations (Jaskula-Sztul et al, *J. Surg. Res.* 2011, 171, 23-27; Yu et al., *Cancer* 2013, 119, 774-781; Ye et al., *Sci. Rep.* 2016, 6, 26510). Prominent examples comprise nonmelanoma skin cancer, neuroendocrine tumors and certain cancers of the hematopoietic system.

In a broader sense, due to the central role of this pathway, the potential use of Notch enhancers is not only limited to the treatment of cancer, but likewise expected to be beneficial in other pathologic conditions that have been shown to be responsive to Notch induction, such as diseases of the skin, muscle or immune system.

To this end, it is highly desirable to develop therapeutic agents that enhance Notch signaling.

Notch Enhancers State of the Art

Current methods to enhance Notch signaling for a potential therapeutic use entail the application of receptor-activating peptides or of small molecules that show Notch-augmenting properties. However, no approved Notch enhancer is available yet in the clinics. Besides, only a small number of according agents is known to date and much less have so far entered a drug development program. Reported small molecule Notch enhancers comprise resveratrol (Pinchot et al., *Cancer* 2011, 117, 1386-1398; Truong et al., *Ann. Surg. Oncol.* 2011, 18, 1506-1511; Yu et al., *Mol. Cancer Ther.* 2013, 12, 1276-1287), valproic acid (Greenblatt et al., *Oncologist* 2007, 12, 942-951; Platta et al., *J. Surg. Res.* 2008, 148, 31-37; Mohammed et al., *Oncologist* 2011, 16, 835-843), hesperetin (Patel et al., *Ann. Surg. Oncol.* 2014, 21, 497-504), chrysin (Yu et al., *Cancer* 2013, 119, 774-778), phenethyl isothiocyanate (Kim et al., *PLoS One* 2011, 6, 10), thiocoraline (Wyche et al., *Cancer Gene Ther.* 2014, 21, 518-525) and N-methylhemeanthidine chloride (Ye et al., *Sci. Rep.* 2016, 6, 26510).

A common drawback associated with most of the mentioned compounds is the lack of potency.

Hence, it is absolutely crucial to provide novel Notch enhancers with high therapeutic efficacy.

The screening of a small library of chemical molecules in a Notch-dependent luciferase reporter assay revealed a novel compound family with Notch-augmenting properties (Reinmiller et al., 2015, EPFL Thesis 6887, published in March 2016), the content of which is herein incorporated by reference.

DESCRIPTION OF THE INVENTION

The present invention covers refined structures to the initially discovered limited set of Notch enhancer molecules. These second generation compounds have been designed and are supposed to exhibit increased potency and greater metabolic stability. Alternatively, they present specific modifications of chemical residues, which are supposed to not impair the Notch-augmenting activity, but yet provide novel molecular features that may turn out to beneficially influence pharmacological and physicochemical parameters addressed in the general drug development process.

Thus, the present invention relates to compounds as defined herein that feature Notch enhancing activity, which can be used in the treatment of pathological conditions that are responsive for Notch-regulation, such as cancer, skin diseases, muscle disorders, and immune system-related disorders such as disorders of the hematopoietic system including the hematologic system in human and veterinary medicine.

The biological activity, e.g. the antiproliferative activity of the claimed compounds can be attributed to but may not be limited to Notch signaling enhancing activity. Thus, the present invention also relates to compounds as defined herein that feature antiproliferative activity, which can be used in the treatment of benign and malignant hyperproliferative disorders in human and veterinary medicine. In particular, the present invention relates to compounds as defined herein for the treatment of immune system-related disorders such as disorders of the hematopoietic system including the hematologic system, such as malignancies of the myeloid lineage, malignant and non-malignant disorders of the skin and mucosa, such as squamous and basal cell carcinoma, actinic keratosis, and hyperproliferative disorders of the skin and mucosa, e.g. cornification disorders, malignant and non-malignant disorders of the muscle, including hyperproliferative disorders of the muscle, such as muscle hyperplasia and muscle hypertrophy, disorders of the neuroendocrine system, such as medullary thyroid cancer, and hyperproliferative disorders of the genitourinary tract, e.g. cervical cancer in human and veterinary medicine.

A first aspect of the present invention relates to compounds of formula I and salts and solvates thereof:

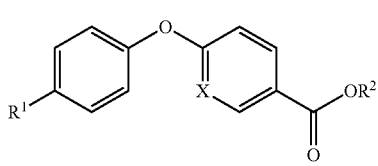

(I)

wherein X is CH or N, $R^1$=$C_1$-$C_{12}$ preferably $C_1$-$C_6$ alkyl, $C_2$-$C_{12}$ preferably $C_2$-$C_6$ alkenyl, $C_2$-$C_{12}$ preferably $C_2$-$C_6$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents in particular independently selected from: —F, —Cl, —Br, —I, —CN, —NCO, —NCS; and $OC_1$—$C_3$ alkyl optionally halogenated or perhalogenated, particularly perfluorinated;

wherein all cycloalkyl, cycloalkenyl, bicycloalkyl, bicycloalkenyl and tricycloalkyl residues can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all alkyl, alkenyl, alkynyl, cycloalkyl, cycloalkenyl, bicycloalkyl, bicycloalkenyl and tricycloalkyl residues can be perhalogenated, particularly perfluorinated;

and wherein $R^1$ is preferably selected from methyl, ethyl, n-propyl, n-butyl, n-pentyl, n-hexyl, iso-propyl, tert-butyl, tert-pentyl, 3-pentyl, —$CF_3$, —$CF_2CF_3$, —$(CF_2)_2CF_3$, —$(CF_2)_3CF_3$, —$CH(CF_3)_2$, —$CF(CF_3)_2$, cyclopropyl, cyclobutyl, cyclopentyl, cyclohexyl, cycloheptyl, norbornyl, bicyclo[2.2.2]octyl, adamantyl, and 9-methylbicyclo[3.3.1]nonyl;

$R^2$=H, $C_1$-$C_6$ alkyl, $C_3$-$C_6$ cycloalkyl, wherein all alkyl residues can be linear or branched, and can be unsubstituted or substituted with one or more substituents in particular independently selected from: —F, —Cl, —Br, —I; and $OC_1$—$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all alkyl and cycloalkyl residues can be perhalogenated, particularly perfluorinated;

and wherein $R^2$ is preferably selected from H, methyl and ethyl.

In some embodiments, the following compounds shown in Table Ia are explicitly excluded from the scope of the invention:

TABLE Ia

| Compound | $R^1$ | $R^2$ | X |
|---|---|---|---|
| I-A | tert-butyl | H | CH |
| I-B | tert-butyl | ethyl | CH |
| I-C | tert-pentyl | H | CH |
| I-D | tert-pentyl | ethyl | CH |
| I-E | cyclo-hexyl | H | CH |
| I-F | cyclo-hexyl | ethyl | CH |
| I-G | adamant-1-yl | H | CH |
| I-H | adamant-1-yl | ethyl | CH |
| I-I | methyl | H | N |
| I-J | methyl | ethyl | N |
| I-K | tert-butyl | H | N |
| I-L | tert-butyl | ethyl | N |
| I-M | tert-pentyl | H | N |
| I-N | tert-pentyl | ethyl | N |
| I-O | cyclo-hexyl | H | N |
| I-P | cyclo-hexyl | ethyl | N |
| I-Q | isopropyl | H | CH |
| I-R | phenyl | H | CH |
| I-S | methyl | H | CH |
| I-T | tert-butyl | methyl | N |
| I-U | methyl | methyl | N |
| I-V | methyl | methyl | CH |
| I-W | methyl | ethyl | CH |
| I-X | n-hexyl | H | CH |
| I-Y | n-octyl | H | CH |
| I-Z | n-dodecyl | H | CH |
| I-AA | iso-propyl | H | N |

Compounds I-A to I-T of Table Ia are known in the art for certain applications in the field of medicine whereas to the best of the inventor's knowledge, compounds I-U to I-AA are not known for any use in medicine. Thus, the invention encompasses any medical use for compounds I-U to I-AA.

Specific examples of compounds falling under the scope of formula I are shown in Table Ib. The compounds in Table Ib are defined by their chemical structure, the indicated nomenclature is only for illustrative purposes.

TABLE Ib

X = CH, $R^2$ = H

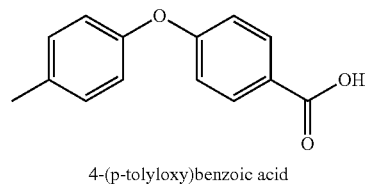 [SMILES: Cc1ccc(Oc2ccc(C(=O)O)cc2)cc1]

001

4-(p-tolyloxy)benzoic acid

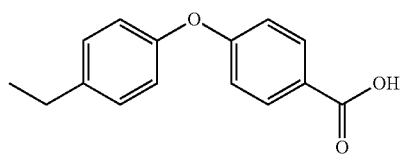

002

4-(4-ethylphenoxy)benzoic acid

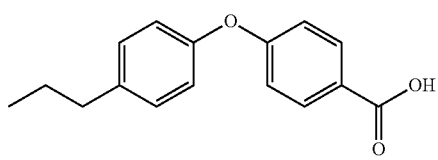

003

4-(4-propylphenoxy)benzoic acid

TABLE Ib-continued 004 4-(4-butylphenoxy)benzoic acid 005 4-(4-pentylphenoxy)benzoic acid 006 4-(4-hexylphenoxy)benzoic acid 007 4-(4-isopropylphenoxy)benzoic acid 008 4-(4-(pentan-3-yl)phenoxy)benzoic acid 009 4-(4-(trifluoromethyl)phenoxy)benzoic acid 010 4-(4-(perfluoroethyl)phenoxy)benzoic acid 011 4-(4-(perfluoropropyl)phenoxy)benzoic acid 012 4-(4-(perfluorobutyl)phenoxy)benzoic acid 013 4-(4-(1,1,1,3,3,3-hexafluoropropan-2-yl)phenoxy)benzoic acid 014 4-(4-(perfluoropropan-2-yl)phenoxy)benzoic acid 015 4-(4-cyclopropylphenoxy)benzoic acid 016 4-(4-cyclobutylphenoxy)benzoic acid 017 4-(4-cyclopentylphenoxy)benzoic acid 018 4-(4-cycloheptylphenoxy)benzoic acid 019 4-(4-((1S,4R)-bicyclo[2.2.1]heptan-2-yl)phenoxy)benzoic acid TABLE Ib-continued

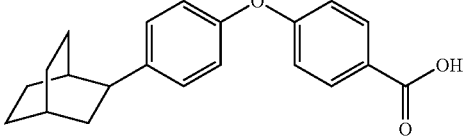 020

4-(4-((1s,4s)-bicyclo[2.2.2]octan-2-yl)phenoxy)benzoic acid

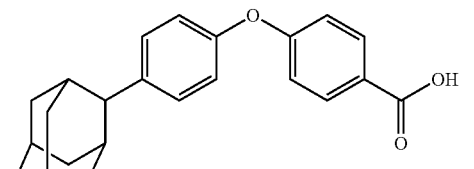 021

4-(4-((1r,3r,5r,7r)-adamantan-2-yl)phenoxy)benzoic acid

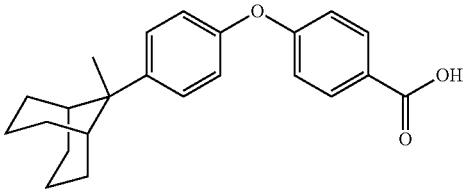 022

4-(4-((1R,5S)-9-methylbicyclo[3.3.1]nonan-9-yl)phenoxy)benzoic acid

X = CH, R² = Me

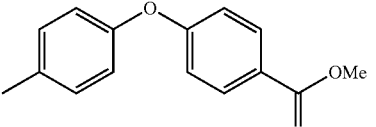 023 methyl 4-(p-tolyloxy)benzoate

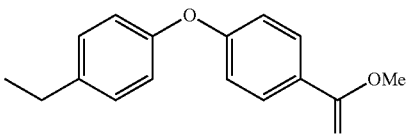 024 methyl 4-(4-ethylphenoxy)benzoate

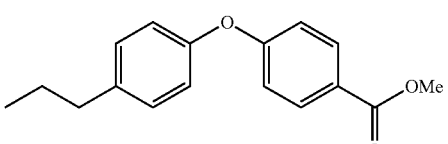 025 methyl 4-(4-propylphenoxy)benzoate

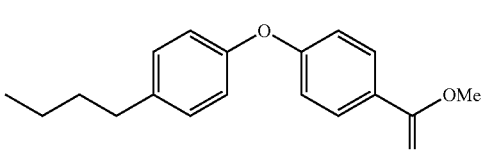 026 methyl 4-(4-butylphenoxy)benzoate

TABLE Ib-continued

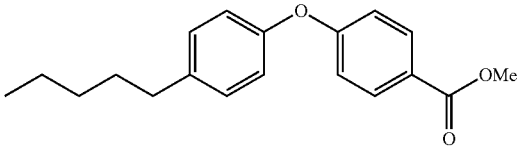 027 methyl 4-(4-pentylphenoxy)benzoate

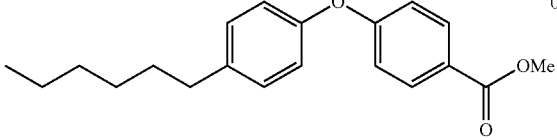 028 methyl 4-(4-hexylphenoxy)benzoate

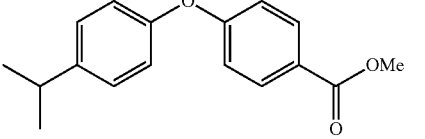 029 methyl 4-(4-isopropylphenoxy)benzoate

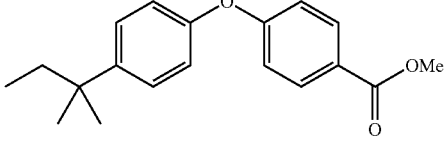 030 methyl 4-(4-(tert-pentyl)phenoxy)benzoate

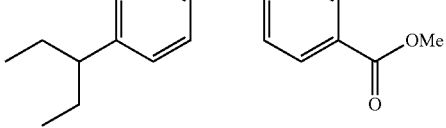 031 methyl 4-(4-(pentan-3-yl)phenoxy)benzoate

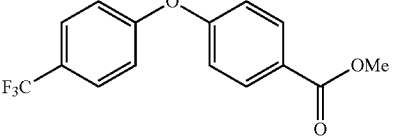 032 methyl 4-(4-(trifluoromethyl)phenoxy)benzoate

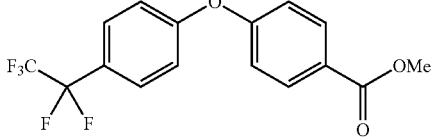 033 methyl 4-(4-(perfluoroethyl)phenoxy)benzoate

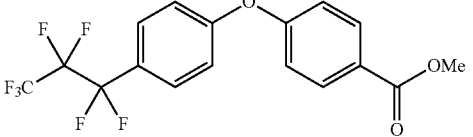 034 methyl 4-(4-(perfluoropropyl)phenoxy)benzoate

TABLE Ib-continued 035 methyl 4-(4-(perfluorobutyl)phenoxy)benzoate 036 methyl 4-(4-(1,1,1,3,3,3-hexafluoropropan-2-yl)phenoxy)benzoate 037 methyl 4-(4-(perfluoropropan-2-yl)phenoxy)benzoate 038 methyl 4-(4-cyclopropylphenoxy)benzoate 039 methyl 4-(4-cyclobutylphenoxy)benzoate 040 methyl 4-(4-cyclopentylphenoxy)benzoate 041 methyl 4-(4-cyclohexylphenoxy)benzoate 042 methyl 4-(4-cycloheptylphenoxy)benzoate 043 methyl 4-(4-((1S,4R)-bicyclo[2.2.1]heptan-2-yl)phenoxy)benzoate 044 methyl 4-(4-((1s,4s)-bicyclo[2.2.2]octan-2-yl)phenoxy)benzoate 045 methyl 4-(4-((3r,5r,7r)-adamantan-1-yl)phenoxy)benzoate 046 methyl 4-(4-((1r,3r,5r,7r)-adamantan-2-yl)phenoxy)benzoate 047 methyl 4-(4-((1R,5S)-9-methylbicyclo[3.3.1]nonan-9-yl)phenoxy)benzoate X = CH, $R^2$ = Et 048 ethyl-4-(p-tolyloxy)benzoate 049 ethyl 4-(4-ethylphenoxy)benzoate TABLE Ib-continued 050 ethyl 4-(4-propylphenoxy)benzoate 051 ethyl 4-(4-butylphenoxy)benzoate 052 ethyl 4-(4-pentylphenoxy)benzoate 053 ethyl 4-(4-hexylphenoxy)benzoate 054 ethyl 4-(4-isopropylphenoxy)benzoate 055 ethyl 4-(4-(pentan-3-yl)phenoxy)benzoate 056 ethyl 4-(4-(trifluoromethyl)phenoxy)benzoate 057 ethyl 4-(4-(perfluoroethyl)phenoxy)benzoate 058 ethyl 4-(4-(perfluoropropyl)phenoxy)benzoate 059 ethyl 4-(4-(perfluorobutyl)phenoxy)benzoate 060 ethyl 4-(4-(1,1,1,3,3,3-hexafluoropropan-2-yl)phenoxy)benzoate 061 ethyl 4-(4-(perfluoropropan-2-yl)phenoxy)benzoate 062 ethyl 4-(4-cyclopropylphenoxy)benzoate 063 ethyl 4-(4-cyclobutylphenoxy)benzoate 064 ethyl 4-(4-cyclopentylphenoxy)benzoate 065 ethyl 4-(4-cycloheptylphenoxy)benzoate TABLE Ib-continued 066 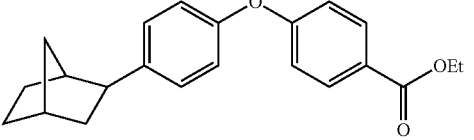
ethyl 4-(4-((1S,4R)-bicyclo[2.2.1]heptan-2-yl)phenoxy)benzoate 067 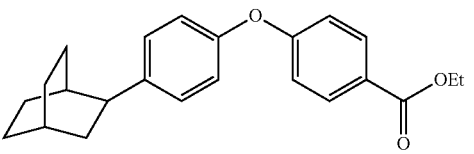
ethyl 4-(4-((1s,4s)-bicyclo[2.2.2]octan-2-yl)phenoxy)benzoate 068 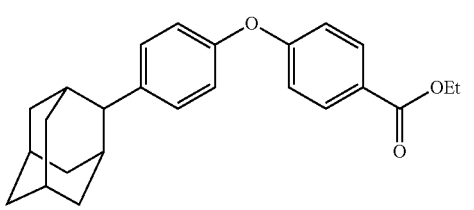
ethyl 4-(4-((1r,3r,5r,7r)-adamantan-2-yl)phenoxy)benzoate 069 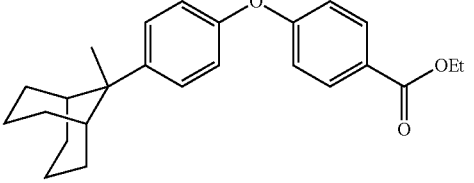
ethyl 4-(4-((1R,5S)-9-methylbicyclo[3.3.1]nonan-9-yl)phenoxy)benzoate

X = N, R² = H

070 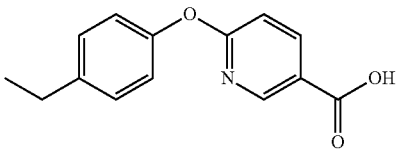
6-(4-ethylphenoxy)nicotinic acid

071 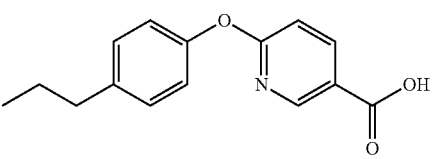
6-(4-propylphenoxy)nicotinic acid

072 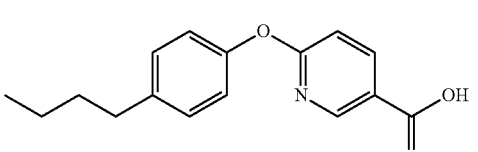
6-(4-butylphenoxy)nicotinic acid

073 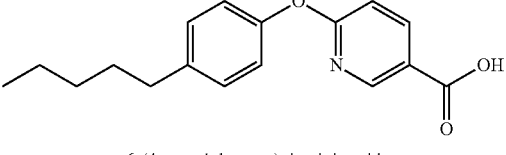
6-(4-pentylphenoxy)nicotinic acid

074 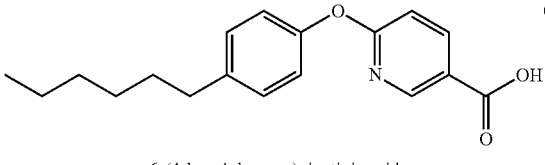
6-(4-hexylphenoxy)nicotinic acid

075 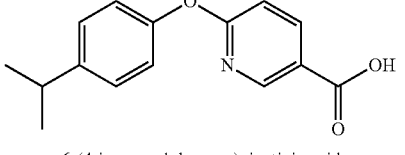
6-(4-isopropylphenoxy)nicotinic acid

076 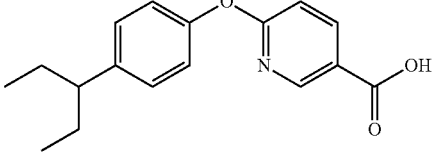
6-(4-(pentan-3-yl)phenoxy)nicotinic acid

077 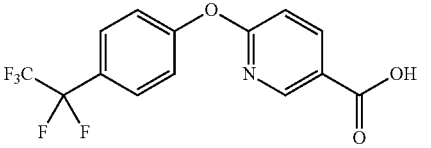
6-(4-(perfluoroethyl)phenoxy)nicotinic acid

078 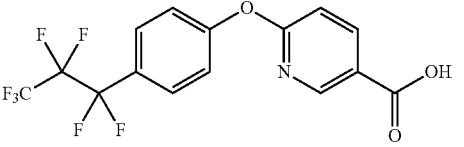
6-(4-(perfluoropropyl)phenoxy)nicotinic acid

079 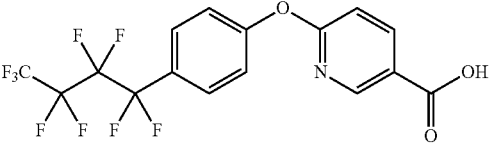
6-(4-(perfluorobutyl)phenoxy)nicotinic acid

080 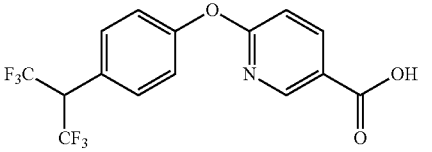
6-(4-(1,1,1,3,3,3-hexafluoropropan-2-yl)phenoxy)nicotinic acid

TABLE Ib-continued 081 6-(4-(perfluoropropan-2-yl)phenoxy)nicotinic acid 082 6-(4-cyclopropylphenoxy)nicotinic acid 083 6-(4-cyclobutylphenoxy)nicotinic acid 084 6-(4-cyclopentylphenoxy)nicotinic acid 085 6-(4-cycloheptylphenoxy)nicotinic acid 086 6-(4-((1S,4R)-bicyclo[2.2.1]heptan-2-yl)phenoxy)nicotinic acid 087 6-(4-((1s,4s)-bicyclo[2.2.2]octan-2-yl)phenoxy)nicotinic acid 088 6-(4-((3r,5r,7r)-adamantan-1-yl)phenoxy)nicotinic acid 089 6-(4-((1r,3r,5r,7r)-adamantan-2-yl)phenoxy)nicotinic acid 090 6-(4-((1R,5S)-9-methylbicyclo[3.3.1]nonan-9-yl)phenoxy)nicotinic acid X = N, R$^2$ = Me 091 methyl 6-(p-tolyloxy)nicotinate 092 methyl 6-(4-ethylphenoxy)nicotinate 093 methyl 6-(4-propylphenoxy)nicotinate 094 methyl 6-(4-butylphenoxy)nicotinate 095 methyl 6-(4-pentylphenoxy)nicotinate TABLE Ib-continued 096 methyl 6-(4-hexylphenoxy)nicotinate 097 methyl 6-(4-isopropylphenoxy)nicotinate 099 methyl 6-(4-(tert-pentyl)phenoxy)nicotinate 100 methyl 6-(4-(pentan-3-yl)phenoxy)nicotinate 101 methyl 6-(4-(trifluoromethyl)phenoxy)nicotinate 102 methyl 6-(4-(perfluoroethyl)phenoxy)nicotinate 103 methyl 6-(4-(perfluoropropyl)phenoxy)nicotinate 104 methyl 6-(4-(perfluorobutyl)phenoxy)nicotinate 105 methyl 6-(4-(1,1,1,3,3,3-hexafluoropropan-2-yl)phenoxy)nicotinate 106 methyl 6-(4-(perfluoropropan-2-yl)phenoxy)nicotinate 107 methyl 6-(4-cyclopropylphenoxy)nicotinate 108 methyl 6-(4-cyclobutylphenoxy)nicotinate 109 methyl 6-(4-cyclopentylphenoxy)nicotinate 110 methyl 6-(4-cyclohexylphenoxy)nicotinate 111 methyl 6-(4-cycloheptylphenoxy)nicotinate 112 methyl 6-(4-((1S,4R)-bicyclo[2.2.1]heptan-2-yl)phenoxy)nicotinate TABLE Ib-continued

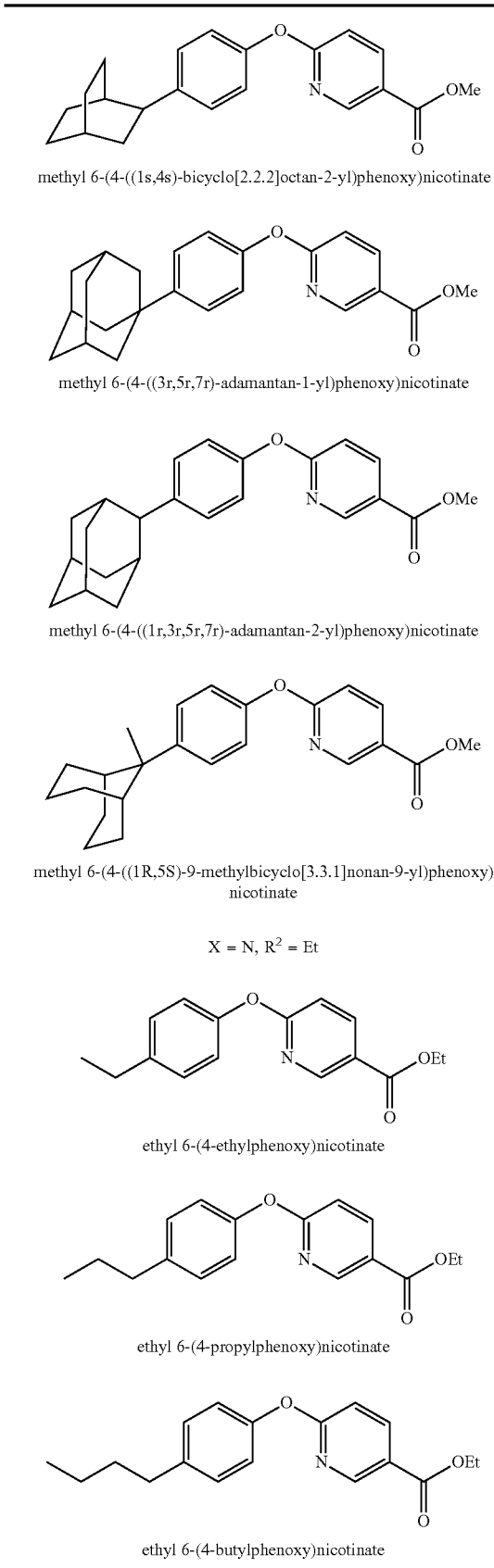

113 methyl 6-(4-((1s,4s)-bicyclo[2.2.2]octan-2-yl)phenoxy)nicotinate 114 methyl 6-(4-((3r,5r,7r)-adamantan-1-yl)phenoxy)nicotinate 115 methyl 6-(4-((1r,3r,5r,7r)-adamantan-2-yl)phenoxy)nicotinate 116 methyl 6-(4-((1R,5S)-9-methylbicyclo[3.3.1]nonan-9-yl)phenoxy)nicotinate X = N, R² = Et 117 ethyl 6-(4-ethylphenoxy)nicotinate 118 ethyl 6-(4-propylphenoxy)nicotinate 119 ethyl 6-(4-butylphenoxy)nicotinate

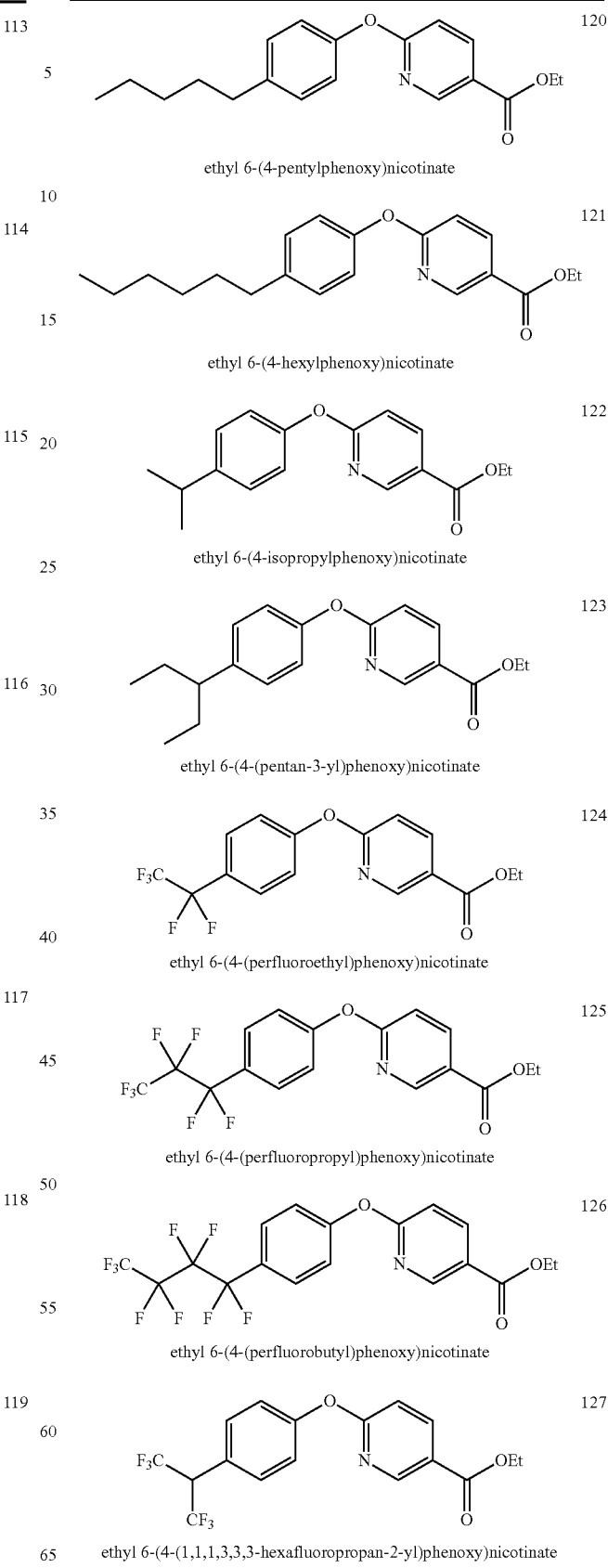

120 ethyl 6-(4-pentylphenoxy)nicotinate 121 ethyl 6-(4-hexylphenoxy)nicotinate 122 ethyl 6-(4-isopropylphenoxy)nicotinate 123 ethyl 6-(4-(pentan-3-yl)phenoxy)nicotinate 124 ethyl 6-(4-(perfluoroethyl)phenoxy)nicotinate 125 ethyl 6-(4-(perfluoropropyl)phenoxy)nicotinate 126 ethyl 6-(4-(perfluorobutyl)phenoxy)nicotinate 127 ethyl 6-(4-(1,1,1,3,3,3-hexafluoropropan-2-yl)phenoxy)nicotinate TABLE Ib-continued

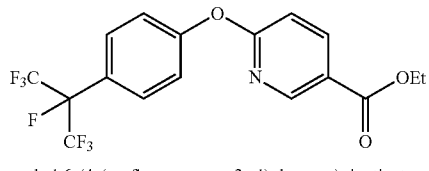
128 ethyl 6-(4-(perfluoropropan-2-yl)phenoxy)nicotinate

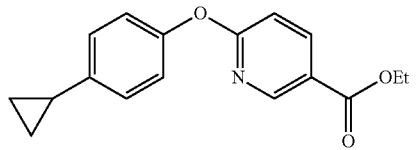
129 ethyl 6-(4-cyclopropylphenoxy)nicotinate

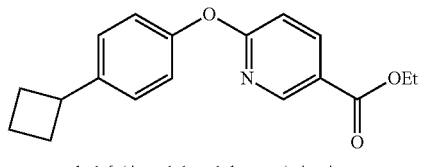
130 ethyl 6-(4-cyclobutylphenoxy)nicotinate

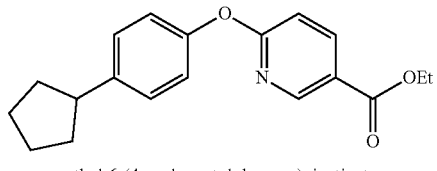
131 ethyl 6-(4-cyclopentylphenoxy)nicotinate

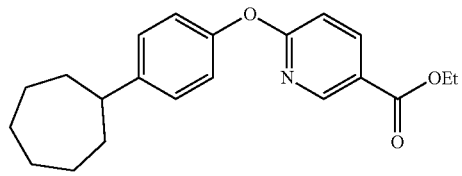
132 ethyl 6-(4-cycloheptylphenoxy)nicotinate

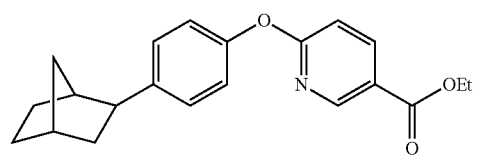
133 ethyl 6-(4-((1S,4R)-bicyclo[2.2.1]heptan-2-yl)phenoxy)nicotinate

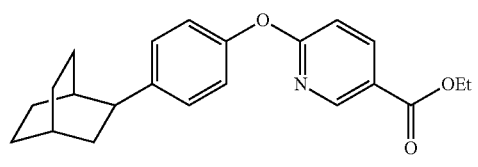
134 ethyl 6-(4-((1s,4s)-bicyclo[2.2.2]octan-2-yl)phenoxy)nicotinate

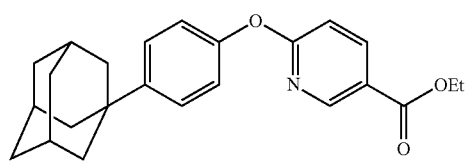
135 ethyl 6-(4-((3r,5r,7r)-adamantan-1-yl)phenoxy)nicotinate

TABLE Ib-continued

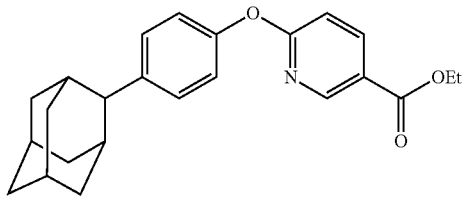
136 ethyl 6-(4-((1r,3r,5r,7r)-adamantan-2-yl)phenoxy)nicotinate

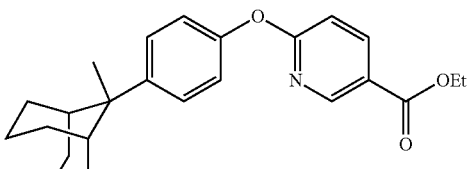
137 ethyl 6-(4-((1R,5S)-9-methylbicyclo[3.3.1]nonan-9-yl)phenoxy)nicotinate Also included are isomers, e.g. enantiomers or diastereomers or mixtures of isomers, salts, particularly pharmaceutically acceptable salts, and solvates of the compounds listed above.

A second aspect of the present invention relates to compounds of formula II and salts and solvates thereof:

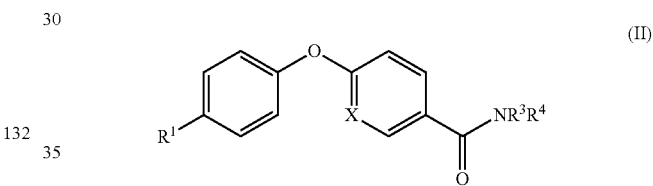
(II)

wherein X and $R^1$ are defined as in formula I, including the preferred definition of $R^1$, $R^3$=H, $C_1$-$C_6$ alkyl, or $C_3$-$C_6$ cycloalkyl, wherein all alkyl residues can be linear or branched, and can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all alkyl and cycloalkyl residues can be perhalogenated, particularly perfluorinated;

and wherein $R^3$ is preferably H or methyl;

$R^4$=H, $C_1$-$C_6$ alkyl, $C_3$-$C_6$ cycloalkyl, OH or $OC_1$—$C_6$ alkyl, wherein all alkyl residues can be linear or branched, and can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein all alkyl and cycloalkyl residues can be perhalogenated, particularly perfluorinated;

and wherein $R^4$ is preferably H, OH or methyl.

In especially preferred embodiments, $R^3$ and $R^4$ are in each case H; H and OH; H and —$CH_3$; or in each case —$CH_3$.

In some embodiments, the following compounds shown in Table IIa are explicitly excluded from the scope of the invention:

TABLE IIa

| Compound | $R^1$ | $R^3$ | $R^4$ | X |
|---|---|---|---|---|
| II-A | tert-butyl | H | H | N |
| II-B | methyl | H | methyl | CH |
| II-C | methyl | methyl | methyl | CH |

Compound II-A and II-B of Table IIa are known in the art for certain applications in the field of medicine whereas to the best of the inventor's knowledge, compound II-C is not known for any use in medicine. Thus, the invention encompasses any medical use for compound II-C.

Specific examples of compounds falling under the scope of formula II are shown in Table IIb. The compounds in Table IIb are defined by their chemical structure, the indicated nomenclature is only for illustrative purposes.

TABLE IIb

X = CH, $R^3$ = H, $R^4$ = H

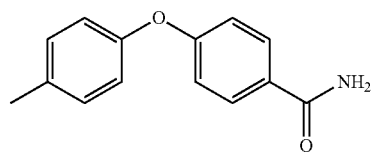 [SMILES: Cc1ccc(Oc2ccc(C(N)=O)cc2)cc1]

138

4-(p-tolyloxy)benzamide

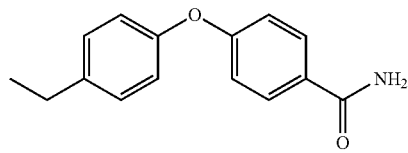 [SMILES: CCc1ccc(Oc2ccc(C(N)=O)cc2)cc1]

139

4-(4-ethylphenoxy)benzamide

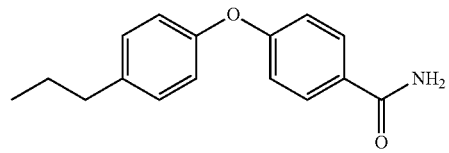 [SMILES: CCCc1ccc(Oc2ccc(C(N)=O)cc2)cc1]

140

4-(4-propylphenoxy)benzamide

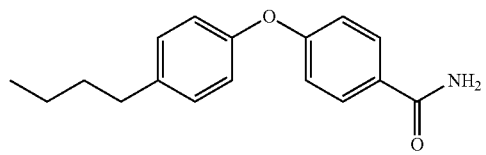

141

4-(4-butylphenoxy)benzamide

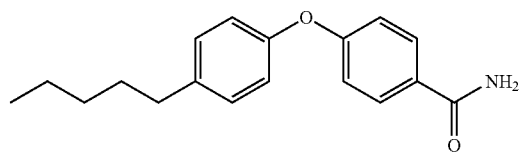

142

4-(4-pentylphenoxy)benzamide

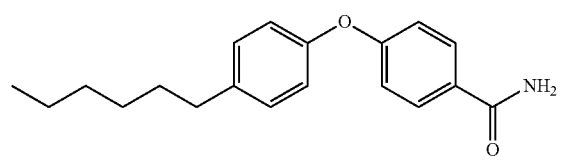 [SMILES: CCCCCCc1ccc(Oc2ccc(C(N)=O)cc2)cc1]

143

TABLE IIb-continued
4-(4-hexylphenoxy)benzamide
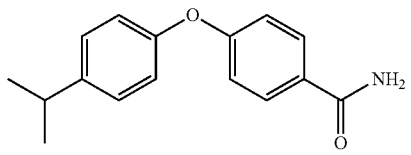 [SMILES: CC(C)c1ccc(Oc2ccc(C(N)=O)cc2)cc1]
144
4-(4-isopropylphenoxy)benzamide
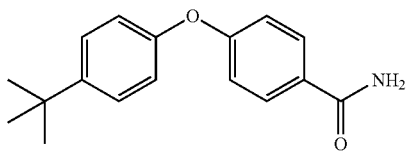 [SMILES: CC(C)(C)c1ccc(Oc2ccc(C(N)=O)cc2)cc1]
145
4-(4-(tert-butyl)phenoxy)benzamide
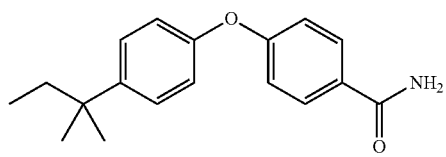 [SMILES: CCC(C)(C)c1ccc(Oc2ccc(C(N)=O)cc2)cc1]
146
4-(4-(tert-pentyl)phenoxy)benzamide
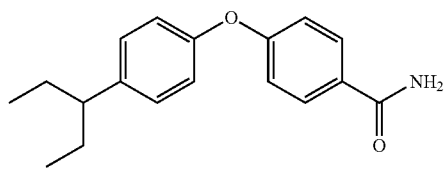 [SMILES: CCC(CC)c1ccc(Oc2ccc(C(N)=O)cc2)cc1]
147
4-(4-(pentan-3-yl)phenoxy)benzamide
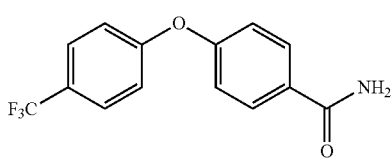 [SMILES: NC(=O)c1ccc(Oc2ccc(C(F)(F)F)cc2)cc1]
148
4-(4-(trifluoromethyl)phenoxy)benzamide
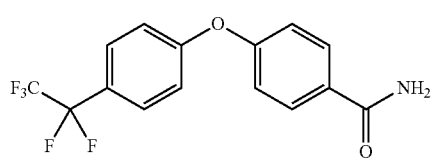 [SMILES: NC(=O)c1ccc(Oc2ccc(C(F)(F)C(F)(F)F)cc2)cc1]
149
4-(4-(perfluoroethyl)phenoxy)benzamide
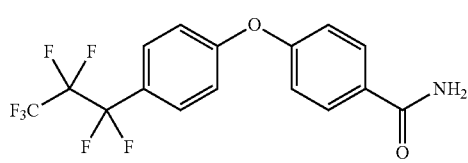 [SMILES: NC(=O)c1ccc(Oc2ccc(C(F)(F)C(F)(F)C(F)(F)F)cc2)cc1]
150
4-(4-(perfluoropropyl)phenoxy)benzamide TABLE IIb-continued

| | |
|---|---|
| 4-(4-(perfluorobutyl)phenoxy)benzamide | 151 |
| 4-(4-(1,1,1,3,3,3-hexafluoropropan-2-yl)phenoxy)benzamide | 152 |
| 4-(4-(perfluoropropan-2-yl)phenoxy)benzamide | 153 |
| 4-(4-cyclopropylphenoxy)benzamide | 154 |
| 4-(4-cyclobutylphenoxy)benzamide | 155 |
| 4-(4-cyclopentylphenoxy)benzamide | 156 |
| 4-(4-cyclohexylphenoxy)benzamide | 157 |

TABLE IIb-continued
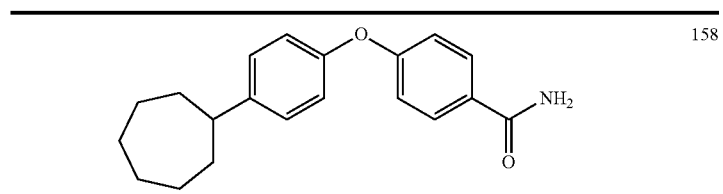
4-(4-cycloheptylphenoxy)benzamide 158
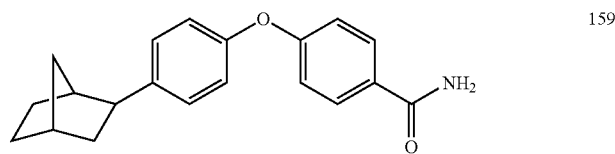
4-(4-((1S,4R)-bicyclo[2.2.1]heptan-2-yl)phenoxy)benzamide 159
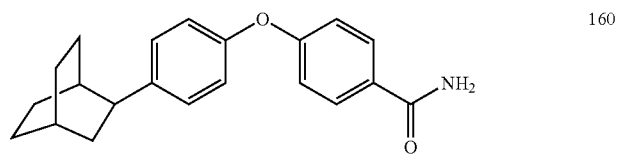
4-(4-((1s,4s)-bicyclo[2.2.2]octan-2-yl)phenoxy)benzamide 160
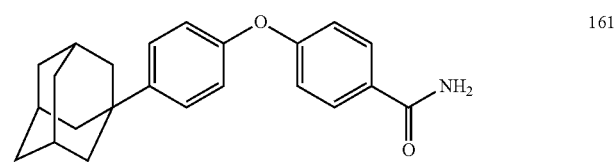
4-(4-((3r,5r,7r)-adamantan-1-yl)phenoxy)benzamide 161
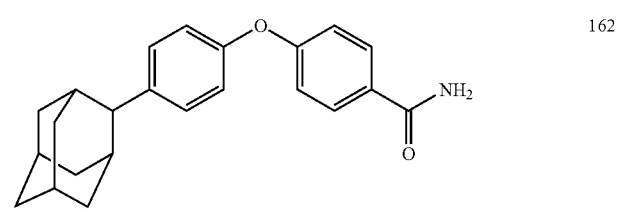
4-(4-((1r,3r,5r,7r)-adamantan-2-yl)phenoxy)benzamide 162
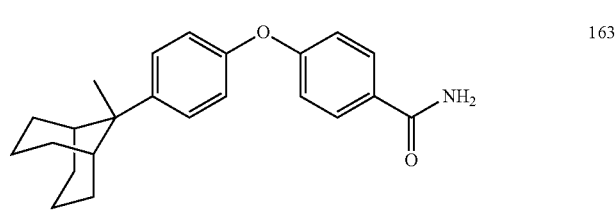
4-(4-((1R,5S)-9-methylbicyclo[3.3.1]nonan-9-yl)phenoxy)benzamide 163
X = CH, $R^3$ = H, $R^4$ = OH
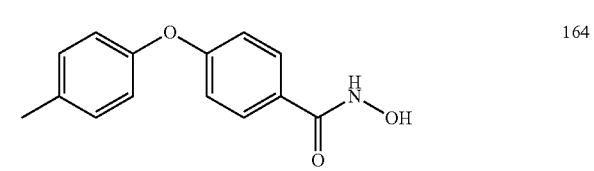
N-hydroxy-4-(p-tolyltoxy)benzamide 164

TABLE IIb-continued
| | |
|---|---|
| 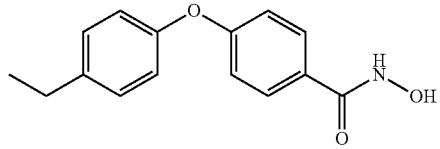 4-(4-ethylphenoxy)-N-hydroxybenzamide | 165 |
| 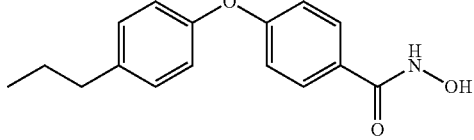 N-hydroxy-4-(4-propylphenoxy)benzamide | 166 |
| 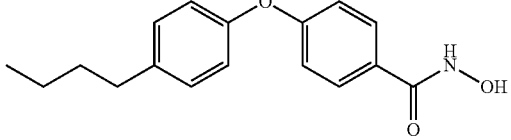 4-(4-butylphenoxy)-N-hydroxybenzamide | 167 |
| 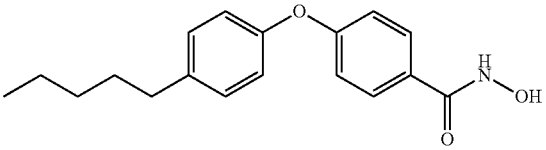 N-hydroxy-4-(4-pentylphenoxy)benzamide | 168 |
| 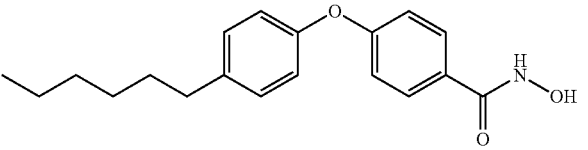 4-(4-hexylphenoxy)-N-hydroxybenzamide | 169 |
| 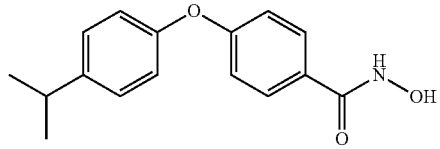 [SMILES: CC(C)c1ccc(Oc2ccc(C(=O)NO)cc2)cc1] N-hydroxy-4-(4-isopropylphenoxy)benzamide | 170 |
| 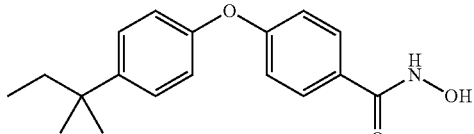 N-hydroxy-4-(4-(tert-pentyl)phenoxy)benzamide | 171 |
| 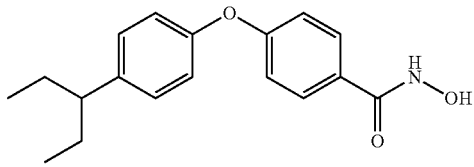 N-hydroxy-4-(4-(pentan-3-yl)phenoxy)benzamide | 172 |

TABLE IIb-continued
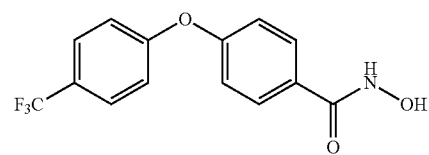
173
N-hydroxy-4-(4-(trifluoromethyl)phenoxy)benzamide
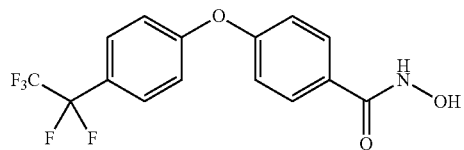 [SMILES: O=C(NO)c1ccc(Oc2ccc(C(F)(F)C(F)(F)F)cc2)cc1]
174
N-hydroxy-4-(4-(perfluoroethyl)phenoxy)benzamide
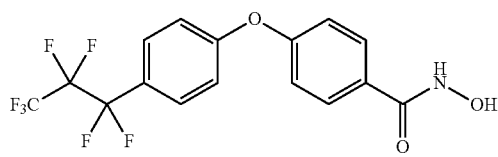 [SMILES: O=C(NO)c1ccc(Oc2ccc(C(F)(F)C(F)(F)C(F)(F)F)cc2)cc1]
175
N-hydroxy-4-(4-(perfluoropropyl)phenoxy)benzamide
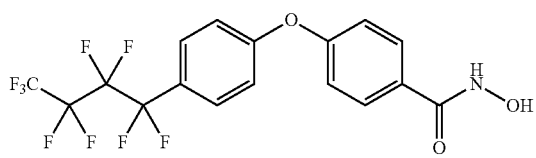 [SMILES: O=C(NO)c1ccc(Oc2ccc(C(F)(F)C(F)(F)C(F)(F)C(F)(F)F)cc2)cc1]
176
N-hydroxy-4-(4-(perfluorobutyl)phenoxy)benzamide
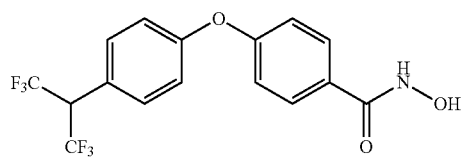 [SMILES: O=C(NO)c1ccc(Oc2ccc(C(C(F)(F)F)C(F)(F)F)cc2)cc1]
177
4-(4-(1,1,1,3,3,3-hexafluoropropan-2-yl)phenoxy)-N-hydroxybenzamide
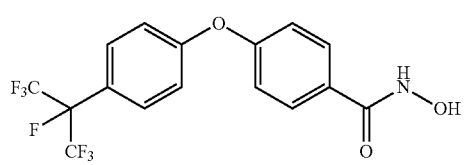 [SMILES: O=C(NO)c1ccc(Oc2ccc(C(F)(C(F)(F)F)C(F)(F)F)cc2)cc1]
178
N-hydroxy-4-(4-(perfluoropropan-2-yl)phenoxy)benzamide
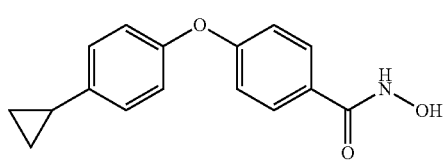 [SMILES: O=C(NO)c1ccc(Oc2ccc(C3CC3)cc2)cc1]
179
4-(4-cyclopropylphenoxy)-N-hydroxybenzamide TABLE IIb-continued

| | |
|---|---|
| 4-(4-cyclobutylphenoxy)-N-hydroxybenzamide | 180 |
| 4-(4-cyclopentylphenoxy)-N-hydroxybenzamide | 181 |
| 4-(4-cyclohexylphenoxy)-N-hydroxybenzamide | 182 |
| 4-(4-cycloheptylphenoxy)-N-hydroxybenzamide | 183 |
| 4-(4-((1S,4R)-bicyclo[2.2.1]heptan-2-yl)phenoxy)-N-hydroxybenzamide | 184 |
| 4-(4-((1s,4s)-bicyclo[2.2.2]octan-2-yl)phenoxy)-N-hydroxybenzamide | 185 |
| 4-(4-((3r,5r,7r)-adamantan-1-yl)phenoxy)-N-hydroxybenzamide | 186 |

TABLE IIb-continued

| | |
|---|---|
| [structure] | 187 |
| 4-(4-((1r,3r,7r)-adamantan-2-yl)phenoxy)-N-hydroxybenzamide | |
| [structure] | 188 |
| N-hydroxy-4-(4-((1R,5S)-9-methylbicyclo[3.3.1]nonan-9-yl)phenoxy)benzamide | |

$X = CH$, $R^3 = H$, $R^4 = Me$

| | |
|---|---|
| [structure] | 189 |
| N-methyl-4-(p-tolyloxy)benzamide | |
| [structure] | 190 |
| 4-(4-ethylphenoxy)-N-methylbenzamide | |
| [structure] | 191 |
| N-methyl-4-(4-propylphenoxy)benzamide | |
| [structure] | 192 |
| 4-(4-butylphenoxy)-N-methylbenzamide | |
| [structure] | 193 |
| N-methyl-4-(4-pentylphenoxy)benzamide | |

TABLE IIb-continued
| | |
|---|---|
| 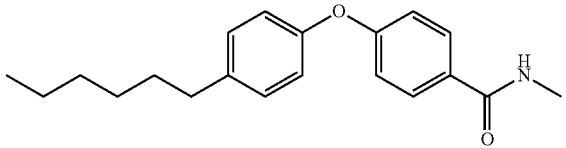 4-(4-hexylphenoxy)-N-methylbenzamide | 194 |
| 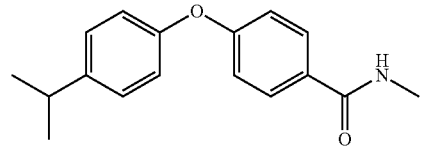 [SMILES: CNC(=O)c1ccc(Oc2ccc(C(C)C)cc2)cc1] 4-(4-isopropylphenoxy)-N-methylbenzamide | 195 |
| 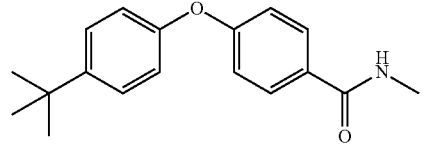 4-(4-(tert-butyl)phenoxy)-N-methylbenzamide | 196 |
| 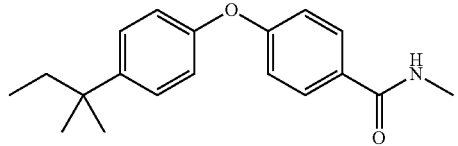 [SMILES: CCC(C)(C)c1ccc(Oc2ccc(C(=O)NC)cc2)cc1] N-methyl-4-(4-(tert-pentyl)phenoxy)benzamide | 197 |
| 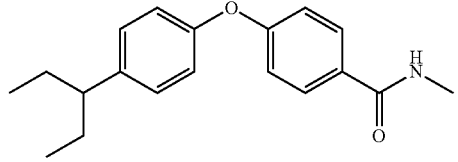 [SMILES: CCC(CC)c1ccc(Oc2ccc(C(=O)NC)cc2)cc1] N-methyl-4-(4-(pentan-3-yl)phenoxy)benzamide | 198 |
| 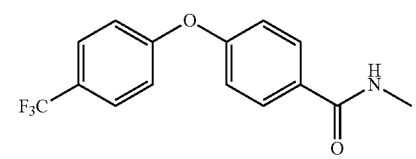 [SMILES: CNC(=O)c1ccc(Oc2ccc(C(F)(F)F)cc2)cc1] N-methyl-4-(4-(trifluoromethyl)phenoxy)benzamide | 199 |
| 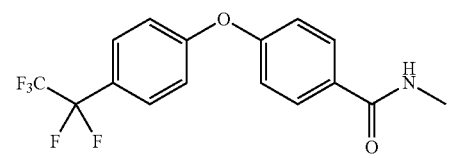 [SMILES: CNC(=O)c1ccc(Oc2ccc(C(F)(F)C(F)(F)F)cc2)cc1] N-4-methyl-4-(4-(perfluoroethyl)phenoxy)benzamide | 200 |
| 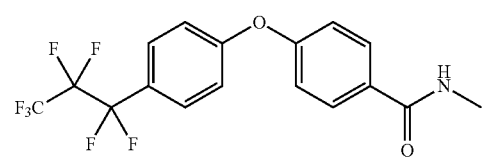 [SMILES: CNC(=O)c1ccc(Oc2ccc(C(F)(F)C(F)(F)C(F)(F)F)cc2)cc1] N-methyl-4-(4-(perfluoropropyl)phenoxy)benzamide | 201 |

TABLE IIb-continued
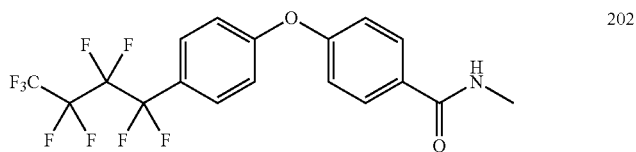
N-methyl-4-(4-(perfluorobutyl)phenoxy)benzamide
202
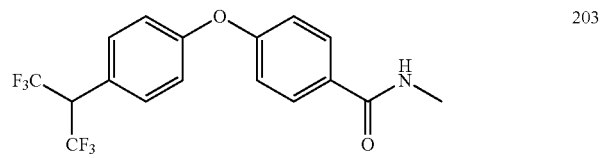
4-(4-(1,1,1,3,3,3-hexafluoropropan-2-yl)phenoxy)-N-methylbenzamide
203
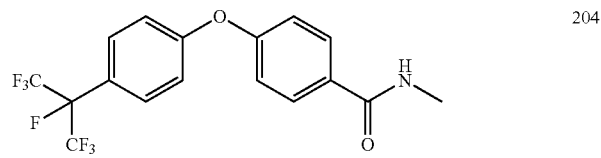
N-methyl-4-(4-(perfluoropropan-2-yl)phenoxy)benzamide
204
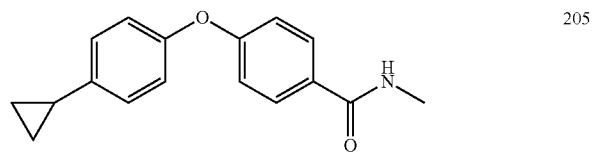
4-(4-cyclopropylphenoxy)-N-methylbenzamide
205
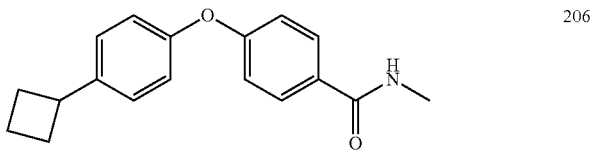
4-(4-cyclobutylphenoxy)-N-methylbenzamide
206
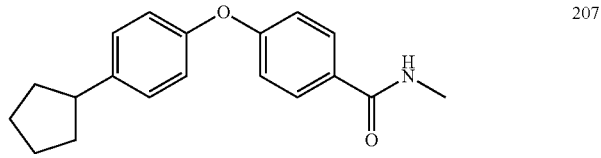
4-(4-cyclopentylphenoxy)-N-methylbenzamide
207
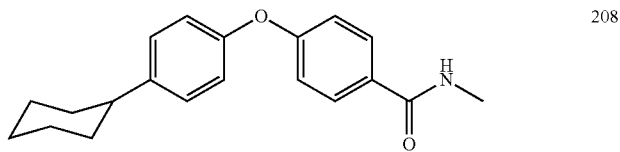
4-(4-cyclohexylphenoxy)-N-methylbenzamide
208

TABLE IIb-continued
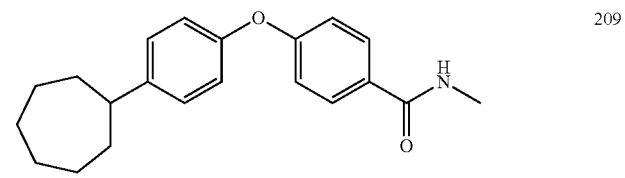
4-(4-cycloheptylphenoxy)-N-methylbenzamide
209
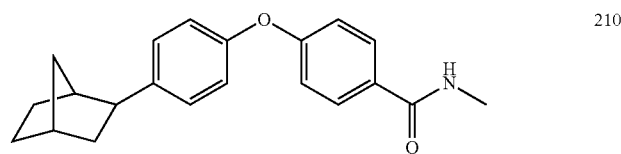
4-(4-((1S,4R)-bicyclo[2.2.1]heptan-2-yl)phenoxy)-N-methylbenzamide
210
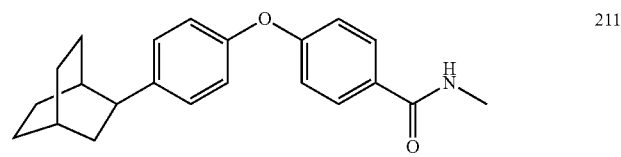
4-(4-((1s,4s)-bicyclo[2.2.2]octan-2-yl)phenoxy)-N-methylbenzamide
211
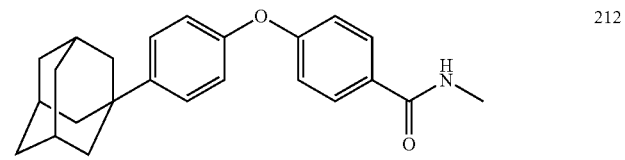
4-(4-((3r,5r,7r)-adamantan-1-yl)phenoxy)-N-methylbenzamide
212
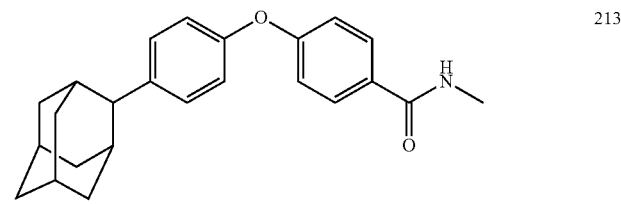
4-(4-((1r,3r,5r,7r)-adamantan-2-yl)phenoxy)-N-methylbenzamide
213
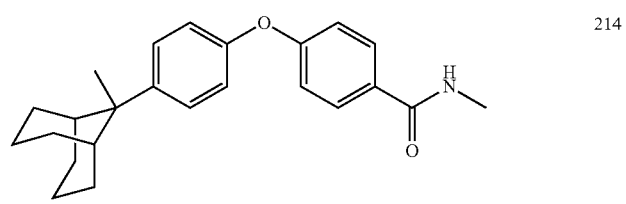
N-methyl-4-(4-((1R,5S)-9-methylbicyclo[3.3.1]nonan-9-yl)phenoxy)benzamide
214
X = CH, $R^3$ = Me, $R^4$ = Me
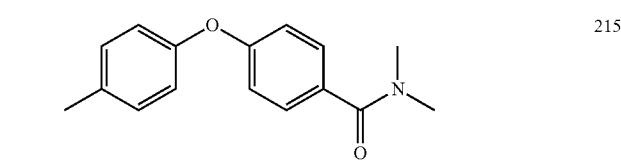
N,N-dimethyl-4-(p-tolyloxy)benzamide
215

TABLE IIb-continued
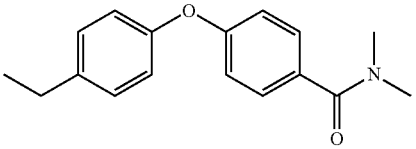 [SMILES: CCc1ccc(Oc2ccc(C(=O)N(C)C)cc2)cc1]
4-(4-ethylphenoxy)-N,N-dimethylbenzamide 216
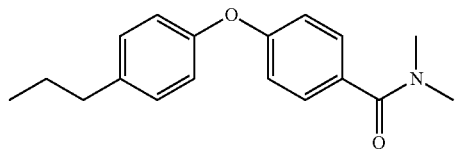
N,N-dimethyl-4-(4-propylphenoxy)benzamide 217
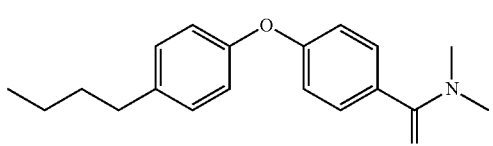
4-(4-butylphenoxy)-N,N-dimethylbenzamide 218
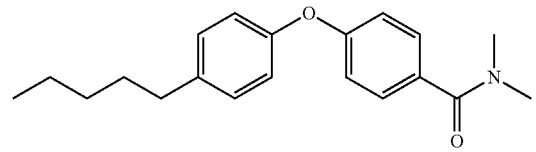 [SMILES: CCCCCc1ccc(Oc2ccc(C(=O)N(C)C)cc2)cc1]
N,N-dimethyl-4-(4-pentylphenoxy)benzamide 219
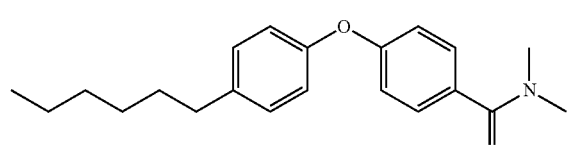
4-(4-hexylphenoxy)-N,N-dimethylbenzamide 220
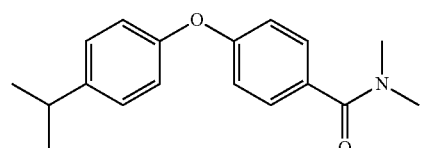
4-(4-isopropylphenoxy)-N,N-dimethylbenzamide 221
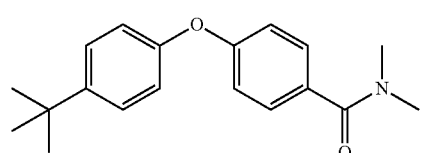
4-(4-(tert-butyl)phenoxy)-N,N-dimethylbenzamide 222
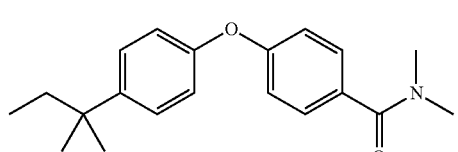
N,N-dimethyl-4-(4-(tert-pentyl)phenoxy)benzamide 223

TABLE IIb-continued

| | |
|---|---|
| 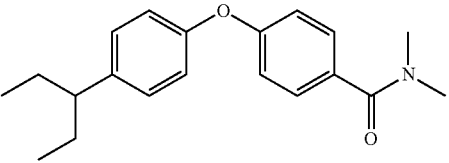 [SMILES: CCC(CC)c1ccc(Oc2ccc(C(=O)N(C)C)cc2)cc1] N,N-dimethyl-4-(4-(pentan-3-yl)phenoxy)benzamide | 224 |
| 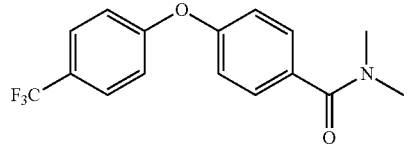 [SMILES: CN(C)C(=O)c1ccc(Oc2ccc(C(F)(F)F)cc2)cc1] N,N-dimethyl-4-(4-(trifluoromethyl)phenoxy)benzamide | 225 |
| 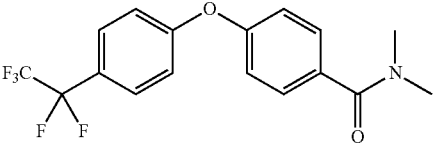 N,N-dimethyl-4-(4-(perfluoroethyl)phenoxy)benzamide | 226 |
| 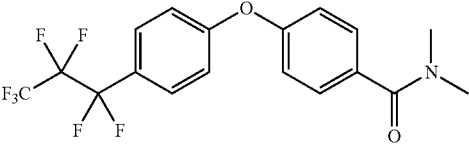 [SMILES: CN(C)C(=O)c1ccc(Oc2ccc(C(F)(F)C(F)(F)C(F)(F)F)cc2)cc1] N,N-dimethyl-4-(4-(perfluoropropyl)phenoxy)benzamide | 227 |
| 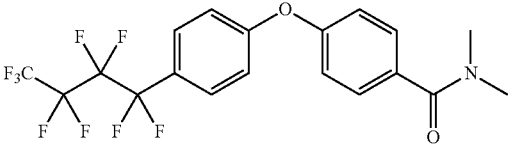 N,N-dimethyl-4-(4-(perfluorobutyl)phenoxy)benzamide | 228 |
| 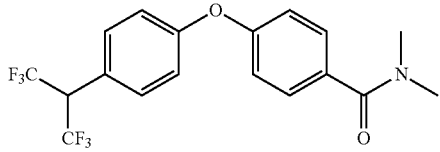 [SMILES: CN(C)C(=O)c1ccc(Oc2ccc(C(C(F)(F)F)C(F)(F)F)cc2)cc1] 4-(4-(1,1,1,3,3,3-hexafluoropropan-2-yl)phenoxy)-N,N-dimethylbenzamide | 229 |
| 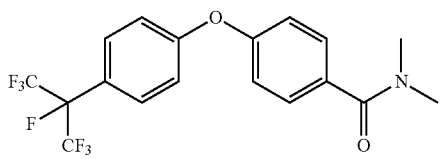 N,N-dimethyl-4-(4-(perfluoropropan-2-yl)phenoxy)benzamide | 230 |
| 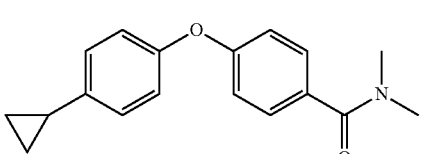 4-(4-cyclopropylphenoxy)-N,N-dimethylbenzamide | 231 |

TABLE IIb-continued
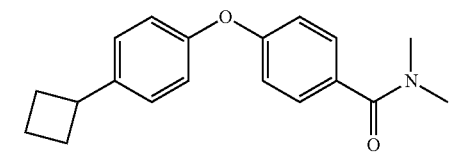
232
4-(4-cyclobutylphenoxy)-N,N-dimethylbenzamide
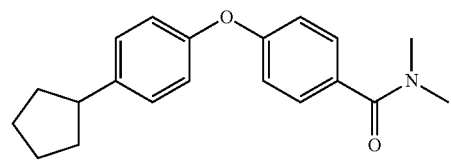
233
4-(4-cyclopentylpheoxy)-N,N-dimethylbenzamide
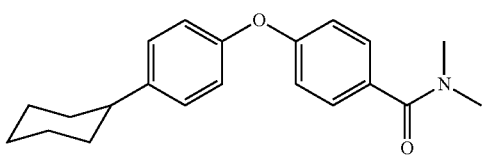
234
4-(4-cyclohexylphenoxy)-N,N-dimethylbenzamide
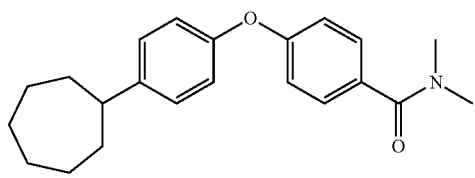 [SMILES: CN(C)C(=O)c1ccc(Oc2ccc(C3CCCCCC3)cc2)cc1]
235
4-(4-cycloheptylphenoxy)-N,N-dimethylbenzamide
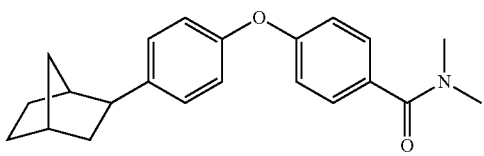 [SMILES: CN(C)C(=O)c1ccc(Oc2ccc(C3CC4CCC3C4)cc2)cc1]
236
4-(4-((1S,4R)-bicyclo[2.2.1]heptan-2-yl)phenoxy)-N,N-dimethylbenzamide
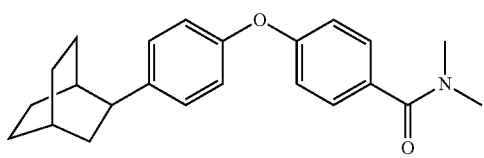
237
4-(4-((1s,4s)-bicyclo[2.2.2]octan-2-yl)phenoxy)-N,N-dimethylbenzamide
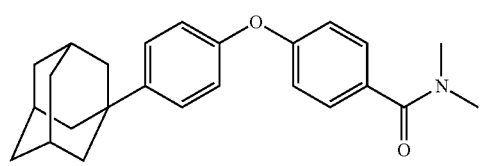
238
4-(4-((3r,5r,7r)-adamantan-1-yl)pheoxy)-N,N-dimethylbenzamide TABLE IIb-continued
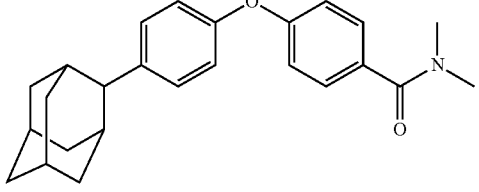
239
4-(4-((1r,3r,5r,7r)-adamantan-2-yl)-phenoxy)-N,N-dimethylbenzamide
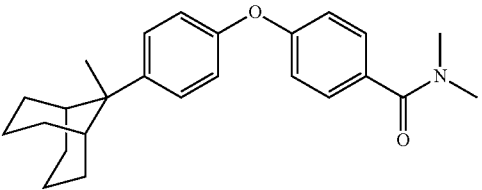
240
N,N-dimethyl-4-(4-((1R,5S)-9-methylbicyclo[3.3.1]nonan-9-yl)phenoxy)benzamide
$X = N, R^3 = H, R^4 = H$
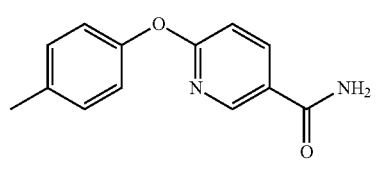
241
6-(p-tolyloxy)nicolinamide
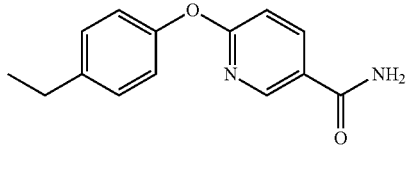
242
6-(4-ethylphenoxy)nicotinamide
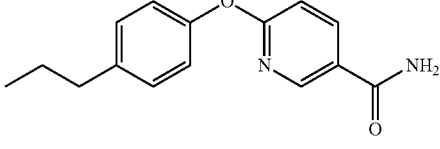
243
6-(4-propylphenoxy)nicotinamide
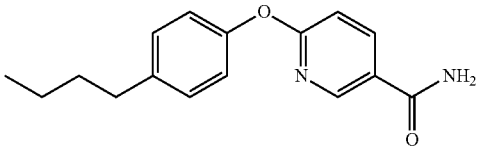
244
6-(4-butylphenoxy)nicotinamide
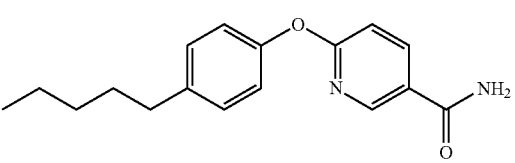 [SMILES: CCCCCc1ccc(Oc2ccc(C(N)=O)cn2)cc1]
245
6-(4-pentylphenoxy)nicotinamide TABLE IIb-continued
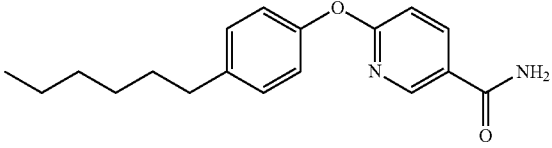 [SMILES: CCCCCCc1ccc(Oc2ccc(C(N)=O)cn2)cc1]
246
6-(4-hexylphenoxy)nicotinamide
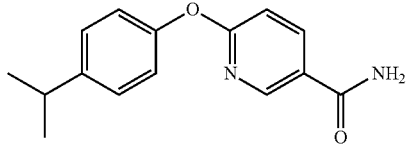 [SMILES: CC(C)c1ccc(Oc2ccc(C(N)=O)cn2)cc1]
247
6-(4-isopropylphenoxy)nicotinamide
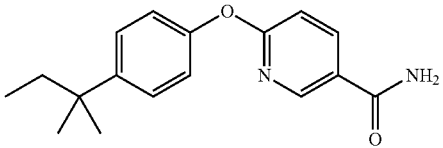 [SMILES: CCC(C)(C)c1ccc(Oc2ccc(C(N)=O)cn2)cc1]
248
6-(4-(tert-pentyl)phenoxy)nicotinamide
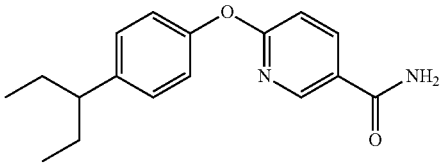
249
6-(4-pentan-3-yl)phenoxy)nicotinamide
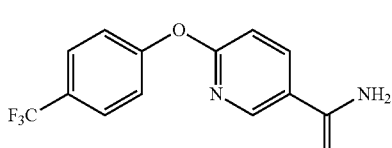
250
6-(4-(trifluoromethyl)phenoxy)nicotinamide
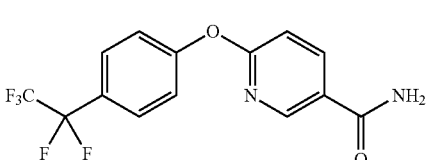
251
6-(4-(perfluoroethyl)phenoxy)nicotinamide
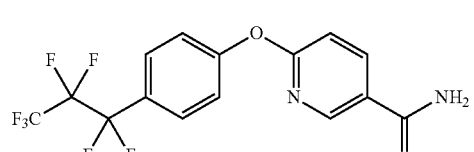
252
6-(4-(perfluoropropyl)phenoxy)nicotinamide
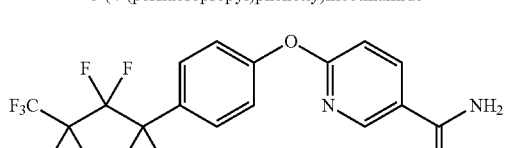
253
6-(4-(perfluorobutyl)phenoxy)nicotinamide TABLE IIb-continued
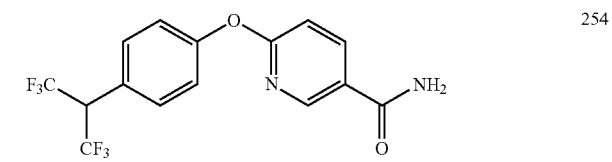
254
6-(4-(1,1,1,3,3,3-hexafluoropropan-2-yl)phenoxy)nicotinamide
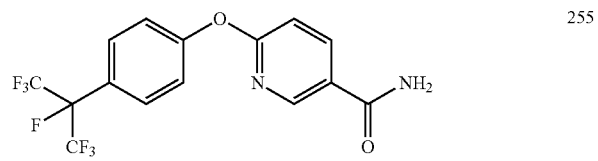
255
(6-(4-(perfluoropropan-2-yl)phenoxy)nicotinamide
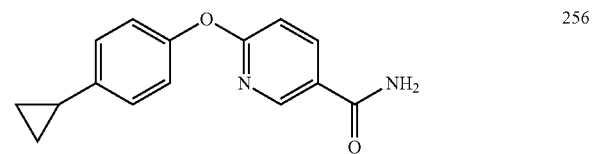
256
6-(4-cyclopropylphenoxy)nicotinamide
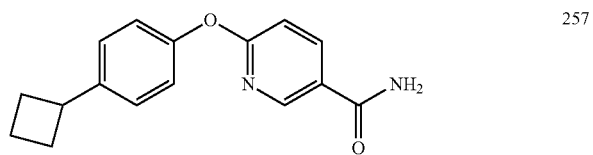
257
6-(4-cyclobutylphenoxy)nicotinamide
258
6-(4-cyclopentylphenoxy)nicotinamide
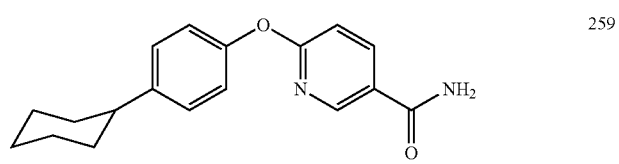
259
6-(4-cyclohexylphenoxy)nicotinamide
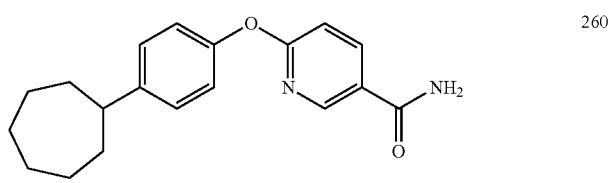
260
6-(4-cycloheptylphenoxy)nicotinamide TABLE IIb-continued
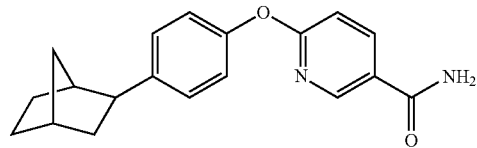 [SMILES: NC(=O)c1ccc(Oc2ccc(C3CC4CCC3C4)cc2)nc1]
6-(4-((1S,4R)-bicyclo[2.2.1]heptan-2-yl)phenoxy)nictinamide
261
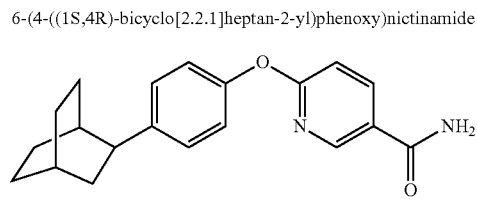
6-(4-((1s,4)-bicyclo[2.2.2]octan-2-yl)phenoxy)nicotinamide
262

6-(4-((3r,5r,7r)-adamantan-1-yl)phenoxy)nicotinamide
263
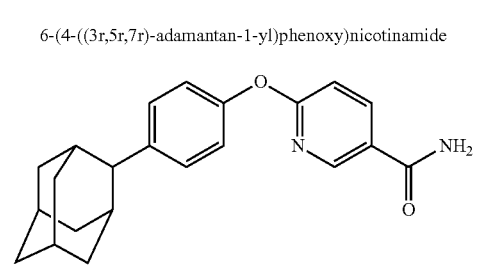
6-(4-((1r,3r,5r,7r)-adamantan-2-yl)phenoxy)nicotinamide
264
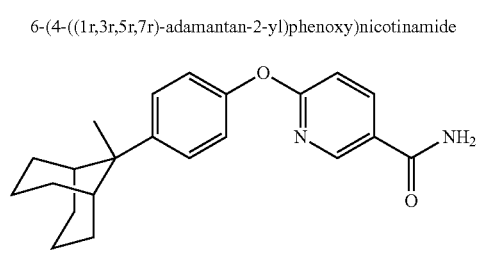
6-(4-((1R,5S)-9-methylbicyclo[3.3.1]nonan-9-yl)phenoxy)nicotinamide
265
X = N, R³ = H, R⁴ = OH
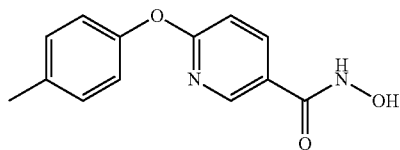 [SMILES: Cc1ccc(Oc2ccc(C(=O)NO)cn2)cc1]
N-hydroxy-6-(p-tolyloxy)nicotinamide
266
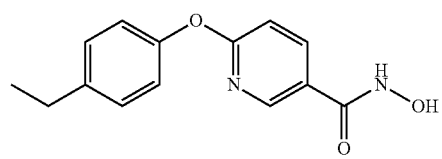 [SMILES: CCc1ccc(Oc2ccc(C(=O)NO)cn2)cc1]
6-(4-ethylphenoxy)-N-hydroxynicotinamide
267

TABLE IIb-continued
| | |
|---|---|
| 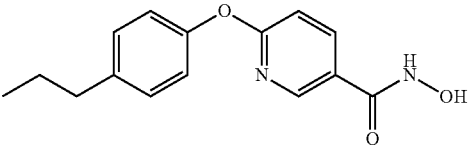 N-hydroxy-6-(4-propylphenoxy)nicotinamide | 268 |
| 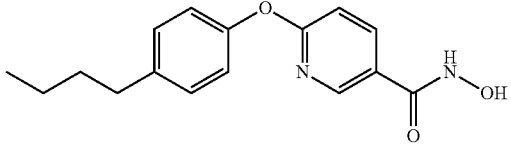 [SMILES: CCCCc1ccc(Oc2ccc(C(=O)NO)cn2)cc1] 6-(4-butylphenoxy)-N-hydroxynicotinamide | 269 |
| 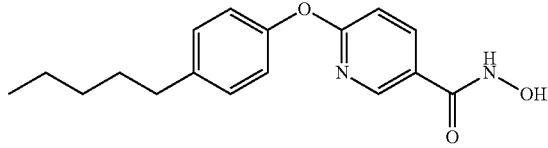 [SMILES: CCCCCc1ccc(Oc2ccc(C(=O)NO)cn2)cc1] N-hydroxy-6-(4-pentylphenoxy)nicotinamide | 270 |
| 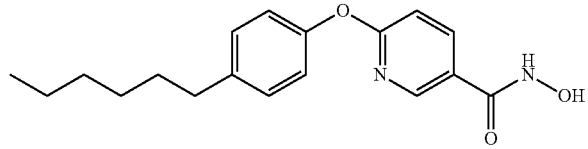 [SMILES: CCCCCCc1ccc(Oc2ccc(C(=O)NO)cn2)cc1] 6-(4-hexylphenoxy)-N-hydroxynicotinamide | 271 |
| 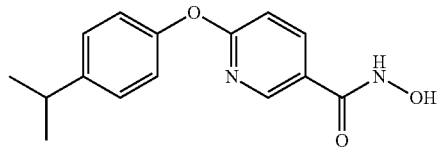 [SMILES: CC(C)c1ccc(Oc2ccc(C(=O)NO)cn2)cc1] N-hydroxy-6-(4-isopropylphenoxy)nicotinamide | 272 |
| 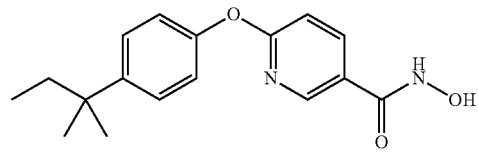 N-hydroxy-6-(4-(tert-pentyl)phenoxy)nicotinamide | 273 |
| 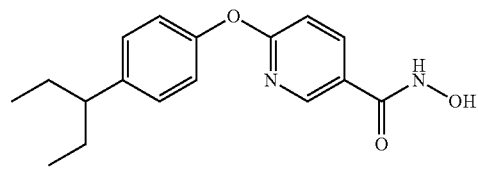 [SMILES: CCC(CC)c1ccc(Oc2ccc(C(=O)NO)cn2)cc1] N-hydroxy-6-(4-(pentan-3-yl)phenoxy)nicotinamide | 274 |
| 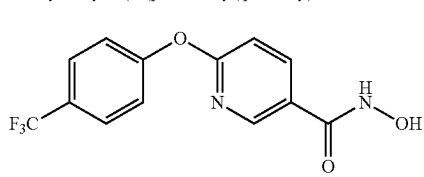 N-hydroxy-6-(4-(trifluoromethyl)phenoxy)nicotinamide | 275 |

TABLE IIb-continued

| | |
|---|---|
| 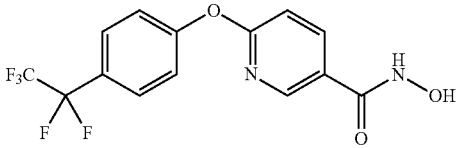 [SMILES: O=C(NO)c1ccc(Oc2ccc(C(F)(F)C(F)(F)F)cc2)nc1] N-hydroxy-6-(4-(perfluoroethyl)phenoxy)nicotinamide | 276 |
| 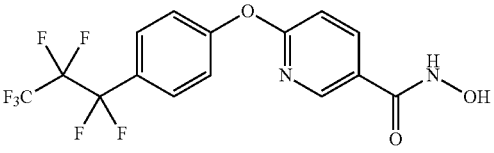 N-hydroxy-6-(4-(perfluoropropyl)phenoxy)nicotinamide | 277 |
| 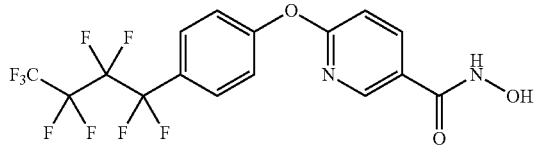 [SMILES: O=C(NO)c1ccc(Oc2ccc(C(F)(F)C(F)(F)C(F)(F)C(F)(F)F)cc2)nc1] 6-(4-(1,1,1,3,3,3-hexafluoropropan-2-yl)phenoxy)-N-hydroxynicotinamide | 278 |
| 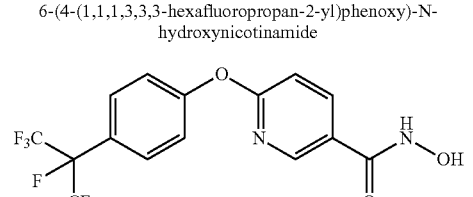 6-(4-(1,1,1,3,3,3-hexafluoropropan-2-yl)phenoxy)-N-hydroxynicotinamide | 279 |
| 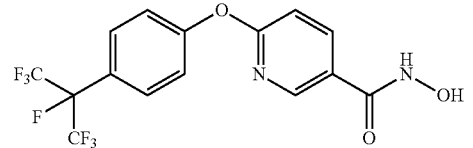 [SMILES: O=C(NO)c1ccc(Oc2ccc(C(F)(C(F)(F)F)C(F)(F)F)cc2)nc1] N-hydroxy-6-(4-(perfluoropropan-2-yl)phenoxy)nicotinamide | 280 |
| 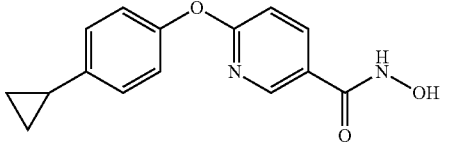 [SMILES: O=C(NO)c1ccc(Oc2ccc(C3CC3)cc2)nc1] 6-(4-cyclopropylphenoxy)-N-hydroxynicotinamide | 281 |
| 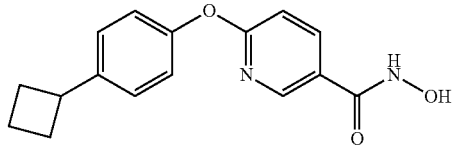 [SMILES: O=C(NO)c1ccc(Oc2ccc(C3CCC3)cc2)nc1] 6-(4-cyclobutylphenoxy)-N-hydroxynicotinamide | 282 |
| 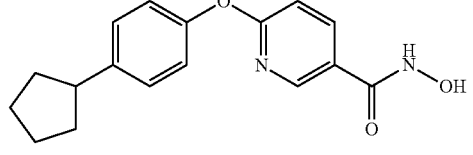 6-(4-cyclopentylphenoxy)-N-hydroxynicotinamide | 283 |

TABLE IIb-continued

| | |
|---|---|
| 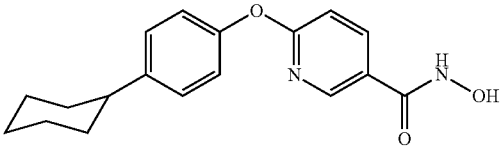 [SMILES: O=C(NO)c1ccc(Oc2ccc(C3CCCCC3)cc2)nc1] 6-(4-cyclohexylphenoxy)-N-hydroxynicotinamide | 284 |
| 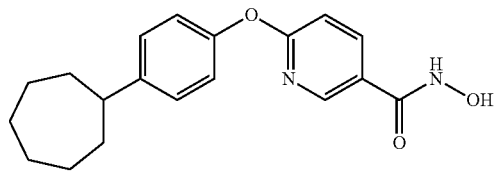 [SMILES: O=C(NO)c1ccc(Oc2ccc(C3CCCCCC3)cc2)nc1] 6-(4-cycloheptylphenoxy)-N-hyeroxynicotinamide | 285 |
| 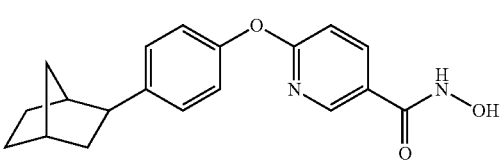 [SMILES: O=C(NO)c1ccc(Oc2ccc(C3CC4CCC3C4)cc2)nc1] 6-(4-((1S,4R)-bicyclo[2.2.1]heptan-2-yl)phenoxy)-N-hydroxynicotinamide | 286 |
| 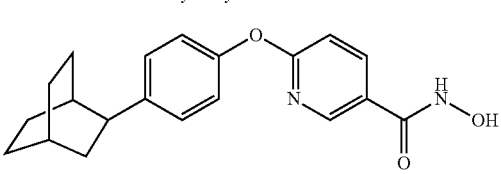 6-(4-((1s,4s)-bicyclo[2.2.2]octan-2-yl)phenoxy)-N-hydroxynicotinamide | 287 |
| 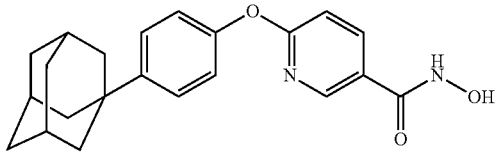 6-(4-((3r,5r,7r)-adamantan-1-yl)phenoxy)-N-hydroxynicotinamide | 288 |
| 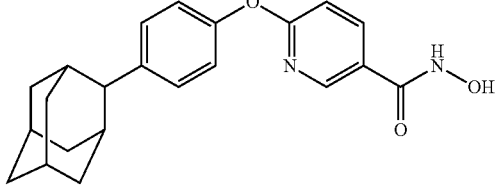 6-(4-((1r,3r,5r,7r)-adamantan-2-yl)phenoxy)-N-hydroxynicotinamide | 289 |
| 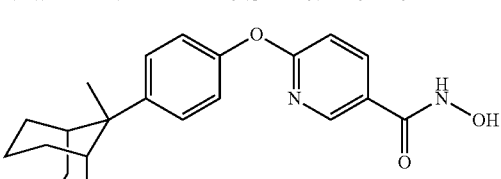 N-hydroxy-6-(4-((1R,5S)-9-methylbicyclo[3.3.1]nonan-9-yl)phenoxy)nicotinamide | 290 |

X = N, R³ = H, R⁴ = Me

TABLE IIb-continued
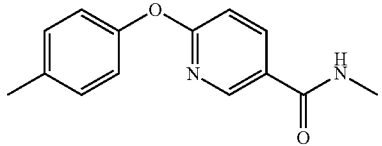
N-methyl-6-(p-tolyloxy)nicotinamide
291
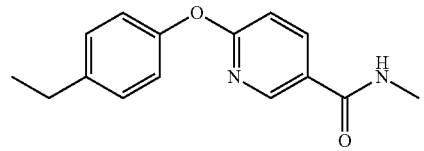 [SMILES: CCc1ccc(Oc2ccc(C(=O)NC)cn2)cc1]
6-(4-ethylphenoxy)-N-mtehylnicotinamide
292
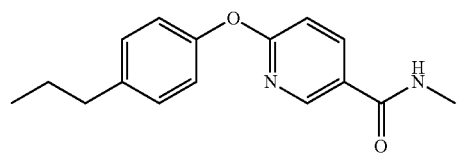
N-methyl-6-(4-propylphenoxy)nicotinamide
293
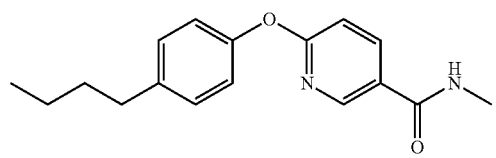 [SMILES: CCCCc1ccc(Oc2ccc(C(=O)NC)cn2)cc1]
6-(4-butylphenoxy)-N-methylnicotinamide
294
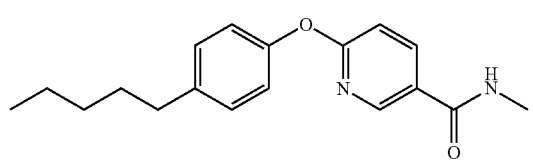
N-methyl-6-(4-pentylphenoxy)nicotinamide
295
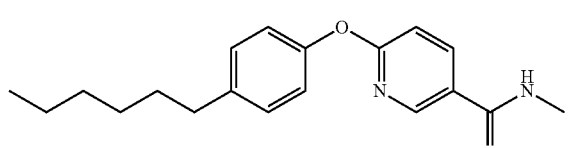
6-(4-hexylphenoxy)-N-methylnicotinamide
296
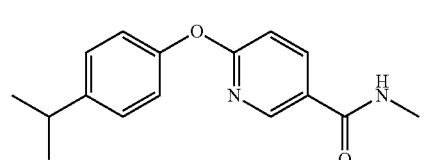
6-(4-isopropylphenoxy)-N-methylnicotinamide
297
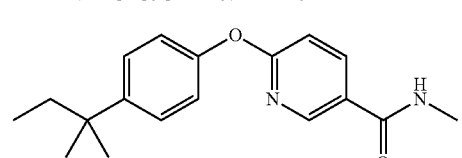
N-methyl-6-(4-(tert-pentyl)phenoxy)nicotinamide
298

TABLE IIb-continued

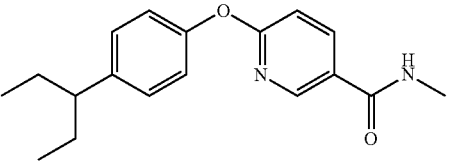 [SMILES: CCC(CC)c1ccc(Oc2ccc(C(=O)NC)cn2)cc1]

N-mtehyl-6-(4-(pentan-3-yl)phenoxy)nicotinamide

299

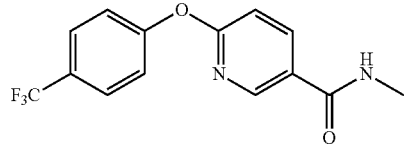 [SMILES: CNC(=O)c1ccc(Oc2ccc(C(F)(F)F)cc2)nc1]

N-methyl-6-(4-(trifluoromethyl)phenoxy)nicotinamide

300

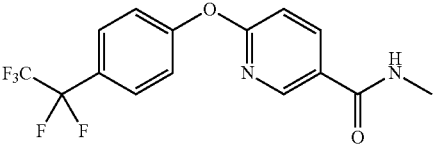

N-methyl-6-(4-(perfluoroethyl)phenoxy)nicotinamide

301

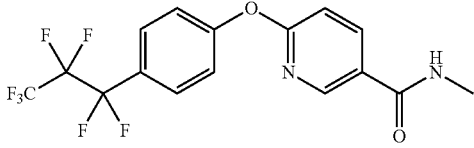

N-methyl-6-(4-(perfluoropropyl)phenoxy)nicotinamide

302

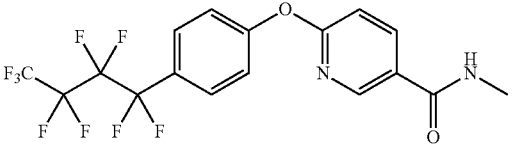

N-methyl-6-(4-(perfluorobutyl)phenoxy)nicotinamide

303

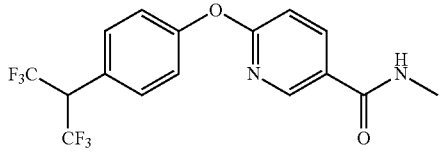 [SMILES: CNC(=O)c1ccc(Oc2ccc(C(C(F)(F)F)C(F)(F)F)cc2)nc1]

6-(4-(1,1,1,3,3,3-hexafluoropropan-2-yl)phenoxy)-N-methylnicotinamide

304

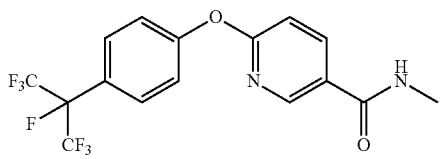 [SMILES: CNC(=O)c1ccc(Oc2ccc(C(F)(C(F)(F)F)C(F)(F)F)cc2)nc1]

N-methyl-6-(4-(perfluoropropan-2-yl)phenoxy)nicotinamide

305

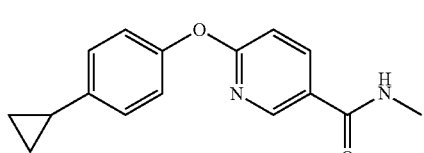

6-(4-cyclopropylphenoxy)-N-mtehylnicotinamide

306

TABLE IIb-continued

| | |
|---|---|
| 6-(4-cyclobutylphenoxy)-N-methylnicotinamide | 307 |
| 6-(4-cyclopentylphenoxy)-N-mtehylnicotinamide | 308 |
| 6-(4-cyclohexylphenoxy)-N-methylnicotinamide | 309 |
| 6-(4-cycloheptylphenoxy)-N-methylnicotinamide | 310 |
| 6-(4-((1S,4R)-bicyclo[2.2.1]heptan-2-yl)phenoxy)-N-methylnicotinamide | 311 |
| 6-(4-((1s,4s)-bicyclo[2.2.2]octan-2-yl)phenoxy)-N-methylnicotinamide | 312 |
| 6-(4-((3r,5r,7r)-adamantan-1-yl)phenoxy)-N-methylnicotinamide | 313 |

TABLE IIb-continued
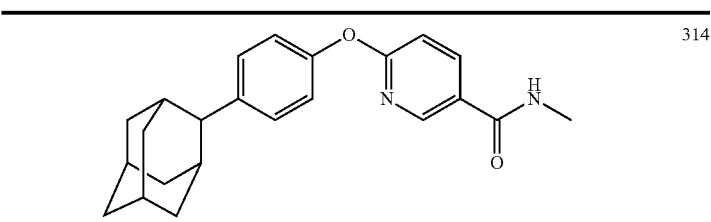
314
6-(4-((1r,3r,5r,7r)-adamantan-2-yl)phenoxy)-N-methylnicotinamide
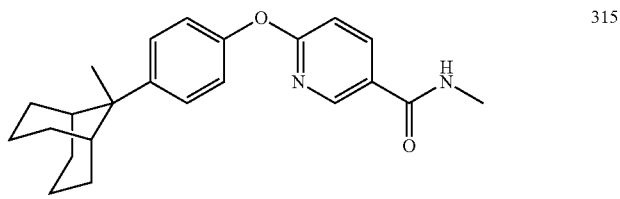
315
N-methyl-6-(4-((1R,5S)-9-methylbicyclo[3.3.1]nonan-9-yl)phenoxy)
nicotinamide
X = N, $R^3$ = Me, $R^4$ = Me
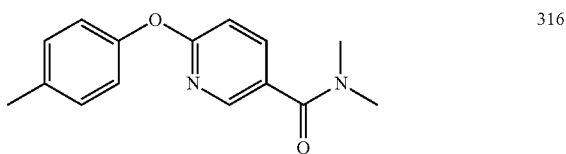
316
N,N-dimethyl-6-(p-tolyloxy)nicotinamide
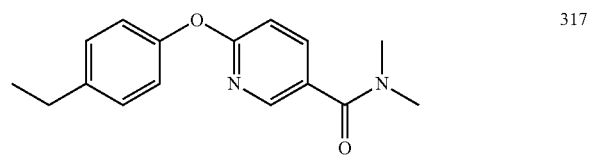
317
6-(4-ethylphenoxy)-N,N-dimethylnicotinamide
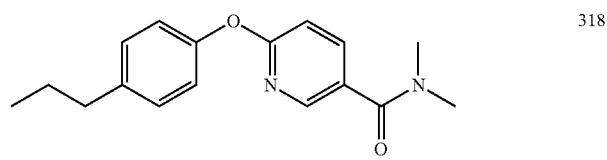
318
N,N-dimethyl-6-(4-propylphenoxy)nicotinamide
319
6-(4-butylphenoxy)-N,N-dimethylnicotinamide
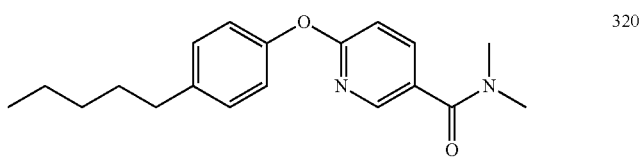
320
N,N-dimethyl-6-(4-pentylphenoxy)nicotinamide TABLE IIb-continued

| | |
|---|---|
| 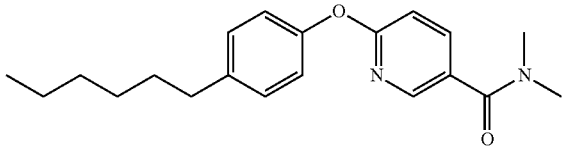 [SMILES: CCCCCCc1ccc(Oc2ccc(C(=O)N(C)C)cn2)cc1] 6-(4-hexylphenoxy)-N,N-dimethylnicotinamide | 321 |
| 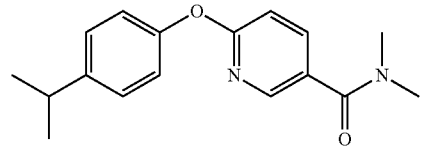 6-(4-isopropylphenoxy)-N,N-dimethylnictinamide | 322 |
| 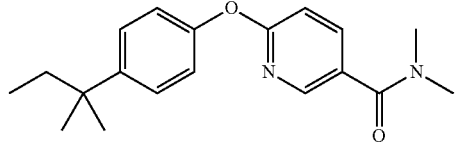 [SMILES: CCC(C)(C)c1ccc(Oc2ccc(C(=O)N(C)C)cn2)cc1] N,N-dimethyl-6-(4-(tert-pentyl)phenoxy)nicotinamide | 323 |
| 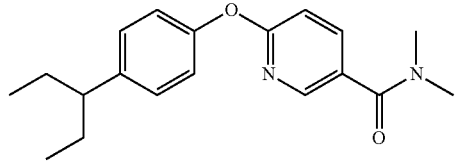 [SMILES: CCC(CC)c1ccc(Oc2ccc(C(=O)N(C)C)cn2)cc1] N,N-dimethyl-6-(4-(pentan-3-yl)phenoxy)nicotinamide | 324 |
| 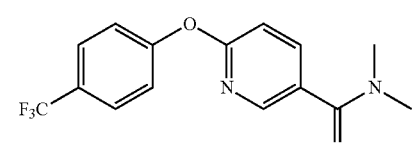 N,N-dimethyl-6-(4-(trifluoromethyl)phenoxy)nicotinamide | 325 |
| 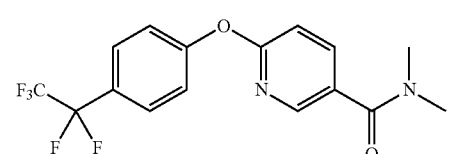 N,N-dimethyl-6-(4-(perfluoroethyl)phenoxy)nicotinamide | 326 |
| 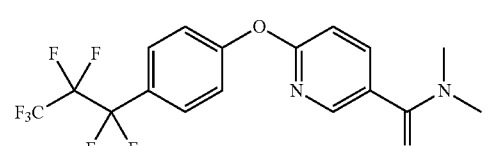 N,N-dimethyl-6-(4-(perfluoropropyl)phenoxy)nicotinamide | 327 |
| 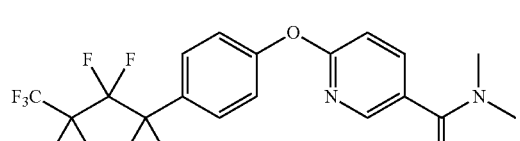 N,N-dimethyl-6-(4-(perfluorobutyl)phenoxy)nicotinamide | 328 |

TABLE IIb-continued

| Structure | # |
|---|---|
| 6-(4-(1,1,1,3,3,3-hexafluoropropan-2-yl)phenoxy)-N,N-dimethylnicotinamide | 329 |
| N,N-dimethyl-6-(4-(perfluoropropan-2-yl)phenoxy)nicotinamide | 330 |
| 6-(4-cyclopropylphenoxy)-N,N-dimethylnicotinamide | 359 |
| 6-(4-cyclobutylphenoxy)-N,N-dimethylnicotinamide | 332 |
| 6-(4-cyclopentylphenoxy)-N,N-dimethylnicotinamide | 333 |
| 6-(4-cyclohexylphenoxy)-N,N-dimethylnicotinamide | 334 |
| 6-(4-cycloheptylphenoxy)-N,N-dimethylnicotinamide | 335 |

TABLE IIb-continued
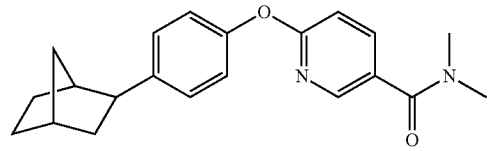 [SMILES: CN(C)C(=O)c1ccc(Oc2ccc(C3CC4CCC3C4)cc2)nc1]
336
6-(4-((1S,4R)-bicyclo[2.2.1]heptan-2-yl)phenoxy)-N,N-dimethylnicotinamide
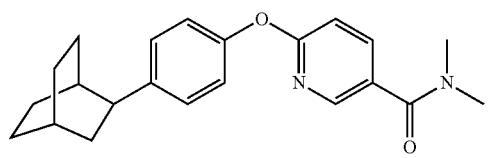 [SMILES: CN(C)C(=O)c1ccc(Oc2ccc(C3CC4CCC3CC4)cc2)nc1]
337
6-(4-((1s,4s)-bicyclo[2.2.2]octan-2-yl)phenoxy)-N,N-dimethylnicotinamide
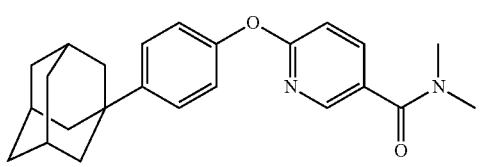 [SMILES: CN(C)C(=O)c1ccc(Oc2ccc(C34CC5CC(CC(C5)C3)C4)cc2)nc1]
338
6-(4-((3r,5r,7r)-adamantan-1-yl)phenoxy)-N,N-dimethylnicotinamide
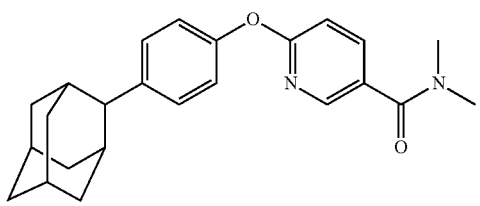 [SMILES: CN(C)C(=O)c1ccc(Oc2ccc(C3C4CC5CC(C4)CC3C5)cc2)nc1]
339
6-(4-((1r,3r,5r,7r)-adamantan-2-yl)phenoxy)-N,N-dimethylnicotinamide
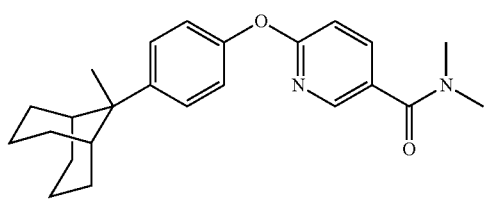 [SMILES: CN(C)C(=O)c1ccc(Oc2ccc(C3(C)C4CCCC3CCC4)cc2)nc1]
340
N,N-dimethyl-6-(4-((1R,5S)-9-methylbicyclo[3.3.1]nonan-9-yl)phenoxy)nicotinamide Also included are isomers) e.g. enantiomers or diastereomers or rotamers or mixtures of isomers, salts, particularly pharmaceutically acceptable salts, and solvates of the compounds listed above.

A third aspect of the present invention relates to compounds of formula III and salts and solvates thereof:

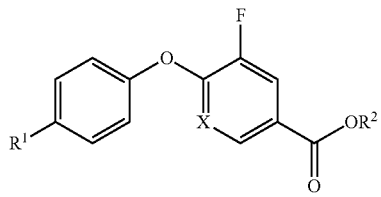

(III)

wherein X, $R^1$ and $R^2$ are defined as in formula I, including the preferred definitions of $R^1$ and $R^2$.

In some embodiments, the following compounds shown in Table IIIa are explicitly excluded from the scope of the invention:

TABLE IIIa

| Compound | $R^1$ | $R^2$ | X |
|---|---|---|---|
| III-A | tert-butyl | H | CH |
| III-B | tert-butyl | ethyl | CH |
| III-C | phenyl | H | CH |

Specific examples of compounds falling under the scope of formula III are shown in Table IIIb. The compounds in Table IIIb are defined by their chemical structure, the indicated nomenclature is only for illustrative purposes.

TABLE IIIb

X = CH, $R^2$ = H

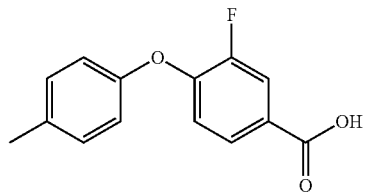

341

3-fluoro-4-(p-tolyloxy)benzoic acid

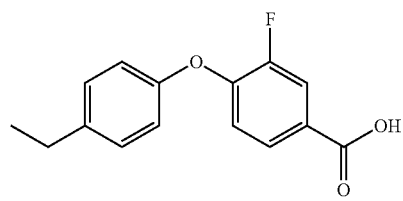 [SMILES: CCc1ccc(Oc2ccc(C(=O)O)cc2F)cc1]

342

4-(4-ethylphenoxy)-3-fluorobenzoic acid

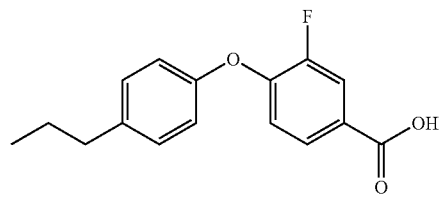

343

3-fluoro-4-(4-propylphenoxy)benzoic acid

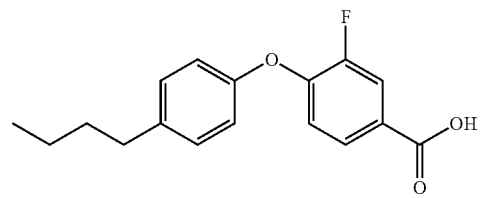

344

4-(4-butylphenoxy)-3-fluorobenzoic acid

TABLE IIIb-continued
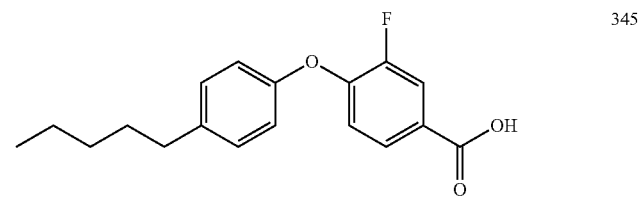
345
3-fluoro-4-(4-pentylphenoxy)benzoic acid
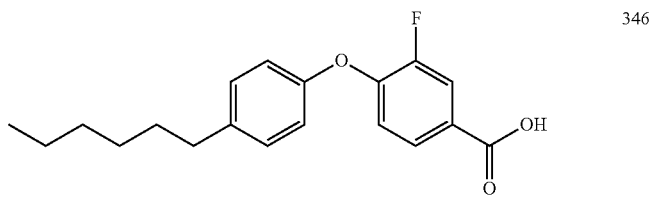
346
3-fluoro-4-(4-hexylphenoxy)benzoic acid
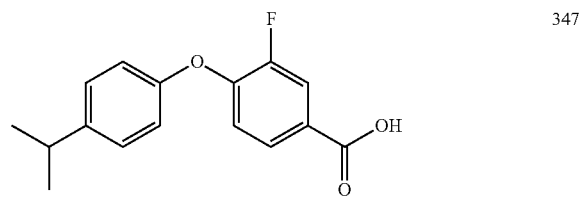
347
3-fluoro-4-(4-isopropylphenoxy)benzoic acid
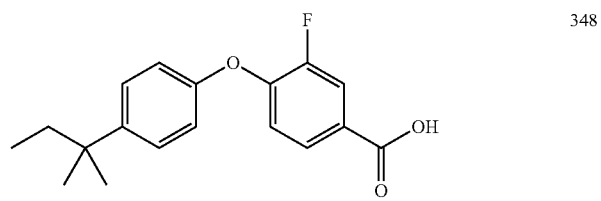
348
3-fluoro-4-(4-(tert-pentyl)phenoxy)benzoic acid
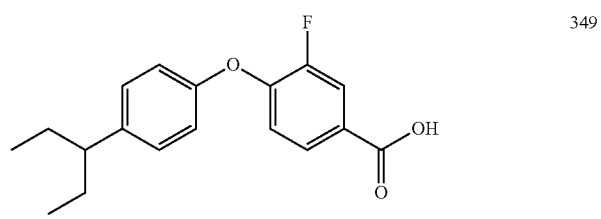
349
3-fluoro-4-(4-(pentan-3-yl)phenoxy)benzoic acid
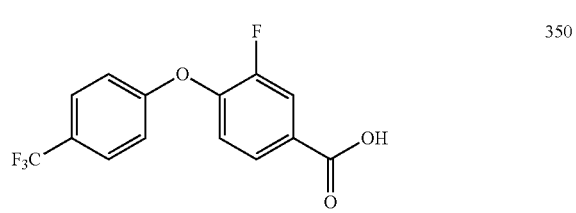
350
3-fluoro-4-(4-(trifluoromethyl)phenoxy)benzoic acid TABLE IIIb-continued
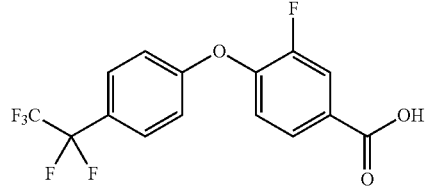 [SMILES: O=C(O)c1ccc(Oc2ccc(C(F)(F)C(F)(F)F)cc2)c(F)c1]
3-fluoro-4-(4-(perfluoroethyl)phenoxy)benzoic acid
351
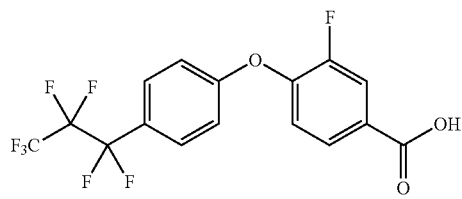
3-fluoro-4-(4-(perfluoropropyl)phenoxy)benzoic acid
352
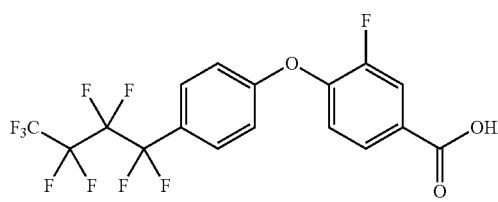 [SMILES: O=C(O)c1ccc(Oc2ccc(C(F)(F)C(F)(F)C(F)(F)C(F)(F)F)cc2)c(F)c1]
3-fluoro-4-(4-(perfluorobutyl)phenoxy)benzoic acid
353
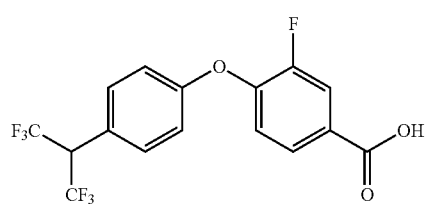
3-fluoro-4-(4-(1,1,1,3,3,3-hexafluoropropan-2-yl)phenoxy)benzoic acid
354
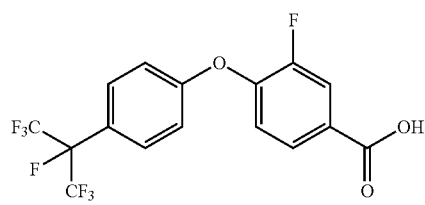
3-fluoro-4-(4-(perfluoropropan-2-yl)phenoxy)benzoic acid
355
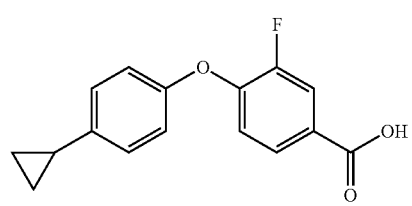 [SMILES: O=C(O)c1ccc(Oc2ccc(C3CC3)cc2)c(F)c1]
4-(4-cyclopropylphenoxy)-3-fluorobenzoic acid
356

TABLE IIIb-continued
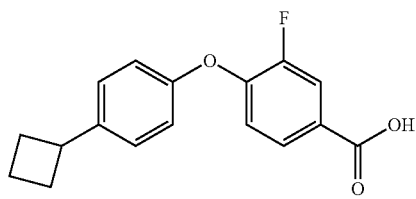 [SMILES: O=C(O)c1ccc(Oc2ccc(C3CCC3)cc2)c(F)c1]
357
4-(4-cyclobutylphenoxy)-3-fluorobenzoic acid
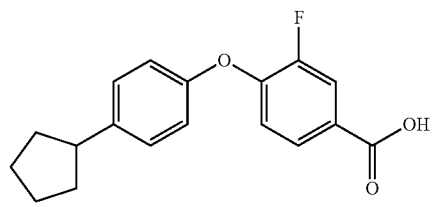
358
4-(4-cyclopentylphenoxy)-3-fluorobenzoic acid
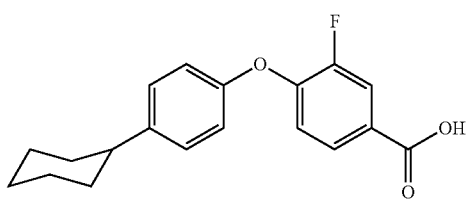 [SMILES: O=C(O)c1ccc(Oc2ccc(C3CCCCC3)cc2)c(F)c1]
359
4-(4-cyclohexylphenoxy)-3-fluorobenzoic acid
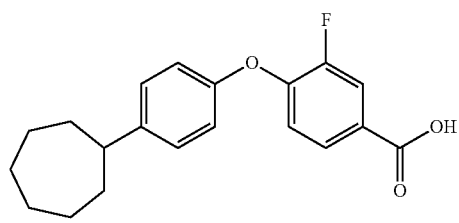
360
4-(4-cycloheptylphenoxy)-3-fluorobenzoic acid
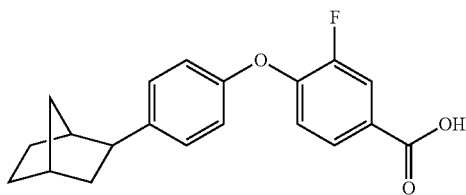
361
4-(4-((1S,4R)-bicyclo[2.2.1]heptan-2-yl)phenoxy)-3-fluorobenzoic acid
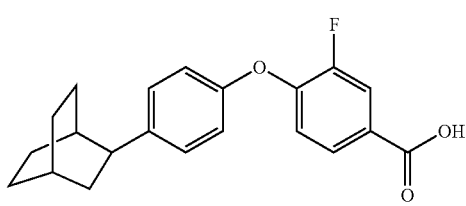 [SMILES: O=C(O)c1ccc(Oc2ccc(C3CC4CCC3CC4)cc2)c(F)c1]
362
4-(4-((1s,4s)-bicyclo[2.2.2]octan-2-yl)phenoxy)-3-fluorobenzoic acid TABLE IIIb-continued
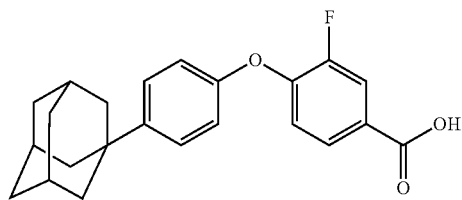
4-(4-((3r,5r,7r)-adamantan-1-yl)phenoxy)-3-fluorobenzoic acid
363
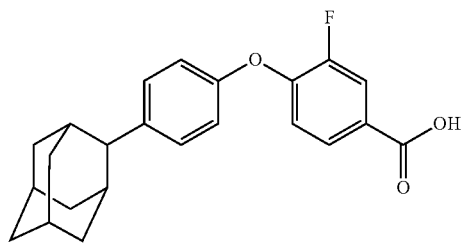 [SMILES: O=C(O)c1ccc(Oc2ccc(C3C4CC5CC(C4)CC3C5)cc2)c(F)c1]
4-(4-((1r,3r,5r,7r)-adamantan-2-yl)phenoxy)-3-fluorobenzoic acid
364
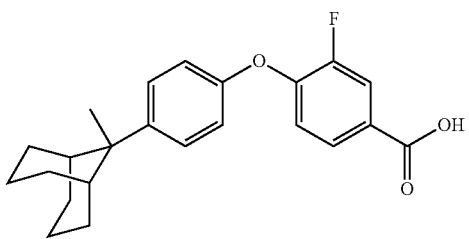 [SMILES: CC1(c2ccc(Oc3ccc(C(=O)O)cc3F)cc2)C2CCCC1CCC2]
3-fluoro-4-(4-((1R,5S)-9-methylbicyclo[3.3.1]nonan-9-yl)phenoxy)benzoic acid
X = CH, $R^2$ = Me
365
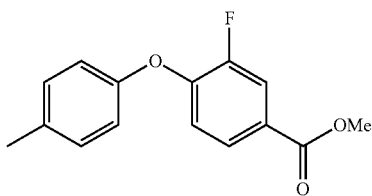 [SMILES: COC(=O)c1ccc(Oc2ccc(C)cc2)c(F)c1]
methyl 3-fluoro-4-(p-tolyloxy)benzoate
366
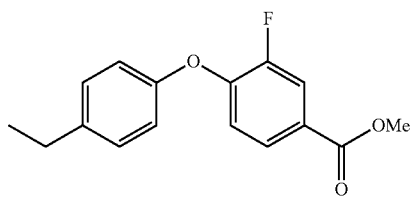 [SMILES: CCc1ccc(Oc2ccc(C(=O)OC)cc2F)cc1]
methyl 4-(4-ethylphenoxy)-3-fluorobenzoate
367
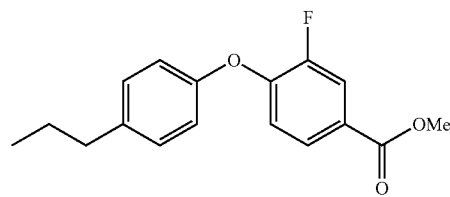 [SMILES: CCCc1ccc(Oc2ccc(C(=O)OC)cc2F)cc1]
methyl 3-fluoro-4-(4-propylphenoxy)benzoate
368

TABLE IIIb-continued
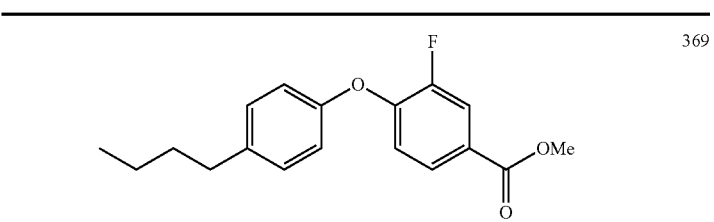
369
methyl 4-(4-butylphenoxy)-3-fluorobenzoate
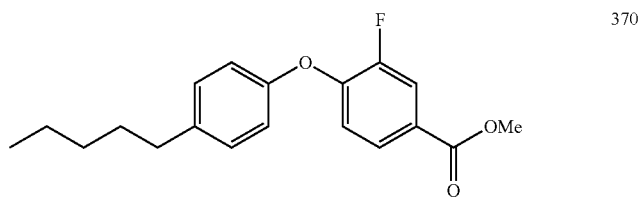
370
methyl 3-fluoro-4-(4-pentylphenoxy)benzoate
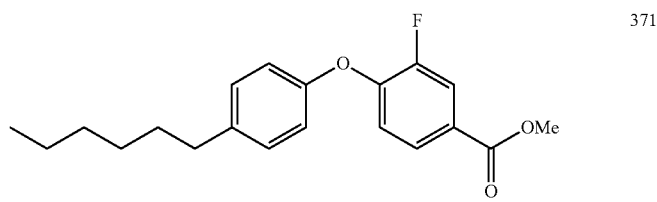
371
methyl 3-fluoro-4-(4-hexylphenoxy)benzoate
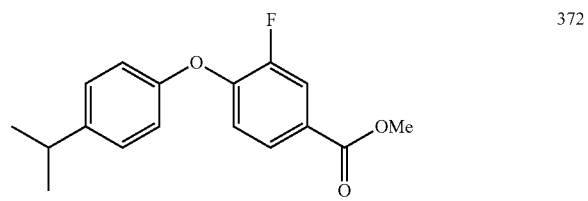
372
methyl 3-fluoro-4-(4-isopropylphenoxy)benzoate
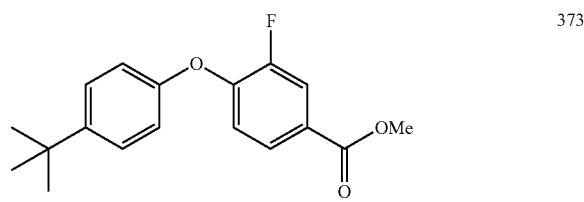
373
methyl 4-(4-(tert-butyl)phenoxy)-3-fluorobenzoate
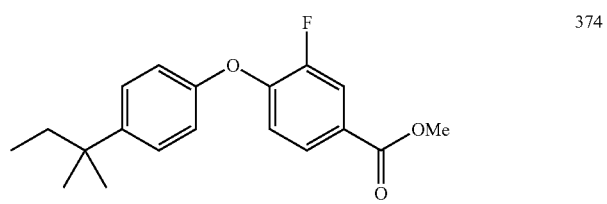
374
methyl 3-fluoro-4-(4-(tert-pentyl)phenoxy)benzoate TABLE IIIb-continued
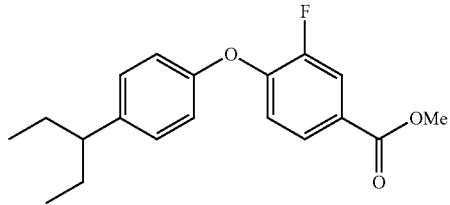 [SMILES: CCC(CC)c1ccc(Oc2ccc(C(=O)OC)cc2F)cc1]
methyl 3-fluoro-4-(4-(pentan-3-yl)phenoxy)benzoate
375
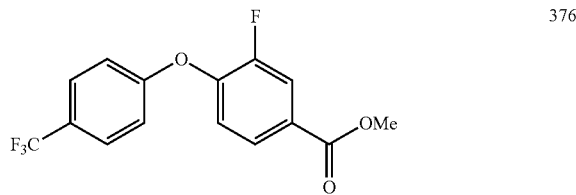
methyl 3-fluoro-4-(4-(trifluoromethyl)phenoxy)benzoate
376
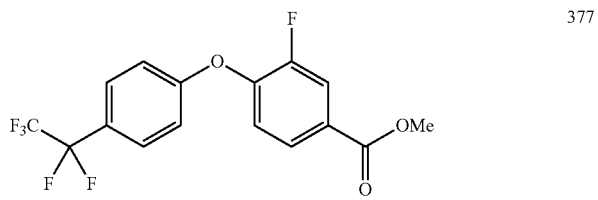
methyl 3-fluoro-4-(4-(perfluoroethyl)phenoxy)benzoate
377
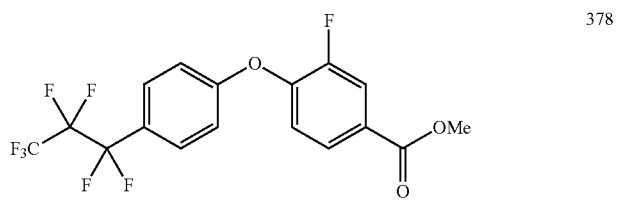
methyl 3-fluoro-4-(4-(perfluoropropyl)phenoxy)benzoate
378
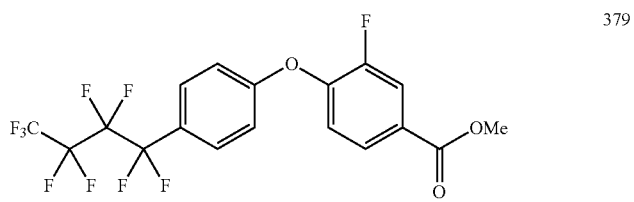
methyl 3-fluoro-4-(4-(perfluorobutyl)phenoxy)benzoate
379
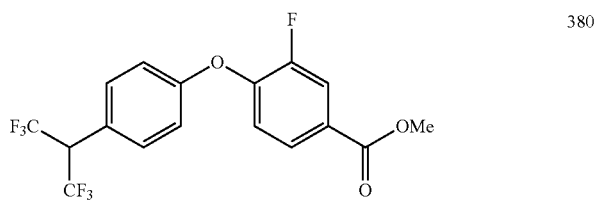
methyl 3-fluoro-4-(4-(1,1,1,3,3,3-hexafluoropropan-2-yl)phenoxy)benzoate
380

TABLE IIIb-continued
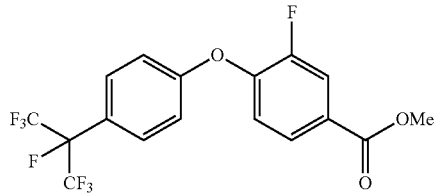
381
methyl 3-fluoro-4-(4-(perfluoropropan-2-yl)phenoxy)benzoate
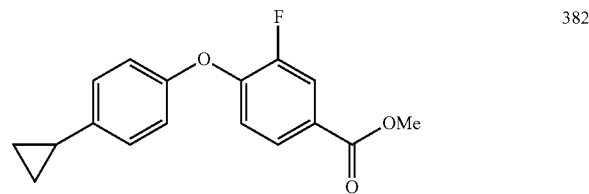
382
methyl 4-(4-cyclopropylphenoxy)-3-fluorobenzoate
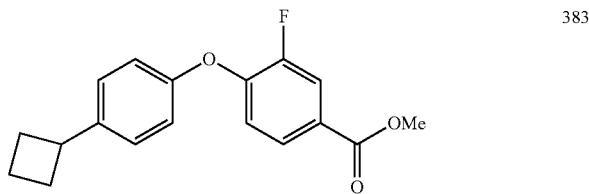
383
methyl 4-(4-cyclobutylphenoxy)-3-fluorobenzoate
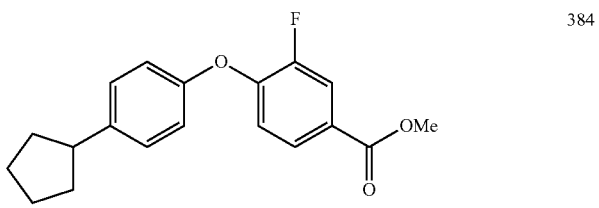
384
methyl 4-(4-cyclopentylphenoxy)-3-fluorobenzoate
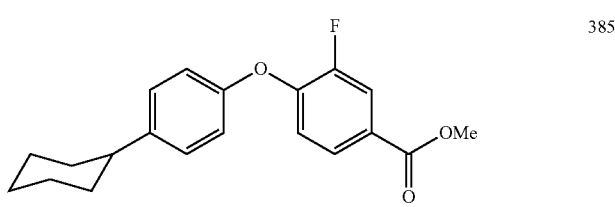
385
methyl 4-(4-cyclohexylphenoxy)-3-fluorobenzoate
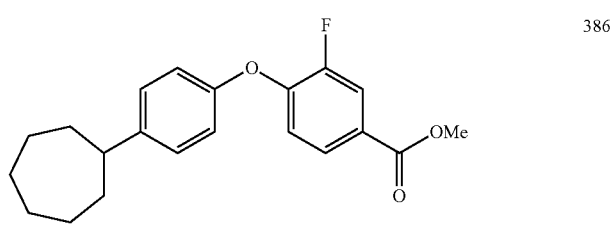
386
methyl 4-(4-cycloheptylphenoxy)-3-fluorobenzoate TABLE IIIb-continued
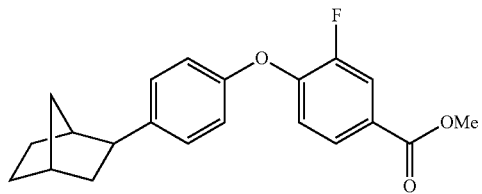
methyl 4-(4-((1S,4R)-bicyclo[2.2.1]heptan-2-yl)phenoxy)-3-fluorobenzoate
387
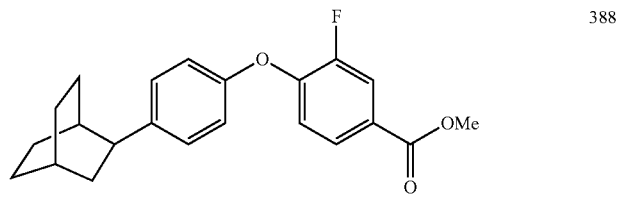
methyl 4-(4-((1s,4s)-bicyclo[2.2.2]octan-2-yl)phenoxy)-3-fluorobenzoate
388
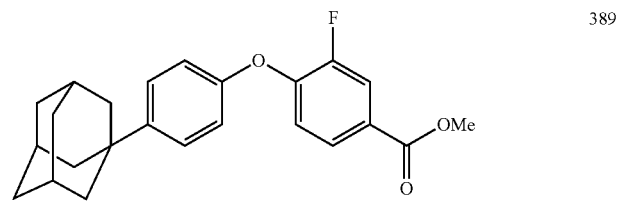
methyl 4-(4-((3r,5r,7r)-adamantan-1-yl)phenoxy)-3-fluorobenzoate
389
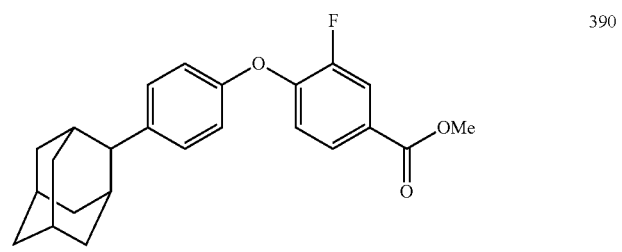
methyl 4-(4-((1r,3r,5r,7r)-adamantan-2-yl)phenoxy)-3-fluorobenzoate
390
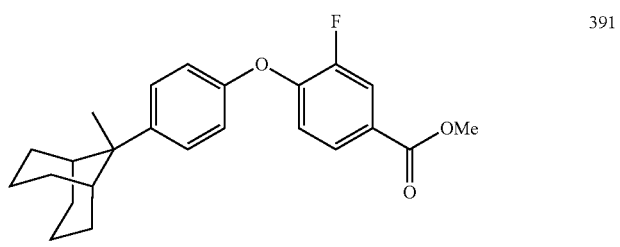
methyl 3-fluoro-4-(4-((1R,5S)-9-methylbicyclo[3.3.1]nonan-9-yl)phenoxy)benzoate
391
X = CH, R² = Et
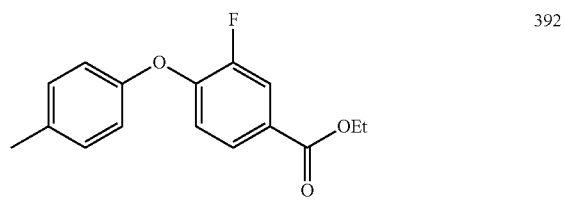
ethyl 3-fluoro-4-(p-tolyloxy)benzoate
392

TABLE IIIb-continued
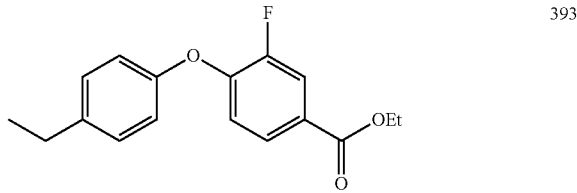
393
ethyl 4-(4-ethylphenoxy)-3-fluorobenzoate
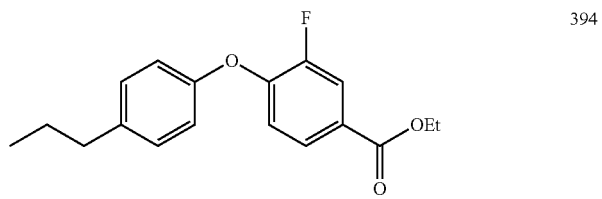
394
ethyl 3-fluoro-4-(4-propylphenoxy)benzoate
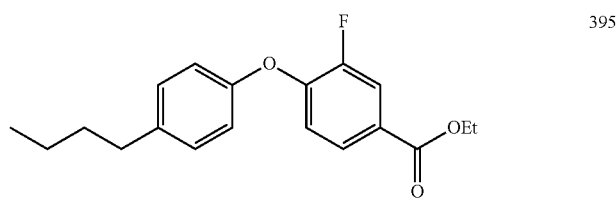
395
ethyl 4-(4-butylphenoxy)-3-fluorobenzoate
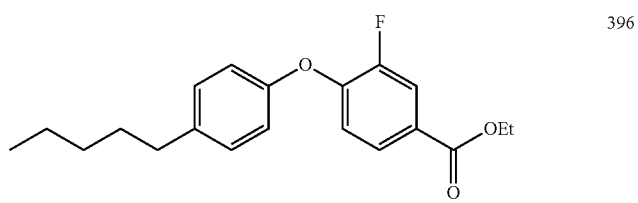
396
ethyl 3-fluoro-4-(4-pentylphenoxy)benzoate
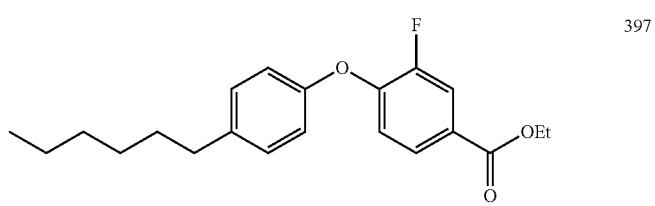
397
ethyl 3-fluoro-4-(4-hexylphenoxy)benzoate
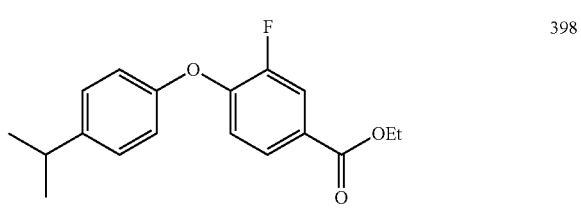
398
ethyl 3-fluoro-4-(4-isopropylphenoxy)benzoate TABLE IIIb-continued
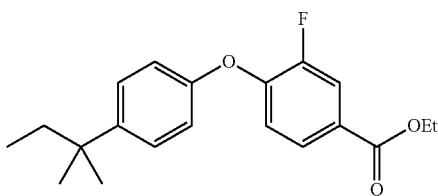 [SMILES: CCOC(=O)c1ccc(Oc2ccc(C(C)(C)CC)cc2)c(F)c1]
399
ethyl 3-fluoro-4-(4-(tert-pentyl)phenoxy)benzoate
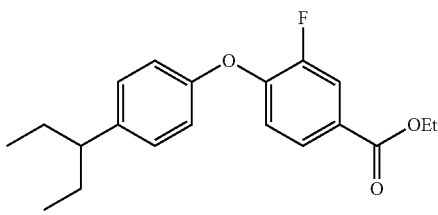 [SMILES: CCOC(=O)c1ccc(Oc2ccc(C(CC)CC)cc2)c(F)c1]
400
ethyl 3-fluoro-4-(4-(pentan-3-yl)phenoxy)benzoate
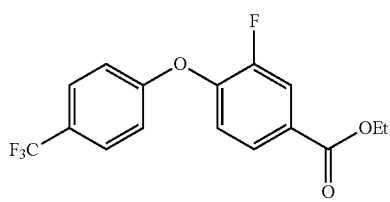
401
ethyl 3-fluoro-4-(4-trifluoromethyl)phenoxy)benzoate
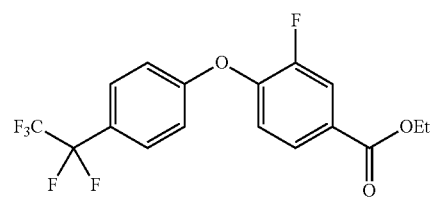 [SMILES: CCOC(=O)c1ccc(Oc2ccc(C(F)(F)C(F)(F)F)cc2)c(F)c1]
402
ethyl 3-fluoro-4-(4-(perfluoroethyl)phenoxy)benzoate
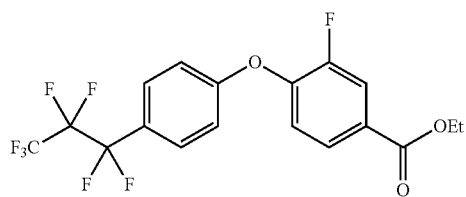
403
ethyl 3-fluoro-4-(4-(perfluoropropyl)phenoxy)benzoate
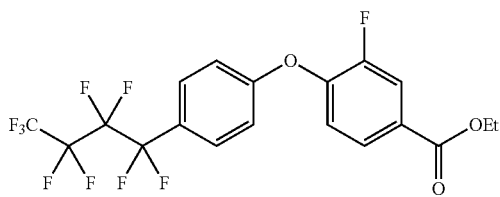 [SMILES: CCOC(=O)c1ccc(Oc2ccc(C(F)(F)C(F)(F)C(F)(F)C(F)(F)F)cc2)c(F)c1]
404
ethyl 3-fluoro-4-(4-(perfluorobutyl)phenoxy)benzoate TABLE IIIb-continued
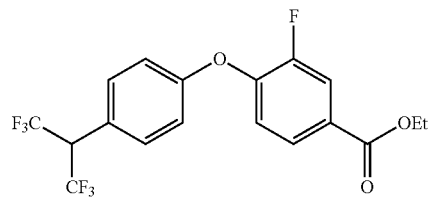
ethyl 3-fluoro-4-(4-(1,1,1,3,3,3-hexafluoropropan-2-yl)phenoxy)benzoate
405
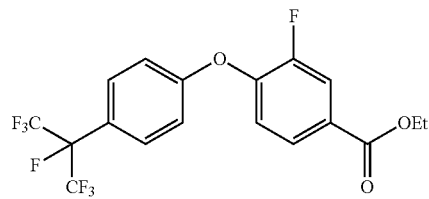
ethyl 3-fluoro-4-(4-(perfluoropropan-2-yl)phenoxy)benzoate
406
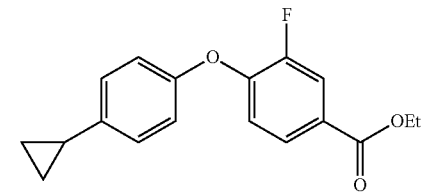 [SMILES: CCOC(=O)c1ccc(Oc2ccc(C3CC3)cc2)c(F)c1]
ethyl 4-(4-cyclopropylphenoxy)-3-fluorobenzoate
407
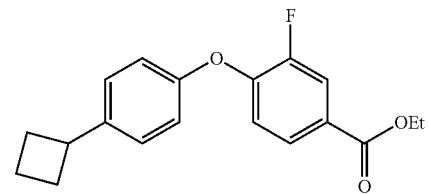 [SMILES: CCOC(=O)c1ccc(Oc2ccc(C3CCC3)cc2)c(F)c1]
ethyl 4-(4-cyclobutylphenoxy)-3-fluorobenzoate
408
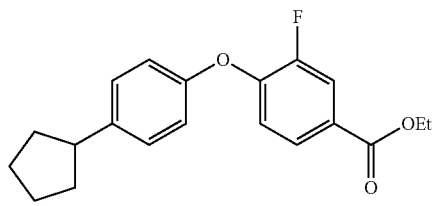 [SMILES: CCOC(=O)c1ccc(Oc2ccc(C3CCCC3)cc2)c(F)c1]
ethyl 4-(4-cyclopentylphenoxy)-3-fluorobenzoate
409
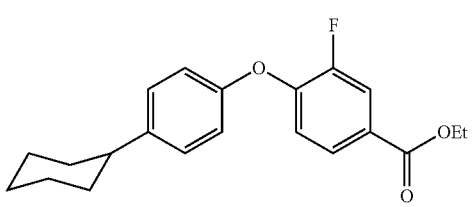 [SMILES: CCOC(=O)c1ccc(Oc2ccc(C3CCCCC3)cc2)c(F)c1]
ethyl 4-(4-cyclohexylphenoxy)-3-fluorobenzoate
410

TABLE IIIb-continued
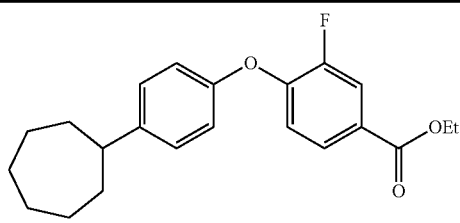
ethyl 4-(4-cycloheptylphenoxy)-3-fluorobenzoate
411
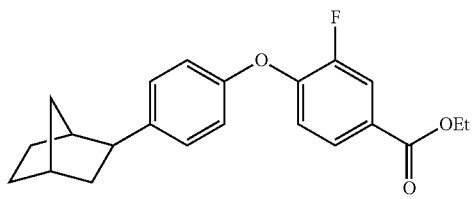
ethyl 4-(4-((1S,4R)-bicyclo[2.2.1]heptan-2-yl)phenoxy)-3-fluorobenzoate
412
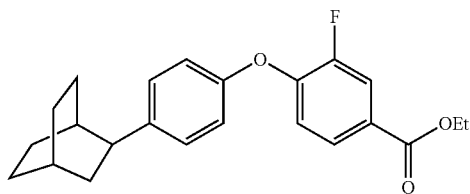 [SMILES: CCOC(=O)c1ccc(Oc2ccc(C3CC4CCC3CC4)cc2)c(F)c1]
ethyl 4-(4-((1s,4s)-bicyclo[2.2.2]octan-2-yl)phenoxy)-3-fluorobenzoate
413
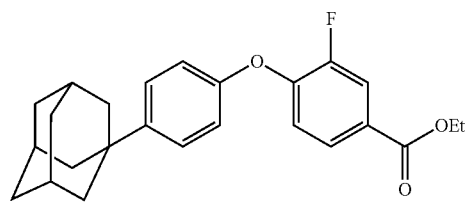 [SMILES: CCOC(=O)c1ccc(Oc2ccc(C34CC5CC(CC(C5)C3)C4)cc2)c(F)c1]
ethyl 4-(4-((3r,5r,7r)-adamantan-1-yl)phenoxy)-3-fluorobenzoate
414
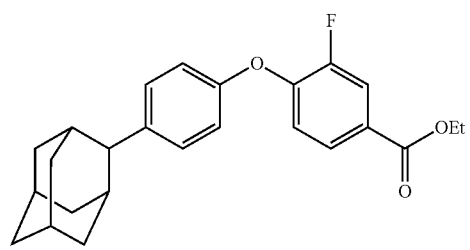 [SMILES: CCOC(=O)c1ccc(Oc2ccc(C3C4CC5CC(C4)CC3C5)cc2)c(F)c1]
ethyl 4-(4-((1r,3r,5r,7r)-adamantan-2-yl)phenoxy)-3-fluorobenzoate
415
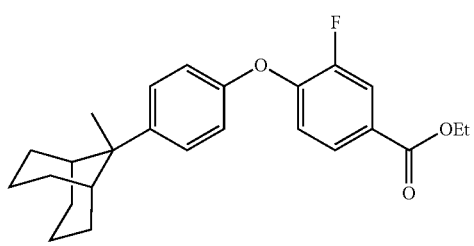
ethyl 3-fluoro-4-(4-((1R,5S)-9-methylbiccyclo[3.3.1]nonan-9-yl)phenoxy)benzoate
$X = N$, $R^2 = H$
416

TABLE IIIb-continued
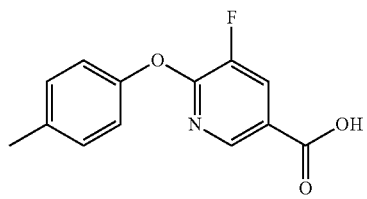 [SMILES: Cc1ccc(Oc2ncc(C(=O)O)cc2F)cc1]
417
5-fluoro-6-(p-tolyloxy)nicotinic acid
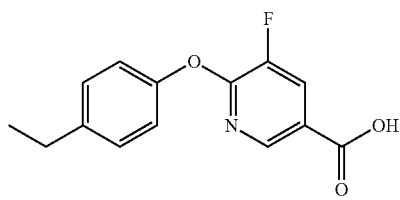 [SMILES: CCc1ccc(Oc2ncc(C(=O)O)cc2F)cc1]
418
6-(4-ethylphenoxy)-5-fluoronicotinic acid
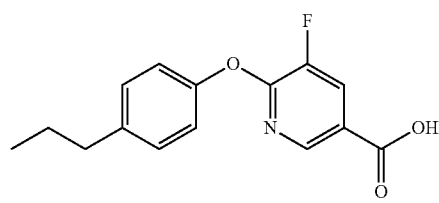 [SMILES: CCCc1ccc(Oc2ncc(C(=O)O)cc2F)cc1]
419
5-fluoro-6-(4-propylphenoxy)nicotinic acid
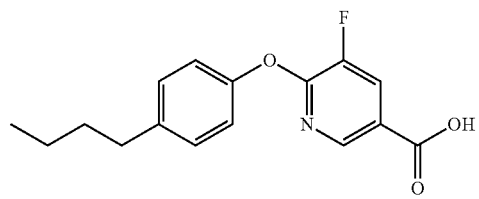
420
6-(4-butylphenoxy)-5-fluoronicotinic acid
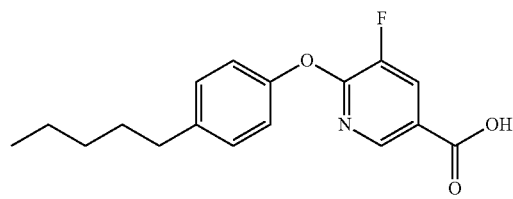 [SMILES: CCCCCc1ccc(Oc2ncc(C(=O)O)cc2F)cc1]
421
5-fluoro-6-(4-pentylphenoxy)nicotinic acid
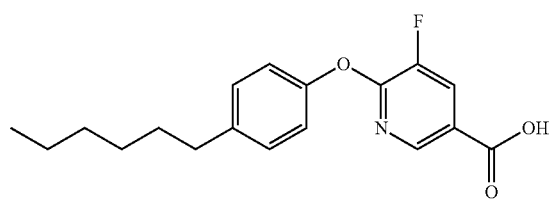 [SMILES: CCCCCCc1ccc(Oc2ncc(C(=O)O)cc2F)cc1]
422
5-fluoro-6-(4-hexylphenoxy)nicotinic acid TABLE IIIb-continued
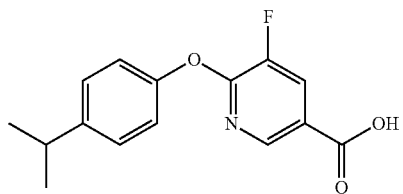 [SMILES: CC(C)c1ccc(Oc2ncc(C(=O)O)cc2F)cc1]
423
5-fluoro-6-(4-isopropylphenoxy)nicotinic acid
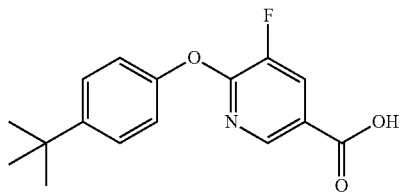 [SMILES: CC(C)(C)c1ccc(Oc2ncc(C(=O)O)cc2F)cc1]
424
6-(4-(tert-butyl)phenoxy)-5-fluoronicotinic acid
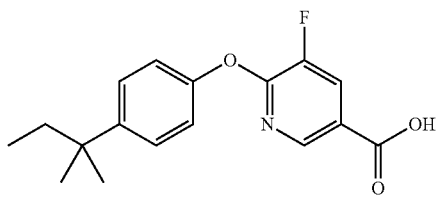 [SMILES: CCC(C)(C)c1ccc(Oc2ncc(C(=O)O)cc2F)cc1]
425
5-fluoro-6-(4-(tert-pentyl)phenoxy)nicotinic acid
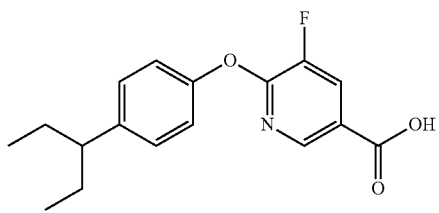 [SMILES: CCC(CC)c1ccc(Oc2ncc(C(=O)O)cc2F)cc1]
426
5-fluoro-6-(4-(pentan-3-yl)phenoxy)nicotinic acid
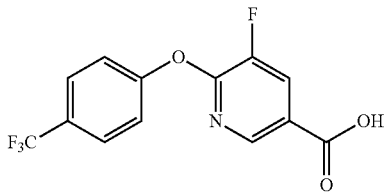
427
5-fluoro-6-(4-(trifluoromethyl)phenoxy)nicotinic acid
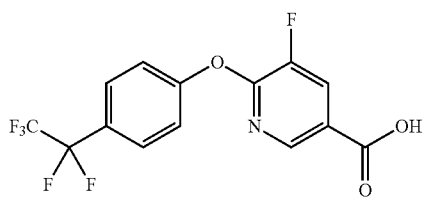
428
5-fluoro-6-(4-(perfluoroethyl)phenoxy)nicotinic acid TABLE IIIb-continued
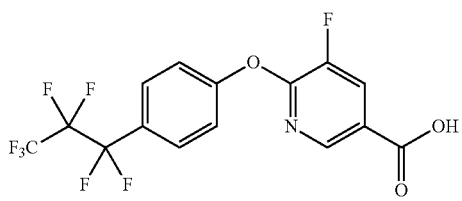
429
5-fluoro-6-(4-(perfluoropropyl)phenoxy)nicotinic acid
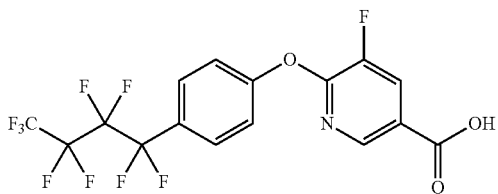 [SMILES: O=C(O)c1cnc(Oc2ccc(C(F)(F)C(F)(F)C(F)(F)C(F)(F)F)cc2)c(F)c1]
430
5-fluoro-6-(4-(perfluorobutyl)phenoxy)nicotinic acid
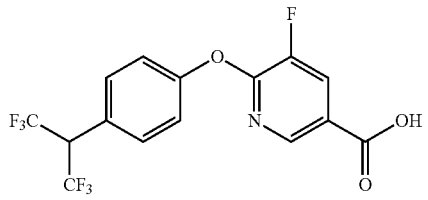
431
5-fluoro-6-(4-(1,1,1,3,3,3-hexafluoropropan-2-yl)phenoxy)nicotinic acid
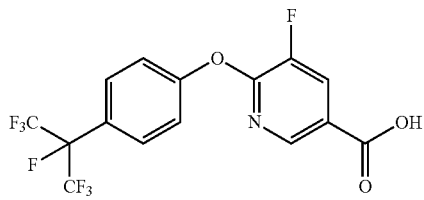 [SMILES: O=C(O)c1cnc(Oc2ccc(C(F)(C(F)(F)F)C(F)(F)F)cc2)c(F)c1]
432
5-fluoro-6-(4-(perfluoropropan-2-yl)phenoxy)nicotinic acid
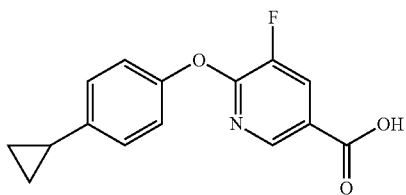
433
6-(4-cyclopropylphenoxy)-5-fluoronicotinic acid
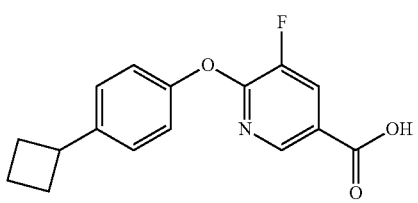 [SMILES: O=C(O)c1cnc(Oc2ccc(C3CCC3)cc2)c(F)c1]
434
6-(4-cyclobutylphenoxy)-5-fluoronicotinic acid TABLE IIIb-continued
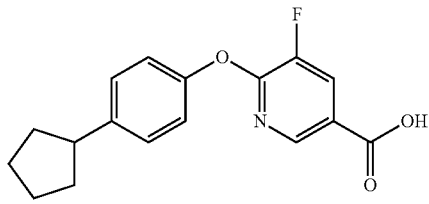
435
6-(4-cyclopentylphenoxy)-5-fluoronicotinic acid
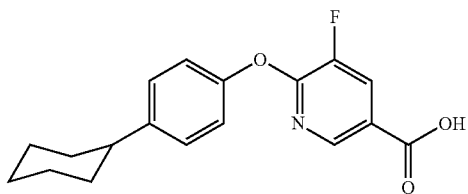
436
6-(4-cyclohexylphenoxy)-5-fluoronicotinic acid
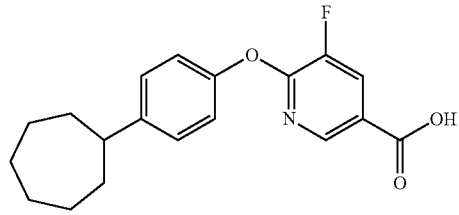
437
6-(4-cylcloheptylphenoxy)-5-fluoronicotinic acid
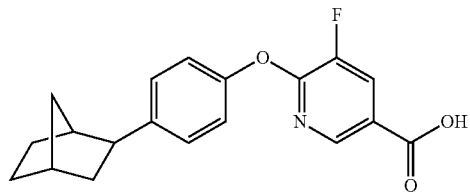 [SMILES: O=C(O)c1cnc(Oc2ccc(C3CC4CCC3C4)cc2)c(F)c1]
438
6-(4-((1S,4R)-bicyclo[2.2.1]heptan-2-yl)phenoxy)-5-fluoronicotinic acid
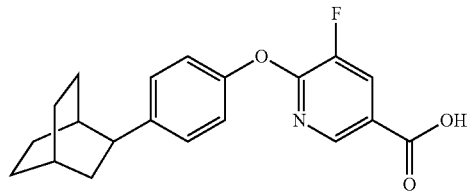
439
6-(4-((1s,4s)-bicyclo[2.2.2]octan-2-yl)phenoxy)-5-fluoronicotinic acid
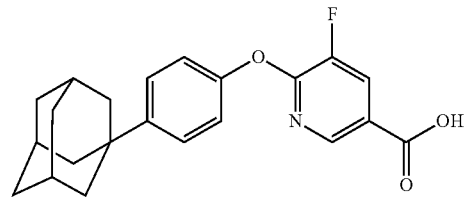 [SMILES: O=C(O)c1cnc(Oc2ccc(C34CC5CC(CC(C5)C3)C4)cc2)c(F)c1]
440
6-(4-((3r,5r,7r)-adamantan-1-yl)phenoxy)-5-fluoronicotinic acid TABLE IIIb-continued
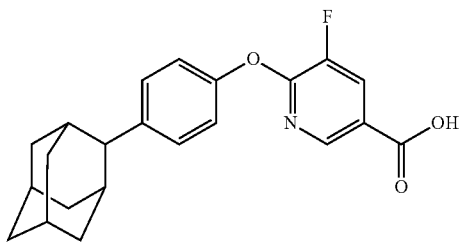
6-(4-((1r,3r,5r,7r)-adamantan-2-yl)phenoxy)-5-fluoronicotinic acid
441
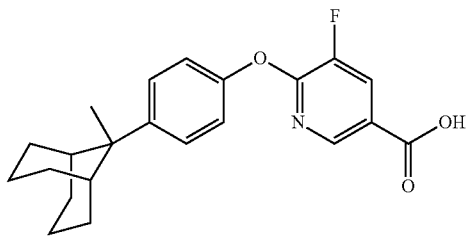 [SMILES: CC1(c2ccc(Oc3ncc(C(=O)O)cc3F)cc2)C2CCCC1CCC2]
5-fluoro-6-(4-((1R,5S)-9-methylbicyclo[3.3.1]nonan-9-yl)phenoxy)nicotinic acid
442
$X = N$, $R^2 = Me$
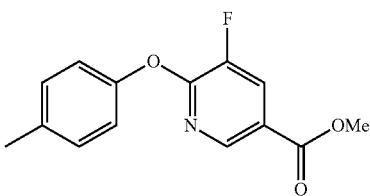
methyl 5-fluoro-6-(p-tolyloxy)nicotinate
443
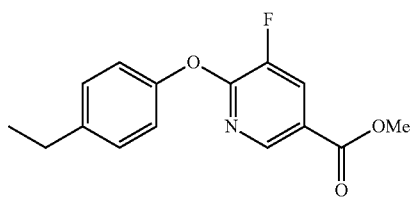 [SMILES: CCc1ccc(Oc2ncc(C(=O)OC)cc2F)cc1]
methyl 6-(4-ethylphenoxy)-5-fluoronicotinate
444
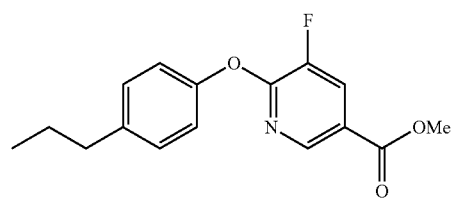 [SMILES: CCCc1ccc(Oc2ncc(C(=O)OC)cc2F)cc1]
methyl 5-fluoro-6-(4-propylphenoxy)nicotinate
445
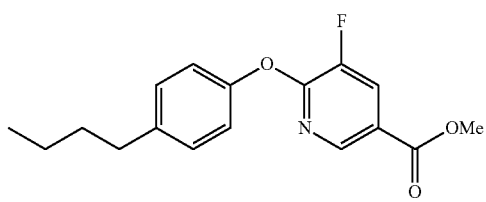 [SMILES: CCCCc1ccc(Oc2ncc(C(=O)OC)cc2F)cc1]
methyl 6-(4-butylphenoxy)5-fluoronicotinate
446

TABLE IIIb-continued
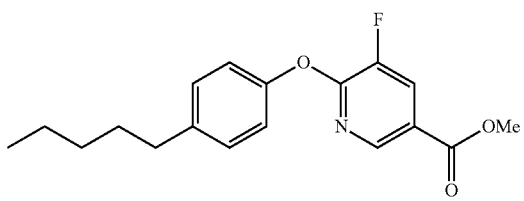 [SMILES: CCCCCc1ccc(Oc2ncc(C(=O)OC)cc2F)cc1]
447
methyl 5-fluoro-6-(4-pentylphenoxy)nicotinate
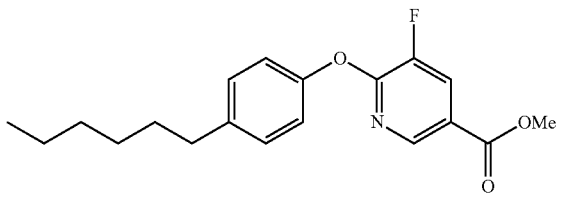 [SMILES: CCCCCCc1ccc(Oc2ncc(C(=O)OC)cc2F)cc1]
448
methyl 5-fluoro-6-(4-hexylphenoxy)nicotinate
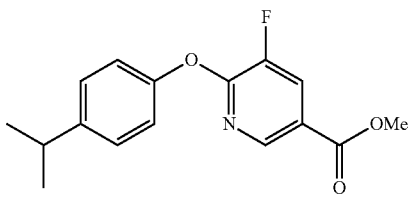 [SMILES: COC(=O)c1cnc(Oc2ccc(C(C)C)cc2)c(F)c1]
449
methyl 5-fluoro-6-(4-isopropylphenoxy)nicotinate
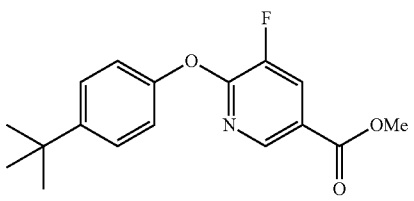 [SMILES: COC(=O)c1cnc(Oc2ccc(C(C)(C)C)cc2)c(F)c1]
450
methyl 6-(4-(tert-butyl)phenoxy)-5-fluoronicotinate
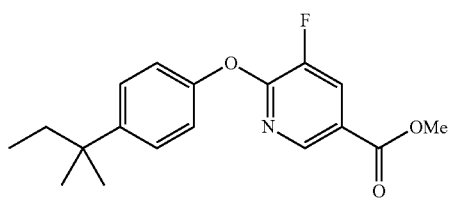 [SMILES: CCC(C)(C)c1ccc(Oc2ncc(C(=O)OC)cc2F)cc1]
451
methyl 5-fluoro-6-(4-(tert-pentyl)phenoxy)nicotinate
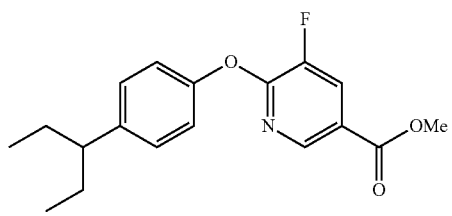 [SMILES: CCC(CC)c1ccc(Oc2ncc(C(=O)OC)cc2F)cc1]
452
methyl 5-fluoro-6-(4-(pentan-3-yl)phenoxy)nicotinate TABLE IIIb-continued
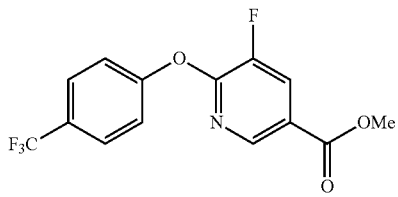 [SMILES: COC(=O)c1cnc(Oc2ccc(C(F)(F)F)cc2)c(F)c1]
methyl 5-fluoro-6-(4-(trifluoromethyl)phenoxy)nicotinate
453
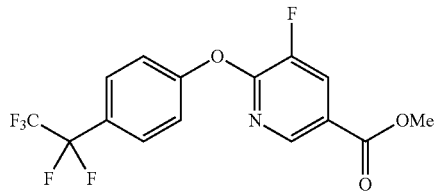
methyl 5-fluoro-6-(4-(perfluoroethyl)phenoxy)nicotinate
454
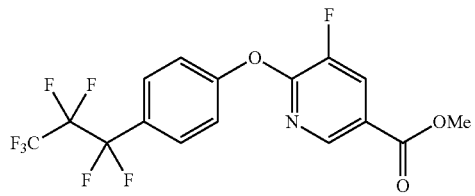 [SMILES: COC(=O)c1cnc(Oc2ccc(C(F)(F)C(F)(F)C(F)(F)F)cc2)c(F)c1]
methyl 5-fluoro-6-(4-(perfluoropropyl)phenoxy)nicotinate
455
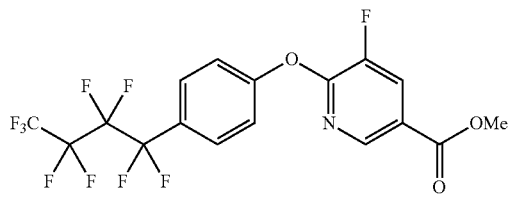 [SMILES: COC(=O)c1cnc(Oc2ccc(C(F)(F)C(F)(F)C(F)(F)C(F)(F)F)cc2)c(F)c1]
methyl 5-fluoro-6-(4-(perfluorobutyl)phenoxy)nicotinate
456
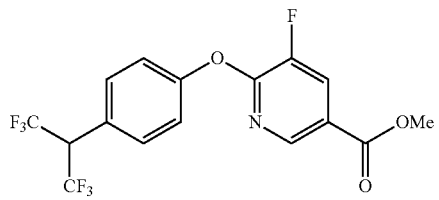
methyl 5-fluoro-6-(4-(1,1,1,3,3,3-hexafluoropropan-2-yl)phenoxy)
nicotinate
457
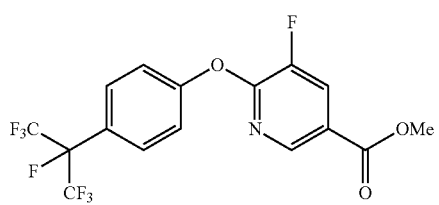
methyl 5-fluoro-6-(4-(perfluoropropan-2-yl)phenoxy)nicotinate
458

TABLE IIIb-continued
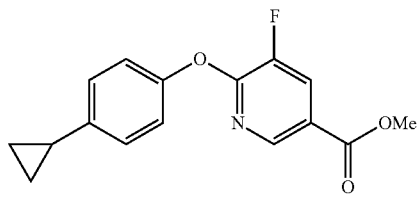 [SMILES: COC(=O)c1cnc(Oc2ccc(C3CC3)cc2)c(F)c1]
459
methyl 6-(4-cyclopropylphenoxy)-5-fluoronicotinate
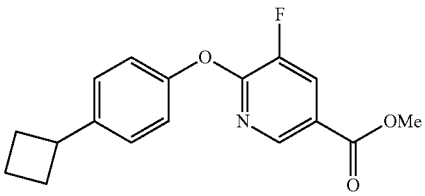 [SMILES: COC(=O)c1cnc(Oc2ccc(C3CCC3)cc2)c(F)c1]
460
methyl 6-(4-cyclobutylphenoxy)-5-fluoronicotinate
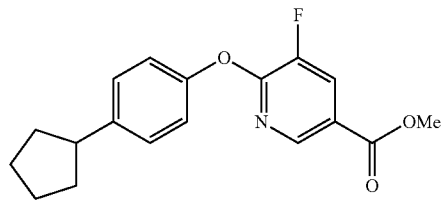 [SMILES: COC(=O)c1cnc(Oc2ccc(C3CCCC3)cc2)c(F)c1]
461
methyl 6-(4-cyclopentylphenoxy)-5-fluoronicotinate
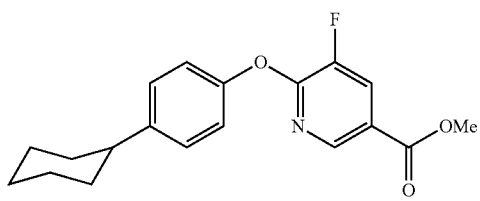
462
methyl 6-(4-cyclohexylphenoxy)-5-fluoronicotinate
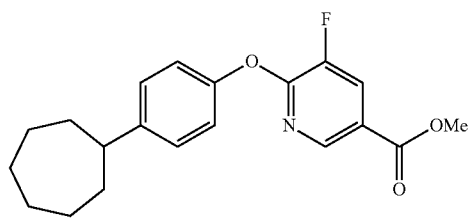 [SMILES: COC(=O)c1cnc(Oc2ccc(C3CCCCCC3)cc2)c(F)c1]
463
methyl 6-(4-cycloheptylphenoxy)-5-fluoronicotinate
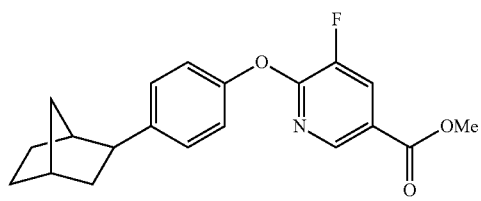 [SMILES: COC(=O)c1cnc(Oc2ccc(C3CC4CCC3C4)cc2)c(F)c1]
464
methyl 6-(4-((1S,4R)-bicyclo[2.2.1]heptan-2-yl)phenoxy)-5-fluoronicotinate TABLE IIIb-continued
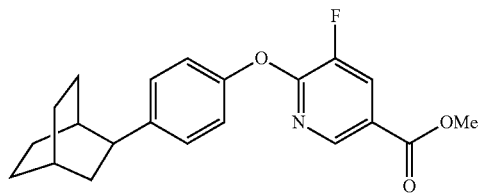 [SMILES: COC(=O)c1cnc(Oc2ccc(C3CC4CCC3CC4)cc2)c(F)c1]
465
methyl 6-(4-((1s,4s)-bicyclo[2.2.2]octan-2-yl)phenoxy)-5-fluoronicotinate
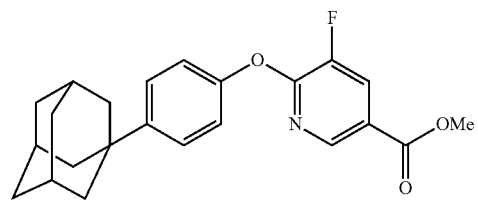 [SMILES: COC(=O)c1cnc(Oc2ccc(C34CC5CC(CC(C5)C3)C4)cc2)c(F)c1]
466
methyl 6-(4-((3r,5r,7r)-adamantan-1-yl)phenoxy)-5-fluoronicotinate
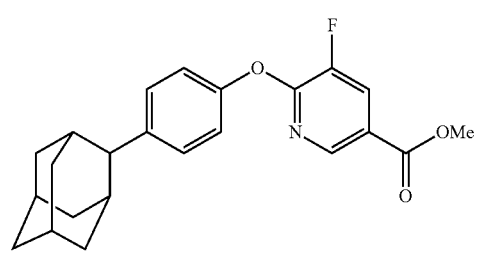
467
methyl 6-(4-((1r,3r,5r,7r)-adamantan-2-yl)phenoxy)-5-fluoronictinate
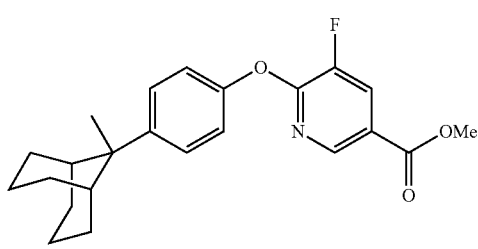 [SMILES: COC(=O)c1cnc(Oc2ccc(C3(C)C4CCCC3CCC4)cc2)c(F)c1]
468
methyl 5-fluoro-6-(4-((1R,5S)-9-methylbicyclo[3.3.1]nonan-9-yl)phenoxy)nicotinate
X = N, R$^2$ = Et
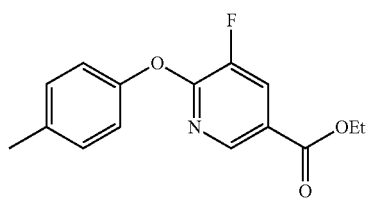 [SMILES: CCOC(=O)c1cnc(Oc2ccc(C)cc2)c(F)c1]
469
ethyl 5-fluoro-6-(p-tolyloxy)nicotinate
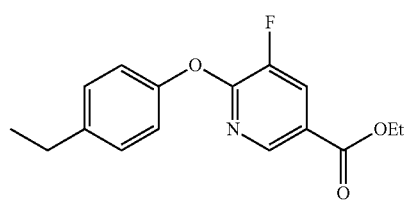 [SMILES: CCOC(=O)c1cnc(Oc2ccc(CC)cc2)c(F)c1]
470
ethyl 6-(4-ethylphenoxy)-5-fluoronicotinate TABLE IIIb-continued
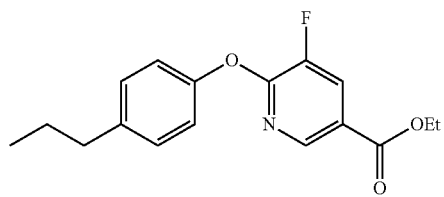 [SMILES: CCCc1ccc(Oc2ncc(C(=O)OCC)cc2F)cc1]
471
ethyl 5-fluoro-6-(4-propylphenoxy)nicotinate
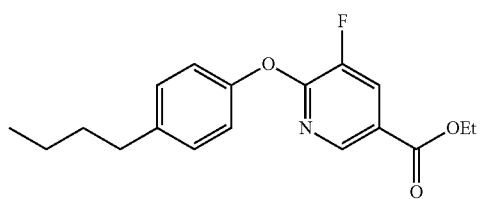 [SMILES: CCCCc1ccc(Oc2ncc(C(=O)OCC)cc2F)cc1]
472
ethyl 6-(4-butylphenoxy)-5-fluoronicotinate
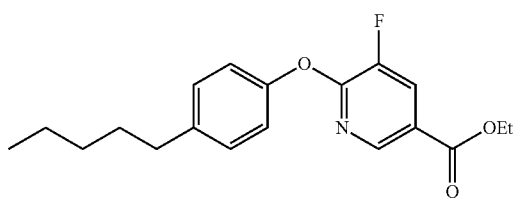 [SMILES: CCCCCc1ccc(Oc2ncc(C(=O)OCC)cc2F)cc1]
473
ethyl 5-fluoro-6-(4-pentylphenoxy)nicotinate
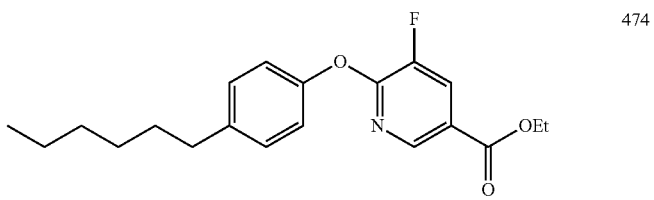
474
ethyl 5-fluoro-6-(4-hexylphenoxy)nicotinate
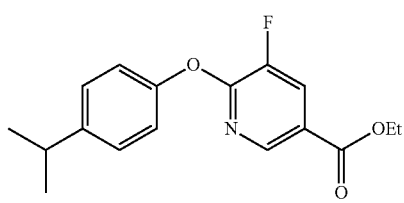
475
ethyl 5-fluoro-6-(4-isopropylphenoxy)nicotinate
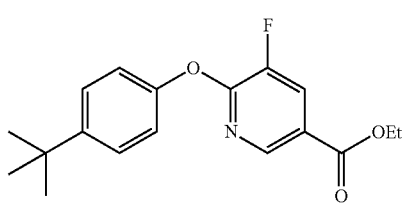 [SMILES: CCOC(=O)c1cnc(Oc2ccc(C(C)(C)C)cc2)c(F)c1]
476
ethyl 6-(4-(tert-butyl)phenoxy)-5-fluoronicotinate TABLE IIIb-continued
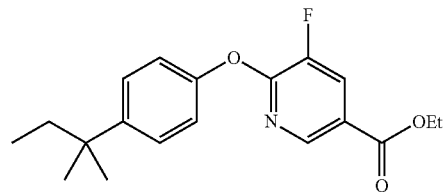 [SMILES: CCOC(=O)c1cnc(Oc2ccc(C(C)(C)CC)cc2)c(F)c1]
ethyl 5-fluoro-6-(4-(tert-pentyl)phenoxy)nicotinate
477
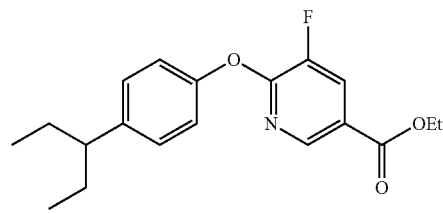 [SMILES: CCOC(=O)c1cnc(Oc2ccc(C(CC)CC)cc2)c(F)c1]
ethyl 5-fluoro-6-(4-(pentan-3-yl)phenoxy)nicotinate
478
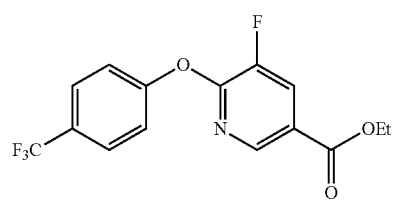 [SMILES: CCOC(=O)c1cnc(Oc2ccc(C(F)(F)F)cc2)c(F)c1]
ethyl 5-fluoro-6-(4-(trifluoromethyl)phenoxy)nicotinate
479
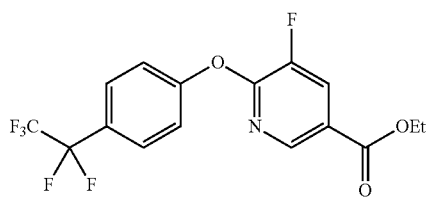 [SMILES: CCOC(=O)c1cnc(Oc2ccc(C(F)(F)C(F)(F)F)cc2)c(F)c1]
ethyl 5-fluoro-6-(4-(perfluoroethyl)phenoxy)nicotinate
480
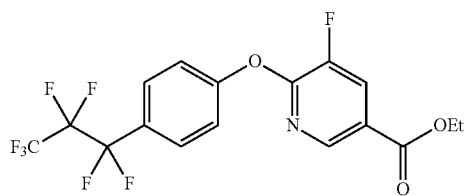 [SMILES: CCOC(=O)c1cnc(Oc2ccc(C(F)(F)C(F)(F)C(F)(F)F)cc2)c(F)c1]
ethyl 5-fluoro-6-(4-(perfluoropropyl)phenoxy)nicotinate
481
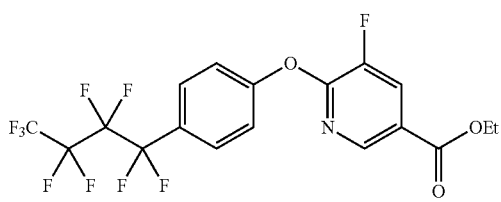
ethyl 5-fluoro-6-(4-(perfluorobutyl)phenoxy)nicotinate
482

TABLE IIIb-continued
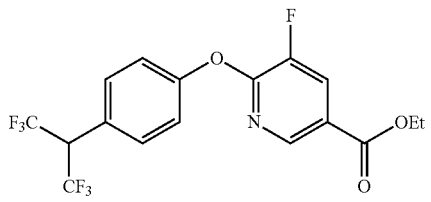 [SMILES: CCOC(=O)c1cnc(Oc2ccc(C(C(F)(F)F)C(F)(F)F)cc2)c(F)c1]
ethyl 5-fluoro-6-(4-(1,1,1,3,3,3-hexafluoropropan-2-yl)phenoxy)nicotinate
483
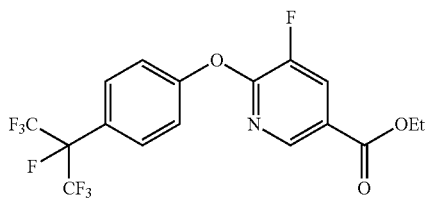 [SMILES: CCOC(=O)c1cnc(Oc2ccc(C(F)(C(F)(F)F)C(F)(F)F)cc2)c(F)c1]
ethyl 5-fluoro-6-(4-(perfluoropropan-2-yl)phenoxy)nicotinate
484
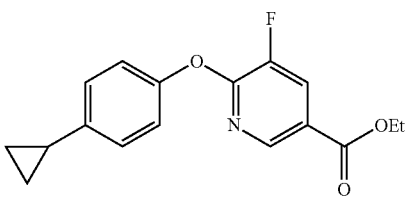
ethyl 6-(4-cyclopropylphenoxy)-5-fluoronictinate
485
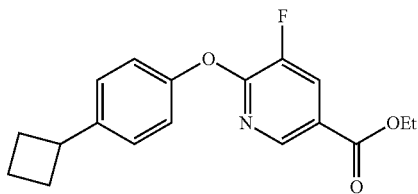 [SMILES: CCOC(=O)c1cnc(Oc2ccc(C3CCC3)cc2)c(F)c1]
ethyl 6-(4-cyclobutylphenoxy)-5-fluoronicotinate
486
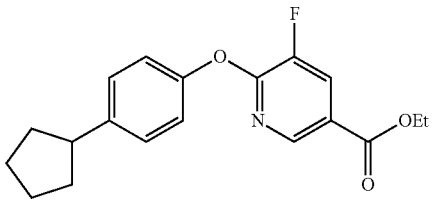
ethyl 6-(4-cyclopentylphenoxy)-5-fluoronicotinate
487
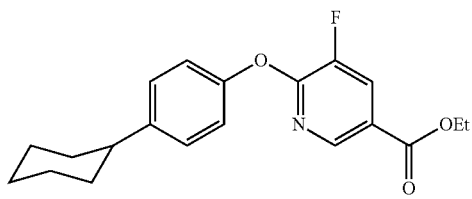
ethyl 6-(4-cyclohexylphenoxy)-5-fluoronicotinate
488

TABLE IIIb-continued
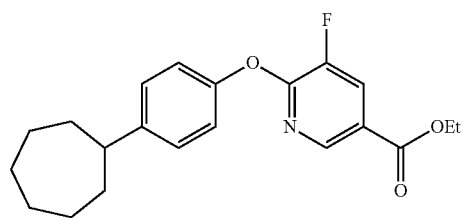 [SMILES: CCOC(=O)c1cnc(Oc2ccc(C3CCCCCC3)cc2)c(F)c1]
489
ethyl 6-(4-cycloheptylphenoxy)-5-fluoronicotinate
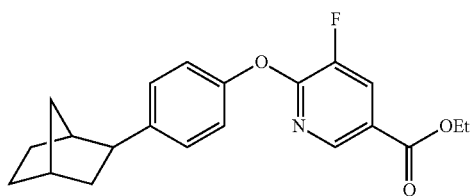 [SMILES: CCOC(=O)c1cnc(Oc2ccc(C3CC4CCC3C4)cc2)c(F)c1]
490
ethyl 6-(4-((1S,4R)-bicyclo[2.2.1]heptan-2-yl)phenoxy)-5-fluoronicotinate
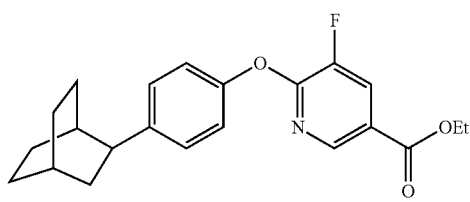
491
ethyl 6-(4-((1s,4s)-bicyclo[2.2.2]octan-2-yl)phenoxy)-5-fluoronicotinate
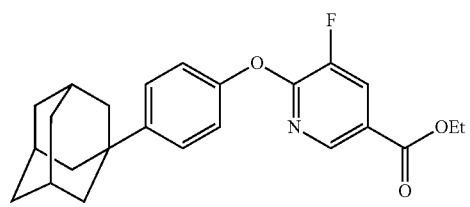 [SMILES: CCOC(=O)c1cnc(Oc2ccc(C34CC5CC(CC(C5)C3)C4)cc2)c(F)c1]
492
ethyl 6-(4-((3r,5r,7r)-adamantan-1-yl)phenoxy)-5-fluoronicotinate
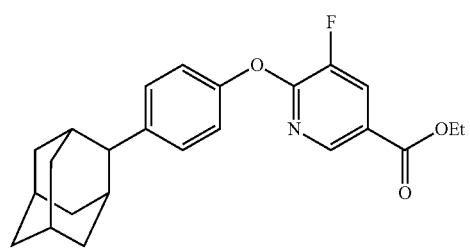
493
ethyl 6-(4-((1r,3r,5r,7r)-adamantan-2-yl)phenoxy)-5-fluoronicotinate TABLE IIIb-continued

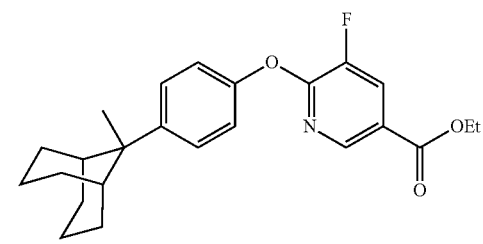

494 ethyl 5-fluoro-6-(4-((1R,5S)-9-methylbicyclo[3.3.1]nonan-9-yl)phenoxy)nicotinate Also included are isomers, e.g. enantiomers or diastereomers or mixtures of isomers, salts, particularly pharmaceutically acceptable salts, and solvates of the compounds listed above.

A fourth aspect of the present invention relates to compounds of formula IV and salts and solvates thereof:

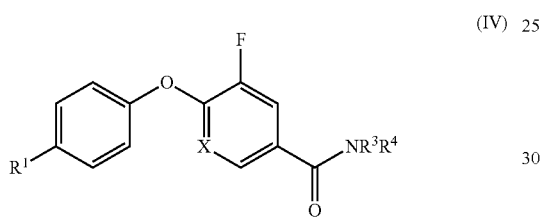

(IV)

wherein X and $R^1$ are defined as in formula I, including the preferred definition of $R^1$, and $R^3$ and $R^4$ are defined as in formula II, including the preferred definitions of $R^3$ and $R^4$.

Specific examples of compounds falling under the scope of formula IV are shown in Table IV. The compounds in Table IV are defined by their chemical structure, the indicated nomenclature is only for illustrative purposes.

TABLE IV

X = CH, $R^3$ = H, $R^4$ = H

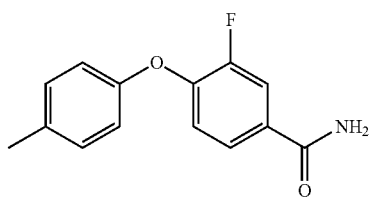 [SMILES: Cc1ccc(Oc2ccc(C(N)=O)cc2F)cc1]

495

3-fluoro-4-(p-tolyloxy)benzamide

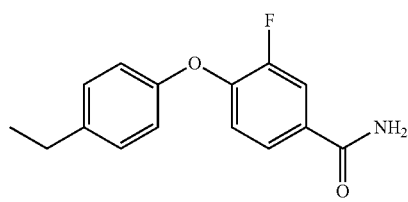

496

4-(4-ethylphenoxy)-3-fluorobenzamide

TABLE IV-continued
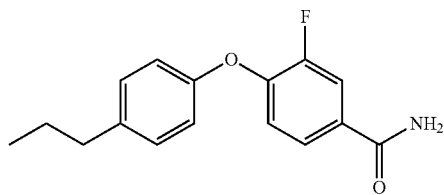 [SMILES: CCCc1ccc(Oc2ccc(C(N)=O)cc2F)cc1]
497
3-fluoro-4-(4-propylphenoxy)benzamide
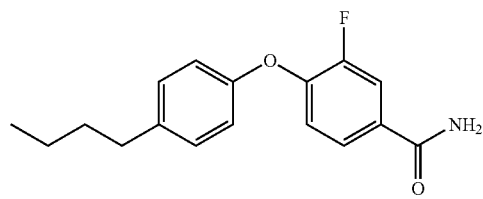 [SMILES: CCCCc1ccc(Oc2ccc(C(N)=O)cc2F)cc1]
498
4-(4-butylphenoxy)-3-fluorobenzamide
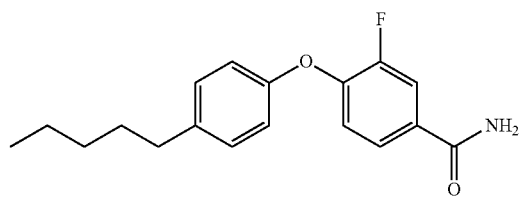 [SMILES: CCCCCc1ccc(Oc2ccc(C(N)=O)cc2F)cc1]
499
3-fluoro-4-(4-pentylphenoxy)benzamide
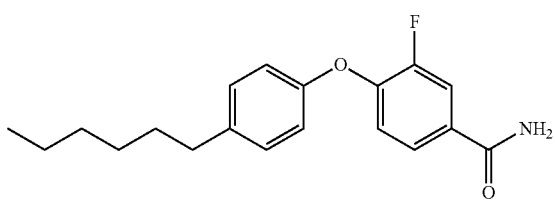 [SMILES: CCCCCCc1ccc(Oc2ccc(C(N)=O)cc2F)cc1]
500
3-fluoro-4-(4-hexylphenoxy)bnezamide
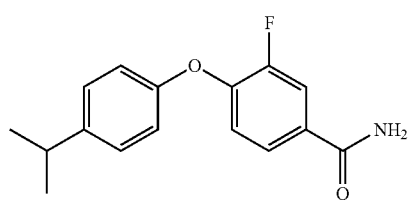 [SMILES: CC(C)c1ccc(Oc2ccc(C(N)=O)cc2F)cc1]
501
3-fluoro-4-(4-isopropylphenoxy)benzamide
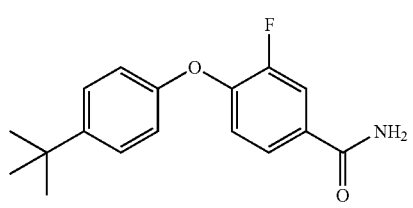 [SMILES: CC(C)(C)c1ccc(Oc2ccc(C(N)=O)cc2F)cc1]
502
4-(4-(tert-butyl)phenoxy)-3-fluorobenzamide

TABLE IV-continued
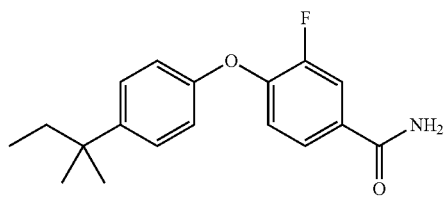 [SMILES: CCC(C)(C)c1ccc(Oc2ccc(C(N)=O)cc2F)cc1]
3-fluoro-4-(4-(tert-pentyl)phenoxy)benzamide  503
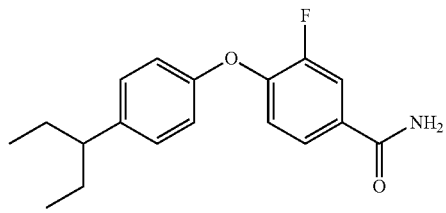 [SMILES: CCC(CC)c1ccc(Oc2ccc(C(N)=O)cc2F)cc1]
3-fluoro-4-(4-(pentan-3-yl)phenoxy)benzamide  504
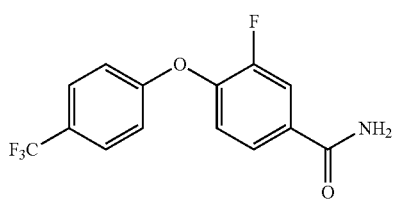 [SMILES: NC(=O)c1ccc(Oc2ccc(C(F)(F)F)cc2)c(F)c1]
3-fluoro-4-(4-(trifluoromethyl)phenoxy)benzamide  505
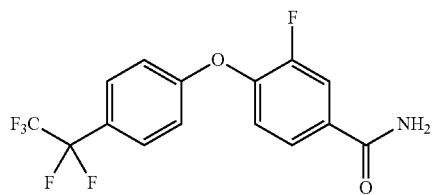 [SMILES: NC(=O)c1ccc(Oc2ccc(C(F)(F)C(F)(F)F)cc2)c(F)c1]
3-fluoro-4-(4-(perfluoroethyl)phenoxy)benzamide  506
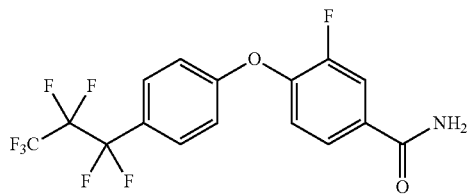 [SMILES: NC(=O)c1ccc(Oc2ccc(C(F)(F)C(F)(F)C(F)(F)F)cc2)c(F)c1]
3-fluoro-4-(4-(perfluoropropyl)phenoxy)benzamide  507
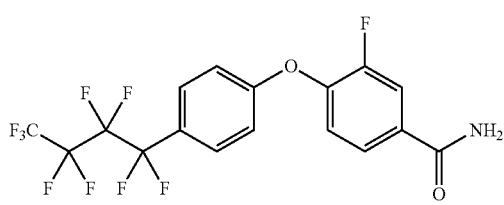 [SMILES: NC(=O)c1ccc(Oc2ccc(C(F)(F)C(F)(F)C(F)(F)C(F)(F)F)cc2)c(F)c1]
3-fluoro-4-(4-(perfluorobutyl)phenoxy)benzamide  508

TABLE IV-continued
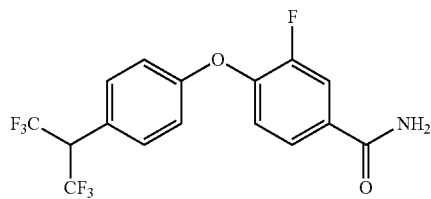
509
3-fluoro-4-(4-(1,1,1,3,3,3-hexafluoropropan-2-yl)phenoxy)benzamide
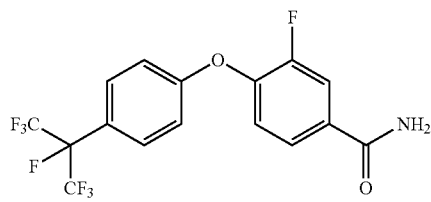 [SMILES: NC(=O)c1ccc(Oc2ccc(C(F)(C(F)(F)F)C(F)(F)F)cc2)c(F)c1]
510
3-fluoro-4-(4-(perfluoropropan-2-yl)phenoxy)benzamide
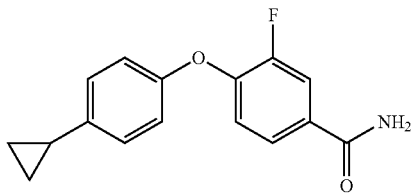 [SMILES: NC(=O)c1ccc(Oc2ccc(C3CC3)cc2)c(F)c1]
511
4-(4-cyclopropylphenoxy)-3-fluorobenzamide
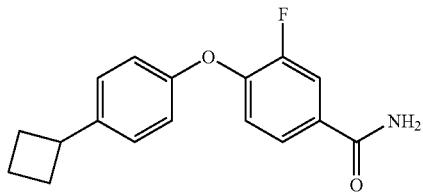 [SMILES: NC(=O)c1ccc(Oc2ccc(C3CCC3)cc2)c(F)c1]
512
4-(4-cyclobutylphenoxy)-3-fluorobenzamide
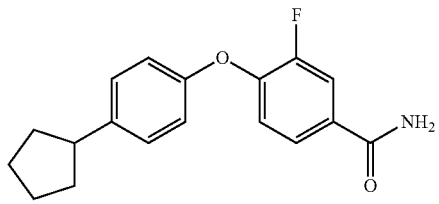 [SMILES: NC(=O)c1ccc(Oc2ccc(C3CCCC3)cc2)c(F)c1]
513
4-(4-cyclopentylphenoxy)-3-fluorobenzamide
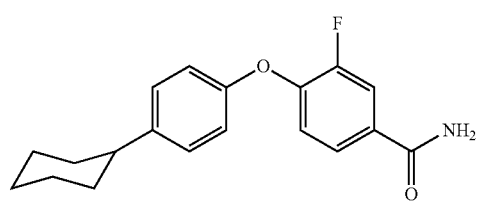 [SMILES: NC(=O)c1ccc(Oc2ccc(C3CCCCC3)cc2)c(F)c1]
514
4-(4-cyclohexylphenoxy)-3-fluorobenzamide TABLE IV-continued
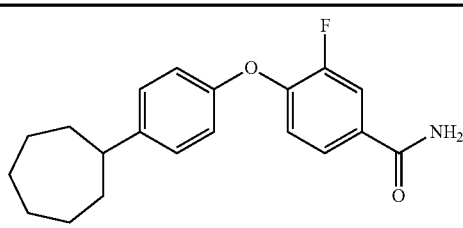
4-(4-cycloheptylphenoxy)-3-fluorobenzamide
515
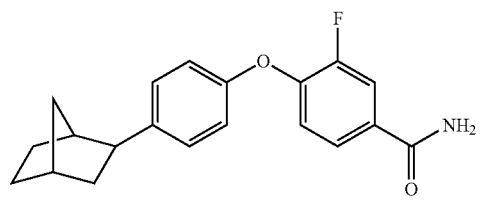 [SMILES: NC(=O)c1ccc(Oc2ccc(C3CC4CCC3C4)cc2)c(F)c1]
4-(4-((1S,4R)-bicyclo[2.2.1]heptan-2-yl)phenoxy)-3-fluorobenzamide
516
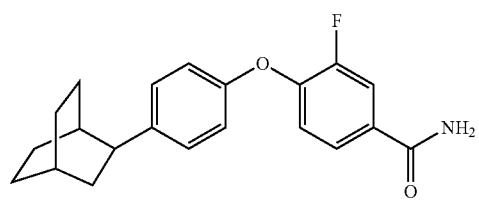 [SMILES: NC(=O)c1ccc(Oc2ccc(C3CC4CCC3CC4)cc2)c(F)c1]
4-(4-((1s,4s)-bicyclo[2.2.2]octan-2-yl)phenoxy)-3-fluorobenzamide
517
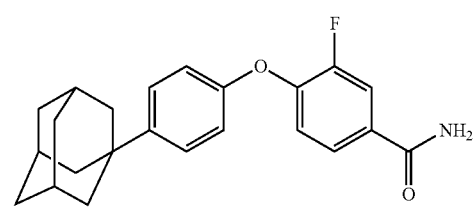 [SMILES: NC(=O)c1ccc(Oc2ccc(C34CC5CC(CC(C5)C3)C4)cc2)c(F)c1]
4-(4-((3r,5r,7r)-adamantan-1-yl)phenoxy)-3-fluorobenzamide
518
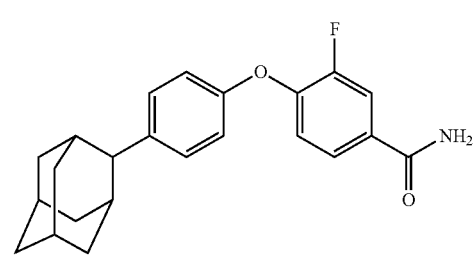 [SMILES: NC(=O)c1ccc(Oc2ccc(C3C4CC5CC(C4)CC3C5)cc2)c(F)c1]
4-(4-((1r,3r,5r,7r)-adamantan-2-yl)phenoxy)-3-fluorobenzamide
519
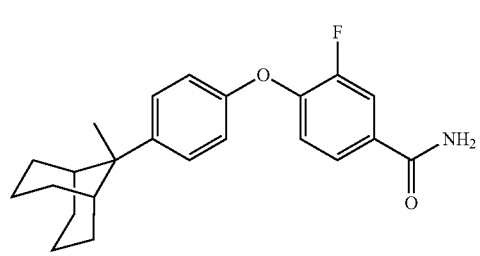 [SMILES: CC1(c2ccc(Oc3ccc(C(N)=O)cc3F)cc2)C2CCCC1CCC2]
3-fluoro-4-(4-((1R,5S)-9-methylbicyclo[3.3.1]nonan-9-yl)phenoxy)benzamide
520
X = CH, R³ = H, R⁴ = OH TABLE IV-continued
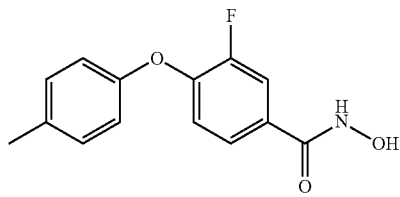 [SMILES: Cc1ccc(Oc2ccc(C(=O)NO)cc2F)cc1]
521
3-fluoro-N-hydroxy-4-(p-tolyloxy)benzamide
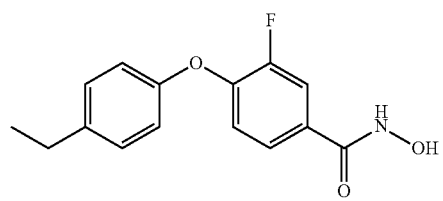
522
4-(4-ethylphenoxy)-3-fluoro-N-hydroxybenzamide
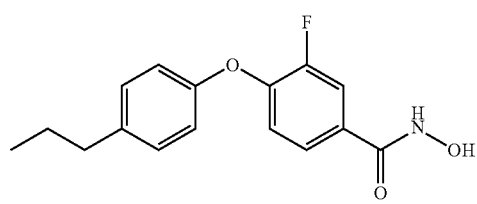 [SMILES: CCCc1ccc(Oc2ccc(C(=O)NO)cc2F)cc1]
523
3-fluoro-N-hydroxy-4-(4-propylphenoxy)benzamide
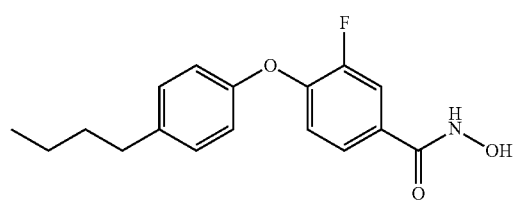 [SMILES: CCCCc1ccc(Oc2ccc(C(=O)NO)cc2F)cc1]
524
4-(4-butylphenoxy)-3-fluoro-N-hydroxybenzamide
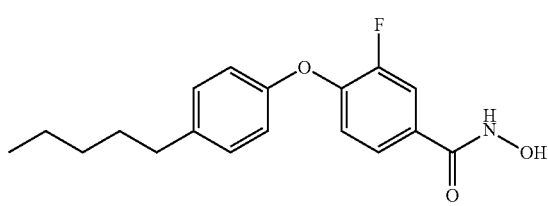 [SMILES: CCCCCc1ccc(Oc2ccc(C(=O)NO)cc2F)cc1]
525
3-fluoro-N-hydroxy-4-(4-pentylphenoxy)benzamide
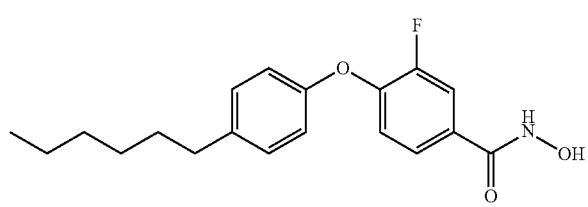
526
3-fluoro-4-(4-hexylphenoxy)-N-hydroxybenzamide TABLE IV-continued

527
3-fluooro-N-hydroxy-4-(4-isopropylphenoxy)benzamide
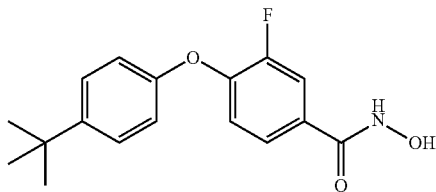 [SMILES: CC(C)(C)c1ccc(Oc2ccc(C(=O)NO)cc2F)cc1]
528
4-(4-(tert-butyl)phenoxy)-3-fluoro-N-hydroxybenzamide
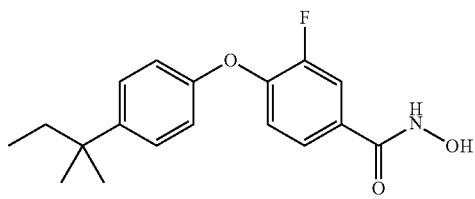 [SMILES: CCC(C)(C)c1ccc(Oc2ccc(C(=O)NO)cc2F)cc1]
529
3-fluoro-N-hydroxy-4-(4-(tert-pentyl)phenoxy)benzamide
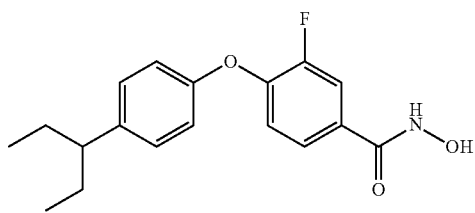
530
3-fluoro-N-hydroxy-4-(4-(pentan-3-yl)phenoxy)benzamide
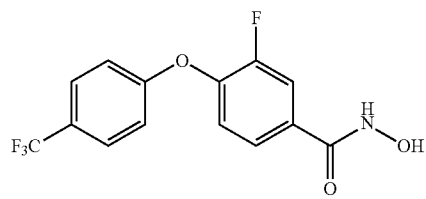 [SMILES: O=C(NO)c1ccc(Oc2ccc(C(F)(F)F)cc2)c(F)c1]
531
3-fluoro-N-hydroxy-4-(4-(trifluoromethyl)phenoxy)benzamide
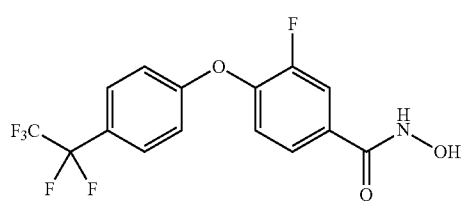 [SMILES: O=C(NO)c1ccc(Oc2ccc(C(F)(F)C(F)(F)F)cc2)c(F)c1]
532
3-fluoro-N-hydroxy-4-(4-(perfluoroethyl)phenoxy)benzamide TABLE IV-continued
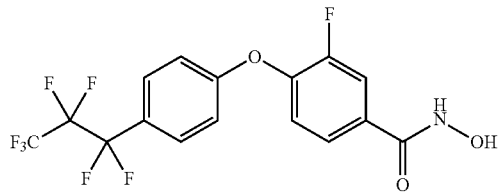
3-fluoro-N-hydroxy-4-(4-(perfluoropropyl)phenoxy)benzamide
533
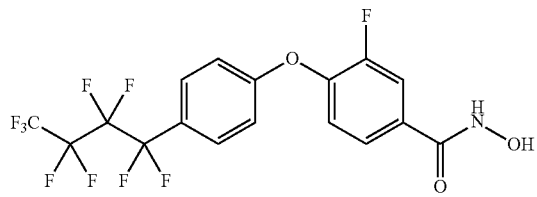 [SMILES: O=C(NO)c1ccc(Oc2ccc(C(F)(F)C(F)(F)C(F)(F)C(F)(F)F)cc2)c(F)c1]
3-fluoro-N-hydroxy-4-(4-(perfluorobutyl)phenoxy)benzamide
534
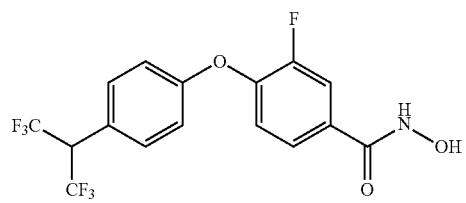
3-fluoro-4-(4-(1,1,1,3,3,3-hexafluoropropan-2-yl)phenoxy)-N-hydroxybenzamide
535
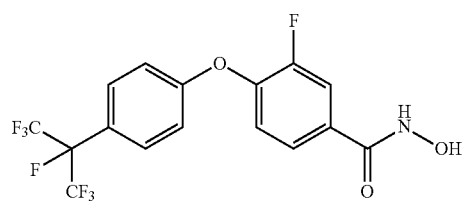
3-fluoro-N-hydroxy-4-(4-(perfluoropropan-2-yl)phenoxy)benzamide
536
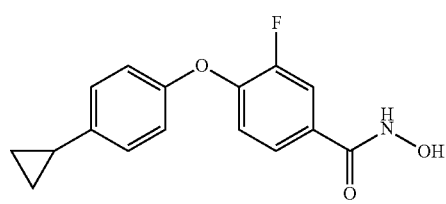 [SMILES: O=C(NO)c1ccc(Oc2ccc(C3CC3)cc2)c(F)c1]
4-(4-cyclopropylphenoxy)-3-fluoro-N-hydroxybenzamide
537
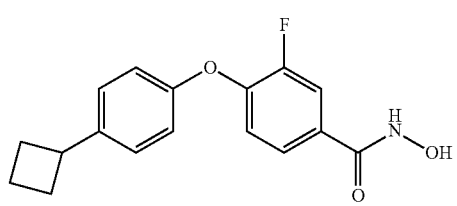 [SMILES: O=C(NO)c1ccc(Oc2ccc(C3CCC3)cc2)c(F)c1]
4-(4-cyclobutylphenoxy)-3-fluoro-N-hydroxybenzamide
538

TABLE IV-continued
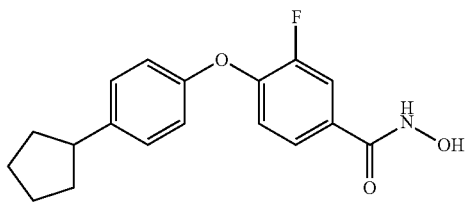 [SMILES: O=C(NO)c1ccc(Oc2ccc(C3CCCC3)cc2)c(F)c1]
4-(4-cyclopentylphenoxy)-3-fluoro-N-hydroxybenzamide      539
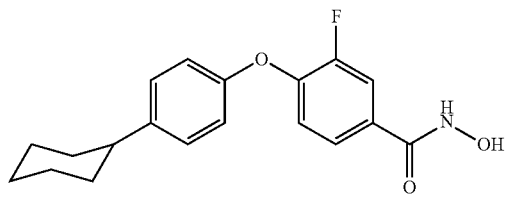
4-(4-cyclohexylphenoxy)-3-fluoro-N-hydroxybenzamide      540
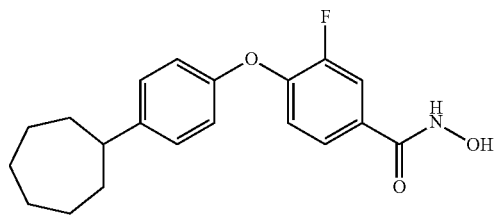
4-(4-cycloheptylphenoxy)-3-fluoro-N-hydroxybenzamide      541
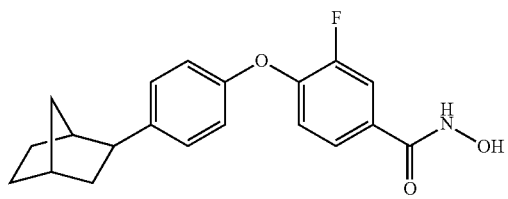 [SMILES: O=C(NO)c1ccc(Oc2ccc(C3CC4CCC3C4)cc2)c(F)c1]
4-(4-((1S,4R)-bicyclo[2.2.1]heptan-2-yl)phenoxy)-3-fluoro-
N-hydroxybenzamide      542
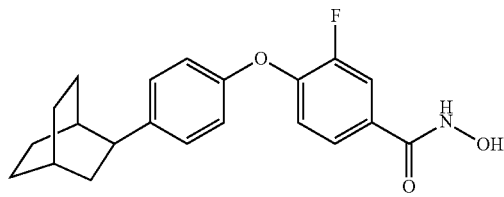 [SMILES: O=C(NO)c1ccc(Oc2ccc(C3CC4CCC3CC4)cc2)c(F)c1]
4-(4-((1s,4s)-bicyclo[2.2.2]octan-2-yl)phenoxy)-3-fluoro-
N-hydroxybenzamide      543
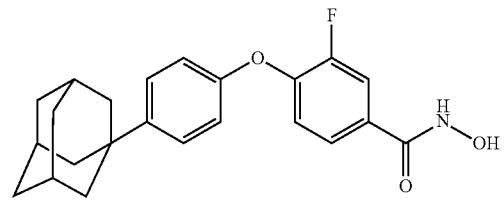 [SMILES: O=C(NO)c1ccc(Oc2ccc(C34CC5CC(CC(C5)C3)C4)cc2)c(F)c1]
4-(4-((3r,5r,7r)-adamantan-1-yl)phenoxy)-3-fluoro-
N-hydroxybenzamide      544

TABLE IV-continued
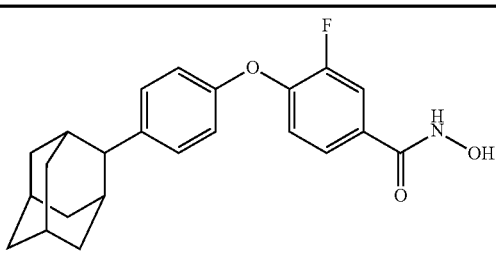
545
4-(4-((1r,3r,5r,7r)-adamantan-2-yl)phenoxy)-3-fluoro-
N-hydroxybenzamide
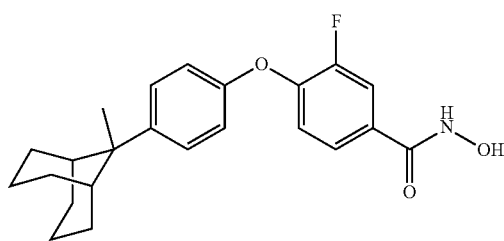 [SMILES: CC1(c2ccc(Oc3ccc(C(=O)NO)cc3F)cc2)C2CCCC1CCC2]
546
3-fluoro-N-hydroxy-4-(4-((1R,5S)-9-methylbicyclo[3.3.1]nonan-9-yl)
phenoxy)benzamide
$X = CH, R^3 = H, R^4 = Me$
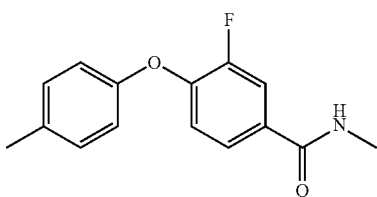
547
3-fluoro-N-mtehyl-4-(p-tolyloxy)benzamide
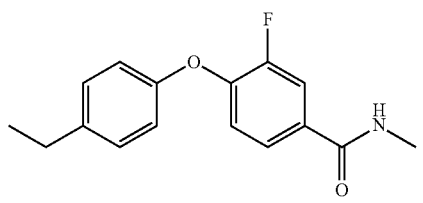 [SMILES: CCc1ccc(Oc2ccc(C(=O)NC)cc2F)cc1]
548
4-(4-ethylphenoxy)-3-fluoro-N-methylbenzamide
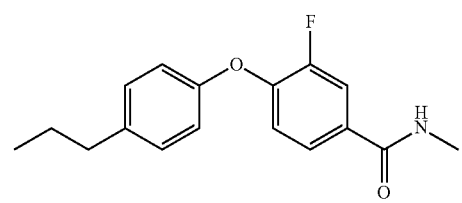 [SMILES: CCCc1ccc(Oc2ccc(C(=O)NC)cc2F)cc1]
549
3-fluoro-N-methyl-4-(4-propylphenoxy)benzamide
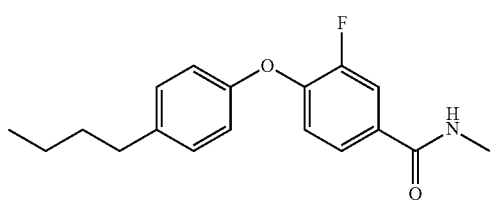 [SMILES: CCCCc1ccc(Oc2ccc(C(=O)NC)cc2F)cc1]
550
4-(4-butylphenoxy)-3-fluoro-N-methylbenzamide TABLE IV-continued
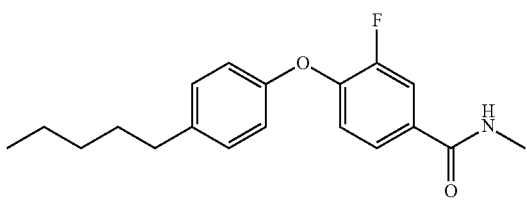 [SMILES: CCCCCc1ccc(Oc2ccc(C(=O)NC)cc2F)cc1]
3-fluoro-N-methyl-4-(4-pentylphenoxy)benzamide 551
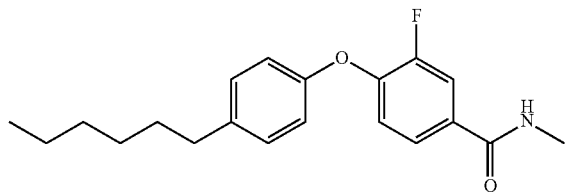
3-fluoro-4-(4-hexylphenoxy)-N-methylbenzamide 552
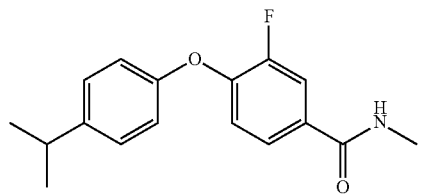 [SMILES: CNC(=O)c1ccc(Oc2ccc(C(C)C)cc2)c(F)c1]
3-fluoro-4-(4-isopropylphenoxy)-N-methylbenzamide 553
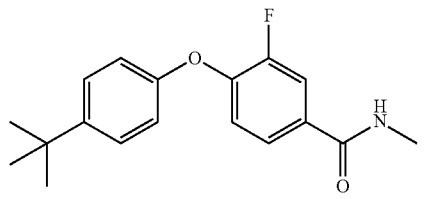 [SMILES: CNC(=O)c1ccc(Oc2ccc(C(C)(C)C)cc2)c(F)c1]
4-(4-(tert-butyl)phenxoy)-3-fluoro-N-methylbenzamide 554
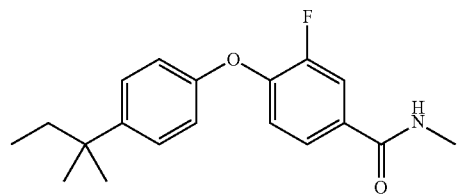 [SMILES: CCC(C)(C)c1ccc(Oc2ccc(C(=O)NC)cc2F)cc1]
3-fluoro-N-methyl-4-(4-(tert-pentyl)phenoxy)benzamide 555
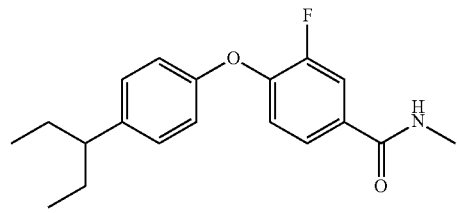
3-fluoro-N-methyl-4-(4-(pentan-3-yl)phenoxy)benzamide 556

TABLE IV-continued
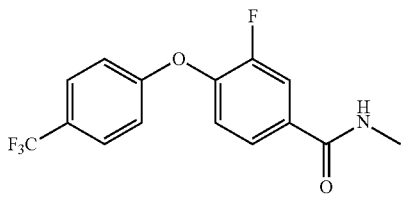 [SMILES: CNC(=O)c1ccc(Oc2ccc(C(F)(F)F)cc2)c(F)c1]
557
3-fluoro-N-methyl-4-(4-(trifluoromethyl)phenoxy)benzamide
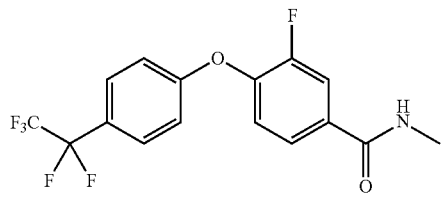
558
3-fluoro-N-methyl-4-(4-(perfluoroethyl)phenoxy)benzamide
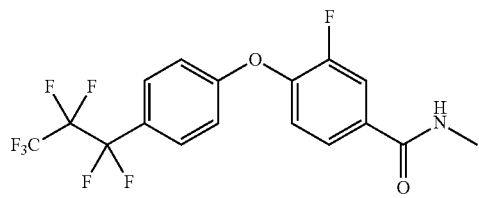 [SMILES: CNC(=O)c1ccc(Oc2ccc(C(F)(F)C(F)(F)C(F)(F)F)cc2)c(F)c1]
559
3-fluoro-N-methyl-4-(4-(perfluoropropyl)phenoxy)benzamide
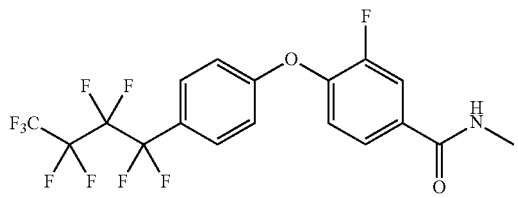
560
3-fluoro-N-methyl-4-(4-(perfluorobutyl)phenoxy)benzamide
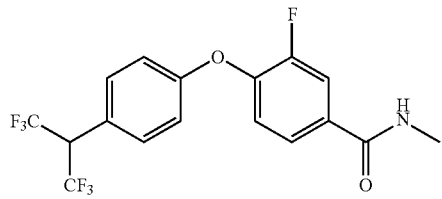
561
3-fluoro-4-(4-(1,1,1,3,3,3-hexafluoropropan-2-yl)phenoxy)-N-methylbenzamide
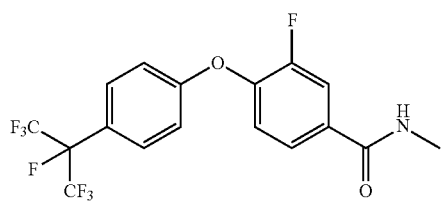
562
3-fluoro-N-methyl-4-(4-(perfluoropropan-2-yl)phenoxy)benzamide TABLE IV-continued
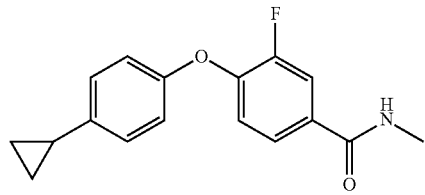 [SMILES: CNC(=O)c1ccc(Oc2ccc(C3CC3)cc2)c(F)c1]
4-(4-cyclopropylphenoxy)-3-fluoro-N-methylbenzamide
563
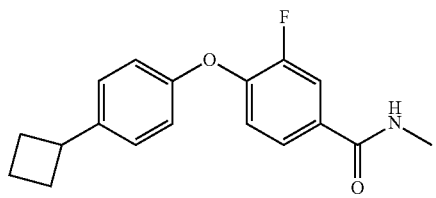 [SMILES: CNC(=O)c1ccc(Oc2ccc(C3CCC3)cc2)c(F)c1]
4-(4-cyclobutylphenoxy)-3-fluoro-N-methylbenzamide
564
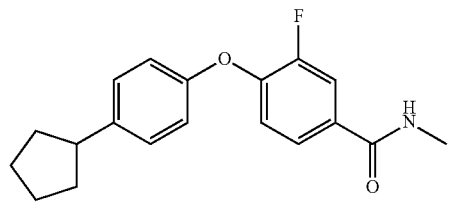
4-(4-cyclopentylphenoxy)-3-fluoro-N-methylbenzamide
565
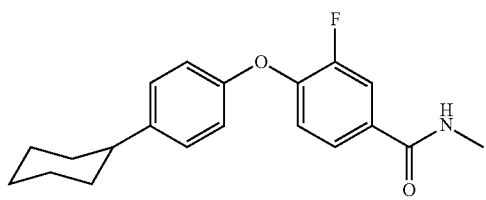 [SMILES: CNC(=O)c1ccc(Oc2ccc(C3CCCCC3)cc2)c(F)c1]
4-(4-cyclohexylphenoxy)-3-fluoro-N-methylbenzamide
566
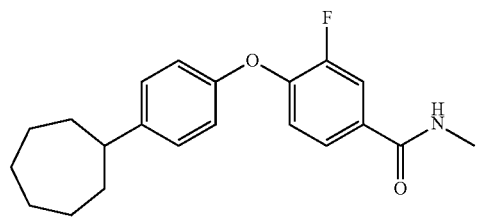
4-(4-cycloheptylphenoxy)-3-fluoro-N-methylbenzamide
567
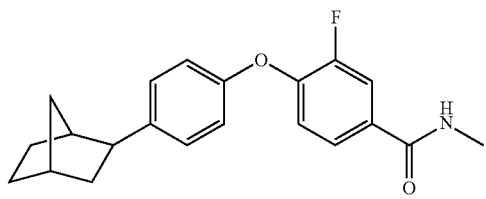 [SMILES: CNC(=O)c1ccc(Oc2ccc(C3CC4CCC3C4)cc2)c(F)c1]
4-(4-((1S,4R)-bicyclo[2.2.1]heptan-2-yl)phenoxy)-3-fluoro-N-methylbenzamide
568

TABLE IV-continued
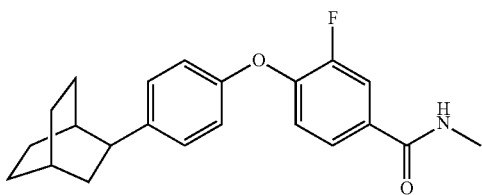
4-(4-((1s,4s)-bicyclo[2.2.2]octan-2-yl)phenoxy)-3-fluoro-N-methylbenzamide
569
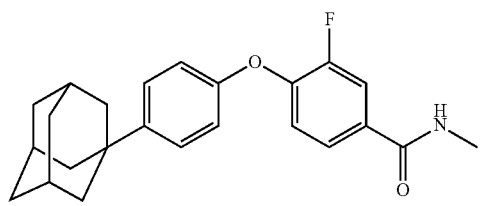
4-(4-((3r,5r,7r)-adamantan-1-yl)phenoxy)-3-fluoro-N-methylbenzamide
570
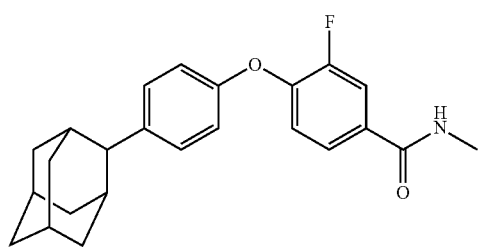
4-(4-((1r,3r,5r,7r)-adamantan-2-yl)phenoxy)-3-fluoro-N-methylbenzamide
571
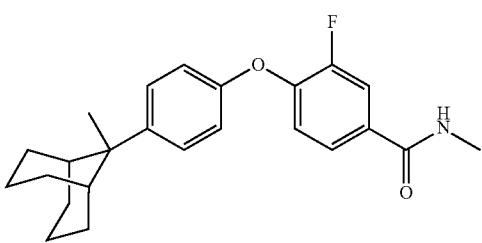
3-fluoro-N-methyl-4-(4-((1R,5S)-9-methylbicyclo[3.3.1]nonan-9-yl)phenoxy)benzamide
572
X = CH, $R^3$ = Me, $R^4$ = Me
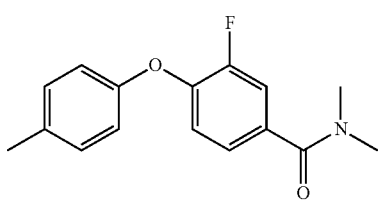
3-fluoro-N,N-dimethyl-4-(p-tolyloxy)benzamide
573

TABLE IV-continued
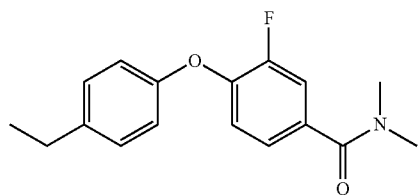
4-(4-ethylphenoxy)-3-fluoro-N,N-dimethylbenzamide
574
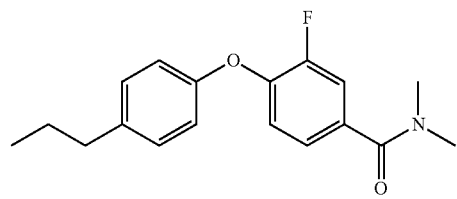 [SMILES: CCCc1ccc(Oc2ccc(C(=O)N(C)C)cc2F)cc1]
3-fluoro-N,N-dimethyl-4-(4-propylphenoxy)benzamide
575
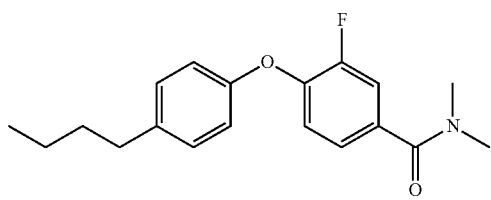 [SMILES: CCCCc1ccc(Oc2ccc(C(=O)N(C)C)cc2F)cc1]
4-(4-butylphenoxy)-3-fluoro-N,N-dimethylbenzamide
576
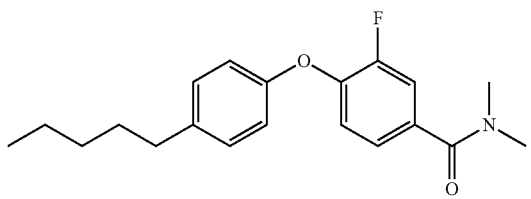 [SMILES: CCCCCc1ccc(Oc2ccc(C(=O)N(C)C)cc2F)cc1]
3-fluoro-N,N-dimethyl-4-(4-pentylphenoxy)benzamide
577
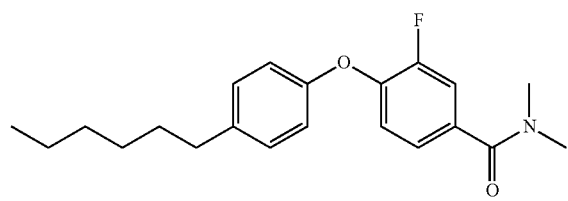
3-fluoro-4-(4-hexylphenoxy)-N,N-dimethylbenzamide
578
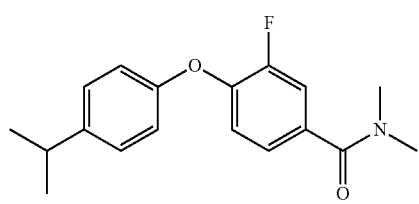 [SMILES: CC(C)c1ccc(Oc2ccc(C(=O)N(C)C)cc2F)cc1]
3-fluoro-4-(4-isopropylphenoxy)-N,N-dimethylbenzamide
579

TABLE IV-continued
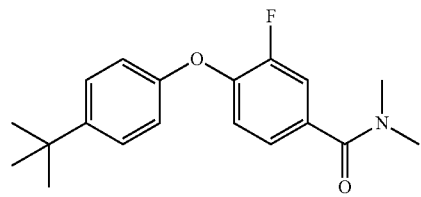
4-(4-(tert-butyl)phenoxy)-3-fluoro-N,N-dimethylbenzamide
580
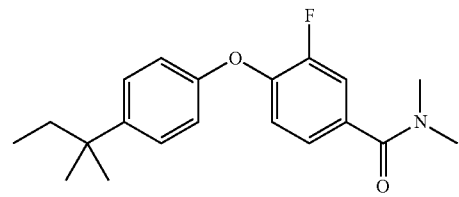 [SMILES: CCC(C)(C)c1ccc(Oc2ccc(C(=O)N(C)C)cc2F)cc1]
3-fluoro-N,N-dimethyl-4-(4-(tert-pentyl)phenoxy)benzamide
581
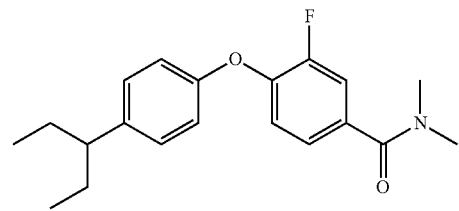
3-fluoro-N,N-dimethyl-4-(4-pentan-3-yl)phenoxy)benzamide
582
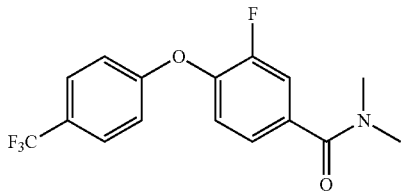
3-fluoro-N,N-dimethyl-4-(4-(trifluoromethyl)phenoxy)benzamide
583
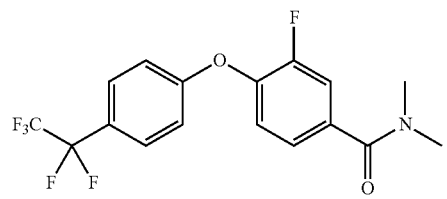
3-fluoro-N,N-dimethyl-4-(4-(perfluoroethyl)phenoxy)benzamide
584
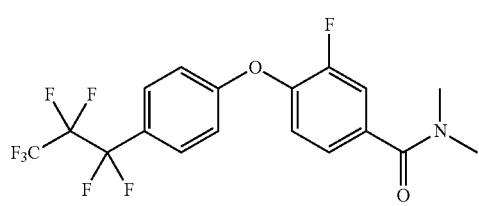 [SMILES: CN(C)C(=O)c1ccc(Oc2ccc(C(F)(F)C(F)(F)C(F)(F)F)cc2)c(F)c1]
3-fluoro-N,N-dimethyl-4-(4-(perfluoropropyl)phenoxy)benzamide
585

TABLE IV-continued
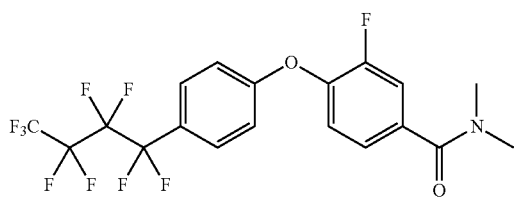 [SMILES: CN(C)C(=O)c1ccc(Oc2ccc(C(F)(F)C(F)(F)C(F)(F)C(F)(F)F)cc2)c(F)c1]
3-fluoro-N,N-dimethyl-4-(4-(perfluorobutyl)phenoxy)benzamide
586
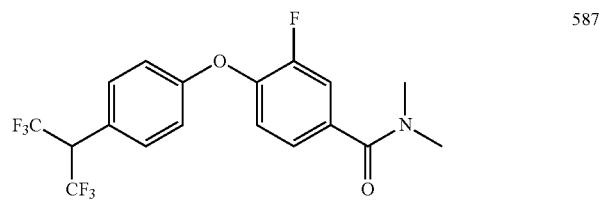
3-fluoro-4-(4-(1,1,1,3,3,3-hexafluoropropan-2-yl)phenoxy)-
N,N-dimethylbenzamide
587
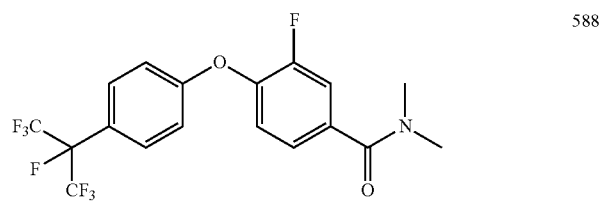
3-fluoro-N,N-dimethyl-4-(4-(perfluoropropan-2-
yl)phenoxy)benzamide
588
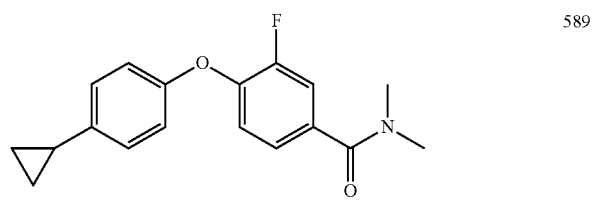
4-(4-cyclopropylphenoxy)-3-fluoro-N,N-dimethylbenzamide
589
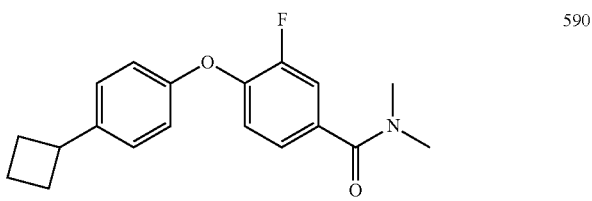
4-(4-cyclobutylphenoxy)-3-fluoro-N,N-dimethylbenzamide
590
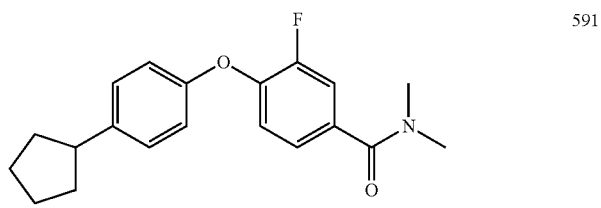
4-(4-cyclopentylphenoxy)-3-fluoro-N,N-dimethylbenzamide
591

TABLE IV-continued

| | |
|---|---|
| 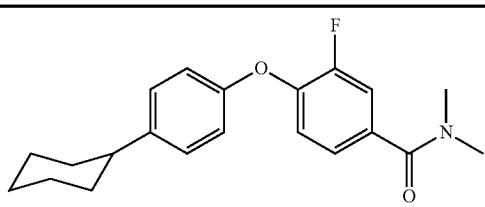<br>4-(4-cyclohexylphenoxy)-3-fluoro-N,N-dimethylbenzamide | 592 |
| 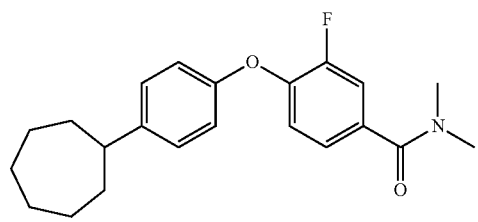<br>4-(4-cycloheptylphenoxy)-3-fluoro-N,N-dimethylbenzamide | 593 |
| 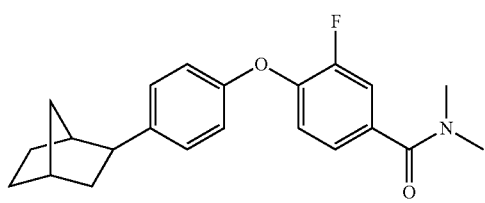 [SMILES: CN(C)C(=O)c1ccc(Oc2ccc(C3CC4CCC3C4)cc2)c(F)c1]<br>4-(4-((1S,4R)-bicyclo[2.2.1]heptan-2-yl)phenoxy-3-fluoro-N,N-dimethylbenzamide | 594 |
| 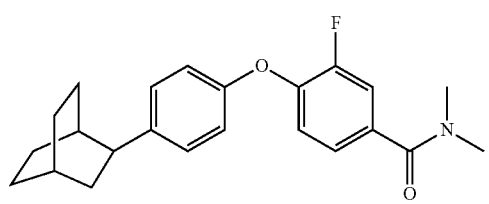 [SMILES: CN(C)C(=O)c1ccc(Oc2ccc(C3CC4CCC3CC4)cc2)c(F)c1]<br>4-(4-((1s,4s)-bicyclo[2.2.2]octan-2-yl)phenoxy)-3-fluoro-N,N-dimethylbenzamide | 595 |
| 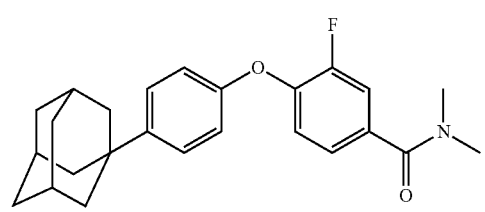 [SMILES: CN(C)C(=O)c1ccc(Oc2ccc(C34CC5CC(CC(C5)C3)C4)cc2)c(F)c1]<br>4-(4-((3r,5r,7r)-adamantan-1-yl)phenoxy)-3-fluoro-N,N-dimethylbenzamide | 596 |
| 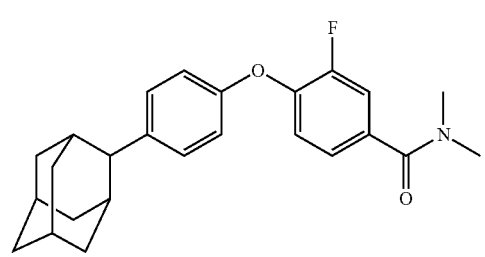 [SMILES: CN(C)C(=O)c1ccc(Oc2ccc(C3C4CC5CC(C4)CC3C5)cc2)c(F)c1]<br>4-(4-((1r,3r,5r,7r)-adamantan-2-yl)phenoxy)-3-fluoro-N,N-dimethylbenzamide | 597 |

TABLE IV-continued
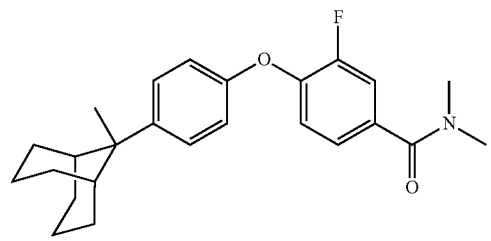 [SMILES: CN(C)C(=O)c1ccc(Oc2ccc(C3(C)C4CCCC3CCC4)cc2)c(F)c1]
598
3-fluoro-N,N-dimethyl-4-(4-((1R,5S)-9-methylbicyclo[3.3.1]nonan-9-yl)phenoxy)benzamide
X = N, R³ = H, R⁴ = H
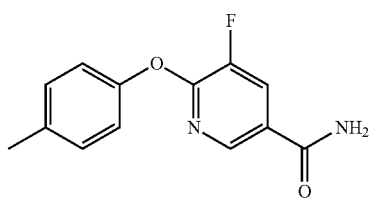 [SMILES: Cc1ccc(Oc2ncc(C(N)=O)cc2F)cc1]
599
5-fluoro-6-(p-tolyloxy)nicotinamide
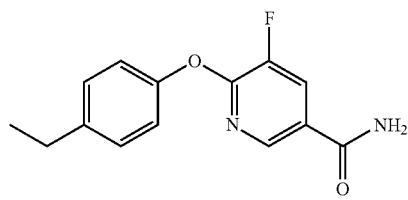 [SMILES: CCc1ccc(Oc2ncc(C(N)=O)cc2F)cc1]
600
6-(4-ethylphenoxy)-5-fluoronicotinamide
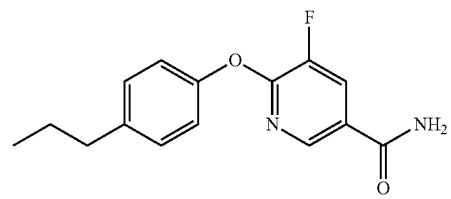
601
5-fluoro-6-(4-propylphenoxy)nicotinamide
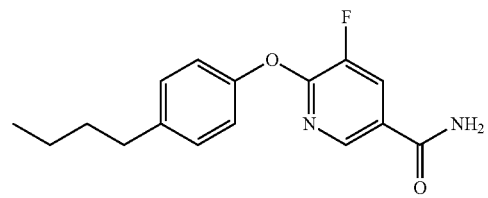
602
6-(4-butylphenoxy)-5-fluoronicotinamide
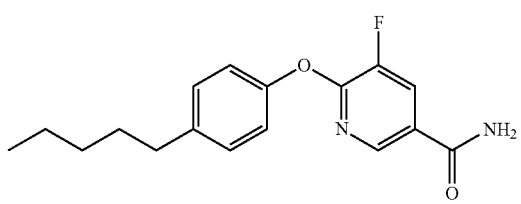 [SMILES: CCCCCc1ccc(Oc2ncc(C(N)=O)cc2F)cc1]
603
5-fluoro-6-(4-pentylphenoxy)nicotinamide TABLE IV-continued
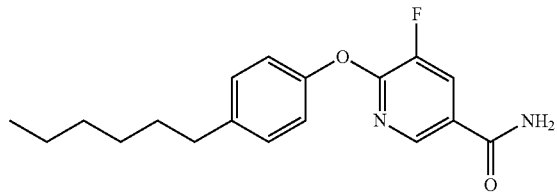 [SMILES: CCCCCCc1ccc(Oc2ncc(C(N)=O)cc2F)cc1]
604
5-fluoro-6-(4-hexylphenoxy)nicotinamide
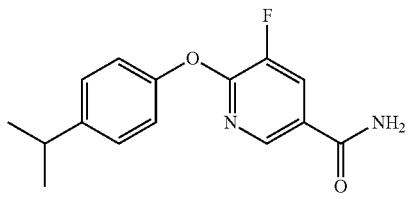 [SMILES: CC(C)c1ccc(Oc2ncc(C(N)=O)cc2F)cc1]
605
5-fluoro-6-(4-isopropylphenoxy)nictinamide
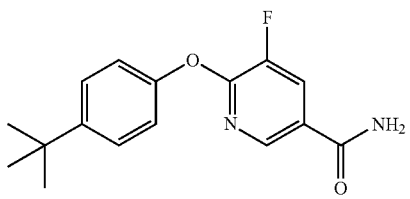
606
6-(4-(tert-butyl)phenoxy)-5-fluoronicotinamide
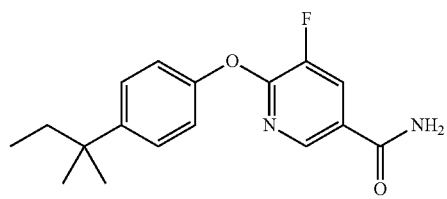 [SMILES: CCC(C)(C)c1ccc(Oc2ncc(C(N)=O)cc2F)cc1]
607
5-fluoro-6-(4-(tert-pentyl)phenoxy)nicotinamide
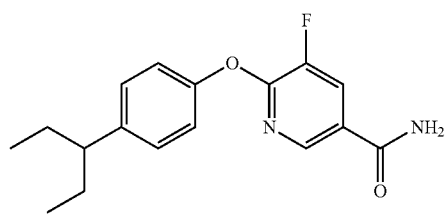 [SMILES: CCC(CC)c1ccc(Oc2ncc(C(N)=O)cc2F)cc1]
608
5-fluoro-6-(4-(pentan-3-yl)phenoxy)nicotinamide
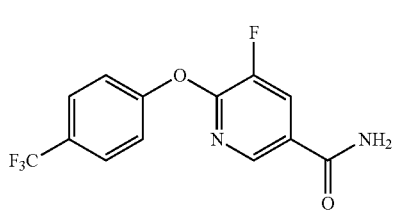 [SMILES: NC(=O)c1cnc(Oc2ccc(C(F)(F)F)cc2)c(F)c1]
609
5-fluoro-6-(4-(trifluoromethyl)phenoxy)nicotinamide TABLE IV-continued
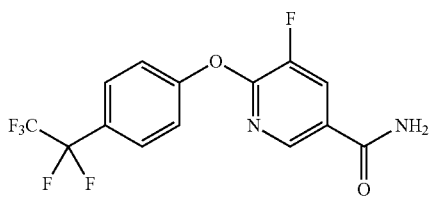 [SMILES: NC(=O)c1cnc(Oc2ccc(C(F)(F)C(F)(F)F)cc2)c(F)c1]
610
5-fluoro-6-(4-(perfluoroethyl)phenoxy)nicotinamdie
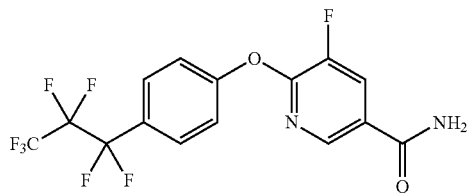
611
5-fluoro-6-(4-(perfluoropropyl)phenoxy)nicotinamide
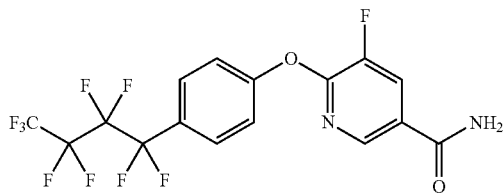 [SMILES: NC(=O)c1cnc(Oc2ccc(C(F)(F)C(F)(F)C(F)(F)C(F)(F)F)cc2)c(F)c1]
612
5-fluoro-6-(4-(perfluorobutyl)phenoxy)nicotinamide
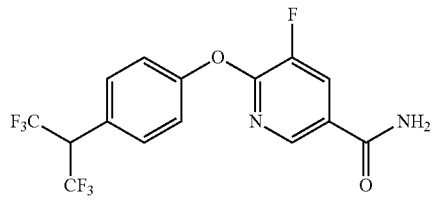 [SMILES: NC(=O)c1cnc(Oc2ccc(C(C(F)(F)F)C(F)(F)F)cc2)c(F)c1]
613
5-fluoro-6-(4-(1,1,1,3,3,3-hexafluoropropan-2-yl)phenoxy)nicotinamide
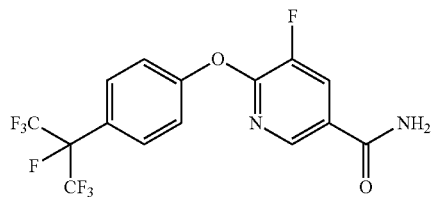 [SMILES: NC(=O)c1cnc(Oc2ccc(C(F)(C(F)(F)F)C(F)(F)F)cc2)c(F)c1]
614
5-fluoro-6-(4-(perfluoropropan-2-yl)phenoxy)nicotinamide
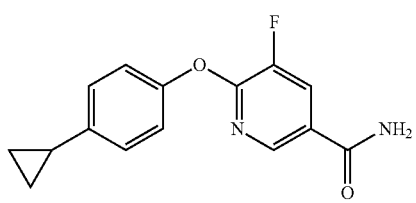 [SMILES: NC(=O)c1cnc(Oc2ccc(C3CC3)cc2)c(F)c1]
615
6-(4-cyclopropylphenoxy)-5-fluoronicotinamide TABLE IV-continued
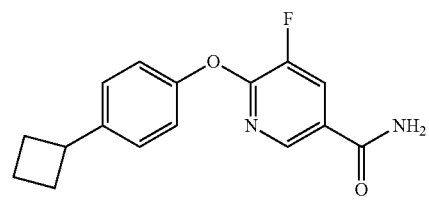 [SMILES: NC(=O)c1cnc(Oc2ccc(C3CCC3)cc2)c(F)c1]
6-(4-cyclobutylphenoxy)-5-fluoronicotinamide
616
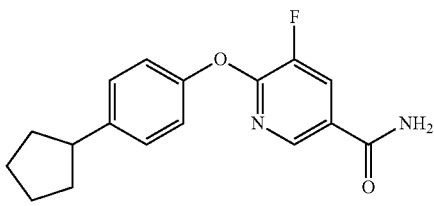 [SMILES: NC(=O)c1cnc(Oc2ccc(C3CCCC3)cc2)c(F)c1]
6-(4-cyclopentylphenoxy)-5-fluoronicotinamide
617
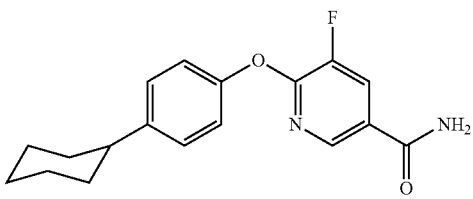 [SMILES: NC(=O)c1cnc(Oc2ccc(C3CCCCC3)cc2)c(F)c1]
6-(4-cyclohexylphenoxy)-5-fluoronicotinamide
618
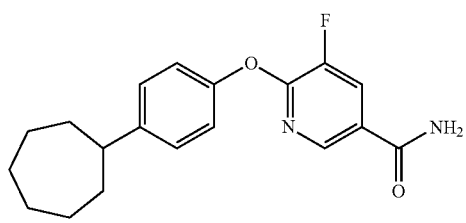 [SMILES: NC(=O)c1cnc(Oc2ccc(C3CCCCCC3)cc2)c(F)c1]
6-(4-cycloheptylphenoxy)-5-fluoronicotinamide
619
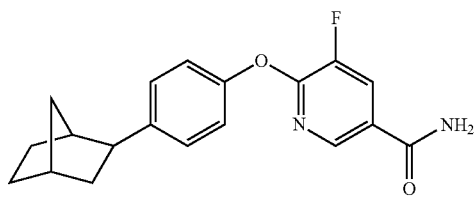 [SMILES: NC(=O)c1cnc(Oc2ccc(C3CC4CCC3C4)cc2)c(F)c1]
6-(4-((1S,4R)-bicyclo[2.2.1]heptan-2-yl)phenoxy)-5-fluoronicotinamide
620
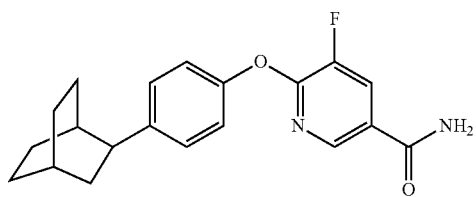 [SMILES: NC(=O)c1cnc(Oc2ccc(C3CC4CCC3CC4)cc2)c(F)c1]
6-(4-((1s,4s)-bicyclo[2.2.2]octan-2-yl)phenoxy)-5-fluoronicotinamide
621

TABLE IV-continued
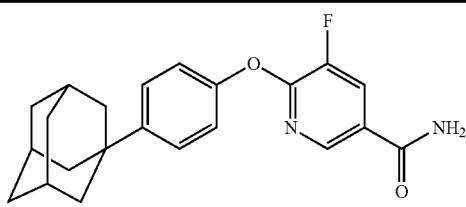
6-(4-((3r,5r,7r)-adamantan-1-yl)phenoxy)-5-fluoronicotinamide
622
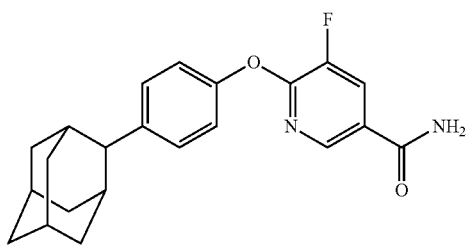 [SMILES: NC(=O)c1cnc(Oc2ccc(C3C4CC5CC(C4)CC3C5)cc2)c(F)c1]
6-(4-((1r,3r,5r,7r)-adamantan-2-yl)phenoxy)-5-fluoronicotinamide
623
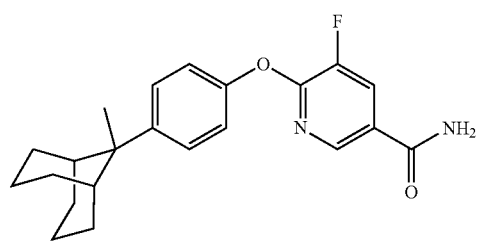 [SMILES: CC1(c2ccc(Oc3ncc(C(N)=O)cc3F)cc2)C2CCCC1CCC2]
5-fluoro-6-(4-((1R,5S)-9-methybicyclo[3.3.1]nonan-9-yl)phenoxy)nicotinamide
624
$X = N$, $R^3 = H$, $R^4 = OH$
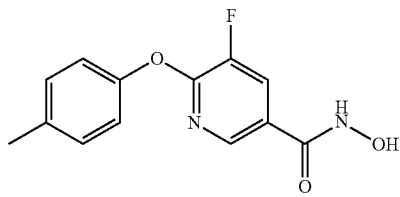 [SMILES: Cc1ccc(Oc2ncc(C(=O)NO)cc2F)cc1]
5-fluoro-N-hydroxy-6-(p-tolyloxy)nicotinamide
625
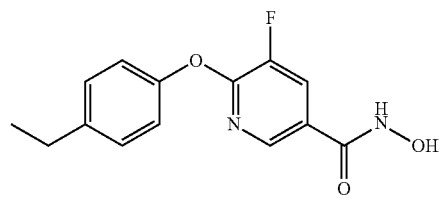 [SMILES: CCc1ccc(Oc2ncc(C(=O)NO)cc2F)cc1]
6-(4-ethylphenoxy)-5-fluoro-N-hydroxynicotinamide
626
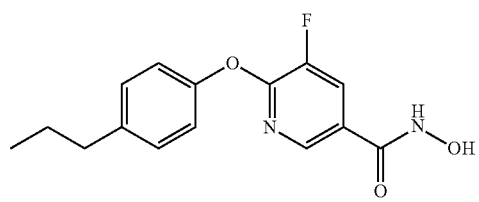 [SMILES: CCCc1ccc(Oc2ncc(C(=O)NO)cc2F)cc1]
5-fluoro-N-hydroxy-6-(4-propylphenoxy)nicotinamide
627

TABLE IV-continued
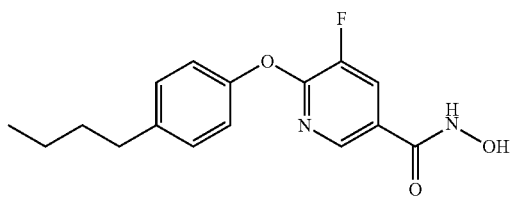 [SMILES: CCCCc1ccc(Oc2ncc(C(=O)NO)cc2F)cc1]
628
6-(4-butylphenoxy)-5-fluoro-N-hydroxynicotinamide
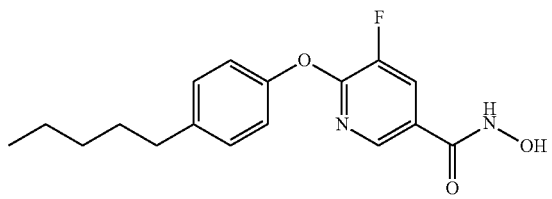 [SMILES: CCCCCc1ccc(Oc2ncc(C(=O)NO)cc2F)cc1]
629
5-fluoro-N-hydroxy-6-(4-pentylphenoxy)nicotinamide
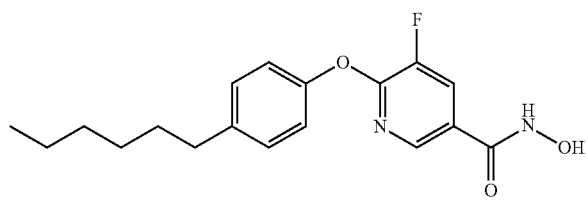 [SMILES: CCCCCCc1ccc(Oc2ncc(C(=O)NO)cc2F)cc1]
630
5-fluoro-6-(4-hexylphenoxy)-N-hydroxynicotinamide
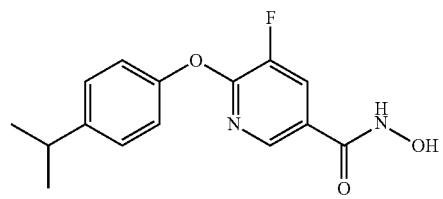 [SMILES: CC(C)c1ccc(Oc2ncc(C(=O)NO)cc2F)cc1]
631
5-fluoro-N-hydroxy-6-(4-isopropylphenoxy)nicotinamide
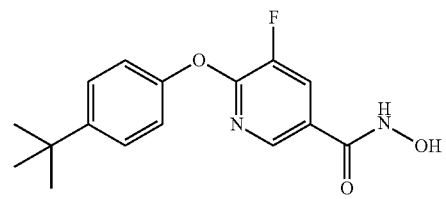 [SMILES: CC(C)(C)c1ccc(Oc2ncc(C(=O)NO)cc2F)cc1]
632
6-(4-(tert-butyl)phenoxy)-5-fluoro-N-hydroxynicotinamide
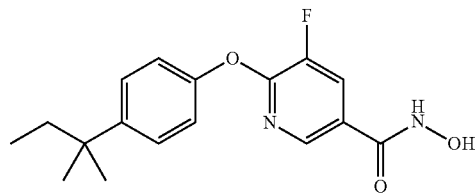 [SMILES: CCC(C)(C)c1ccc(Oc2ncc(C(=O)NO)cc2F)cc1]
633

TABLE IV-continued
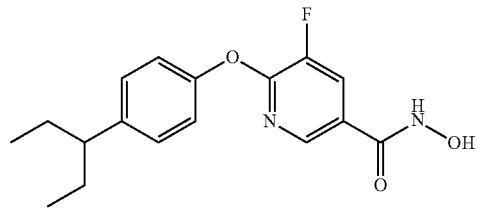
5-fluoro-N-hydroxy-6-(4-(pentan-3-yl)phenoxy)nicotinamide
634
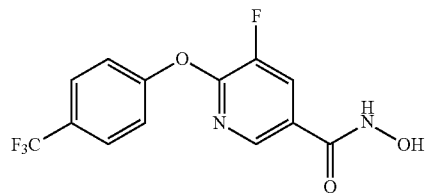 [SMILES: O=C(NO)c1cnc(Oc2ccc(C(F)(F)F)cc2)c(F)c1]
5-fluoro-N-hydroxy-6-(4-(trifluoromethyl)phenoxy)nicotinamide
635
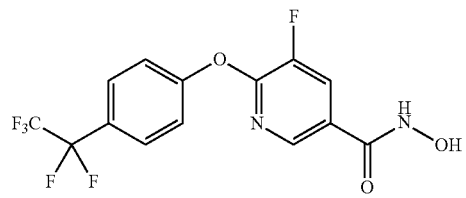
5-fluoro-N-hydroxy-6-(4-(perfluoroethyl)phenoxy)nicotinamide
636
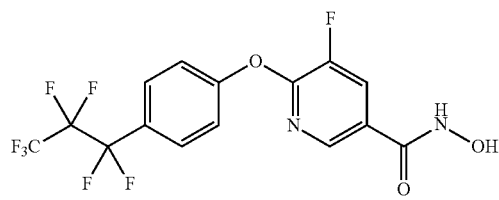 [SMILES: O=C(NO)c1cnc(Oc2ccc(C(F)(F)C(F)(F)C(F)(F)F)cc2)c(F)c1]
5-fluoro-N-hydroxy-6-(4-(perfluoropropyl)phenoxy)nicotinamide
637
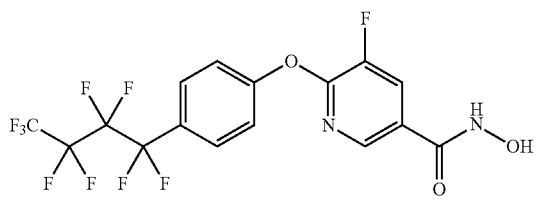
5-fluoro-N-hydroxy-6-(4-(perfluorobutyl)phenoxy)nicotinamide
638
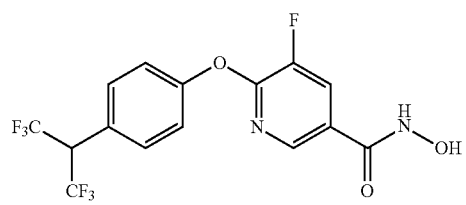
5-fluoro-6-(4-(1,1,1,3,3,3-hexafluoropropan-2-yl)phenoxy)-N-hydroxynicotinamide
639

TABLE IV-continued
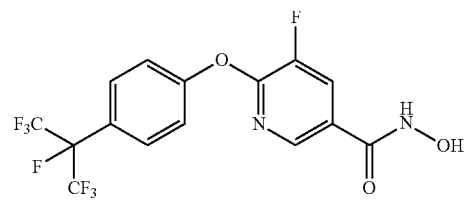 [SMILES: O=C(NO)c1cnc(Oc2ccc(C(F)(C(F)(F)F)C(F)(F)F)cc2)c(F)c1]
640
5-fluoro-N-hydroxy-6-(4-(perfluoropropan-2-yl)phenoxy)nicotinamide
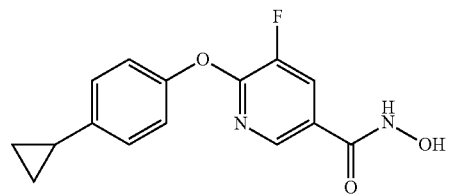 [SMILES: O=C(NO)c1cnc(Oc2ccc(C3CC3)cc2)c(F)c1]
641
6-(4-cyclopropylphenoxy)-5-fluoro-N-hydroxynicotinamide
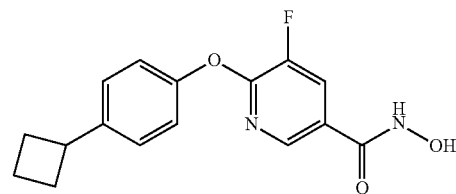 [SMILES: O=C(NO)c1cnc(Oc2ccc(C3CCC3)cc2)c(F)c1]
642
6-(4-cyclobutylphenoxy)-5-fluoro-N-hydroxynicotinamide
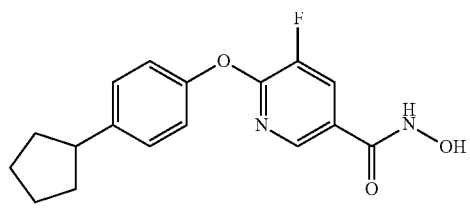 [SMILES: O=C(NO)c1cnc(Oc2ccc(C3CCCC3)cc2)c(F)c1]
643
6-(4-cyclopentylphenoxy)-5-fluoro-N-hydroxynicotinamide
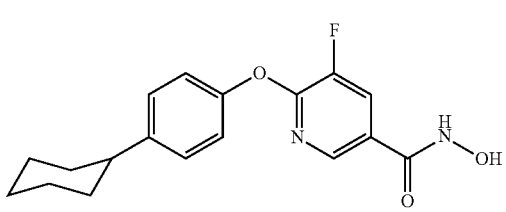
644
6-(4-cyclohexylphenoxy)-5-fluoro-N-hydroxynicotinamide
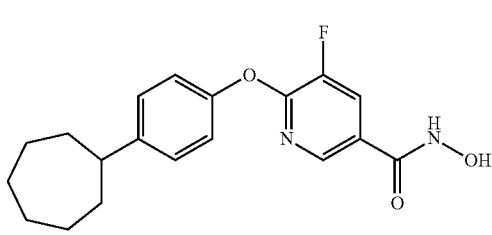 [SMILES: O=C(NO)c1cnc(Oc2ccc(C3CCCCCC3)cc2)c(F)c1]
645
6-(4-cycloheptylphenoxy)-5-fluoro-N-hydroxynicotinamide TABLE IV-continued
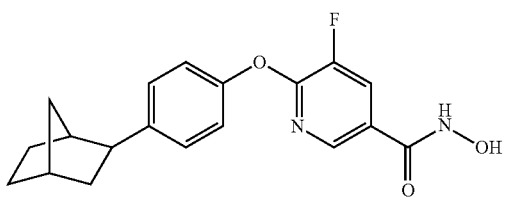 [SMILES: O=C(NO)c1cnc(Oc2ccc(C3CC4CCC3C4)cc2)c(F)c1]
646
6-(4-((1S,4R)-bicyclo[2.2.1]heptan-2-yl)phenoxy)-5-fluoro-
N-hydroxynicotinamide
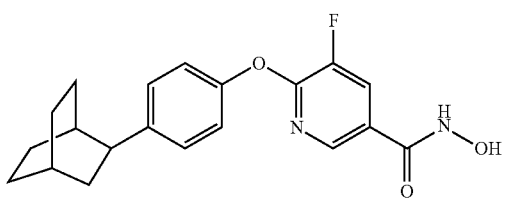
647
6-(4-((1s,4s)-bicyclo[2.2.2]octan-2-yl)phenoxy)-5-fluoro-
N-hydroxynicotinamide
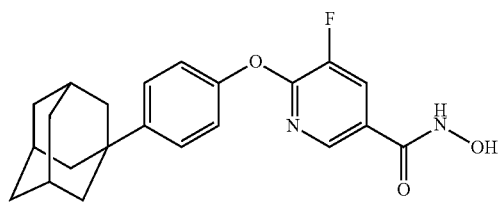 [SMILES: O=C(NO)c1cnc(Oc2ccc(C34CC5CC(CC(C5)C3)C4)cc2)c(F)c1]
648
6-(4-((3r,5r,7r)-adamantan-1-yl)phenoxy)-5-fluoro-
N-hydroxynictinamide
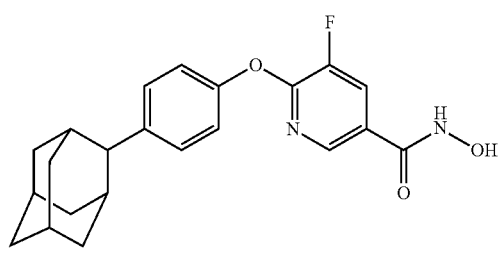 [SMILES: O=C(NO)c1cnc(Oc2ccc(C3C4CC5CC(C4)CC3C5)cc2)c(F)c1]
649
6-(4-((1r,3r,5r,7r)-adamantan-2-yl)phenoxy)-5-fluoro-
N-hydroxynicotinamide
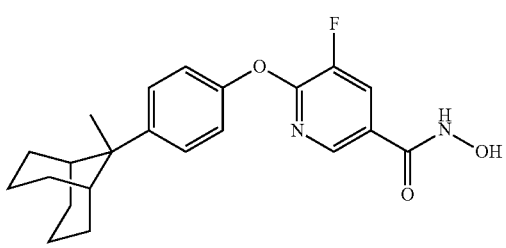 [SMILES: CC1(c2ccc(Oc3ncc(C(=O)NO)cc3F)cc2)C2CCCC1CCC2]
650
5-fluoro-N-hydroxy-6-(4-((1R,5S)-9-methylbicyclo[3.3.1]nonan-9-yl)
phenoxy)nicotinamide
X = N, R$^3$ = H, R$^4$ = Me TABLE IV-continued
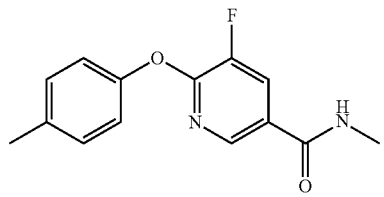
651
5-fluoro-N-methyl-6-(p-tolyloxy)nicotinamide
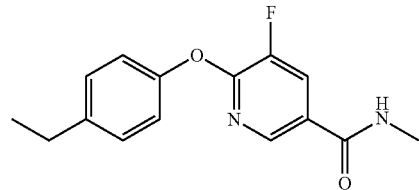 [SMILES: CCc1ccc(Oc2ncc(C(=O)NC)cc2F)cc1]
652
6-(4-ethylphenoxy)-5-fluoro-N-mtehylnictinamide
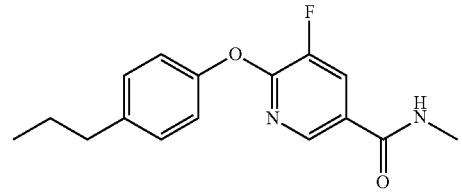 [SMILES: CCCc1ccc(Oc2ncc(C(=O)NC)cc2F)cc1]
653
5-fluoro-N-methyl-6-(4-propylphenoxy)nicotinamide
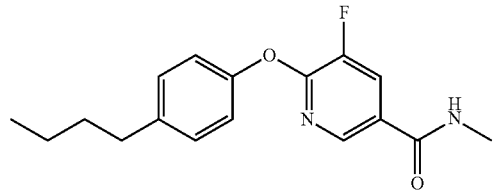 [SMILES: CCCCc1ccc(Oc2ncc(C(=O)NC)cc2F)cc1]
654
6-(4-butylphenoxy)-5-fluoro-N-methylnictinamide
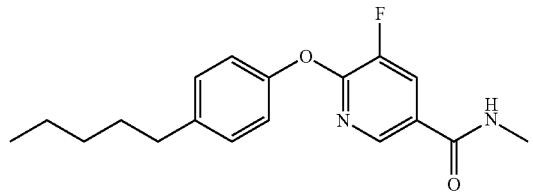 [SMILES: CCCCCc1ccc(Oc2ncc(C(=O)NC)cc2F)cc1]
655
5-fluoro-N-methyl-6-(4-pentylphenoxy)nicotnamide
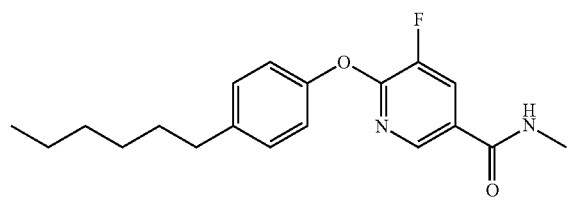 [SMILES: CCCCCCc1ccc(Oc2ncc(C(=O)NC)cc2F)cc1]
656
5-fluoro-6-(4-hexylphenoxy)-N-methylnicotinamide TABLE IV-continued
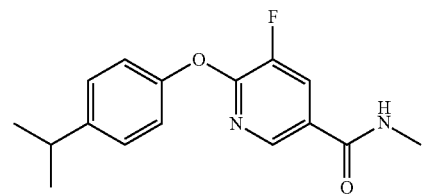 [SMILES: CNC(=O)c1cnc(Oc2ccc(C(C)C)cc2)c(F)c1]
657
5-fluoro-6-(4-isopropylphenoxy)-N-methylnicotinamide
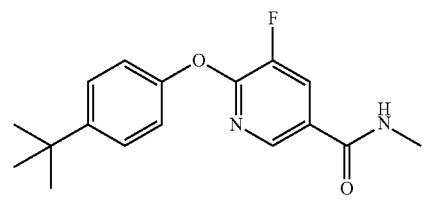 [SMILES: CNC(=O)c1cnc(Oc2ccc(C(C)(C)C)cc2)c(F)c1]
658
6-(4-(tert-butyl)phenoxy)-5-fluoro-N-methylnicotinamide
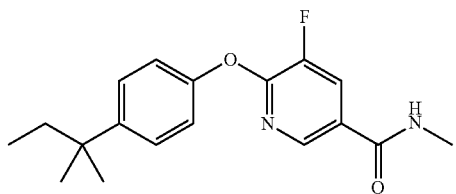
659
5-fluoro-N-methyl-6-(4-(tert-pentyl)phenoxy)nicotinamide
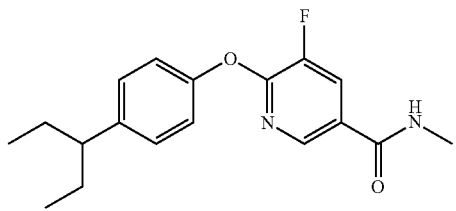 [SMILES: CCC(CC)c1ccc(Oc2ncc(C(=O)NC)cc2F)cc1]
660
5-fluoro-N-methyl-6-(4-(pentan-3-yl)phenoxy)nicotinamide
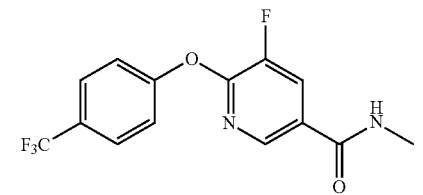 [SMILES: CNC(=O)c1cnc(Oc2ccc(C(F)(F)F)cc2)c(F)c1]
661
5-fluoro-N-methyl-6-(4-(trifluoromethyl)phenoxy)nicotinamide
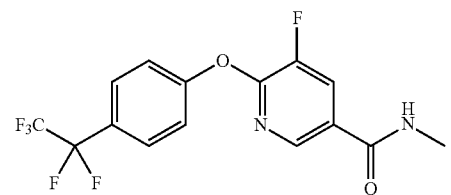 [SMILES: CNC(=O)c1cnc(Oc2ccc(C(F)(F)C(F)(F)F)cc2)c(F)c1]
662
5-fluoro-N-methyl-6-(4-(perfluoroethyl)phenoxy)nicotinamide TABLE IV-continued
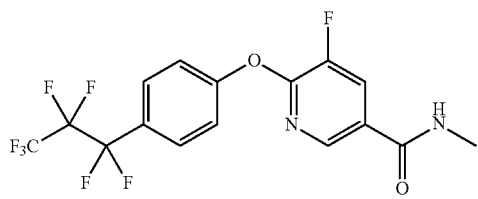 [SMILES: CNC(=O)c1cnc(Oc2ccc(C(F)(F)C(F)(F)C(F)(F)F)cc2)c(F)c1]
663
5-fluoro-N-methyl-6-(4-(perfluoropropyl)phenoxy)nicotinamide
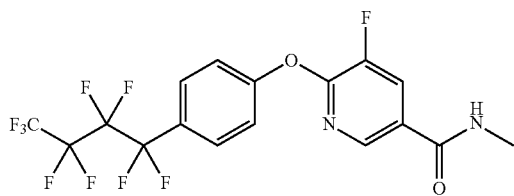
664
5-fluoro-N-methyl-6-(4-(perfluorobutyl)phenoxy)nicotinamide
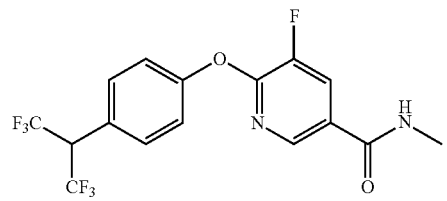
665
5-fluoro-6-(4-(1,1,1,3,3,3-hexafluoropropan-2-yl)phenoxy)-N-methylnicotinamide
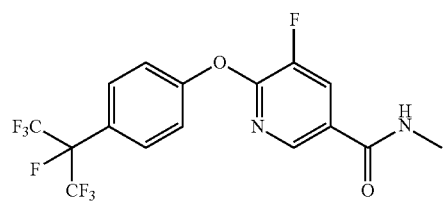
666
5-fluoro-N-methyl-6-(4-(perfluoropropan-2-yl)phenoxy)nicotinamide
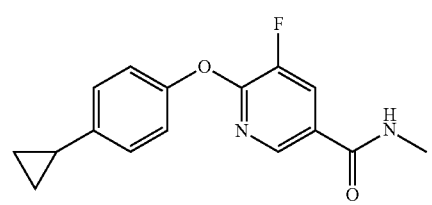
667
6-(4-cyclopropylphenoxy)-5-fluoro-N-methylnicotinamide
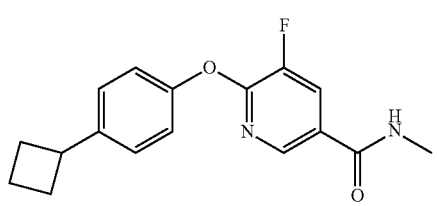
668
6-(4-cyclobutylphenoxy)-6-fluoro-N-methylnicotinamide TABLE IV-continued
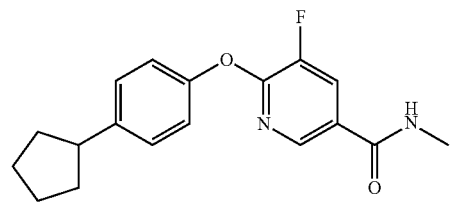 [SMILES: CNC(=O)c1cnc(Oc2ccc(C3CCCC3)cc2)c(F)c1]
6-(4-cyclopentylphenoxy)-5-fluoro-N-methylnicotinamide 669
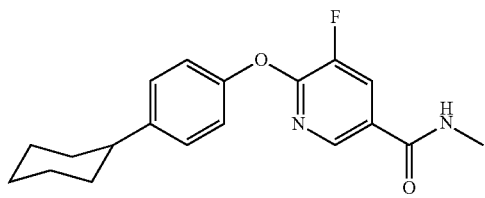 [SMILES: CNC(=O)c1cnc(Oc2ccc(C3CCCCC3)cc2)c(F)c1]
6-(4-cyclohexylphenoxy)-5-fluoro-N-methylnicotinamide 670
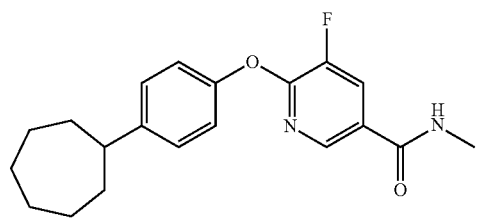 [SMILES: CNC(=O)c1cnc(Oc2ccc(C3CCCCCC3)cc2)c(F)c1]
6-(4-cycloheptylphenoxy)-5-fluoro-N-methylnicotinamide 671
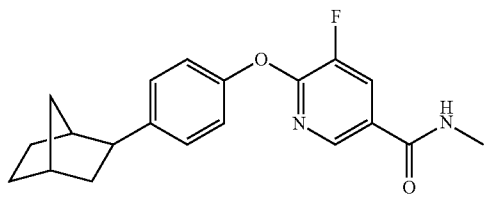 [SMILES: CNC(=O)c1cnc(Oc2ccc(C3CC4CCC3C4)cc2)c(F)c1]
6-(4-((1S,4R)-bicyclo[2.2.1]heptan-2-yl)phenoxy)-5-fluoro-N-methylnicotinamide 672
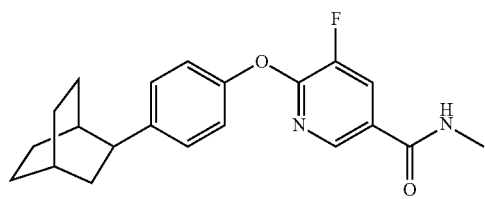
6-(4-((1s,4s)-bicyclo[2.2.2]octan-2-yl)phenoxy)-5-fluoro-N-methylnictinamide 673
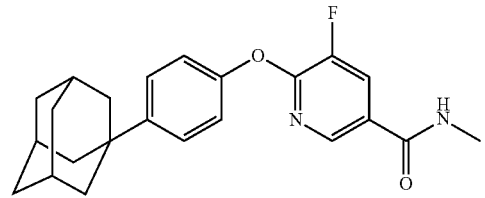
6-(4-((3r,5r,7r)-adamantan-1-yl)phenoxy)-5-fluoro-N-methylnicotinamide 674

TABLE IV-continued
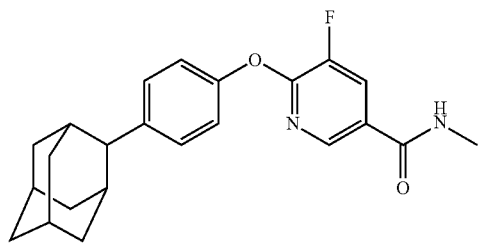
6-(4-((1r,3r,5r,7r)-adamantan-2-yl)phenoxy)-5-fluoro-N-methylnicotinamide
675
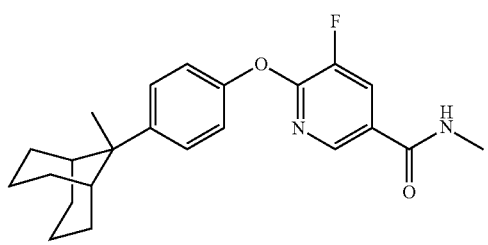 [SMILES: CNC(=O)c1cnc(Oc2ccc(C3(C)C4CCCC3CCC4)cc2)c(F)c1]
5-fluoro-N-methyl-6-(4-((1R,5S)-9-methylbicyclo[3.3.1]nonan-9-yl)phenoxy)nicotinamide
676
$X = N$, $R^3 = Me$, $R^4 = Me$
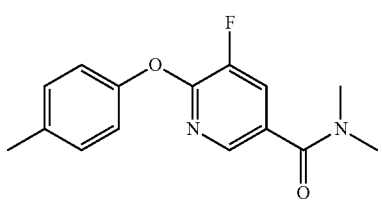
5-fluoro-N,N-dimethyl-6-(p-tolyloxy)nicotinamide
677
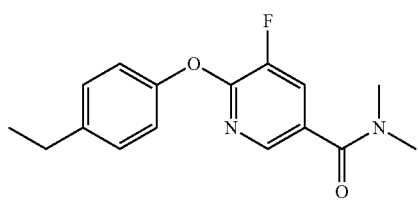 [SMILES: CCc1ccc(Oc2ncc(C(=O)N(C)C)cc2F)cc1]
6-(4-ethylphenoxy)-5-fluoro-N,N-dimethylnicotinamide
678
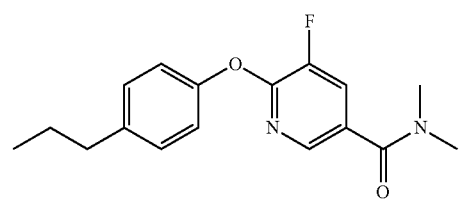
5-fluoro-N,N-dimethyl-6-(4-propylphenoxy)nicotinamide
679
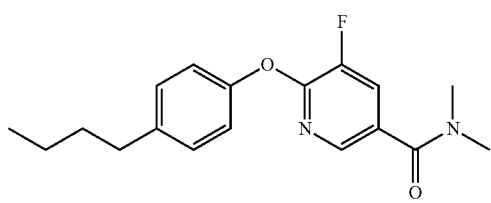 [SMILES: CCCCc1ccc(Oc2ncc(C(=O)N(C)C)cc2F)cc1]
6-(4-butylphenoxy)-5-fluoro-N,N-dimethylnicotinamide
680

TABLE IV-continued
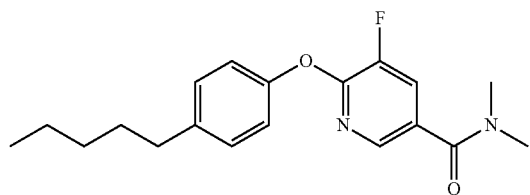 [SMILES: CCCCCc1ccc(Oc2ncc(C(=O)N(C)C)cc2F)cc1]
5-fluoro-N,N-dimethyl-6-(4-pentylphenoxy)nicotinamide
681
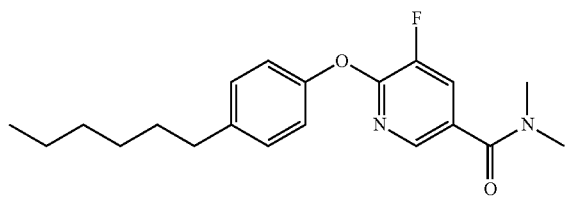 [SMILES: CCCCCCc1ccc(Oc2ncc(C(=O)N(C)C)cc2F)cc1]
5-fluoro-6-(4-hexylphenoxy)-N,N-dimethylnicotinamide
682
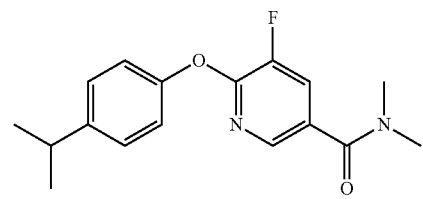
5-fluoro-6-(4-isopropylphenoxy)-N,N-dimethylnicotinamide
683
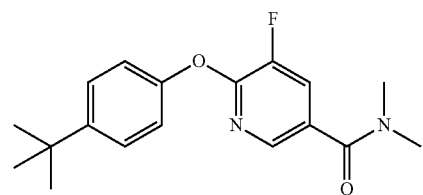 [SMILES: CN(C)C(=O)c1cnc(Oc2ccc(C(C)(C)C)cc2)c(F)c1]
6-(4-(tert-butyl)phenoxy)-5-fluoro-N,N-dimethylnicotinamide
684
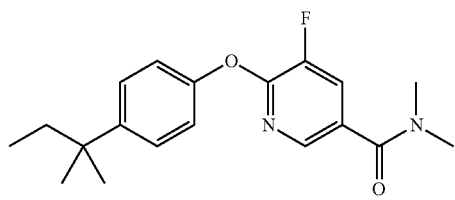
5-fluoro-N,N-dimethyl-6-(4-(tert-pentyl)phenoxy)nicotinamide
685
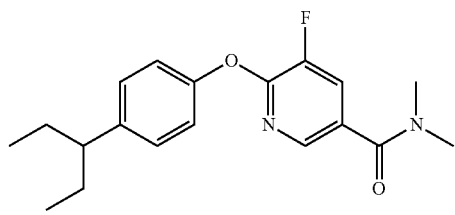 [SMILES: CCC(CC)c1ccc(Oc2ncc(C(=O)N(C)C)cc2F)cc1]
5-fluoro-N,N-dimethyl-6-(4-(pentan-3-yl)phenoxy)nicotinamide
686

TABLE IV-continued

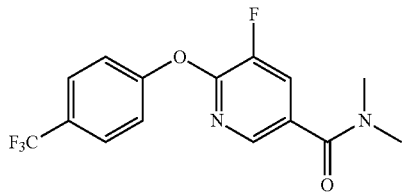 [SMILES: CN(C)C(=O)c1cnc(Oc2ccc(C(F)(F)F)cc2)c(F)c1]

687

5-fluoro-N,N-dimethyl-6-(4-(trifluoromethyl)phenoxy)nicotinamide

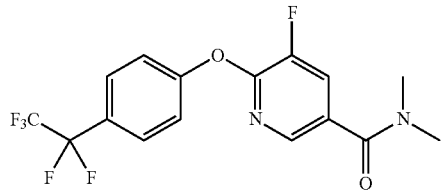

688

5-fluoro-N,N-dimethyl-6-(4-(perfluoroethyl)phenoxy)nicotinamide

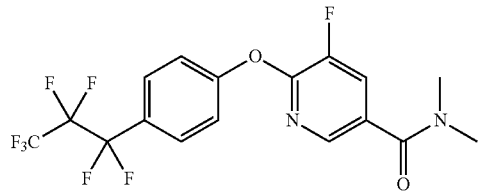 [SMILES: CN(C)C(=O)c1cnc(Oc2ccc(C(F)(F)C(F)(F)C(F)(F)F)cc2)c(F)c1]

689

5-fluoro-N,N-dimethyl-6-(4-(perfluoropropyl)phenoxy)nicotinamide

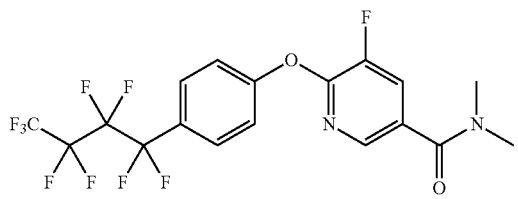 [SMILES: CN(C)C(=O)c1cnc(Oc2ccc(C(F)(F)C(F)(F)C(F)(F)C(F)(F)F)cc2)c(F)c1]

690

5-fluoro-N,N-dimethyl-6-(4-(perfluorobutyl)phenoxy)nicotinamide

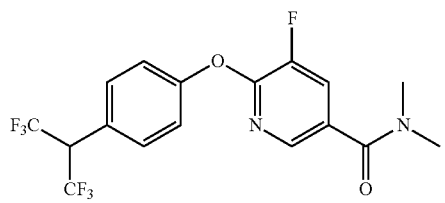

691

5-fluoro-6-(4-(1,1,1,3,3,3-hexafluoropropan-2-yl)phenoxy)-
N,N-dimethylnicotinamide

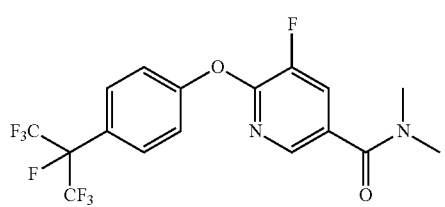 [SMILES: CN(C)C(=O)c1cnc(Oc2ccc(C(F)(C(F)(F)F)C(F)(F)F)cc2)c(F)c1]

692

5-fluoro-N,N-dimethyl-6-(4-(perfluoropropan-2-
yl)phenoxy)nicotinamide

TABLE IV-continued
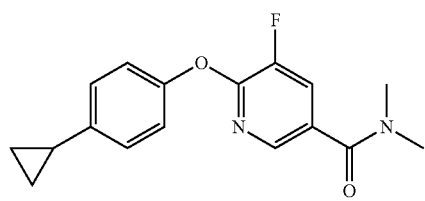
6-(4-cyclopropylphenoxy)-5-fluoro-N,N-dimethylnicotinamide
693
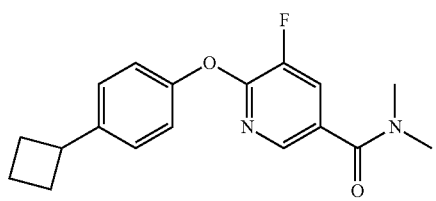
6-(4-cyclobutylphenoxy)-5-fluoro-N,N-dimethylnicotinamide
694
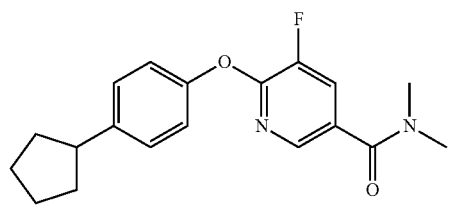 [SMILES: CN(C)C(=O)c1cnc(Oc2ccc(C3CCCC3)cc2)c(F)c1]
6-(4-cyclopentylphenoxy)-5-fluoro-N,N-dimethylnicotinamide
695
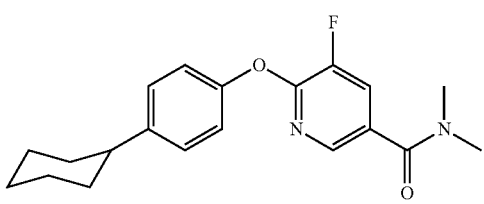 [SMILES: CN(C)C(=O)c1cnc(Oc2ccc(C3CCCCC3)cc2)c(F)c1]
6-(4-cyclohexylphenoxy)-5-fluoro-N,N-dimethylnicotinamide
696
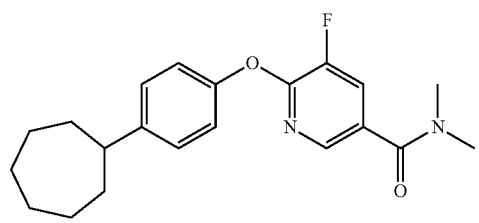 [SMILES: CN(C)C(=O)c1cnc(Oc2ccc(C3CCCCCC3)cc2)c(F)c1]
6-(4-cycloheptylphenoxy)-5-fluoro-N,N-dimethylnicotinamide
697
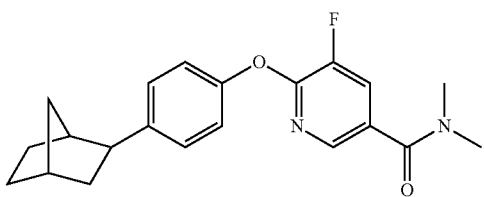 [SMILES: CN(C)C(=O)c1cnc(Oc2ccc(C3CC4CCC3C4)cc2)c(F)c1]
6-(4-((1S,4R)-bicyclo[2.2.1]heptan-2-yl)phenoxy)-5-fluoro-N,N-dimethylnicotinamide
698

TABLE IV-continued

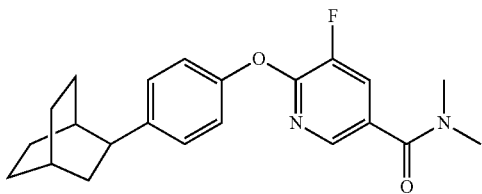 [SMILES: CN(C)C(=O)c1cnc(Oc2ccc(C3CC4CCC3CC4)cc2)c(F)c1]

699

6-(4-((1s,4s)-bicyclo[2.2.2]octan-2-yl)phenoxy)-5-fluoro-N,N-dimethylnicotinamide

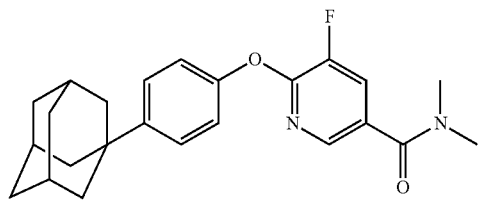 [SMILES: CN(C)C(=O)c1cnc(Oc2ccc(C34CC5CC(CC(C5)C3)C4)cc2)c(F)c1]

700

6-(4-((3r,5r,7r)-adamantan-1-yl)phenoxy)-5-fluoro-N,N-dimethylnicotinamide

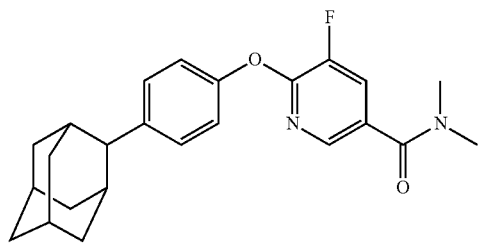

701

6-(4-((1r,3r,5r,7r)-adamantan-2-yl)phenoxy)-5-fluoro-N,N-dimethylnictinamide

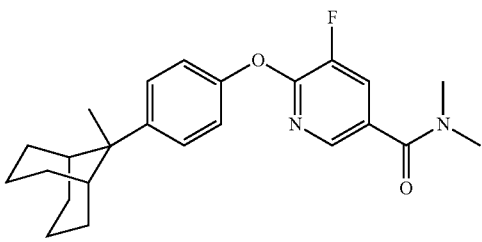 [SMILES: CN(C)C(=O)c1cnc(Oc2ccc(C3(C)C4CCCC3CCC4)cc2)c(F)c1]

702

5-fluoro-N,N-dimethyl-6-(4-((1R,5S)-9-methylbicyclo[3.3.1]nonan-9-yl)phenoxy)nicotinamide Also included are isomers, e.g. enantiomers or diastereomers or rotamers or mixtures of isomers, salts, particularly pharmaceutically acceptable salts, and solvates of the compounds listed above.

A fifth aspect of the present invention relates to compounds of formula V and salts and solvates thereof:

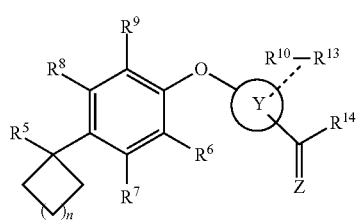

(V)

wherein n=0-5, which comprises cyclopropyl (n=0), cyclobutyl (n=1), cyclopentyl (n=2), cyclohexyl (n=3), cycloheptyl (n=4) and cyclooctyl (n=5), wherein the said cyclopropyl, cyclobutyl, cyclopentyl, cyclohexyl, cycloheptyl and cyclooctyl groups can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein the said cyclopropyl, cyclobutyl, cyclopentyl, cyclohexyl, cycloheptyl and cyclooctyl groups can be perhalogenated, particularly perfluorinated;

and wherein n is preferably 0 as constituting cyclopropyl, particularly as constituting cyclopropyl being unsubstituted;

$R^5$=$C_1$-$C_{12}$ preferably $C_1$-$C_6$ alkyl, $C_2$-$C_{12}$ preferably $C_2$-$C_6$ alkenyl, $C_2$-$C_{12}$ preferably $C_2$-$C_6$ alkynyl, $C_3$-$C_8$ cycloalkyl, $C_3$-$C_8$ cycloalkenyl, wherein all alkyl, alkenyl and alkynyl residues can be linear or branched, and are perhalogenated, particularly perfluorinated, and wherein all cycloalkyl and cycloalkenyl residues are perhalogenated, particularly perfluorinated;

or wherein all alkyl, alkenyl and alkynyl residues can be linear or branched, and can be unsubstituted or substituted with one or more substituents in particular independently selected from: —F, —Cl, —Br, —I, —CN, —NCO, —NCS; and $OC_1$—$C_3$ alkyl optionally halogenated or perhalogenated, particularly perfluorinated;

and wherein all cycloalkyl and cycloalkenyl residues can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein $R^5$ is preferably —$CF_3$ or —$CF_2CF_3$;

$R^6$-$R^9$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

wherein $R^6$-$R^8$ each are preferably H, and $R^9$ is preferably —H, —F, —Cl, or —$CH_3$;

Y=a six-membered aromatic ring selected from benzene, pyridine, pyrimidine, pyridazine or pyrazine;

wherein the benzene ring is not substituted, or it is substituted with one to four of the substituents independently selected from $R^{10}$-$R^{13}$, and wherein the pyridine ring is not substituted, or it is substituted at the carbon positions with one to three of the substituents independently selected from $R^{10}$-$R^{12}$, and wherein preferably the N-atom of the pyridine ring is in ortho-position relative to the ether bond, and wherein the pyrimidine ring is not substituted, or it is substituted at the carbon positions with one or two of the substituents independently selected from $R^{10}$-$R^{11}$, and wherein preferably an N-atom of the pyrimidine ring is in ortho-position relative to the ether bond, and wherein the pyridazine ring is not substituted, or it is substituted at the carbon positions with one or two of the substituents independently selected from $R^{10}$-$R^{11}$, and wherein preferably an N-atom of the pyridazine ring is in ortho-position relative to the ether bond, and wherein the pyrazine ring is not substituted, or it is substituted at the carbon positions with one or two of the substituents independently selected from $R^{10}$-$R^{11}$, and wherein preferably an N-atom of the pyrazine ring is in ortho-position relative to the ether bond, wherein preferably Y=benzene or pyridine being not substituted with any of the residues selected from $R^{10}$-$R^3$, or being substituted with one of the substituents selected from $R^{10}$-$R^{13}$ being F at the carbon atom in ortho-position relative to the ether bond;

$R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated;

Z=O or S, and preferably Z=O;

$R^{14}$=$OR^2$ or $NR^3R^4$ wherein $R^2$ is defined as in formula I including the preferred definition of $R^2$ as H, methyl or ethyl;

wherein $R^3$ and $R^4$ are defined as in formula II, including the preferred definitions of $R^3$ as H or —$CH_3$ and $R^4$ as H, OH or —$CH_3$;

In a particularly preferred embodiment of the compounds of formula V, the present invention relates to compounds of formula Va and salts and solvates thereof:

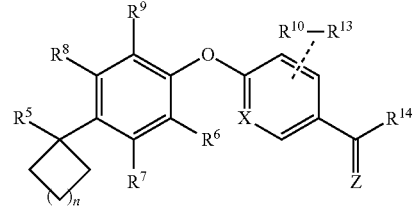

(Va)

wherein n is defined as in formula V, including the preferred definition of n being n=0 as constituting cyclopropyl, particularly as constituting cyclopropyl being unsubstituted, wherein Z is defined as in formula V, including the preferred definition of Z as Z=O, wherein $R^5$ is defined as in formula V, including all preferred definitions of $R^5$, $R^6$-$R^9$ are defined as in formula V, including all preferred definitions of $R^6$-$R^9$, wherein $R^{14}$ is defined as in formula V, wherein X is N or $CR^{13}$, and wherein $R^{10}$-$R^{13}$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from —F, —Cl, —Br, —I; and $C_1$-$C_3$ alkyl such as —$CH_3$ optionally halogenated or perhalogenated, particularly perfluorinated such as —$CF_3$; and $OC_1$—$C_3$ alkyl optionally halogenated or perhalogenated, particularly perfluorinated.

Specific examples of compounds falling under the scope of formula V are shown in Table V. The compounds in Table V are defined by their chemical structure, the indicated nomenclature is only for illustrative purposes.

TABLE V

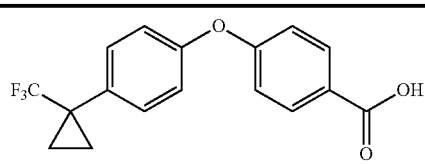

703

4-(4-(1-(trifluoromethyl)cyclopropyl)phenoxy) benzoic acid

TABLE V-continued

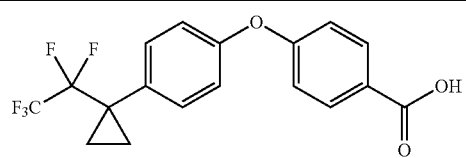

704

4-(4-(1-(perfluoroethyl)cyclopropyl)phenoxy)
benzoic acid

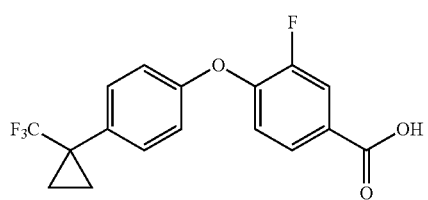 [SMILES: O=C(O)c1ccc(Oc2ccc(C3(C(F)(F)F)CC3)cc2)c(F)c1]

705

3-fluoro-4-(4-(1-(trifluoromethyl)cyclopropyl)phenoxy)
benzoic acid

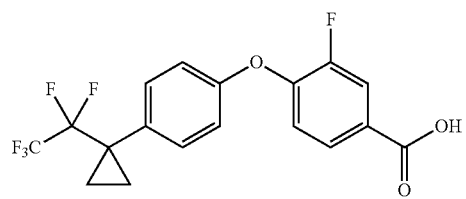 [SMILES: O=C(O)c1ccc(Oc2ccc(C3(C(F)(F)C(F)(F)F)CC3)cc2)c(F)c1]

706

3-fluoro-4-(4-(1-(perfluoroethyl)cyclopropyl)phenoxy)
benzoic acid

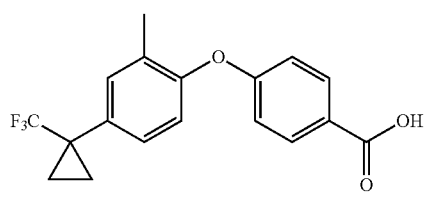 [SMILES: Cc1cc(C2(C(F)(F)F)CC2)ccc1Oc1ccc(C(=O)O)cc1]

707

4-(2-methyl-4-(1-trifluoromethyl)cyclopropyl)phenoxy)
benzoic acid

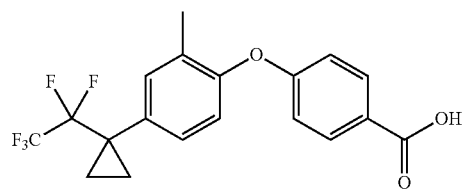 [SMILES: Cc1cc(C2(C(F)(F)C(F)(F)F)CC2)ccc1Oc1ccc(C(=O)O)cc1]

708

4-(2-methyl-4-(1-(perfluoroethyl)cyclopropyl)phenoxy)
benzoic acid

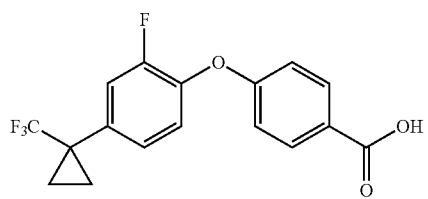

709

4-(2-fluoro-4-(1-(trifluoromethyl)cyclopropyl)phenoxy)
benzoic acid

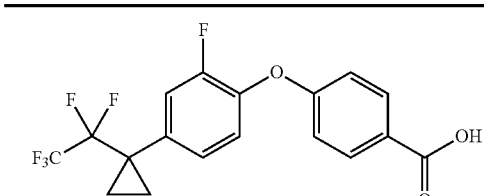

710

4-(2-fluoro-4-(1-(perfluoroethyl)cyclopropyl)phenoxy)
benzoic acid

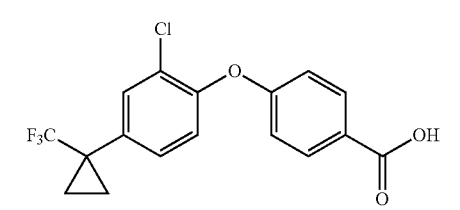 [SMILES: O=C(O)c1ccc(Oc2ccc(C3(C(F)(F)F)CC3)cc2F)cc1]

711

4-(2-chloro-4-(1-(trifluoromethyl)cyclopropyl)phenoxy)
benzoic acid

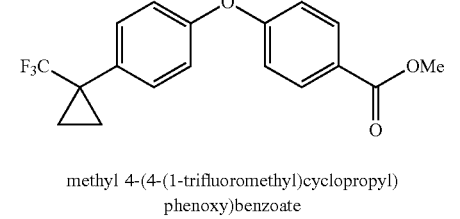

712 methyl 4-(4-(1-trifluoromethyl)cyclopropyl)
phenoxy)benzoate

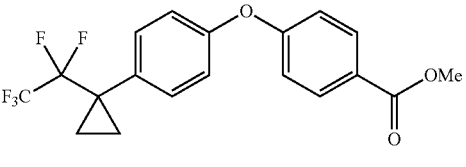 [SMILES: COC(=O)c1ccc(Oc2ccc(C3(C(F)(F)C(F)(F)F)CC3)cc2)cc1]

713 methyl 4-(4-(1-(perfluoroethyl)cyclopropyl)
phenoxy)benzoate

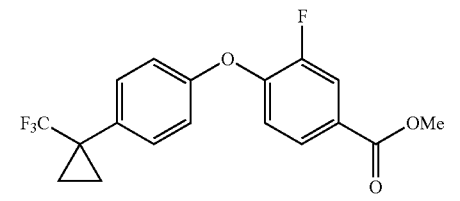 [SMILES: COC(=O)c1ccc(Oc2ccc(C3(C(F)(F)F)CC3)cc2)c(F)c1]

714 methyl 3-fluoro-4-(4-(1-(trifluoromethyl)cyclopropyl)
phenoxy)benzoate

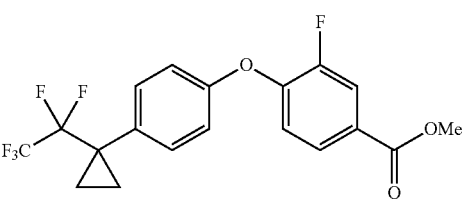 [SMILES: COC(=O)c1ccc(Oc2ccc(C3(C(F)(F)C(F)(F)F)CC3)cc2)c(F)c1]

715 methyl 3-fluoro-4-(4-(1-(perfluoroethyl)cyclopropyl)
phenoxy)benzoate

TABLE V-continued

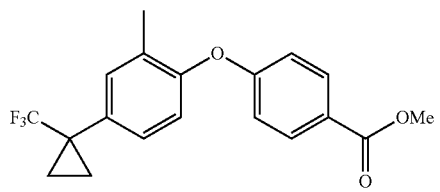 [SMILES: COC(=O)c1ccc(Oc2ccc(C3(C(F)(F)F)CC3)cc2C)cc1]

716 methyl 4-(2-methyl-4-(1-(trifluoromethyl)cyclopropyl)
phenoxy)benzoate

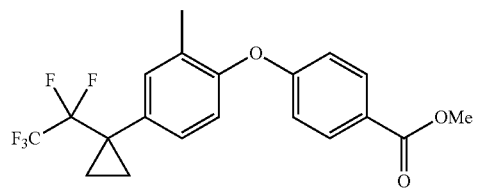 [SMILES: COC(=O)c1ccc(Oc2ccc(C3(C(F)(F)C(F)(F)F)CC3)cc2C)cc1]

717 methyl 4-(2-methyl-4-(1-(perfluoroethyl)cyclopropyl)
phenoxy)benzoate

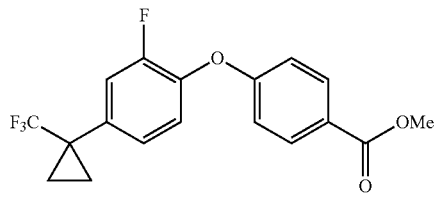

718 methyl 4-(2-fluoro-4-(1-(trifluoromethyl)cyclopropyl)
phenoxy)benzoate

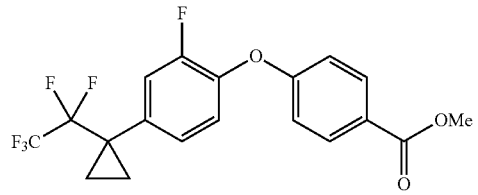

719 methyl 4-(2-fluoro-4-(1-(perfluoroethyl)cyclopropyl)
phenoxy)benzoate

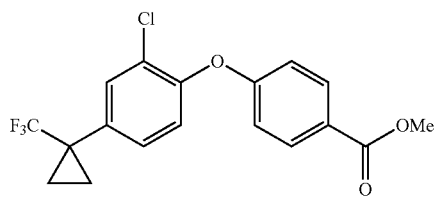 [SMILES: COC(=O)c1ccc(Oc2ccc(C3(C(F)(F)F)CC3)cc2F)cc1]

720 methyl 4-(2-chloro-4-(1-(trifluoromethyl)cyclopropyl)
phenoxy)benzoate

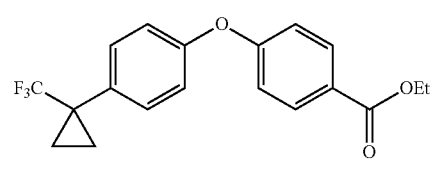 [SMILES: CCOC(=O)c1ccc(Oc2ccc(C3(C(F)(F)F)CC3)cc2)cc1]

721 ethyl 4-(4-(1-(trifluoromethyl)cyclopropyl)
phenoxy)benzoate

TABLE V-continued

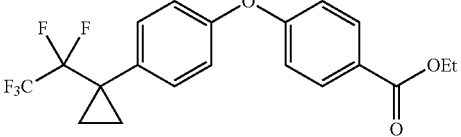

722 ethyl 4-(4-(1-perfluoroethyl)cyclopropyl)
pheoxy)benzoate

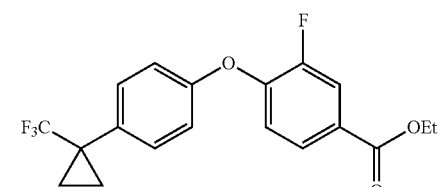

723 ethyl 3-fluoro-4-(4-(1-(trifluoromethyl)cyclopropyl)
phenoxy)benzoate

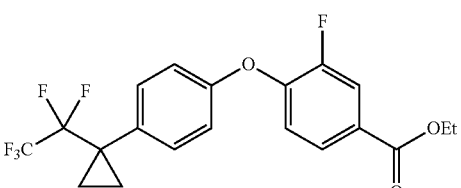

724 ethyl 3-fluoro-4-(4-(1-(perfluoroethyl)cyclopropyl)
phenoxy)benzoate

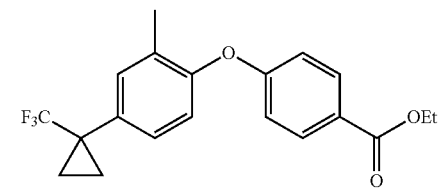 [SMILES: CCOC(=O)c1ccc(Oc2ccc(C3(C(F)(F)F)CC3)cc2C)cc1]

725 ethyl 4-(2-methyl-4-(1-(trifluoromethyl)cyclopropyl)
phenoxy)benzoate

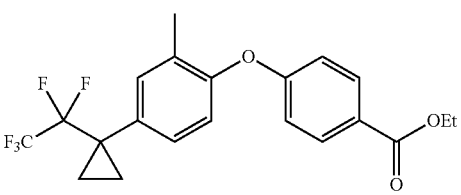 [SMILES: CCOC(=O)c1ccc(Oc2ccc(C3(C(F)(F)C(F)(F)F)CC3)cc2C)cc1]

726 ethyl 4-(2-methyl-4-(1-(perfluoroethyl)cyclopropyl)
phenoxy)benzoate

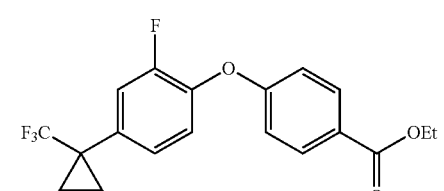

727 ethyl 4-(2-fluoro-4-(1-(trifluoromethyl)cyclopropyl)
phenoxy)benozate

TABLE V-continued

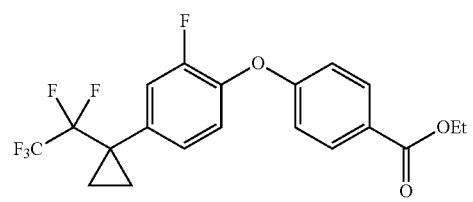

ethyl 4-(2-fluoro-4-(1-(perfluoroethyl)cyclopropyl)
phenoxy)benzoate

728

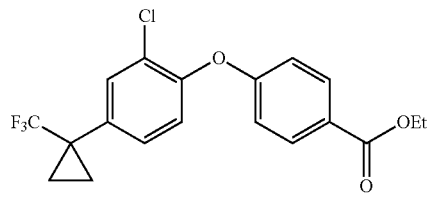 [SMILES: CCOC(=O)c1ccc(Oc2ccc(C3(C(F)(F)F)CC3)cc2F)cc1]

ethyl 4-(2-chloro-4-(1-(trifluoromethyl)cyclopropyl)
phenoxy)benzoate

729

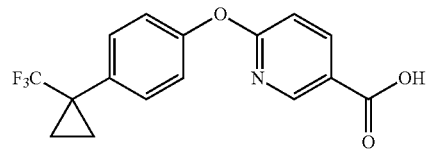 [SMILES: O=C(O)c1ccc(Oc2ccc(C3(C(F)(F)F)CC3)cc2)nc1]

6-(4-(1-(trifluoromethyl)cyclopropyl)phenoxy)
phenoxy)nicotinic acid

730

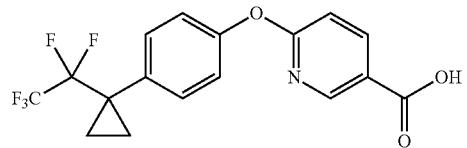 [SMILES: O=C(O)c1ccc(Oc2ccc(C3(C(F)(F)C(F)(F)F)CC3)cc2)nc1]

6-(4-(1-(perfluoroethyl)cyclopropyl)phenoxy)
phenoxy)nicotinic acid

731

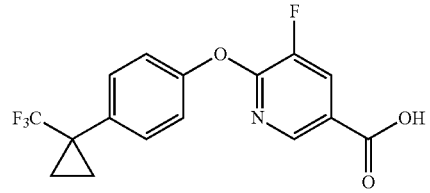 [SMILES: O=C(O)c1cnc(Oc2ccc(C3(C(F)(F)F)CC3)cc2)c(F)c1]

5-fluoro-6-(4-(1-(trifluoromethyl)cyclopropyl)phenoxy)
phenoxy)nicotinic acid

732

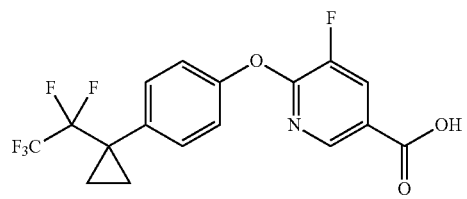 [SMILES: O=C(O)c1cnc(Oc2ccc(C3(C(F)(F)C(F)(F)F)CC3)cc2)c(F)c1]

5-fluoro-6-(4-(1-(perfluoroethyl)cyclopropyl)phenoxy)
phenoxy)nicotinic acid

733

TABLE V-continued

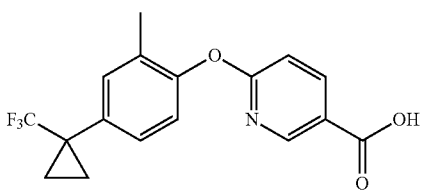 [SMILES: Cc1cc(C2(C(F)(F)F)CC2)ccc1Oc1ccc(C(=O)O)cn1]

6-(2-methyl-4-(1-(trifluoromethyl)cyclopropyl)phenoxy)
phenoxy)nicotinic acid

734

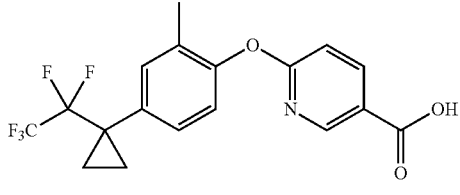 [SMILES: Cc1cc(C2(C(F)(F)C(F)(F)F)CC2)ccc1Oc1ccc(C(=O)O)cn1]

6-(2-methyl-4-(1-(perfluoroethyl)cyclopropyl)phenoxy)
phenoxy)nicotinic acid

735

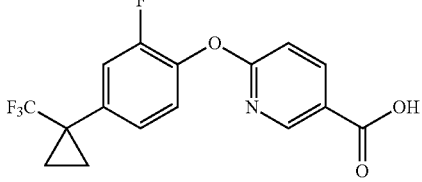

6-(2-fluoro-4-(1-(trifluoromethyl)cyclopropyl)phenoxy)
phenoxy)nicotinic acid

736

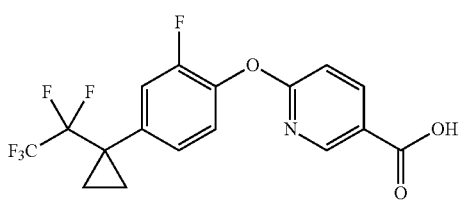 [SMILES: O=C(O)c1ccc(Oc2ccc(C3(C(F)(F)C(F)(F)F)CC3)cc2F)nc1]

6-(2-fluoro-4-(1-(perfluoroethyl)cyclopropyl)phenoxy)
phenoxy)nicotinic acid

737

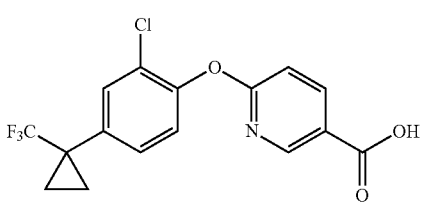

6-(2-chloro-4-(1-(trifluoromethyl)cyclopropyl)phenoxy)
phenoxy)nicotinic acid

738

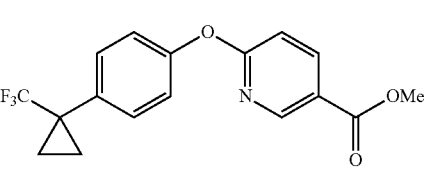

methyl 6-(4-(1-(trifluoromethyl)cyclopropyl)
phenoxy)nicotinate

739

TABLE V-continued

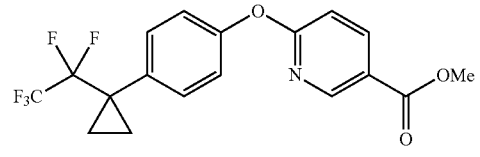

740 methyl 6-(4-(1-(perfluoroethyl)cyclopropyl)
phenoxy)nicotinate

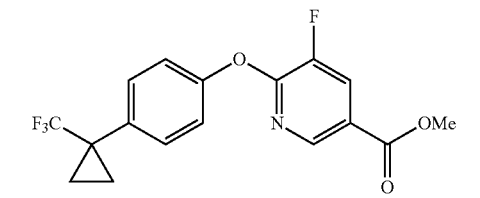 [SMILES: COC(=O)c1cnc(Oc2ccc(C3(C(F)(F)F)CC3)cc2)c(F)c1]

741 methyl 5-fluoro-6-(4-(1-(trifluoromethyl)cyclopropyl)
phenoxy)nicotinate

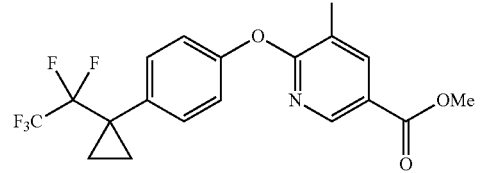

742 methyl 5-fluoro-6-(4-(1-(perfluoroethyl)cyclopropyl)
phenoxy)nicotinate

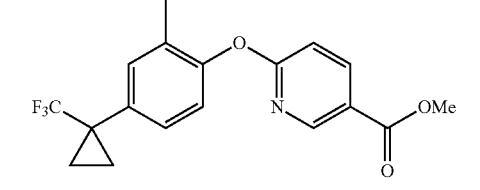 [SMILES: COC(=O)c1ccc(Oc2ccc(C3(C(F)(F)F)CC3)cc2C)nc1]

743 methyl 6-(2-methyl-4-(1-(trifluoromethyl)cyclopropyl)
phenoxy)nicotinate

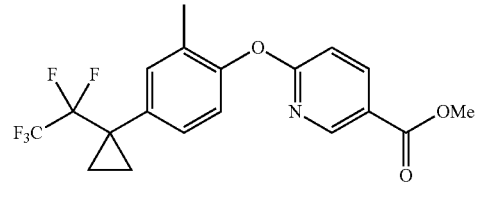 [SMILES: COC(=O)c1ccc(Oc2ccc(C3(C(F)(F)C(F)(F)F)CC3)cc2C)nc1]

744 methyl 6-(2-methyl-4-(1-(perfluoroethyl)cyclopropyl)
phenoxy)nicotinate

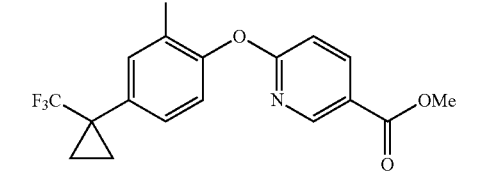

745 methyl 6-(2-fluoro-4-(1-(trifluoromethyl)cyclopropyl)
phenoxy)nicotinate

TABLE V-continued

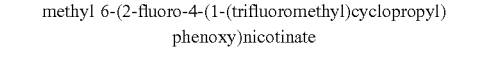

746 methyl 6-(2-fluoro-4-(1-(perfluoroethyl)cyclopropyl)
phenoxy)nicotinate

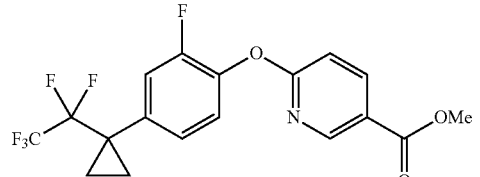

747 methyl 6-(2-chloro-4-(1-(trifluoromethyl)cyclopropyl)
phenoxy)nicotinate

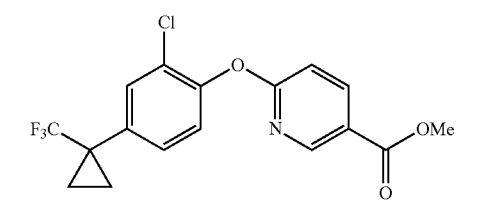

748 ethyl 6-(4-(1-(trifluoromethyl)cyclopropyl)
phenoxy)nicotinate

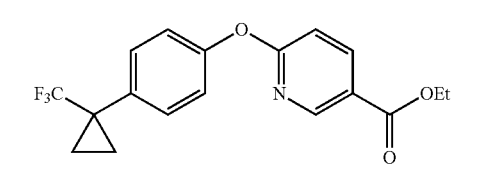 [SMILES: CCOC(=O)c1ccc(Oc2ccc(C3(C(F)(F)F)CC3)cc2)nc1]

749 ethyl 6-(4-(1-(perfluoroethyl)cyclopropyl)
phenoxy)nicotinate

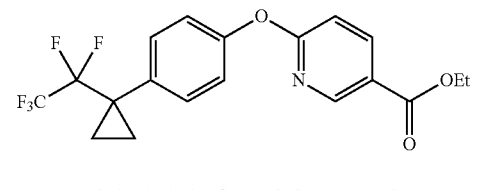 [SMILES: CCOC(=O)c1ccc(Oc2ccc(C3(C(F)(F)C(F)(F)F)CC3)cc2)nc1]

750 ethyl 5-fluoro-6-(4-(1-(trifluoromethyl)cyclopropyl)
phenoxy)nicotinate

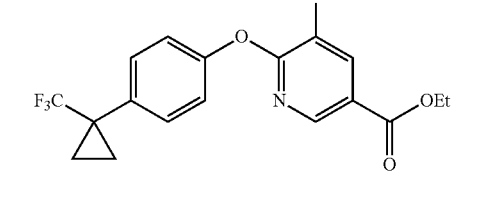

751 ethyl 5-fluoro-6-(4-(1-(perfluoroethyl)cyclopropyl)
phenoxy)nicotinate

TABLE V-continued

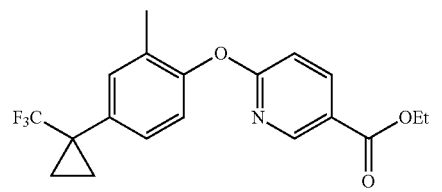 [SMILES: CCOC(=O)c1ccc(Oc2ccc(C3(C(F)(F)F)CC3)cc2C)nc1]

ethyl 6-(2-methyl-4-(1-(trifluoromethyl)cyclopropyl)
phenoxy)nicotinate
752

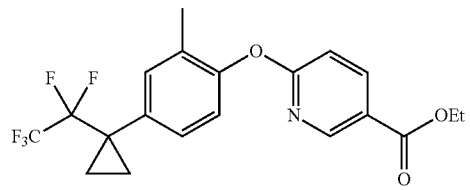 [SMILES: CCOC(=O)c1ccc(Oc2ccc(C3(C(F)(F)C(F)(F)F)CC3)cc2C)nc1]

ethyl 6-(2-methyl-4-(1-(perfluoroethyl)cyclopropyl)
phenoxy)nicotinate
753

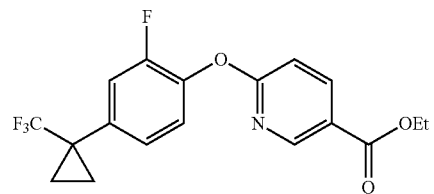 [SMILES: CCOC(=O)c1ccc(Oc2ccc(C3(C(F)(F)F)CC3)cc2F)nc1]

ethyl 6-(2-fluoro-4-(1-(trifluoromethyl)cyclopropyl)
phenoxy)nicotinate
754

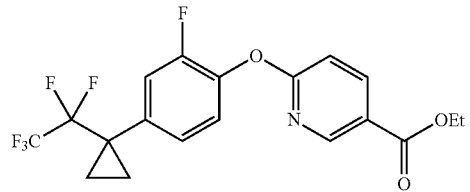 [SMILES: CCOC(=O)c1ccc(Oc2ccc(C3(C(F)(F)C(F)(F)F)CC3)cc2F)nc1]

ethyl 6-(2-fluoro-4-(1-(perfluoroethyl)cyclopropyl)
phenoxy)nicotinate
755

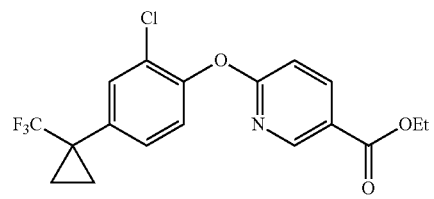

ethyl 6-(2-chloro-4-(1-(trifluoromethyl)cyclopropyl)
phenoxy)nicotinate
756

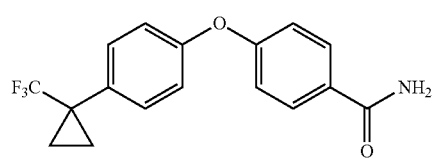 [SMILES: NC(=O)c1ccc(Oc2ccc(C3(C(F)(F)F)CC3)cc2)cc1]

4-(4-(1-(trifluoromethyl)cyclopropyl)
phenoxy)benzamide
757

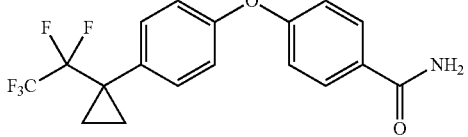

4-(4-(1-(perfluoroethyl)cyclopropyl)
phenoxy)benzamide
758

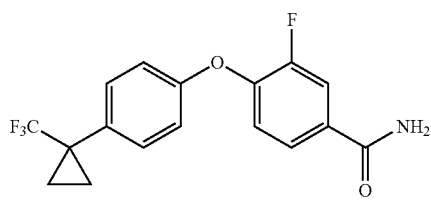 [SMILES: NC(=O)c1ccc(Oc2ccc(C3(C(F)(F)F)CC3)cc2)c(F)c1]

3-fluoro-4-(4-(1-(trifluoromethyl)cyclopropyl)
phenoxy)benzamide
759

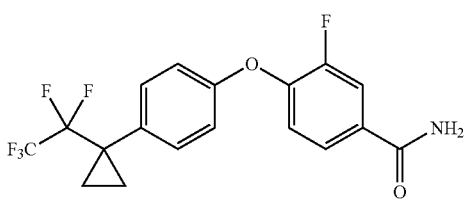 [SMILES: NC(=O)c1ccc(Oc2ccc(C3(C(F)(F)C(F)(F)F)CC3)cc2)c(F)c1]

3-fluoro-4-(4-(1-(perfluoroethyl)cyclopropyl)
phenoxy)benzamide
760

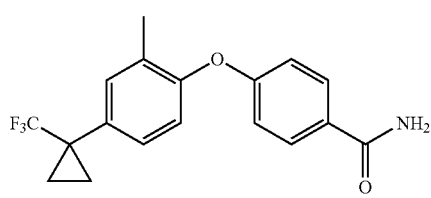 [SMILES: Cc1cc(C2(C(F)(F)F)CC2)ccc1Oc1ccc(C(N)=O)cc1]

4-(2-methyl-4-(1-(trifluoromethyl)cyclopropyl)
phenoxy)benzamide
761

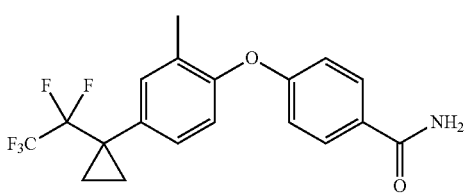 [SMILES: Cc1cc(C2(C(F)(F)C(F)(F)F)CC2)ccc1Oc1ccc(C(N)=O)cc1]

4-(2-methyl-4-(1-(perfluoroethyl)cyclopropyl)
phenoxy)benzamide
762

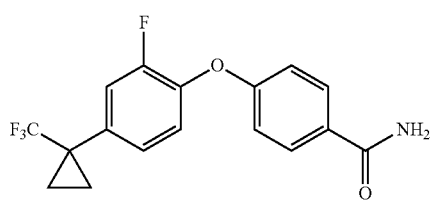 [SMILES: NC(=O)c1ccc(Oc2ccc(C3(C(F)(F)F)CC3)cc2F)cc1]

4-(2-fluoro-4-(1-(trifluoromethyl)cyclopropyl)
phenoxy)benzamide
763

TABLE V-continued

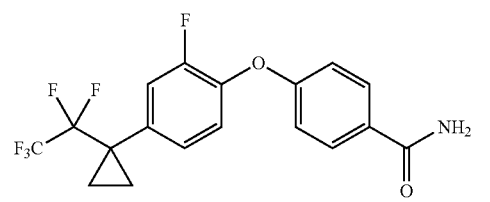 [SMILES: NC(=O)c1ccc(Oc2ccc(C3(C(F)(F)C(F)(F)F)CC3)cc2F)cc1]

4-(2-fluoro-4-(1-(perfluoroethyl)cyclopropyl)
phenoxy)benzamide

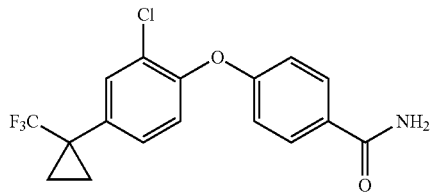 [SMILES: NC(=O)c1ccc(Oc2ccc(C3(C(F)(F)F)CC3)cc2Cl)cc1]

4-(2-chloro-4-(1-(trifluoromethyl)cyclopropyl)
phenoxy)benzamide

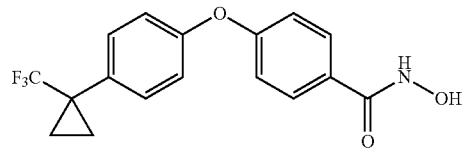 [SMILES: O=C(NO)c1ccc(Oc2ccc(C3(C(F)(F)F)CC3)cc2)cc1]

N-hydroxy-4-(4-(1-(trifluoromethyl)cyclopropyl)
phenoxy)benzamide

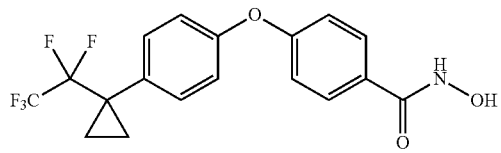 [SMILES: O=C(NO)c1ccc(Oc2ccc(C3(C(F)(F)C(F)(F)F)CC3)cc2)cc1]

N-hydroxy-4-(4-(1-(perfluoroethyl)cyclopropyl)
phenoxy)benzamide

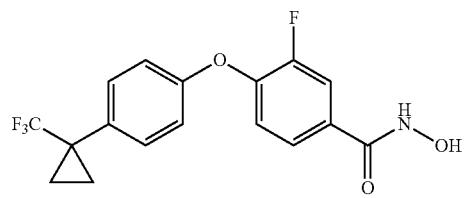 [SMILES: O=C(NO)c1ccc(Oc2ccc(C3(C(F)(F)F)CC3)cc2)c(F)c1]

3-fluoro-N-hydroxy-4-(4-(1-(trifluoromethyl)cyclopropyl)
phenoxy)benzamide

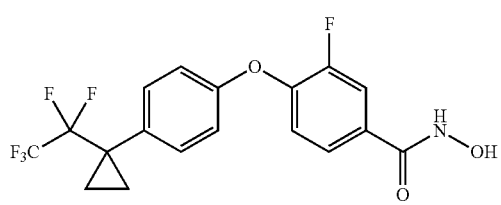 [SMILES: O=C(NO)c1ccc(Oc2ccc(C3(C(F)(F)C(F)(F)F)CC3)cc2)c(F)c1]

3-fluoro-N-hydroxy-4-(4-(1-(perfluoroethyl)cyclopropyl)
phenoxy)benzamide

TABLE V-continued

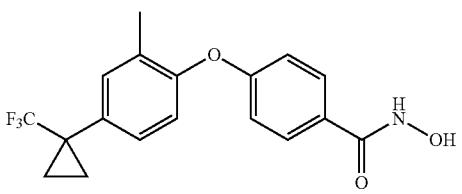 [SMILES: Cc1cc(C2(C(F)(F)F)CC2)ccc1Oc1ccc(C(=O)NO)cc1]

N-hydroxy-4-(2-methyl-4-(1-(trifluoromethyl)cyclopropyl)
phenoxy)benzamide

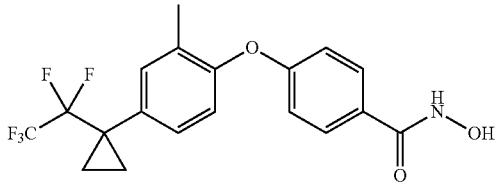 [SMILES: Cc1cc(C2(C(F)(F)C(F)(F)F)CC2)ccc1Oc1ccc(C(=O)NO)cc1]

N-hydroxy-4-(2-methyl-4-(1-(perfluoroethyl)cyclopropyl)
phenoxy)benzamide

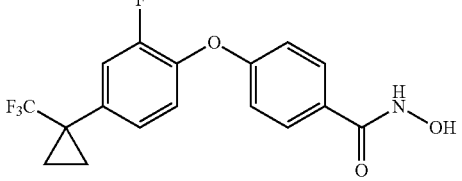

4-(2-fluoro-4-(1-(trifluoromethyl)cyclopropyl)phenoxy)-
N-hydroxybenzamide

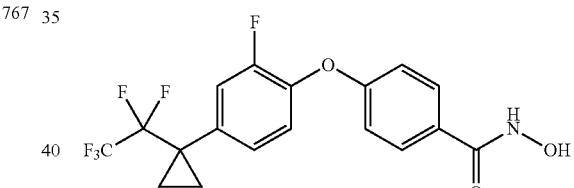

4-(2-fluoro-4-(1-(perfluoroethyl)cyclopropyl)phenoxy)-
N-hydroxybenzamide

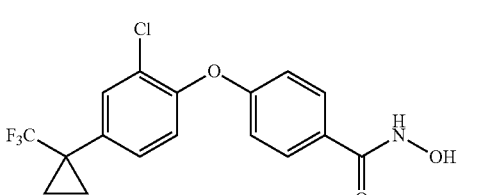

4-(2-chloro-4-(1-(trifluoromethyl)cyclopropyl)phenoxy)-
N-hydroxybenzamide

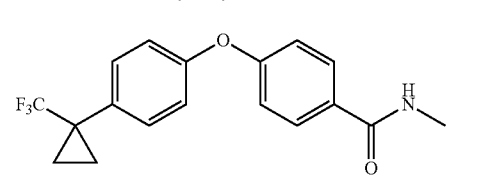 [SMILES: CNC(=O)c1ccc(Oc2ccc(C3(C(F)(F)F)CC3)cc2)cc1]

N-methyl-4-(4-(1-(trifluoromethyl)cyclopropyl)
phenoxy)benzamide

TABLE V-continued

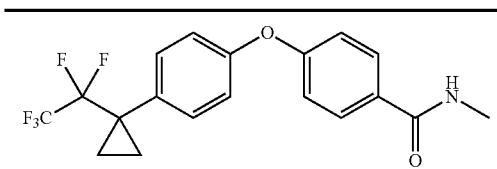

N-methyl-4-(4-(1-(perfluoroethyl)cyclopropyl)
phenoxy)benzamide
776

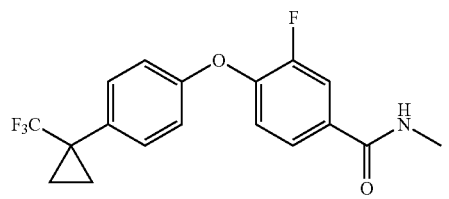 [SMILES: CNC(=O)c1ccc(Oc2ccc(C3(C(F)(F)F)CC3)cc2)c(F)c1]

3-fluoro-N-methyl-4-(4-(1-(trifluoromethyl)cyclopropyl)
phenoxy)benzamide
777

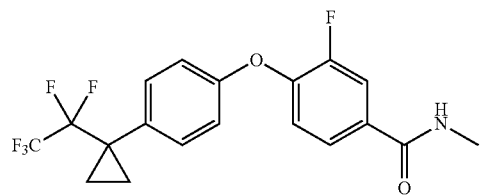 [SMILES: CNC(=O)c1ccc(Oc2ccc(C3(C(F)(F)C(F)(F)F)CC3)cc2)c(F)c1]

3-fluoro-N-methyl-4-(4-(1-(perfluoroethyl)cyclopropyl)
phenoxy)benzamide
778

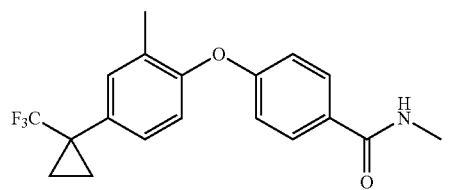

N-mtehyl-4-(2-methyl-4-(1-(trifluoromethyl)cyclopropyl)
phenoxy)benzamide
779

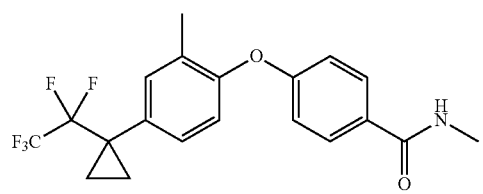 [SMILES: CNC(=O)c1ccc(Oc2ccc(C3(C(F)(F)C(F)(F)F)CC3)cc2C)cc1]

N-methyl-4-(2-methyl-4-(1-(perfluoroethyl)cyclopropyl)
phenoxy)benzamide
780

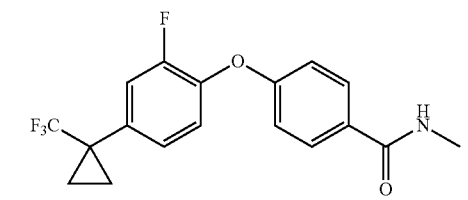 [SMILES: CNC(=O)c1ccc(Oc2ccc(C3(C(F)(F)F)CC3)cc2F)cc1]

4-(2-fluoro-4-(1-(trifluoromethyl)cyclopropyl)phenoxy)-
N-methylbenzamide
781

TABLE V-continued

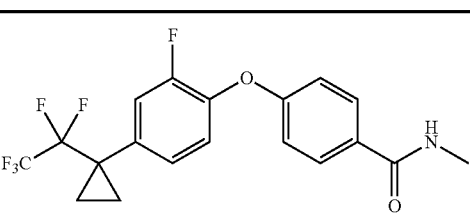

4-(2-fluoro-4-(1-(perfluoroethyl)cyclopropyl)phenoxy)-
N-methylbenzamide
782

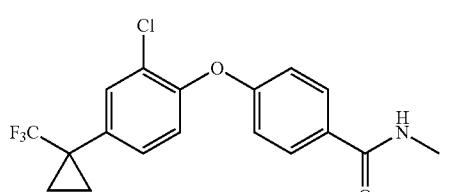

4-(2-chloro-4-(1-(trifluoromethyl)cyclopropyl)phenoxy)-
N-methylbenzamide
783

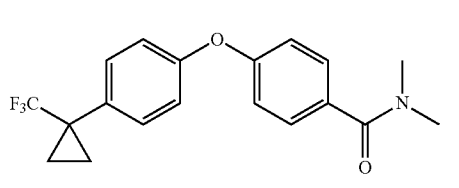

N,N-dimethyl-4-(4-(1-(trifluoromethyl)cyclopropyl)
phenoxy)benzamide
784

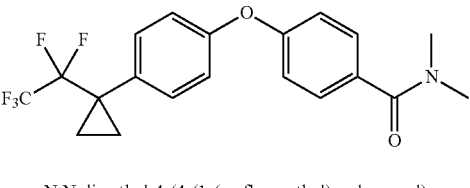

N,N-dimethyl-4-(4-(1-(perfluoroethyl)cyclopropyl)
phenoxy)benzamide
785

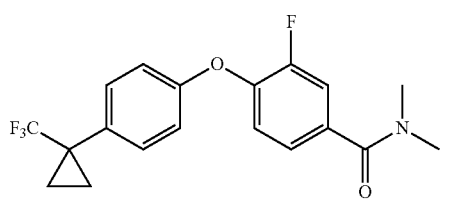 [SMILES: CN(C)C(=O)c1ccc(Oc2ccc(C3(C(F)(F)F)CC3)cc2)c(F)c1]

3-fluoro-N,N-dimethyl-4-(4-(1-(trifluoromethyl)cyclopropyl)
phenoxy)benzamide
786

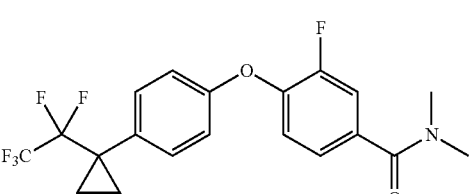

3-fluoro-N,N-dimethyl-4-(4-(1-(perfluoroethyl)cyclopropyl)
phenoxy)benzamide
787

TABLE V-continued

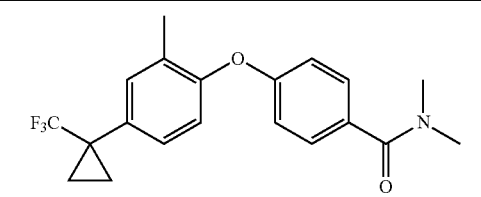

788

N,N-dimethyl-4-(2-methyl-4-(1-(trifluoromethyl)cyclopropyl)
phenoxy)benzamide

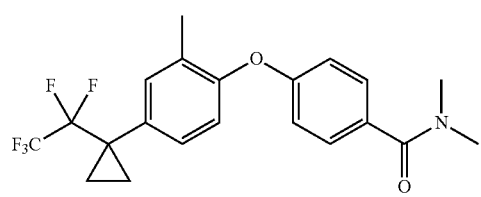 [SMILES: Cc1cc(C2(C(F)(F)C(F)(F)F)CC2)ccc1Oc1ccc(C(=O)N(C)C)cc1]

789

N,N-dimethyl-4-(2-methyl-4-(1-(perfluoroethyl)cyclopropyl)
phenoxy)benzamide

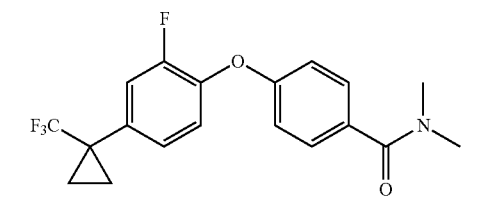

790

4-(2-fluoro-4-(1-(trifluoromethyl)cyclopropyl)phenoxy)-
N,N-dimethylbenzamide

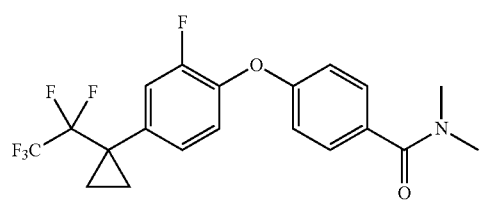 [SMILES: CN(C)C(=O)c1ccc(Oc2ccc(C3(C(F)(F)C(F)(F)F)CC3)cc2F)cc1]

791

4-(2-fluoro-4-(1-(perfluoroethyl)cyclopropyl)phenoxy)-
N,N-dimethylbenzamide

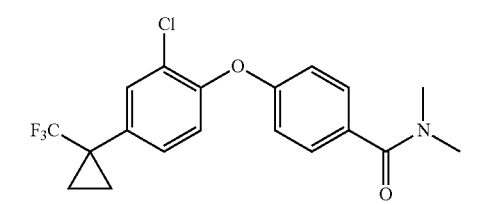 [SMILES: CN(C)C(=O)c1ccc(Oc2ccc(C3(C(F)(F)F)CC3)cc2Cl)cc1]

792

4-(2-chloro-4-(1-(trifluoromethyl)cyclopropyl)phenoxy)-
N,N-dimethylbenzamide

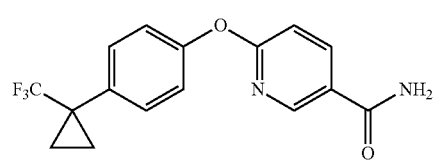

793

6-(4-(1-(trifluoromethyl)cyclopropyl)
phenoxy)nicotinamide

TABLE V-continued

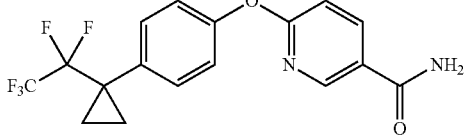

794

6-(4-(1-(perfluoroethyl)cyclopropyl)
phenoxy)nicotinamide

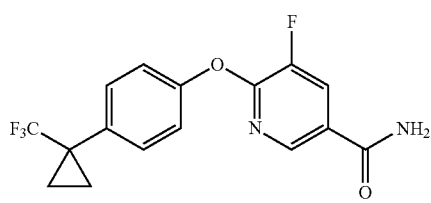 [SMILES: NC(=O)c1cnc(Oc2ccc(C3(C(F)(F)F)CC3)cc2)c(F)c1]

795

5-fluoro-6-(4-(1-(trifluoromethyl)cyclopropyl)
phenoxy)nicotinamide

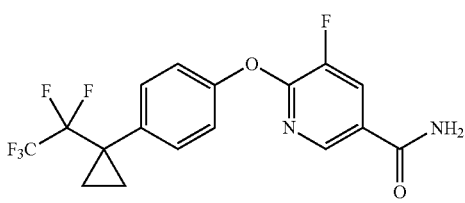 [SMILES: NC(=O)c1cnc(Oc2ccc(C3(C(F)(F)C(F)(F)F)CC3)cc2)c(F)c1]

796

5-fluoro-6-(4-(1-(perfluoroethyl)cyclopropyl)
phenoxy)nicotinamide

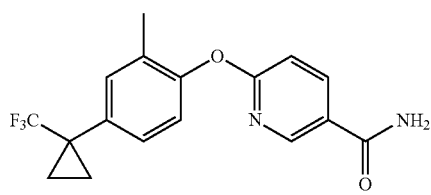 [SMILES: Cc1cc(C2(C(F)(F)F)CC2)ccc1Oc1ccc(C(N)=O)cn1]

797

6-(2-methyl-4-(1-(trifluoromethyl)cyclopropyl)
phenoxy)nicotinamide

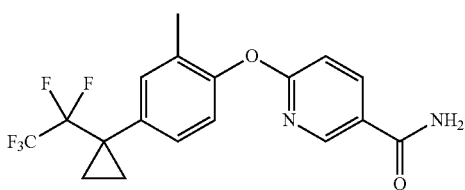 [SMILES: Cc1cc(C2(C(F)(F)C(F)(F)F)CC2)ccc1Oc1ccc(C(N)=O)cn1]

798

6-(2-methyl-4-(1-(perfluoroethyl)cyclopropyl)
phenoxy)nicotinamide

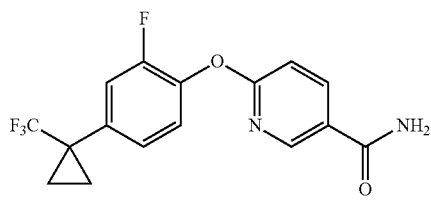 [SMILES: NC(=O)c1ccc(Oc2ccc(C3(C(F)(F)F)CC3)cc2F)nc1]

799

6-(2-fluoro-4-(1-(trifluoromethyl)cyclopropyl)
phenoxy)nicotinamide

TABLE V-continued

800

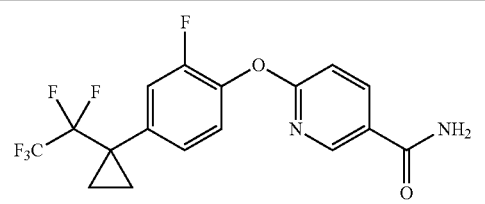 [SMILES: NC(=O)c1ccc(Oc2ccc(C3(C(F)(F)C(F)(F)F)CC3)cc2F)nc1]

6-(2-fluoro-4-(1-(perfluoroethyl)cyclopropyl)
phenoxy)nicotinamide

801

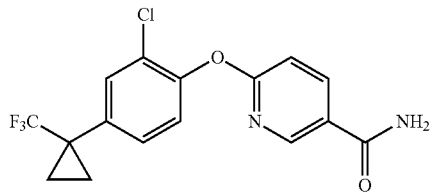 [SMILES: NC(=O)c1ccc(Oc2ccc(C3(C(F)(F)F)CC3)cc2Cl)nc1]

6-(2-chloro-4-(1-(trifluoromethyl)cyclopropyl)
phenoxy)nicotinamide

802

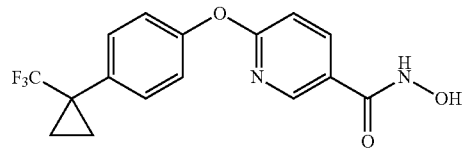 [SMILES: O=C(NO)c1ccc(Oc2ccc(C3(C(F)(F)F)CC3)cc2)nc1]

N-hydroxy-6-(4-(1-(trifluoromethyl)cyclopropyl)
phenoxy)nicotinamide

803

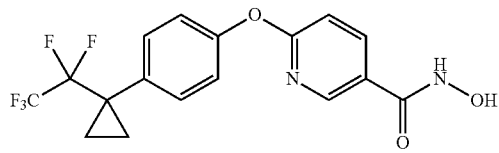 [SMILES: O=C(NO)c1ccc(Oc2ccc(C3(C(F)(F)C(F)(F)F)CC3)cc2)nc1]

N-hydroxy-6-(4-(1-(perfluoroethyl)cyclopropyl)
phenoxy)nicotinamide

804

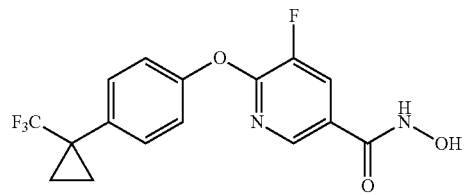 [SMILES: O=C(NO)c1cnc(Oc2ccc(C3(C(F)(F)F)CC3)cc2)c(F)c1]

5-fluoro-N-hydroxy-6-(4-(1-(trifluoromethyl)cyclopropyl)
phenoxy)nicotinamide

805

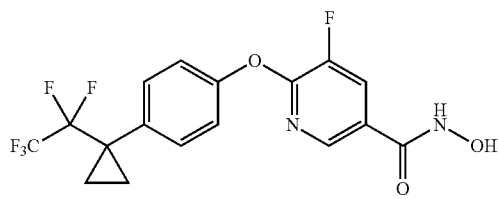 [SMILES: O=C(NO)c1cnc(Oc2ccc(C3(C(F)(F)C(F)(F)F)CC3)cc2)c(F)c1]

5-fluoro-N-hydroxy-6-(4-(1-(perfluoroethyl)cyclopropyl)
phenoxy)nicotinamide

TABLE V-continued

806

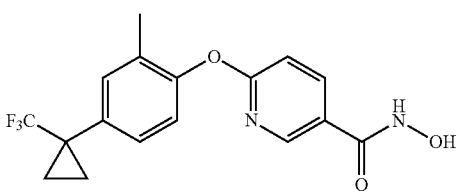 [SMILES: Cc1cc(C2(C(F)(F)F)CC2)ccc1Oc1ccc(C(=O)NO)cn1]

N-hydroxy-6-(2-methyl-4-(1-(trifluoroemthyl)cyclopropyl)
phenoxy)nicotinamide

807

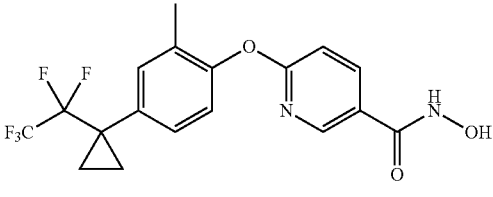 [SMILES: Cc1cc(C2(C(F)(F)C(F)(F)F)CC2)ccc1Oc1ccc(C(=O)NO)cn1]

N-hydroxy-6-(2-methyl-4-(1-(perfluoroethyl)cyclopropyl)
phenoxy)nicotinamide

808

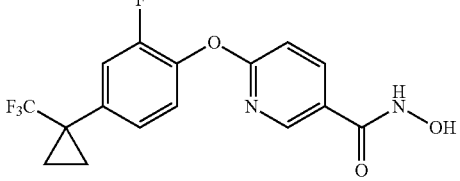

6-(2-fluoro-4-(1-(trifluoromethyl)cyclopropyl)phenoxy)-
N-hydroxynicotinamide

809

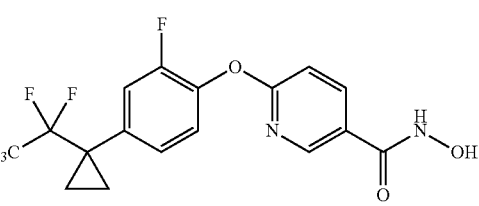

6-(2-fluoro-4-(1-(perfluoroethyl)cyclopropyl)phenoxy)-
N-hydroxynicotinamide

810

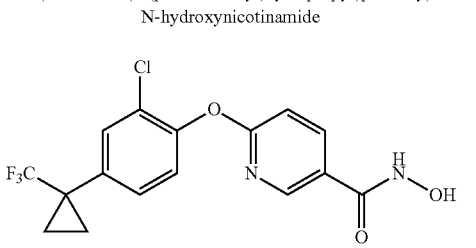

6-(2-chloro-4-(1-(trifluoromethyl)cyclopropyl)phenoxy)-
N-hydroxynicotinamide

811

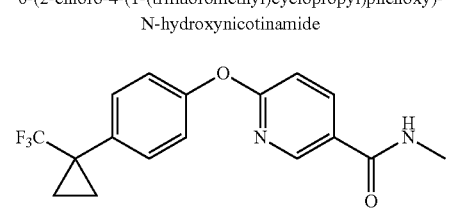

N-methyl-4-(4-(1-(trifluoromethyl)cyclopropyl)
phenoxy)benzamide

TABLE V-continued

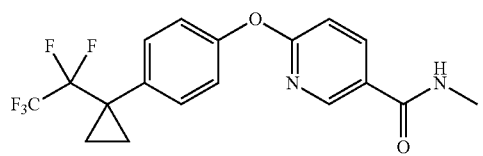 [SMILES: CNC(=O)c1ccc(Oc2ccc(C3(C(F)(F)C(F)(F)F)CC3)cc2)nc1]

812

N-methyl-4-(4-(1-(perfluoroethyl)cyclopropyl)
phenoxy)benzamide

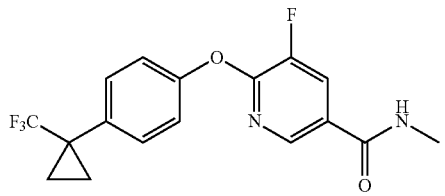

813

3-fluoro-N-methyl-4-(4-(1-(trifluoromethyl)cyclopropyl)
phenoxy)benzamide

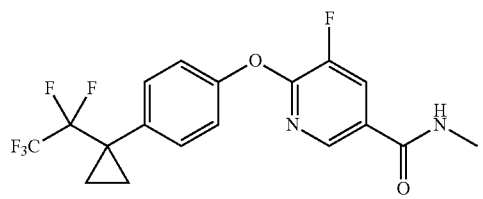 [SMILES: CNC(=O)c1cnc(Oc2ccc(C3(C(F)(F)C(F)(F)F)CC3)cc2)c(F)c1]

814

3-fluoro-N-methyl-4-(4-(1-(perfluoroethyl)cyclopropyl)
phenoxy)benzamide

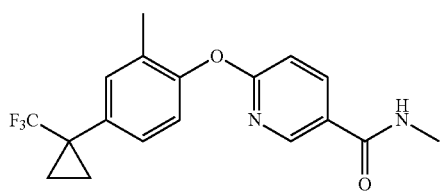

815

N-methyl-4-(2-methyl-4-(1-(trifluoromethyl)cyclopropyl)
phenoxy)benzamide

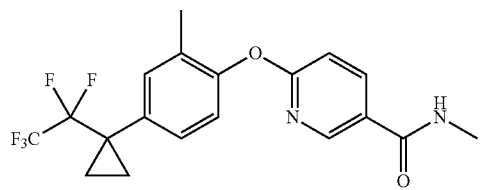 [SMILES: CNC(=O)c1ccc(Oc2ccc(C3(C(F)(F)C(F)(F)F)CC3)cc2C)nc1]

816

N-methyl-4-(2-methyl-4-(1-(perfluoroethyl)cyclopropyl)
phenoxy)benzamide

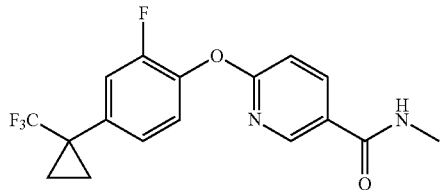 [SMILES: CNC(=O)c1ccc(Oc2ccc(C3(C(F)(F)F)CC3)cc2F)nc1]

817

4-(2-fluoro-4-(1-(trifluoromethyl)cyclopropyl)phenoxy)-
N-methylbenzamide

TABLE V-continued

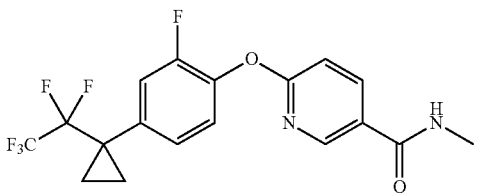 [SMILES: CNC(=O)c1ccc(Oc2ccc(C3(C(F)(F)C(F)(F)F)CC3)cc2F)nc1]

818

4-(2-fluoro-4-(1-(perfluoroethyl)cyclopropyl)phenoxy)-
N-methylbenzamide

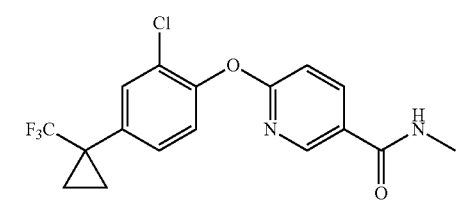 [SMILES: CNC(=O)c1ccc(Oc2ccc(C3(C(F)(F)F)CC3)cc2Cl)nc1]

819

4-(2-chloro-4-(1-(trifluoromethyl)cyclopropyl)phenoxy)-
N-methylbenzamide

+get,862

820

N,N-idmethyl-6-(4-(1-(trifluoromethyl)cyclopropyl)
phenoxy)nicotinamide

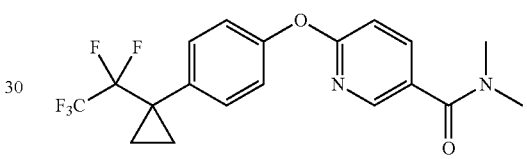

821

N,N-dimethyl-6-(4-(1-(perfluoroethyl)cyclopropyl)
phenoxy)nicotinamide

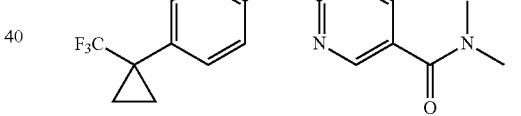

822

5-fluoro-N,N-dimethyl-6-(4-(1-(trifluoromethyl)cyclopropyl)
phenoxy)nicotinamide

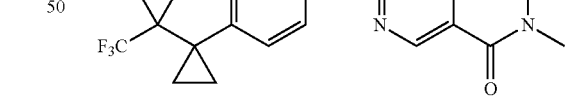

823

5-fluoro-N,N-dimethyl-6-(4-(1-(perfluoroethyl)cyclopropyl)
phenoxy)nicotinamide

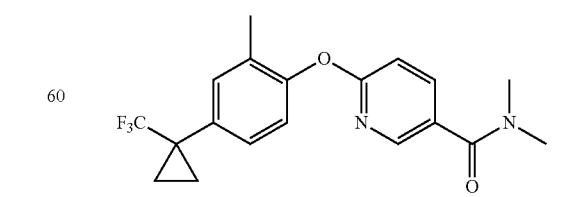

824

N,N-dimethyl-6-(2-methyl-4-(1-(trifluoromethyl)cyclopropyl)
phenoxy)nicotinamide TABLE V-continued

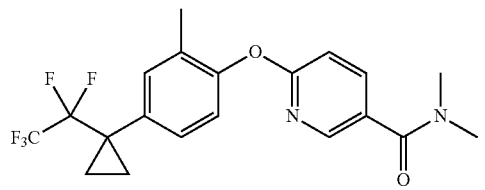 [SMILES: Cc1cc(C2(C(F)(F)C(F)(F)F)CC2)ccc1Oc1ccc(C(=O)N(C)C)cn1]

825

N,N-dimethyl-6-(2-methyl-4-(1-(perfluoroethyl)cyclopropyl)phenoxy)nicotinamide

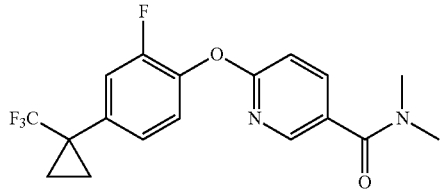 [SMILES: CN(C)C(=O)c1ccc(Oc2ccc(C3(C(F)(F)F)CC3)cc2F)nc1]

826

6-(2-fluoro-4-(1-(trifluoromethyl)cyclopropyl)phenoxy)-N,N-dimethylnicotinamide

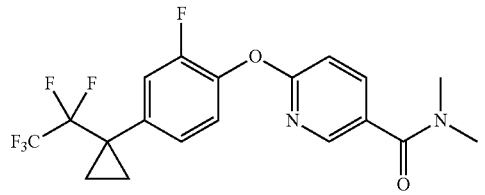 [SMILES: CN(C)C(=O)c1ccc(Oc2ccc(C3(C(F)(F)C(F)(F)F)CC3)cc2F)nc1]

827

6-(2-fluoro-4-(1-(perfluoroethyl)cyclopropyl)phenoxy)-N,N-dimethylnicotinamide

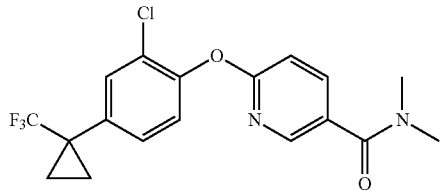 [SMILES: CN(C)C(=O)c1ccc(Oc2ccc(C3(C(F)(F)F)CC3)cc2Cl)nc1]

828

6-(2-chloro-4-(1-(trifluoromethyl)cyclopropyl)phenoxy)-N,N-dimethylnicotinamide

Also included are isomers, e.g. enantiomers or diastereomers or rotamers or mixtures of isomers, salts, particularly pharmaceutically acceptable salts, and solvates of the compounds listed above.

Further Definitions:

The term "$C_1$-$C_{12}$ alkyl" comprises all isomers of the corresponding saturated aliphatic hydrocarbon groups containing one to twelve carbon atoms; this includes methyl, ethyl, n-propyl, iso-propyl, n-butyl, sec-butyl, iso-butyl, tert-butyl, n-pentyl, sec-pentyl, 3-pentyl, 2-methylbutyl, iso-pentyl, 2-methylbut-2-yl, 3-methylbut-2-yl, all hexyl-isomers, all heptyl-isomers, all octyl-isomers, all nonyl-isomers, all decyl-isomers, all undecyl-isomers and all dodecyl-isomers.

The term "$C_2$-$C_{12}$ alkenyl" comprises all isomers of the corresponding unsaturated olefinic hydrocarbon groups containing two to twelve carbon atoms linked by one or more double bonds; this includes vinyl, all propenyl-isomers, all butenyl-isomers, all pentenyl-isomers, all hexenyl-isomers, all heptenyl-isomers, all octenyl-isomers, all nonenyl-isomers, all decenyl-isomers, all undecenyl-isomers and all dodecenyl-isomers.

The term "$C_2$-$C_{12}$ alkynyl" comprises all isomers of the corresponding unsaturated olefinic hydrocarbon groups containing two to twelve carbon atoms linked by one or more triple bonds; this includes ethynyl, all propynyl-isomers, all butynyl-isomers, all pentynyl-isomers, all hexynyl-isomers, all heptynyl-isomers, all octynyl-isomers, all nonynyl-isomers, all decynyl-isomers, all undecynyl-isomers and all dodecynyl-isomers. The term "alkynyl" also includes compounds having one or more triple bonds and one or more double bonds.

The term "$C_3$-$C_8$ cycloalkyl" comprises the corresponding saturated hydrocarbon groups containing three to eight carbon atoms arranged in a monocyclic ring structure; this includes cyclopropyl, cyclobutyl, cyclopentyl, cyclohexyl, cycloheptyl, cyclooctyl.

The term "$C_3$-$C_8$ cycloalkenyl" comprises the corresponding unsaturated non-aromatic, anti-aromatic or aromatic hydrocarbon groups containing three to eight carbon atoms arranged in a monocyclic ring structure and linked by one or more double bonds; this includes cyclopropenyl, all cyclobutenyl-isomers, all cyclopentenyl-isomers, all cyclohexenyl-isomers, all cycloheptenyl-isomers, all cyclooctenyl-isomers.

The term "$C_4$-$C_{12}$ bicycloalkyl" comprises the corresponding saturated hydrocarbon groups containing four to twelve carbon atoms arranged in a bicyclic ring structure; The term "$C_6$-$C_{12}$ bicycloalkenyl" comprises the corresponding unsaturated hydrocarbon groups containing six to twelve carbon atoms arranged in a bicyclic ring structure and linked by one or more double bonds;

The term "$C_5$-$C_{14}$ tricycloalkyl" comprises the corresponding saturated hydrocarbon groups containing five to fourteen carbon atoms arranged in a tricyclic ring structure;

The term "perhalogenated" relates to the exhaustive halogenation of the carbon scaffold; according residues comprise the corresponding perfluorinated, perchlorinated, perbrominated and periodinated groups. Preferably, the term "perhalogenated" relates to perfluorinated or perchlorinated groups, more preferably to perfluorinated groups.

The following contains definitions of terms used in this specification. The initial definition provided for a group or term herein applies to that group or term throughout the present specification, individually or as part of another group, unless otherwise indicated.

The compounds of the present invention may form salts, which are also within the scope of this invention. Reference to a compound of the invention herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the substituents comprise an acid moiety such as a carboxyl group). Also included herein are quaternary ammonium salts such as alkylammonium salts. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, tert-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science* 1977, 66 (2), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Furthermore, in the case of the compounds of the invention which contain an asymmetric carbon atom, the invention relates to the D form, the L form and D,L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms.

Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

Also included are solvates and hydrates of the compounds of the invention and solvates and hydrates of their pharmaceutically acceptable salts.

The term "compound" as used herein is meant to include all stereoisomers, geometric isomers, tautomers, rotamers, and isotopes of the structures depicted, unless otherwise indicated.

In some embodiments, the compound can be provided as a prodrug. The term "prodrug", as employed herein, denotes a compound, which, upon administration to a subject, undergoes chemical conversion by metabolic or chemical processes to yield a compound of the invention, or a salt and/or solvate thereof.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

Pharmaceutical Methods

The compounds according to the invention have been found to have pharmacologically important properties, which can be used therapeutically. The compounds of the invention can be used alone, in combination with each other or in combination with other active compounds.

In certain embodiments, compounds of the present invention may be enhancers of Notch signalling.

The communication between cells via Notch signaling (reviewed in Kopan et al., Cell 2009, 137, 216-233; Bray, Nat. Rev. Mol. Cell Biol. 2016, 17, 722-735) is in the first step mediated by two types of transmembrane proteins: The Notch receptors being distributed within the cell membrane of the signal-receiving cell and the Notch ligands covering the membrane of the signal-sending cell. Mechanistically, Notch signaling is activated by receptor-ligand interaction, which leads to the proteolytic release of the intra cellular domain (NICD) of the membrane bound Notch receptor into the inside of the signal receiving cell. Subsequent translocation of NICD into the nucleus in turn leads to the transcriptional activation of certain and cell type specific genes. The Notch-mediated alteration of the previous gene-expression program of a cell is manifested in according cellular changes, which represent the response of the cell to a Notch signal.

The activation level of Notch signaling can be quantified in vitro most reliably by measuring the expression levels of Notch specific target genes. This can be accomplished by the quantification of corresponding mRNA or protein of a particular Notch target gene. Alternatively, cells can be genetically modified to carry a luciferase gene as an artificial Notch target gene, which is expressed in dependence of Notch activity. In this setting, Notch signaling levels can be quantified by measuring the luciferase-derived bioluminescence values.

An according Notch-reporter assay, i.e. a luciferase-based luminescence readout, was used here to quantify the ability of the claimed small molecules to augment Notch signaling in a cellular system. For this purpose, HeLa cells, obtainable from the American Type Culture Collection (ATCC) under the accession number ATCC-CCL-2, were transiently transfected for 24 hours using FuGENE® HD (Promega, # E2311) as transfection reagent with expression vectors of a membrane-tethered form of the constitutively active intracellular domain of the human Notch1 receptor (hNotch1ΔE) to activate the signaling cascade (BPS Bioscience, human analogue to Notch Pathway Reporter Kit #60509 component C), a Firefly luciferase being expressed under the control of a Notch-responsive promoter to monitor Notch signaling (BPS Bioscience, Notch Pathway Reporter Kit #60509, CSL luciferase reporter vector from component A not premixed with Renilla luciferase vector), and a Renilla luciferase being constitutively expressed in a Notch signaling independent manner to include a measure for the cell number per sample (Promega, pRL-SV40, # E2231). HeLa cells were cultivated according to the protocol of the provider in DMEM medium (Fisherscientific, #11584456) containing 10% fetal bovine serum (Fisherscientific, #15517589). The transfection was carried out in a 100 mm-culture dish (StarLab, # CC7682-3394) with cells being properly attached to the plate at a cell confluency of 80-90% in a total volume of 7 mL culture medium. Per dish to be transfected, a transfection mix was prepared by adding to 238 µL Opti-MEM (Fisherscientific, #10149832) 40 µL of the hNotch1ΔE expression vector (100 ng/µL), 80 µL of the CSL luciferase reporter vector (40 ng/µL), 4 µL of the pRL-SV40-Renilla luciferase vector (10 ng/L), and in the last step 18.1 µL of FuGENE® HD. After addition of FuGENE® HD the transfection mix was let stand for 15 min at room temperature and hereafter equally distributed into the culture dish. Subsequently, i.e. after 24 hours of transfection, the transfected cells (10.000 cells per well) were incubated with the test-compounds at a final concentration of 10 µM (diluted from 10 mM stock-solutions in DMSO to a final DMSO concentration of 0.1% v/v) or with the empty carrier DMSO at 0.1% v/v as control for 20 hours in 96-well plates suitable for luminescence readouts (CORNING, #3610). Hereafter, the cells were lysed with 30 µL per well of Passive Lysis Buffer (Promega, # E194A, component of Dual-Luciferase® Reporter Assay System, # E1910) and the Firefly as well as Renilla luciferase values were measured with a luminescence reader with applying 15 µL per well each of the corresponding enzyme substrates needed to create the luminescence signals (Promega, Dual-Luciferase® Reporter Assay System, # E1910).

The suitability of the assays for monitoring Notch signaling was controlled by additionally including a generally accepted commercial Notch inhibitor, i.e. DAPT, as negative control, as well as the reported Notch enhancer resveratrol (RES) as positive control (Pinchot et al., Cancer 2011, 117, 1386-1398; Truong et al., Ann. Surg. Oncol. 2011, 18, 1506-1511; Yu et al., Mol. Cancer Ther. 2013, 12, 1276-1287). Both control compounds were likewise tested at 10 µM.

Per single experiment the measurement was performed in six replicates per compound. For every compound, this experiment was repeated in three or more independent replicates. The values of the Notch-reporter luciferase were normalized by division through the corresponding individual Notch-independent Renilla values in order to eliminate the impact of variation in the absolute cell-numbers in between the samples. For every individual plate, a second normalization was performed against the equally weighted arithmetic mean (here abbreviated as AVE) of the six associated Renilla-normalized DMSO-control values within a single experiment in order to obtain the relative values to a baseline level of 1.0. Two independent outlier analyses were performed according to the methods by Peirce and Chauvenet (Ross, Journal of Engineering Technology 2003, 1-12). Outliers confirmed by at least one of the methods were excluded from the calculations but not more than one value out of six per compound within a single experiment. The weighted arithmetic mean (here abbreviated as $AVE_w$) for each compound was calculated from the double-normalized values over all independent replicates of the single experiments comprising the six replicates each. The corresponding standard deviation for the weighted arithmetic mean was calculated according to the method described by Bronstein et al. (Bronstein, Semendjajew, Musiol, Mühlig, Taschenbuch der Mathematik, $5^{th}$ edition 2001 (German), publisher: Verlag Harri Deutsch, Frankfurt am Main and Thun) and was combined with the Gauß' error propagation associated with the performed calculation for the normalization. The resulting standard deviation is herein referred to as "combined standard deviation".

A compound is considered as a Notch augmenting molecule, i.e. an enhancer of Notch signaling, if the weighted arithmetic mean of the luminescence values after subtraction of the corresponding combined standard deviation amounts to 1.1 or higher, in particular to 1.2 or higher, 1.3 or higher, 1.4 or higher, 1.5 or higher, 1.7 or higher, and 2.0 or higher relative to the overall basis level of 1.0. The overall basis level was calculated as the weighted arithmetic mean of all double-normalized values from the DMSO control measurements in analogy to the calculations performed for the test-compounds. The corresponding combined standard deviation for the DMSO values amounts to less than $1 \cdot 10^{-2}$.

According to the method described above, several molecules falling under the scope of the five compound families herein defined in formula I, formula II, formula III, formula IV and formula V have been identified as enhancers of Notch signaling. The so far identified Notch enhancers relate to the compounds listed in Table VI. The entries of Table VI are categorized by the corresponding weighted arithmetic mean of the compounds falling into the activity ranges as indicated.

TABLE VI

Notch reporter assay

| Activity Range | Entry | Compound | Specification |
|---|---|---|---|
| $AVE_w \geq 2.0$ | 1 | 030 | |
| | 2 | 186 | |
| | 3 | 322 | |
| $1.7 \leq AVE_w < 2.0$ | 4 | 003 | |
| | 5 | 005 | |
| | 6 | 027 | |
| | 7 | 043 | |
| | 8 | 045 | |
| | 9 | 051 | |
| | 10 | 114 | |
| | 11 | 272 | |
| | 12 | 284 | |
| | 13 | 288 | |
| | 14 | 318 | |
| $1.4 \leq AVE_w < 1.7$ | 15 | 004 | |
| | 16 | 026 | |
| | 17 | 041 | |
| | 18 | 050 | |
| | 19 | 052 | |
| | 20 | 067 | |
| | 21 | 071 | |
| | 22 | 072 | |
| | 23 | 073 | |
| | 24 | 075 | |
| | 25 | 117 | |
| | 26 | 120 | |
| | 27 | 134 | |
| | 28 | 216 | |
| | 29 | 266 | |
| | 30 | 269 | |
| | 31 | 291 | |
| | 32 | 297 | |
| | 33 | 317 | |
| | 34 | 336 | |
| | 35 | 337 | |
| | 36 | 385 | |
| | 37 | 394 | |
| | 38 | 395 | |
| | 39 | 410 | |
| | 40 | 544 | |
| | 41 | 820 | |
| $1.5 \pm 0.0$ | 42 | RES | Positive control |
| $1.3 \leq AVE_w < 1.4$ | 43 | 044 | |
| | 44 | 066 | |
| | 45 | 122 | |
| | 46 | 168 | |
| | 47 | 182 | |
| | 48 | 184 | |
| | 49 | 268 | |
| | 50 | 286 | |
| | 51 | 292 | |
| | 52 | 319 | |
| | 53 | 334 | |
| | 54 | 344 | |
| $1.2 \leq AVE_w < 1.3$ | 55 | 007 | |
| | 56 | 019 | |
| | 57 | 025 | |
| | 58 | 091 | |
| | 59 | 092 | |
| | 60 | 133 | |
| | 61 | 166 | |
| | 62 | 195 | |
| | 63 | 217 | |
| | 64 | 222 | |
| | 65 | 241 | |
| | 66 | 242 | |
| | 67 | 247 | |
| | 68 | 273 | |
| | 69 | 275 | |
| | 70 | 316 | |
| | 71 | 325 | |
| | 72 | 363 | |
| | 73 | 396 | |
| | 74 | 784 | |
| $1.1 \leq AVE_w < 1.2$ | 75 | 086 | |
| | 76 | 118 | |
| | 77 | 159 | |
| | 78 | 170 | |
| | 79 | 171 | |
| | 80 | 189 | |
| | 81 | 215 | |
| | 82 | 221 | |
| | 83 | 234 | |
| | 84 | 267 | |
| | 85 | 287 | |
| | 86 | 300 | |
| | 87 | 323 | |
| | 88 | 343 | |
| | 89 | 374 | |
| | 90 | 399 | |
| | 91 | 451 | |
| | 92 | 644 | |
| | 93 | 703 | |
| | 94 | 712 | |
| | 95 | 721 | |
| | 96 | 730 | |
| $1.0 \pm 0.0$ | 97 | DMSO | Baseline control |
| $0.1 \pm 0.0$ | 98 | DAPT | Negative control |

Several other molecules have not been identified as enhancers of Notch signaling according to the above method.

In the course of the evaluation of molecules falling under formula I, formula II, formula III, formula IV and formula V in further cellular assays, results indicate that compounds of said molecule families exhibit growth inhibiting properties in hyperproliferative processes. In some cases, the growth inhibiting properties correlate with Notch enhancing properties, in other cases the growth inhibiting properties do not correlate with Notch enhancing properties.

The biological activity of the claimed compounds can be attributed to but may not be limited to Notch signaling enhancing activity. The secondary mechanisms of the claimed compounds leading to antiproliferative effects can be used alternatively or in combination with the Notch enhancing properties in medicinal treatments, preferably in the treatment of hyperproliferative disorders including cancer and non-malignant hyperproliferative disorders.

The antiproliferative activities of compounds falling under formula I, formula II, formula III, formula IV and formula V were investigated on cells or cell lines originating from a disorder of the myeloid cell compartment, the neuroendocrine system, the cervix, and the mucosal epithelium, as well as from the skin epithelium. To this end, HL-60 cells, TT cells, HeLa cells, CAL-27 cells and human primary epidermal keratinocytes (HPEK) were seeded into 96-well plates suitable for fluorescence assays (CORNING #3598) at following initial cell numbers: 1000 cells per well for HL-60; 9000 cells per well for TT; 2000 cells per well for HeLa, 2000 cells per well for CAL-27, 2000 cells per well for HPEK. The cells were treated with compounds at indicated final concentrations (diluted from the 1000× stock-solutions in DMSO to a final DMSO concentration of 0.1% v/v) or with the empty carrier DMSO at 0.1% v/v as control for 5 days. At day 5 after starting the treatments the cells were subjected to the alamarBlue® Proliferation Assay (Bio-Rad Serotec GmbH, BUF012B) according to the protocol of the manufacturer. The readout was taken with a multi-well plate-reader in the fluorescence mode with applying a filter for excitation at 560 nm (band width 10 nm) and for emission at 590 nm (band width 10 nm). Resveratrol (RES) treatment was included as control for growth inhibition.

The assays were performed in duplicate or more replicates of independent single experiments each containing a six-fold replicate for every condition. For every individual plate, the measured fluorescence intensity values of the conditions with compound treatment were normalized against the corresponding equally weighted arithmetic mean of the fluorescence intensity values of the six DMSO treated control wells in order to obtain the relative values to a baseline level of 1.0. The statistical calculations were performed in analogy to the luciferase assay as described above. To this end, two independent outlier analyses were performed according to the methods by Peirce and Chauvenet (Ross, *Journal of Engineering Technology* 2003, 1-12). Outliers confirmed by at least one of the methods were excluded from the calculations but not more than one value out of six per compound within a single experiment. The weighted arithmetic mean $AVE_w$ for each compound was calculated from the normalized values over all independent replicates of the single experiments comprising the six replicates each. The corresponding standard deviation for the weighted arithmetic mean was calculated according to the method described by Bronstein et al. (Bronstein, Semendjajew, Musiol, Mühlig, Taschenbuch der Mathematik, $5^{th}$ edition 2001 (German), publisher: Verlag Harri Deutsch, Frankfurt am Main and Thun) and was combined with the Gauß' error propagation associated with the performed calculation for the normalization. The resulting standard deviation is herein referred to as "combined standard deviation".

In certain embodiments, the compounds of the present invention may be growth inhibitors in hyperproliferative processes, including malignant and non-malignant hyperproliferative processes.

In one embodiment, several compounds of the invention were found to inhibit the growth of HL-60 cells (human acute myeloid leukemia cells) obtainable from the Deutsche Sammlung von Mikroorganismen und Zellkulturen GmbH (DSMZ) under the accession number ACC 3. HL-60 cells were cultivated according to the protocol of the provider in RPMI 1640 medium (Fisherscientific, #11554526) containing 10% fetal bovine serum (Fisherscientific, #15517589).

A compound is considered as a growth inhibitor of HL-60 cells, if—at a reference concentration of 20 µM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling under the scope of the five compound families herein defined in formula I, formula II, formula III, formula IV and formula V have been identified as growth inhibitors of HL-60 cells. The so far identified HL-60 growth inhibitors relate to the compounds listed in Table VII. The entries of Table VII are categorized by the corresponding weighted arithmetic means of the compounds falling into the activity ranges as indicated.

TABLE VII

Proliferation assay with HL-60 cells at 20 µM

| Activity Range | Entry | Compound | Specification |
|---|---|---|---|
| 1.0 ± 0.0 | 1 | DMSO | Baseline control |
| $0.8 < AVE_w \le 0.9$ | 2 | 002 | |
| | 3 | 030 | |
| | 4 | 054 | |
| | 5 | 072 | |
| | 6 | 073 | |
| | 7 | 075 | |
| | 8 | 087 | |
| | 9 | 092 | |
| | 10 | 165 | |
| | 11 | 245 | |
| | 12 | 248 | |
| | 13 | 298 | |
| | 14 | 300 | |
| | 15 | 316 | |
| | 16 | 317 | |
| | 17 | 325 | |
| | 18 | 337 | |
| | 19 | 374 | |
| | 20 | 385 | |
| | 21 | 395 | |
| | 22 | 399 | |
| | 23 | 427 | |
| | 24 | 477 | |
| | 25 | 592 | |
| | 26 | 712 | |
| | 27 | 723 | |
| | 28 | 731 | |
| | 29 | 738 | |
| | 30 | 739 | |
| | 31 | 740 | |
| | 32 | 792 | |
| | 33 | 793 | |
| | 34 | 811 | |
| | 35 | 812 | |
| | 36 | 819 | |
| $0.7 < AVE_w \le 0.8$ | 37 | 041 | |
| | 38 | 134 | |
| | 39 | 215 | |
| | 40 | 223 | |
| | 41 | 322 | |
| | 42 | 410 | |
| | 43 | 440 | |
| | 44 | 488 | |
| | 45 | 581 | |
| | 46 | 674 | |
| | 47 | 685 | |
| | 48 | 756 | |
| | 49 | 785 | |
| | 50 | 786 | |
| | 51 | 822 | |
| $0.6 < AVE_w \le 0.7$ | 52 | 067 | |
| | 53 | 217 | |
| | 54 | 222 | |
| | 55 | 334 | |
| | 56 | 336 | |
| | 57 | 414 | |
| | 58 | 492 | |
| | 59 | 700 | |
| | 60 | 821 | |
| | 61 | 828 | |
| $0.4 < AVE_w \le 0.6$ | 62 | 043 | |
| | 63 | 044 | |
| | 64 | 045 | |
| | 65 | 066 | |
| | 66 | 133 | |
| | 67 | 159 | |

TABLE VII-continued

Proliferation assay with HL-60 cells at 20 μM

| Activity Range | Entry | Compound | Specification |
|---|---|---|---|
| | 68 | 164 | |
| | 69 | 167 | |
| | 70 | 218 | |
| | 71 | 221 | |
| | 72 | 236 | |
| | 73 | 238 | |
| | 74 | 313 | |
| | 75 | 318 | |
| | 76 | 319 | |
| | 77 | 320 | |
| | 78 | 323 | |
| | 79 | 389 | |
| | 80 | 721 | |
| | 81 | 722 | |
| | 82 | 729 | |
| | 83 | 784 | |
| | 84 | 820 | |
| 0.4 ± 0.0 | 85 | RES 20 μM | Control |
| $0.2 < AVE_w \le 0.4$ | 86 | 161 | |
| | 87 | 210 | |
| | 88 | 211 | |
| | 89 | 237 | |
| | 90 | 596 | |
| $0.0 \le AVE_w \le 0.2$ | 91 | 166 | |
| | 92 | 168 | |
| | 93 | 170 | |
| | 94 | 171 | |
| | 95 | 182 | |
| | 96 | 184 | |
| | 97 | 185 | |
| | 98 | 186 | |
| | 99 | 216 | |
| | 100 | 266 | |
| | 101 | 267 | |
| | 102 | 268 | |
| | 103 | 269 | |
| | 104 | 270 | |
| | 105 | 272 | |
| | 106 | 273 | |
| | 107 | 275 | |
| | 108 | 284 | |
| | 109 | 286 | |
| | 110 | 287 | |
| | 111 | 288 | |
| | 112 | 529 | |
| | 113 | 540 | |
| | 114 | 544 | |
| | 115 | 633 | |
| | 116 | 644 | |
| | 117 | 648 | |
| | 118 | 766 | |
| | 119 | 767 | |
| | 120 | 768 | |
| | 121 | 774 | |
| | 122 | 802 | |
| | 123 | 803 | |
| | 124 | 804 | |
| | 125 | 810 | |

In one embodiment, several compounds of the invention were found to inhibit the growth of CAL-27 cells (human tongue squamous cell carcinoma cells) obtainable from the Deutsche Sammlung von Mikroorganismen und Zellkulturen GmbH (DSMZ) under the accession number ACC 446. CAL-27 cells were cultivated according to the protocol of the provider (but at 5% instead of 10% $CO_2$) in DMEM medium (Fisherscientific, #11584456) containing 10% fetal bovine serum (Fisherscientific, #15517589).

A compound is considered as a growth inhibitor of CAL-27 cells, if—at a reference concentration of 20 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the three compound families herein defined in formula II, formula IV and formula V have been identified as growth inhibitors of CAL-27 cells. The so far identified CAL-27 growth inhibitors relate to the compounds listed in Table VIIIa and VIIIb. The entries of Table VIIIa and VIIIb are categorized by the corresponding weighted arithmetic means of the compounds falling into the activity ranges as indicated.

TABLE VIIIa

Proliferation assay with CAL-27 cells at 20 μM

| Activity Range | Entry | Compound | Specification |
|---|---|---|---|
| 1.0 ± 0.0 | 1 | DMSO | Baseline control |
| 0.9 ± 0.0 | 2 | RES 20 μM | Control |
| $0.8 < AVE_w \le 0.9$ | 3 | 236 | |
| | 4 | 300 | |
| | 5 | 596 | |
| | 6 | 820 | |
| | 7 | 822 | |
| $0.7 < AVE_w \le 0.8$ | 8 | 164 | |
| | 9 | 210 | |
| | 10 | 313 | |
| | 11 | 774 | |
| $0.6 < AVE_w \le 0.7$ | 12 | 167 | |
| | 13 | 238 | |
| $0.4 < AVE_w \le 0.6$ | 14 | 211 | |
| | 15 | 237 | |
| | 16 | 266 | |
| 0.4 ± 0.0 | 17 | RES 40 μM | Control |
| $0.2 < AVE_w \le 0.4$ | 18 | 166 | |
| | 19 | 170 | |
| | 20 | 182 | |
| | 21 | 267 | |
| | 22 | 287 | |
| | 23 | 288 | |
| | 24 | 768 | |
| $0.0 \le AVE_w \le 0.2$ | 25 | 168 | |
| | 26 | 171 | |
| | 27 | 184 | |
| | 28 | 185 | |
| | 29 | 186 | |
| | 30 | 268 | |
| | 31 | 269 | |
| | 32 | 270 | |
| | 33 | 272 | |
| | 34 | 273 | |
| | 35 | 275 | |
| | 36 | 284 | |
| | 37 | 286 | |
| | 38 | 529 | |
| | 39 | 540 | |
| | 40 | 544 | |
| | 41 | 633 | |
| | 42 | 644 | |
| | 43 | 648 | |
| | 44 | 766 | |
| | 45 | 767 | |
| | 46 | 802 | |
| | 47 | 803 | |
| | 48 | 804 | |
| | 49 | 810 | |

TABLE VIIIb

Proliferation assay with CAL-27 cells at 40 μM

| Activity Range | Entry | Compound | Specification |
|---|---|---|---|
| 1.0 ± 0.0 | 1 | DMSO | Baseline control |
| 0.9 ± 0.0 | 2 | RES 24M | Control |
| $0.8 < AVE_w \leq 0.9$ | 3 | 300 | |
| | 4 | 334 | |
| $0.7 < AVE_w \leq 0.8$ | 5 | 722 | |
| $0.6 < AVE_w \leq 0.7$ | 6 | 159 | |
| 0.5 ± 0.0 | 7 | RES 40 μM | Control |
| $0.2 < AVE_w \leq 0.4$ | 8 | 161 | |
| | 9 | 237 | |
| | 10 | 729 | |
| | 11 | 768 | |
| $0.0 \leq AVE_w \leq 0.2$ | 12 | 166 | |
| | 13 | 167 | |
| | 14 | 210 | |
| | 15 | 272 | |
| | 16 | 287 | |

In one embodiment, several compounds of the invention were found to inhibit the growth of TT cells (human medullary thyroid carcinoma cells) obtainable from the American Type Culture Collection (ATCC) under the accession number ATCC-CRL-1803. TT cells were cultivated according to the protocol of the provider in F-12K medium (Fisherscientific, #11580556, or ATCC, # ATCC-30-2004) containing 10% fetal bovine serum (Fisherscientific, #15517589).

A compound is considered as a growth inhibitor of TT cells, if—at a reference concentration of 40 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the three compound families herein defined in formula II, formula IV and formula V have been identified as growth inhibitors of TT cells. The so far identified TT growth inhibitors relate to the compounds listed in Table IX. The entries of Table IX are categorized by the corresponding weighted arithmetic means of the compounds falling into the activity ranges as indicated.

TABLE IX

Proliferation assay with TT cells at 40 μM

| Activity Range | Entry | Compound | Specification |
|---|---|---|---|
| 1.0 ± 0.0 | 1 | DMSO | Baseline control |
| 0.9 ± 0.0 | 2 | RES 20 μM | Control |
| $0.8 < AVE_w \leq 0.9$ | 3 | 159 | |
| | 4 | 309 | |
| | 5 | 334 | |
| 0.8 ± 0.0 | 6 | RES 40 μM | Control |
| $0.7 < AVE_w \leq 0.8$ | 7 | 748 | |
| $0.6 < AVE_w \leq 0.7$ | 8 | 210 | |
| $0.4 < AVE_w \leq 0.6$ | 9 | 161 | |
| | 10 | 237 | |
| $0.2 < AVE_w \leq 0.4$ | 11 | 166 | |
| | 12 | 167 | |
| | 13 | 171 | |
| | 14 | 182 | |
| | 15 | 186 | |
| | 16 | 287 | |
| | 17 | 540 | |
| | 18 | 544 | |
| | 19 | 644 | |
| | 20 | 729 | |
| $0.0 \leq AVE_w \leq 0.2$ | 21 | 272 | |
| | 22 | 284 | |
| | 23 | 288 | |
| | 24 | 768 | |

In one embodiment, several compounds of the invention were found to inhibit the growth of HeLa cells (human cervical adenocarcinoma cells) obtainable from the American Type Culture Collection (ATCC) under the accession number ATCC-CCL-2. HeLa cells were cultivated according to the protocol of the provider in DMEM medium (Fisherscientific, #11584456) containing 10% fetal bovine serum (Fisherscientific, #15517589).

A compound is considered as a growth inhibitor of HeLa cells, if—at a reference concentration of 40 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the compound family herein defined in formula II have been identified as growth inhibitors of HeLa cells. The so far identified HeLa growth inhibitors relate to the compounds listed in Table X. The entries of Table X are categorized by the corresponding weighted arithmetic means of the compounds falling into the activity ranges as indicated.

TABLE X

Proliferation assay with HeLa cells at 40 μM

| Activity Range | Entry | Compound | Specification |
|---|---|---|---|
| 1.0 ± 0.0 | 1 | DMSO | Baseline control |
| 0.9 ± 0.0 | 2 | RES 20 μM | Control |
| $0.4 < AVE_w \leq 0.6$ | 3 | 166 | |
| 0.4 ± 0.0 | 4 | RES 40 μM | Control |
| $0.2 < AVE_w \leq 0.4$ | 5 | 167 | |
| | 6 | 287 | |
| $0.0 \leq AVE_w \leq 0.2$ | 7 | 272 | |

In one embodiment, several compounds of the invention were found to inhibit the growth of human epidermal keratinocyte progenitors, (HPEKp, pooled), obtainable from CELLnTEC Advanced Cell Systems AG under the accession number HPEKp. HPEKp cells were cultivated according to the protocol of the provider in CnT-Prime epithelial culture medium (CELLnTEC, # CnT-PR, a fully defined, low calcium formulation, completely free of animal or human-derived components) without addition of further components.

A compound is considered as a growth inhibitor of HPEKp cells, if—at a reference concentration of 10 µM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the four compound families herein defined in formula II, formula III, formula IV and formula V have been identified as growth inhibitors of HPEKp cells. The so far identified HPEKp growth inhibitors relate to the compounds listed in Table XI. The entries of Table XI are categorized by the corresponding weighted arithmetic means of the compounds falling into the activity ranges as indicated.

TABLE XI

Proliferation assay with HPEKp cells at 10 µM

| Activity Range | Entry | Compound | Specification |
|---|---|---|---|
| $1.0 \pm 0.0$ | 1 | DMSO | Baseline control |
| $0.8 < AVE_w \leq 0.9$ | 3 | 140 | |
| | 4 | 374 | |
| | 5 | 731 | |
| | 6 | 747 | |
| | 7 | 749 | |
| | 8 | 801 | |
| $0.7 < AVE_w \leq 0.8$ | 10 | 312 | |
| | 11 | 323 | |
| | 12 | 424 | |
| | 13 | 721 | |
| | 14 | 819 | |
| | 15 | 828 | |
| $0.6 < AVE_w \leq 0.7$ | 16 | 086 | |
| | 17 | 190 | |
| | 18 | 334 | |
| $0.4 < AVE_w \leq 0.6$ | 19 | 112 | |
| | 20 | 722 | |
| $0.4 \pm 0.0$ | 21 | RES 10 µM | Control |
| $0.2 < AVE_w \leq 0.4$ | 22 | 389 | |
| | 23 | 440 | |
| | 24 | 540 | |
| $0.0 \leq AVE_w \leq 0.2$ | 25 | 159 | |
| | 26 | 182 | |
| | 27 | 185 | |
| | 28 | 273 | |
| | 29 | 287 | |
| | 30 | 644 | |
| | 31 | 810 | |

Preliminary results from a single proliferation assay of six replicates per condition using cells derived from murine muscle tissue show that compounds of the invention may exhibit antiproliferative activity on muscle cells. Compounds were tested on C2C12 cells using the alamarBlue® proliferation assay in analogy to the above described method with seeding the cells at an initial number of 2000 cells per 96-well and a duration of treatment with compounds for 3 days.

In one embodiment, two compounds of the invention were found so far to inhibit the growth of C2C12 cells (murine myoblast cells) obtainable from the Deutsche Sammlung von Mikroorganismen und Zellkulturen GmbH (DSMZ) under the accession number ACC 565. C2C12 cells were cultivated according to the protocol of the provider in RPMI 1640 medium (Fisherscientific, #11554526) containing 10% fetal bovine serum (Fisherscientific, #15517589).

A compound is considered as a growth inhibitor of C2C12 cells, if—at a reference concentration of 40 µM—the equally weighted arithmetic mean (AVE) of the six normalized fluorescence intensity values after addition of the corresponding standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the equally weighted arithmetic mean (AVE) of the six normalized values from the DMSO control measurements in analogy to the calculations performed for the test-compounds. The corresponding standard deviations for the tested compounds were calculated including the Gauß' error propagation associated with the performed calculation for the normalization and amounts for the DMSO values to less than $3 \cdot 10^{-2}$. Outlier analyses were performed as described above.

According to the method described above, molecules falling so far under the scope of the two compound families herein defined in formula II and formula V have been identified as growth inhibitors of C2C12 cells. The so far identified C2C12 growth inhibitors relate to the compounds listed in Table XII. The entries of Table XII are categorized by the corresponding equally weighted arithmetic means of the compounds falling into the activity ranges as indicated.

TABLE XII

Proliferation assay with C2C12 cells at 40 µM

| Activity Range | Entry | Compound | Specification |
|---|---|---|---|
| $1.0 \pm 0.0$ | 1 | DMSO | Baseline control |
| $0.8 < AVE \leq 0.9$ | 2 | 748 | |
| $0.3 \pm 0.0$ | 3 | RES 40 µM | Control |
| $0.2 < AVE \leq 0.4$ | 4 | 288 | |

Preliminary results from a single proliferation assay of six replicates per condition using squamous cell carcinoma (SCC) cells derived from the human oral mucosa may confirm that compounds of the invention exhibit antiproliferative activity on SCC of the mucosal epithelium. Compounds were tested on BHY cells using the alamarBlue® proliferation assay in analogy to the above described method with seeding the cells at an initial number of 4000 cells per 96-well and a duration of treatment with compounds for 3 days.

In one embodiment, several compounds of the invention were found to inhibit the growth of BHY cells (human oral squamous cell carcinoma cells) obtainable from the Deutsche Sammlung von Mikroorganismen und Zellkulturen GmbH (DSMZ) under the accession number ACC 404. BHY cells were cultivated according to the protocol of the provider (but at 5% instead of 10% $CO_2$) in DMEM medium (Fisherscientific, #11584456) containing 10% fetal bovine serum (Fisherscientific, #15517589).

A compound is considered as a growth inhibitor of BHY cells, if—at a reference concentration of 40 µM—the equally weighted arithmetic mean (AVE) of the six normalized fluorescence intensity values after addition of the corresponding standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean ($AVE_w$) of all normalized values from the DMSO control measurements. The corresponding combined standard deviation for the DMSO values amounts to less than $1\cdot 10^{-2}$. The corresponding standard deviations for the tested compounds were calculated including the Gauß' error propagation associated with the performed calculation for the normalization. The weighted arithmetic mean ($AVE_w$) and the combined standard deviation for RES was calculated in analogy to DMSO. Outlier analyses were performed as described above.

According to the method described above, molecules falling so far under the scope of the two compound families herein defined in formula II and formula IV have been identified as growth inhibitors of BHY cells. The so far identified BHY growth inhibitors relate to the compounds listed in Table XIII. The entries of Table XIII are categorized by the corresponding equally weighted arithmetic means of the compounds falling into the activity ranges as indicated.

TABLE XIII

Proliferation assay with BHY cells at 40 µM

| Activity Range | Entry | Compound | Specification |
|---|---|---|---|
| 1.0 ± 0.0 | 1 | DMSO | Baseline control |
| 0.6 < AVE ≤ 0.7 | 2 | 644 | |
| 0.6 ± 0.0 | 3 | RES 40 µM | Control |
| 0.4 < AVE ≤ 0.6 | 4 | 171 | |
| 0.2 < AVE ≤ 0.4 | 5 | 182 | |
|  | 6 | 186 | |
|  | 7 | 272 | |
|  | 8 | 284 | |
|  | 9 | 288 | |
|  | 10 | 544 | |
|  | 11 | 633 | |
| 0.0 ≤ AVE ≤ 0.2 | 12 | 540 | |

In one aspect, the present invention relates to the treatment of skin, skin appendages, mucosa, mucosal appendages, cornea, and all kinds of epithelial tissue. The term "skin" relates to tissue including epidermis and dermis. The term "mucosa" relates to mucous and submucous tissues including oral mucosa, nasal mucosa, ocular mucosa, mucosa of the ear, respiratory mucosa, genital mucosa, urothelial mucosa, anal mucosa and rectal mucosa. The term "appendages" relates to tissue including hair follicles, hair, fingernails, toenails and glands including sebaceous glands, sweat glands, e.g. apocrine or eccrine sweat glands and mammary glands.

In one embodiment, the present invention relates to treatment of non-melanoma skin cancer and pre-cancerous lesions, such as basal cell carcinoma (BCC), squamous cell carcinoma (SCC), e.g. cutaneous SCC, lung SCC, head and neck SCC, oral SCC, esophageal SCC, cervical SCC, periocular SCC, SCC of the thyroid, SCC of the penis, SCC of the vagina, SCC of the prostate, SCC of the bladder, sebaceous gland carcinoma, Merkel cell carcinoma, angiosarcoma, cutaneous B-cell lymphoma, cutaneous T-cell lymphoma, dermatofibrosarcoma, actinic keratosis (AK) or Bowen's disease (BD).

In a further embodiment, the present invention relates to the treatment of skin and mucosal disorders with cornification defects (keratoses) and/or abnormal keratinocyte proliferation, such as Psoriasis, Darier's disease, Lichen planus, Lupus erythematosus, Ichthyosis or Verruca vulgaris (senilis).

In a further embodiment, the invention relates to the treatment of skin and mucosal diseases related to and caused by viral infections, such as warts, HPV-related warts, papillomas, HPV-related papillomas, papillomatoses and HPV-related papillomatoses, e.g. Verruca (plantar warts), Verruca plana (flat warts/plane warts), Verruca filiformis (filiform warts), mosaic warts, periungual warts, subungual warts, oral warts, genital warts, fibroepithelial papilloma, intracanalicular papilloma, intraductal papilloma, inverted papilloma, basal cell papilloma, squamous papilloma, cutaneous papilloma, fibrovasular papilloma, plexus papilloma, nasal papilloma, pharyngeal papilloma, Papillomatosis cutis carcinoides, Papillomatosis cutis lymphostatica, Papillomatosis confluens et *reticularis* or laryngeal papillomatosis (respiratory papillomatosis), Herpes-related diseases, e.g. Herpes labialis, Herpes genitalis, Herpes zoster, Herpes corneae or Kaposi's sarcoma.

In a further embodiment, the invention relates to the treatment of atopic dermatitis.

In a further embodiment, the invention relates to the treatment of acne.

In a further embodiment, the invention relates to the treatment of wounds of the skin, wherein the process of wound healing is accelerated.

A further aspect of the present invention relates to the treatment of immune system-related disorders. The term "immune system-related" as used herein applies to a pathological condition of the hematopoietic system including the hematologic system, as well as to the intervention into proliferation, differentiation and/or activation of cell lineages of the hematopoietic system including the hematologic system in order to modulate an immune response (immune modulation).

Examples are diseases of the hematopoietic system including the hematologic system, such as malignancies of the myeloid lineage, e.g. chronic myelomonocytic leukemia (CMML) or acute myeloid leukemia (AML), including acute promyelocytic leukemia (APL); malignancies of the lymphoid lineage, e.g. B-cell acute lymphoblastic leukemia (B-ALL), pre-B-cell acute lymphoblastic leukemia (pre-B-ALL), Hodgkin lymphoma or myeloma; or acute lymphoblastic and acute myeloid mixed lineage leukemia with MLL gene translocation.

Furthermore, the compounds of the invention may be used in immunotherapy, alone or together with other immunotherapeutic methods or compounds, or as adjuvant for immunotherapy. The term "immunotherapy" as used herein applies to activation-immunotherapy in patients without immune deficiency or with acquired or congenital immune deficiency, and as immune recovery to enhance the functionality of the immune system in the response against pathogens or pathologically transformed endogenous cells, such as cancer cells.

The term "other immunotherapy methods" as used herein applies to vaccinations, antibody treatment, cytokine therapy, the use of immune checkpoint inhibitors and immune response-stimulating drugs, as well as to autologous transplantations of genetically modified or non-modified immune cells, which may be stimulated with intercellular signals, or signaling molecules, or antigens, or antibodies, i.e. adoptive immune-cell transfer.

Specific examples are activation of peripheral T-lymphocytes in order to amplify an immune response, particularly the stimulation of proliferation and/or cytokine production and/or secretion upon antigen recognition in order to amplify an immune response, such as the activation of B-lymphocytes in order to amplify an immune response, particularly the stimulation of proliferation and/or antibody production and/or secretion, such as the enhancement of an immune response through augmentation of the number of specific immune-cell subtypes, by regulation of differentiation and/or cell fate decision during immune-cell development, as for example to augment the number of marginal zone B-cells, or T-helper (Th) subsets in particular Th1, Th2 and regulatory T-cells; or the use as vaccine adjuvant.

A still further aspect of the invention relates to the treatment of muscular diseases including diseases of skeletal muscle, cardiac muscle and smooth muscle.

In one embodiment, the invention relates to the treatment of muscular dystrophies (MD).

Specific examples are Duchenne MD, Becker MD, congenital MD, Limb-Girdle MD, facioscapulohumeral MD, Emery-Dreifuss MD, distal MD, myotonic MD or oculopharyngeal MD.

In a further embodiment, the invention relates to the treatment of hyperproliferative disorders of the muscle, including myoblastoma, rhabdomyoma, and rhabdomyosarcoma, as well as muscle hyperplasia and muscle hypertrophy.

In a further embodiment, the compounds of the invention may be used for muscle regeneration after pathologic muscle degeneration or atrophy, e.g. caused by traumata, caused by muscle ischemia or caused by inflammation, in aging-related muscle-atrophy or in disease-related muscle atrophy such as myositis and fibromyositis or poliomyelitis.

A still further aspect relates to the treatment of disorders of the neuroendocrine system such as cancer of the neuroendocrine system, comprising neuroendocrine small cell carcinomas, neuroendocrine large cell carcinomas and carcinoid tumors, e.g. of the brain, thyroid, pancreas, gastrointestinal tract, liver, esophagus, and lung, such as neuroendocrine tumor of the pituitary gland, neuroendocrine tumor of the adrenal gland, medullary thyroid cancer (MTC), C-cell hyperplasia, anaplastic thyroid cancer (ATC), parathyroid adenoma, intrathyroidal nodules, insular carcinoma, hyalinizing trabecular neoplasm, paraganglioma, small-cell lung cancer (SCLC), lung carcinoid tumors, neuroblastoma, gastrointestinal carcinoid, Goblet-cell carcinoid, pancreatic carcinoid, gastrinoma, glucagenoma, somatostatinoma, VIPoma, insulinoma, non-functional islet cell tumor, multiple endocrine neoplasia type-1, or pulmonary carcinoid.

A still further aspect relates to the treatment of cancers or precancerous lesions of the brain, pancreas, liver, thyroid, genitourinary tract and endothelial tissue, including glioma, mixed glioma, glioblastoma multiforme, astrocytoma, anaplastic astrocytoma, glioblastoma, oligodendroglioma, anaplastic oligodendroglioma, anaplastic oligoastrocytoma, ependymoma, anaplastic ependymoma, myxopapillary ependymoma, subependymoma, brain stem glioma, optic nerve glioma, and forebrain tumors, pancreatic adenocarcinoma, pancreatic ductal adenocarcinoma, pancreatic acinar cell carcinoma, pancreatic pseudopapillary neoplasm, pancreatic intraductal papillary-mucinous neoplasm, pancreatic mucinous cystadenocarcinoma, pancreatoblastoma and pancreatic intraepithelial neoplesia, hepatocellular carcinoma, fibrolamellar hepatocellular carcinoma, papillary thyroid cancer and follicular thyroid cancer, cervical cancer and angiosarcoma.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. The term "treating" also encompasses post-treatment care.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

The compounds of the invention may be used in human and veterinary medicine, which includes the treatment of companion animals, e.g. horses, dogs, cats, rabbits, guinea pigs, birds, fishes; and livestock, e.g. cattle, poultry, pig, sheep, goat, donkey, yak and camel.

Pharmaceutical Compositions

The present invention further provides pharmaceutical compositions comprising a compound as described herein or a pharmaceutically acceptable salt thereof for use in medicine, e.g. in human or veterinary medicine. In some embodiments, the composition further comprises a pharmaceutically acceptable carrier.

An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are topical or systemical including enteral, oral, rectal, and parenteral, as infusion and injection, intravenous, intra-arterial, intraperitoneal, intramuscular, intracardial, epidural, intracerebral, intracerebroventricular, intraosseous, intra-articular, intraocular, intravitreal, intrathecal, intravaginal, intracavernous, intravesical, subcutaneous, intradermal, transdermal, transmucosal, inhalative, intranasal, buccal, sublingual and intralesional preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, gels, hydrogels, ointments, creams, lotions, shampoos, lip balms, mouthwashs, foams, pastes, tinctures, dermal patches and tapes, forms in occlusion or in combination with time release drug delivery systems, with electrophoretic dermal delivery systems including implants and devices, and with jet injectors, liposome and transfersome vesicles, vapors, sprays, syrups, juices or drops and eye drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable, synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia.

Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na-N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy, as sequence therapy or as simultaneous combination therapy, with further active agents, e.g. therapeutically active compounds useful in the treatment of the above indicated disorders. These therapeutically active compounds may include but are not limited to chemotherapeutic agents such as nucleoside analogs, e.g. Cytarabin, Gemcitabine, Azathioprine, Mercaptopurine, Fluorouracil, Thioguanine, Hydroxyurea, Azacitidine, Capecitabine, Doxifluridine, and Methotrexate; such as platinum-based drugs, e.g. Cisplatin, Oxaliplatin, Carboplatin and Nedaplatin; such as anthracyclines, e.g. Doxorubicin, Epirubicin, Valrubicin, Idarubicin, Daunorubicin, Sabarubicin, Pixantrone and Mitoxantrone; such as peptide antibiotics, e.g. Actinomycin and Bleomycin; such as alkylating agents e.g. Mechlorethamine, Chlorambucil, Melphalan, Nitrosoureas, Dacarbazine, Temozolomide and Cyclophosphamide; such as antimitotic agents including taxanes and vinca alkaloids, e.g. Docetaxel, Paclitaxel, Abraxane, Cabazitaxel, Vinblastine, Vindesine, Vinorelbine and Vincristine; such as topoisomerase inhibitors, e.g. Irinotecan, Topotecan, Teniposide and Etoposide; and targeted therapeutic agents such as kinase inhibitors, regulators i.e. inhibitors and activators of signaling pathways including growth factor signaling, cytokine signaling, NF-kappaB signaling, AP1 signaling, JAK/STAT signaling, EGFR signaling, TGF-beta signaling, Notch signaling, Wnt signaling, Hedgehog signaling, hormone and nuclear receptor signaling, e.g. Erlotinib, Lapatinib, Dasatinib, Imatinib, Afatinib, Vemurafenib, Dabrafenib, Nilotinib, Cetuximab, Trametinib, Palbociclib, Cobimetinib, Cabozantinib, Pegaptanib, Crizotinib, Olaparib, Panitumumab, Cabozantinib, Ponatinib, Regorafenib, Entrectinib, Ranibizumab, Ibrutinib, Trastuzumab, Rituximab, Alemtuzumab, Gefitinib, Bevacizumab, Lenvatinib, Bosutinib, Axitinib, Pazopanib, Everolimus, Temsirolimus, Ruxolitinib, Tofacitinib, Sorafenib, Sunitinib, Aflibercept, Bortezomib, Vandetanib; Vismodegib and Sonidegib; retinoids such as retinol, tretinoin, isotretinoin, alitretinoin, bexarotene, tazarotene, acitretin, adapalene and etretinate; hormone signaling modulators including estrogen receptor modulators, androgen receptor modulators and aromatase inhibitors e.g. Raloxifene, Tamoxifen, Fulvestrant, Lasofoxifene, Toremifene, Bicalutamide, Flutamide, Anastrozole, Letrozole and Exemestane; histone deacetylase inhibitors, e.g. Vorinostat, Romidepsin, Panobinostat, Belinostat and Chidamide; and Ingenol mebutate; and other Notch enhancers not encompassed by the compounds of the present invention, e.g. Valproic acid, Resveratrol, hesperetin, chrysin, phenethyl isothiocyanate, thiocoraline, N-methylhemeanthidine chloride and Notch Signaling-activating peptides or antibodies; and immune response modulating agents e.g. Imiquimod, Ipilimumab, Atezolizumab, Ofatumumab, Rituximab, Nivolumab and Pembrolizumab; and anti-inflammatory agents including glucocorticoids and non-steroidal anti-inflammatory drugs, e.g. cortisol-based preparations, Dexamethason, Betamethason, Prednisone, Prednisolone, Methylprednisolone, Triamcinolon-hexacetonid, Mometasonfuroat, Clobetasolpropionat, acetylsalicylic acid, salicylic acid and other salicylates, Diflunisal, Ibuprofen, Dexibuprofen, Naproxen, Fenoprofen, Ketoprofen, Dexketoprofen, Loxoprofen, Flurbiprofen, Oxaprozin, Indomethacin, Ketorolac, Tolmetin, Diclofenac, Etodolac, Aceclofenac, Nabumetone, Sulindac, Mefenamic acid, Meclofenamic acid, Flufenamic acid, Tolfenamic acid, Celecoxib, Parecoxib, Etoricoxib and Firocoxib; and ACE inhibitors; and beta-blockers; and myostatin inhibitors; and PDE-5 inhibitors; and antihistamines. For a combination therapy, the active ingredients may be formulated as compositions containing several active ingredients in a single dose form and/or as kits containing individual active ingredients in separate dose forms. The active ingredients used in combination therapy may be co-administered or administered separately.

The compounds of the invention may be administered as antibody-drug conjugates.

The compounds of the invention may be administered in combination with surgery, cryotherapy, electrodessication, radiotherapy, photodynamic therapy, laser therapy, chemotherapy, targeted therapy, immunotherapy, gene therapy, antisense therapy, cell-based transplantation therapy, stem cell therapy, physical therapy and occupational therapy.

The compounds of the invention falling under the scope of formula I, formula II, formula III, formula IV and formula V can be synthesized in analogy to the methods described in Reinmüller et al., 2015, EPFL Thesis 6887 by a coupling step to establish the diaryl ether scaffold, which can be prepared by a method of reacting a phenol and an electron-deficient aryl halide in the presence of a base such as potassium carbonate or cesium carbonate in a non-protic organic solvent such as DMSO or DMF at room temperature or at elevated temperature or reflux, preferably at 80° C. or 100° C., with optional assistance of microwave irradiation (Li et al., Org. Lett. 2003, 5, 2169-2171);

or by a method of reacting a phenol and a nitroarene in the presence of a base such as potassium carbonate or cesium carbonate in a non-protic organic solvent such as DMSO or DMF at elevated temperature or reflux, with assistance of microwave irradiation (Sarkate et al., Synlett 2013, 24, 1513-1516);

or by a method of reacting an aryl silyl ether with an electron-deficient aryl halide in the presence of a base such as DBU and trace water in a non-protic organic solvent such as DMSO or DMF at elevated temperature or reflux (Yeom et al., Synlett 2007, 146-150);

or by a method of reacting a phenol with a diaryliodonium triflate or tosylate in the presence of a base such as potassium carbonate or cesium carbonate in a non-protic organic solvent such as acetonitrile at ambient or elevated temperature (Kakinuma et al., Synthesis 2013, 45, 183-184);

or by a method of reacting under Buchwald-Hartwig conditions a phenol with an aryl halide in the presence of a transition metal-based catalyst system such as palladium(II) acetate, an organophosphorus-based ligand such as dppf, a base such as potassium phosphate in an organic solvent such as toluene at elevated temperature or reflux (Burgos et al., Angew. Chem. Int. Ed. 2006, 45, 4321-4326);

or by a method of reacting under Chan-Lam conditions a phenol with an arylboronic acid or ester in the presence of air, a copper-based catalyst system such as copper(II) acetate, a base such as pyridine or triethylamine in a non-protic organic solvent such as DCM, chloroform at ambient temperature (Evans et al., Tetrahedron Letters 1998, 39, 2937-2940);

wherein all said methods of preparation may require a subsequent derivatisation step by standard chemical procedures known to the person skilled in the art, such as saponification, hydrolysis, esterification or amidation to obtain the corresponding carboxylic acids, esters, primary amides, secondary amides, tertiary amides, hydroxamic acids and hydroxamates.

For example, the corresponding carboxylic acids are synthesized by saponification of the corresponding benzoate esters, fluorobenzoate esters, nicotinate esters, or fluoronicotinate esters in the presence of potassium hydroxide or sodium hydroxide in a binary solvent mixture of water and an alcohol, preferably ethanol, or water and tetrahydrofuran at ambient or elevated temperature (Becker et al., Organikum, 22nd edition 2004 (German), pp. 488, publisher: Wiley-VCH Weinheim);

the esters, primary amides, secondary amides, tertiary amides, and hydroxamic acids are synthesized by in situ transformation of the corresponding benzoic acid, fluorobenzoic acid, nicotinic acid, or fluoronicotinic acid to the corresponding acid chlorides in the presence of thionyl chloride and catalytic amounts of DMF in toluene at ambient or elevated temperature, preferably at 80° C., and under inert gas atmosphere, followed by the addition of the respective nucleophile, i.e. alcohol, ammonia, secondary amine, tertiary amine, or hydroxylamine in the presence or absence of a non-nucleophilic base such as triethylamine, at ambient temperature under inert gas atmosphere (Becker et al., Organikum, 22nd edition 2004 (German), pp. 459, publisher: Wiley-VCH Weinheim).

The perfluoroalkylcyclopropyl moiety associated with the compounds of the invention falling under the scope of formula V is synthesized in three steps according to the procedure described in Barnes-Seeman et al., ACS Med. Chem. Lett. 2013, 4, 514-516; first, a bromoperfluoroalkenylbenzene such as 1-bromo-4-(3,3,3-trifluoroprop-1-en-2-yl)benzene or 1-bromo-4-(3,3,4,4,4-pentafluorobut-1-en-2-yl)benzene is obtained by a method of reacting 1-(4-bromophenyl)-2,2,2-trifluoroethan-1-one or 1-(4-bromophenyl)-2,2,3,3,3-pentafluoropropan-1-one, respectively, in the presence of methanesulfonyl chloride and a base such as potassium fluoride in a crown ether such as 18-crown-6 in a non-protic organic solvent such as DMF at elevated temperature, preferably at 80° C.;

second, a bromophenylperfluoroalkyldihydropyrazole such as 3-(4-bromophenyl)-3-(trifluoromethyl)-4,5-dihydro-3H-pyrazole or 3-(4-bromophenyl)-3-(perfluoroethyl)-4,5-dihydro-3H-pyrazole is obtained by a method of reacting a bromoperfluoroalkenylbenzene such as 1-bromo-4-(3,3,3-trifluoroprop-1-en-2-yl)benzene or 1-bromo-4-(3,3,4,4,4-pentafluorobut-1-en-2-yl)benzene, respectively, in the presence of diazomethane in an ether such as diethyl ether or methyl tert-butyl ether at ambient temperature;

and third, the perfluoroalkylcyclopropylarylbromide such as 1-bromo-4-(1-(trifluoromethyl)cyclopropyl)benzene or 1-bromo-4-(1-(perfluoroethyl)cyclopropyl)benzene is obtained by a method of reacting 3-(4-bromophenyl)-3-(trifluoromethyl)-4,5-dihydro-3H-pyrazole or 3-(4-bromophenyl)-3-(perfluoroethyl)-4,5-dihydro-3H-pyrazole, respectively, in an organic solvent such as toluene or xylenes or a mixture thereof.

The obtained perfluoroalkylcyclopropylarylbromide can subsequently be converted into the corresponding phenol for one of the above said coupling reactions with an electron-deficient aryl halide, a nitroarene, a diaryliodonium triflate or tosylate by a method of reaction in the presence of a transition metal-based catalyst system such as Pd2dba3, an organophosphorus-based ligand such as 2-di-tert-butylphosphino-2',4',6'-triisopropylbiphenyl (t-Bu XPhos), a base such as potassium hydroxide or sodium hydroxide in a biphasic solvent system such as water/dioxane or water/toluene at elevated temperature or reflux, preferably at 100° C., and under an inert gas atmosphere (Anderson et al., J. Am. Chem. Soc. 2006, 128, 10694-10695);

or by a method of reaction in the presence of a copper-based catalyst system such as CuI, a pyridyl based ligand such as 2-methylquinolin-8-ol or preferably 8-hydroxyquinoline-N-oxide, and tetrabutyl-ammonium hydroxide or preferably cesium hydroxide monohydrate in a non-protic organic solvent such as DMSO or DMF at elevated temperature or reflux, preferably at 110° C., and under an inert gas atmosphere (Paul et al., Synthesis 2010, 4268-4272; Yang et el., Org. Lett. 2011, 13, 4340-4343).

The compounds of the invention falling under the scope of formula I, formula II, formula III, formula IV and formula V, as well as intermediates, can be isolated by column chromatography using silica gel as stationary phase and common organic solvents such as petroleum ether, ethyl acetate, dichloromethane, methanol, or acetic acids as eluent, preferably as binary or tertiary solvent mixtures thereof; or by crystallization from common organic solvents such as petroleum ether, ethyl acetate, dichloromethane, chloroform, methanol, ethanol, toluene, or tert-butyl methyl ether, and mixtures thereof.

The compounds of the invention falling under the scope of formula I, formula II, formula III, formula IV and formula V, as well as starting materials and intermediates, can be identified by conventional methods such as nuclear magnetic resonance (NMR) spectroscopy, mass spectrometry (MS), or thin layer chromatography (TLC).

Chemical Synthesis

The compounds of the invention falling under the scope of formula I, formula II, formula III, formula IV and formula V can be synthesized and purified by those persons skilled in the art and are preferably synthesized according to the general procedure A, or general procedure B, or general procedure C, or general procedure D, respectively, and according to the detailed synthesis procedures described herein;

Abbreviations
Ac acetyl
BRSM based on recovered starting material (yield)
Bu butyl
$\delta$ chemical shift in parts per million (ppm)
dba dibenzylideneacetone
DCE 1,2-dichloroethane
DCM dichloromethane
DMF N,N-dimethylformamide
DMSO dimethyl sulfoxide
Et ethyl
ESI electron spray ionization
M mol/L
Me methyl
Ms methanesulfonyl
PE petroleum ether
TBAF tetrabutylammonium fluoride
THF tetrahydrofuran
TMS trimethylsilyl General Procedure A: Synthesis of Diaryl Ether Esters Diaryl ether esters according to formula I, formula III, and formula V can be prepared by nucleophilic aromatic substitution, e.g. by reaction of an alkyl 4-fluorobenzoate, or an alkyl 3,4-difluorobenzoate, or an alkyl 6-chloronicotinate, or an alkyl 6-chloro-5-fluoronicotinate, with a phenol derivative (nucleophile, see Table XIV) in the presence of a base like potassium carbonate in a solvent like dimethyl sulfoxide at a temperature between 80° C. and 150° C. and in an inert atmosphere such as argon.

General Procedure B: Synthesis of Diaryl Ether Acids

Diaryl ether acids according to formula I, formula III, and formula V can be prepared by saponification, e.g. by reaction of the corresponding diaryl ether esters with an aqueous base solution like sodium hydroxide (nucleophile, see Table XIV) in a solvent like ethanol, methanol, tetrahydrofuran or a mixture thereof at a temperature between room temperature and reflux.

General Procedure C: Synthesis of Diaryl Ether Esters

Diaryl ether esters according to formula I, formula III, and formula V can be prepared by esterification via the corresponding acid chloride, e.g by reaction of a diaryl ether acid with thionyl chloride in the presence of catalytic amounts of DMF in a solvent like toluene at a temperature between 50° C. and 100° C. and in an inert atmosphere such as argon. After removal of the volatiles, the such obtained acid chloride intermediate is reacted with the alcohol corresponding to the desired ester (nucleophile, see Table XIV) in the presence of an organic base like triethylamine at a temperature between 0° C. and room temperature and in an inert atmosphere such as argon.

Alternatively, diaryl ether esters according to formula I, formula III, and formula V can be prepared by esterification via the corresponding acid chloride, e.g. by reaction of a diaryl ether acid with thionyl chloride in the presence of the alcohol corresponding to the desired ester (nucleophile, see Table XIV), preferably as the solvent at a temperature between 50° C. and reflux.

General Procedure D: Synthesis of Diaryl Ether Amides

Diaryl ether amides according to formula II, formula IV, and formula V can be prepared by amidation via the corresponding acid chloride, e.g by reaction of a diaryl ether acid with thionyl chloride in the presence of catalytic amounts of DMF in a solvent like toluene at a temperature between 50° C. and 100° C. and in an inert atmosphere such as argon. After removal of the volatiles, the such obtained acid chloride intermediate is reacted with the amine corresponding to the desired amide (nucleophile, see Table XIV) in a solvent like methanol, ethanol, or tetrahydrofuran at a temperature between 0° C. and room temperature and in an inert atmosphere such as argon. The presence of an organic base like triethylamine is needed if the hydrochloride salt of the amine is used.

TABLE XIV

List of Synthesized compounds

| Compound Number | m/z | ESI Ion Type | General Procedure | Nucleophile used in the General Procedure |
|---|---|---|---|---|
| 002 | 241.17 | [M − H]⁻ | B | NaOH |
| 003 | 255.18 | [M − H]⁻ | B | NaOH |
| 004 | 269.18 | [M − H]⁻ | B | NaOH |
| 005 | 283.21 | [M − H]⁻ | B | NaOH |
| 019 | 307.28 | [M − H]⁻ | B | NaOH |
| 020 | 321.34 | [M − H]⁻ | B | NaOH |
| 023 | 243.09 | [M + H]⁺ | C | methanol |
| 024 | 257.10 | [M + H]⁺ | C | methanol |
| 025 | 271.11 | [M + H]⁺ | C | methanol |
| 026 | 285.13 | [M + H]⁺ | C | methanol |
| 027 | 299.20 | [M + H]⁺ | C | methanol |
| 029 | 271.11 | [M + H]⁺ | C | methanol |
| 030 | 299.20 | [M + H]⁺ | C | methanol |
| 041 | 311.21 | [M + H]⁺ | C | methanol |
| 043 | 323.24 | [M + H]⁺ | C | methanol |
| 044 | 337.25 | [M + H]⁺ | C | methanol |
| 045 | 362.32 | [M + H]⁺ | C | methanol |
| 048 | 257.11 | [M + H]⁺ | A | 4-methylphenol |
| 049 | 271.12 | [M + H]⁺ | A | 4-ethylphenol |
| 050 | 285.15 | [M + H]⁺ | A | 4-n-propylphenol |
| 051 | 299.21 | [M + H]⁺ | A | 4-n-butylphenol |
| 052 | 313.26 | [M + H]⁺ | A | 4-n-pentylphenol |
| 054 | 285.15 | [M + H]⁺ | A | 4-isopropylphenol |
| 056 | 311.17 | [M + H]⁺ | A | 4-(trifluoromethyl)phenol |
| 066 | 337.25 | [M + H]⁺ | A | (±)-4-(bicyclo[2.2.1]heptan-2-yl)phenol (7:1 endo:exo) |
| 067 | 351.26 | [M + H]⁺ | A | (±)-4-(bicyclo[2.2.2]octan-2-yl)phenol |
| 070 | 244.00 | [M − H]⁻ | B | NaOH |
| 071 | 258.09 | [M − H]⁻ | B | NaOH |
| 072 | 272.11 | [M − H]⁻ | B | NaOH |
| 073 | 286.16 | [M − H]⁻ | B | NaOH |
| 075 | 258.10 | [M − H]⁻ | B | NaOH |
| 086 | 308.25 | [M − H]⁻ | B | NaOH |
| 087 | 322.30 | [M − H]⁻ | B | NaOH |
| 091 | 244.07 | [M + H]⁺ | C | methanol |
| 092 | 258.09 | [M + H]⁺ | C | methanol |
| 093 | 272.11 | [M + H]⁺ | C | methanol |
| 094 | 286.15 | [M + H]⁺ | C | methanol |
| 095 | 300.19 | [M + H]⁺ | C | methanol |
| 097 | 272.11 | [M + H]⁺ | C | methanol |
| 099 | 300.19 | [M + H]⁺ | C | methanol |
| 101 | 298.09 | [M + H]⁺ | C | methanol |
| 110 | 312.19 | [M + H]⁺ | C | methanol |
| 112 | 324.22 | [M + H]⁺ | C | methanol |
| 113 | 338.24 | [M + H]⁺ | C | methanol |
| 114 | 364.29 | [M + H]⁺ | C | methanol |
| 117 | 272.12 | [M + H]⁺ | A | 4-ethylphenol |
| 118 | 286.16 | [M + H]⁺ | A | 4-n-propylphenol |
| 119 | 300.20 | [M + H]⁺ | A | 4-n-butylphenol |
| 120 | 314.24 | [M + H]⁺ | A | 4-n-pentylphenol |
| 122 | 286.16 | [M + H]⁺ | A | 4-isopropylphenol |
| 133 | 338.24 | [M + H]⁺ | A | (±)-4-(bicyclo[2.2.1]heptan-2-yl)phenol (7:1 endo:exo) |
| 134 | 352.28 | [M + H]⁺ | A | (±)-4-(bicyclo[2.2.2]octan-2-yl)phenol |
| 138 | 228.10 | [M + H]⁺ | D | ammonia |
| 139 | 242.10 | [M + H]⁺ | D | ammonia |
| 140 | 256.12 | [M + H]⁺ | D | ammonia |
| 141 | 270.11 | [M + H]⁺ | D | ammonia |
| 142 | 284.16 | [M + H]⁺ | D | ammonia |
| 144 | 256.12 | [M + H]⁺ | D | ammonia |
| 145 | 270.12 | [M + H]⁺ | D | ammonia |
| 146 | 284.16 | [M + H]⁺ | D | ammonia |
| 157 | 296.20 | [M + H]⁺ | D | ammonia |
| 159 | 308.22 | [M + H]⁺ | D | ammonia |
| 160 | 322.26 | [M + H]⁺ | D | ammonia |
| 161 | 348.27 | [M + H]⁺ | D | ammonia |
| 164 | 244.07 | [M + H]⁺ | D | hydroxylamine |
| 165 | 258.09 | [M + H]⁺ | D | hydroxylamine |
| 166 | 272.11 | [M + H]⁺ | D | hydroxylamine |
| 167 | 286.15 | [M + H]⁺ | D | hydroxylamine |
| 168 | 300.19 | [M + H]⁺ | D | hydroxylamine |
| 170 | 272.11 | [M + H]⁺ | D | hydroxylamine |
| 171 | 300.19 | [M + H]⁺ | D | hydroxylamine |
| 182 | 312.20 | [M + H]⁺ | D | hydroxylamine |
| 184 | 324.22 | [M + H]⁺ | D | hydroxylamine |
| 185 | 338.25 | [M + H]⁺ | D | hydroxylamine |
| 186 | 364.36 | [M + H]⁺ | D | hydroxylamine |
| 190 | 256.12 | [M + H]⁺ | D | methylamine |
| 191 | 270.12 | [M + H]⁺ | D | methylamine |
| 192 | 284.15 | [M + H]⁺ | D | methylamine |
| 193 | 298.21 | [M + H]⁺ | D | methylamine |
| 195 | 270.12 | [M + H]⁺ | D | methylamine |
| 196 | 284.15 | [M + H]⁺ | D | methylamine |
| 197 | 298.22 | [M + H]⁺ | D | methylamine |
| 208 | 310.23 | [M + H]⁺ | D | methylamine |
| 210 | 322.26 | [M + H]⁺ | D | methylamine |
| 211 | 336.28 | [M + H]⁺ | D | methylamine |
| 212 | 362.30 | [M + H]⁺ | D | methylamine |
| 215 | 256.12 | [M + H]⁺ | D | dimethylamine |
| 216 | 270.12 | [M + H]⁺ | D | dimethylamine |
| 217 | 284.16 | [M + H]⁺ | D | dimethylamine |
| 218 | 298.21 | [M + H]⁺ | D | dimethylamine |
| 219 | 312.23 | [M + H]⁺ | D | dimethylamine |
| 221 | 284.15 | [M + H]⁺ | D | dimethylamine |
| 222 | 298.21 | [M + H]⁺ | D | dimethylamine |
| 223 | 312.24 | [M + H]⁺ | D | dimethylamine |
| 234 | 324.27 | [M + H]⁺ | D | dimethylamine |
| 236 | 336.28 | [M + H]⁺ | D | dimethylamine |
| 237 | 350.30 | [M + H]⁺ | D | dimethylamine |
| 238 | 376.33 | [M + H]⁺ | D | dimethylamine |
| 241 | 229.09 | [M + H]⁺ | D | ammonia |
| 242 | 243.09 | [M + H]⁺ | D | ammonia |
| 243 | 257.11 | [M + H]⁺ | D | ammonia |
| 244 | 271.12 | [M + H]⁺ | D | ammonia |
| 245 | 285.15 | [M + H]⁺ | D | ammonia |
| 247 | 257.11 | [M + H]⁺ | D | ammonia |
| 248 | 285.16 | [M + H]⁺ | D | ammonia |
| 250 | 283.04 | [M + H]⁺ | D | ammonia |
| 259 | 297.17 | [M + H]⁺ | D | ammonia |
| 261 | 309.21 | [M + H]⁺ | D | ammonia |
| 262 | 323.26 | [M + H]⁺ | D | ammonia |
| 263 | 349.29 | [M + H]⁺ | D | ammonia |
| 266 | 245.07 | [M + H]⁺ | D | hydroxylamine |
| 267 | 259.09 | [M + H]⁺ | D | hydroxylamine |
| 268 | 273.11 | [M + H]⁺ | D | hydroxylamine |
| 269 | 287.14 | [M + H]⁺ | D | hydroxylamine |
| 270 | 301.18 | [M + H]⁺ | D | hydroxylamine |
| 272 | 273.12 | [M + H]⁺ | D | hydroxylamine |
| 273 | 301.19 | [M + H]⁺ | D | hydroxylamine |
| 275 | 299.08 | [M + H]⁺ | D | hydroxylamine |
| 284, | 313.20 | [M + H]⁺ | D | hydroxylamine |
| 286 | 325.21 | [M + H]⁺ | D | hydroxylamine |
| 287 | 339.24 | [M + H]⁺ | D | hydroxylamine |
| 288 | 365.29 | [M + H]⁺ | D | hydroxylamine |
| 291 | 243.10 | [M + H]⁺ | D | methylamine |
| 292 | 257.11 | [M + H]⁺ | D | methylamine |
| 293 | 271.12 | [M + H]⁺ | D | methylamine |
| 294 | 285.15 | [M + H]⁺ | D | methylamine |
| 295 | 299.21 | [M + H]⁺ | D | methylamine |
| 297 | 271.12 | [M + H]⁺ | D | methylamine |
| 298 | 299.21 | [M + H]⁺ | D | methylamine |
| 300 | 297.08 | [M + H]⁺ | D | methylamine |
| 309 | 311.22 | [M + H]⁺ | D | methylamine |
| 311 | 323.25 | [M + H]⁺ | D | methylamine |
| 312 | 337.26 | [M + H]⁺ | D | methylamine |
| 313 | 363.32 | [M + H]⁺ | D | methylamine |
| 316 | 257.11 | [M + H]⁺ | D | dimethylamine |
| 317 | 271.12 | [M + H]⁺ | D | dimethylamine |
| 318 | 285.15 | [M + H]⁺ | D | dimethylamine |
| 319 | 299.21 | [M + H]⁺ | D | dimethylamine |
| 320 | 313.24 | [M + H]⁺ | D | dimethylamine |
| 322 | 285.16 | [M + H]⁺ | D | dimethylamine |
| 323 | 313.25 | [M + H]⁺ | D | dimethylamine |

TABLE XIV-continued

List of Synthesized compounds

| Compound Number | m/z | ESI Ion Type | General Procedure | Nucleophile used in the General Procedure |
|---|---|---|---|---|
| 325 | 311.13 | [M + H]⁺ | D | dimethylamine |
| 334 | 325.26 | [M + H]⁺ | D | dimethylamine |
| 336 | 337.26 | [M + H]⁺ | D | dimethylamine |
| 337 | 351.28 | [M + H]⁺ | D | dimethylamine |
| 338 | 377.32 | [M + H]⁺ | D | dimethylamine |
| 341 | 245.13 | [M − H]⁻ | B | NaOH |
| 342 | 259.15 | [M − H]⁻ | B | NaOH |
| 343 | 273.17 | [M − H]⁻ | B | NaOH |
| 344 | 287.18 | [M − H]⁻ | B | NaOH |
| 345 | 301.21 | [M − H]⁻ | B | NaOH |
| 347 | 273.15 | [M − H]⁻ | B | NaOH |
| 348 | 301.24 | [M − H]⁻ | B | NaOH |
| 350 | 299.12 | [M − H]⁻ | B | NaOH |
| 359 | 313.24 | [M − H]⁻ | B | NaOH |
| 363 | 365.39 | [M − H]⁻ | B | NaOH |
| 374 | 317.22 | [M + H]⁺ | C | methanol |
| 385 | 329.24 | [M + H]⁺ | C | methanol |
| 389 | 381.34 | [M + H]⁺ | C | methanol |
| 392 | 275.09 | [M + H]⁺ | A | 4-methylphenol |
| 393 | 289.13 | [M + H]⁺ | A | 4-ethylphenol |
| 394 | 303.17 | [M + H]⁺ | A | 4-n-propylphenol |
| 395 | 317.23 | [M + H]⁺ | A | 4-n-butylphenol |
| 396 | 331.24 | [M + H]⁺ | A | 4-n-pentylphenol |
| 398 | 303.19 | [M + H]⁺ | A | 4-isopropylphenol |
| 399 | 331.25 | [M + H]⁺ | A | 4-tert-pentylphenol |
| 401 | 329.17 | [M + H]⁺ | A | 4-(trifluoromethyl)phenol |
| 410 | 343.28 | [M + H]⁺ | A | 4-cyclohexylphenol |
| 414 | 395.33 | [M + H]⁺ | A | 4-(1-adamantyl)phenol |
| 417 | 246.12 | [M − H]⁻ | B | NaOH |
| 423 | 274.15 | [M − H]⁻ | B | NaOH |
| 424 | 288.17 | [M − H]⁻ | B | NaOH |
| 425 | 304.16 | [M + H]⁺ | B | NaOH |
| 427 | 300.10 | [M − H]⁻ | B | NaOH |
| 436 | 314.24 | [M − H]⁻ | B | NaOH |
| 440 | 368.29 | [M + H]⁺ | B | NaOH |
| 451 | 318.21 | [M + H]⁺ | C | methanol |
| 462 | 330.23 | [M + H]⁺ | C | methanol |
| 466 | 382.29 | [M + H]⁺ | C | methanol |
| 469 | 276.08 | [M + H]⁺ | A | 4-methylphenol |
| 475 | 304.15 | [M + H]⁺ | A | 4-isopropylphenol |
| 476 | 318.20 | [M + H]⁺ | A | 4-tert-butylphenol |
| 477 | 332.24 | [M + H]⁺ | A | 4-tert-pentylphenol |
| 479 | 330.14 | [M + H]⁺ | A | 4-(trifluoromethyl)phenol |
| 488 | 344.24 | [M + H]⁺ | A | 4-cyclohexylphenol |
| 492 | 396.29 | [M + H]⁺ | A | 4-(1-adamantyl)phenol |
| 503 | 302.20 | [M + H]⁺ | D | ammonia |
| 514 | 314.20 | [M + H]⁺ | D | ammonia |
| 518 | 366.29 | [M + H]⁺ | D | ammonia |
| 529 | 318.21 | [M + H]⁺ | D | hydroxylamine |
| 540 | 330.23 | [M + H]⁺ | D | hydroxylamine |
| 544 | 382.30 | [M + H]⁺ | D | hydroxylamine |
| 555 | 316.23 | [M + H]⁺ | D | methylamine |
| 566 | 328.25 | [M + H]⁺ | D | methylamine |
| 570 | 380.31 | [M + H]⁺ | D | methylamine |
| 581 | 330.26 | [M + H]⁺ | D | dimethylamine |
| 592 | 342.28 | [M + H]⁺ | D | dimethylamine |
| 596 | 394.33 | [M + H]⁺ | D | dimethylamine |
| 607 | 303.19 | [M + H]⁺ | D | ammonia |
| 618 | 315.21 | [M + H]⁺ | D | ammonia |
| 622 | 367.36 | [M + H]⁺ | D | ammonia |
| 633 | 319.21 | [M + H]⁺ | D | hydroxylamine |
| 644 | 331.21 | [M + H]⁺ | D | hydroxylamine |
| 648 | 383.27 | [M + H]⁺ | D | hydroxylamine |
| 659 | 317.22 | [M + H]⁺ | D | methylamine |
| 670 | 329.25 | [M + H]⁺ | D | methylamine |
| 674 | 381.31 | [M + H]⁺ | D | methylamine |
| 685 | 331.25 | [M + H]⁺ | D | dimethylamine |
| 696 | 343.28 | [M + H]⁺ | D | dimethylamine |
| 700 | 395.31 | [M + H]⁺ | D | dimethylamine |
| 703 | 321.22 | [M − H]⁻ | B | NaOH |
| 704 | 371.30 | [M − H]⁻ | B | NaOH |
| 705 | 339.22 | [M − H]⁻ | B | NaOH |
| 711 | 355.21 | [M − H]⁻ | B | NaOH |
| 712 | 337.16 | [M + H]⁺ | C | methanol |
| 714 | 353.31 | [M − H]⁻ | C | methanol |
| 721 | 351.20 | [M + H]⁺ | A | 4-(1-trifluoromethyl)cyclopropyl)phenol |
| 722 | 401.25 | [M + H]⁺ | A | 4-(1-perfluoroethyl)cyclopropyl)phenol |
| 723 | 369.24 | [M + H]⁺ | A | 4-(1-trifluoromethyl)cyclopropyl)phenol |
| 729 | 385.18 | [M + H]⁺ | A | 2-chloro-4-(1-(trifluoromethyl)cyclopropyl)phenol |
| 730 | 322.22 | [M − H]⁻ | B | NaOH |
| 731 | 374.19 | [M + H]⁺ | B | NaOH |
| 732 | 340.21 | [M − H]⁻ | B | NaOH |
| 738 | 358.13 | [M + H]⁺ | B | NaOH |
| 739 | 338.17 | [M + H]⁺ | C | methanol |
| 740 | 388.21 | [M + H]⁺ | C | methanol |
| 741 | 356.19 | [M + H]⁺ | C | methanol |
| 747 | 372.15 | [M + H]⁺ | C | methanol |
| 748 | 352.21 | [M + H]⁺ | A | 4-(1-trifluoromethyl)cyclopropyl)phenol |
| 749 | 402.25 | [M + H]⁺ | A | 4-(1-perfluoroethyl)cyclopropyl)phenol |
| 750 | 370.20 | [M + H]⁺ | A | 4-(1-trifluoromethyl)cyclopropyl)phenol |
| 756 | 386.17 | [M + H]⁺ | A | 2-chloro-4-(1-(trifluoromethyl)cyclopropyl)phenol |
| 757 | 322.18 | [M + H]⁺ | D | ammonia |
| 759 | 340.18 | [M + H]⁺ | D | ammonia |
| 766 | 338.17 | [M + H]⁺ | D | hydroxylamine |
| 767 | 388.22 | [M + H]⁺ | D | hydroxylamine |
| 768 | 356.19 | [M + H]⁺ | D | hydroxylamine |
| 774 | 372.19 | [M + H]⁺ | D | hydroxylamine |
| 775 | 336.20 | [M + H]⁺ | D | methylamine |
| 777 | 354.19 | [M + H]⁺ | D | methylamine |
| 784 | 350.21 | [M + H]⁺ | D | dimethylamine |
| 785 | 400.26 | [M + H]⁺ | D | dimethylamine |
| 786 | 368.22 | [M + H]⁺ | D | dimethylamine |
| 792 | 384.23 | [M + H]⁺ | D | dimethylamine |
| 793 | 323.17 | [M + H]⁺ | D | ammonia |
| 794 | 373.21 | [M + H]⁺ | D | ammonia |
| 795 | 341.17 | [M + H]⁺ | D | ammonia |
| 801 | 357.14 | [M + H]⁺ | D | ammonia |
| 802 | 339.17 | [M + H]⁺ | D | hydroxylamine |
| 803 | 389.22 | [M + H]⁺ | D | hydroxylamine |
| 804 | 357.17 | [M + H]⁺ | D | hydroxylamine |
| 810 | 373.17 | [M + H]⁺ | D | hydroxylamine |
| 811 | 337.18 | [M + H]⁺ | D | methylamine |
| 812 | 387.23 | [M + H]⁺ | D | methylamine |
| 813 | 355.20 | [M + H]⁺ | D | methylamine |
| 819 | 371.17 | [M + H]⁺ | D | methylamine |
| 820 | 351.21 | [M + H]⁺ | D | dimethylamine |
| 821 | 401.26 | [M + H]⁺ | D | dimethylamine |
| 822 | 369.21 | [M + H]⁺ | D | dimethylamine |
| 828 | 385.21 | [M + H]⁺ | D | dimethylamine |

Synthesis of Representative Compounds
Compound 005:

4-(4-Pentylphenoxy)benzoic Acid

Following general procedure B, to a solution of ethyl 4-(4-pentylphenoxy)benzoate (1.69 g, 5.4 mmol) in THF (25 mL) and MeOH (3 mL) was added 2 M aqueous NaOH (10 mL, 20 mmol) and the reaction was stirred at room temperature for 48 hours. The organic solvents were evaporated and the residue acidified with 5 M aqueous HCl to adjust a pH of 1-2. The aqueous layer was extracted with EtOAc (3×). The combined organics were washed with brine (1×), dried over Na$_2$SO$_4$, filtered and concentrated in vacuo. The residue was purified by recrystallization from hot EtOAc to give the title compound as colorless solid (1.21 g, 79%). $^1$H NMR (300 MHz, CDCl$_3$) δ 8.12-8.01 (m, 2H), 7.25-7.15 (m, 2H), 7.05-6.94 (m, 4H), 2.68-2.57 (m, 2H), 1.72-1.56 (m, 2H), 1.46-1.33 (m, 2H), 1.38-1.23 (m, 2H), 0.97-0.86 (m, 3H). $^{13}$C NMR (75 MHz, CDCl$_3$) δ 171.9, 163.3, 153.2, 139.7, 132.5, 130.0, 123.3, 120.4, 117.0, 35.4, 31.6, 31.4, 22.7, 14.2. HRMS (C$_{18}$H$_{19}$O$_3^-$): expected: 283.1339; found: 283.1326.

Compound 030:

Methyl 4-(4-(tert-Pentyl)phenoxy)benzoate

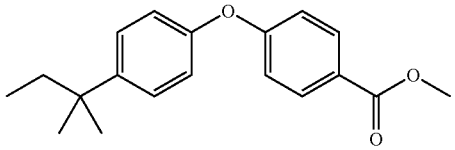 [SMILES: CCC(C)(C)c1ccc(Oc2ccc(C(=O)OC)cc2)cc1]

Following general procedure C, to a solution of 4-(4-(tert-pentyl)phenoxy)benzoic acid (122 mg, 0.43 mmol) in MeOH (2 mL) was added SOCl$_2$ (0.1 mL, 1.4 mmol) at 0° C. and the reaction was then stirred at 80° C. in a sealed vessel for 3 hours in an argon atmosphere. The reaction was cooled to room temperature and quenched by the addition of saturated aqueous NaHCO$_3$. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 90% PE-EtOAc gradient to give the title compound as colorless oil (120 mg, 94%). $^1$H NMR (300 MHz, CDCl$_3$) δ 8.05-7.94 (m, 2H), 7.39-7.28 (m, 2H), 7.04-6.92 (m, 4H), 3.89 (s, 3H), 1.65 (q, J=7.4 Hz, 2H), 1.30 (s, 6H), 0.71 (t, J=7.4 Hz, 3H). $^{13}$C NMR (75 MHz, CDCl$_3$) δ 166.8, 162.3, 153.1, 146.0, 131.8, 127.6, 124.3, 119.7, 117.2, 52.1, 37.8, 37.1, 28.7, 9.3. HRMS (C$_{19}$H$_{23}$O$_3^+$): expected: 299.1642; found: 299.1640.

Compound 044:

(+)-Methyl 4-(4-(bicyclo[2.2.2]octan-2-yl)phenoxy) benzoate

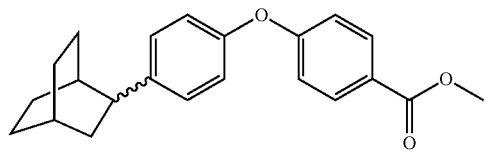 [SMILES: COC(=O)c1ccc(Oc2ccc(C3CC4CCC3CC4)cc2)cc1]

Following general procedure C, to a solution of (±)-4-(4-(Bicyclo[2.2.2]octan-2-yl)phenoxy)benzoic acid (30.3 mg, 0.1 mmol) in toluene (1 mL) was added one drop of DMF followed by SOCl$_2$ (0.02 mL, 0.3 mmol) at room temperature and the reaction was then stirred at 80° C. for 3.5 hours in an argon atmosphere. The reaction was cooled to room temperature and the volatiles evaporated on a rotary evaporator. A solution of NEt$_3$ (0.2 mL, 1.4 mmol) in MeOH (1 mL) was added and the reaction was stirred at room temperature overnight in an argon atmosphere. The reaction was quenched by the addition of 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 85% PE-EtOAc gradient to give the title compound as colorless oil (29.3 mg, 93%). $^1$H NMR (300 MHz, CDCl$_3$) δ 8.05-7.94 (m, 2H), 7.35-7.21 (m, 2H), 7.06-6.91 (m, 4H), 3.89 (s, 3H), 3.11-2.94 (m, 1H), 2.01 (dddd, J=12.9, 10.6, 3.9, 1.9 Hz, 1H), 1.85-1.45 (m, 10H), 1.43-1.23 (m, 1H). $^{13}$C NMR (75 MHz, CDCl$_3$) δ 166.8, 162.3, 153.3, 143.1, 131.8, 129.3, 124.3, 120.0, 117.1, 52.1, 41.4, 32.6, 31.2, 27.6, 26.1, 25.4, 24.9, 20.6. HRMS (C$_{22}$H$_{25}$O$_3^+$): expected: 337.1798; found: 337.1778.

Compound 051:

Ethyl 4-(4-butylphenoxy)benzoate

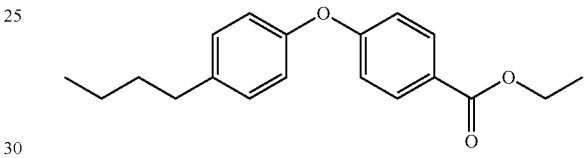

Following general procedure A, to 4-butylphenol (1.75 mL, 11.4 mmol) and K$_2$CO$_3$ (1.89 g, 13.7 mmol) in DMSO (18 mL) was added ethyl 4-fluorobenzoate (1.35 mL, 9.2 mmol) and the reaction was then stirred at 120° C. for 3 days in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over Na$_2$SO$_4$, filtered and concentrated in vacuo. The residue was purified by silica gel flash chromatography eluting with a 100% to 70% PE-DCM gradient to give the title compound as colorless oil (1.72 g, 63%). $^1$H NMR (300 MHz, CDCl$_3$) δ 8.05-7.94 (m, 2H), 7.24-7.13 (m, 2H), 7.02-6.91 (m, 4H), 4.36 (q, J=7.1 Hz, 2H), 2.67-2.56 (m, 2H), 1.69-1.53 (m, 2H), 1.47-1.23 (m, 5H), 0.95 (t, J=7.3 Hz, 3H). $^{13}$C NMR (75 MHz, CDCl$_3$) δ 166.3, 162.3, 153.5, 139.4, 131.7, 130.0, 124.7, 120.1, 117.1, 60.9, 35.1, 33.8, 22.5, 14.5, 14.1. HRMS (C$_{19}$H$_{23}$O$_3^+$): expected: 299.1642; found: 299.1642.

Compound 071:

6-(4-Propylphenoxy)nicotinic Acid

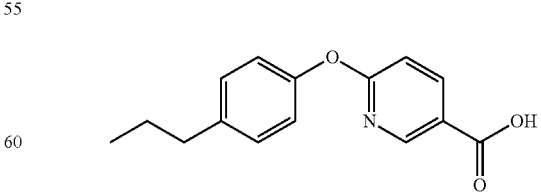

Following general procedure B, to a solution of ethyl 6-(4-propylphenoxy)nicotinate (2.11 g, 7.4 mmol) in EtOH (15 mL) was added 2 M aqueous NaOH (10 mL, 20 mmol) and the reaction was stirred at room temperature for 48 hours. The reaction was acidified with 5 M aqueous HCl to adjust a pH of 1-2. The aqueous layer was extracted with EtOAc (3×). The combined organics were washed with brine (1×), dried over Na$_2$SO$_4$, filtered and concentrated in vacuo. The residue was purified by recrystallization from hot EtOAc to give the title compound as colorless solid (1.26 g, 66%). $^1$H NMR (300 MHz, CDCl$_3$) δ 11.01 (br, s, 1H), 8.92 (dd, J=2.4, 0.7 Hz, 1H), 8.31 (dd, J=8.7, 2.4 Hz, 1H), 7.28-7.18 (m, 2H), 7.12-7.02 (m, 2H), 6.94 (dd, J=8.7, 0.7 Hz, 1H), 2.61 (dd, J=8.7, 6.7 Hz, 2H), 1.76-1.58 (m, 2H), 0.97 (t, J=7.3 Hz, 3H). $^{13}$C NMR (75 MHz, CDCl$_3$) δ 170.5, 167.4, 151.4, 151.2, 141.2, 140.2, 129.9, 121.3, 120.3, 110.9, 37.6, 24.6, 14.0. HRMS (C$_{15}$H$_{14}$NO$_3^-$): expected: 256.0979; found: 256.0979.

Compound 114:

Methyl 6-(4-(adamantan-1-yl)phenoxy)nicotinate

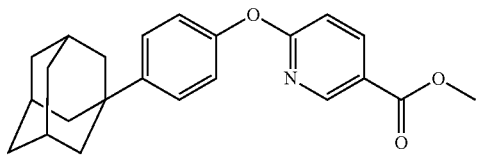 [SMILES: COC(=O)c1ccc(Oc2ccc(C34CC5CC(CC(C5)C3)C4)cc2)nc1]

Following general procedure C, to a solution of 6-(4-(adamantan-1-yl)phenoxy)nicotinic acid (170 mg, 0.49 mmol) in MeOH (2 mL) was added SOCl$_2$ (0.1 mL, 1.37 mmol) at room temperature and the reaction was then stirred at 80° C. in a sealed vessel for 3.5 hours in an argon atmosphere. The reaction was cooled to room temperature and quenched by the addition of saturated aqueous NaHCO$_3$. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 90% PE-EtOAc gradient to give the title compound as colorless solid (47 mg, 27%). $^1$H NMR (300 MHz, CDCl$_3$) δ 8.84 (dd, J=2.4, 0.7 Hz, 1H), 8.25 (dd, J=8.6, 2.4 Hz, 1H), 7.46-7.35 (m, 2H), 7.15-7.04 (m, 2H), 6.90 (dd, J=8.6, 0.7 Hz, 1H), 3.91 (s, 3H), 2.11 (p, j=3.0 Hz, 4H), 1.93 (d, J=2.9 Hz, 6H), 1.87-1.68 (m, 6H). $^{13}$C NMR (75 MHz, CDCl$_3$) δ 166.7, 165.6, 150.9, 150.5, 148.4, 140.5, 126.3, 121.0, 120.7, 110.7, 52.2, 43.3, 36.8, 36.0, 29.0. HRMS (C$_{23}$H$_{26}$NO$_3^+$): expected: 364.1907; found: 364.1900.

Compound 117:

Ethyl 6-(4-Ethylphenoxy)nicotinate

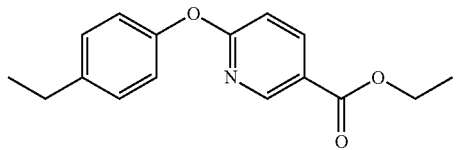 [SMILES: CCOC(=O)c1ccc(Oc2ccc(CC)cc2)nc1]

Following general procedure A, to 4-ethylphenol (1.36 g, 11.1 mmol) and K$_2$CO$_3$ (1.89 g, 13.7 mmol) in DMSO (18 mL) was added ethyl 6-chloronicotinate (1.65 mL, 10.9 mmol) and the reaction was then stirred at 80° C. for 48 hours in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over Na$_2$SO$_4$, filtered and concentrated in vacuo. The residue was purified by silica gel flash chromatography eluting with a 90% to 60% PE-MeOH gradient to give the title compound as colorless oil (1.78 g, 60%). $^1$H NMR (300 MHz, CDCl$_3$) δ 8.83 (dd, J=2.4, 0.7 Hz, 1H), 8.25 (dd, J=8.6, 2.4 Hz, 1H), 7.28-7.20 (m, 2H), 7.11-7.00 (m, 2H), 6.90 (dd, J=8.7, 0.8 Hz, 1H), 4.37 (q, J=7.1 Hz, 2H), 2.68 (q, J=7.6 Hz, 2H), 1.38 (t, J=7.1 Hz, 3H), 1.26 (t, J=7.6 Hz, 3H). $^{13}$C NMR (75 MHz, CDCl$_3$) δ 166.8, 165.2, 151.3, 150.5, 141.4, 140.6, 129.3, 121.4, 121.3, 110.7, 61.2, 28.4, 15.6, 14.4. HRMS (C$_{16}$H$_{18}$NO$_3^+$): expected: 272.1281; found: 272.1271.

Compound 159:

(±)-4-(4-(Bicyclo[2.2.1]heptan-2-yl)phenoxy)benzamide, Mixture of Endo and Exo

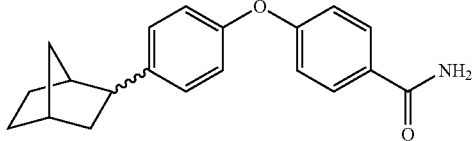 [SMILES: NC(=O)c1ccc(Oc2ccc(C3CC4CCC3C4)cc2)cc1]

Following general procedure D, to a solution of (±)-4-(4-(bicyclo[2.2.1]heptan-2-yl)phenoxy)benzoic acid (50.2 mg, 0.16 mmol) in toluene (0.8 mL) was added one drop of DMF followed by SOCl$_2$ (0.04 mL, 0.55 mmol) at room temperature and the reaction was then stirred at 80° C. for 3 hours in an argon atmosphere. The reaction was cooled to room temperature and the volatiles evaporated on a rotary evaporator. 2 M ammonia in MeOH (0.6 mL, 1.3 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 10% PE-EtOAc gradient to give the title compound as colorless solid (46.6 mg, 93%, 6:1 mixture endo:exo). $^1$H NMR (300 MHz, CDCl$_3$, mixture of rotamers 0.3:1, and diastereoisomers 6:1) δ 7.82-7.72 (m, 2H), 7.26-7.13 (m, 2H), 7.08-6.91 (m, 4H), 6.05 (s, 2H), 3.20 (major diastereomer, tt, J=14.0, 4.8 Hz, 0.85H), 2.79-2.70 (minor diastereomer, m, 0.15H), 2.46-2.29 (major diastereomer, m, 1.7H), 2.28-2.14 (minor diastereomer, m, 0.3H), 2.12-1.10 (m, 8H). $^{13}$C NMR (75 MHz, CDCl$_3$, mixture of rotamers 0.3:1, and diastereoisomers 6:1) δ 169.0, 161.5, 161.4, 153.5, 153.3, 144.1, 140.1, 139.9, 129.8, 129.7, 129.5, 128.6, 127.5, 127.4, 119.9, 119.7, 119.6, 117.6, 117.5, 117.4, 50.3, 46.9, 46.6, 45.6, 43.6, 43.1, 42.7, 42.4, 42.2, 42.1, 41.6, 41.1, 40.7, 39.4, 37.7, 37.7, 37.0, 36.7, 36.4, 36.2, 34.6, 30.7, 30.3, 29.0, 24.7, 24.6, 23.0. HRMS (C$_{20}$H$_{22}$NO$_2^+$): expected: 308.1645; found: 308.1624.

Compound 186:

4-(4-(Adamantan-1-yl)phenoxy)-N-hydroxybenzamide

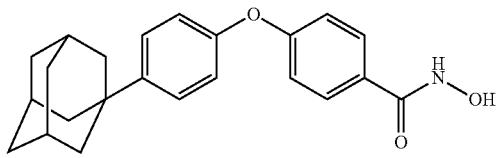 [SMILES: O=C(NO)c1ccc(Oc2ccc(C34CC5CC(CC(C5)C3)C4)cc2)cc1]

Following general procedure D, to a solution of 4-(4-(adamantantan-1-yl)phenoxy)benzoic acid (200 mg, 0.57 mmol) in toluene (2 mL) was added two drops of DMF followed by SOCl$_2$ (0.1 mL, 1.37 mmol) at room temperature and the reaction was then stirred at 80° C. for 3.5 hours in an argon atmosphere. The reaction was cooled to room temperature and the volatiles evaporated on a rotary evaporator. Hydroxylamine hydrochloride (208 mg, 3 mmol) in a solution of NEt$_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed first with 1 M aqueous HCl (1×) then washed with brine (1×), dried over Na$_2$SO$_4$, filtered and concentrated in vacuo. The residue was purified by silica gel flash chromatography eluting with a 90% to 30% PE-EtOAc gradient to give the title compound as colorless solid (176 mg, 84%). $^1$H NMR (300 MHz, CDCl$_3$/DMSO-d$_6$) δ 11.10 (s, 1H), 8.87 (s, 1H), 7.80-7.69 (m, 2H), 7.37-7.26 (m, 2H), 6.98-6.86 (m, 4H), 2.09-2.01 (m, 4H), 1.85 (d, J=2.8 Hz, 6H), 1.81-1.63 (m, 6H). $^{13}$C NMR (75 MHz, CDCl$_3$/DMSO-d$_6$) δ 163.8, 159.7, 152.9, 146.7, 128.6, 126.7, 126.0, 118.9, 116.7, 42.6, 36.1, 35.3, 28.2. HRMS (C$_{23}$H$_{24}$NO$_3$$^-$): expected: 362.1761; found: 362.1672.

Compound 195:

4-(4-Isopropylphenoxy)-N-methylbenzamide

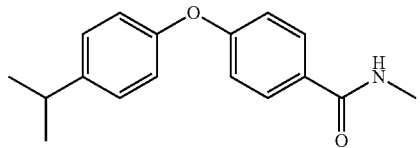

Following general procedure D, to a solution of 4-(4-isopropylphenoxy)benzoic acid (177 mg, 0.7 mmol) in toluene (2.5 mL) was added two drops of DMF followed by SOCl$_2$ (0.15 mL, 2.1 mmol) at room temperature and the reaction was then stirred at 80° C. for 3 hours in an argon atmosphere. The reaction was cooled to room temperature and the volatiles evaporated on a rotary evaporator. 33 wt % methylamine in EtOH (2 mL, 16 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 40% PE-EtOAc gradient to give the title compound as colorless solid (178 mg, 94%). $^1$H NMR (300 MHz, CDCl$_3$) δ 7.78-7.67 (m, 2H), 7.27-7.16 (m, 2H), 7.01-6.90 (m, 4H), 6.31 (s, 1H), 2.98 (d, J=4.6 Hz, 3H), 2.90 (hept, J=6.9 Hz, 1H), 1.26 (d, J=6.9 Hz, 6H). $^{13}$C NMR (75 MHz, CDCl$_3$) δ 167.8, 160.8, 153.8, 145.1, 128.8, 128.8, 127.9, 119.8, 117.5, 33.6, 26.9, 24.2. HRMS (C$_{17}$H$_{18}$NO$_2$$^-$): expected: 268.1343; found: 268.1384.

Compound 222:

4-(4-(tert-Butyl)phenoxy)-N,N-dimethylbenzamide

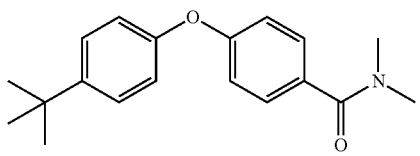 [SMILES: CN(C)C(=O)c1ccc(Oc2ccc(C(C)(C)C)cc2)cc1]

Following general procedure D, to a solution of 4-(4-(tert-butyl)phenoxy)benzoic acid (154 mg, 0.57 mmol) in toluene (2.5 mL) was added two drops of DMF followed by SOCl$_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5 mmol) was added and the reaction was stirred at room temperature overnight in an argon atmosphere.

The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 40% PE-EtOAc gradient to give the title compound as colorless oil (166 mg, 98%). $^1$H NMR (300 MHz, CDCl$_3$) δ 7.44-7.31 (m, 4H), 7.03-6.91 (m, 4H), 3.06 (s, 6H), 1.33 (s, 9H). $^{13}$C NMR (75 MHz, CDCl$_3$) δ 171.4, 159.1, 153.9, 147.0, 130.6, 129.2, 126.8, 119.2, 117.8, 39.9 (br), 35.6 (br), 34.5, 31.6. HRMS (C$_{19}$H$_{24}$NO$_2$$^+$): expected: 298.1802; found: 298.1820.

Compound 241:

6-(p-Tolyloxy)nicotinamide

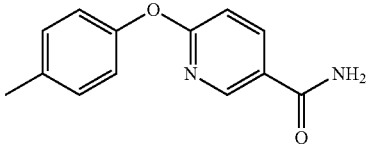 [SMILES: Cc1ccc(Oc2ccc(C(N)=O)cn2)cc1]

Following general procedure D, to a solution of 6-(p-tolyloxy)nicotinic acid (148 mg, 0.66 mmol) in toluene (2.5 mL) was added two drops of DMF followed by SOCl$_2$ (0.12 mL, 1.6 mmol) at room temperature and the reaction was then stirred at 80° C. for 3.5 hours in an argon atmosphere. The reaction was cooled to room temperature and the volatiles evaporated on a rotary evaporator. 2 M ammonia in MeOH (3 mL, 1.3 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 20% PE-EtOAc gradient to give the title compound as colorless solid (104 mg, 70%). $^1$H NMR (300 MHz, CDCl$_3$/DMSO-d$_6$, mixture of rotamers 0.3:1) δ 8.89 (d, J=2.5 Hz, 0.25H, minor rotamer), 8.65 (d, J=2.4 Hz, 0.75H, major rotamer), 8.25 (dt, J=8.6, 2.9 Hz, 1H), 7.96 (br, s, 1H), 7.49 (d, J=8.4 Hz, 0.25H, minor rotamer), 7.27 (br, s, 1H), 7.21 (d, i=8.2 Hz, 2H), 7.06-6.97 (m, 2H), 6.93 (d, J=8.6 Hz, 0.75H, major rotamer), 2.35 (s, 3H). $^{13}$C NMR (75 MHz, CDCl$_3$/DMSO-d$_6$, mixture of rotamers 0.3:1) δ 166.6, 165.9 (minor rotamer), 165.4. (major rotamer), 153.3 (minor rotamer), 151.5 (major rotamer), 149.7 (minor rotamer), 148.0 (major rotamer), 139.5 (major rotamer), 138.9 (minor rotamer), 134.4, 130.3, 129.3 (minor rotamer), 125.2 (major rotamer), 124.1 (minor rotamer), 121.4, 110.5 (major rotamer), 20.9. HRMS (C$_{13}$H$_{13}$N$_2$O$_2$$^+$): expected: 229.0972; found: 229.0978.

Compound 275:

N-Hydroxy-6-(4-(trifluoromethyl)phenoxy)nicotinamide

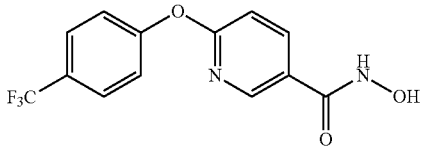 [SMILES: O=C(NO)c1ccc(Oc2ccc(C(F)(F)F)cc2)nc1]

Following general procedure D, to a solution of 6-(4-(trifluoromethyl)phenoxy)nicotinic acid (62.9 mg, 0.22 mmol) in toluene (1.5 mL) was added two drops of DMF followed by SOCl$_2$ (0.06 mL, 0.82 mmol) at room temperature and the reaction was then stirred at 80° C. for 3 hours in an argon atmosphere. The reaction was cooled to room temperature and the volatiles evaporated on a rotary evaporator. Hydroxylamine hydrochloride (94 mg, 1.35 mmol) in a solution of NEt$_3$ (0.5 mL, 3.6 mmol) and MeOH (1 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 40% PE-EtOAc (+0.2% AcOH) gradient to give the title compound as colorless solid (42.7 mg, 65%). $^1$H NMR (300 MHz, CDCl$_3$/DMSO-d$_6$) δ 11.29 (s, 1H), 9.07 (s, 1H), 8.52 (d, J=2.4 Hz, 1H), 8.19 (dd, J=8.6, 2.4 Hz, 1H), 7.69 (d, J=8.4 Hz, 2H), 7.29 (d, J=8.4 Hz, 2H), 7.06 (d, J=8.5 Hz, 1H). $^{13}$C NMR (75 MHz, CDCl$_3$/DMSO-d$_6$) δ 163.6, 161.9, 156.2 (d, J=1.5 Hz), 146.4, 138.8, 126.6 (q, j=3.8 Hz), 125.6 (q, j=32.4 Hz), 124.2, 123.8 (q, j=273.0 Hz), 121.5, 111.1. HRMS (C$_{13}$Hs$_{83}$N$_2$O$_3$$^-$): expected: 297.0492; found: 297.0597.

Compound 284:

6-(4-Cyclohexylphenoxy)-N-hydroxynicotinamide

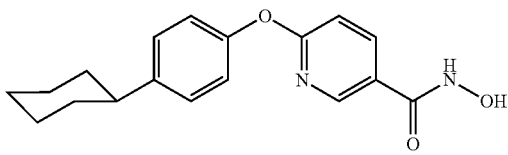 [SMILES: O=C(NO)c1ccc(Oc2ccc(C3CCCCC3)cc2)nc1]

Following general procedure D, to a solution of 6-(4-cyclohexylphenoxy)nicotinic acid (150 mg, 0.5 mmol) in toluene (2 mL) was added two drops of DMF followed by SOCl$_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. Hydroxylamine hydrochloride (208 mg, 3 mmol) in a solution of NEt$_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 95% PE-EtOAc gradient to give the title compound as colorless solid (150 mg, 95%). $^1$H NMR (300 MHz, CDCl$_3$/DMSO-d$_6$) δ 11.27 (s, 1H), 9.05 (s, 1H), 8.54 (s, 1H), 8.20-8.06 (m, 1H), 7.23 (d, j=8.0 Hz, 2H), 7.02 (d, J=8.0 Hz, 2H), 6.95 (d, J=8.6 Hz, 1H), 1.86 (d, j=8.3 Hz, 4H), 1.74 (d, J=12.6 Hz, 1H), 1.43 (q, J=11.3, 10.1 Hz, 4H), 1.35-1.16 (m, 2H). $^{13}$C NMR (75 MHz, CDCl$_3$/DMSO-d$_6$) δ 163.4, 160.9, 149.8, 145.2, 142.8, 137.1, 126.2, 122.0, 119.5, 109.0, 41.9, 32.7, 25.0, 24.2. HRMS (C$_{18}$H$_{21}$N$_2$O$_3$$^+$): expected: 313.1547; found: 313.1622.

Compound 297:

6-(4-Isopropylphenoxy)-N-methylnicotinamide

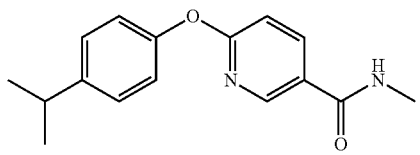

Following general procedure D, to a solution of 6-(4-isopropylphenoxy)nicotinic acid (151 mg, 0.6 mmol) in toluene (2.5 mL) was added two drops of DMF followed by SOCl$_2$ (0.1 mL, 1.5 mmol) at room temperature and the reaction was then stirred at 80° C. for 3 hours in an argon atmosphere. 33 wt % methylamine in EtOH (2.5 mL, 20 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 20% PE-EtOAc gradient to give the title compound as colorless solid (150 mg, 96%). $^1$H NMR (300 MHz, CDCl$_3$) δ 8.55 (dd, J=2.5, 0.7 Hz, 1H), 8.11 (dd, J=8.6, 2.5 Hz, 1H), 7.32-7.21 (m, 2H), 7.11-7.00 (m, 2H), 6.90 (dd, J=8.6, 0.7 Hz, 1H), 6.47 (d, J=5.3 Hz, 1H), 2.98 (d, J=4.7 Hz, 3H), 2.94 (hept, J=7.0 Hz, 1H), 1.27 (d, J=6.9 Hz, 6H). 13C NMR (75 MHz, CDCl$_3$) δ 166.1, 165.8, 151.4, 146.6, 145.9, 139.0, 127.8, 125.3, 121.1, 111.0, 33.7, 26.9, 24.1. HRMS (C$_{16}$H$_{19}$N$_2$O$_2$$^+$): expected: 271.1441; found: 271.1491.

Compound 322:

6-(4-Isopropylphenoxy)-N,N-dimethylnicotinamide

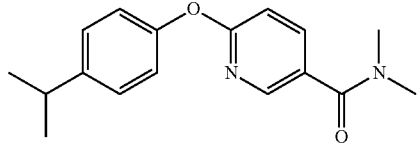 [SMILES: CC(C)c1ccc(Oc2ccc(C(=O)N(C)C)cn2)cc1]

Following general procedure D, to a solution of 6-(4-isopropylphenoxy)nicotinic acid (156 mg, 0.6 mmol) in toluene (2.5 mL) was added two drops of DMF followed by SOCl$_2$ (0.1 mL, 1.5 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5.4 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 30% PE-EtOAc gradient to give the title compound as colorless oil (169 mg, 98%). $^1$H NMR (300 MHz, CDCl$_3$) δ 8.28 (dd, J=2.4, 0.8 Hz, 1H), 7.79 (dd, J=8.5, 2.4 Hz, 1H), 7.31-7.20 (m, 2H), 7.11-7.00 (m, 2H), 6.91 (dd, J=8.5, 0.7 Hz, 1H), 3.07 (s, 6H), 2.92 (hept, J=7.0 Hz, 1H), 1.26 (d, J=6.9 Hz, 6H). $^{13}$C NMR (75 MHz, CDCl$_3$) δ 168.9, 164.5, 151.4, 146.8, 145.6, 139.2, 127.7, 126.6, 121.0, 111.0, 39.7 (br), 35.6 (br), 33.6, 24.1. HRMS (C$_{17}$H$_{21}$N$_2$O$_2$$^+$): expected: 285.1598; found: 285.1643.

Compound 344:

4-(4-(Butylphenoxy)-3-fluorobenzoic Acid

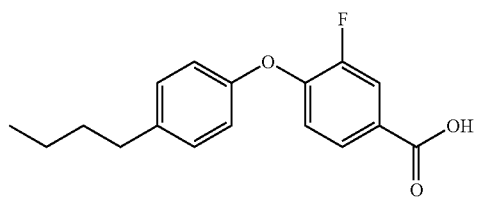 [SMILES: CCCCc1ccc(Oc2ccc(C(=O)O)cc2F)cc1]

Following general procedure B, to a solution of ethyl 4-(4-butylphenoxy)-3-fluorobenzoate (1.42 g, 4.5 mmol) in EtOH (9 mL) was added 2 M aqueous NaOH (5 mL, 10 mmol) and the reaction was stirred at room temperature overnight. 1 M aqueous HCl was added to adjust a pH of 1-2. The aqueous layer was extracted with EtOAc (3×). The combined organics were washed with brine (2×), dried over Na$_2$SO$_4$, filtered and concentrated in vacuo. The residue was purified by recrystallization from hot EtOAc to give the title compound as colorless solid (0.56 g, 43%). $^1$H NMR (300 MHz, CDCl$_3$) δ 11.18 (br, s, 1H), 7.91 (dd, J=11.0, 2.0 Hz, 1H), 7.82 (ddd, J=8.6, 2.0, 1.1 Hz, 1H), 7.26-7.15 (m, 2H), 7.04-6.88 (m, 3H), 2.68-2.57 (m, 2H), 1.70-1.54 (m, 2H), 1.47-1.23 (m, 2H), 0.95 (t, J=7.3 Hz, 3H). $^{13}$C NMR (75 MHz, CDCl$_3$) δ 171.0 (d, J=2.5 Hz), 153.3, 152.9 (d, J=249.5 Hz), 150.8 (d, J=11.0 Hz), 139.7, 130.1, 127.3 (d, J=3.5 Hz), 124.3 (d, J=6.5 Hz), 119.4, 118.9 (d, J=19.9 Hz), 118.6 (d, J=1.4 Hz), 35.1, 33.8, 22.5, 14.1. HRMS (C$_{17}$H$_{16}$FO$_3$$^-$): expected: 287.1089; found: 287.1062.

Compound 395:

Ethyl 4-(4-butylphenoxy)-3-fluorobenzoate

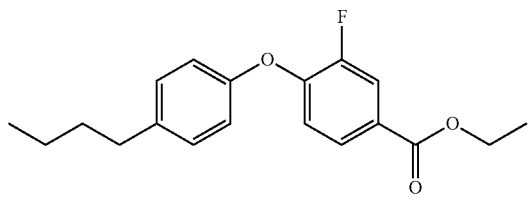 [SMILES: CCCCc1ccc(Oc2ccc(C(=O)OCC)cc2F)cc1]

Following general procedure A, to 4-butylphenol (1.75 mL, 11.4 mmol) and K$_2$CO$_3$ (1.90 g, 13.8 mmol) in DMSO (18 mL) was added ethyl 3,4-difluorobenzoate (1.37 mL, 9 mmol) and the reaction was then stirred at 80° C. for 24 hours in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over Na$_2$SO$_4$, filtered and concentrated in vacuo. The residue was purified by silica gel flash chromatography eluting with a 100% to 80% PE-DCM gradient to give the title compound as colorless oil (1.80 g, 63%). $^1$H NMR (300 MHz, CDCl$_3$) δ 7.84 (dd, j=11.2, 2.0 Hz, 1H), 7.75 (ddd, J=8.5, 2.0, 1.2 Hz, 1H), 7.23-7.12 (m, 2H), 7.01-6.88 (m, 3H), 4.37 (q, J=7.1 Hz, 2H), 2.67-2.55 (m, 2H), 1.68-1.52 (m, 2H), 1.46-1.23 (m, 5H), 0.94 (t, J=7.3 Hz, 3H). $^{13}$C NMR (75 MHz, CDCl$_3$) δ 165.4 (d, J=2.6 Hz), 153.7, 153.0 (d, J=249.0 Hz), 149.5 (d, J=11.2 Hz), 139.3, 129.9, 126.4 (d, J=3.5 Hz), 126.0 (d, J=6.3 Hz), 119.0, 119.0 (d, J=1.4 Hz), 118.3 (d, J=19.9 Hz), 61.3, 35.1, 33.8, 22.5, 14.4, 14.1. HRMS (C$_{19}$H$_{22}$FO$_3$$^+$): expected: 317.1548; found: 317.1549.

Compound 451:

Methyl 5-fluoro-6-(4-(tert-pentyl)phenoxy)nicotinate

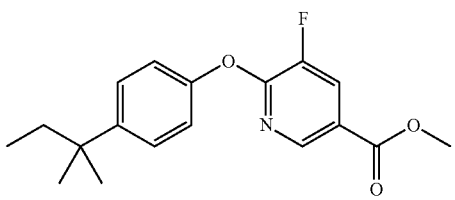

Following general procedure C, to a solution of 5-fluoro-6-(4-(tert-pentyl)phenoxy)nicotinic acid (100 mg, 0.33 mmol) in MeOH (2 mL) was added SOCl$_2$ (0.1 mL, 1.4 mmol) at 0° C. and the reaction was then stirred at 80° C. for 3 hours in an argon atmosphere. The reaction was cooled to room temperature and quenched by the addition of saturated aqueous NaHCO$_3$. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 90% PE-EtOAc gradient to give the title compound as colorless solid (30 mg, 29%). $^1$H NMR (300 MHz, CDCl$_3$) δ 8.56 (d, J=1.9 Hz, 1H), 8.02 (dd, J=10.0, 1.9 Hz, 1H), 7.43-7.31 (m, 2H), 7.17-7.04 (m, 2H), 3.92 (s, 3H), 1.66 (q, J=7.4 Hz, 2H), 1.31 (s, 6H), 0.72 (t, J=7.4 Hz, 3H). $^{13}$C NMR (75 MHz, CDCl$_3$) δ 164.8 (d, J=1.6 Hz), 155.7 (d, J=11.1 Hz), 150.4, 147.1 (d, J=261.8 Hz), 146.9, 144.4 (d, J=6.1 Hz), 127.4, 125.0 (d, J=17.0 Hz), 122.1 (d, J=1.7 Hz), 120.7, 52.6, 37.9, 37.1, 28.6, 9.3. HRMS (C$_{18}$H$_{21}$FNO$_3^+$): expected: 318.1500; found: 318.1555.

Compound 544:

4-(4-(Adamantan-1-yl)phenoxy)-3-fluoro-N-hydroxybenzamide

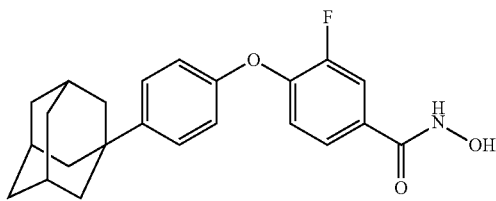

Following general procedure D, to a solution of 4-(4-(adamantan-1-yl)phenoxy)-3-fluorobenzoic acid (110 mg, 0.3 mmol) in toluene (2 mL) was added two drops of DMF followed by SOCl$_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. NEt$_3$ (0.7 mL, 5.1 mmol) and hydroxylamine hydrochloride (148 mg, 2.1 mmol) in MeOH (1.5 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography twice, eluting first with a 100% to 40% PE-EtOAc gradient and then with a 100% to 97% DCM-MeOH gradient to give the title compound as colorless solid (60 mg, 52%). $^1$H NMR (300 MHz, CDCl$_3$/DMSO-d$_6$) δ 11.23 (s, 1H), 9.00 (s, 1H), 7.68 (dd, J=11.6, 2.0 Hz, 1H), 7.57 (ddd, J=8.5, 2.1, 1.1 Hz, 1H), 7.37-7.25 (m, 2H), 6.97 (t, J=8.4 Hz, 1H), 6.96-6.86 (m, 2H), 2.12-1.97 (m, 4H), 1.84 (d, J=2.9 Hz, 6H), 1.80-1.63 (m, 6H). $^{13}$C NMR (75 MHz, CDCl$_3$/DMSO-d$_6$) δ 162.4, 153.2, 152.4 (d, J=247.5 Hz), 146.6, 146.3 (d, J=11.1 Hz), 128.4 (d, J=5.7 Hz), 126.0, 123.5, 119.5, 117.4, 115.5 (d, J=19.6 Hz), 42.6, 36.1, 35.3, 28.2. HRMS (C$_{23}$H$_{23}$FNO$_3^-$): expected: 380.1667; found: 380.1541.

Compound 644:

6-(4-Cyclohexylphenoxy)-5-fluoro-N-hydroxynicotinamide

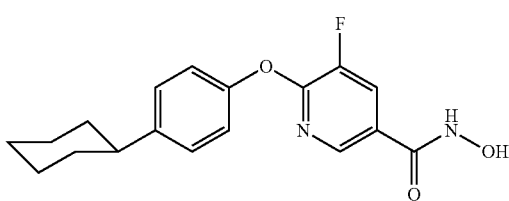 [SMILES: O=C(NO)c1cnc(Oc2ccc(C3CCCCC3)cc2)c(F)c1]

Following general procedure D, to a solution of 6-(4-cyclohexylphenoxy)-5-fluoronicotinic acid (120 mg, 0.4 mmol) in toluene (2.5 mL) was added two drops of DMF followed by SOCl$_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. Hydroxylamine hydrochloride (208 mg, 3 mmol) in a solution of NEt$_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 100% to 30% PE-EtOAc gradient to give the title compound as colorless solid (110 mg, 88%). $^1$H NMR (300 MHz, CDCl$_3$/DMSO-d$_6$) δ 11.32 (s, 1H), 9.12 (s, 1H), 8.28 (d, J=1.9 Hz, 1H), 8.06-7.94 (m, 1H), 7.26-7.15 (m, 2H), 7.08-6.97 (m, 2H), 1.88-1.75 (m, 4H), 1.75-1.64 (m, 1H), 1.48-1.31 (m, 4H), 1.31-1.13 (m, 2H). $^{13}$C NMR (75 MHz, CDCl$_3$/DMSO-d$_6$) δ 161.0, 153.2 (d, j=11.3 Hz), 150.4, 146.3 (d, i=259.6 Hz), 144.4, 140.6, 127.4, 124.5, 123.1 (d, J=16.7 Hz), 120.7, 43.2, 34.0, 26.2, 25.5. HRMS (C$_{18}$H$_{18}$FN$_2$O$_3^-$): expected: 329.1307; found: 329.1279.

Compound 703:

4-(4-(1-Trifluoromethyl)cyclopropyl)phenoxy)benzoic Acid

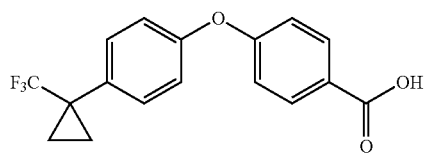 [SMILES: O=C(O)c1ccc(Oc2ccc(C3(C(F)(F)F)CC3)cc2)cc1]

Following general procedure B, to a solution of ethyl 4-(4-(1-(trifluoromethyl)cyclopropyl)phenoxy)benzoate (0.86 g, 2.5 mmol) in EtOH (20 mL) was added 2 M aqueous NaOH (10 mL, 20 mmol) and the reaction was stirred at room temperature overnight. 1 M aqueous HCl was added to adjust a pH of 1-2. The aqueous layer was extracted with EtOAc (3×). The combined organics were washed with brine (2×), dried over Na$_2$SO$_4$, filtered and concentrated in vacuo. The residue was purified by silica gel flash chromatography eluting with a 90% to 75% PE-EtOAc (+0.2% AcOH) gradient to give the title compound as slightly yellow solid (0.75 g, 95%). $^1$H NMR (300 MHz, CDCl$_3$) δ 11.15 (br, s, 1H), 8.15-8.04 (m, 2H), 7.54-7.43 (m, 2H), 7.09-6.98 (m, 4H), 1.38 (dd, J=6.7, 5.1 Hz, 2H), 1.07-1.01 (m, 2H). $^{13}$C NMR (75 MHz, CDCl$_3$) δ 171.8, 162.3, 155.7, 133.2, 132.6, 132.5, 126.5 (q, J=273.4 Hz), 124.0, 119.9, 117.8, 27.8 (q, J=33.7 Hz), 10.0 (q, J=2.4 Hz). HRMS (C$_{17}$H$_{12}$F$_3$O$_3^-$): expected: 321.0744; found: 321.0712.

Compound 712:

Methyl 4-(4-(1-(trifluoromethyl)cyclopropyl)phenoxy)benzoate

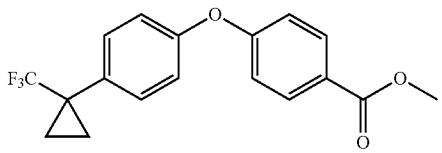 [SMILES: COC(=O)c1ccc(Oc2ccc(C3(C(F)(F)F)CC3)cc2)cc1]

Following general procedure C, to a solution of 4-(4-(1-(Trifluoromethyl)cyclopropyl)phenoxy)benzoic acid (112 mg, 0.35 mmol) in toluene (2 mL) was added two drops of DMF followed by $SOCl_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. A solution of $NEt_3$ (0.6 mL, 4.4 mmol) in MeOH (1.2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 85% PE-EtOAc gradient to give the title compound as colorless oil (176 mg, 93%). $^1$H NMR (300 MHz, $CDCl_3$) δ 8.07-7.96 (m, 2H), 7.52-7.41 (m, 2H), 7.07-6.95 (m, 4H), 3.90 (s, 3H), 1.41-1.31 (m, 2H), 1.09-0.97 (m, 2H). $^{13}$C NMR (75 MHz, $CDCl_3$) δ 166.7, 161.4, 156.0, 133.1, 132.2, 131.9, 126.4 (q, J=273.0 Hz), 125.0, 119.7, 117.9, 52.2, 27.8 (q, J=33.6 Hz), 10.0 (q, J=2.5 Hz). HRMS ($C_{18}H_{16}F_3O_3^+$): expected: 337.1046; found: 337.1036.

Compound 729:

Ethyl 4-(2-chloro-4-(1-(trifluoromethyl)cyclopropyl) phenoxy)-benzoate

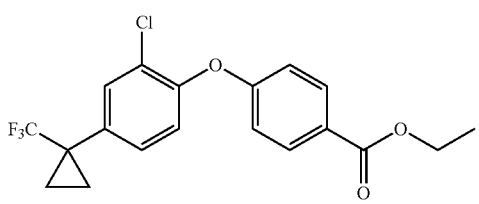 [SMILES: CCOC(=O)c1ccc(Oc2ccc(C3(C(F)(F)F)CC3)cc2Cl)cc1]

Following general procedure A, to 2-chloro-4-(1-(trifluoromethyl)cyclopropyl)phenol (245 mg, 1.5 mmol) and $K_2CO_3$ (220 mg, 1.6 mmol) in DMSO (2 mL) was added ethyl 4-fluorobenzoate (0.15 mL, 1.1 mmol) and the reaction was then stirred at 120° C. for 2 days in an argon atmosphere. $K_2CO_3$ (220 mg, 1.6 mmol) was added and the reaction was then stirred at 150° C. for 9 hours in an argon atmosphere. The reaction was cooled to room temperature and quenched by the addition of water. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 70% PE-DCM gradient to give the title compound as yellow oil (100 mg, 18%). $^1$H NMR (300 MHz, $CDCl_3$) δ 8.08-7.97 (m, 2H), 7.58 (d, J=2.1 Hz, 1H), 7.41-7.27 (m, 1H), 7.03 (d, J=8.4 Hz, 1H), 7.03-6.88 (m, 2H), 4.36 (q, J=7.1 Hz, 2H), 1.44-1.33 (m, 5H), 1.11-1.00 (m, 2H). $^{13}$C NMR (75 MHz, $CDCl_3$) δ 166.0, 160.7, 151.3, 133.9, 133.8, 131.7, 131.1, 126.2, 126.0 (q, J=273.4 Hz), 125.5, 121.6, 116.8, 60.9, 27.6 (q, J=33.1 Hz), 14.4, 10.0 (q, J=2.3 Hz). HRMS ($C_{19}H_{17}ClF_3O_3^+$): expected: 385.0813; found: 385.0796.

Compound 730:

6-(4-(1-(Trifluoromethyl)cyclopropyl)phenoxy)nicotinic Acid

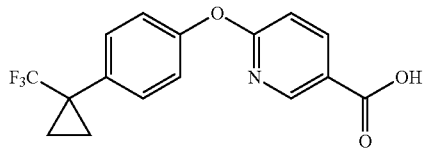

Following general procedure B, to a solution of ethyl 6-(4-(1-(trifluoromethyl)cyclopropyl)phenoxy)nicotinate (1.47 g, 4.2 mmol) in EtOH (20 mL) was added 2 M aqueous NaOH (10 mL, 20 mmol) and the reaction was stirred at room temperature overnight. 1 M aqueous HCl was added to adjust a pH of 1-2. The aqueous layer was extracted with EtOAc (3×). The combined organics were washed with brine (2×), dried over $Na_2SO_4$, filtered and concentrated in vacuo. The residue was purified by silica gel flash chromatography eluting with a 90% to 75% PE-EtOAc (+0.2% AcOH) gradient to give the title compound as colorless solid (1.21 g, 90%). $^1$H NMR (300 MHz, $CDCl_3$/DMSO-$d_6$) δ 12.16 (s, 1H), 8.80 (d, J=2.4 Hz, 1H), 8.30 (dd, =8.6, 2.3 Hz, 1H), 7.51 (dd, J=8.1, 1.6 Hz, 2H), 7.19-7.08 (m, 2H), 6.97 (d, J=8.6 Hz, 1H), 1.41-1.30 (m, 2H), 1.18-1.02 (m, 2H). $^{13}$C NMR (75 MHz, $CDCl_3$/DMSO-$d_6$) δ 166.1, 165.3, 152.9, 149.8, 140.5, 132.2, 132.2, 125.9 (q, J=273.1 Hz), 121.8, 120.7, 110.5, 27.1 (q, J=33.5 Hz), 9.3 (q, J=2.4 Hz). HRMS ($C_{16}H_{13}F_3NO_3+$): expected: 324.0842; found: 324.0847.

Compound 749:

Ethyl 6-(4-(1-(perfluoroethyl)cyclopropyl)phenoxy) nicotinate

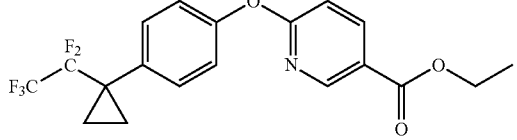

Following general procedure A, to 4-(1-(perfluoroethyl)cyclopropyl)phenol (330 mg, 1.3 mmol) and $K_2CO_3$ (305 mg, 2.2 mmol) in DMSO (2.7 mL) was added ethyl 6-chloronicotinate (0.2 mL, 1.3 mmol) and the reaction was then stirred at 80° C. for 3 days in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over $Na_2SO_4$, filtered and concentrated in vacuo. The residue was purified by silica gel flash chromatography eluting with a 100% to 90% PE-EtOAc gradient to give the title compound as yellow oil (445 mg, 88%). $^1$H NMR (300 MHz, CDCl$_3$) δ 8.83 (dd, J=2.4, 0.7 Hz, 1H), 8.28 (dd, J=8.6, 2.4 Hz, 1H), 7.48 (d, J=8.6 Hz, 2H), 7.14-7.07 (m, 2H), 6.93 (dd, J=8.6, 0.7 Hz, 1H), 4.38 (q, J=7.1 Hz, 2H), 1.43-1.34 (m, 5H), 1.12-1.04 (m, 2H). $^{13}$C NMR (75 MHz, CDCl$_3$) δ 166.14, 165.10, 153.39, 150.44, 140.84, 133.21, 133.12, 121.86, 121.20, 111.12, 61.31, 25.88 (t, J=23.9 Hz), 14.42, 10.02 (t, J=4.0 Hz). The two multiplets of the CF$_2$ (tq) and the CF$_3$ (qt) are too weak to be resolved. HRMS (C$_{19}$H$_{17}$F$_5$NO$_3^+$): expected: 402.1123; found: 402.1124.

Compound 784:

N,N-Dimethyl-4-(4-(1-(trifluoromethyl)cyclopropyl)phenoxy)-benzamide

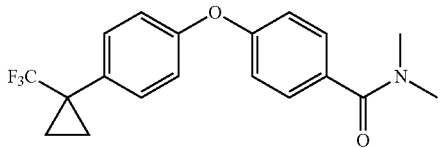 [SMILES: CN(C)C(=O)c1ccc(Oc2ccc(C3(C(F)(F)F)CC3)cc2)cc1]

Following general procedure D, to a solution of 4-(4-(1-(Trifluoromethyl)cyclopropyl)phenoxy)benzoic acid (101 mg, 0.3 mmol) in toluene (2 mL) was added two drops of DMF followed by SOCl$_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (1.2 mL, 2.5 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 15% PE-EtOAc gradient to give the title compound as colorless oil (110 mg, 100%). $^1$H NMR (300 MHz, CDCl$_3$) δ 7.48-7.37 (m, 4H), 7.06-6.92 (m, 4H), 3.06 (d, j=9.8 Hz, 6H), 1.39-1.28 (m, 2H), 1.07-0.95 (m, 2H). $^{13}$C NMR (75 MHz, CDCl$_3$) δ 171.2, 158.2, 156.7, 133.0, 131.6, 131.4, 129.3, 126.5 (q, J=272.1 Hz), 119.0, 118.6, 39.8 (br), 35.6 (br), 27.7 (q, J=33.7 Hz), 10.0 (q, J=2.5 Hz). HRMS (C$_{19}$H$_{19}$F$_3$NO$_2^+$): expected: 350.1363; found: 350.1351.

Compound 820:

N,N-Dimethyl-6-(4-(1-(trifluoromethyl)cyclopropyl)phenoxy)-nicotinamide

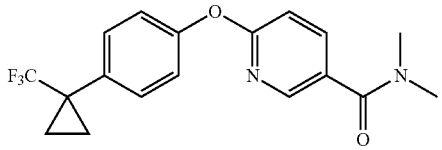

Following general procedure D, to a solution of 6-(4-(1-(trifluoromethyl)cyclopropyl)phenoxy)nicotinic acid (162 mg, 0.5 mmol) in toluene (2 mL) was added two drops of DMF followed by SOCl$_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with a 90% to 30% PE-EtOAc gradient to give the title compound as colorless solid (172 mg, 100%). $^1$H NMR (300 MHz, CDCl$_3$) δ 8.28 (dd, J=2.4, 0.8 Hz, 1H), 7.82 (dd, J=8.5, 2.4 Hz, 1H), 7.54-7.44 (m, 2H), 7.16-7.06 (m, 2H), 6.96 (dd, J=8.5, 0.8 Hz, 1H), 3.18-2.96 (m, 6H), 1.40-1.29 (m, 2H), 1.10-0.98 (m, 2H). $^{13}$C NMR (75 MHz, CDCl$_3$) δ 168.8, 163.9, 153.5, 146.7, 139.3, 132.7, 132.7, 127.1, 126.3 (q, J=274.0 Hz), 121.0, 111.4, 39.7 (br), 35.63 (br), 27.7 (q, J=33.6 Hz), 9.8 (q, J=2.5 Hz). HRMS (C$_{18}$H$_{18}$F$_3$N$_2$O$_2^+$): expected: 351.1315; found: 351.1293.

Synthesis of Intermediates (±)-4-(Bicyclo[2.2.1]heptan-2-yl)phenol, Mixture of Endo and Exo

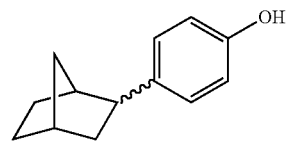 [SMILES: Oc1ccc(C2CC3CCC2C3)cc1]

To a solution of 4-acetoxystyrene (3 mL, 20 mmol) in dicyclopentadiene (3 mL, 22 mmol) was added hydroquinone (10 mg, 0.1 mmol). The reaction vessel was purged with argon and sealed. The reaction mixture was stirred at 160° C. for 24 h. The reaction mixture was filtered through silica and washed with DCM. The solution was concentrated in vacuo and used in the next step without further purification.

The resulting oil was dissolved in EtOAc (40 mL). Under an argon atmosphere, palladium on charcoal (5% Pd, 0.2 g, 0.1 mmol) was added and the reaction vessel was flushed with H$_2$. The reaction was stirred strongly for 22 h at room temperature. The reaction mixture was then purged back with argon, filtered through celite, washed with EtOAc, and concentrated in vacuo. The crude mixture was then filtered on silica (PE/EtOAc), concentrated in vacuo and used in the next step without further purification.

The resulting oil was dissolved in EtOH (40 mL), and 2 M aqueous NaOH (20 mL, 40 mmol) was added. The reaction mixture was stirred for 17 h at room temperature. The reaction was quenched with 1 M aqueous HCl. The aqueous layer was extracted with EtOAc (3×). The combined organics were washed with brine (1×), dried over Na$_2$SO$_4$, filtered and concentrated in vacuo. The residue was purified by silica gel flash chromatography eluting with 100% to 0% PE-DCM gradient. Recrystallization in hot PE afforded the title compound as white needles (1.5 g, 40% over three steps, 7:1 mixture endo:exo)

(±)-4-(Bicyclo[2.2.2]octan-2-yl)phenol

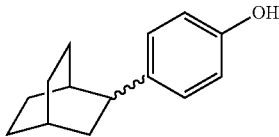 [SMILES: Oc1ccc(C2CC3CCC2CC3)cc1]

To a solution of 4-acetoxystyrene (3 mL, 20 mmol) in cyclohexadiene (2.1 mL, 22 mmol) was added hydroquinone (10 mg, 0.1 mmol). The reaction vessel was purged with argon and sealed. The reaction mixture was stirred at 160° C. for 24 h. The reaction mixture was filtered through silica and washed with DCM. The solution was concentrated in vacuo and used in the next step without further purification.

The resulting oil was dissolved in EtOAc (40 mL). Under an argon atmosphere, palladium on charcoal (5% Pd, 0.2 g, 0.1 mmol) was added and the reaction vessel was flushed with $H_2$. The reaction was stirred strongly for 22 h. The reaction mixture was then purged back with argon, filtered through celite, washed with EtOAc, and concentrated in vacuo. The crude mixture was then filtered on silica (PE/DCM), concentrated in vacuo and used in the next step without further purification.

The resulting oil was dissolved in EtOH (40 mL), and 2 M aqueous NaOH (20 mL, 40 mmol) was added. The reaction mixture was stirred for 17 h at room temperature. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 0% PE-DCM gradient. Recrystallization in hot PE afforded the title compound as white needles (0.6 g, 15% over three steps)

4-(1-(Trifluoromethyl)cyclopropyl)phenol

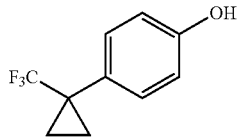 [SMILES: Oc1ccc(C2(C(F)(F)F)CC2)cc1]

Following a procedure from Anderson, K. W. et al., *J. Am. Chem. Soc.*, 2006, 128 (33), 10694-10695, to a solution of KOH (2.6 g, 46.3 mmol), $Pd_2dba_3$ (278 mg, 0.30 mmol), and di-tert-butyl-[2-(2,4,6-triisopropylphenyl)phenyl]phosphate (510 mg, 1.20 mmol) in degassed 1,4-dioxane (7.5 mL) and water (7.5 mL) under argon was added 1-bromo-4-(1-(trifluoromethyl)cyclopropyl)benzene (3.98 g, 15.0 mmol). The reaction vessel was then sealed and immerged in a preheated oil bath at 100° C. The reaction was stirred for 4-10 h. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 90% PE-EtOAc gradient to give the title compound as a yellow oil (3.0 g, 99%).

2-Chloro-4-(1-(trifluoromethyl)cyclopropyl)phenol

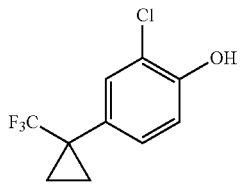

To a solution of 4-(1-(trifluoromethyl)cyclopropyl)phenol (1.03 g, 5.1 mmol) in DCE (25 mL) under argon at 0° C. were added N-chlorosuccinimide (737 mg, 5.52 mmol) and aluminium trichloride (740 mg, 5.55 mmol). The reaction mixture was stirred at 0° C. for 3 h, before being quenched with water. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 80% PE-EtOAc gradient to give the title compound as a yellow oil (380 mg, 31%).

6-Chloro-5-fluoronicotinic Acid

To a solution of 2-chloro-3-fluoro-5-methylpyridine (512 mg, 3.52 mmol) in pyridine (2.5 mL) and water (2.5 mL) was added one portion of potassium permanganate (1.1 g, 6.9 mmol). The reaction mixture was heated to 100° C. Two more equal portion of potassium permanganate (for a total of 3.3 g, 20.7 mmol) were added after respectively 1 h and 2 h of stirring at 100° C. When needed, the solid accumulated in the condenser were washed down with water and pyridine. After another 1 h of stirring at 100° C., the reaction mixture was cooled down to room temperature. The reaction mixture was quenched with saturated aqueous $Na_2S_2O_3$ and stirred 30 minutes. The mixture was filtered, then acidified to pH 2 with HCl 5 M. The aqueous layer was extracted with EtOAc (3×). The combined organics were washed with brine (1×), dried over $Na_2SO_4$, filtered and concentrated in vacuo. The residue was purified by silica gel flash chromatography eluting with 90% to 70% PE-EtOAc gradient to give the title compound as a white solid (300 mg, 49%).

6-Chloro-5-fluoronicotinic Acid Ethyl Ester

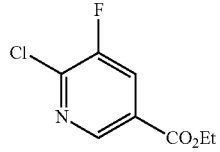

To a solution of 6-chloro-5-fluoronicotinic acid (5.1 g, 29.1 mmol) in EtOH (150 mL) at 0° C. was added SOCl$_2$ (4.5 mL, 61.7 mmol). The mixture was heated at reflux for 4 h. The reaction mixture was allowed to cool down to room temperature, and the reaction was quenched with saturated aqueous NaHCO$_3$. The aqueous layer was extracted with EtOAc (3×). The combined organics were washed with brine (1×), dried over Na$_2$SO$_4$, filtered and concentrated in vacuo. The residue was purified by silica gel flash chromatography eluting with 100% to 80% PE-EtOAc gradient to give the title compound as a white solid (5.28 mg, 89%).

1-(4-Bromophenyl)-N-cyclohexylethan-1-imine

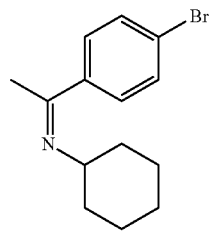 [SMILES: C/C(=N/C1CCCCC1)c1ccc(Br)cc1]

Following a procedure from Mercadante, M. A., et al., Chemical Science, 2014, 5, 3983-3994, to a solution of 4'-bromoacetophenone (10.0 g, 50.2 mmol) and p-toluenesulfonic acid monohydrate (100 mg, 0.53 mmol) in toluene (70 mL) was added cyclohexylamine (6.1 mL, 53.5 mmol) and the mixture was stirred at reflux with a Dean-Stark for 21 h. The reaction mixture was allowed to cool down to room temperature and PE was added (100 mL). The p-toluenesulfonic acid precipitated and could be filtered off. The solid was washed with PE (2×). The filtrate was concentrate in vacuo to afford crude product that was recrystallized from hot PE to give the title compound as slightly yellow flakes (12.4 g, 88%).

(Iodomethyl)dimethylphenylsilane

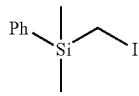

Following a procedure from Mercadante, M. A., et al., Chemical Science, 2014, 5, 3983-3994, to a solution of (chloromethyl)dimethylphenylsilane (4.9 mL, 27 mmol) in acetone (30 mL) was added sodium iodide (7.1 g, 47.3 mmol). The reaction mixture was then stirred at reflux for 19 h. The mixture was concentrated in vacuo, filtered over celite, and the solid washed with PE (60 mL). The solution was concentrated in vacuo. The residue was purified by silica gel flash chromatography eluting with 100% to 70% PE-DCM gradient to give the title compound as a yellow oil (7.1 g, 95%).

1-(4-Bromophenyl)-3-(dimethyl(phenyl)silyl)propan-1-one

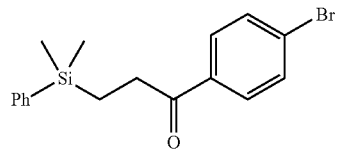

Following a procedure from Mercadante, M. A., et al., Chemical Science, 2014, 5, 3983-3994, to a solution of 1-(4-bromophenyl)-N-cyclohexylethan-1-imine (5.6 g, 20 mmol) in THF (10 mL) at 0° C. was slowly added freshly prepared LDA in THF (approximatively 1.5 M, 15 mL, 22 mmol) dropwise. The mixture was stirred 1 h at 0° C. before adding (iodomethyl)dimethylphenylsilane (6.1 g, 22 mmol). The reaction was stirred for another 1 h at 0° C. before quenching with a buffer aqueous solution of sodium acetate (29.5 g, 360 mmol), acetic acid (10.3 mL, 180 mmol) in water (11 mL). The mixture was stirred for 15 minutes before being diluted with water. The aqueous layer was extracted with EtOAc (3×). The combined organics were washed with brine (1×), dried over Na$_2$SO$_4$, filtered and concentrated in vacuo. The residue was purified by silica gel flash chromatography eluting with 100% to 95% PE-EtOAc gradient to give the title compound as a yellow solid (5.24 g, 75%).

Trimethyl(perfluoroethyl)silane

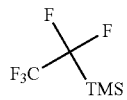

A solution of n-BuLi (2.3 M in cyclohexane, 9 mL, 20.7 mmol) in THF (40 mL) was stirred at −90° C. (Acetone/N$_2$). The system was purged with an atmosphere of pentafluoroethane and the system was kept between −78° C. and −90° C. for 1 h, then slowly warmed to −65° C. and stirred for another 0.5 h. A solution of TMSCl (2.55 mL, 20 mmol) in THF (5 mL) was added and the mixture was allowed to warm-up slowly in the acetone bath and stirred for 15 h at room temperature. The solution was then distilled to obtain the title compound as a solution in THF (65 mL).

4-(1-(Perfluoroethyl)cyclopropyl)phenol

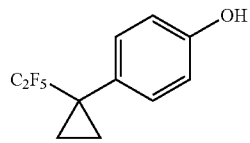

Following a procedure from Mercadante, M. A., et al., Chemical Science, 2014, 5, 3983-3994, to the solution of trimethyl(perfluoroethyl)silane in THF previously obtained (60 mL) at 0° C. was added 1-(4-bromophenyl)-3-(dimethyl(phenyl)silyl)propan-1-one (4.9 g, 14.2 mmol). The mixture was stirred for 10 minutes and TBAF (1 M solution in THF, 0.14 mL, 0.14 mmol) was added and the reaction mixture was stirred at room temperature for 7.5 h. The reaction mixture was cooled down to 0° C., water (1.4 mL) and TBAF (1 M solution in THF, 1.4 mL, 1.4 mmol) were added and the reaction mixture was stirred at room temperature for 14 h. The reaction was quenched with water. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 95% PE-EtOAc gradient to give 3-(4-bromophenyl)-5-(dimethyl (phenyl) silyl)-1,1,1,2,2-pentafluoropentan-3-ol as a mixture with the starting 1-(4-bromophenyl)-3-(dimethyl(phenyl)silyl)propan-1-one (4.9 g, 1:1 ratio by NMR) due to similar polarity.

To a solution of the previous alcohol/ketone mixture (4.5 g, containing approximatively 5.5 mmol of 3-(4-bromophenyl)-5-(dimethyl(phenyl)silyl)-1,1,1,2,2-pentafluoropentan-3-ol) in THF (25 mL) at 0° C. was added NaH (60 wt % in oil, 565 mg, 14.1 mmol). The mixture was stirred at room temperature for 45 minutes. The reaction was cooled down to 0° C. and MsCl (0.9 mL, 11.6 mmol) was added dropwise. After stirring at room temperature for 2 h, the reaction mixture was cooled down to 0° C. and quenched with water. The aqueous layer was extracted with EtOAc (3×). The combined organics were washed with water, saturated aqueous $NaHCO_3$, brine (1×), dried over $Na_2SO_4$, filtered and concentrated in vacuo.

To the resulting oil at 0° C. was added a mixture of pyridine (0.9 mL, 11.2 mmol) and 1,1,1,3,3,3-Hexafluoropropan-2-ol (8 mL). The flask was sealed and the reaction mixture was stirred for 12.5 h. The reaction was quenched with water. The aqueous layer was extracted with PE (3×). The combined organics were washed with aqueous HCl 1 M, water, saturated aqueous $NaHCO_3$ and brine (1×), dried over $Na_2SO_4$, filtered and concentrated in vacuo (water bath at 25° C., no lower than 200 mbar, the desired product is volatile). The residue was purified by silica gel flash chromatography eluting with 100% PE to give 1-bromo-4-(1-(perfluoroethyl)cyclopropyl)benzene. As it is a highly volatile product, the PE was not fully removed and the product was directly subjected to the next step. By further eluting the column with 9:1 PE/EtOAc, 1.7 g of the starting 1-(4-bromophenyl)-3-(dimethyl(phenyl)silyl)propan-1-one was recovered.

Following a procedure from Anderson, K. W. et al., J. Am. Chem. Soc., 2006, 128 (33), 10694-10695, to a solution of KOH (900 m16.0 mmol), $Pd_2dba_3$ (93 mg, 0.10 mmol), and di-tert-butyl-[2-(2,4,6-triisopropylphenyl)phenyl]phosphate (170 mg, 0.40 mmol) in degassed 1,4-dioxane (2 mL) and water (2 mL) under argon was added 1-bromo-4-(1-(perfluoroethyl)cyclopropyl)benzene (obtained in the previous step) in 1,4-dioxane (0.5 mL) and water (0.5 mL). The reaction vessel was then sealed and immerged in a pre-heated oil bath at 100° C. The reaction was stirred for 4-10 h. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 90% PE-EtOAc gradient to give the title compound as a yellow oil (1.04 g, 29% over 4 steps, 44% BRSM).

The compounds listed in Table XIV have been identified by TLC using pre-coated silica TLC sheets and common organic solvents such as petroleum ether, ethyl acetate, dichloromethane, methanol, or acetic acids as eluent, preferably as binary or tertiary solvent mixtures thereof, UV light at a wavelength of 254 or 366 nm, and/or common staining solutions such as phosphomolybdic acid, potassium permanganate, or ninhydrin.

The compounds listed in Table XIV have furthermore been identified by mass spectrometry using formic acid in the mobile phase for detection of positive ions, while no additive was used for negative ions. Ammonium Carbonate was used if the molecule was difficult to ionize. Representative compounds have also been identified by nuclear magnetic resonance spectroscopy. Chemical shifts (δ) were reported in parts per million (ppm) relative to residual solvent peaks rounded to the nearest 0.01 ppm for proton and 0.1 ppm for carbon (ref.: $CHCl_3$[$^1$H: 7.26 ppm, $^{13}$C: 77.2 ppm], DMSO [$^1$H: 2.50 ppm, 13C: 39.5 ppm]). Coupling constants (J) were reported in Hz to the nearest 0.1 Hz. Peak multiplicity was indicated as follows: s (singlet), d (doublet), t (triplet), q (quartet), hept (heptet), m (multiplet), and br (broad).

The invention claimed is:
1. A method for the treatment of a malignant or precancerous hyperproliferative disorder by inhibiting the growth of cells associated with said malignant and precancerous hyperproliferative disorder, comprising administering a therapeutically effective amount of an active agent to a subject in need thereof, wherein the active agent is selected from
(i) a compound of formula I,

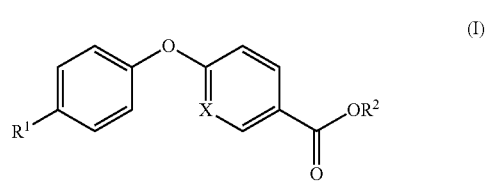

wherein X is CH or N,
$R^1=C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl,
wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$—$C_3$ alkyl optionally halogenated or perhalogenated,
wherein all cycloalkyl, cycloalkenyl, bicycloalkyl, bicycloalkenyl and tricycloalkyl residues can be unsubstituted or substituted with one or more substituents independently selected from: —F, —Cl, —Br, —I, —CN, —NCO, —NCS; and $C_1C_3$ alkyl optionally halogenated or perhalogenated, and $OC_1$—$C_3$ alkyl optionally halogenated or perhalogenated,
wherein all alkyl, alkenyl, alkynyl, cycloalkyl, cycloalkenyl, bicycloalkyl, bicycloalkenyl and tricycloalkyl residues can be perhalogenated;
$R^2$=H, $C_1$-$C_6$ alkyl, $C_3$-$C_6$ cycloalkyl,
wherein all alkyl residues can be linear or branched, and can be unsubstituted or substituted with one or more substituents independently selected from: —F, —Cl, —Br, —I;
and $OC_1$—$C_3$ alkyl optionally halogenated or perhalogenated,
wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all alkyl and cycloalkyl residues can be perhalogenated;

or a salt or solvate thereof, (ii) a compound of formula II,

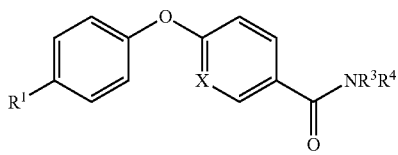

(II)

wherein X and $R^1$ are defined as in formula I, $R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I;

and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$—$C_3$ alkyl optionally halogenated or perhalogenated, wherein all alkyl and cycloalkyl residues can be perhalogenated;

$R^4$=$C_1$-$C_6$ alkyl, $C_3$-$C_6$ cycloalkyl, OH or $OC_1$—$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all alkyl and cycloalkyl residues can be perhalogenated, or a salt or solvate thereof, wherein when $R^4$ is $C_1$-$C_6$ alkyl, the alkyl residues can be linear or branched, and are substituted with one or more substituents independently selected from: F, Cl, Br, I;

and $C_1$-$C_3$ alkyl halogenated or perhalogenated; and $OC_1$—$C_3$ alkyl optionally halogenated or perhalogenated, (iii) a compound of formula III,

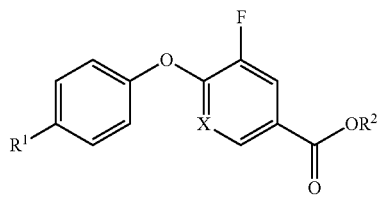

(III)

wherein X, $R^1$ and $R^2$ are defined as in formula I, or a salt or solvate thereof, (iv) a compound of formula IV,

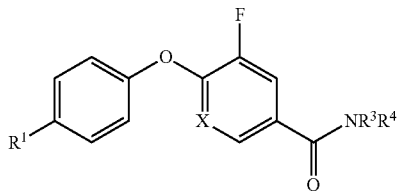

(IV)

wherein X and $R^1$ are defined as in formula I, and $R^3$ and $R^4$ are defined as in formula II, or a salt or solvate thereof, (v) a compound of formula V,

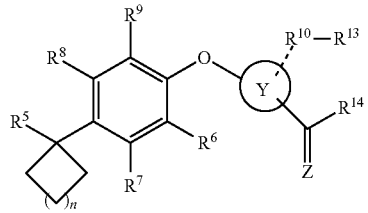

(V)

wherein n=0-5, which comprises cyclopropyl (n=0), cyclobutyl (n=1), cyclopentyl (n=2), cyclohexyl (n=3), cycloheptyl (n=4) and cyclooctyl (n=5), wherein the said cyclopropyl, cyclobutyl, cyclopentyl, cyclohexyl, cycloheptyl and cyclooctyl groups can be unsubstituted or substituted with one or more substituents independently selected from: —F, —Cl, —Br, —I, —CN, —NCO, —NCS; and $C_1$-$C_3$ alkyl optionally halogenated or perhalogenated; and $OC_1$—$C_3$ alkyl optionally halogenated or perhalogenated, wherein the said cyclopropyl, cyclobutyl, cyclopentyl, cyclohexyl, cycloheptyl and cyclooctyl groups can be perhalogenated;

$R^5$=$C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, wherein all alkyl, alkenyl and alkynyl residues can be linear or branched, and are perhalogenated, and wherein all cycloalkyl and cycloalkenyl residues are perhalogenated, or wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$—$C_3$ alkyl optionally halogenated or perhalogenated, and wherein all cycloalkyl and cycloalkenyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$—$C_3$ alkyl optionally halogenated or perhalogenated, $R^6$-$R^9$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from: —F, —Cl, —Br, —I; and $C_1$-$C_3$ alkyl optionally halogenated or perhalogenated, and $OC_1$—$C_3$ alkyl optionally halogenated or perhalogenated, Y=a six-membered aromatic ring selected from benzene, pyridine, pyrimidine, pyridazine or pyrazine;

wherein the benzene ring is not substituted, or it is substituted with one to four of the substituents independently selected from $R^{10}$-$R^{13}$, and wherein the pyridine ring is not substituted, or it is substituted at the carbon positions with one to three of the substituents independently selected from $R^{10}$-$R^{12}$, and wherein the N-atom of the pyridine ring may be in ortho-position relative to the ether bond, and wherein the pyrimidine ring is not substituted, or it is substituted at the carbon positions with one or two of the substituents independently selected from $R^{10}$-$R^{11}$, and wherein the N-atoms of the pyrimidine ring may be in ortho-position relative to the ether bond, and wherein the pyridazine ring is not substituted, or it is substituted at the carbon positions with one or two of the substituents independently selected from $R^{10}$-$R^{11}$, and wherein an N-atom of the pyridazine ring may be in ortho-position relative to the ether bond, and wherein the pyrazine ring is not substituted, or it is substituted at the carbon positions with one or two of the substituents independently selected from $R^{10}$-$R^{11}$, and wherein an N-atom of the pyrazine ring may be in ortho-position relative to the ether bond, $R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from —F, —Cl, —Br, —I; and $C_1$-$C_3$ alkyl optionally halogenated or perhalogenated; and $OC_1$—$C_3$ alkyl optionally halogenated or perhalogenated, Z=O or S, $R^{14}$=$OR^2$ or $NR^3R^4$ wherein $R^2$ is defined as in formula I, and wherein $R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$—$C_3$ alkyl optionally halogenated or perhalogenated, wherein all alkyl and cycloalkyl residues can be perhalogenated;

and wherein $R^4$=H, $C_1$-$C_6$ alkyl, $C_3$-$C_6$ cycloalkyl, OH or $OC_1$—$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all alkyl and cycloalkyl residues can be perhalogenated, or a salt or solvate thereof, wherein the hyperproliferative disorder is cancer or a precancerous lesion selected from the group consisting of cancer or precancerous lesions of the neuroendocrine system, brain, pancreas, liver, thyroid, genitourinary tract, endothelial tissue, skin, mucosa, skin and mucosal appendages, cornea, epithelial tissues, muscle, hematopoietic system, hematologic system, myeloid lineage, lymphoid lineage, lung, gastrointestinal tract, glands, head and neck, respiratory tract, bladder, epidermis, dermis, submucosa, urothelium, genitals, hair follicles, sebaceous glands, sweat glands, esophagus, tongue, cervix, forebrain, pituitary gland, and adrenal gland, mammary gland, ear, ocular mucosa, oral mucosa, nasal mucosa, anal mucosa, rectal mucosa, and cancer related to fingernails and toenails.

2. The method according to claim 1, wherein the cancer is cancer of the neuroendocrine system selected from the group consisting of small cell carcinomas, large cell carcinomas and carcinoid tumors.

3. The method according to claim 1, wherein the cancer is selected from the group consisting of cancers or precancerous lesions of the brain, pancreas, liver, thyroid, genitourinary tract and endothelial tissue, squamous cell carcinoma, basal cell carcinoma, medullary thyroid cancer, and cervical cancer.

4. The method according to claim 1, wherein the hyperproliferative disorder is a disorder of the skin, mucosa, skin and mucosal appendages, cornea, and epithelial tissues.

5. The method according to claim 1, wherein the hyperproliferative disorder is a hyperproliferative disorder of the muscle.

6. The method of claim 1, wherein in the compound of Formula I, II, III and IV, $R^1$ is selected from the group consisting of methyl, ethyl, n-propyl, n-butyl, n-pentyl, n-hexyl, iso-propyl, tert-butyl, tert-pentyl, 3-pentyl, —$CF_3$, —$CF_2CF_3$, —$(CF_2)_2CF_3$, —$(CF_2)_3CF_3$, —$CH(CF_3)_2$, —$CF(CF_3)_2$, cyclopropyl, cyclobutyl, cyclopentyl, cyclohexyl, cycloheptyl, norbornyl, bicyclo[2.2.2]octyl, adamantyl, and 9-methylbicyclo[3.3.1]nonyl.

7. The method of claim 1, wherein in the compound of Formula I, III and V, $R^2$ is selected from the group consisting of H, methyl and ethyl wherein said methyl and ethyl is optionally fluorinated or perfluorinated.

8. The method of claim 1, wherein in the compound of Formula II, IV and V, $R^3$ is H or methyl, wherein said methyl is optionally fluorinated or perfluorinated.

9. The method of claim 1, wherein in the compound of Formula II, IV and V, $R^4$ is selected from the group consisting of H, OH and methyl wherein said methyl is fluorinated or perfluorinated.

10. The method of claim 1, wherein in the compound of Formula V, n is 0 as constituting cyclopropyl.

11. The method of claim 10, wherein said cyclopropyl is unsubstituted.

12. The method of claim 1, wherein in the compound of Formula V, $R^5$ is a perfluorinated alkyl, alkenyl, alkynyl, cycloalkyl or cycloalkenyl residue.

13. The method of claim 1, wherein in the compound of Formula V, $R^5$ is —$CF_3$ or —$CF_2CF_3$.

14. The method of claim 1, wherein in the compound of Formula V, $R^6$-$R^8$ are H and $R^9$ is selected from the group consisting of —H, —F, —Cl or —$CH_3$.

15. The method of claim 1, wherein in the compound of Formula V, Y=benzene or pyridine being not substituted with any of the residues selected from $R^{10}$-$R^{13}$, or being substituted with one of the substituents selected from $R^{10}$-$R^{13}$ being —F at the carbon atom in ortho-position relative to the ether bond.

16. The method of claim 1, wherein in the compound of Formula V, Z=0.

17. The method of claim 1, wherein the disorder is selected from the group consisting of a hyperproliferative disorder of the skin and mucosa, a hyperproliferative disorder of the muscle and a hyperproliferative disorder of the genitourinary tract.

18. The method of claim 1, wherein the subject is a human subject.

19. The method of claim 1, wherein all alkyl residues of $R^4$ can be linear or branched, and are substituted with one or more substituents independently selected from the group consisting of —F, —Cl, —Br, —I; $OC_1$—$C_3$ alkyl and halogenated $C_1$-$C_3$ alkyl.

20. The method according to claim 19, wherein said $C_1$-$C_3$ alkyl is perhalogenated, and said $OC_1$—$C_3$ alkyl is halogenated or perhalogenated.

21. A method for inhibiting the growth of malignant or precancerous cells in subjects with a hyperproliferative disorder, comprising administering a therapeutically effective amount of an active agent to a subject in need thereof, wherein the active agent is selected from (i) a compound of formula I,

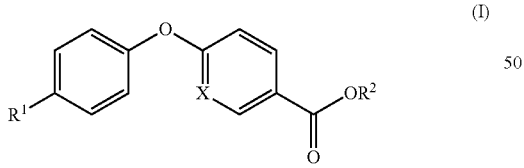

wherein X is CH or N,
$R^1$=$C_1$-$C_{12}$alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl,
wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$—$C_3$ alkyl optionally perhalogenated,
wherein all cycloalkyl, cycloalkenyl, bicycloalkyl, bicycloalkenyl and tricycloalkyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$—$C_3$ alkyl optionally halogenated or perhalogenated,
wherein all alkyl, alkenyl, alkynyl, cycloalkyl, cycloalkenyl, bicycloalkyl, bicycloalkenyl and tricycloalkyl residues can be perhalogenated;
$R^2$=H, $C_1$-$C_6$ alkyl, $C_3$-$C_6$ cycloalkyl,
wherein all alkyl residues can be linear or branched, and can be unsubstituted or substituted with one or more substituents independently selected from: —F, —Cl, —Br, —I;
and $OC_1$—$C_3$ alkyl optionally halogenated or perhalogenated,
wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated,
wherein all alkyl and cycloalkyl residues can be perhalogenated;
or a salt or solvate thereof, (ii) a compound of formula II,

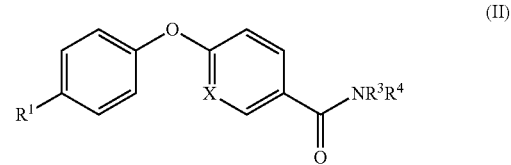

wherein X and $R^1$ are defined as in formula I,
$R^3$=H, $C_1$-$C_6$ alkyl, or $C_3$-$C_6$ cycloalkyl,
wherein all alkyl residues can be linear or branched, and can be unsubstituted or substituted with one or more substituents independently selected from: —F, —Cl, —Br, —I;
and $C_1$-$C_3$ alkyl optionally halogenated or perhalogenated; and $OC_1$—$C_3$ alkyl optionally halogenated or perhalogenated,
wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$—$C_3$ alkyl optionally halogenated or perhalogenated,
wherein all alkyl and cycloalkyl residues can be perhalogenated;
$R^4$=$C_1$-$C_6$alkyl, $C_3$-$C_6$ cycloalkyl, OH or $OC_1$—$C_6$alkyl,
wherein all alkyl residues can be linear or branched, and can be unsubstituted or substituted with one or more substituents independently selected from: —F, —Cl, —Br, —I;
and $C_1$-$C_3$ alkyl optionally halogenated or perhalogenated; and $OC_1$—$C_3$ alkyl optionally halogenated or perhalogenated,
wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all alkyl and cycloalkyl residues can be perhalogenated;
or a salt or solvate thereof,
wherein when $R^4$ is $C_1$-$C_6$ alkyl, the alkyl residues can be linear or branched, and are substituted with one or more substituents independently selected from: —F, —Cl, —Br, —I;
and $C_1$-$C_3$ alkyl halogenated or perhalogenated; and $OC_1$—$C_3$ alkyl optionally halogenated or perhalogenated,
(iii) a compound of formula III,

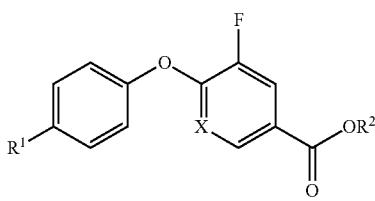

wherein X, $R^1$ and $R^2$ are defined as in formula I,
or a salt or solvate thereof,
(iv) a compound of formula IV,

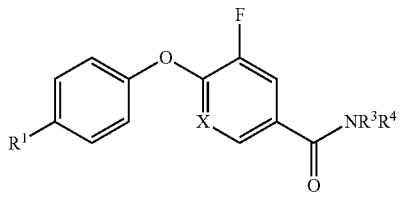

wherein X and $R^1$ are defined as in formula I,
and $R^3$ and $R^4$ are defined as in formula II,
or a salt or solvate thereof,
(v) a compound of formula V,

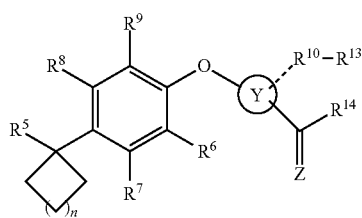

wherein n=0-5, which comprises cyclopropyl (n=0), cyclobutyl (n=1), cyclopentyl (n=2), cyclohexyl (n=3), cycloheptyl (n=4) and cyclooctyl (n=5),
wherein the said cyclopropyl, cyclobutyl, cyclopentyl, cyclohexyl, cycloheptyl and cyclooctyl groups can be unsubstituted or substituted with one or more substituents independently selected from: —F, —Cl, —Br, —I, —CN, —NCO, —NCS; and $C_1$-$C_3$ alkyl optionally halogenated or perhalogenated; and $OC_1$—$C_3$ alkyl optionally halogenated or perhalogenated,
wherein the said cyclopropyl, cyclobutyl, cyclopentyl, cyclohexyl, cycloheptyl and cyclooctyl groups can be perhalogenated;

$R^5$=$C_1$-$C_{12}$alkyl, $C_2$-$C_{12}$ alkenyl, $C_2$-$C_{12}$ alkynyl, $C_3$-$C_8$ cycloalkyl, $C_3$-$C_8$ cycloalkenyl,
wherein all alkyl, alkenyl and alkynyl residues can be linear or branched, and are perhalogenated,
and wherein all cycloalkyl and cycloalkenyl residues are perhalogenated,
or wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$—$C_3$ alkyl optionally halogenated or perhalogenated,
and wherein all cycloalkyl and cycloalkenyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$—$C_3$ alkyl optionally halogenated or perhalogenated,
$R^6$-$R^9$ are independently from each other selected from —H, —F, —Cl, —Br, —I, linear or branched $C_1$-$C_4$ alkyl, linear or branched $C_2$-$C_4$ alkenyl, $C_2$—$C_4$ alkynyl, $C_3$-$C_5$ cycloalkyl, and wherein all alkyl, alkenyl, alkynyl and cycloalkyl residues can be unsubstituted or substituted with one or more substituents independently selected from: —F, —Cl, —Br, —I; and $C_1$—$C_3$ alkyl optionally halogenated or perhalogenated, and $OC_1$—$C_3$ alkyl optionally halogenated or perhalogenated,
Y=a six-membered aromatic ring selected from benzene, pyridine, pyrimidine, pyridazine or pyrazine;
wherein the benzene ring is not substituted, or it is substituted with one to four of the substituents independently selected from $R^{10}$-$R^{13}$,
and wherein the pyridine ring is not substituted, or it is substituted at the carbon positions with one to three of the substituents independently selected from $R^{10}$-$R^{12}$, and wherein the N-atom of the pyridine ring may be in ortho-position relative to the ether bond,
and wherein the pyrimidine ring is not substituted, or it is substituted at the carbon positions with one or two of the substituents independently selected from $R^{10}$-$R^{11}$, and wherein the N-atoms of the pyrimidine ring may be in ortho-position relative to the ether bond,
and wherein the pyridazine ring is not substituted, or it is substituted at the carbon positions with one or two of the substituents independently selected from $R^{10}$-$R^{11}$, and wherein an N-atom of the pyridazine ring may be in ortho-position relative to the ether bond,
and wherein the pyrazine ring is not substituted, or it is substituted at the carbon positions with one or two of the substituents independently selected from $R^{10}$-$R^{11}$ and wherein an N-atom of the pyrazine ring may be in ortho-position relative to the ether bond,
$R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from —F, —Cl, —Br, —I; and $C_1$-$C_3$ alkyl optionally halogenated or perhalogenated; and $OC_1$—$C_3$ alkyl optionally halogenated or perhalogenated,
Z=O or S,
$R^{14}$=$OR^2$ or $NR^3R^4$
wherein $R^2$ is defined as in formula I,
and wherein $R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$—$C_3$ alkyl optionally halogenated or perhalogenated, wherein all alkyl and cycloalkyl residues can be perhalogenated;

and wherein $R^4$=H, $C_1$—$C_6$ alkyl, $C_3$-$C_6$ cycloalkyl, OH or $OC_1$—$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$—$C_3$ alkyl optionally halogenated or perhalogenated, wherein all alkyl and cycloalkyl residues can be perhalogenated;

or a salt or solvate thereof, wherein the hyperproliferative disorder is cancer or a precancerous lesion selected from the group consisting of squamous cell carcinoma, basal cell carcinoma, small cell carcinomas, large cell carcinomas and carcinoid tumors, leukemia, lymphoma, myeloma, non-melanoma skin cancer and precancerous lesions, medullary thyroid cancer, cervical cancer, adenocarcinoma, ductal adenocarcinoma, sarcoma, and cancer associated with, accompanied by and/or caused by viral infections.

22. The method according to claim 1, wherein the hyperproliferative disorder is a hyperproliferative disorder associated with, accompanied by and/or caused by viral infection.

23. A method for inhibiting the growth of malignant and precancerous cells in a subject, comprising administering a therapeutically effective amount of an active agent to a subject in need thereof, wherein the active agent is selected from the group consisting of:

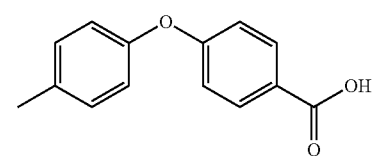

4-(p-tolyoxy)benzoic acid

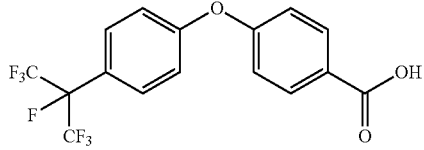

4-(4-(perfluoropropan-2-yl)phenoxy)benzoic acid

-continued

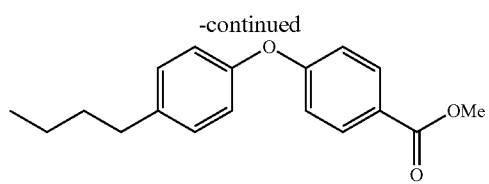

methyl 4-(4-butylphenoxy)benzoate

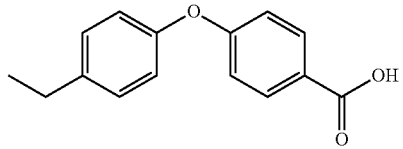

4-(4-ethylphenoxy)benzoic acid

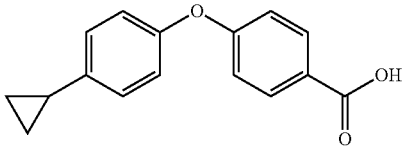

4-(4-cyclopropylphenoxy)benzoic acid

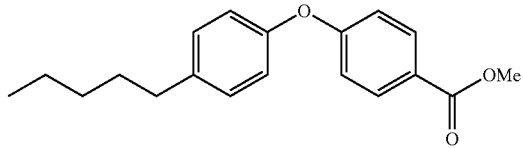

methyl 4-(4-pentylphenoxy)benzoate

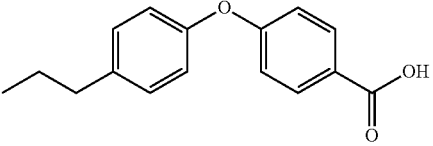

4-(4-propylphenoxy)benzoic acid

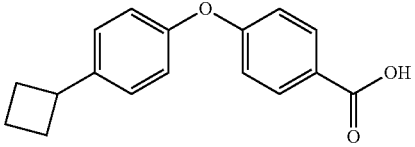

4-(4-cyclobutylphenoxy)benzoic acid

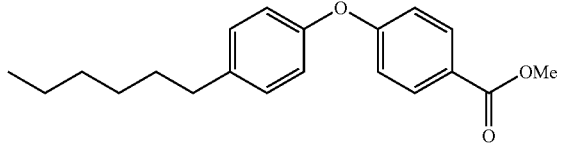

methyl 4-(4-hexylphenoxy)benzoate

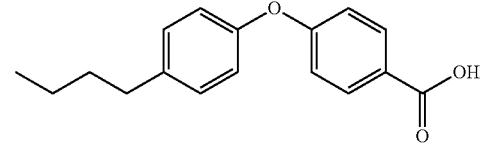

4-(4-butylphenoxy)benzoic acid

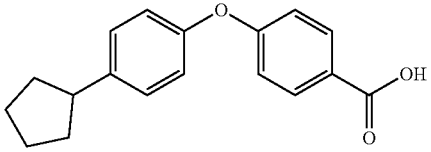

4-(4-cyclopentylphenoxy)benzoic acid

287

-continued

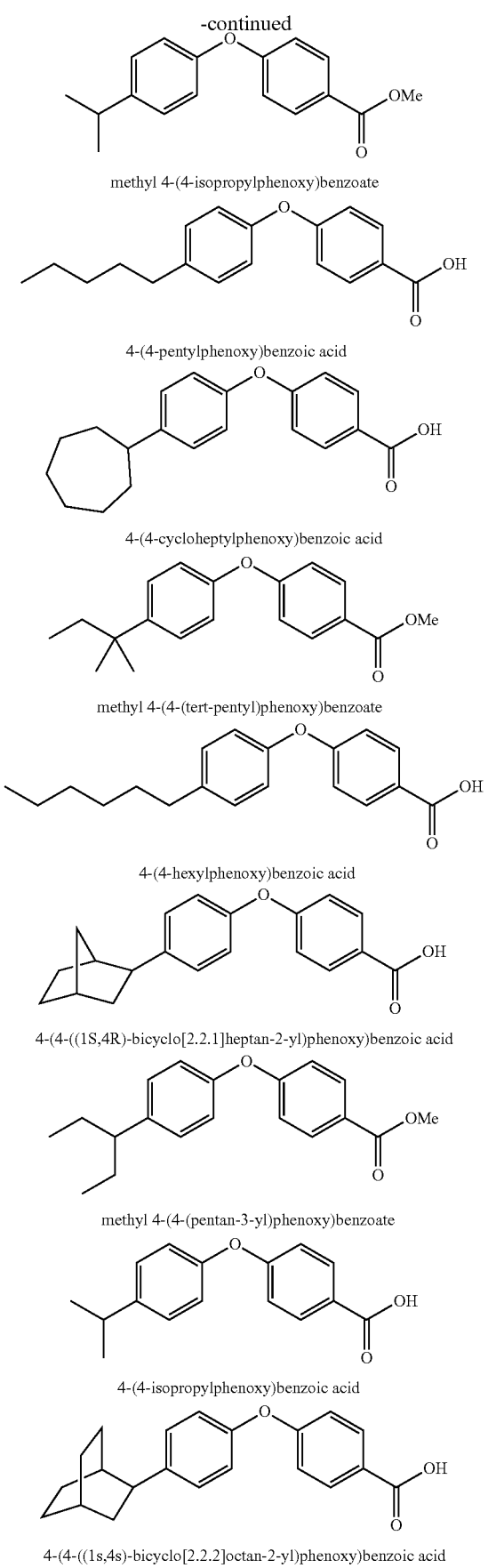

methyl 4-(4-isopropylphenoxy)benzoate 4-(4-pentylphenoxy)benzoic acid 4-(4-cycloheptylphenoxy)benzoic acid methyl 4-(4-(tert-pentyl)phenoxy)benzoate 4-(4-hexylphenoxy)benzoic acid 4-(4-((1S,4R)-bicyclo[2.2.1]heptan-2-yl)phenoxy)benzoic acid methyl 4-(4-(pentan-3-yl)phenoxy)benzoate 4-(4-isopropylphenoxy)benzoic acid 4-(4-((1s,4s)-bicyclo[2.2.2]octan-2-yl)phenoxy)benzoic acid

288

-continued

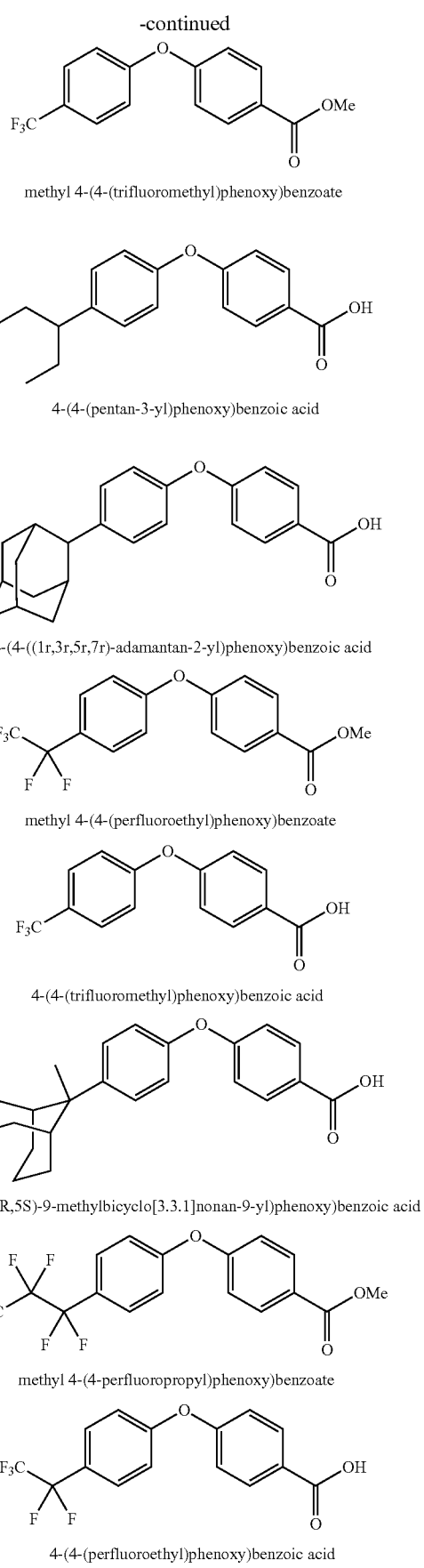

methyl 4-(4-(trifluoromethyl)phenoxy)benzoate 4-(4-(pentan-3-yl)phenoxy)benzoic acid 4-(4-((1r,3r,5r,7r)-adamantan-2-yl)phenoxy)benzoic acid methyl 4-(4-(perfluoroethyl)phenoxy)benzoate 4-(4-(trifluoromethyl)phenoxy)benzoic acid 4-(4-((1R,5S)-9-methylbicyclo[3.3.1]nonan-9-yl)phenoxy)benzoic acid methyl 4-(4-perfluoropropyl)phenoxy)benzoate 4-(4-(perfluoroethyl)phenoxy)benzoic acid -continued methyl 4-(4-(perfluorobutyl)phenoxy)benzoate 4-(4-(perfluoropropyl)phenoxy)benzoic acid methyl 4-(p-tolyloxy)benzoate methyl 4-(4-(1,1,1,3,3,3-hexafluoropropan-2-yl)phenoxy)benozate 4-(4-(perfluorobutyl)phenoxy)benzoic acid methyl 4-(4-ethylphenoxy)benzoate methyl 4-(4-(perfluoropropan-2-yl)phenoxy)benzoate 4-(4-(1,1,1,3,3,3-hexafluoropropan-2-yl)phenoxy)benzoic acid methyl 4-(4-propylphenoxy)benzoate -continued methyl 4-(4-cyclopropylphenoxy)benzoate methyl 4-(4-cyclobutylphenoxy)benzoate ethyl 4-(4-butylphenoxy)benzoate ethyl 4-(4-cyclopentylphenoxy)benzoate methyl 4-(4-cyclopentylphenoxy)benzoate ethyl 4-(4-pentylphenoxy)benzoate ethyl 4-(4-cycloheptylphenoxy)benzoate methyl 4-(4-cyclohexylphenoxy)benzoate ethyl 4-(4-hexylphenoxy)benzoate -continued

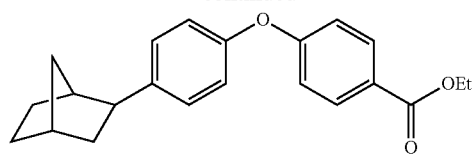

ethyl 4-(4-((1S,4R)-bicyclo[2.2.1]heptan-2-yl)phenoxy)benzoate

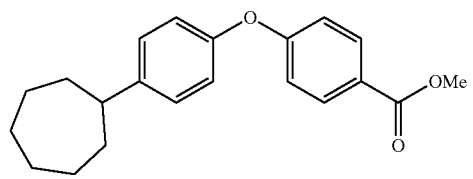

methyl 4-(4-cycloheptylphenoxy)benzoate

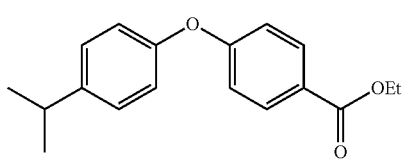

ethyl 4-(4-isopropylphenoxy)benzoate

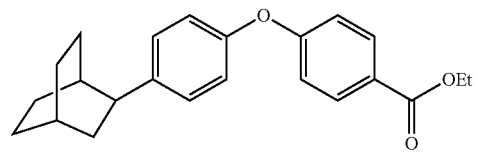

ethyl 4-(4-((1s,4s)-bicyclo[2.2.2]octan-2-yl)phenoxy)benzoate

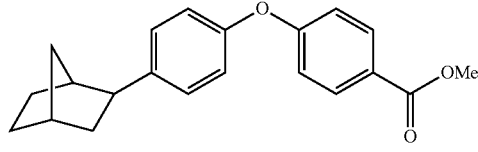

methyl 4-(4-((1S,4R)-bicyclo[2.2.1]heptan-2-yl)phenoxy)benzoate

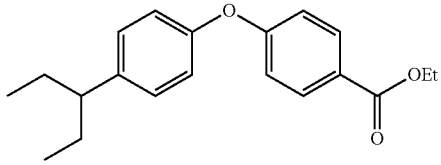

ethyl 4-(4-(pentan-3-yl)phenoxy)benzoate

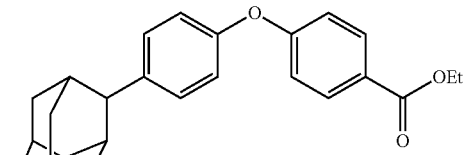

ethyl 4-(4-((1r,3r,5r,7r)-adamantan-2-yl)phenoxy)benzoate

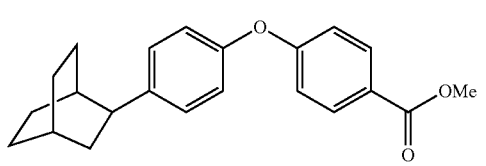

methyl 4-(4-((1s,4s)-bicyclo[2.2.2]octan-2-yl)phenoxy)benzoate

-continued

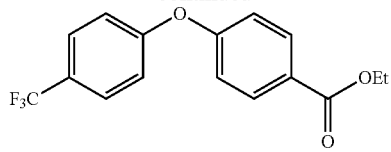

ethyl 4-(4-(trifluoromethyl)phenoxy)benzoate

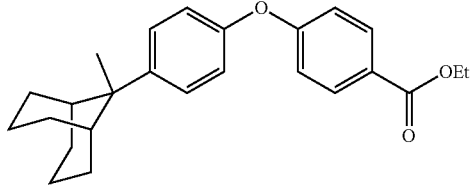

ethyl 4-(4-((1R,5S)-9-methylbicyclo[3.3.1]nonan-9-yl)phenoxy benzoate

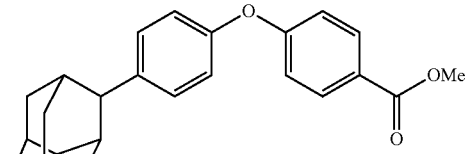

methyl 4-(4-((3r,5r,7r)-adamantan-1-yl)phenoxy)benzoate

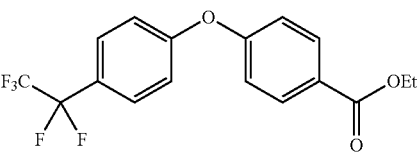

ethyl 4-(4-(perfluoroethyl)phenoxy)benzoate

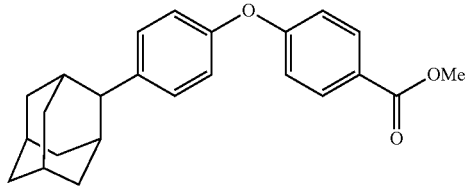

methyl 4-(4-((1r,3r,5r,7r)-adamantan-2-yl)phenoxy)benzoate

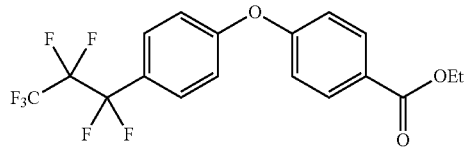

ethyl 4-(4-perfluoropropyl)phenoxy)benzoate

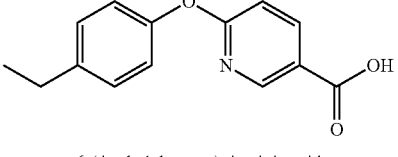

6-(4-ethylphenoxy)nicotinic acid

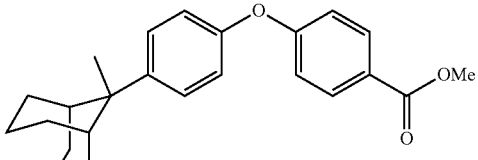

methyl 4-(4-((1R,5S)-9-methylbicyclo[3.3.1]nonan-9-yl)phenoxy)benzoate

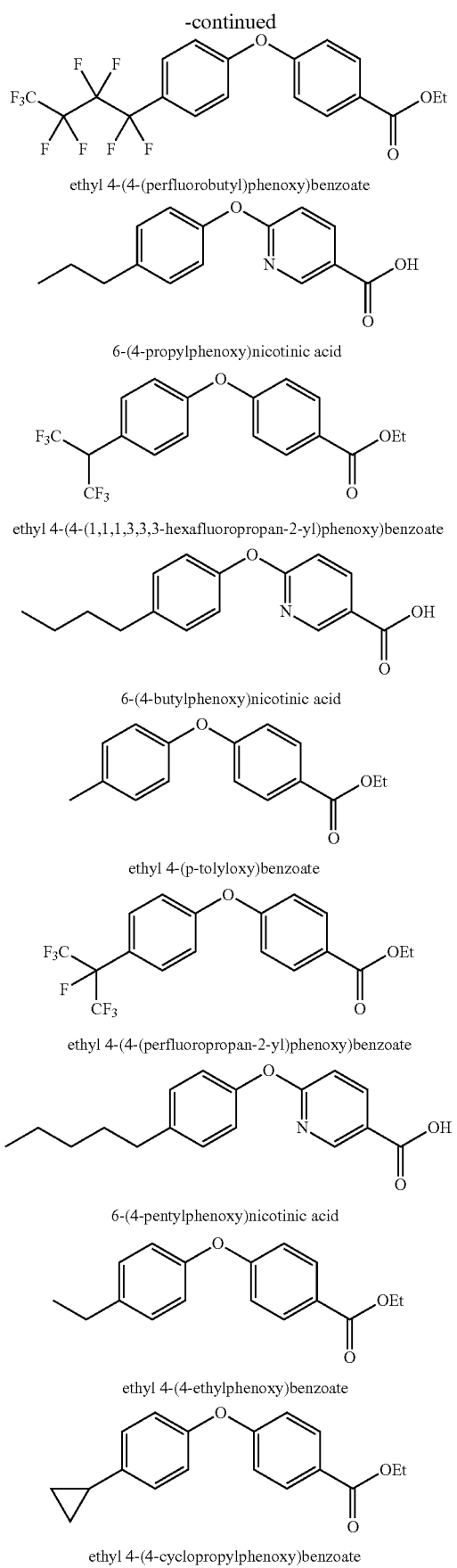
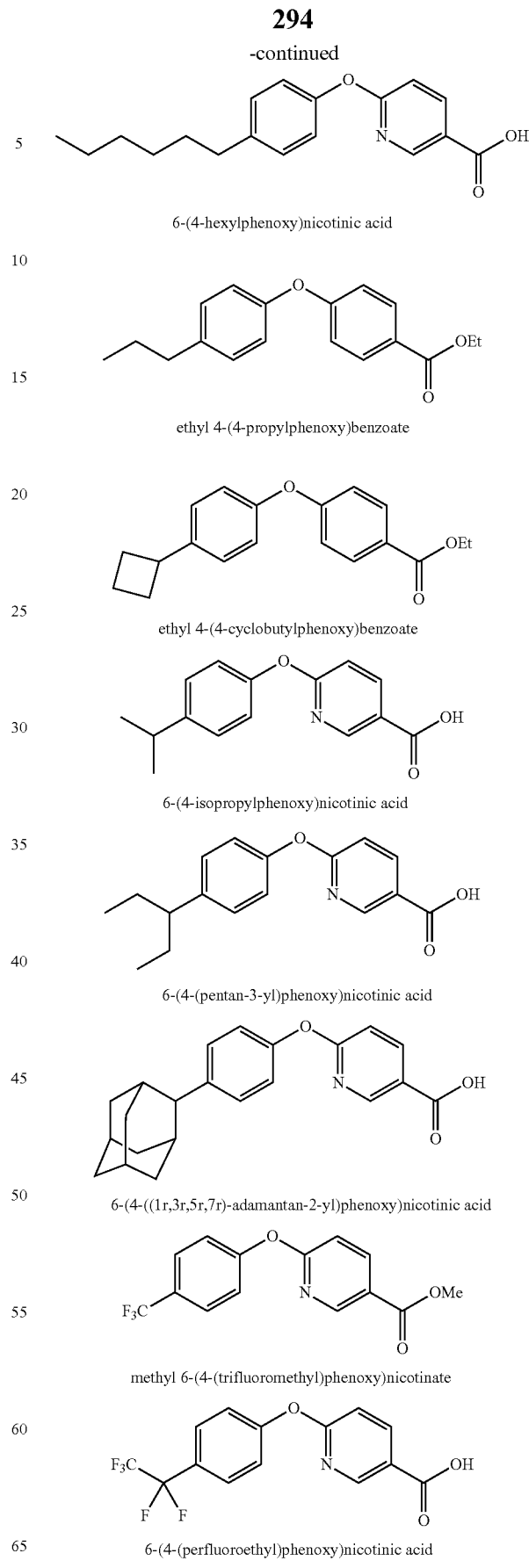

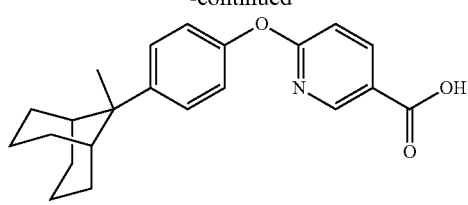

6-(4-((1R,5S)-9-methylbicyclo[3.3.1]nonan-9-yl)phenoxy)nicotinic acid

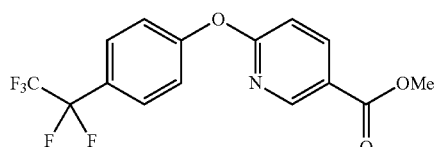

methyl 6-(4-(perfluoroethyl)phenoxy)nicotinate

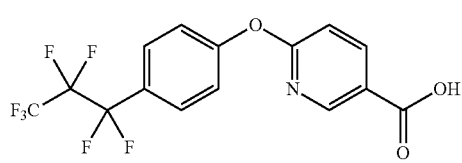

6-(4-(perfluoropropyl)phenoxy)nicotinic acid

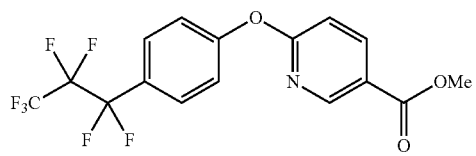

methyl 6-(4-(perfluoropropyl)phenoxy)nicotinate

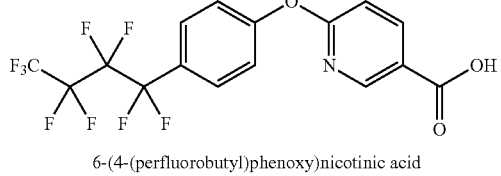

6-(4-(perfluorobutyl)phenoxy)nicotinic acid

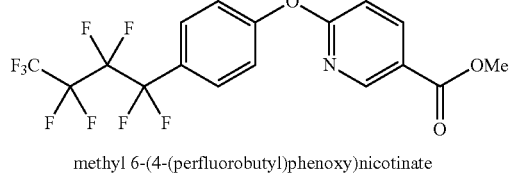

methyl 6-(4-(perfluorobutyl)phenoxy)nicotinate

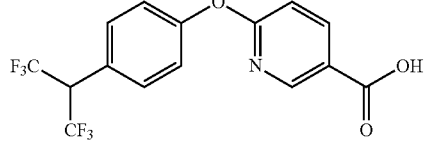

6-(4-(1,1,1,3,3,3-hexafluoropropan-2-yl)phenoxy)nicotinic acid

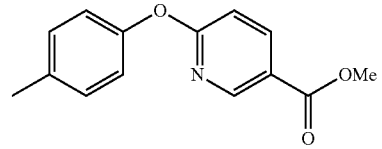

methyl 6-(p-tolyloxy)nicotinate

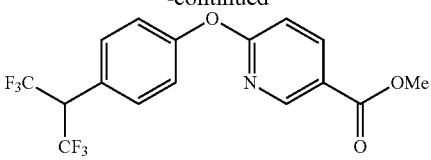

methyl 6-(4-(1,1,1,3,3,3-hexafluoropropan-2-yl)phenoxy)nicotinate

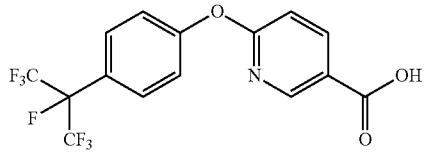

6-(4-(perfluoropropan-2-yl)phenoxy)nicotinic acid

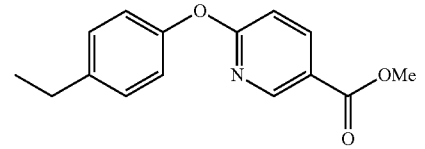

methyl 6-(4-ethylphenoxy)nicotinate

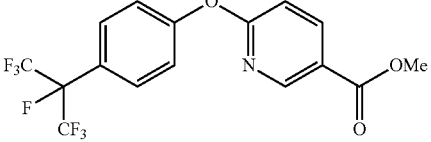

methyl 6-(4-(perfluoropropan-2-yl)phenoxy)nicotinate

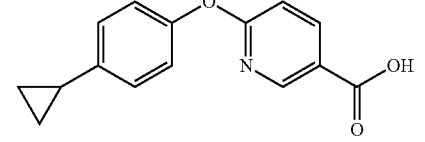

6-(4-cyclopropylphenoxy)nicotinic acid

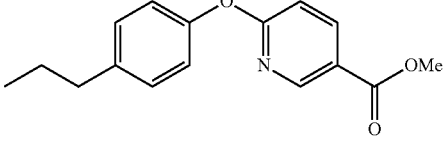

methyl 6-(4-propylphenoxy)nicotinate

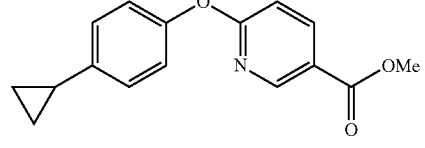

methyl 6-(4-cyclopropylphenoxy)nicotinate

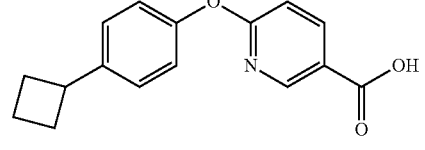

6-(4-cyclobutylphenoxy)nicotinic acid

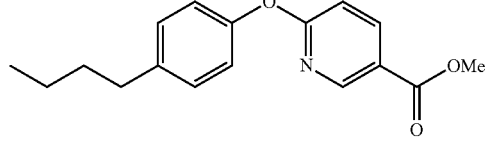

methyl 6-(4-butylphenoxy)nicotinate

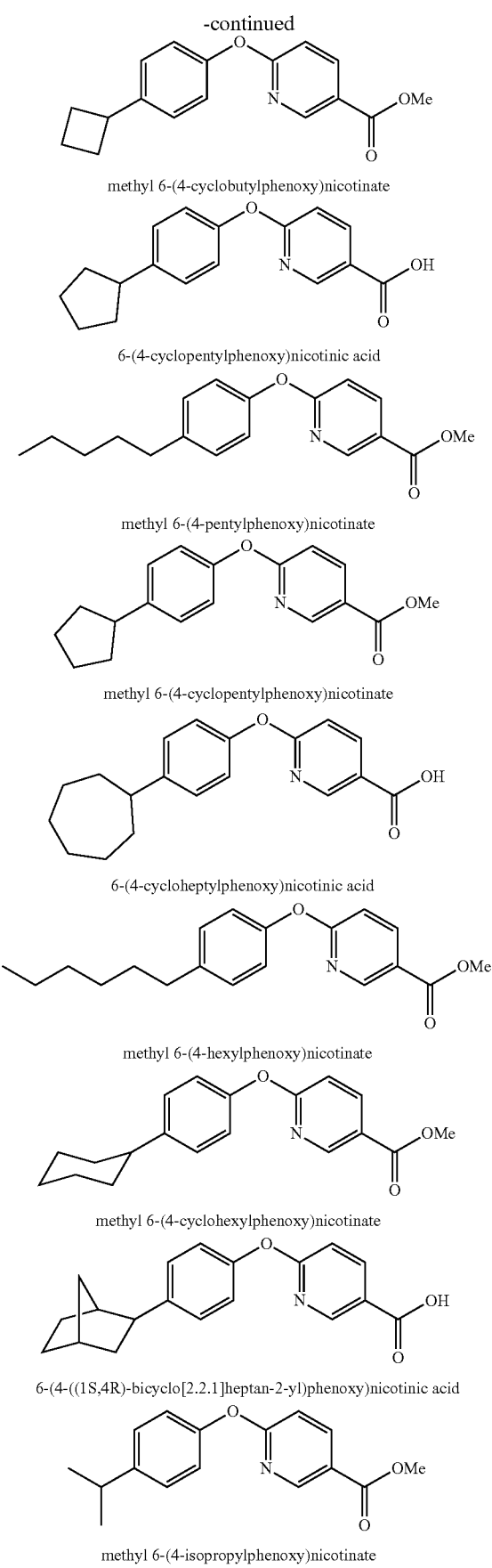
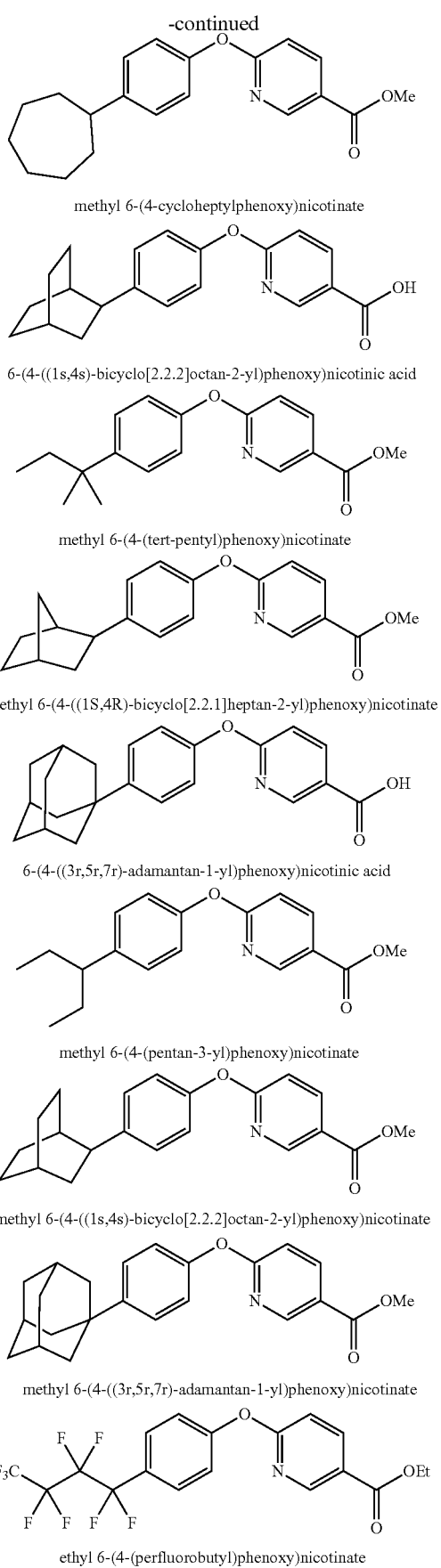

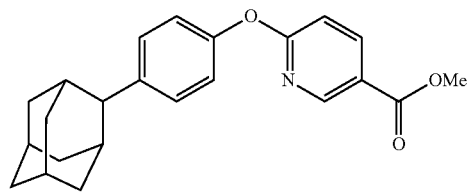

methyl 6-(4-((1r,3r,5r,7r)-adamantan-2-yl)phenoxy)nicotinate

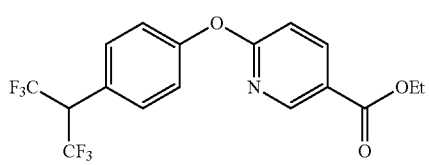

ethyl 6-(4-(1,1,1,3,3,3-hexafluoropropan-2-yl)phenoxy)nicotinate

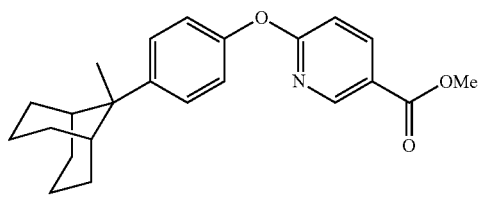

methyl 6-((1R,5S)-9-methylbicyclo[3.3.1]nonan-9-yl)phenoxy)nicotinate

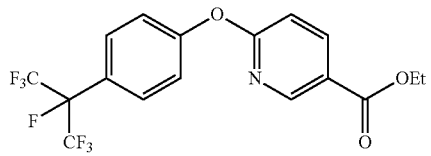

ethyl 6-(4-(perfluoropropan-2-yl)phenoxy)nicotinate

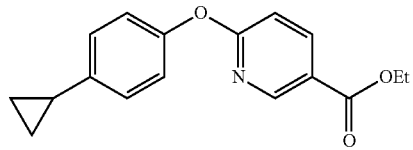

ethyl 6-(4-cyclopropylphenoxy)nicotinate

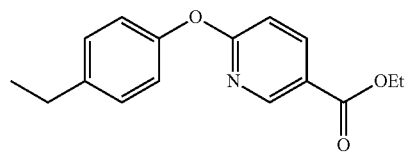

ethyl 6-(4-ethylphenoxy)nicotinate

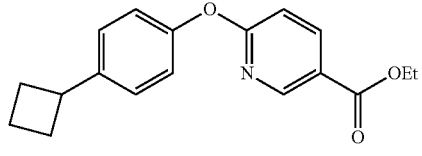

ethyl 6-(4-cyclobutylphenoxy)nicotinate

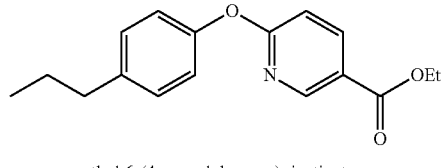

ethyl 6-(4-propylphenoxy)nicotinate

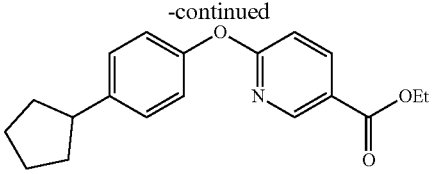

ethyl 6-(4-cyclopentylphenoxy)nicotinate

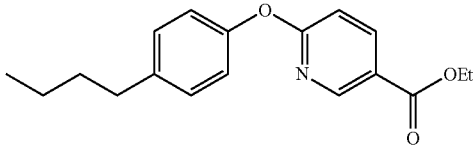

ethyl 6-(4-butylphenoxy)nicotinate

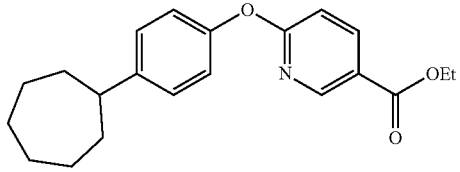

ethyl 6-(4-cycloheptylphenoxy)nicotinate

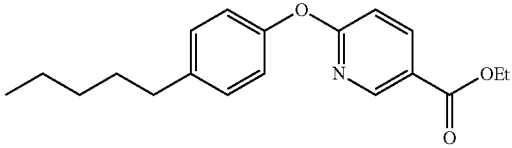

ethyl 6-(4-pentylphenoxy)nicotinate

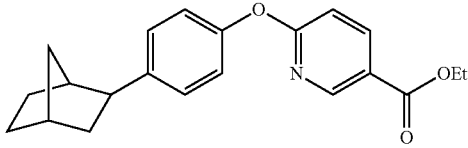

ethyl 6-(4-((1S,4R)-bicyclo[2.2.1]heptan-2-yl)phenoxy)nicotinate

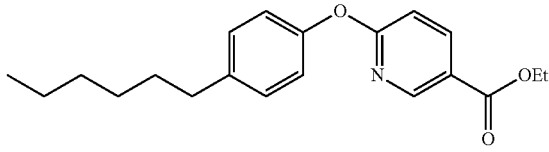

ethyl 6-(4-hexylphenoxy)nicotinate

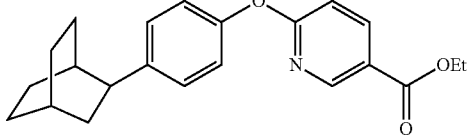

ethyl 6-(4-((1s,4s)-bicyclo[2.2.2]octan-2-yl)phenoxy)nicotinate

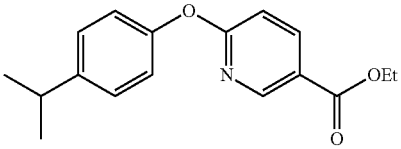

ethyl 6-(4-isopropylphenoxy)nicotinate

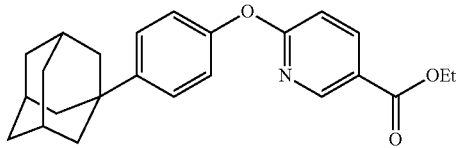

ethyl 6-(4-((3r,5r,7r)-adamantan-1-yl)phenoxy)nicotinate

-continued

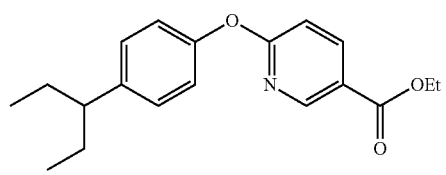

ethyl 6-(4-(pentan-3-yl)phenoxy)nicotinate

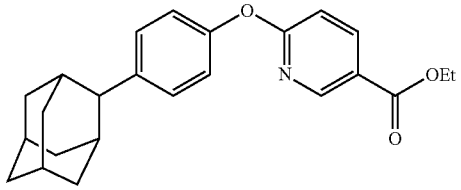

ethyl 6-(4-((1r,3r,5r,7r)-adamantan-2-yl)phenoxy)nicotinate

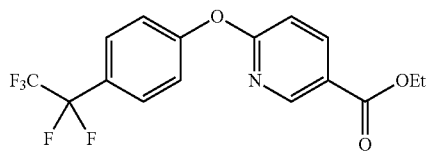

ethyl 6-(4-(perfluoroethyl)phenoxy)nicotinate

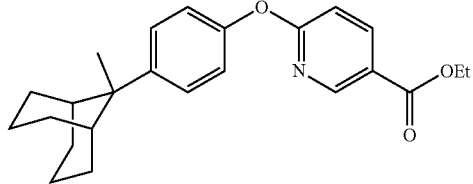

ethyl 6-(4-((1R,5S)-9-methylbicyclo[3.3.1]nonan-9-yl)phenoxy)nicotinate

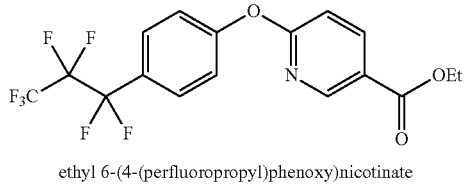

ethyl 6-(4-(perfluoropropyl)phenoxy)nicotinate

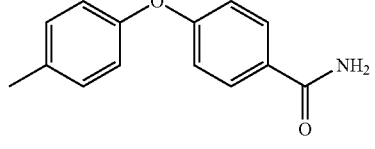

4-(p-tolyloxy)benzamide

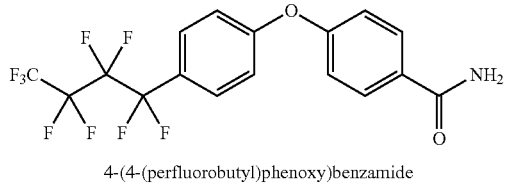

4-(4-(perfluorobutyl)phenoxy)benzamide

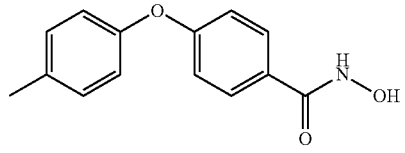

N-hydroxy-4-(p-tolyloxy)benzamide

-continued

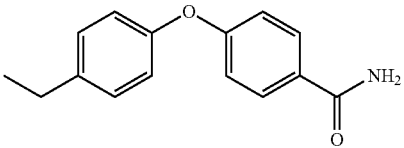

4-(4-ethylphenoxy)benzamide

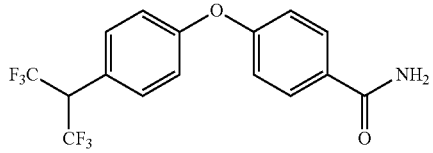

4-(4-(1,1,1,3,3,3-hexafluoropropan-2-yl)phenoxy)benzamide

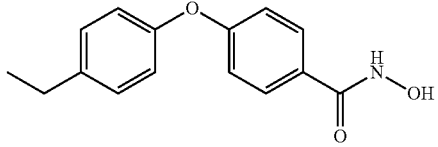

4-(4-ethylphenoxy)-N-hydroxybenzamide

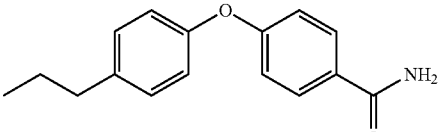

4-(4-propylphenoxy)benzamide

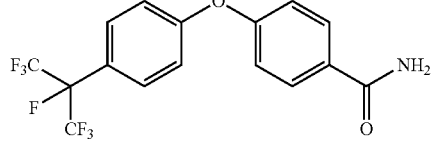

4-(4-(perfluoropropan-2-yl)phenoxy)benzamide

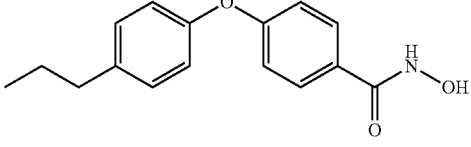

N-hydroxy-4-(4-propylphenoxy)benzamide

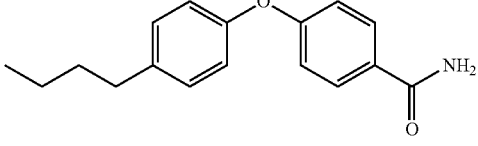

4-(4-butylphenoxy)benzamide

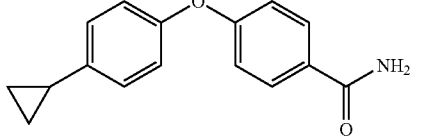

4-(4-cyclopropyl)phenoxy)benzamide

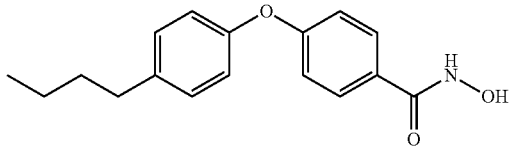

4-(4-butylphenoxy)-N-hydroxybenzamide 4-(4-pentylphenoxy)benzamide 4-(4-cyclobutylphenoxy)benzamide N-hydroxy-4-(4-pentylphenoxy)benzamide 4-(4-hexylphenoxy)benzamide 4-(4-cyclopentylphenoxy)benzamide 4-(4-hexylphenoxy)-N-hydroxybenzamide 4-(4-isopropylphenoxy)benzamide 4-(4-cyclohexylphenoxy)benzamide N-hydroxy-4-(4-isopropylphenoxy)benzamide 4-(4-(tert-butyl)phenoxy)benzamide 4-(4-cycloheptylphenoxy)benzamide N-hydroxy-4-(4-(tert-pentyl)phenoxy)benzamide 4-(4-(tert-pentyl)phenoxy)benzamide 4-(4-((1S,4R)-bicyclo[2.2.1]heptan-2-yl)phenoxy)benzamide N-hydroxy-4-(4-(pentan-3-yl)phenoxy)benzamide 4-(4-(pentan-3-yl)phenoxy)benzamide 4-(4-((1s,4s)-bicyclo[2.2.2]octan-2-yl)phenoxy)benzamide -continued N-hydroxy-4-(4-(trifluoromethyl)phenoxy)benzamide 4-(4-(trifluoromethyl)phenoxy)benzamide 4-(4-((3r,5r,7r)-adamantan-1-yl)phenoxy)benzamide N-hydroxy-4(4-(perfluoroethyl)phenoxy)benzamide 4-(4-(perfluoroethyl)phenoxy)benzamide 4-(4-((1r,3r,5r,7r)-adamantan-2-yl)phenoxy)benzamide N-hydroxy-4-(4-(perfluoropropyl)phenoxy)benzamide 4-(4-(perfluoropropyl)phenoxy)benzamide -continued 4-(4-((1R,5S)-9-methylbicyclo[3.3.1]nonan-9-yl)phenoxy)benzamide N-hydroxy-4-(4-(perfluorobutyl)phenoxy)benzamide 4-(4-(1,1,1,3,3,3-hexafluoropropan-2-yl)phenoxy)-N-hydroxybenzamide N-methyl-4-(p-tolyloxy)benzamide N-methyl-4-(4-perfluorobutyl)phenoxy)benzamide N-hydroxy-4-(4-(perfluoropropan-2-yl)phenoxy)benzamide 4-(4-ethylphenoxy)-N-methylbenzamide 4-(4-(1,1,1,3,3,3-hexafluoropropan-2-yl)phenoxy)-N-methylbenzamide

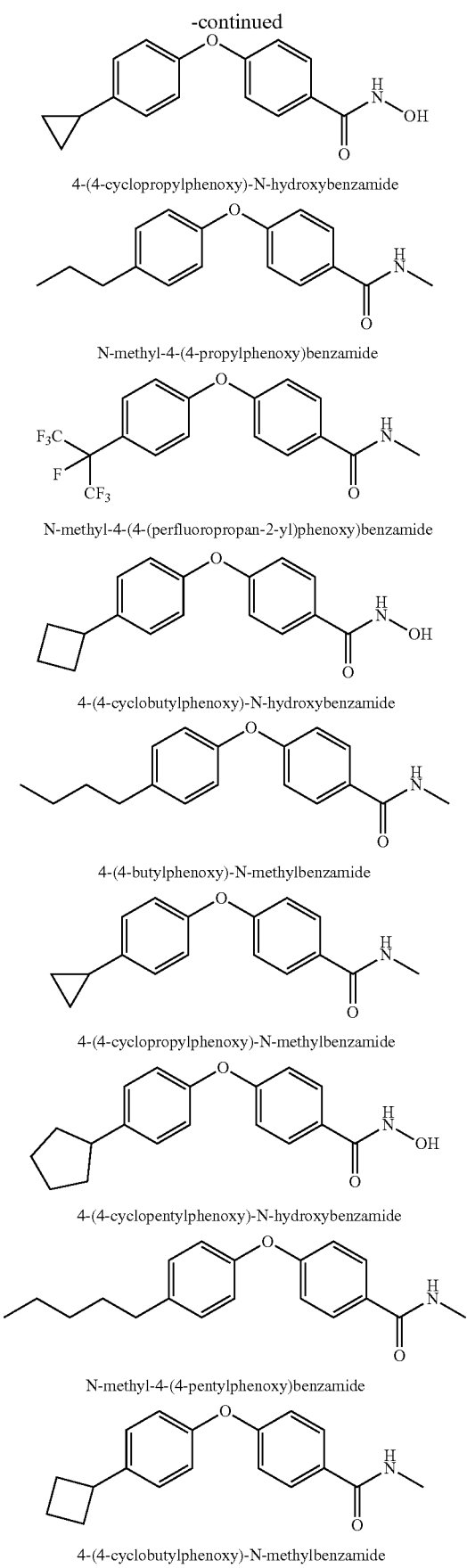
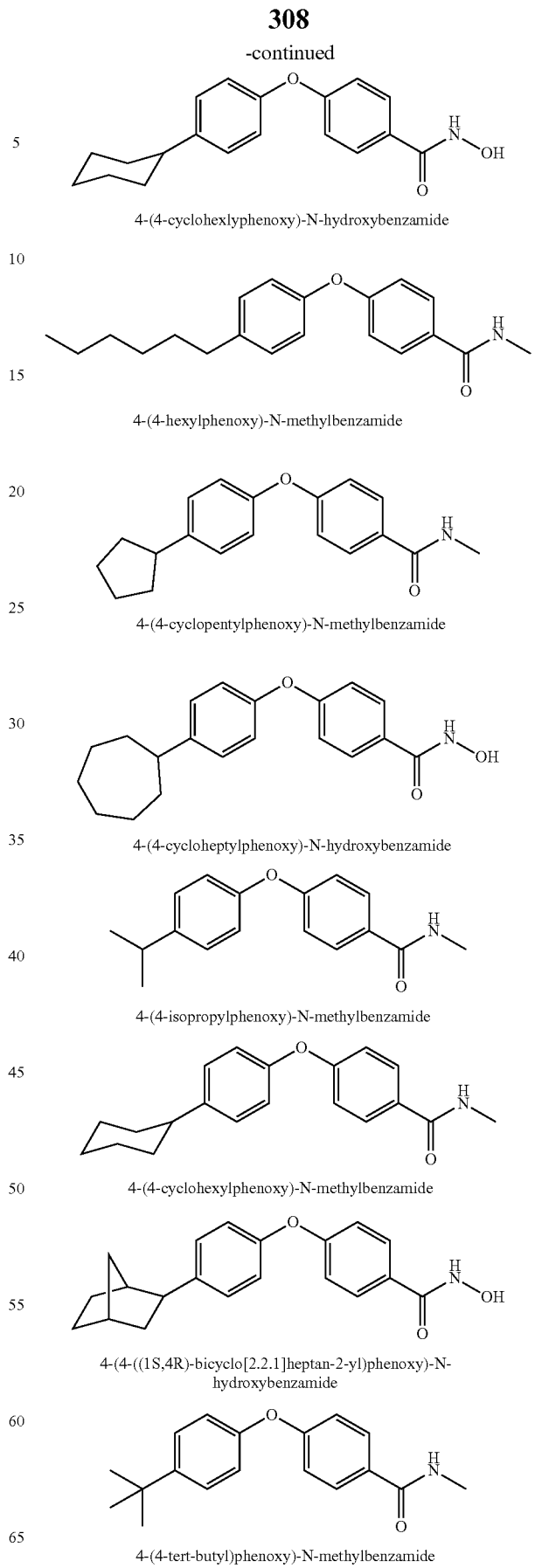

-continued

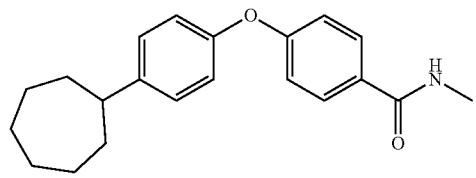

4-(4-cycloheptylphenoxy)-N-methylbenzamide

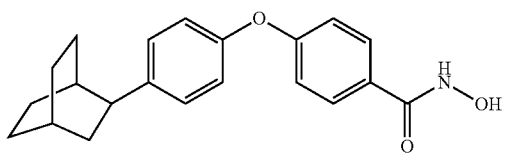

4-(4-((1s,4s)-bicyclo[2.2.2]octan-2-yl)phenoxy)-N-hydroxybenzamide

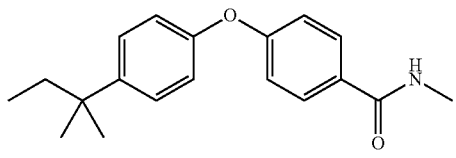

N-methyl-4-(4-(tert-phenyl)phenoxy)benzamide

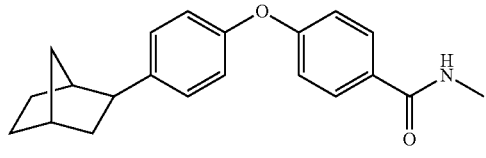

4-(4-((1S,4R)-bicyclo[2.2.1]heptan-2-yl)phenoxy)-N-methylbenzamide

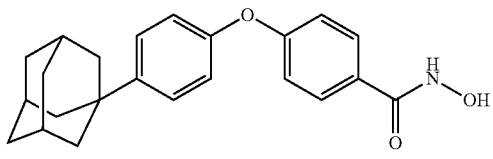

4-(4-((3r,5r,7r)-adamantan-1-yl)phenoxy)-N-hydroxybenzamide

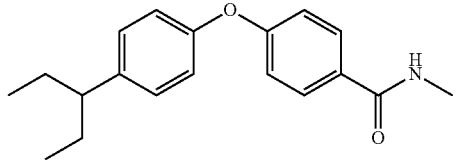

N-methyl-4-(4-(pentan-3-yl)phenoxy)benzamide

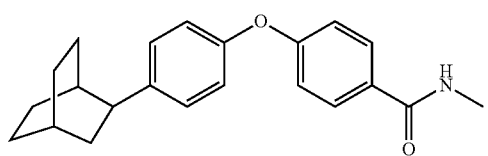

4-(4-((1s,4s)-bicyclo[2.2.2]octan-2-yl)phenoxy)-N-methylbenzamide

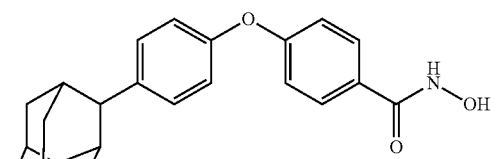

4-(4-((1r,3r,5r,7r)-adamantan-2-yl)phenoxy)-N-hydroxybenzamide

-continued

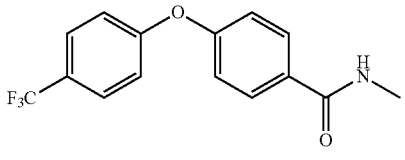

N-methyl-4-(4-(trifluoromethyl)phenoxy)benzamide

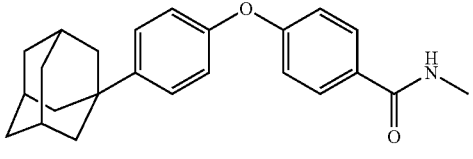

4-(4-((3r,5r,7r)-adamantan-1-yl)phenoxy)-N-methylbenzamide

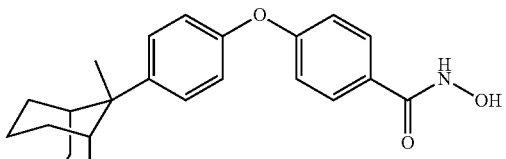

N-hydroxy-4-(4-((1R,5S)-9-methylbicylo[3.3.1]nonan-9-yl)phenoxy)benzamide

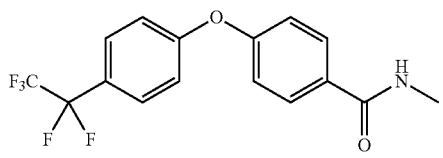

N-methyl-4-(4-(perfluoroethyl)phenoxy)benzamide

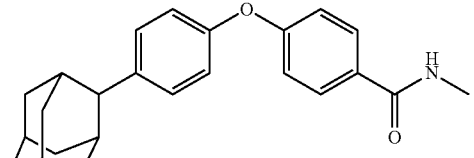

4-(4-((1r,3r,5r,7r)-adamantan-2-yl)phenoxy)-N-methylbenzamide

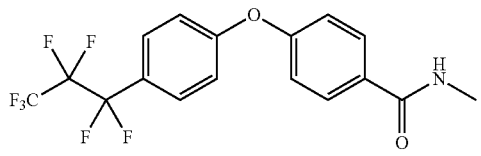

N-methyl-4-(4-(perfluoropropyl)phenoxy)benzamide

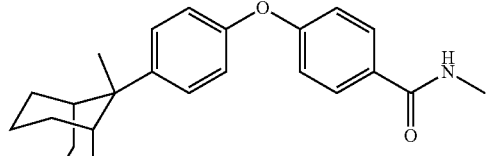

N-methyl-4-(4-((1R,5S)-9-methylbicyclo[3.3.1]nonan-9-yl)phenoxy)benzamide

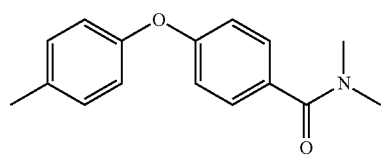

N,N-dimethyl-4-(p-tolyloxy)benzamide

-continued

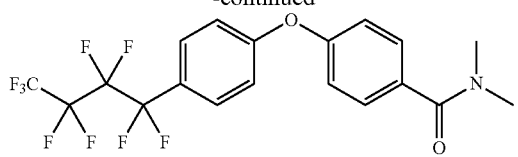

N-N-dimethyl-4(4-perfluorobutyl)phenoxy)benzamide

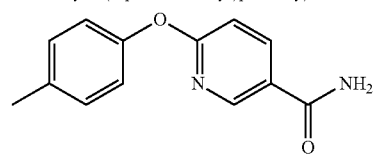

6-(p-tolyloxy)nicotinamide

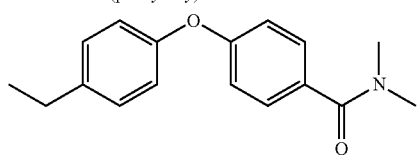

4-(4-ethylphenoxy)-N,N-dimethylbenzamide

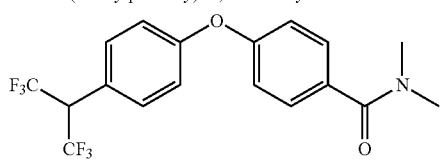

4-(4-(1,1,1,3,3,3-hexafluoropropan-2-yl)phenoxy)-N,N-dimethylbenzamide

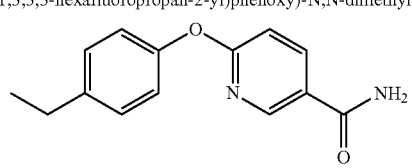

6-(4-ethylphenoxy)nicotinamide

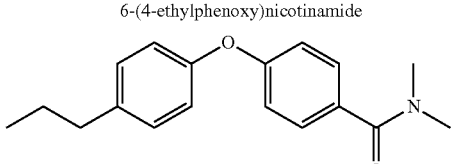

N,N-dimethyl-4-(4-propylphenoxy)benzamide

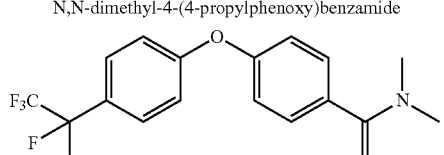

N,N-dimethyl-4-(4-(perfluoropropan-2-yl)phenoxy)benzamide

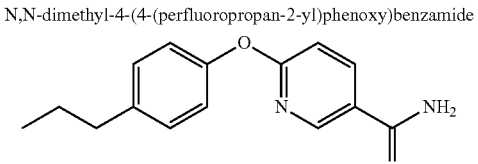

6-(4-propylphenoxy)nicotinamide

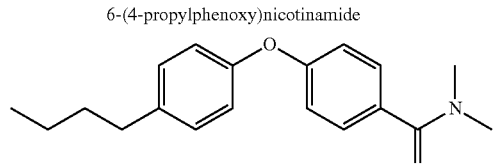

4-(4-butylphenoxy)-N,N-dimethylbenzamide

-continued

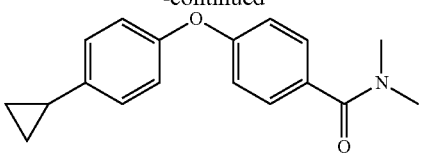

4-(4-cyclopropylphenoxy)-N,N-dimethylbenzamide

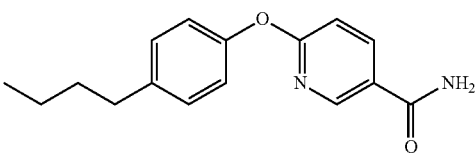

6-(4-butylphenoxy)nicotinamide

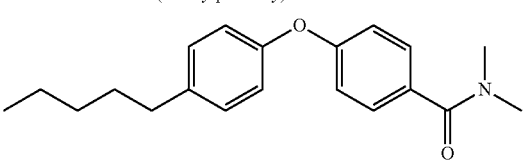

N,N-dimethyl-4-(4-pentylphenoxy)benzamide

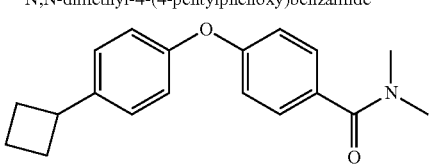

4-(4-cyclobutylphenoxy)-N,N-dimethylbenzamide

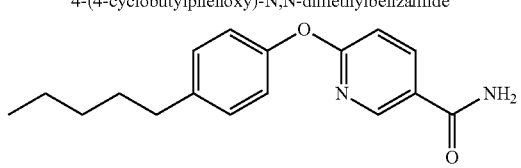

6-(4-pentylphenoxy)nicotinamide

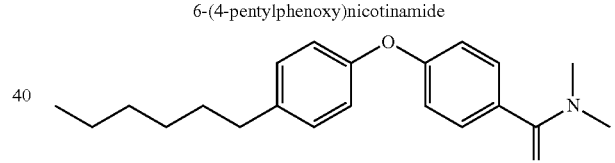

4-(4-hexylphenoxy)-N,N-dimethylbenzamide

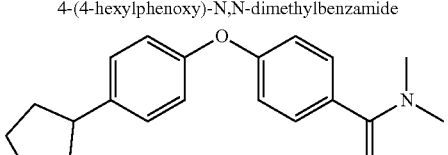

4-(4-cyclopentylphenoxy)-N,N-dimethylbenzamide

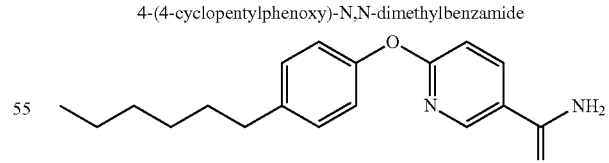

6-(4-hexylphenoxy)nicotinamide

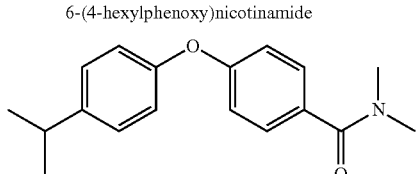

4-(4-isopropylphenoxy)-N,N-dimethylbenzamide

-continued

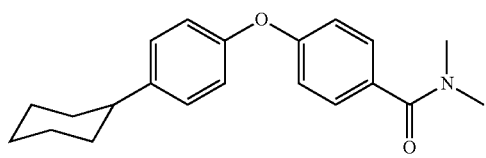
4-(4-cyclohexylphenoxy)-N,N-dimethylbenzamide

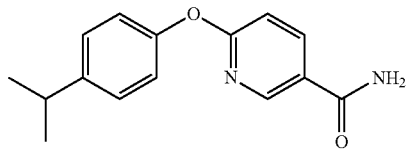
6-(4-isopropylphenoxy)nicotinamide

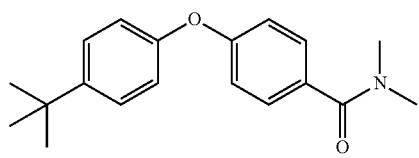
4-(4-(tert-butyl)phenoxy-N,N-dimethylbenzamide

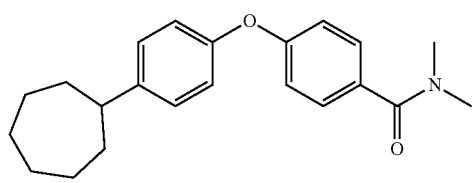
4-(4-cycloheptylphenoxy)-N,N-dimethylbenzamide

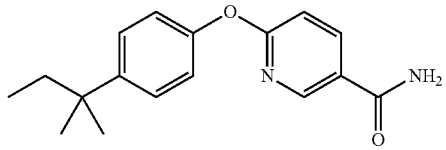
6-(4-(tert-pentyl)phenoxy)nicotinamide

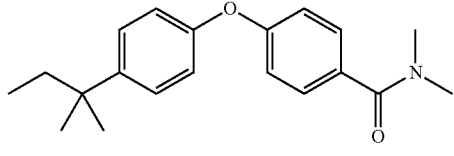
N,N-dimethyl-4-(4-(tert-pentyl)phenoxy)benzamide

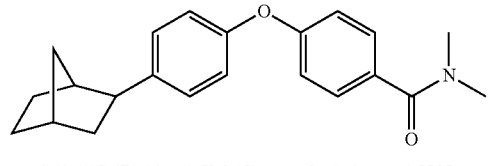
4-(4-((1S,4R)-bicyclo[2.2.1]heptan-2-yl)phenoxy)-N,N-dimethylbenzamide

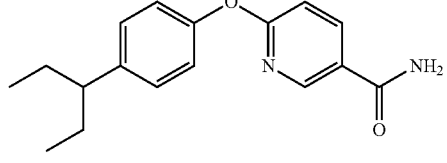
6-(4-(pentan-3-yl)phenoxy)nicotinamide

-continued

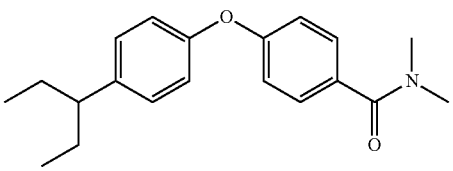
N,N-dimethyl-4-(4-(pentan-3-yl)phenoxy)benzamide

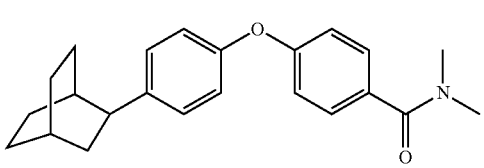
4-(4-((1s,4s)-bicyclo[2.2.2]octan-2-yl)phenoxy)-N,N-dimethylbenzamide

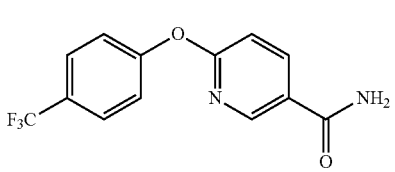
6-(4-(trifluoromethyl)phenoxy)nicotinamide

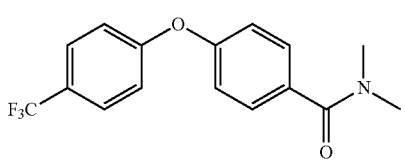
N,N-dimethyl-4-(4-(trifluoromethyl)phenoxy)benzamide

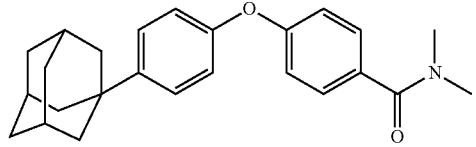
4-(4-((3r,5r,7r)-adamantan-1-yl)phenoxy)-N,N-dimethylbenzamide

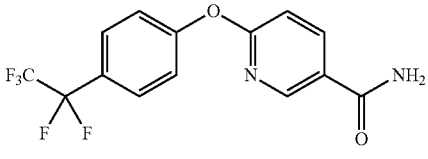
6-(4-(perfluoroethyl)phenoxy)nicotinamide

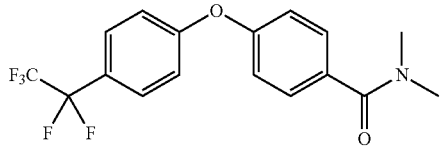
N,N-dimethyl-4-(4-(perfluoroethyl)phenoxy)benzamide

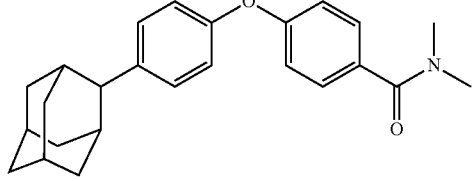
4-(4-((1r,3r,5r,7r)-adamantan-2-yl)phenoxy)-N,N-dimethylbenzamide

-continued

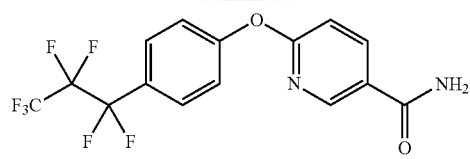

6-(4-(perfluoropropyl)phenoxy)nicotinamide

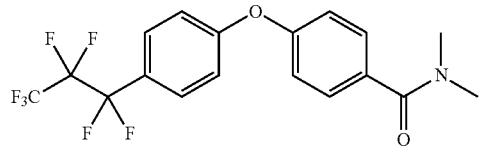

N,N-dimethyl-4-(4-(perfluoropropyl)phenoxy)benzamide

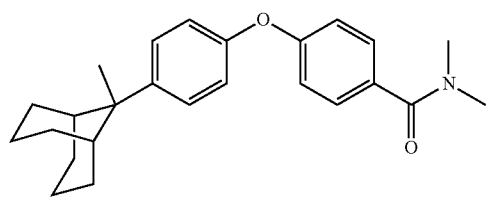

N,N-dimethyl-4-(4-((1R,5S)-9-methylbicyclo[3.3.1]nonan-9-yl)phenoxy)benzamide

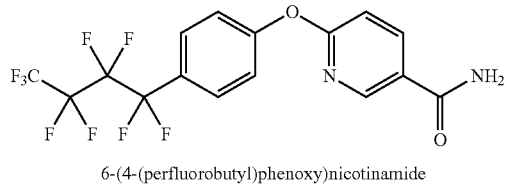

6-(4-(perfluorobutyl)phenoxy)nicotinamide

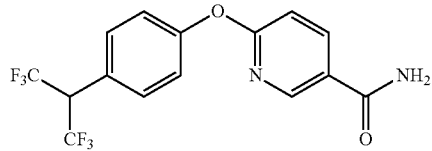

6-(4-(1,1,1,3,3,3-hexafluoropropan-2-yl)phenoxy)nicotinamide

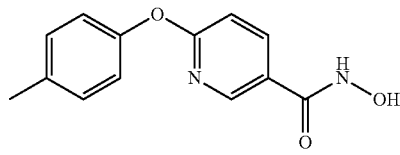

N-hydroxy-6-(p-tolyoxy)nicotinamide

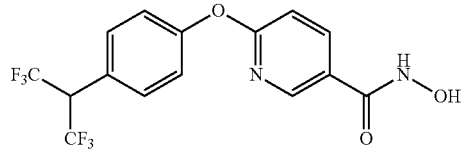

6-(4-(1,1,1,3,3,3-hexafluoropropan-2-yl)phenoxy)-N-hydroxynicotinamide

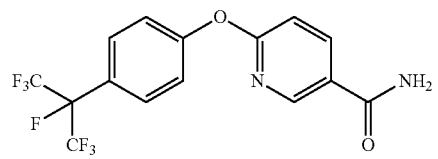

6-(4-(perfluoropropan-2-yl)phenoxy)nicotinamide

-continued

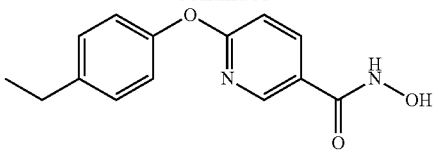

6-(4-ethylphenoxy)-N-hydroxynicotinamide

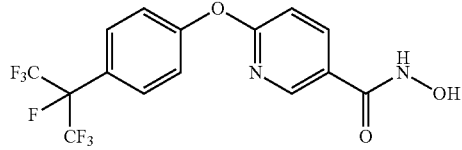

N-hydroxy-6-(4-(perfluoropropan-2-yl)phenoxy)nicotinamide

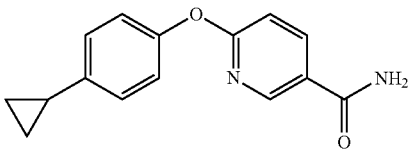

6-(4-cyclopropylphenoxy)nicotinamide

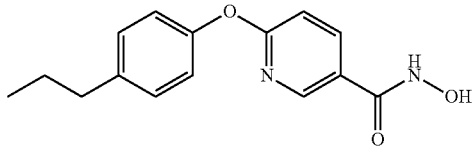

N-hydroxy-6-(4-propylphenoxy)nicotinamide

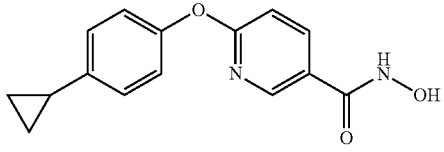

6-(4-cyclopropylphenoxy)-N-hydroxynicotinamide

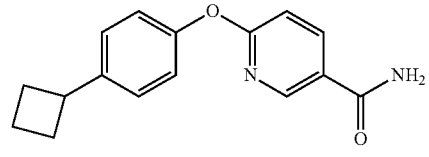

6-(4-cyclobutylphenoxy)nicotinamide

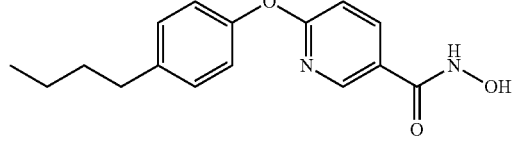

6-(4-butylphenoxy)-N-hydroxynicotinamide

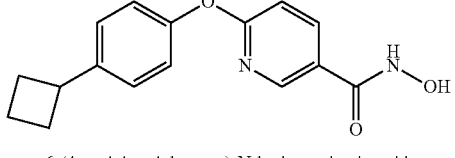

6-(4-cyclobutylphenoxy)-N-hydroxynicotinamide

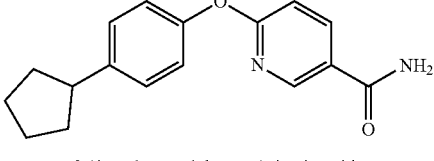

6-(4-cyclopentylphenoxy)nicotinamide

-continued

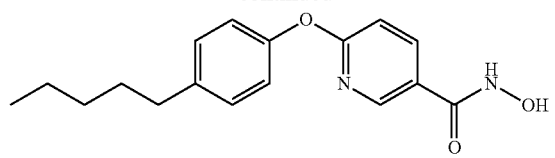

N-hydroxy-6-(4-pentylphenoxy)nicotinamide

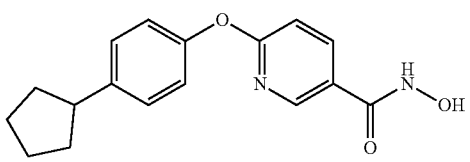

6-(4-cyclopentylphenoxy)-N-hydroxynicotinamide

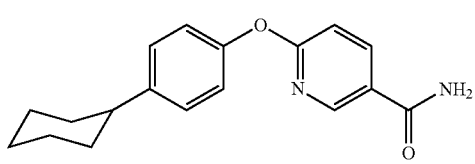

6-(4-cyclohexylphenoxy)nicotinamide

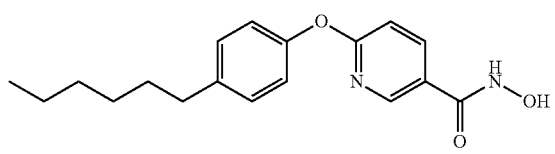

6-(4-hexylphenoxy)-N-hydroxynicotinamide

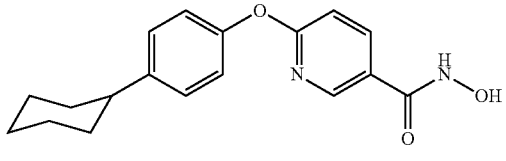

6-(4-cyclohexylphenoxy)-N-hydroxynicotinamide

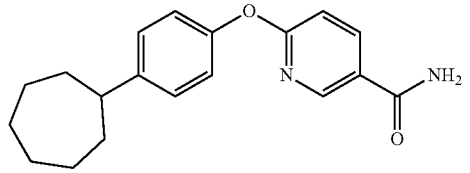

6-(4-cycloheptylphenoxy)nicotinamide

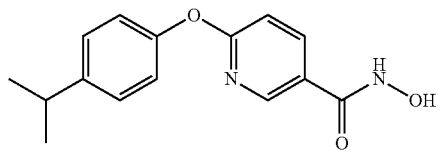

N-hydroxy-6-(4-isopropylphenoxy)nicotinamide

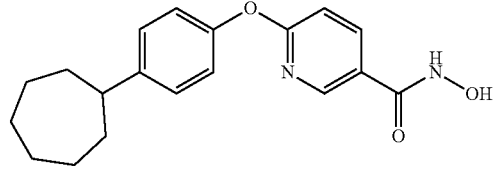

6-(4-cycloheptylphenoxy)-N-hydroxynicotinamide

-continued

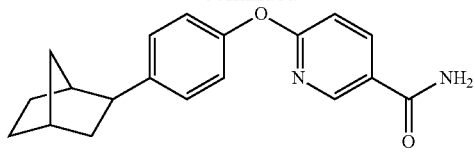

6-(4-((1S,4R)-bicyclo[2.2.1]heptan-2-yl)phenoxy)nicotinamide

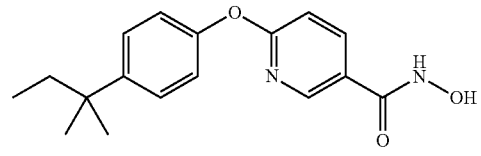

N-hydroxy-6-(4-(tert-pentyl)phenoxy)nicotinamide

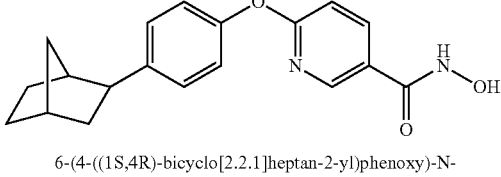

6-(4-((1S,4R)-bicyclo[2.2.1]heptan-2-yl)phenoxy)-N-hydroxynicotinamide

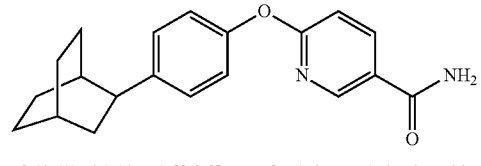

6-(4-((1s,4s)-bicyclo[2.2.2]octan-2-yl)phenoxy)nicotinamide

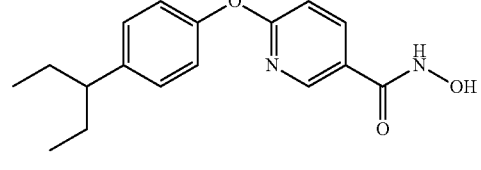

N-hydroxy-6-(4-(pentan-3-yl)phenoxy)nicotinamide

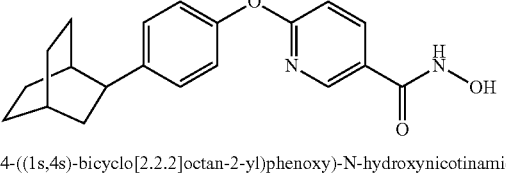

6(4-((1s,4s)-bicyclo[2.2.2]octan-2-yl)phenoxy)-N-hydroxynicotinamide

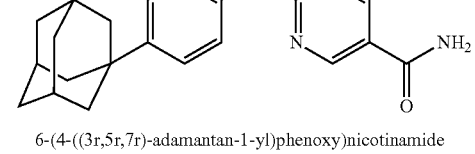

6-(4-((3r,5r,7r)-adamantan-1-yl)phenoxy)nicotinamide

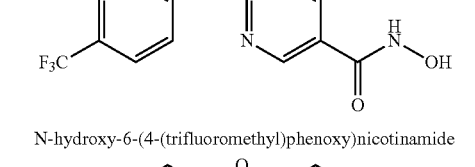

N-hydroxy-6-(4-(trifluoromethyl)phenoxy)nicotinamide

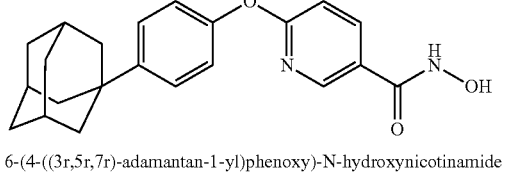

6-(4-((3r,5r,7r)-adamantan-1-yl)phenoxy)-N-hydroxynicotinamide

-continued

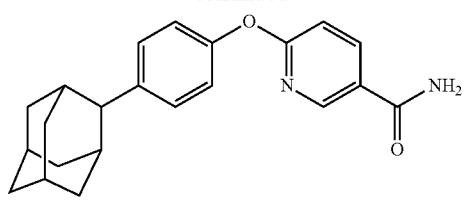

6-(4-((1r,3r,5r,7r)-adamantan-2-yl)phenoxy)nicotinamide

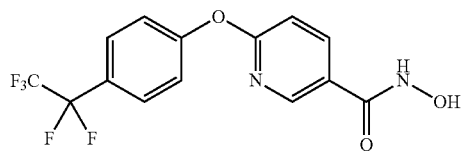

N-hydroxy-6-(4-(perfluoroethyl)phenoxy)nicotinamide

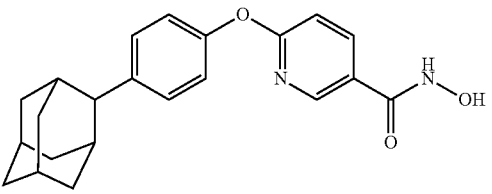

6-(4-((1r,3r,5r,7r)-adamantan-2-yl)phenoxy)-N-hydroxynicotinamide

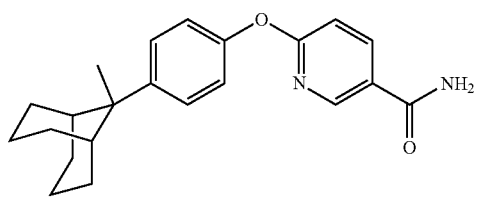

6-(4-((1R,5S)-9-methylbicyclo[3.3.1]nonan-9-yl)phenoxy)nicotinamide

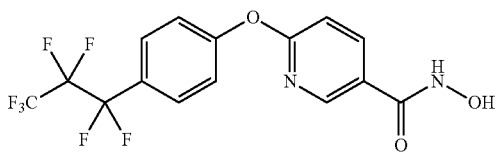

N-hydroxy-6-(4-(perfluoropropyl)phenoxy)nicotinamide

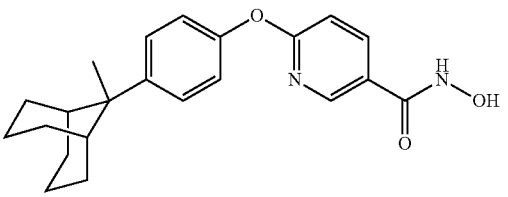

N-hydroxy-6-(4-((1R,5S)-9-methylbicyclo[3.3.1]nonan-9-yl)phenoxy)nicotinamide

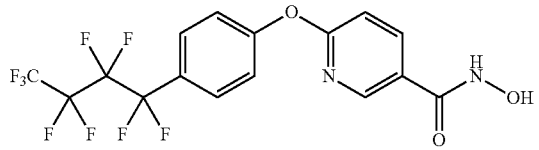

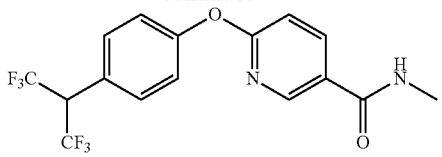

N-methyl-6-(p-tolyoxy)nicotinamide

-continued

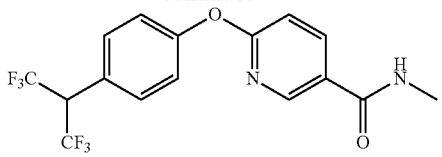

6-(4-(1,1,1,3,3,3-hexafluoropropan-2-yl)phenoxy)-N-methylnicotinamide

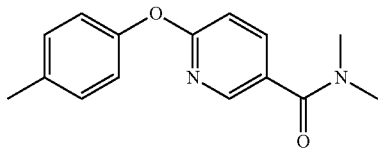

N,N-dimethyl-6-(p-tolyloxy)nicotinamide

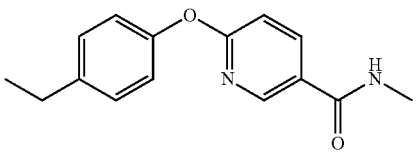

6-(4-ethylphenoxy)-N-methylnicotinamide

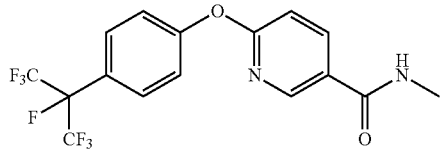

N-methyl-6-(4-(perfluoropropan-2-yl)phenoxy)nicotinamide

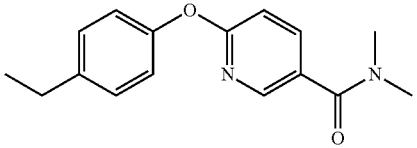

6-(4-ethylphenoxy)-N,N-dimethylnicotinamide

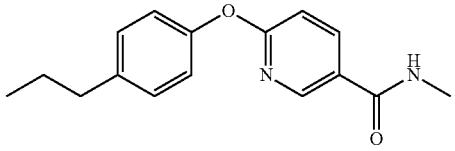

N-methyl-6-(4-propylphenoxy)nicotinamide

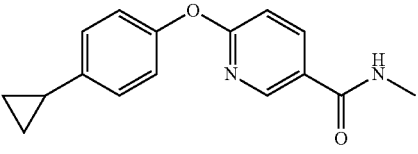

6-(4-cyclopropylphenoxy)-N-methylnicotinamide

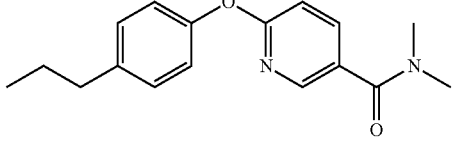

N,N-dimethyl-6-(4-propylphenoxy)nicotinamide

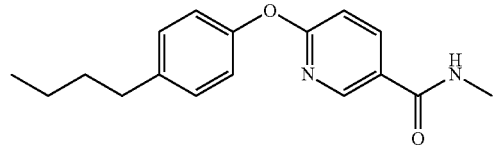

6-(4-butylphenoxy)-N-methylnicotinamide

-continued

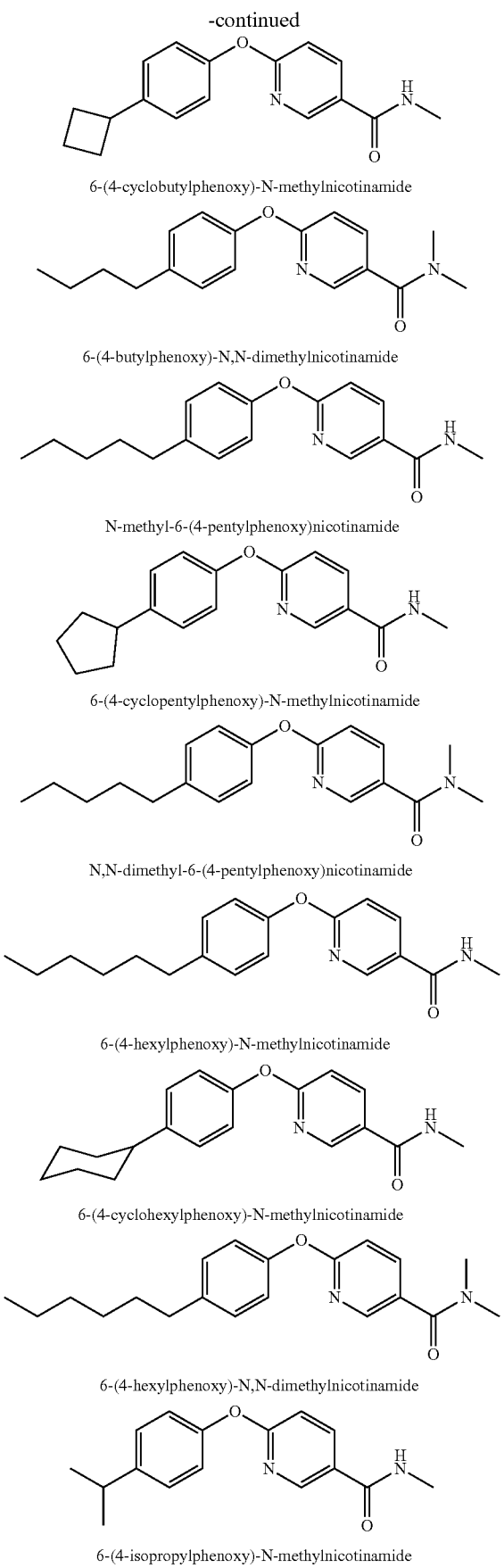

6-(4-cyclobutylphenoxy)-N-methylnicotinamide 6-(4-butylphenoxy)-N,N-dimethylnicotinamide N-methyl-6-(4-pentylphenoxy)nicotinamide 6-(4-cyclopentylphenoxy)-N-methylnicotinamide N,N-dimethyl-6-(4-pentylphenoxy)nicotinamide 6-(4-hexylphenoxy)-N-methylnicotinamide 6-(4-cyclohexylphenoxy)-N-methylnicotinamide 6-(4-hexylphenoxy)-N,N-dimethylnicotinamide 6-(4-isopropylphenoxy)-N-methylnicotinamide -continued

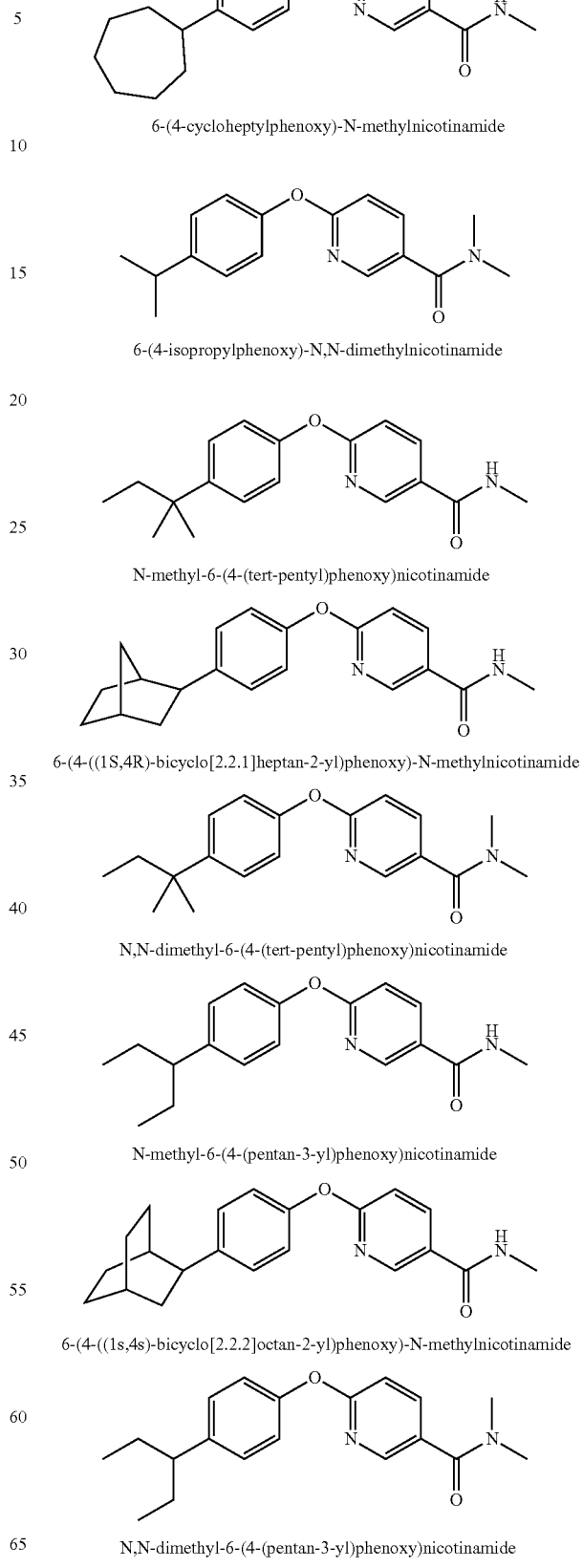

6-(4-cycloheptylphenoxy)-N-methylnicotinamide 6-(4-isopropylphenoxy)-N,N-dimethylnicotinamide N-methyl-6-(4-(tert-pentyl)phenoxy)nicotinamide 6-(4-((1S,4R)-bicyclo[2.2.1]heptan-2-yl)phenoxy)-N-methylnicotinamide N,N-dimethyl-6-(4-(tert-pentyl)phenoxy)nicotinamide N-methyl-6-(4-(pentan-3-yl)phenoxy)nicotinamide 6-(4-((1s,4s)-bicyclo[2.2.2]octan-2-yl)phenoxy)-N-methylnicotinamide N,N-dimethyl-6-(4-(pentan-3-yl)phenoxy)nicotinamide

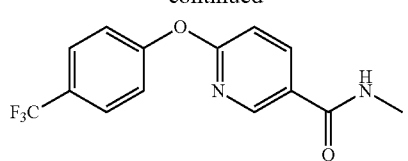

N-methyl-6-(4-(trifluoromethyl)phenoxy)nicotinamide

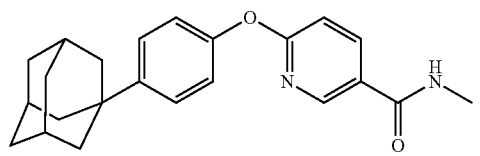

6-(4-((3r,5r,7r)-adamantan-1-yl)phenoxy)-N-methylnicotinamide

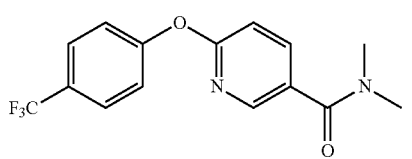

N,N-dimethyl-6-(4-(trifluoromethyl)phenoxy)nicotinamide

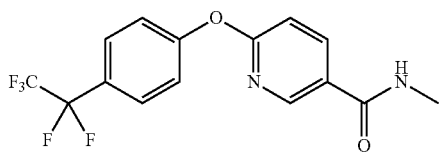

N-methyl-6-(4-(perfluoroethyl)phenoxy)nicotinamide

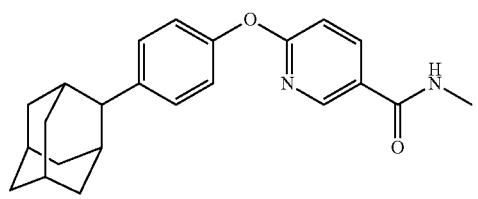

6-(4-((1r,3r,5r,7r)-adamantan-2-yl)phenoxy)-N-methylnicotinamide

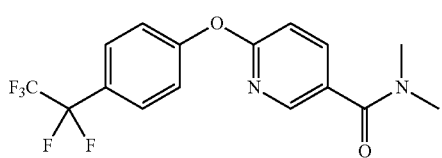

N,N-dimethyl-6-(4-(perfluoroethyl)phenoxy)nicotinamide

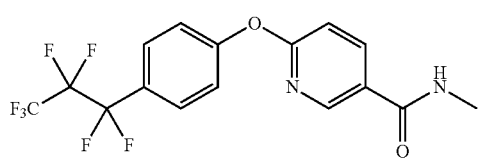

N-methyl-6-(4-(perfluoropropyl)phenoxy)nicotinamide

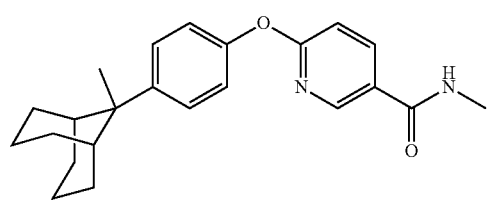

N-methyl-6-(4-((1R,5S)-9-methylbicyclo[3.3.1]nonan-9-yl)phenoxy)nicotinamide

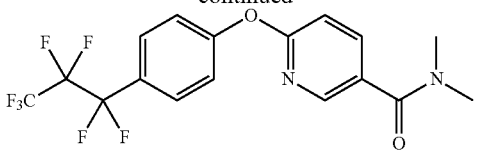

N,N-dimethyl-6-(4-(perfluoropropyl)phenoxy)nicotinamide

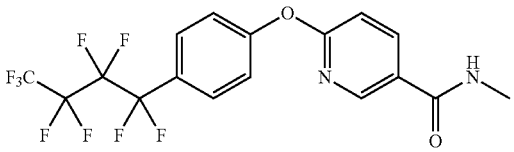

N-methyl-6-(4-(perfluorobutyl)phenoxy)nicotinamide

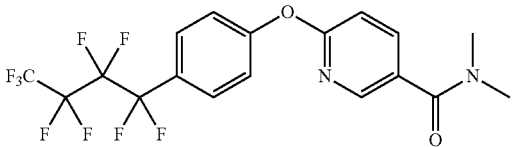

N,N-dimethyl-6-(4-(perfluorobutyl)phenoxy)nicotinamide

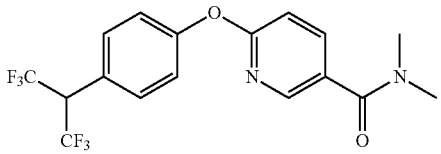

6-(4-(1,1,1,3,3,3-hexafluoropropan-2-yl)phenoxy)-N,N-dimethylnicotinamide

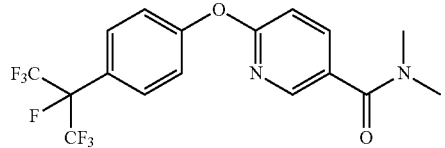

N,N-dimethyl-6-(4-(perfluoropropan-2-yl)phenoxy)nicotinamide

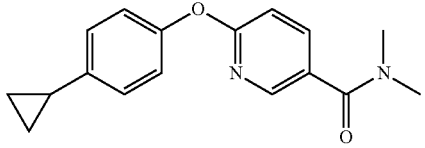

6-(4-cyclopropylphenoxy)-N,N-dimethylnicotinamide

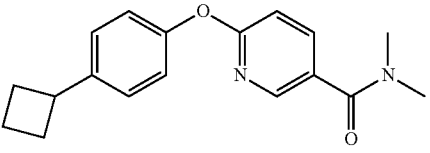

6-(4-cyclobutylphenoxy)-N,N-dimethylnicotinamide

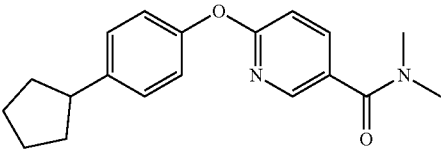

6-(4-cyclopentylphenoxy)-N,N-dimethylnicotinamide

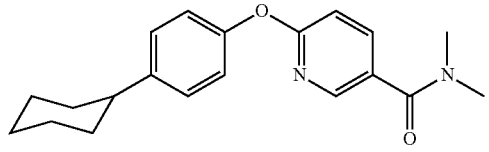

6-(4-cyclohexylphenoxy)-N,N-dimethylnicotinamide

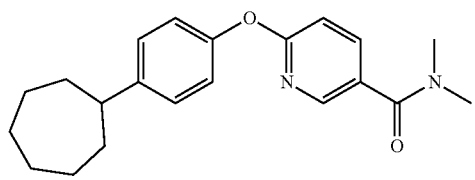

6-(4-cycloheptylphenoxy)-N,N-dimethylnicotinamide

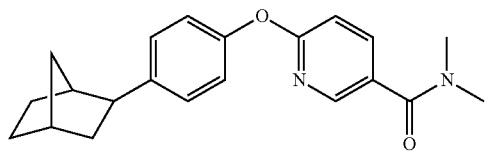

6-(4-((1S,4R)-bicyclo[2.2.1]heptan-2-yl)phenoxy)-N,N-dimethylnicotinamide

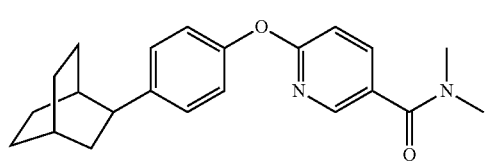

6-(4-((1s,4s)-bicyclo[2.2.2]octan-2-yl)phenoxy)-N,N-dimethylnicotinamide

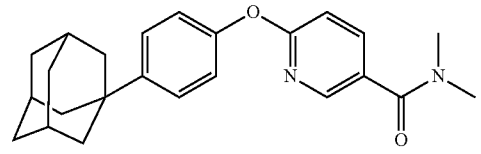

6-(4-((3r,5r,7r)-adamantan-1-yl)phenoxy)-N,N-dimethylnicotinamide

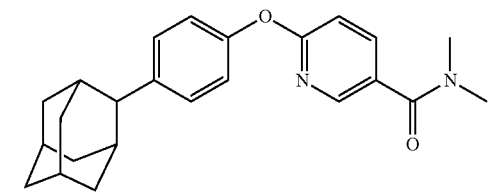

6-(4-((1r,3r,5r,7r)-adamantan-2-yl)phenoxy)-N,N-dimethylnicotinamide

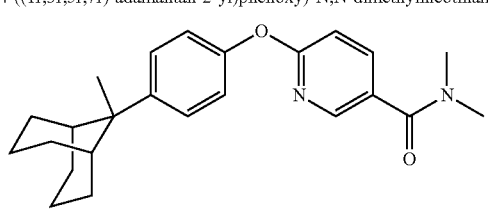

N,N-dimethyl-6-(4-((1R,5S)-9-methylbicyclo[3.3.1]nonan-9-yl)phenoxy)nicotinamide

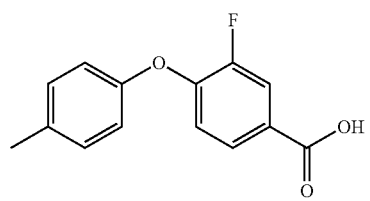

3-fluoro-4-(p-tolyoxy)benzoic acid

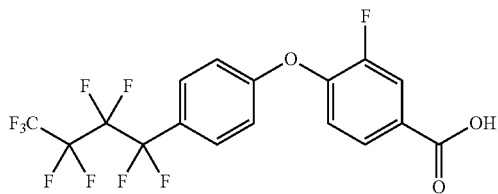

3-fluoro-4-(4-(perfluorobutyl)phenoxy)benzoic acid

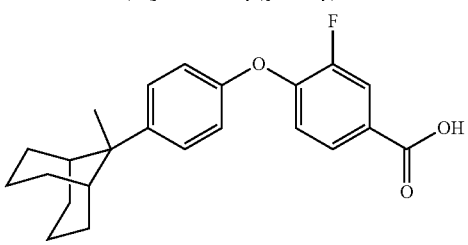

3-fluoro-4-(4-((1R,5S)-9-methylbicyclo[3.3.1]nonan-9-yl)phenoxy)benzoic acid

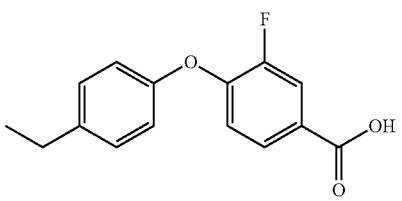

4-(4-ethylphenoxy)-3-fluorobenzoic acid

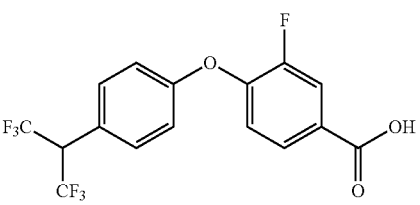

3-fluoro-4-(4-(1,1,1,3,3,3-hexafluoropropan-2-yl)phenoxy)benzoic acid

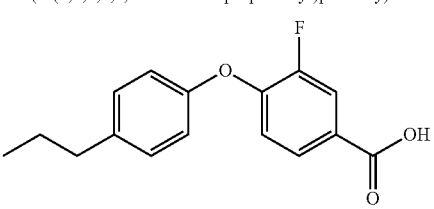

3-fluoro-4-(4-propylphenoxy)benzoic acid

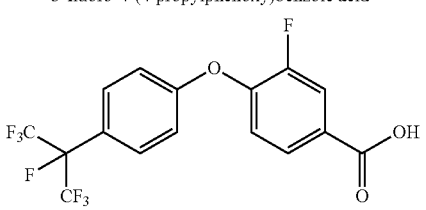

3-fluoro-4-(4-(perfluoropropan-2-yl)phenoxy)benzoic acid

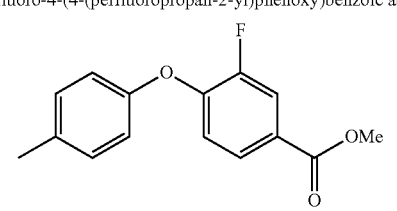

methyl 3-fluoro-4-(p-tolyloxy)benzoate

-continued

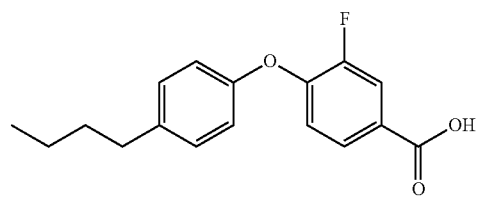

4-(4-butylphenoxy)-3-fluorobenzoic acid

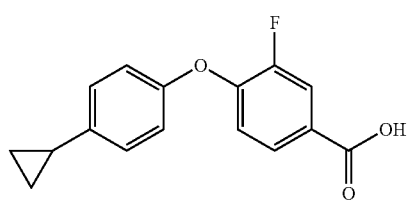

4-(4-cyclopropylphenoxy)-3-fluorobenzoic acid

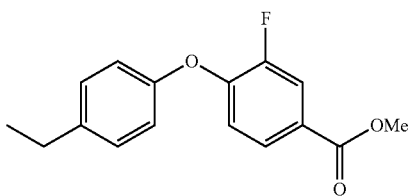

methyl 4-(4-ethylphenoxy)-3-fluorobenzoate

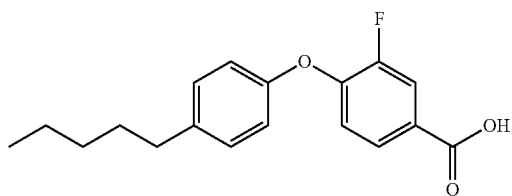

3-fluoro-4-(4-pentylphenoxy)benzoic acid

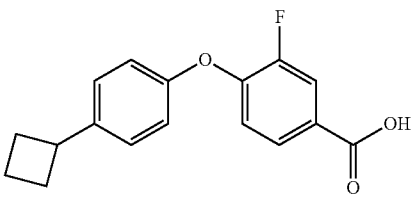

4-(4-cyclobutylphenoxy)-3-fluorobenzoic acid

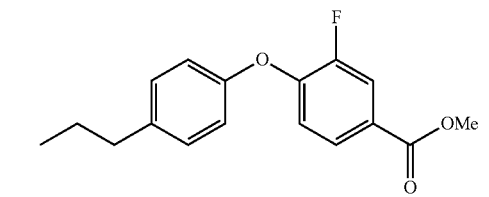

methyl 3-fluoro-4-(4-propylphenoxy)benzoate

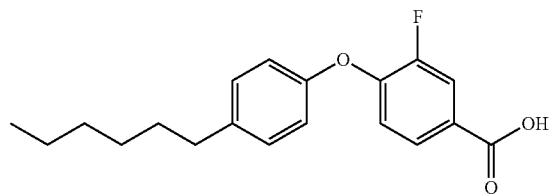

3-fluoro-4-(4-hexylphenoxy)benzoic acid

-continued

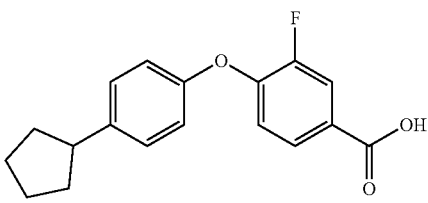

4-(4-cyclopentylphenoxy)-3-fluorobenzoic acid

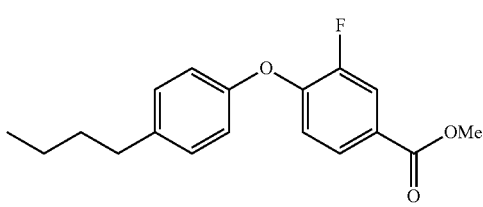

methyl 4-(4-butylphenoxy)-3-fluorobenzoate

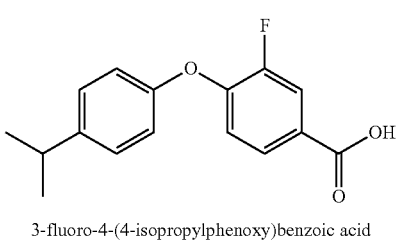

3-fluoro-4-(4-isopropylphenoxy)benzoic acid

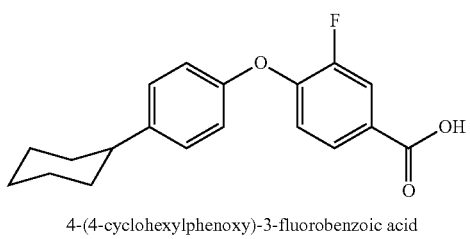

4-(4-cyclohexylphenoxy)-3-fluorobenzoic acid

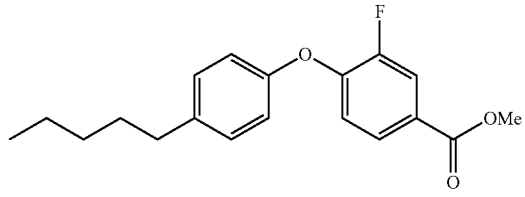

methyl 3-fluoro-4-(4-pentylphenoxy)benzoate

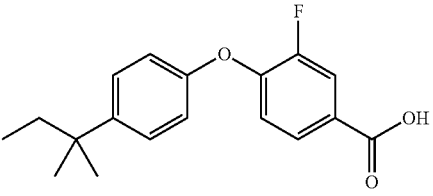

3-fluoro-4-(4-(tert-pentyl)phenoxy)benzoic acid

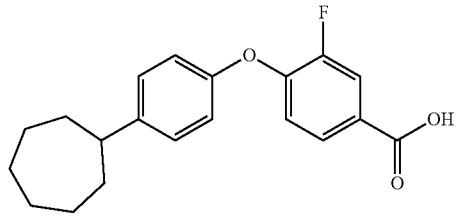

4-(4-cycloheptylphenoxy)-3-fluorobenzoic acid

-continued

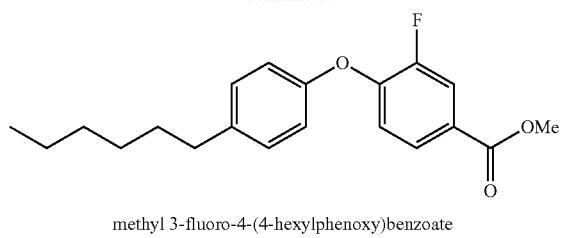

methyl 3-fluoro-4-(4-hexylphenoxy)benzoate

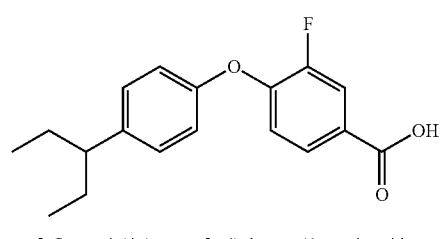

3-fluoro-4-(4-(pentan-3-yl)phenoxy)benzoic acid

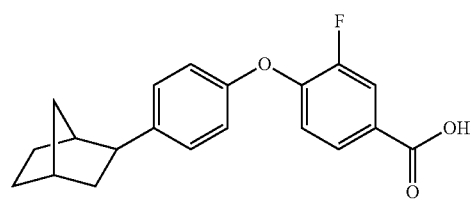

4-(4-((1S,4R)-bicyclo[2.2.1]heptan-2-yl)phenoxy)-3-fluorobenzoic acid

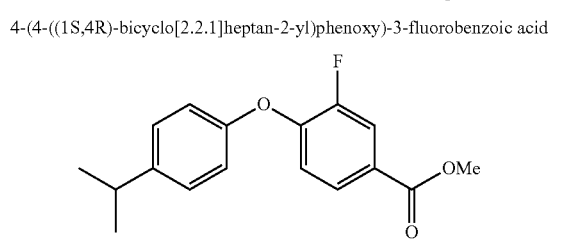

methyl 3-fluoro-4-(4-isopropylphenoxy)benzoate

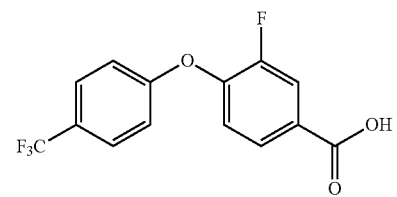

3-fluoro-4-(4-(trifluoromethyl)phenoxy)benzoic acid

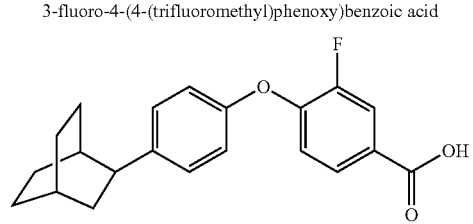

4-(4-((1s,4s)-bicyclo[2.2.2]octan-2-yl)phenoxy)-3-fluorobenzoic acid

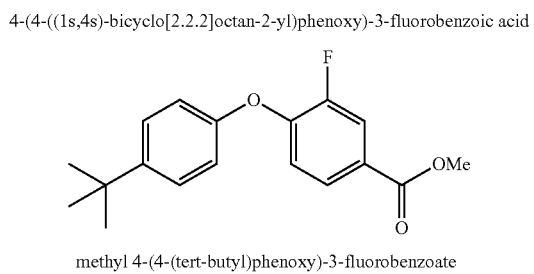

methyl 4-(4-(tert-butyl)phenoxy)-3-fluorobenzoate

-continued

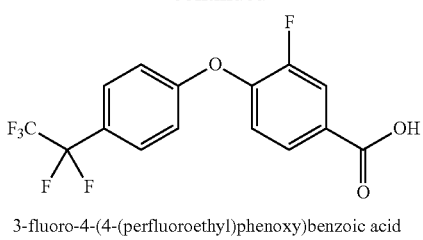

3-fluoro-4-(4-(perfluoroethyl)phenoxy)benzoic acid

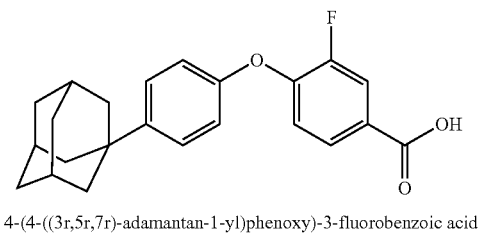

4-(4-((3r,5r,7r)-adamantan-1-yl)phenoxy)-3-fluorobenzoic acid

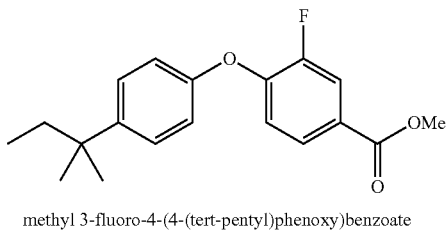

methyl 3-fluoro-4-(4-(tert-pentyl)phenoxy)benzoate

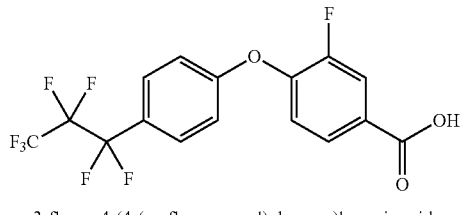

3-fluoro-4-(4-(perfluoropropyl)phenoxy)benzoic acid

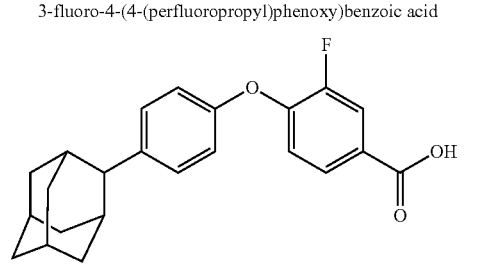

4-(4-((1r,3r,5r,7r)-adamantan-2-yl)phenoxy)-3-fluorobenzoic acid

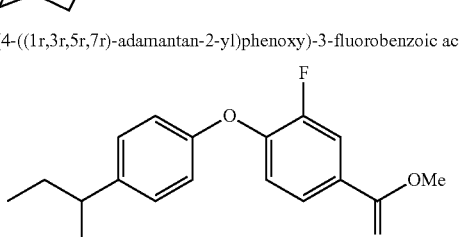

methyl 3-fluoro-4-(4-(pentan-3-yl)phenoxy)benzoate

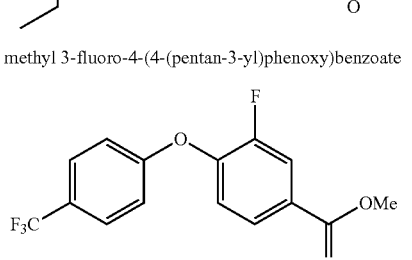

methyl 3-fluoro-4-(4-(trifluoromethyl)phenoxy)benzoate

-continued

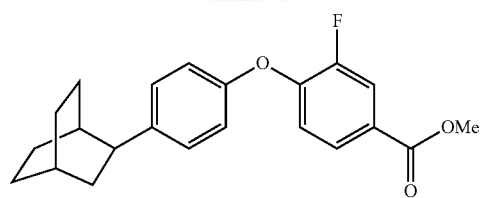

methyl 4-(4-((1s,4s)-bicyclo[2.2.2]octan-2-yl)phenoxy)-3-fluorobenzoate

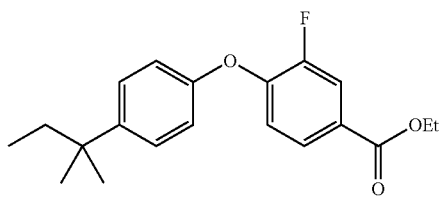

ethyl 3-fluoro-4-(4-(tert-pentyl)phenoxy)benzoate

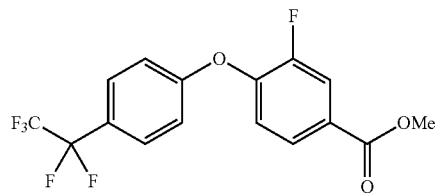

methyl 3-fluoro-4-(4-(perfluoroethyl)phenoxy)benzoate

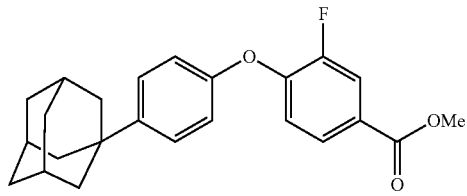

methyl 4-(4-((3r,5r,7r)-adamantan-1-yl)phenoxy)-3-fluorobenzoate

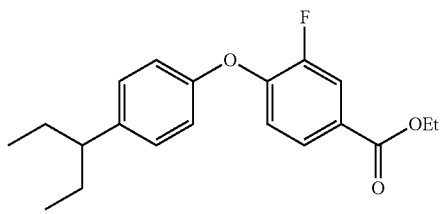

ethyl 3-fluoro-4-(4-(pentan-3-yl)phenoxy)benzoate

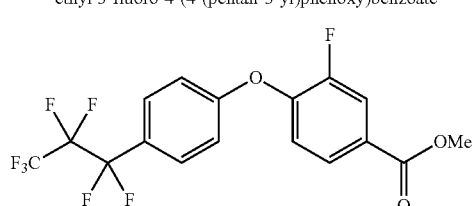

methyl 3-fluoro-4-(4-(perfluoropropyl)phenoxy)benzoate

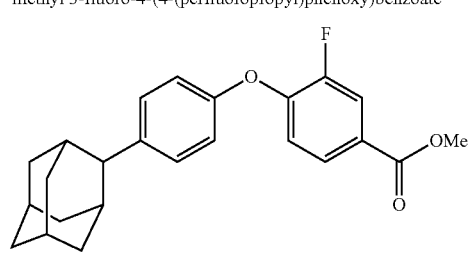

methyl 4-(4-((1r,3r,5r,7r)-adamantan-2-yl)phenoxy)-3-fluorobenzoate

-continued

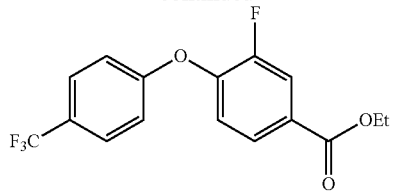

ethyl 3-fluoro-4-(4-(trifluoromethyl)phenoxy)benzoate

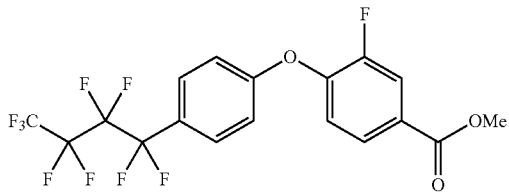

methyl 3-fluoro-4-(4-(perfluorobutyl)phenoxy)benzoate

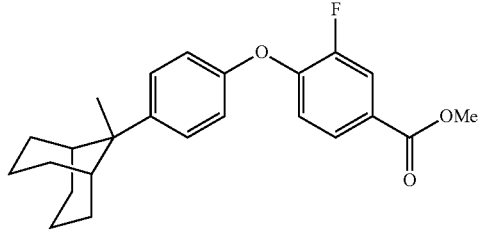

methyl 3-fluoro-4-(4-((1R,5S)-9-methylbicyclo[3.3.1]nonan-9-yl)phenoxy)benzoate

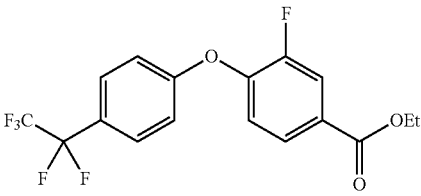

ethyl 3-fluoro-4-(4-(perfluoroethyl)phenoxy)benzoate

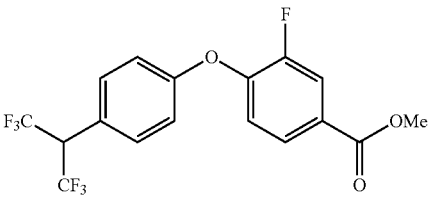

methyl 3-fluoro-4-(4-(1,1,1,3,3,3-hexafluoropropan-2-yl)phenoxy)benzoate

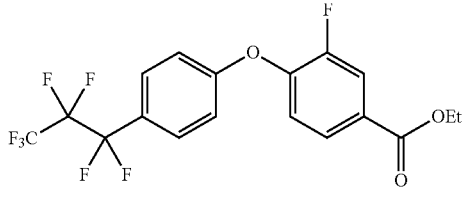

ethyl 3-fluoro-4-(4-(perfluoropropyl)phenoxy)benzoate

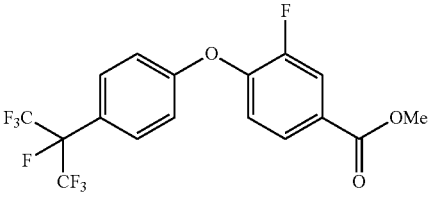

methyl 3-fluoro-4-(4-(perfluoropropan-2-yl)phenoxy)benzoate

-continued

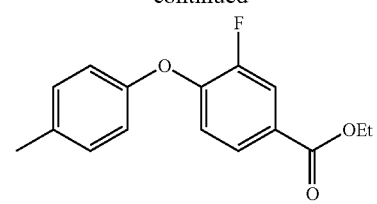
ethyl 3-fluoro-4-(p-tolyloxy)benzoate

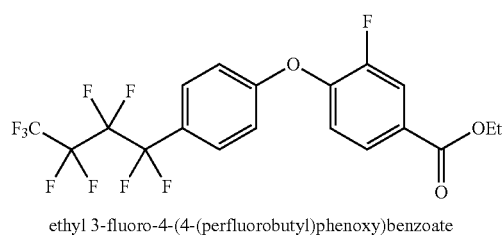
ethyl 3-fluoro-4-(4-(perfluorobutyl)phenoxy)benzoate

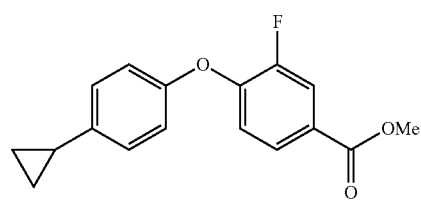
methyl 4-(4-cyclopropylphenoxy)-3-fluorobenzoate

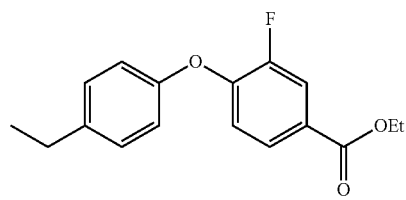
ethyl 4-(4-ethylphenoxy)-3-fluorobenzoate

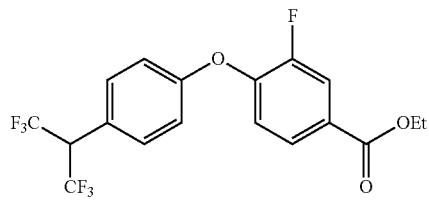
ethyl 3-fluoro-4-(4-(1,1,1,3,3,3-hexafluoropropan-2-yl)phenoxy)benzoate

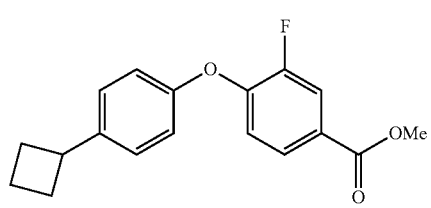
methyl 4-(4-cyclobutylphenoxy)-3-fluorobenzoate

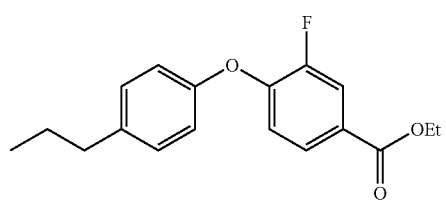
ethyl 3-fluoro-4-(4-propylphenoxy)benzoate

-continued

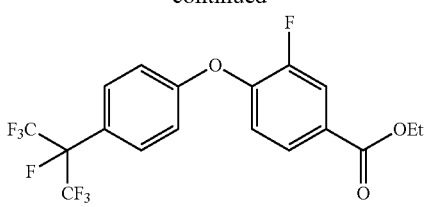
ethyl 3-fluoro-4-(4-(perfluoropropan-2-yl)phenoxy)benzoate

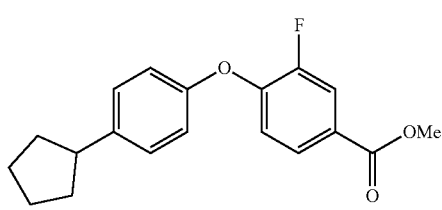
methyl 4-(4-cyclopentylphenoxy)-3-fluorobenzoate

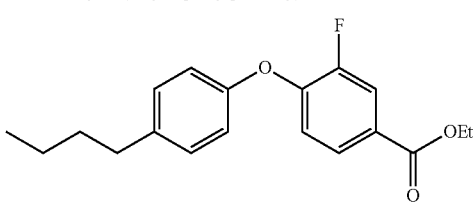
ethyl 4-(4-butylphenoxy)-3-fluorobenzoate

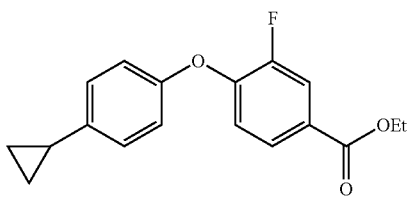
ethyl 4-(4-cyclopropylphenoxy)-3-fluorobenzoate

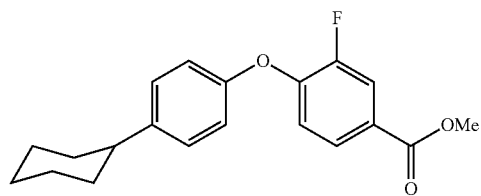
methyl 4-(4-cyclohexylphenoxy)-3-fluorobenzoate

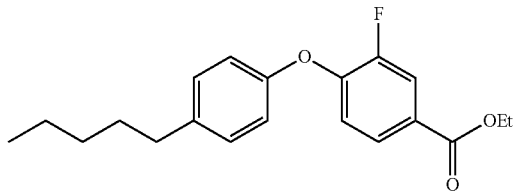
ethyl 3-fluoro-4-(4-pentylphenoxy)benzoate

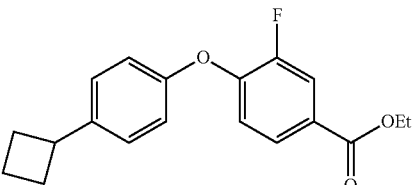
ethyl 4-(4-cyclobutylphenoxy)-3-fluorobenzoate

-continued

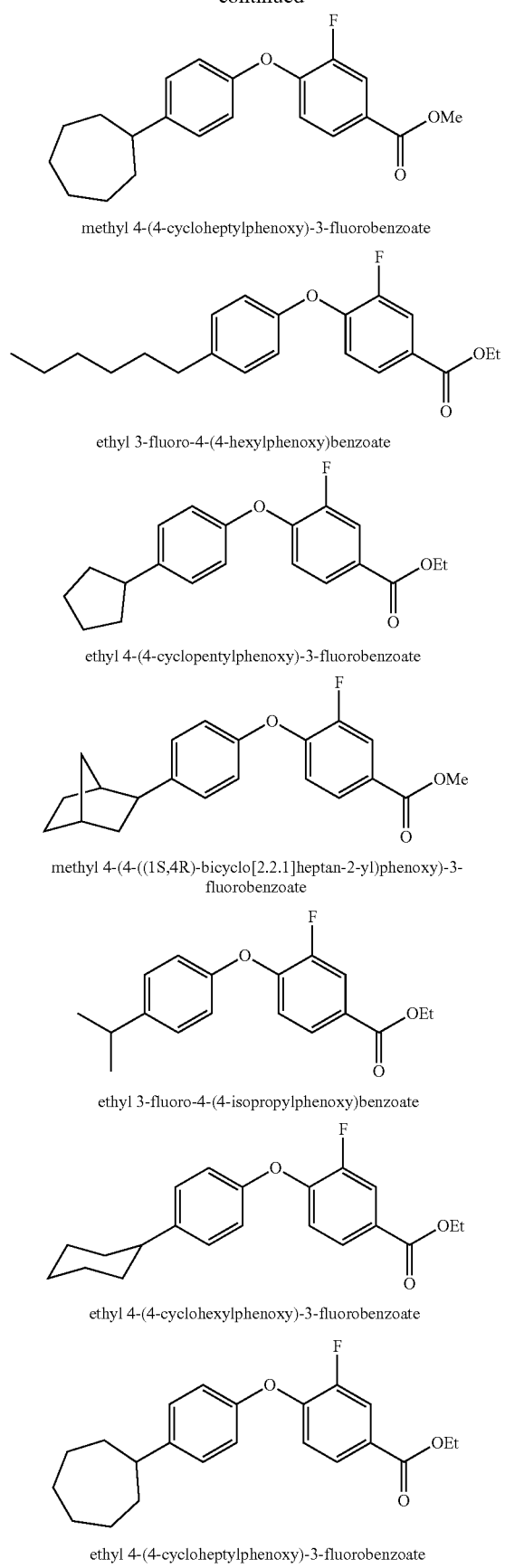

methyl 4-(4-cycloheptylphenoxy)-3-fluorobenzoate ethyl 3-fluoro-4-(4-hexylphenoxy)benzoate ethyl 4-(4-cyclopentylphenoxy)-3-fluorobenzoate methyl 4-(4-((1S,4R)-bicyclo[2.2.1]heptan-2-yl)phenoxy)-3-fluorobenzoate ethyl 3-fluoro-4-(4-isopropylphenoxy)benzoate ethyl 4-(4-cyclohexylphenoxy)-3-fluorobenzoate ethyl 4-(4-cycloheptylphenoxy)-3-fluorobenzoate -continued

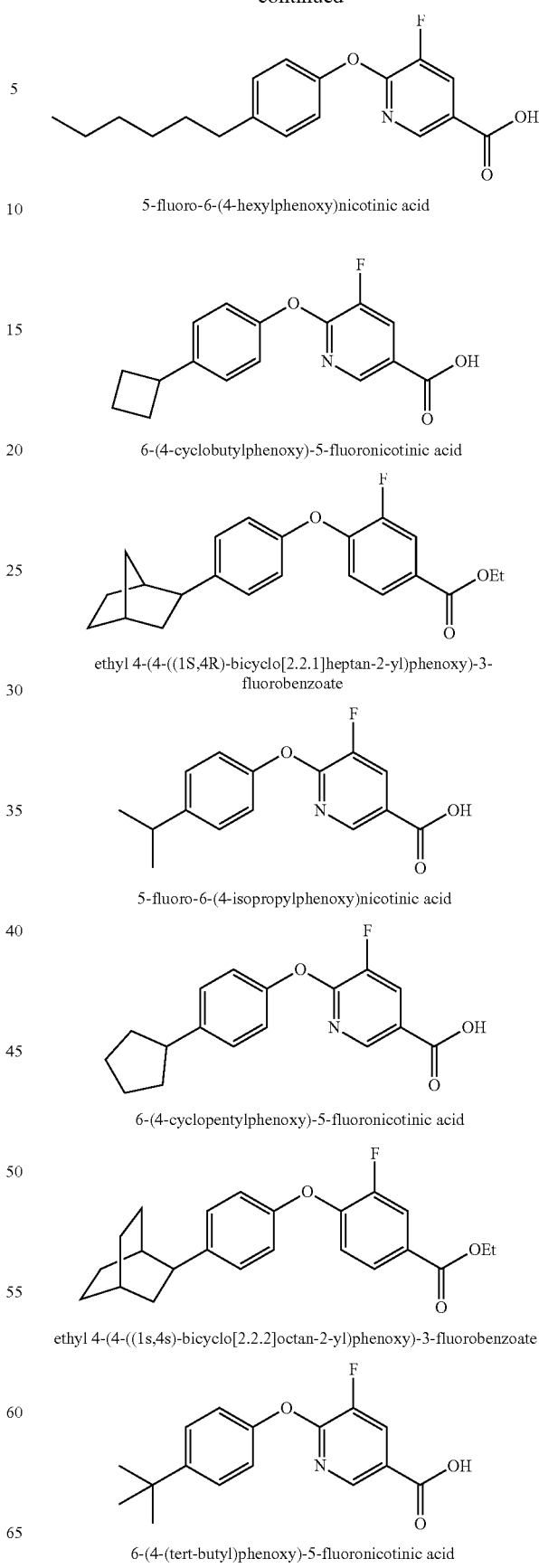

5-fluoro-6-(4-hexylphenoxy)nicotinic acid 6-(4-cyclobutylphenoxy)-5-fluoronicotinic acid ethyl 4-(4-((1S,4R)-bicyclo[2.2.1]heptan-2-yl)phenoxy)-3-fluorobenzoate 5-fluoro-6-(4-isopropylphenoxy)nicotinic acid 6-(4-cyclopentylphenoxy)-5-fluoronicotinic acid ethyl 4-(4-((1s,4s)-bicyclo[2.2.2]octan-2-yl)phenoxy)-3-fluorobenzoate 6-(4-(tert-butyl)phenoxy)-5-fluoronicotinic acid -continued

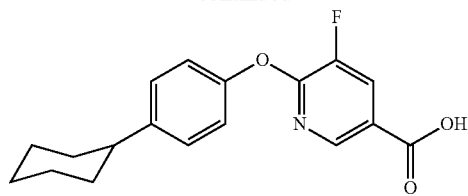

6-(4-cyclohexylphenoxy)-5-fluoronicotinic acid

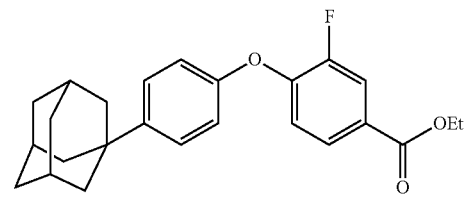

ethyl 4-(4-((3r,5r,7r)-adamantan-1-yl)phenoxy)-3-fluorobenzoate

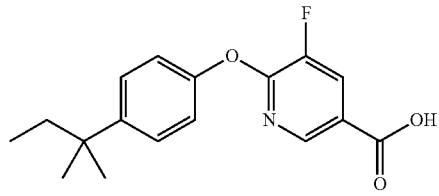

5-fluoro-6-(4-(tert-pentyl)phenoxy)nicotinic acid

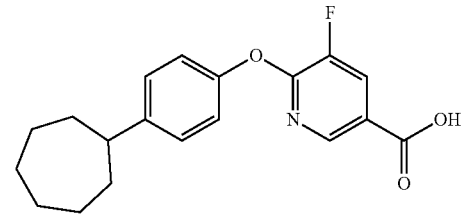

6-(4-cycloheptylphenoxy)-5-fluoronicotinic acid

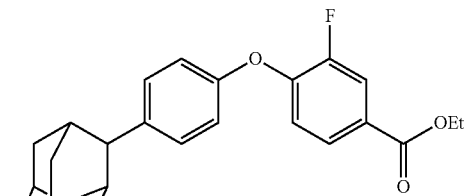

ethyl 4-(4-((1r,3r,5r,7r)-adamantan-2-yl)phenoxy)-3-fluorobenzoate

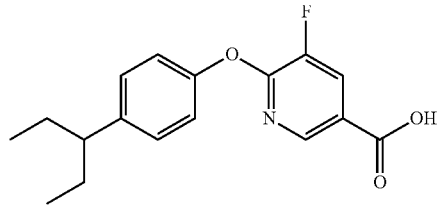

5-fluoro-6-(4-(pentan-3-yl)phenoxy)nicotinic acid

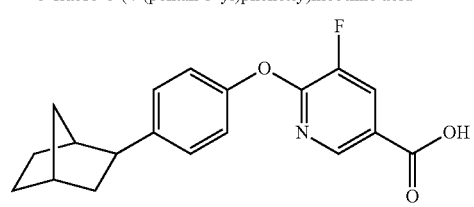

6-(4-((1S,4R)-bicyclo[2.2.1]heptan-2-yl)phenoxy)-5-fluoronicotinic acid

-continued

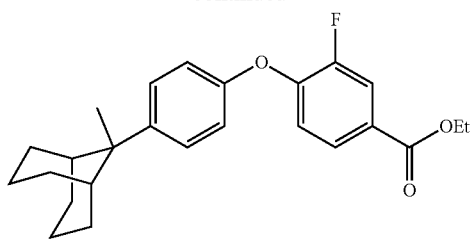

ethyl 3-fluoro-4-(4-((1R,5S)-9-methylbicyclo[3.3.1]nonan-9-yl)phenoxy)benzoate

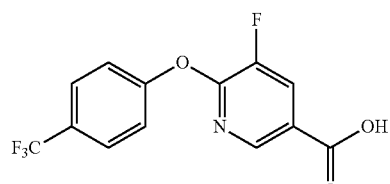

5-fluoro-6-(4-(trifluoromethyl)phenoxy)nicotinic acid

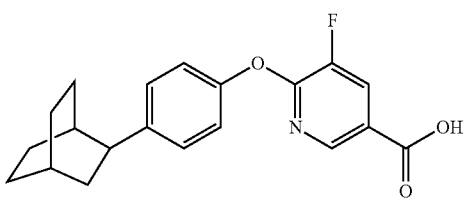

6-(4-((1s,4s)-bicyclo[2.2.2]octan-2-yl)phenoxy)-5-fluoronicotinic acid

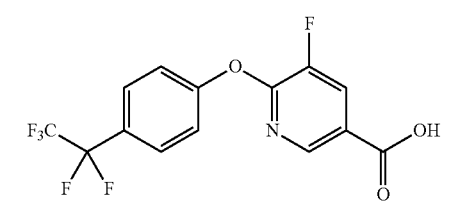

5-fluoro-6-(4-(perfluoroethyl)phenoxy)nicotinic acid

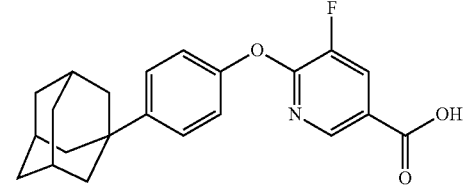

6-(4-((3r,5r,7r)-adamantan-1-yl)phenoxy)-5-fluoronicotinic acid

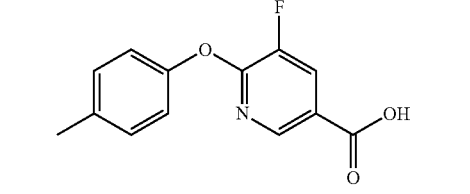

5-fluoro-6-(p-tolyloxy)nicotinic acid

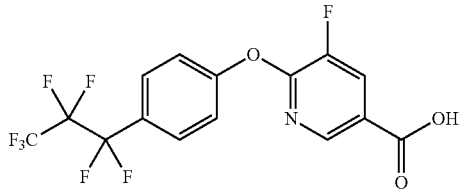

5-fluoro-6-(4-(perfluoropropyl)phenoxy)nicotinic acid

-continued

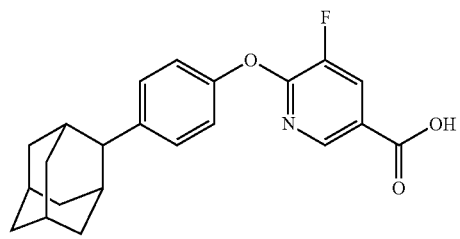

6-(4-((1r,3r,5r,7r)-adamantan-2-yl)phenoxy)-5-fluoronicotinic acid

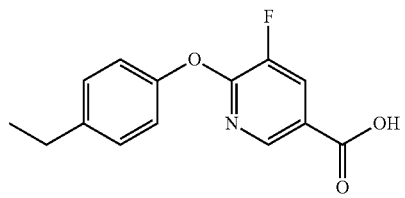

6-(4-ethylphenoxy)-5-fluoronicotinic acid

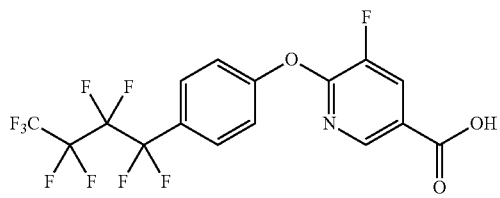

5-fluoro-6-(4-(perfluorobutyl)phenoxy)nicotinic acid

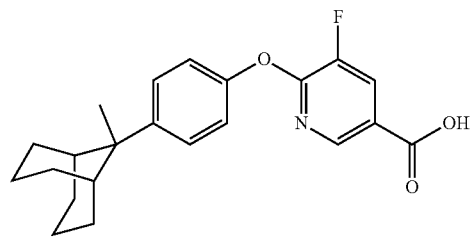

5-fluoro-6-(4-((1R,5S)-9-methylbicyclo[3.3.1]nonan-9-yl)phenoxy)nicotinic acid

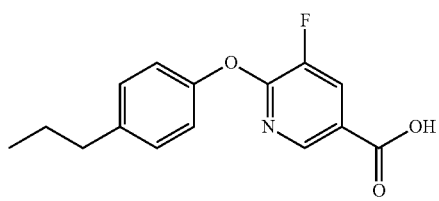

5-fluoro-6-(4-propylphenoxy)nicotinic acid

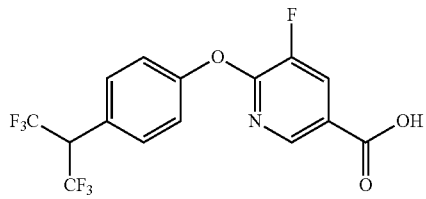

5-fluoro-6-(4-(1,1,1,3,3,3-hexafluoropropan-2-yl)phenoxy)nicotinic acid

-continued

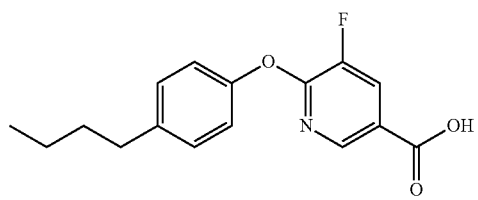

6-(4-butylphenoxy)-5-fluoronicotinic acid

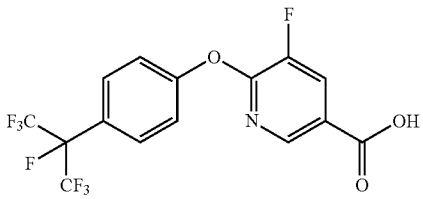

5-fluoro-6-(4-(perfluoropropan-2-yl)phenoxy)nicotinic acid

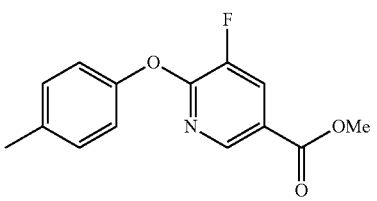

methyl 5-fluoro-6-(p-tolyloxy)nicotinate

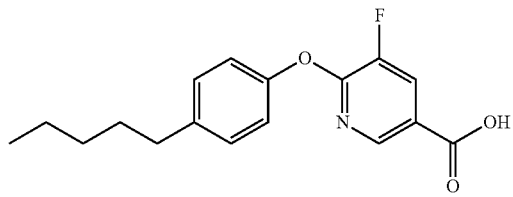

5-fluoro-6-(4-pentylphenoxy)nicotinic acid

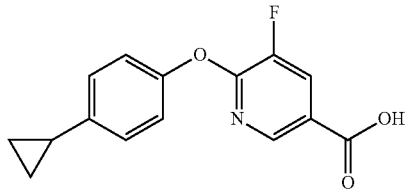

6-(4-cyclopropylphenoxy)-5-fluoronicotinic acid

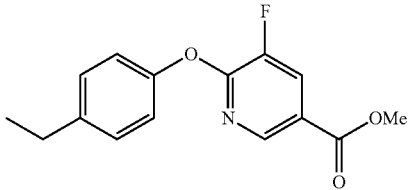

methyl 6-(4-ethylphenoxy)-5-fluoronicotinate

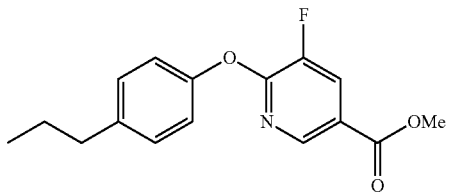

methyl 5-fluoro-6-(4-propylphenoxy)nicotinate

-continued

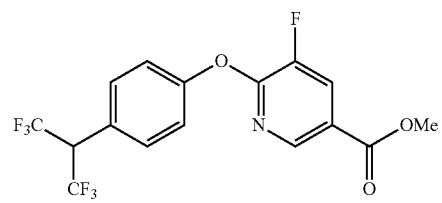

methyl 5-fluoro-6-(4-(1,1,1,3,3,3-hexafluoropropan-2-yl)phenoxy)nicotinate

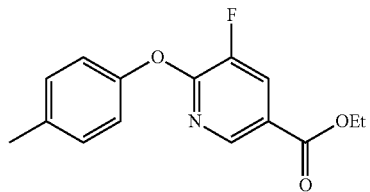

ethyl 5-fluoro-6-(p-tolyloxy)nicotinate

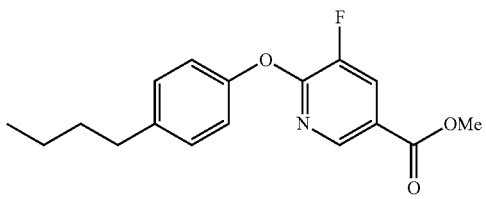

methyl 6-(4-butylphenoxy)-5-fluoronicotinate

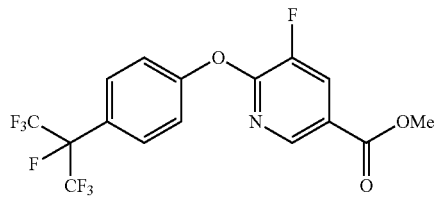

methyl 5-fluoro-6-(4-(perfluoropropan-2-yl)phenoxy)nicotinate

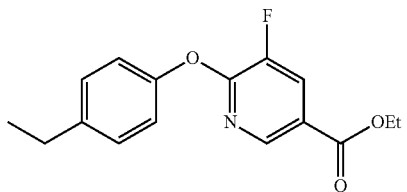

ethyl 6-(4-ethylphenoxy)-5-fluoronicotinate

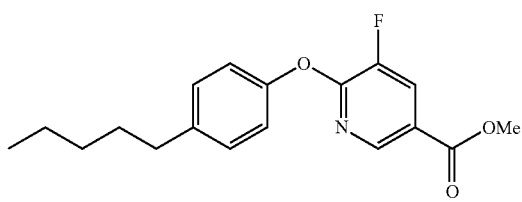

methyl 5-fluoro-6-(4-pentylphenoxy)nicotinate

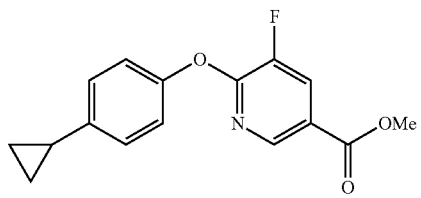

methyl 6-(4-cyclopropylphenoxy)-5-fluoronicotinate

-continued

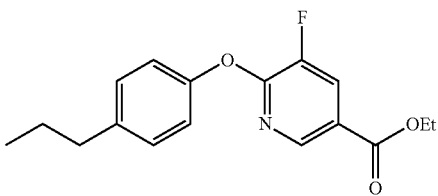

ethyl 5-fluoro-6-(4-propylphenoxy)nicotinate

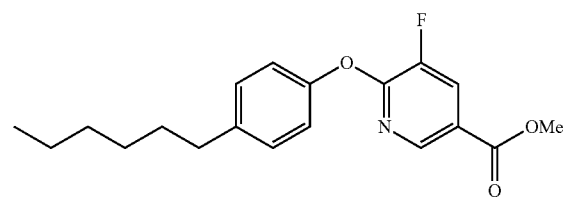

methyl 5-fluoro-6-(4-hexylphenoxy)nicotinate

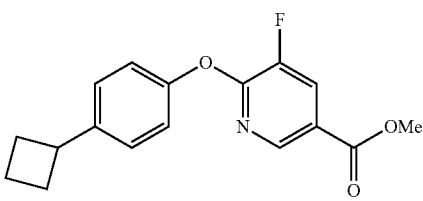

methyl 6-(4-cyclobutylphenoxy)-5-fluoronicotinate

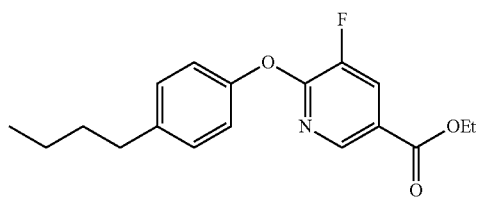

ethyl 6-(4-butylphenoxy)-5-fluoronicotinate

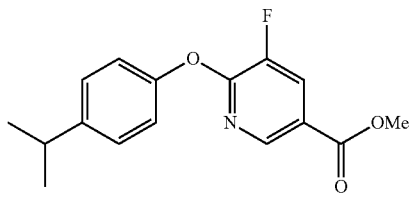

methyl 5-fluoro-6-(4-isopropylphenoxy)nicotinate

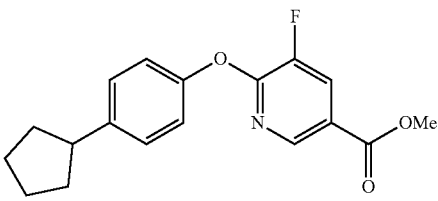

methyl 6-(4-cyclopentylphenoxy)-5-fluoronicotinate

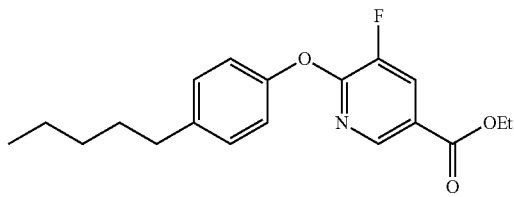

ethyl 5-fluoro-6-(4-pentylphenoxy)nicotinate

-continued

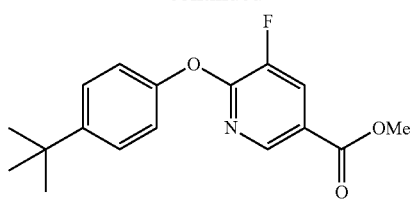

methyl 6-(4-(tert-butyl)phenoxy)-5-fluoronicotinate

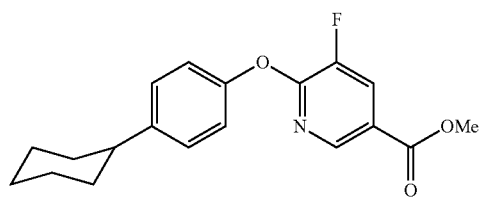

methyl 6-(4-cyclohexylphenoxy)-5-fluoronicotinate

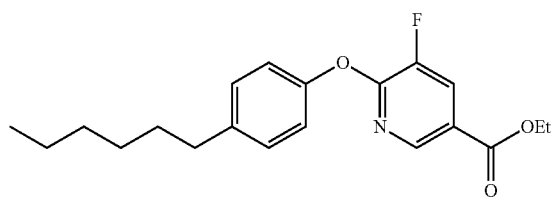

ethyl 5-fluoro-6-(4-hexylphenoxy)nicotinate

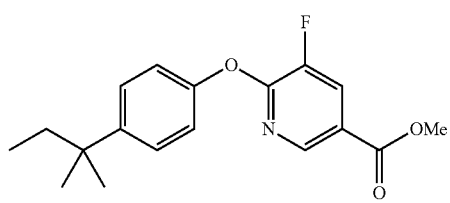

methyl 5-fluoro-6-(4-(tert-pentyl)phenoxy)nicotinate

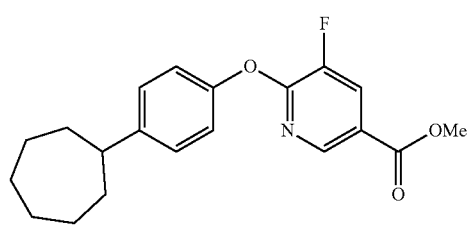

methyl 6-(4-cycloheptylphenoxy)-5-fluoronicotinate

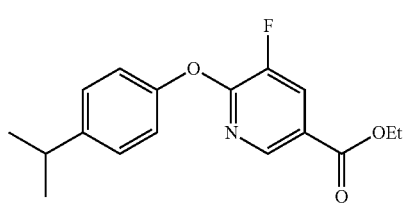

ethyl 5-fluoro-6-(4-isopropylphenoxy)nicotinate

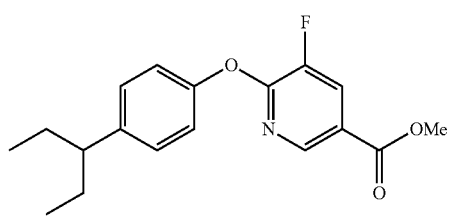

methyl 5-fluoro-6-(4-(pentan-3-yl)phenoxy)nicotinate

-continued

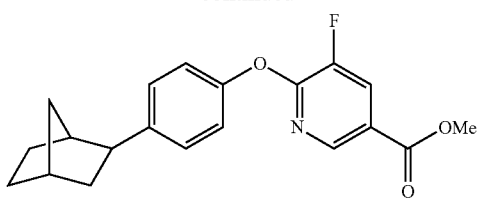

methyl 6-(4-((1S,4R)-bicyclo[2.2.1]heptan-2-yl)phenoxy)-5-fluoronicotinate

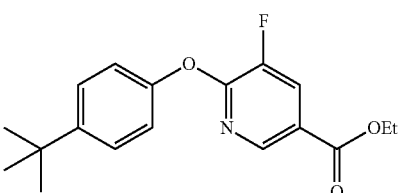

ethyl 6-(4-(tert-butyl)phenoxy)-5-fluoronicotinate

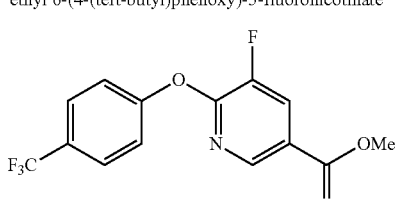

methyl 5-fluoro-6-(4-(trifluoromethyl)phenoxy)nicotinate

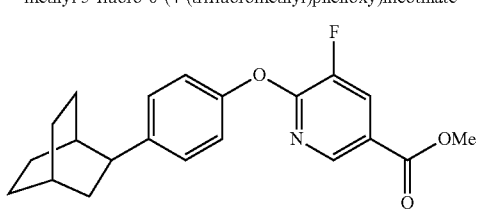

methyl 6-(4-((1s,4s)-bicyclo[2.2.2]octan-2-yl)phenoxy)-5-fluoronicotinate

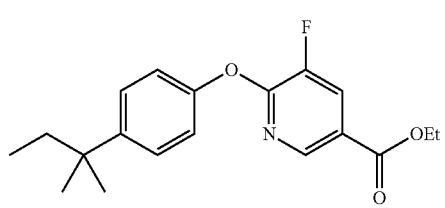

ethyl 5-fluoro-6-(4-(tert-pentyl)phenoxy)nicotinate

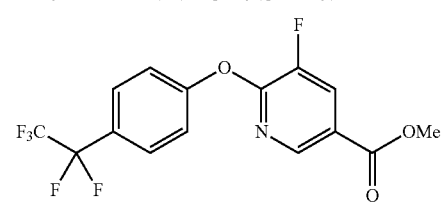

methyl 5-fluoro-6-(4-(perfluoroethyl)phenoxy)nicotinate

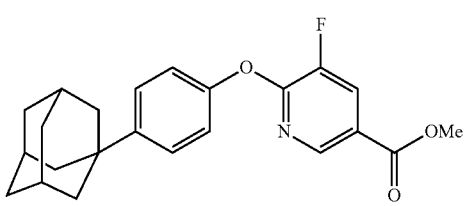

methyl 6-(4-((3r,5r,7r)-adamantan-1-yl)phenoxy)-5-fluoronicotinate

-continued

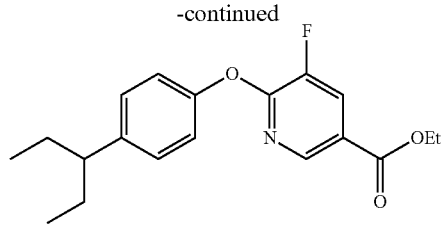

ethyl 5-fluoro-6-(4-(pentan-3-yl)phenoxy)nicotinate

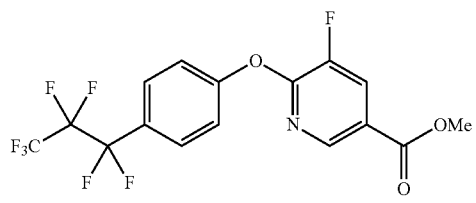

methyl 5-fluoro-6-(4-(perfluoropropyl)phenoxy)nicotinate

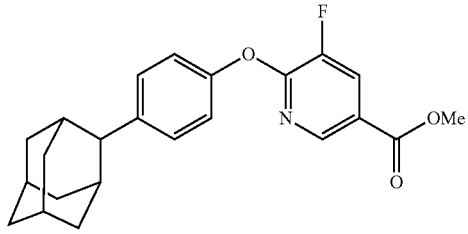

methyl 6-(4-((1r,3r,5r,7r)-adamantan-2-yl)phenoxy)-5-fluoronicotinate

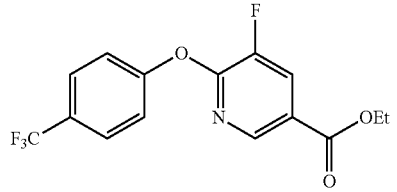

ethyl 5-fluoro-6-(4-(trifluoromethyl)phenoxy)nicotinate

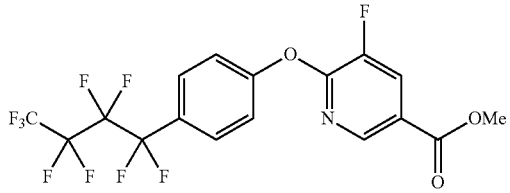

methyl 5-fluoro-6-(4-(perfluorobutyl)phenoxy)nicotinate

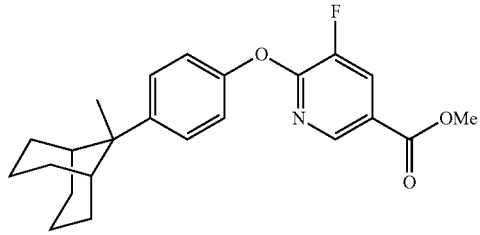

methyl 5-fluoro-6-(4-((1R,5S)-9-methylbicyclo[3.3.1]nonan-9-yl)phenoxy)nicotinate

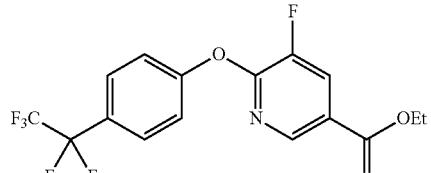

ethyl 5-fluoro-6-(4-(perfluoroethyl)phenoxy)nicotinate

-continued

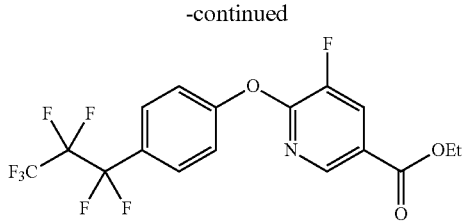

ethyl 5-fluoro-6-(4-(perfluoropropyl)phenoxy)nicotinate

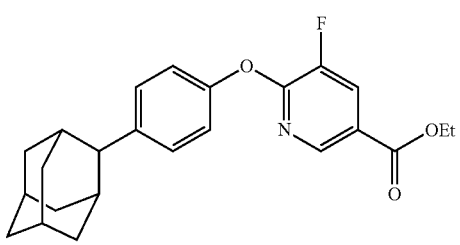

ethyl 6-(4-((1r,3r,5r,7r)-adamantan-2-yl)phenoxy)-5-fluoronicotinate

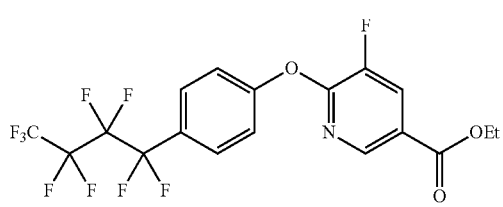

ethyl 5-fluoro-6-(4-(perfluorobutyl)phenoxy)nicotinate

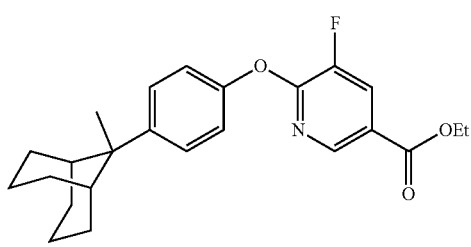

ethyl 5-fluoro-6-(4-((1R,5S)-9-methylbicyclo[3.3.1]nonan-9-yl)phenoxy)nicotinate

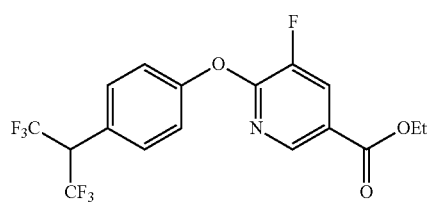

ethyl 5-fluoro-6-(4-(1,1,1,3,3,3-hexafluoropropan-2-yl)phenoxy)nicotinate

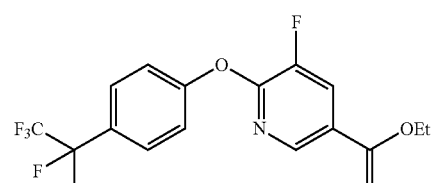

ethyl 5-fluoro-6-(4-(perfluoropropan-2-yl)phenoxy)nicotinate

-continued

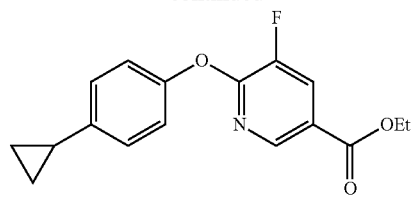

ethyl 6-(4-cyclopropylphenoxy)-5-fluoronicotinate

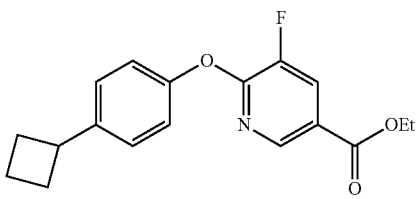

ethyl 6-(4-cyclobutylphenoxy)-5-fluoronicotinate

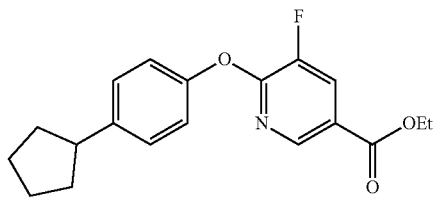

ethyl 6-(4-cyclopentylphenoxy)-5-fluoronicotinate

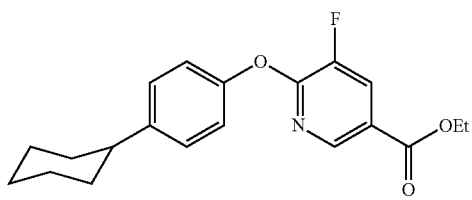

ethyl 6-(4-cyclohexylphenoxy)-5-fluoronicotinate

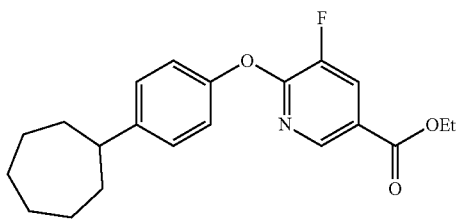

ethyl 6-(4-cycloheptylphenoxy)-5-fluoronicotinate

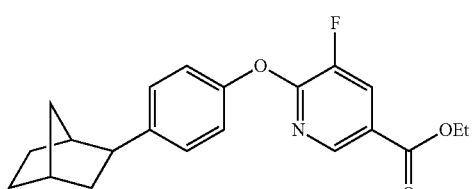

ethyl 6-(4-((1S,4R)-bicyclo[2.2.1]heptan-2-yl)phenoxy)-5-fluoronicotinate

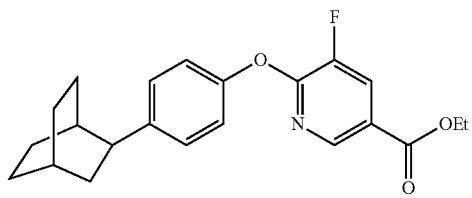

ethyl 6-(4-((1s,4s)-bicyclo[2.2.2]octan-2-yl)phenoxy)-5-fluoronicotinate

-continued

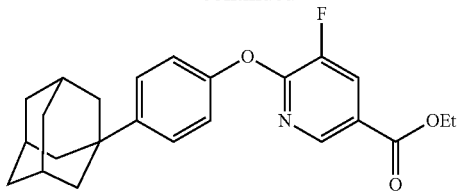

ethyl 6-(4-((3r,5r,7r)-adamantan-1-yl)phenoxy)-5-fluoronicotinate

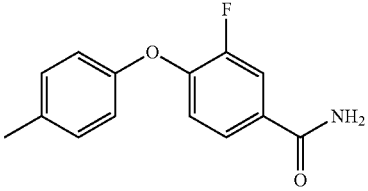

3-fluoro-4-(p-tolyloxy)benzamide

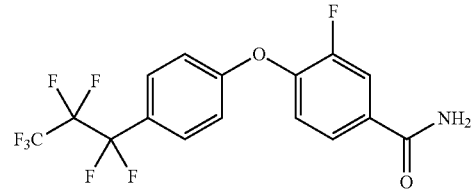

3-fluoro-4-(4-(perfluoropropyl)phenoxy)benzamide

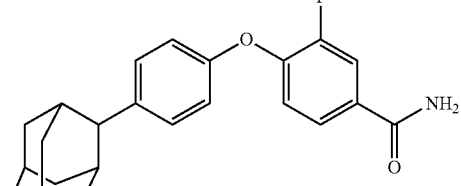

4-(4-((1r,3r,5r,7r)-adamantan-2-yl)phenoxy)-3-fluorobenzamide

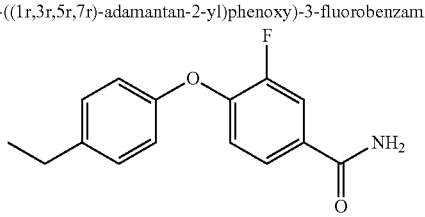

4-(4-ethylphenoxy)-3-fluorobenzamide

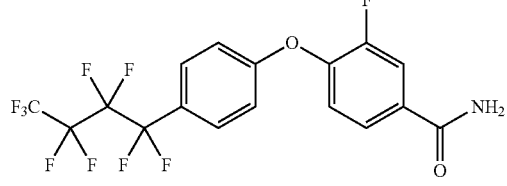

3-fluoro-4-(4-(perfluorobutyl)phenoxy)benzamide

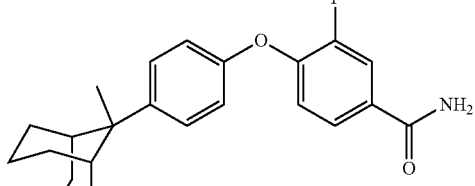

3-fluoro-4-(4-((1R,5S)-9-methylbicyclo[3.3.1]nonan-9-yl)phenoxy)benzamide

-continued

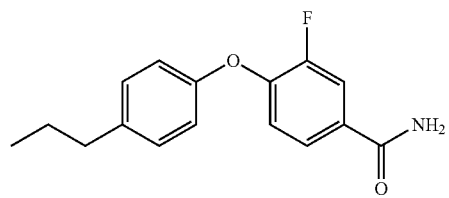
3-fluoro-4-(4-(propylphenoxy)benzamide

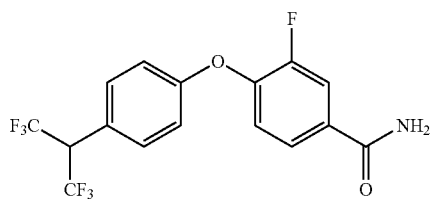
3-fluoro-4-(4-(1,1,1,3,3,3-hexafluoropropan-2-yl)phenoxy)benzamide

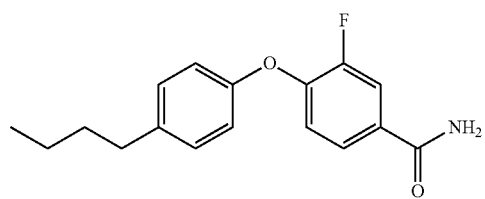
4-(4-butylphenoxy)-3-fluorobenzamide

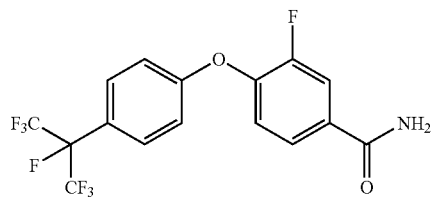
3-fluoro-4-(4-(perfluoropropan-2-yl)phenoxy)benzamide

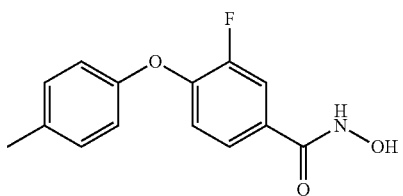
3-fluoro-N-hydroxy-4-(p-tolyloxy)benzamide

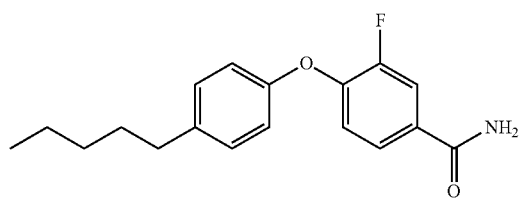
3-fluoro-4-(4-pentylphenoxy)benzamide

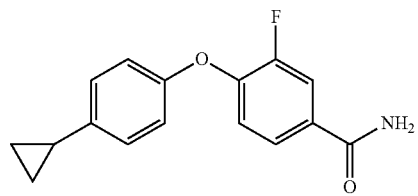
4-(4-cyclopropylphenoxy)-3-fluorobenzamide

-continued

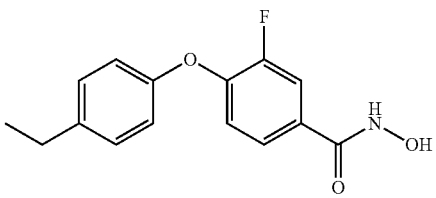
4-(4-ethylphenoxy)-3-fluoro-N-hydroxybenzamide

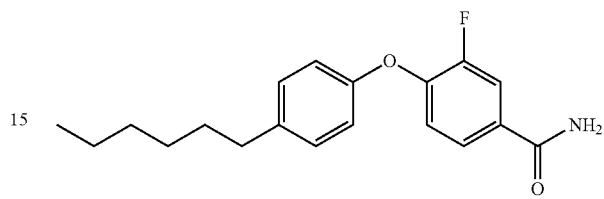
3-fluoro-4-(4-hexylphenoxy)benzamide

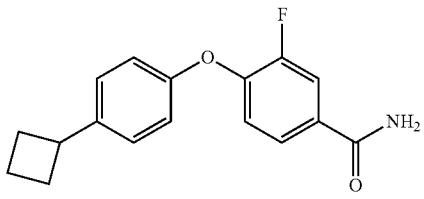
4-(4-cyclobutylphenoxy)-3-fluorobenzamide

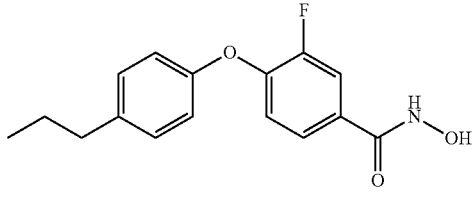
3-fluoro-N-hydroxy-4-(4-propylphenoxy)benzamide

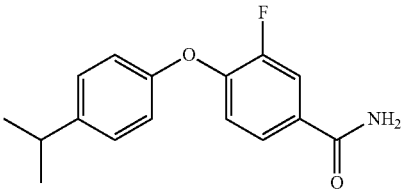
3-fluoro-4-(4-isopropylphenoxy)benzamide

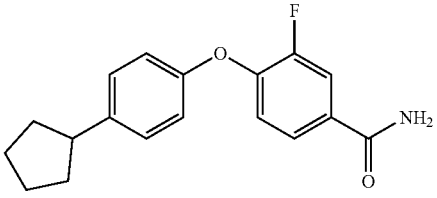
4-(4-cyclopentylphenoxy)-3-fluorobenzamide

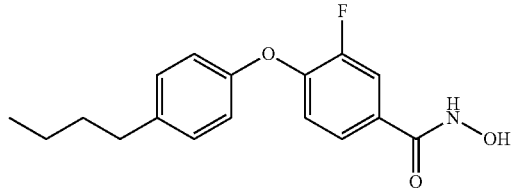
4-(4-butylphenoxy)-3-fluoro-N-hydroxybenzamide

-continued

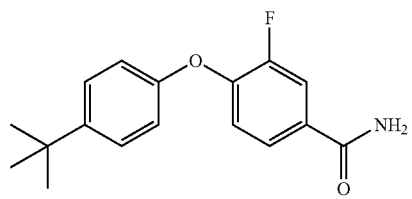
4-(4-(tert-butyl)phenoxy)-3-fluorobenzamide

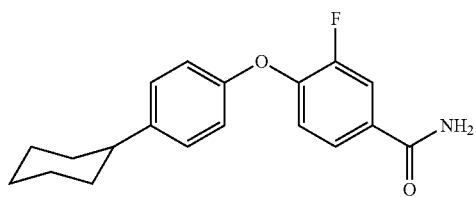
4-(4-cyclohexylphenoxy)-3-fluorobenzamide

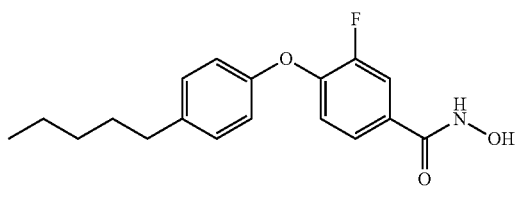
3-fluoro-N-hydroxy-4-(4-pentylphenoxy)benzamide

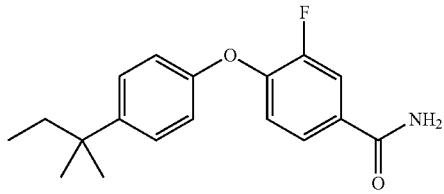
3-fluoro-4-(4-(tert-pentyl)phenoxy)benzamide

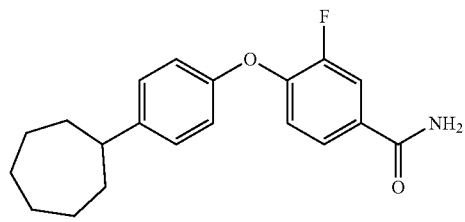
4-(4-cycloheptylphenoxy)-3-fluorobenzamide

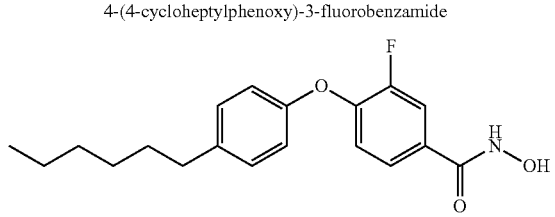
3-fluoro-4-(4-hexylphenoxy)-N-hydroxybenzamide

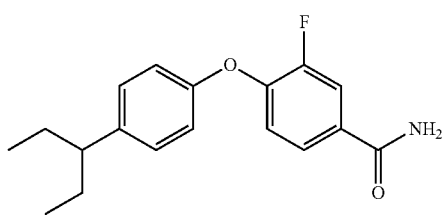
3-fluoro-4-(4-pentan-3-yl)phenoxy)benzamide

-continued

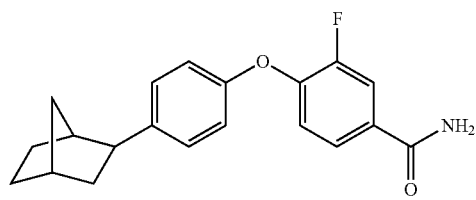
4-(4-((1S,4R)-bicyclo[2.2.1]heptan-2-yl)phenoxy)-3-fluorobenzamide

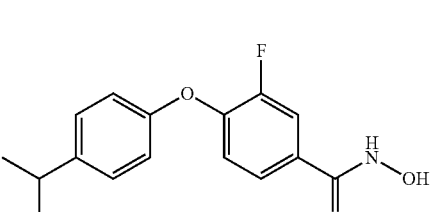
3-fluoro-N-hydroxy-4-(4-isopropylphenoxy)benzamide

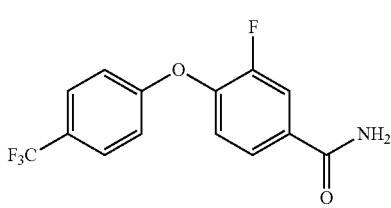
3-fluoro-4-(4-(trifluoromethyl)phenoxy)benzamide

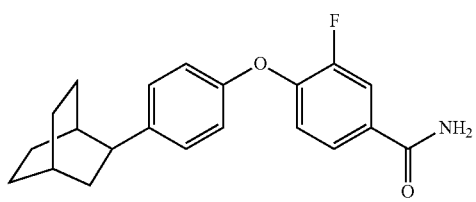
4-(4-((1s,4s)-bicyclo[2.2.2]octan-2-yl)phenoxy)-3-fluorobenzamide

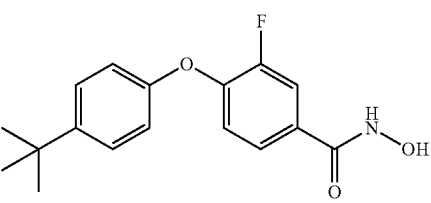
4-(4-(tert-butyl)phenoxy)-3-fluoro-N-hydroxybenzamide

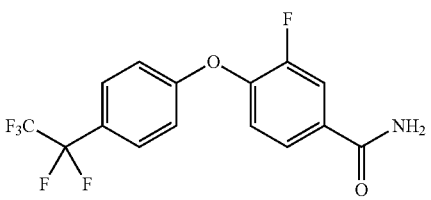
3-fluoro-4-(4-(perfluoroethyl)phenoxy)benzamide

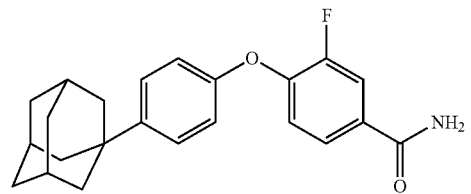
4-(4-((3r,5r,7r)-adamantan-1-yl)phenoxy)-3-fluorobenzamide

-continued

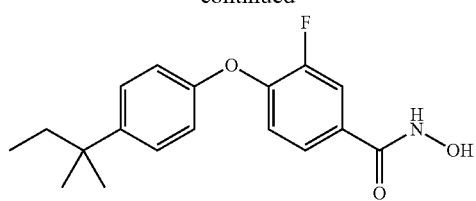

3-fluoro-N-hydroxy-4-(4-(tert-pentyl)phenoxy)benzamide

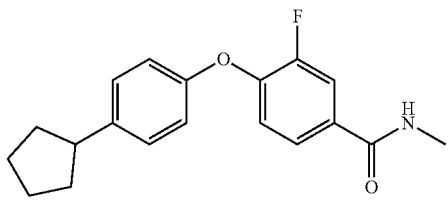

4-(4-cyclopentylphenoxy)-3-fluoro-N-methylbenzamide

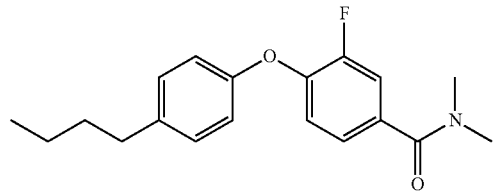

4-(4-butylphenoxy)-3-fluoro-N,N-dimethylbenzamide

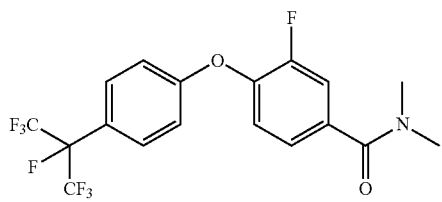

3-fluoro-N,N-dimethyl-4-(4-(perfluoropropan-2-yl)phenoxy)benzamide

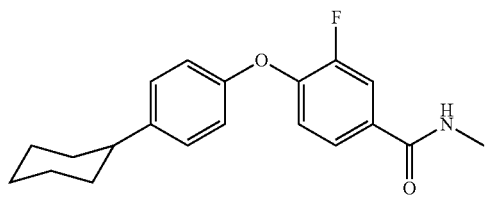

4-(4-cyclohexylphenoxy)-3-fluoro-N-methylbenzamide

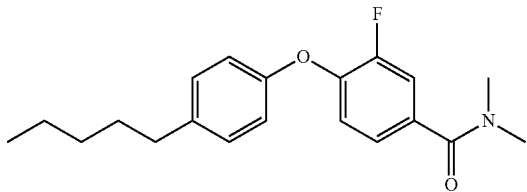

3-fluoro-N,N-dimethyl-4-(4-pentylphenoxy)benzamide

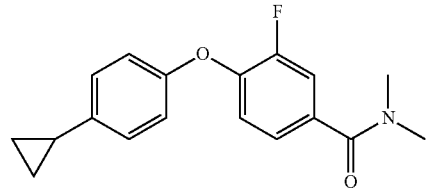

4-(4-cyclopropylphenoxy)-3-fluoro-N,N-dimethylbenzamide

-continued

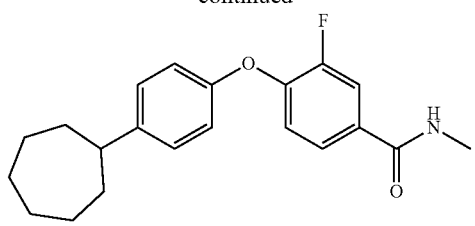

4-(4-cycloheptylphenoxy)-3-fluoro-N-methylbenzamide

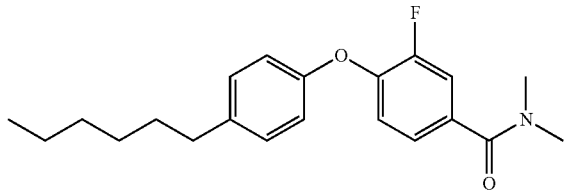

3-fluoro-4-(4-hexylphenoxy)-N,N-dimethylbenzamide

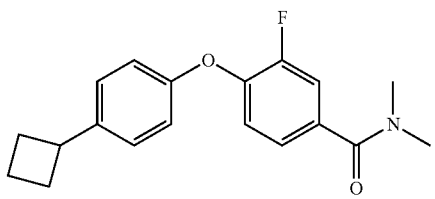

4-(4-cyclobutylphenoxy)-3-fluoro-N,N-dimethylbenzamide

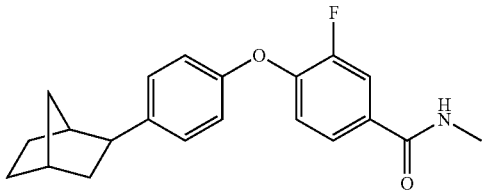

4-(4-((1S,4R)-bicyclo[2.2.1]heptan-2-yl)phenoxy)-3-fluoro-N-methylbenzamide

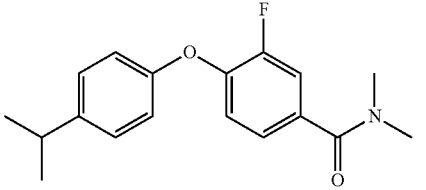

3-fluoro-4-(4-isopropylphenoxy)-N,N-dimethylbenzamide

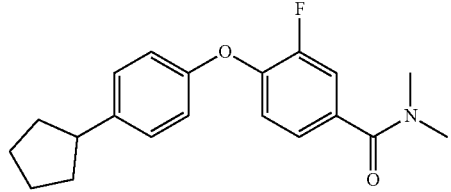

4-(4-cyclopentylphenoxy)-3-fluoro-N,N-dimethylbenzamide

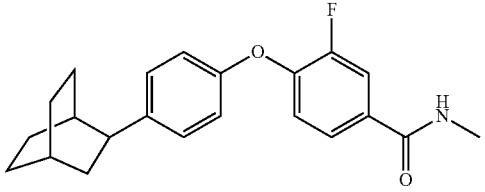

4-(4-((1s,4s)-bicyclo[2.2.2]octan-2-yl)phenoxy)-3-fluoro-N-methylbenzamide

-continued

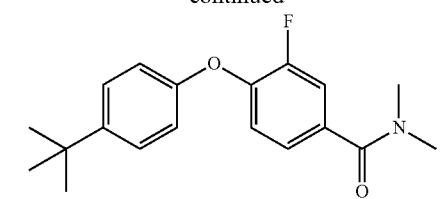

4-(4-(tert-butyl)phenoxy)-3-fluoro-N,N-dimethylbenzamide

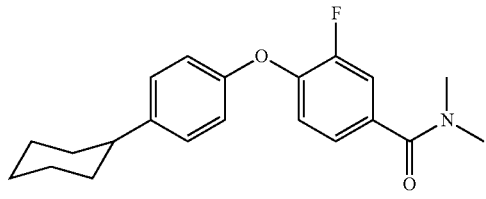

4-(4-cyclohexylphenoxy)-3-fluoro-N,N-dimethylbenzamide

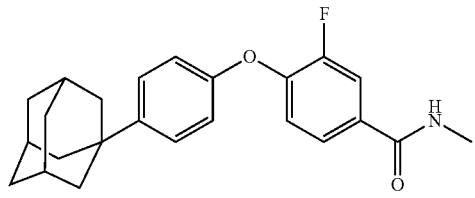

4-(4-((3r,5r,7r)-adamantan-1-yl)phenoxy)-3-fluoro-N-methylbenzamide

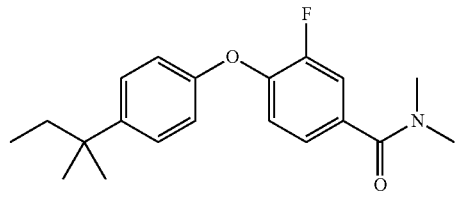

3-fluoro-N,N-dimethyl-4-(4-(tert-pentyl)phenoxy)benzamide

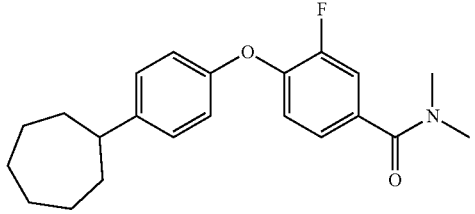

4-(4-cycloheptylphenoxy)-3-fluoro-N,N-dimethylbenzamide

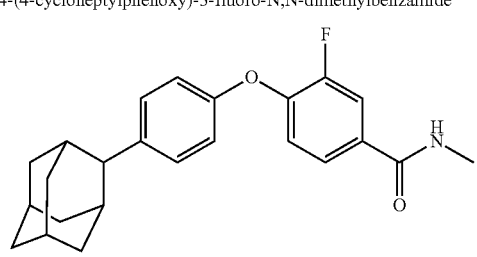

4-(4-((1r,3r,5r,7r)-adamantan-2-yl)phenoxy)-3-fluoro-N-methylbenzamide

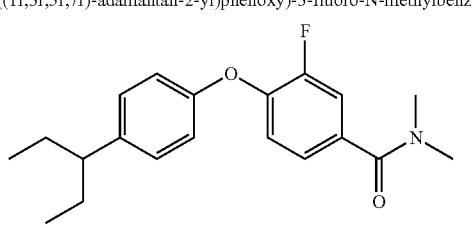

3-fluoro-N,N-dimethyl-4-(4-(pentan-3-yl)phenoxy)benzamide

-continued

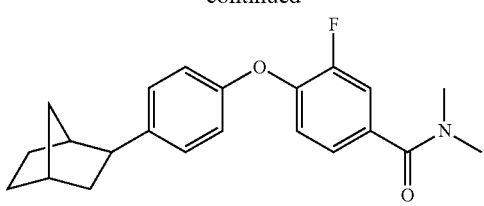

4-(4-((1S,4R)-bicyclo[2.2.1]heptan-2-yl)phenoxy)-3-fluoro-N,N-dimethylbenzamide

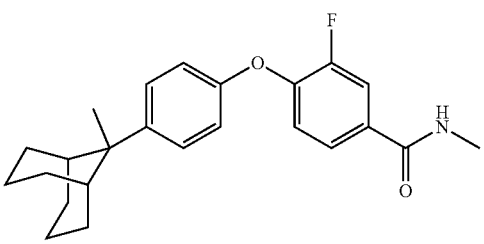

3-fluoro-N-methyl-4-(4-((1R,5S)-9-methylbicyclo[3.3.1]nonan-9-yl)phenoxy)benzamide

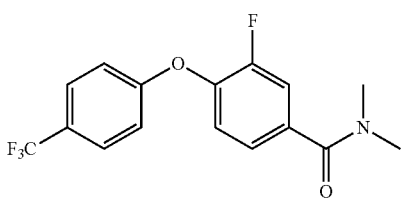

3-fluoro-N,N-dimethyl-4-(4-(trifluoromethyl)phenoxy)benzamide

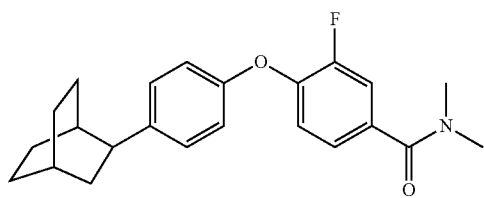

4-(4-((1s,4s)-bicyclo[2.2.2]octan-2-yl)phenoxy)-3-fluoro-N,N-dimethylbenzamide

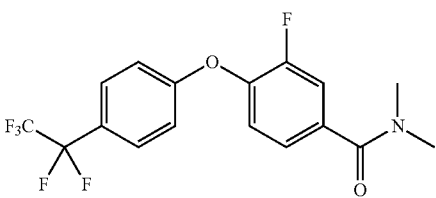

3-fluoro-N,N-dimethyl-4-(4-(perfluoroethyl)phenoxy)benzamide

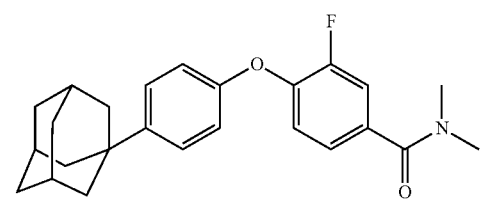

4-(4-((3r,5r,7r)-adamantan-1-yl)phenoxy)-3-fluoro-N,N-dimethylbenzamide

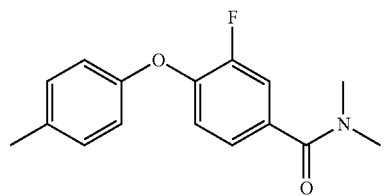

3-fluoro-N,N-dimethyl-4-(p-tolyloxy)benzamide

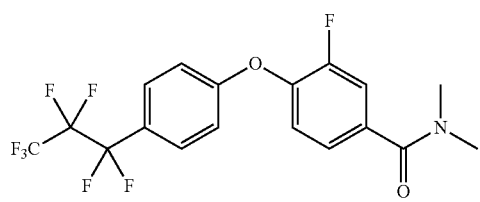

3-fluoro-N,N-dimethyl-4-(4-(perfluoropropyl)phenoxy)benzamide

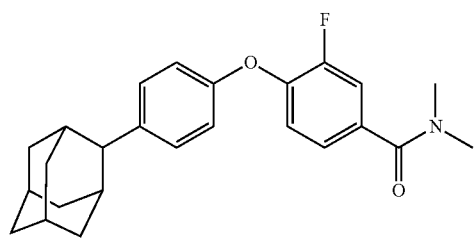

4-(4-((1r,3r,5r,7r)-adamantan-2-yl)phenoxy)-3-fluoro-N,N-dimethylbenzamide

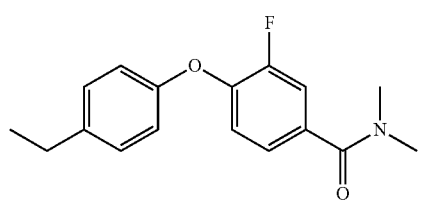

4-(4-ethylphenoxy)-3-fluoro-N,N-dimethylbenzamide

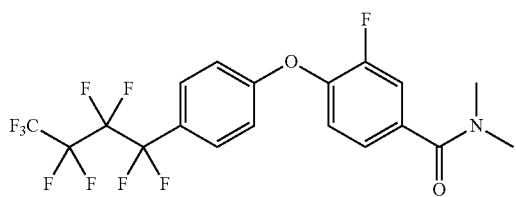

3-fluoro-N,N-dimethyl-4-(4-(perfluorobutyl)phenoxy)benzamide

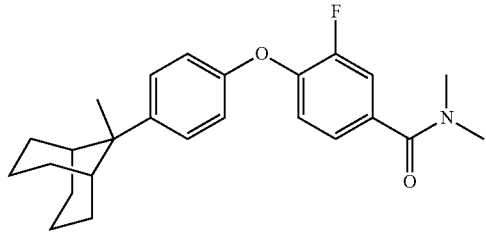

3-fluoro-N,N-dimethyl-4-(4-((1R,5S)-9-methylbicyclo[3.3.1]nonan-9-yl)phenoxy)benzamide

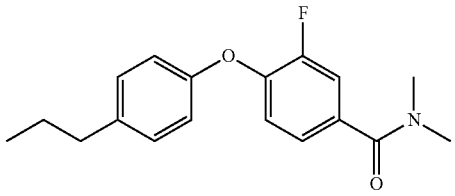

3-fluoro-N,N-dimethyl-4-(4-propylphenoxy)benzamide

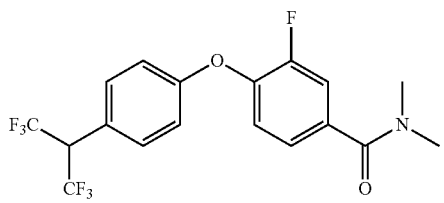

3-fluoro-4-(4-(1,1,1,3,3,3-hexafluoropropan-2-yl)phenoxy)-N,N-dimethylbenzamide

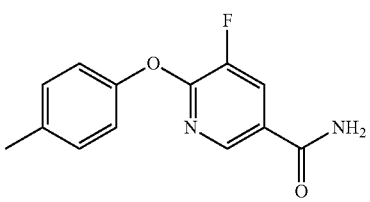

5-fluoro-6-(p-tolyloxy)nicotinamide

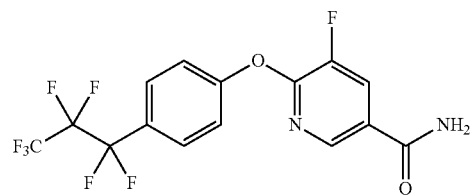

5-fluoro-6-(4-(perfluoropropyl)phenoxy)nicotinamide

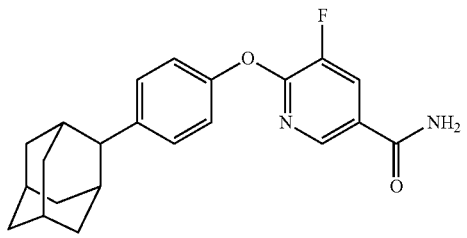

6-(4-((1r,3r,5r,7r)-adamantan-2-yl)phenoxy)-5-fluoronicotinamide

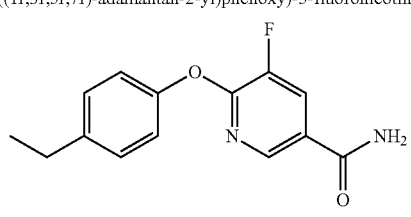

6-(4-ethylphenoxy)-5-fluoronicotinamide

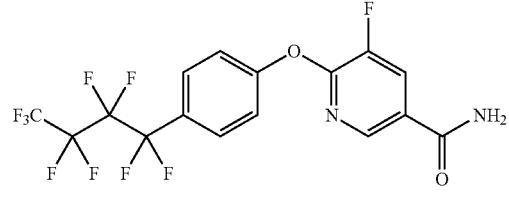

5-fluoro-6-(4-(perfluorobutyl)phenoxy)nicotinamide

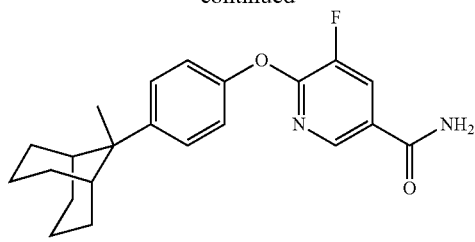

5-fluoro-6-(4-((1R,5S)-9-methylbicyclo[3.3.1]nonan-9-yl)phenoxy)nicotinamide

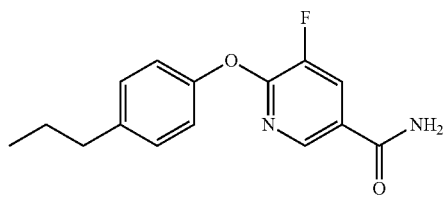

5-fluoro-6-(4-propylphenoxy)nicotinamide

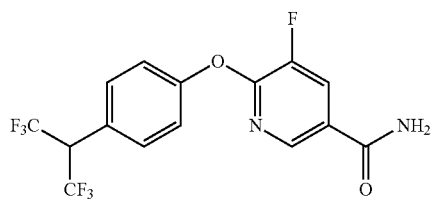

5-fluoro-6-(4-(1,1,1,3,3,3-hexafluoropropan-2-yl)phenoxy)nicotinamide

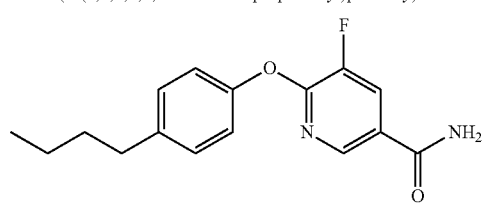

6-(4-butylphenoxy)-5-fluoronicotinamide

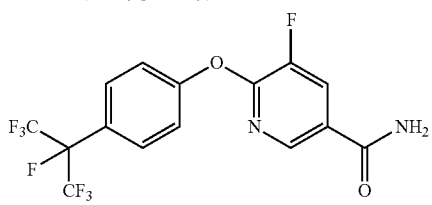

5-fluoro-6-(4-(perfluoropropan-2-yl)phenoxy)nicotinamide

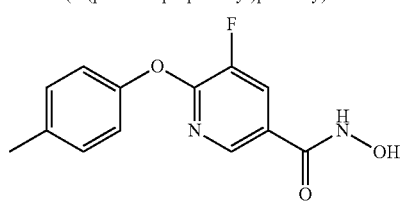

5-fluoro-N-hydroxy-6-(p-tolyloxy)nicotinamide

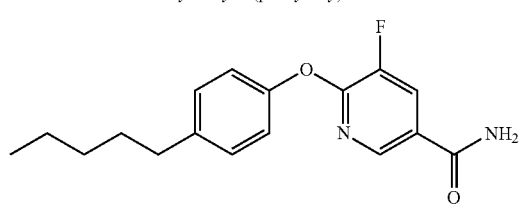

5-fluoro-6-(4-pentylphenoxy)nicotinamide

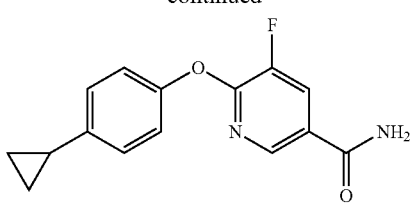

6-(4-cyclopropylphenoxy)-5-fluoronicotinamide

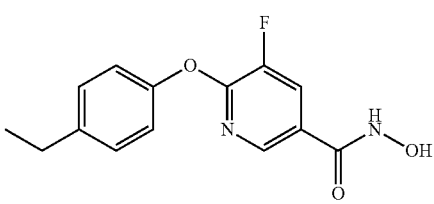

6-(4-ethylphenoxy)-5-fluoro-N-hydroxynicotinamide

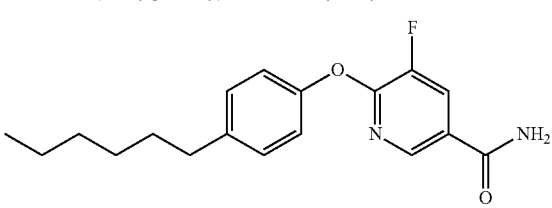

5-fluoro-6-(4-hexylphenoxy)nicotinamide

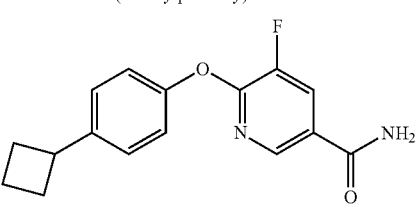

6-(4-cyclobutylphenoxy)-5-fluoronicotinamide

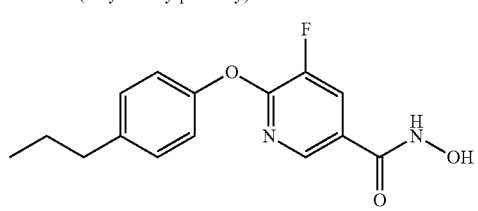

5-fluoro-N-hydroxy-6-(4-propylphenoxy)nicotinamide

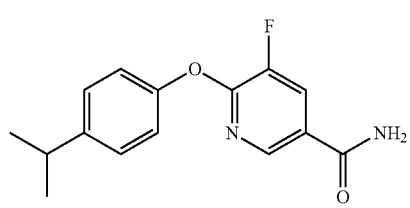

5-fluoro-6-(4-isopropylphenoxy)nicotinamide

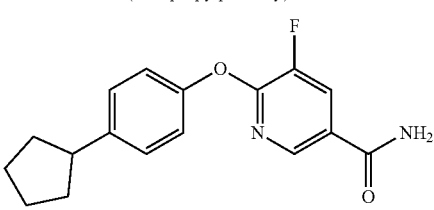

6-(4-cyclopentylphenoxy)-5-fluoronicotinamide

-continued

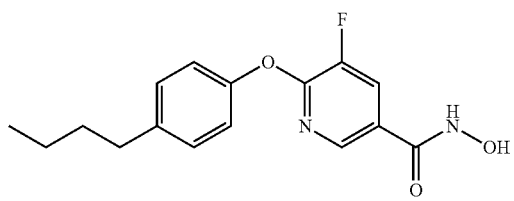

6-(4-butylphenoxy)-5-fluoro-N-hydroxynicotinamide

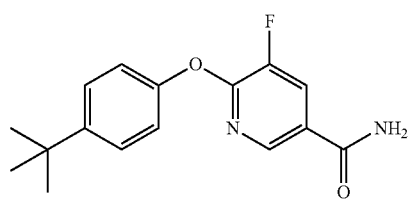

6-(4-(tert-butyl)phenoxy)-5-fluoronicotinamide

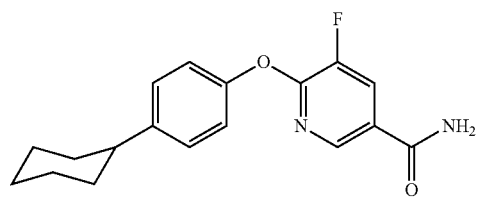

6-(4-cyclohexylphenoxy)-5-fluoronicotinamide

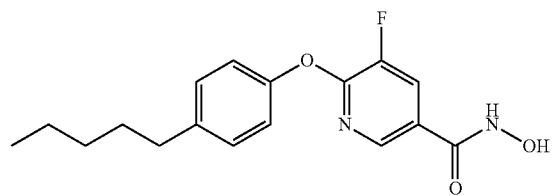

5-fluoro-N-hydroxy-6-(4-pentylphenoxy)nicotinamide

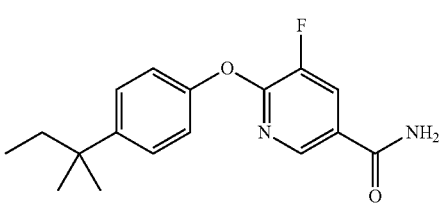

5-fluoro-6-(4-(tert-pentyl)phenoxy)nicotinamide

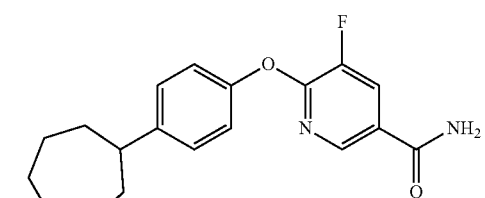

6-(4-cycloheptylphenoxy)-5-fluoronicotinamide

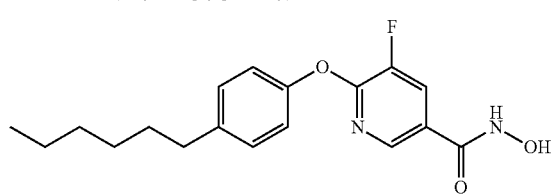

5-fluoro-6-(4-hexylphenoxy)-N-hydroxynicotinamide

-continued

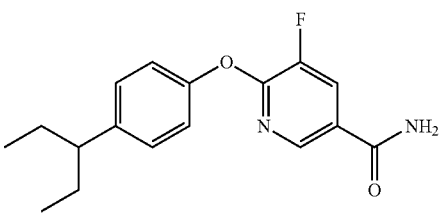

5-fluoro-6-(4-(pentan-3-yl)phenoxy)nicotinamide

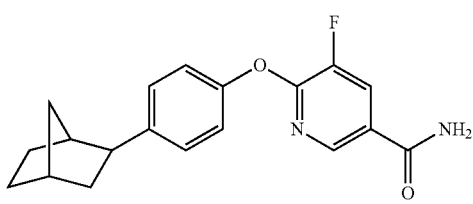

6-(4-((1S,4R)-bicyclo[2.2.1]heptan-2-yl)phenoxy)-5-fluoronicotinamide

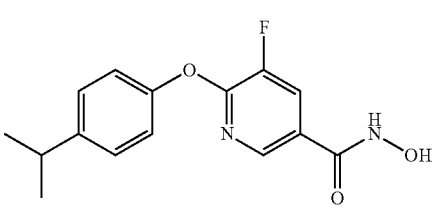

5-fluoro-N-hydroxy-6-(4-isopropylphenoxy)nicotinamide

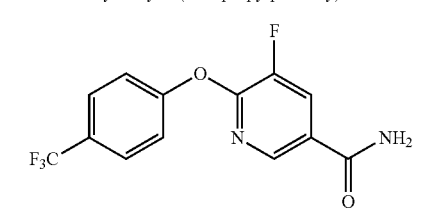

5-fluoro-6-(4-(trifluoromethyl)phenoxy)nicotinamide

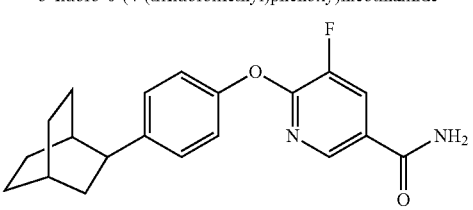

6-(4-((1s,4s)-bicyclo[2.2.2]octan-2-yl)phenoxy)-5-fluoronicotinamide

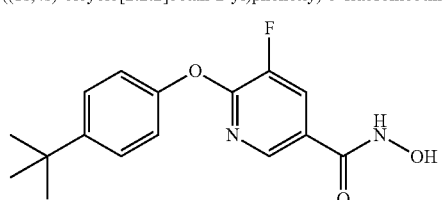

6-(4-(tert-butyl)phenoxy)-5-fluoro-N-hydroxynicotinamide

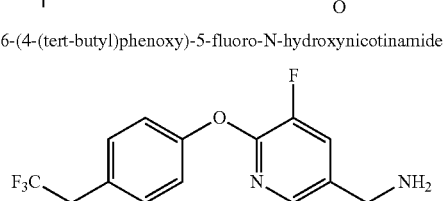

5-fluoro-6-(4-(perfluoroethyl)phenoxy)nicotinamide

-continued

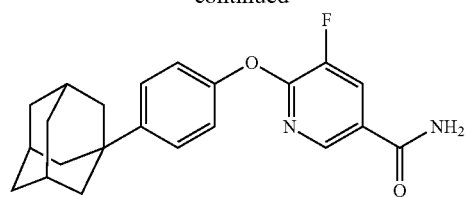

6-(4-((3r,5r,7r)-adamantan-1-yl)phenoxy)-5-fluoronicotinamide

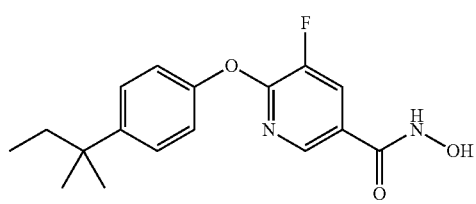

5-fluoro-N-hydroxy-6-(4-(pentan-3-yl)phenoxy)nicotinamide

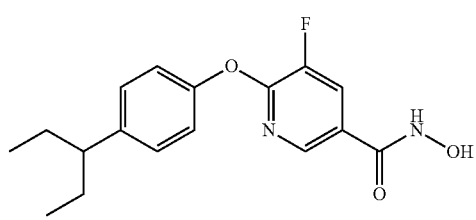

5-fluoro-N-hydroxy-6-(4-(pentan-3-yl)phenoxy)nicotinamide

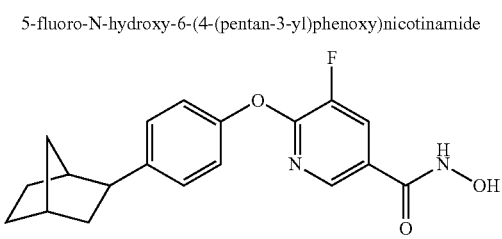

6-(4-((1S,4R)-bicyclo[2.2.1]heptan-2-yl)phenoxy)-5-fluoro-N-hydroxynicotinamide

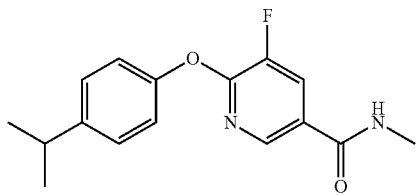

5-fluoro-6-(4-isopropylphenoxy)-N-methylnicotinamide

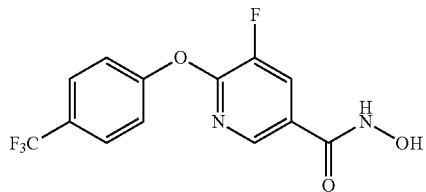

5-fluoro-N-hydroxy-6-(4-(trifluoromethyl)phenoxy)nicotinamide

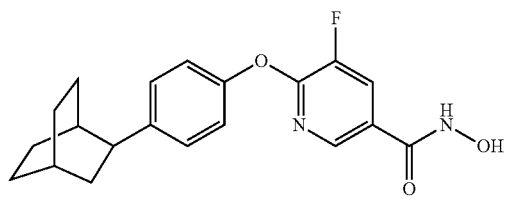

6-(4-((1s,4s)-bicyclo[2.2.2]octan-2-yl)phenoxy)-5-fluoro-N-hydroxynicotinamide

-continued

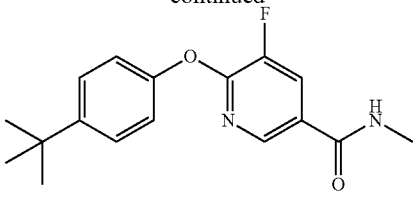

6-(4-(tert-butyl)phenoxy)-5-fluoro-N-methylnicotinamide

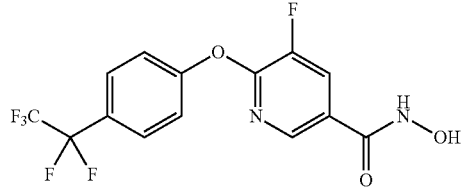

5-fluoro-N-hydroxy-6-(4-(perfluoroethyl)phenoxy)nicotinamide

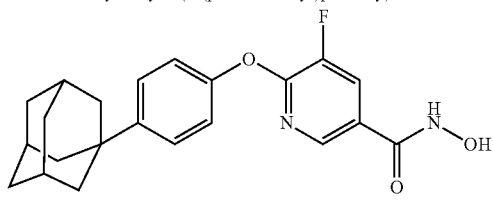

6-(4-((3r,5r,7r)-adamantan-1-yl)phenoxy)-5-fluoro-N-hydroxynicotinamide

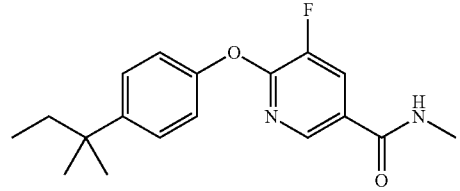

5-fluoro-N-methyl-6-(4-(tert-pentyl)phenoxy)nicotinamide

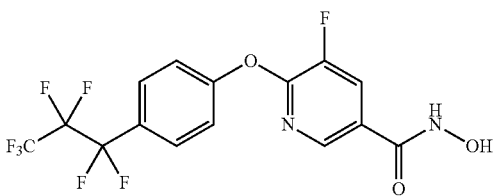

5-fluoro-N-hydroxy-6-(4-(perfluoropropyl)phenoxy)nicotinamide

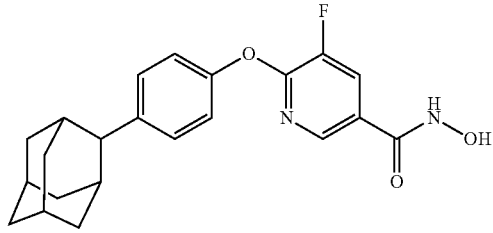

6-(4-((1r,3r,5r,7r)-adamantan-2-yl)phenoxy)-5-fluoro-N-hydroxynicotinamide

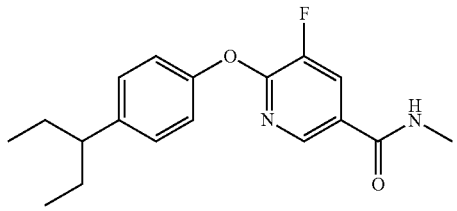

5-fluoro-N-methyl-6-(4-(pentan-3-yl)phenoxy)nicotinamide

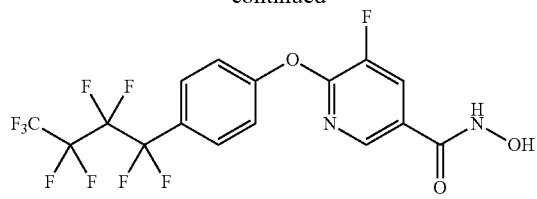

5-fluoro-N-hydroxy-6-(4-(perfluorobutyl)phenoxy)nicotinamide

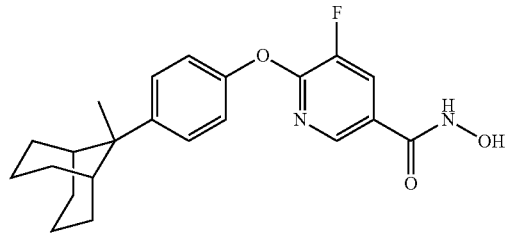

5-fluoro-N-hydroxy-6-(4-((1R,5S)-9-methylbicyclo[3.3.1]nonan-9-yl)phenoxy)nicotinamide

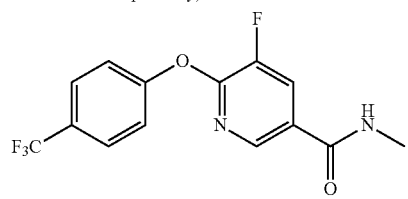

5-fluoro-N-methyl-6-(4-(trifluoromethyl)phenoxy)nicotinamide

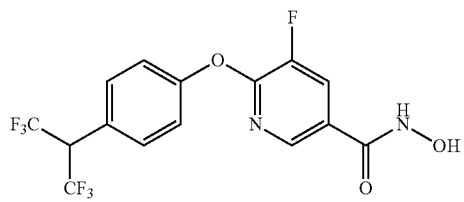

5-fluoro-6-(4-(1,1,1,3,3,3-hexafluoropropan-2-yl)phenoxy)-N-hydroxynicotinamide

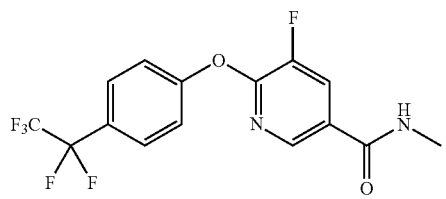

5-fluoro-N-methyl-6-(4-(perfluoroethyl)phenoxy)nicotinamide

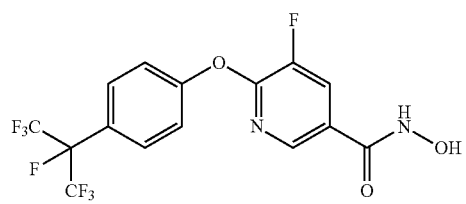

5-fluoro-N-hydroxy-6-(4-(perfluoropropan-2-yl)phenoxy)nicotinamide

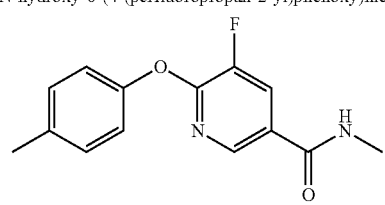

5-fluoro-N-methyl-6-(p-tolyloxy)nicotinamide

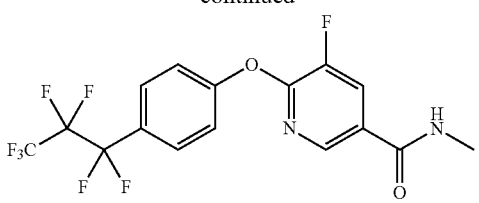

5-fluoro-N-methyl-6-(4-(perfluoropropyl)phenoxy)nicotinamide

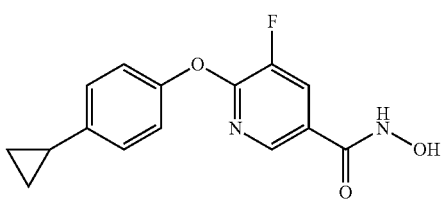

6-(4-cyclopropylphenoxy)-5-fluoro-N-hydroxynicotinamide

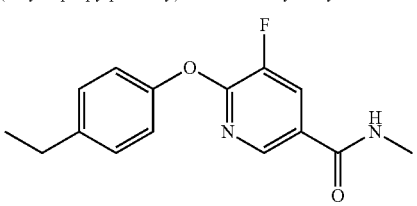

6-(4-ethylphenoxy)-5-fluoro-N-methylnicotinamide

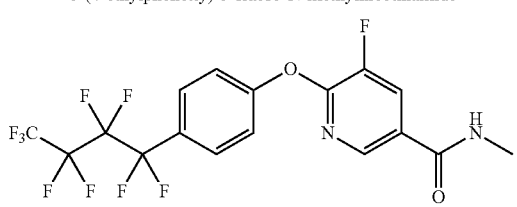

5-fluoro-N-methyl-6-(4-(perfluorobutyl)phenoxy)nicotinamide

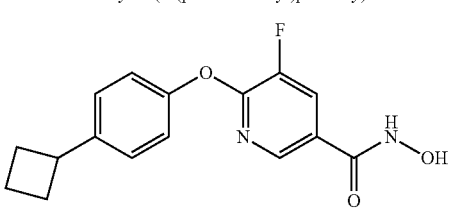

6-(4-cyclobutylphenoxy)-5-fluoro-N-hydroxynicotinamide

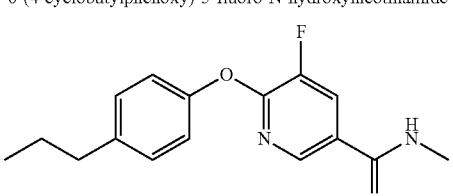

5-fluoro-N-methyl-6-(4-propylphenoxy)nicotinamide

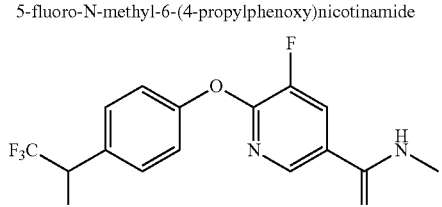

5-fluoro-6-(4-(1,1,1,3,3,3-hexafluoropropan-2-yl)phenoxy)-N-methylnicotinamide

-continued

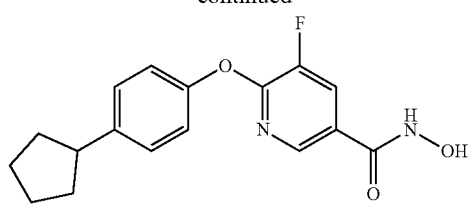

6-(4-cyclopentylphenoxy)-5-fluoro-N-hydroxynicotinamide

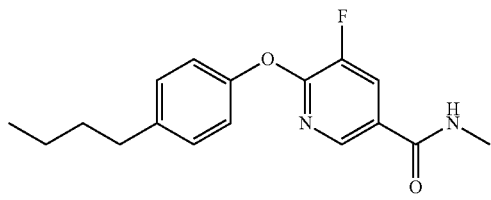

6-(4-butylphenoxy)-5-fluoro-N-methylnicotinamide

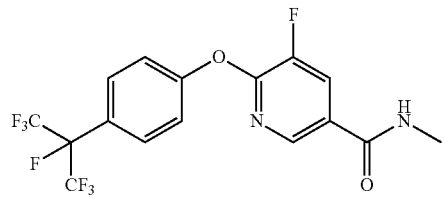

5-fluoro-N-methyl-6-(4-(perfluoropropan-2-yl)phenoxy)nicotinamide

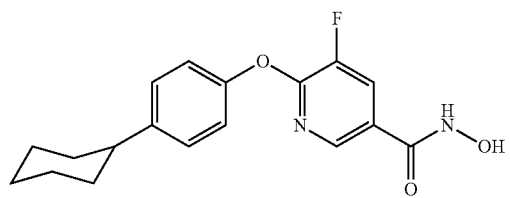

6-(4-cyclohexylphenoxy)-5-fluoro-N-hydroxynicotinamide

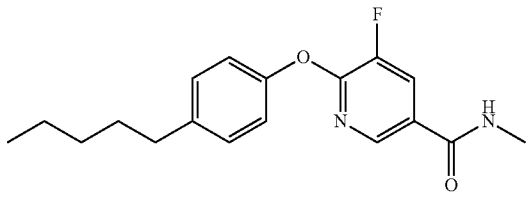

5-fluoro-N-methyl-6-(4-pentylphenoxy)nicotinamide

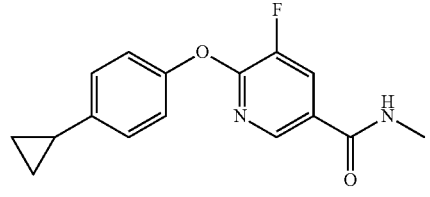

6-(4-cyclopropylphenoxy)-5-fluoro-N-methylnicotinamide

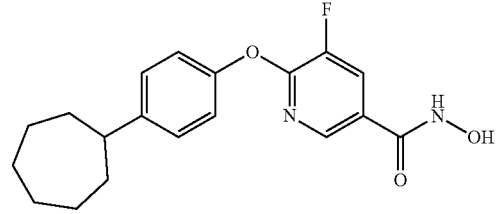

6-(4-cycloheptylphenoxy)-5-fluoro-N-hydroxynicotinamide

-continued

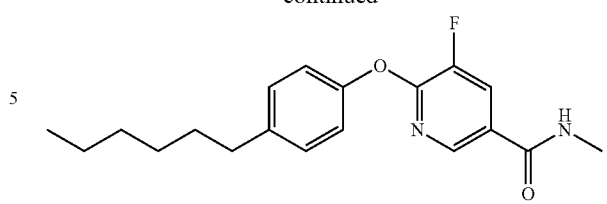

5-fluoro-6-(4-hexylphenoxy)-N-methylnicotinamide

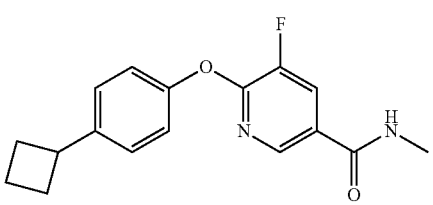

6-(4-cyclobutylphenoxy)-5-fluoro-N-methylnicotinamide

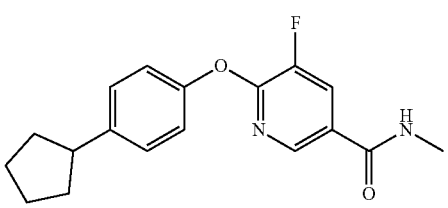

6-(4-cyclopentylphenoxy)-5-fluoro-N-methylnicotinamide

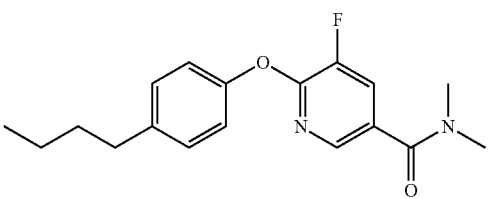

6-(4-butylphenoxy)-5-fluoro-N,N-dimethylnicotinamide

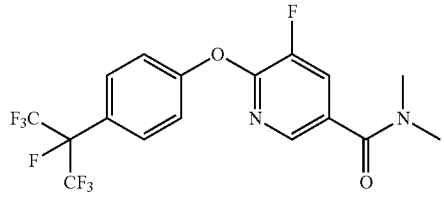

5-fluoro-N,N-dimethyl-6-(4-(perfluoropropan-2-yl)phenoxy)nicotinamide

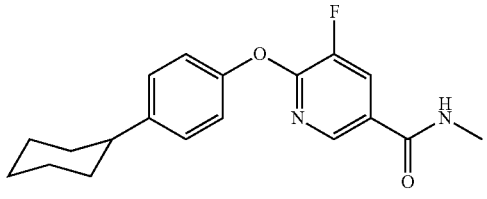

6-(4-cyclohexylphenoxy)-5-fluoro-N-methylnicotinamide

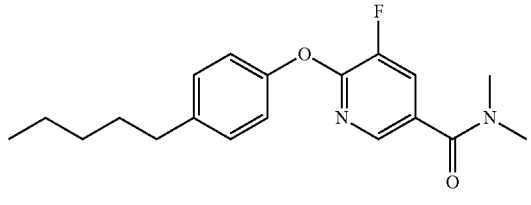

5-fluoro-N,N-dimethyl-6-(4-pentylphenoxy)nicotinamide

-continued

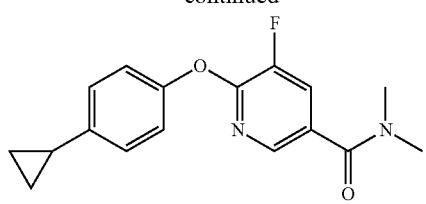

6-(4-cyclopropylphenoxy)-5-fluoro-N,N-dimethylnicotinamide

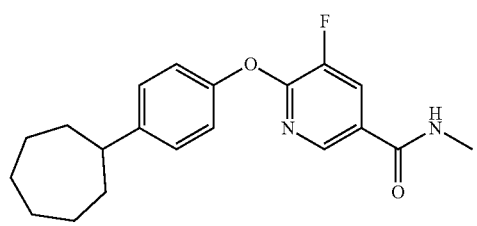

6-(4-cycloheptylphenoxy)-5-fluoro-N-methylnicotinamide

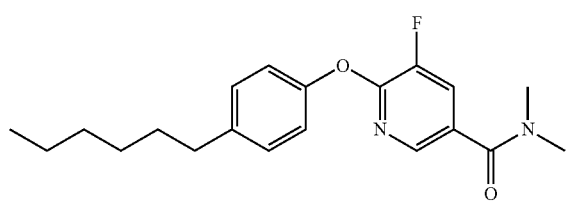

5-fluoro-6-(4-hexylphenoxy)-N,N-dimethylnicotinamide

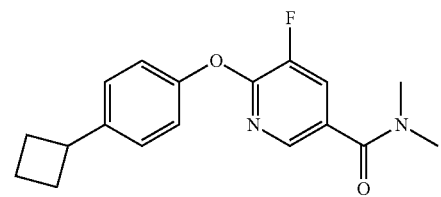

6-(4-cyclobutylphenoxy)-5-fluoro-N,N-dimethylnicotinamide

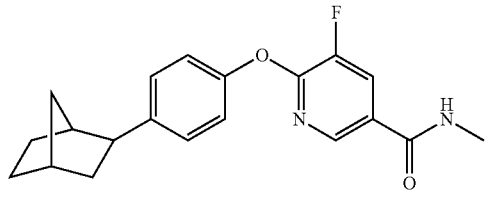

6-(4-((1S,4R)-bicyclo[2.2.1]heptan-2-yl)phenoxy)-5-fluoro-N-methylnicotinamide

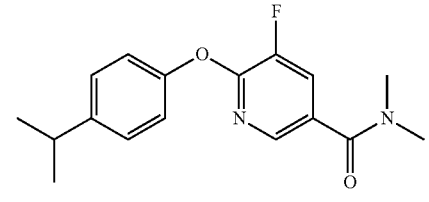

5-fluoro-6-(4-isopropylphenoxy)-N,N-dimethylnicotinamide

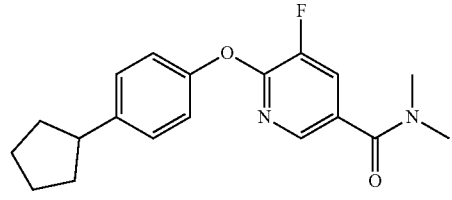

6-(4-cyclopentylphenoxy)-5-fluoro-N,N-dimethylnicotinamide

-continued

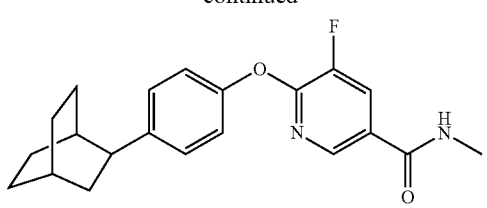

6-(4-((1s,4s)-bicyclo[2.2.2]octan-2-yl)phenoxy)-5-fluoro-N-methylnicotinamide

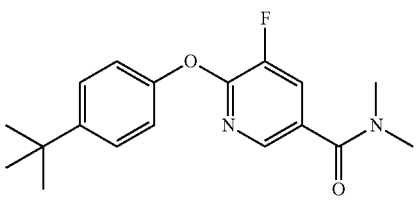

6-(4-(tert-butyl)phenoxy)-5-fluoro-N,N-dimethylnicotinamide

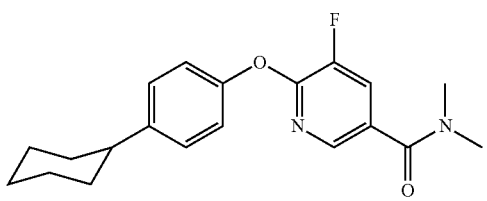

6-(4-cyclohexylphenoxy)-5-fluoro-N,N-dimethylnicotinamide

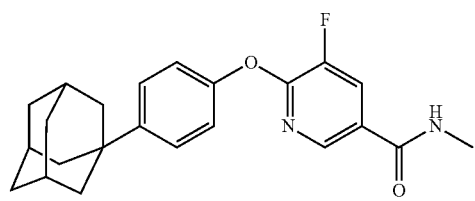

6-(4-((3r,5r,7r)-adamantan-1-yl)phenoxy)-5-fluoro-N-methylnicotinamide

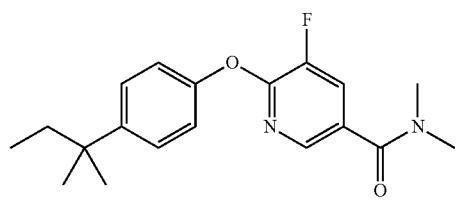

5-fluoro-N,N-dimethyl-6-(4-(tert-pentyl)phenoxy)nicotinamide

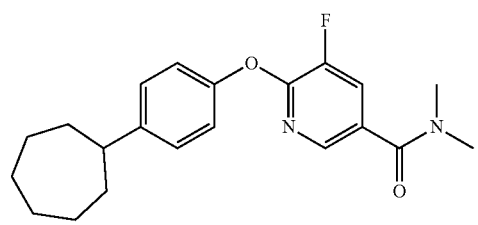

6-(4-cycloheptylphenoxy)-5-fluoro-N,N-dimethylnicotinamide

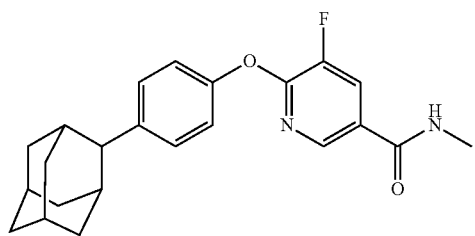

6-(4-(((1r,3r,5r,7r)-adamantan-2-yl)phenoxy)-5-fluoro-N-methylnicotinamide

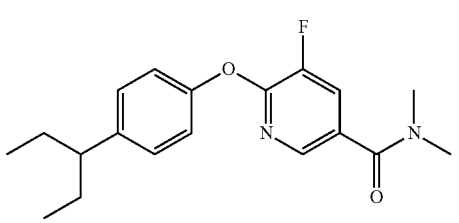

5-fluoro-N,N-dimethyl-6-(4-(pentan-3-yl)phenoxy)nicotinamide

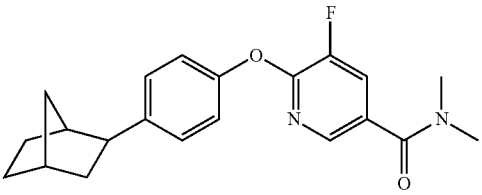

6-(4-((1S,4R)-bicyclo[2.2.1]heptan-2-yl)phenoxy)-5-fluoro-N,N-dimethylnicotinamide

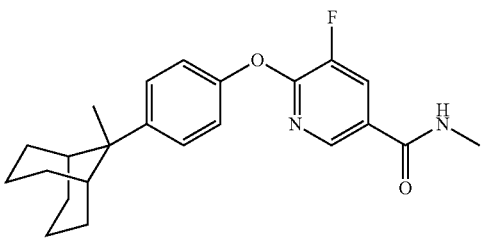

5-fluoro-N-methyl-6-(4-((1R,5S)-9-methylbicyclo[3.3.1]nonan-9-yl)phenoxy)nicotinamide

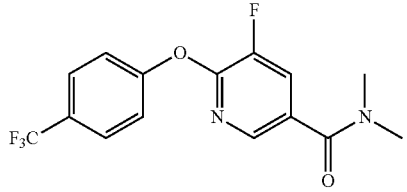

5-fluoro-N,N-dimethyl-6-(4-(trifluoromethyl)phenoxy)nicotinamide

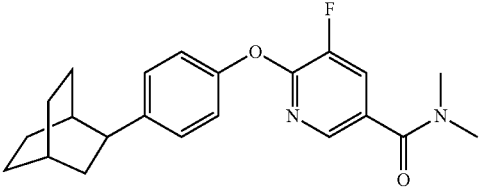

6-(4-((1s,4s)-bicyclo[2.2.2]octan-2-yl)phenoxy)-5-fluoro-N,N-dimethylnicotinamide

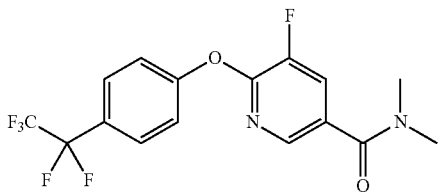

5-fluoro-N,N-dimethyl-6-(4-(perfluoroethyl)phenoxy)nicotinamide

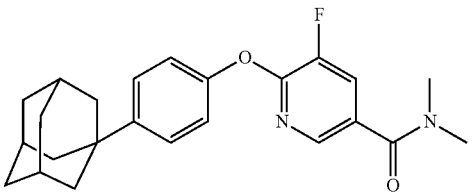

6-(4-(((3r,5r,7r)-adamantan-1-yl)phenoxy)-5-fluoro-N,N-dimethylnicotinamide

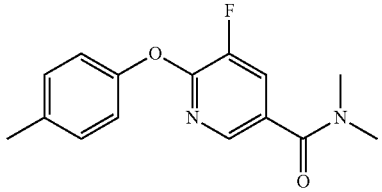

5-fluoro-N,N-dimethyl-6-(p-tolyloxy)nicotinamide

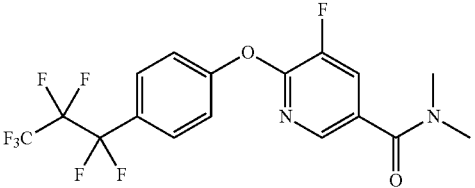

5-fluoro-N,N-dimethyl-6-(4-(perfluoropropyl)phenoxy)nicotinamide

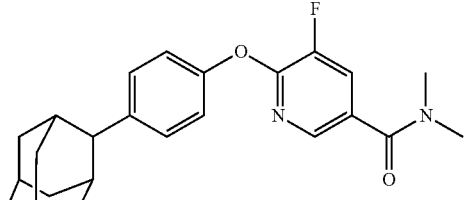

6-(4-(((1r,3r,5r,7r)-adamantan-2-yl)phenoxy)-5-fluoro-N,N-dimethylnicotinamide

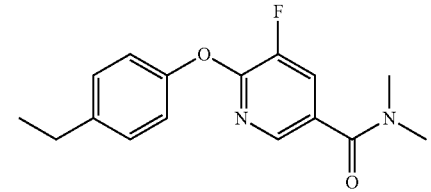

6-(4-ethylphenoxy)-5-fluoro-N,N-dimethylnicotinamide

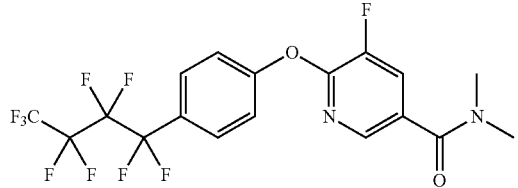

5-fluoro-N,N-dimethyl-6-(4-(perfluorobutyl)phenoxy)nicotinamide

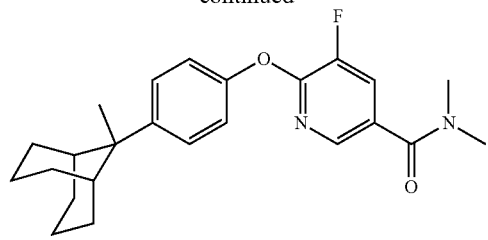

5-fluoro-N,N-dimethyl-6-(4-((1R,5S)-9-methylbicyclo[3.3.1]nonan-9-yl)phenoxy)nicotinamide

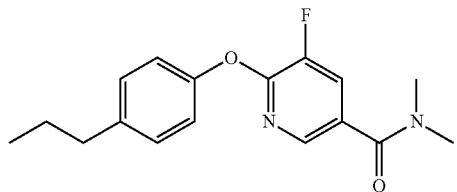

5-fluoro-N,N-dimethyl-6-(4-propylphenoxy)nicotinamide

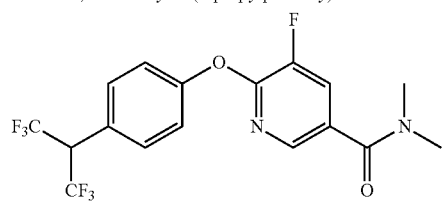

5-fluoro-6-(4-(1,1,1,3,3,3-hexafluoropropan-2-yl)phenoxy)-N,N-dimethylnicotinamide

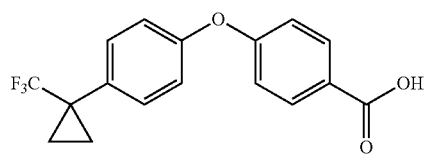

4-(4-(1-(trifluoromethyl)cyclopropyl)phenoxy)benzoic acid

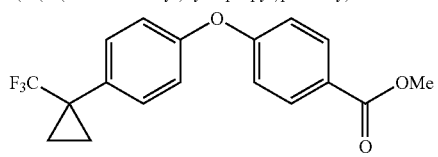

methyl 4-(4-(1-(trifluoromethyl)cyclopropyl)phenoxy)benzoate

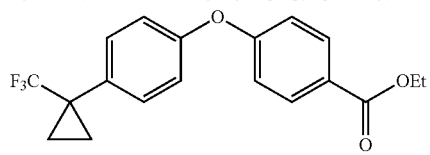

ethyl 4-(4-(1-(trifluoromethyl)cyclopropyl)phenoxy)benzoate

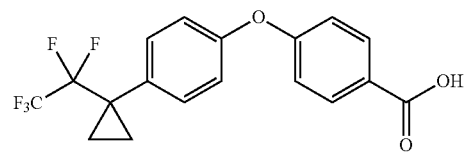

4-(4-(1-(perfluoroethyl)cyclopropyl)phenoxy)benzoic acid

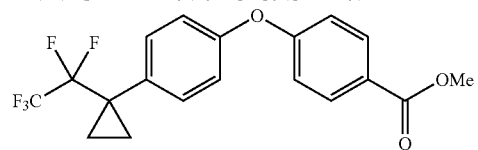

methyl 4-(4-(1-(perfluoroethyl)cyclopropyl)phenoxy)benzoate

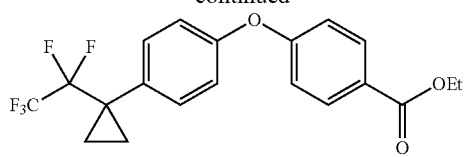

ethyl 4-(4-(1-(perfluoroethyl)cyclopropyl)phenoxy)benzoate

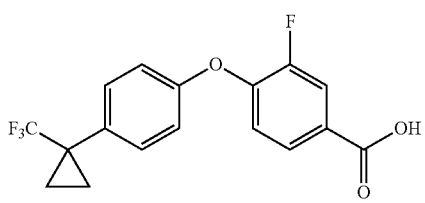

3-fluoro-4-(4-(1-(trifluoromethyl)cyclopropyl)phenoxy)benzoic acid

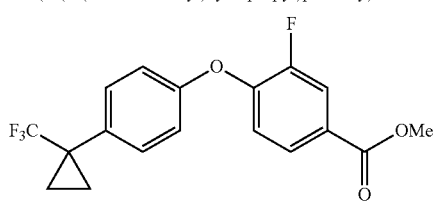

methyl 3-fluoro-4-(4-(1-(trifluoromethyl)cyclopropyl)phenoxy)benzoate

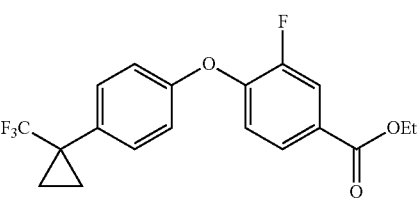

ethyl 3-fluoro-4-(4-(1-(trifluoromethyl)cyclopropyl)phenoxy)benzoate

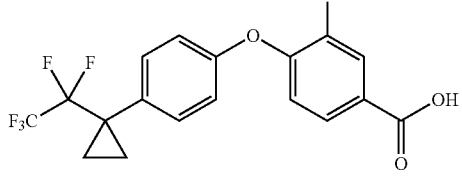

3-fluoro-4-(4-(1-(perfluoroethyl)cyclopropyl)phenoxy)benzoic acid

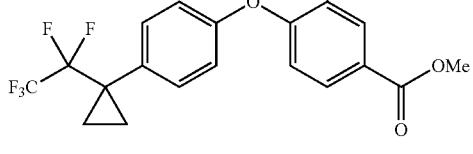

methyl 3-fluoro-4-(4-(1-(perfluoroethyl)cyclopropyl)phenoxy)benzoate

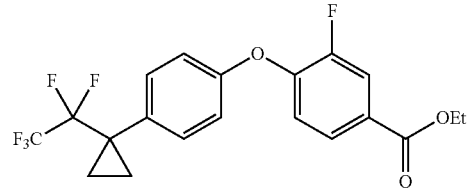

ethyl 3-fluoro-4-(4-(1-(perfluoroethyl)cyclopropyl)phenoxy)benzoate

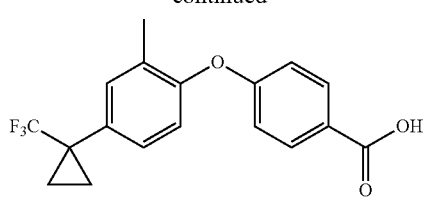

4-(2-methyl-4-(1-(trifluoromethyl)cyclopropyl)phenoxy)benzoic acid

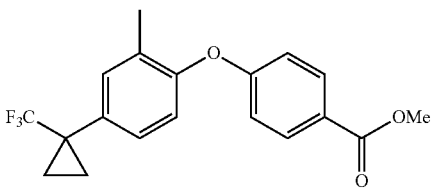

methyl 4-(2-methyl-4-(1-(trifluoromethyl)cyclopropyl)phenoxy)benzoate

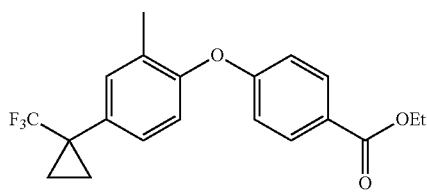

ethyl 4-(2-methyl-4-(1-(trifluoromethyl)cyclopropyl)phenoxy)benzoate

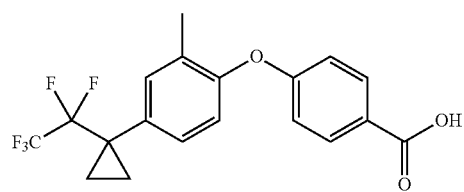

4-(2-methyl-4-(1-(perfluoroethyl)cyclopropyl)phenoxy)benzoic acid

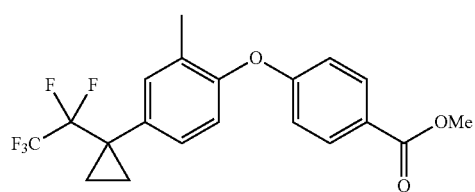

methyl 4-(2-methyl-4-(1-(perfluoroethyl)cyclopropyl)phenoxy)benzoate

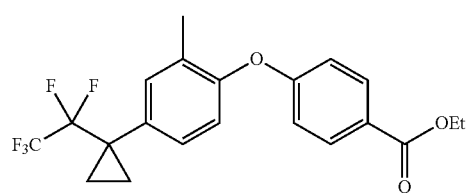

ethyl 4-(2-methyl-4-(1-(perfluoroethyl)cyclopropyl)phenoxy)benzoate

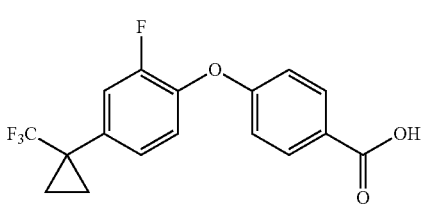

4-(2-fluoro-4-(1-(trifluoromethyl)cyclopropyl)phenoxy)benzoic acid

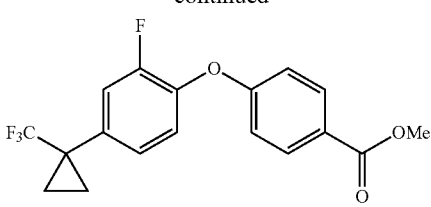

methyl 4-(2-fluoro-4-(1-(trifluoromethyl)cyclopropyl)phenoxy)benzoate

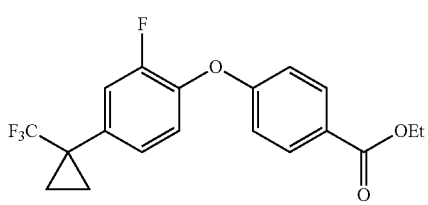

ethyl 4-(2-fluoro-4-(1-(trifluoromethyl)cyclopropyl)phenoxy)benzoate

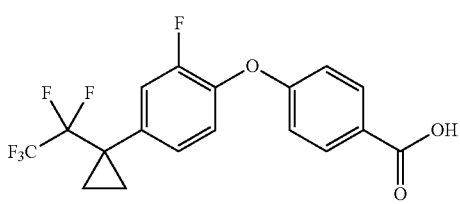

4-(2-fluoro-4-(1-(perfluoroethyl)cyclopropyl)phenoxy)benzoic acid

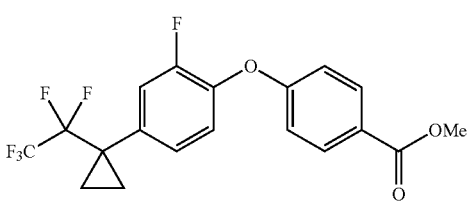

methyl 4-(2-fluoro-4-(1-(perfluoroethyl)cyclopropyl)phenoxy)benzoate

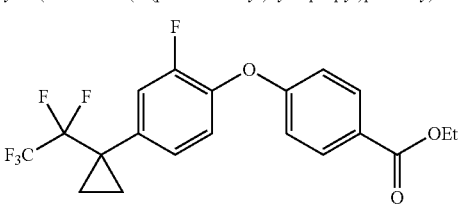

ethyl 4-(2-fluoro-4-(1-(perfluoroethyl)cyclopropyl)phenoxy)benzoate

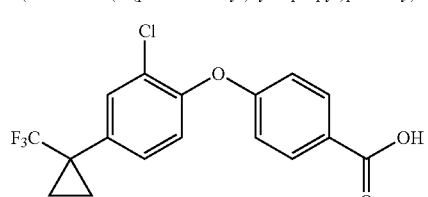

4-(3-chloro-4-(1-(trifluoromethyl)cyclopropyl)phenoxy)benzoic acid

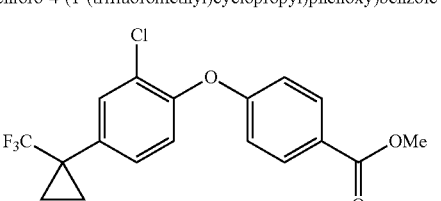

methyl 4-(2-chloro-4-(1-(trifluoromethyl)cyclopropyl)phenoxy)benzoate

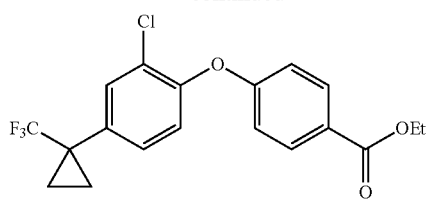

ethyl 4-(2-chloro-4-(1-(trifluoromethyl)cyclopropyl)phenoxy)benzoate

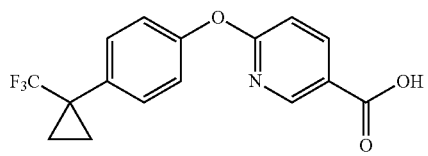

6-(4-(1-(trifluoromethyl)cyclopropyl)phenoxy)nicotinic acid

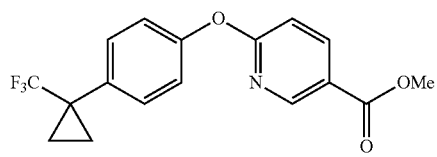

methyl 6-(4-(1-(trifluoromethyl)cyclopropyl)phenoxy)nicotinate

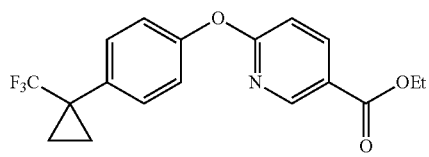

ethyl 6-(4-(1-(trifluoromethyl)cyclopropyl)phenoxy)nicotinate

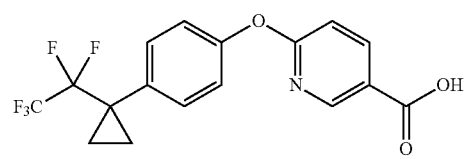

6-(4-(1-(perfluoroethyl)cyclopropyl)phenoxy)nicotinic acid

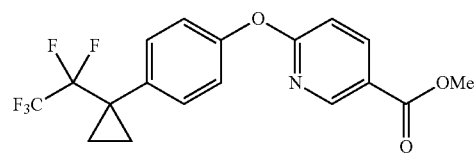

methyl 6-(4-(1-(perfluoroethyl)cyclopropyl)phenoxy)nicotinate

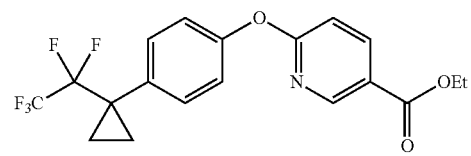

ethyl 6-(4-(1-(perfluoroethyl)cyclopropyl)phenoxy)nicotinate

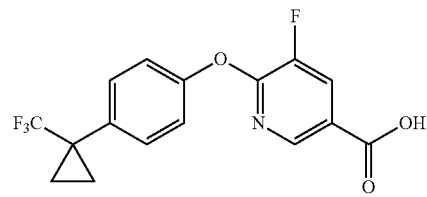

5-fluoro-6-(4-(1-(trifluoromethyl)cyclopropyl)phenoxy)nicotinic acid

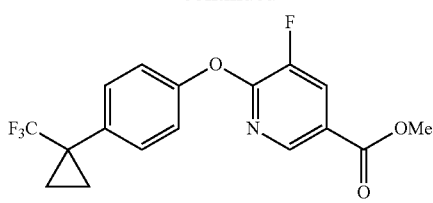

methyl 5-fluoro-6-(4-(1-(trifluoromethyl)cyclopropyl)phenoxy)nicotinate

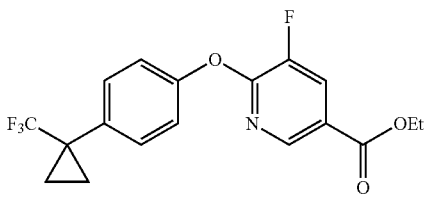

ethyl 5-fluoro-6-(4-(1-(trifluoromethyl)cyclopropyl)phenoxy)nicotinate

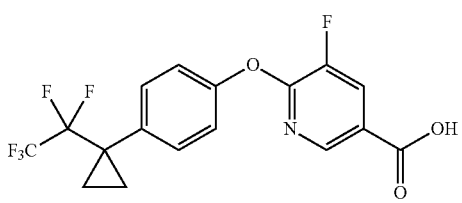

5-fluoro-6-(4-(1-(perfluoroethyl)cyclopropyl)phenoxy)nicotinic acid

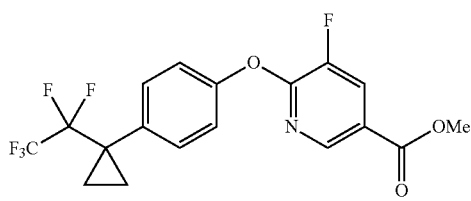

methyl 5-fluoro-6-(4-(1-(perfluoroethyl)cyclopropyl)phenoxy)nicotinate

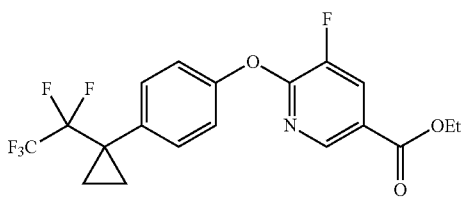

ethyl 5-fluoro-6-(4-(1-(perfluoroethyl)cyclopropyl)phenoxy)nicotinate

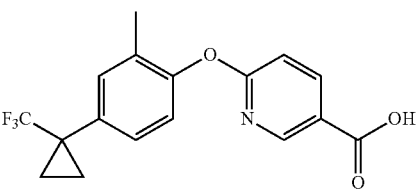

6-(2-methyl-4-(1-(trifluoromethyl)cyclopropyl)phenoxy)nicotinic acid

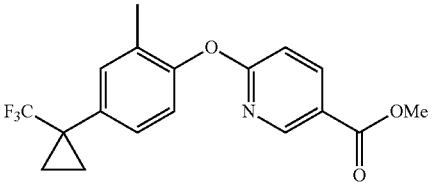

methyl 6-(2-methyl-4-(1-(trifluoromethyl)cyclopropyl)phenoxy)nicotinate

-continued

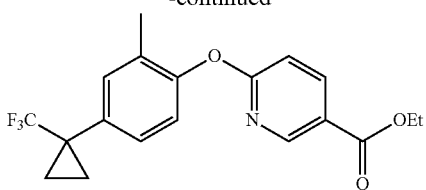

ethyl 6-(2-methyl-4-(1-(trifluoromethyl)cyclopropyl)phenoxy)nicotinate

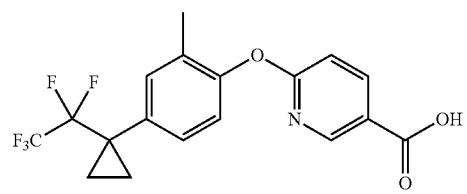

6-(2-methyl-4-(1-(perfluoroethyl)cyclopropyl)phenoxy)nicotinic acid

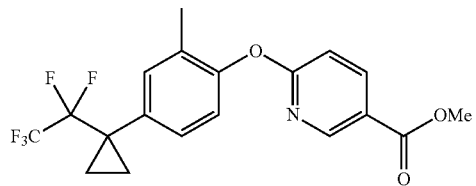

methyl 6-(2-methyl-4-(1-(perfluoroethyl)cyclopropyl)phenoxy)nicotinate

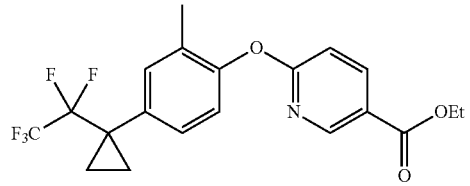

ethyl 6-(2-methyl-4-(1-(perfluoroethyl)cyclopropyl)phenoxy)nicotinate

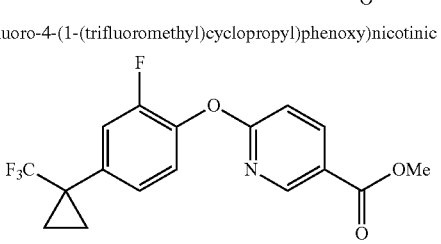

6-(2-fluoro-4-(1-(trifluoromethyl)cyclopropyl)phenoxy)nicotinic acid

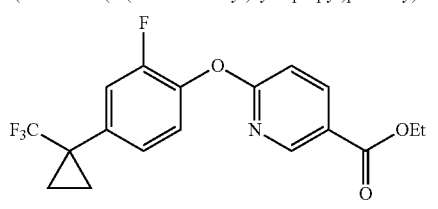

methyl 6-(2-fluoro-4-(1-(trifluoromethyl)cyclopropyl)phenoxy)nicotinate

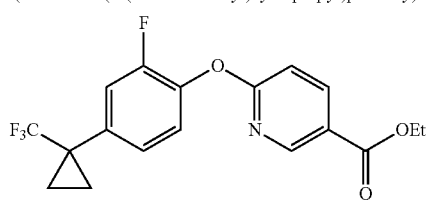

ethyl 6-(2-fluoro-4-(1-(trifluoromethyl)cyclopropyl)phenoxy)nicotinate

-continued

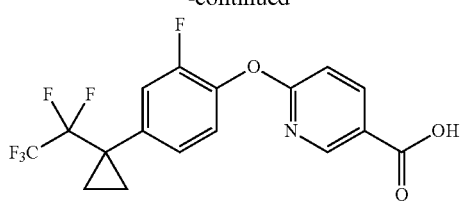

6-(2-fluoro-4-(1-(perfluoroethyl)cyclopropyl)phenoxy)nicotinic acid

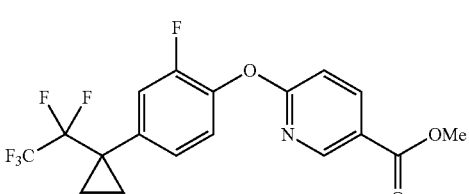

methyl 6-(2-fluoro-4-(1-perfluoroethyl)cyclopropyl)phenoxy)nicotinate

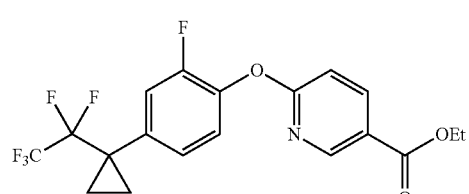

ethyl 6-(2-fluoro-4-(1-(perfluoroethyl)cyclopropyl)phenoxy)nicotinate

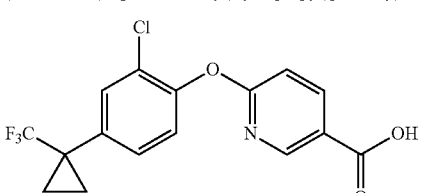

6-(2-chloro-4-(1-(trifluoromethyl)cyclopropyl)phenoxy)nicotinic acid

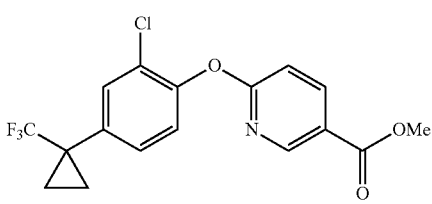

methyl 6-(2-chloro-4-(1-(trifluoromethyl)cyclopropyl)phenoxy)nicotinate

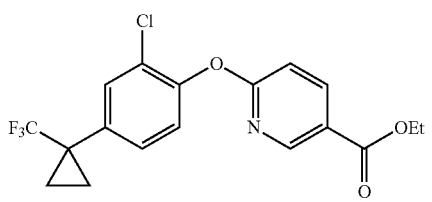

ethyl 6-(2-chloro-4-(1-(trifluoromethyl)cyclopropyl)phenoxy)nicotinate

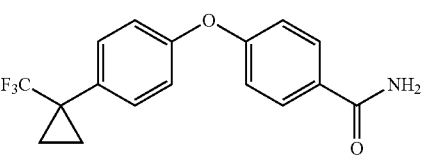

4-(4-(1-(trifluoromethyl)cyclopropyl)phenoxy)benzamide

-continued

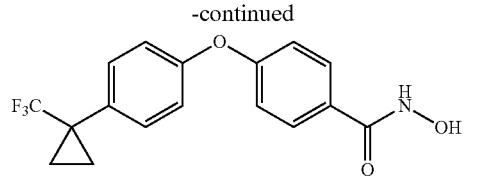

N-hydroxy-4-(4-(1-(trifluoromethyl)cyclopropyl)phenoxy)benzamide

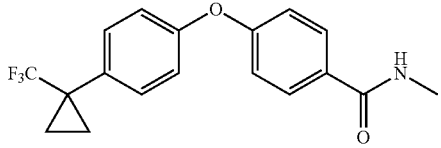

N-methyl-4-(4-(1-(trifluoromethyl)cyclopropyl)phenoxy)benzamide

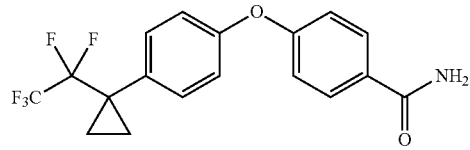

4-(4-(1-(perfluoroethyl)cyclopropyl)phenoxy)benzamide

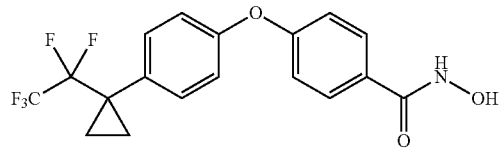

N-hydroxy-4-(4-(1-(perfluoroethyl)cyclopropyl)phenoxy)benzamide

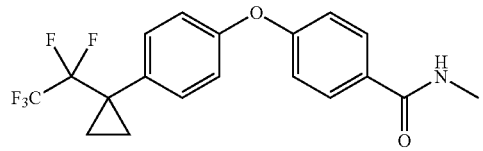

N-methyl-4-(4-(1-perfluoroethyl)cyclopropyl)phenoxy)benzamide

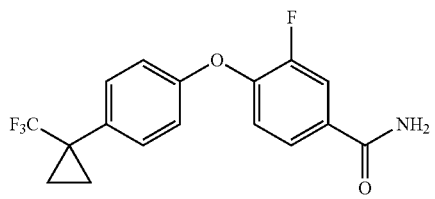

3-fluoro-4-(4-(1-(trifluoromethyl)cyclopropyl)phenoxy)benzamide

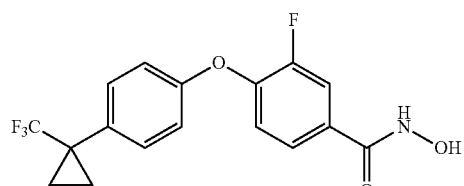

3-fluoro-N-hydroxy-4-(4-(1-(trifluoromethyl)cyclopropyl)phenoxy)
benzamide

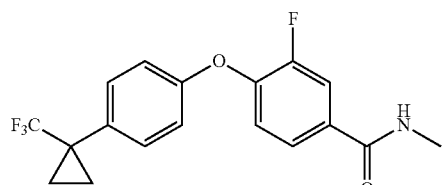

3-fluoro-N-methyl-4-(4-(1-(trifluoromethyl)cyclopropyl)phenoxy)
benzamide

-continued

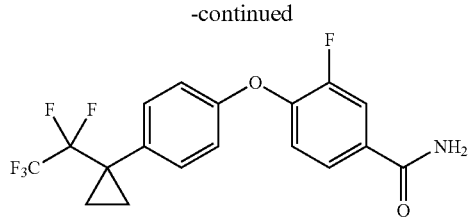

3-fluoro-4-(4-(1-(perfluoroethyl)cyclopropyl)phenoxy)benzamide

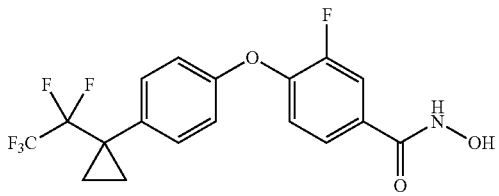

3-fluoro-N-hydroxy-4-(4-(1-(perfluoroethyl)cyclopropyl)phenoxy)
benzamide

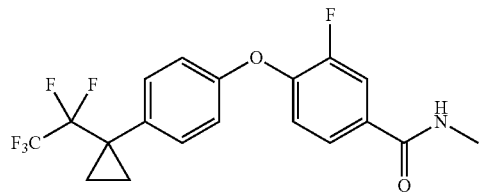

3-fluoro-N-methyl-4-(4-(1-(perfluoroethyl)cyclopropyl)phenoxy)
benzamide

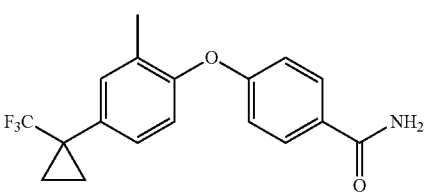

4-(2-methyl-4-(1-(trifluoromethyl)cyclopropyl)phenoxy)benzamide

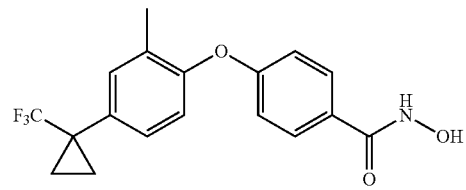

N-hydroxy-4-(2-methyl-4-(1-(trifluoromethyl)cyclopropyl)phenoxy)
benzamide

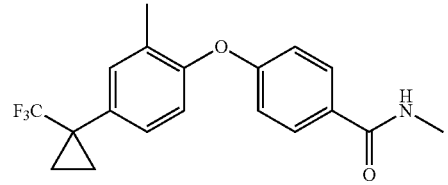

N-methyl-4-(2-methyl-4-(1-(trifluoromethyl)cyclopropyl)phenoxy)
benzamide

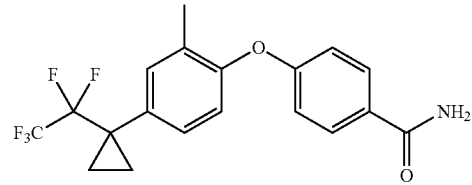

4-(2-methyl-4-(1-(perfluoroethyl)cyclopropyl)phenoxy)benzamide

-continued

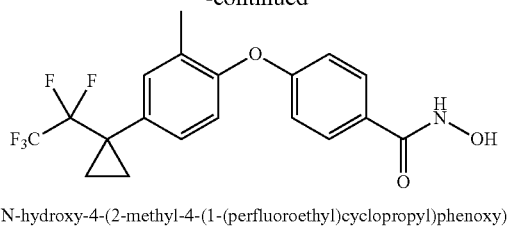

N-hydroxy-4-(2-methyl-4-(1-(perfluoroethyl)cyclopropyl)phenoxy)benzamide

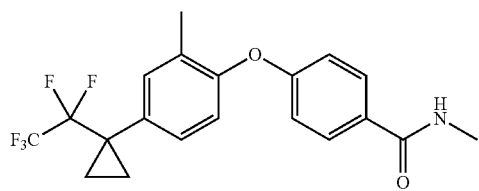

N-methyl-4-(2-methyl-4-(1-(perfluoroethyl)cyclopropyl)phenoxy)benzamide

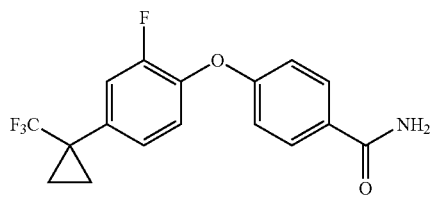

4-(2-fluoro-4-(1-(trifluoromethyl)cyclopropyl)phenoxy)benzamide

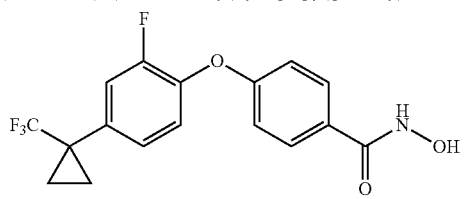

4-(2-fluoro-4-(1-(trifluoromethyl)cyclopropyl)phenoxy)-N-hydroxybenzamide

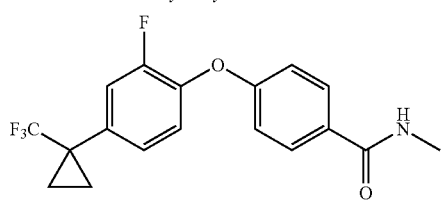

4-(2-fluoro-4-(1-(trifluoromethyl)cyclopropyl)phenoxy)-N-methylbenzamide

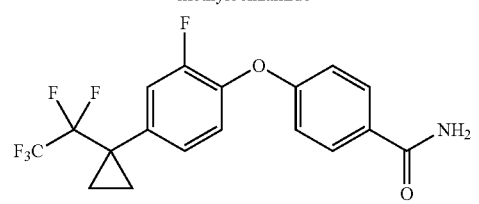

4-(2-fluoro-4-(1-(perfluoroethyl)cyclopropyl)phenoxy)benzamide

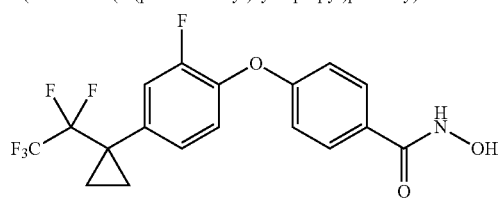

4-(2-fluoro-4-(1-(perfluoroethyl)cyclopropyl)phenoxy)-N-hydroxybenzamide

-continued

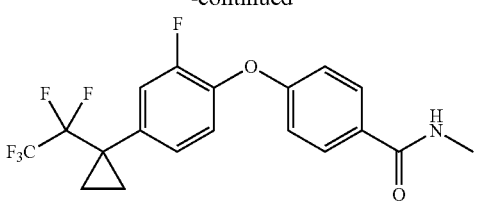

4-(2-fluoro-4-(1-(perfluoroethyl)cyclopropyl)phenoxy)-N-methylbenzamide

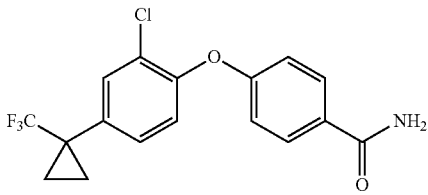

4-(2-chloro-4-(1-(trifluoromethyl)cyclopropyl)phenoxy)benzamide

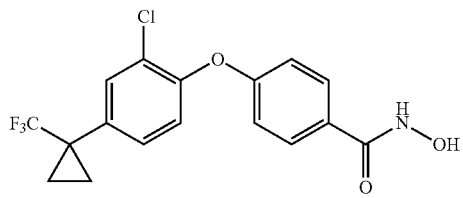

4-(2-chloro-4-(1-(trifluoromethyl)cyclopropyl)phenoxy)-N-hydroxybenzamide

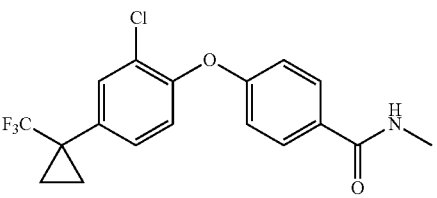

4-(2-chloro-4-(1-(trifluoromethyl)cyclopropyl)phenoxy)-N-methylbenzamide

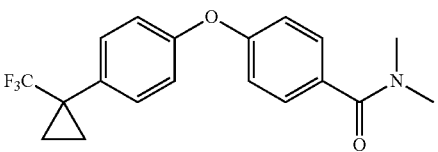

N,N-dimethyl-4-(4-(1-(trifluoromethyl)cyclopropyl)phenoxy)benzamide

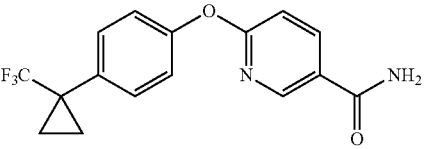

6-(4-(trifluoromethyl)cyclopropyl)phenoxy)nicotinamide

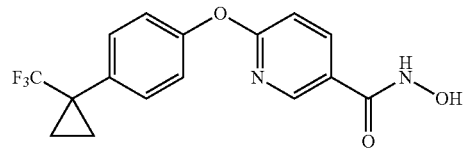

N-hydroxy-6-(4-(1-(trifluoromethyl)cyclopropyl)phenoxy)nicotinamide

-continued

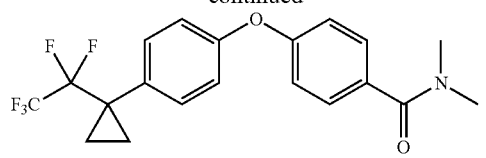

N-N-dimethyl-4-(4-(1-(perfluoroethyl)cyclopropyl)phenoxy)benzamide

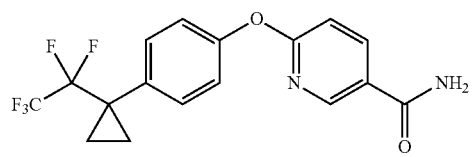

6-(4-(1-(perfluoroethyl)cyclopropyl)phenoxy)nicotinamide

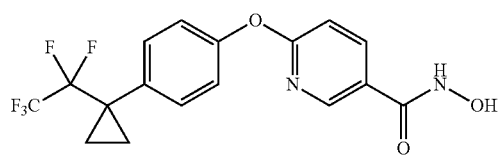

N-hydroxy-6-(4-(1-perfluoroethyl)cyclopropyl)phenoxy)nicotinamide

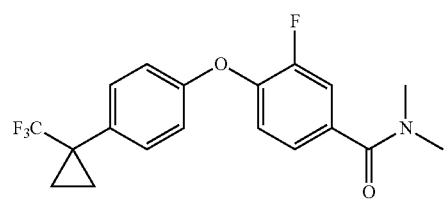

3-fluoro-N,N-dimethyl-4-(4-(1-(trifluoromethyl)cyclopropyl)phenoxy)
benzamide

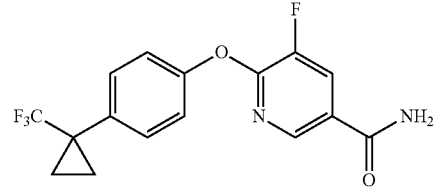

5-fluoro-6-(4-(1-(trifluoromethyl)cyclopropyl)phenoxy)nicotinamide

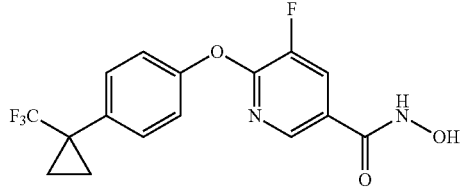

5-fluoro-N-hydroxy-6-(4-(1-(trifluoromethyl)cyclopropyl)phenoxy)
nicotinamide

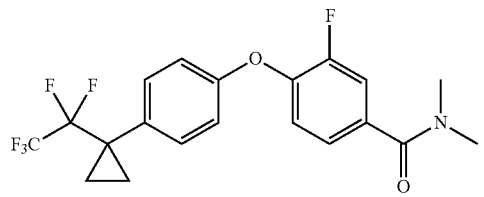

3-fluoro-N,N-dimethyl-4-(4-(1-(perfluoroethyl)cyclopropyl)phenoxy)
benzamide

-continued

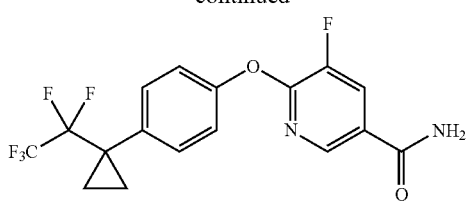

5-fluoro-6-(4-(1-(perfluoroethyl)cyclopropyl)phenoxy)nicotinamide

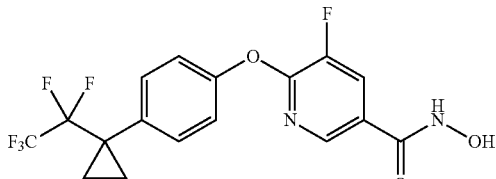

5-fluoro-N-hydroxy-6-(4-(1-(perfluoroethyl)cyclopropyl)phenoxy)
nicotinamide

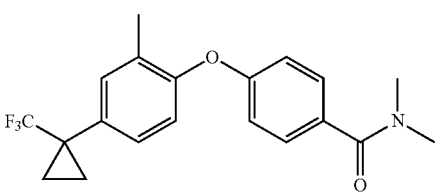

N,N-dimethyl-4-(2-methyl-4-(1-(trifluoromethyl)cyclopropyl)phenoxy)
benzamide

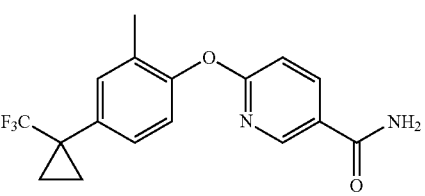

6-(2-methyl-4-(1-(trifluoromethyl)cyclopropyl)phenoxy)nicotinamide

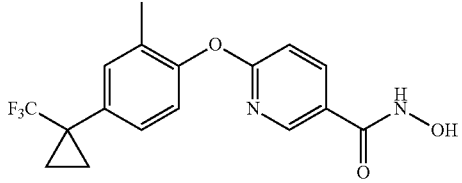

N-hydroxy-6-(2-methyl-4-(1-(trifluoromethyl)cyclopropyl)phenoxy)
nicotinamide

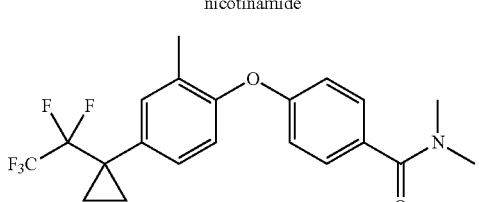

N,N-dimethyl-4-(2-methyl-4-(1-perfluoroethyl)cyclopropyl)phenoxy)
benzamide

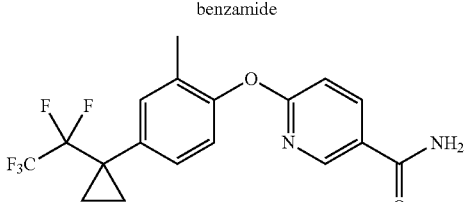

6-(2-methyl-4-(1-(perfluoroethyl)cyclopropyl)phenoxy)nicotinamide

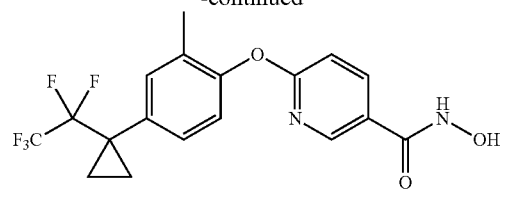

N-hydroxy-6-(2-methyl-4-(1-(perfluoroethyl)cyclopropyl)phenoxy)nicotinamide

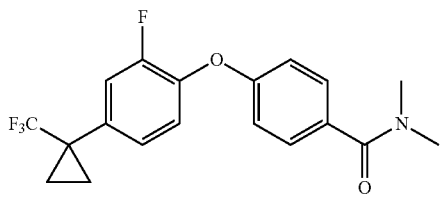

4-(2-fluoro-4-(1-(trifluoromethyl)cyclopropyl)phenoxy)-N,N,-dimethylbenzamide

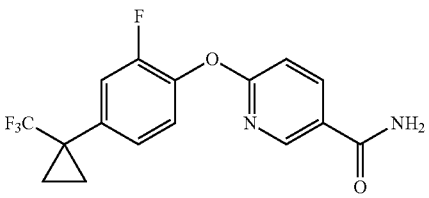

6-(2-fluoro-4-(1-(trifluoromethyl)cyclopropyl)phenoxy)nicotinamide

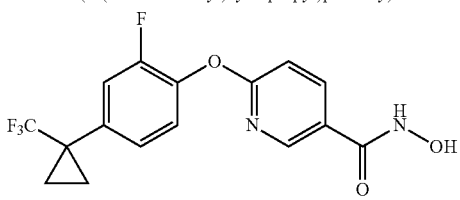

6-(2-fluoro-4-(1-(trifluoromethyl)cyclopropyl)phenoxy)-N-hydroxynicotinamide

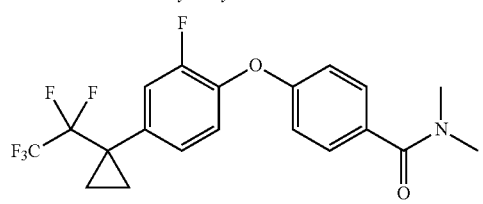

4-(2-fluoro-4-(1-(perfluoroethyl)cyclopropyl)phenoxy)-N,N-dimethylbenzamide

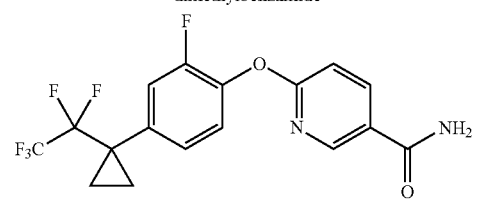

6-(2-fluoro-4-(1-(perfluoroethyl)cyclopropyl)phenoxy)nicotinamide

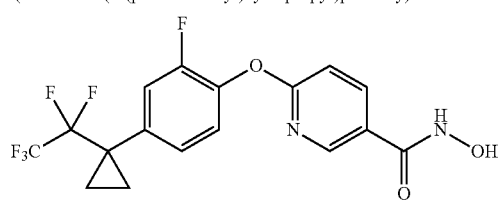

6-(2-fluoro-4-(1-(perfluoroethyl)cyclopropyl)phenoxy)-N-hydroxynicotinamide

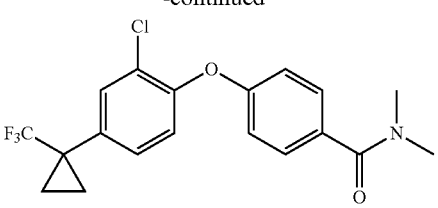

4-(2-chloro-4-(1-(trifluoromethyl)cyclopropyl)phenoxy)-N,N-dimethylbenzamide

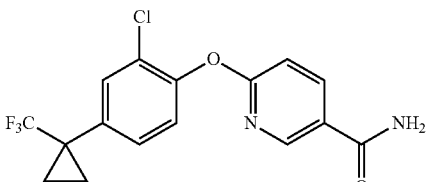

6-(2-chloro-4-(1-(trifluoromethyl)cyclopropyl)phenoxy)nicotinamide

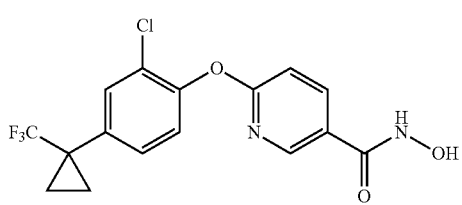

6-(2-chloro-4-(1-(trifluoromethyl)cyclopropyl)phenoxy)-N-hydroxynicotinamide

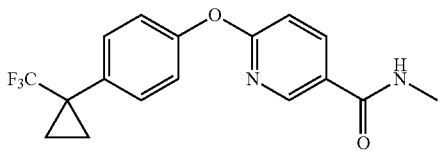

N-methyl-4-(4-(1-(trifluoromethyl)cyclopropyl)phenoxy)benzamide

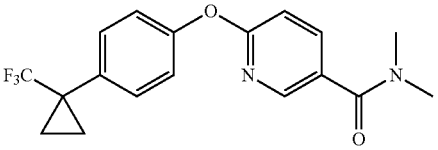

N,N-dimethyl-6-(4-(1-(trifluoromethyl)cyclopropyl)phenoxy)nicotinamide

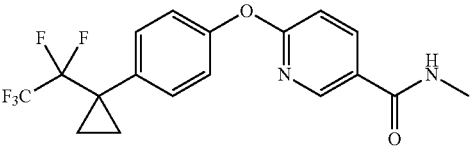

N-methyl-4-(4-(1-(perfluoroethyl)cyclopropyl)phenoxy)benzamide

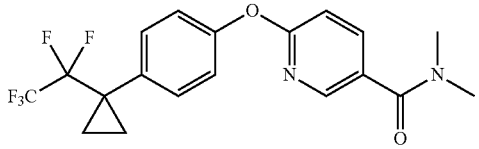

N,N-dimethyl-6-(4-(1-(perfluoroethyl)cyclopropyl)phenoxy)nicotinamide

-continued

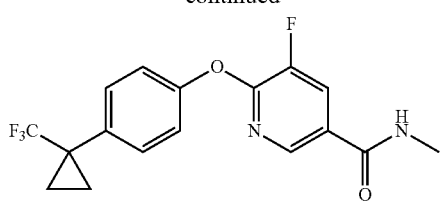

3-fluoro-N-methyl-4-(4-(1-(trifluoromethyl)cyclopropyl)phenoxy)
benzamide

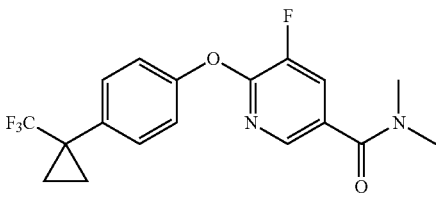

5-fluoro-N,N-dimethyl-6-(4-(1-(trifluoromethyl)cyclopropyl)phenoxy)
nicotinamide

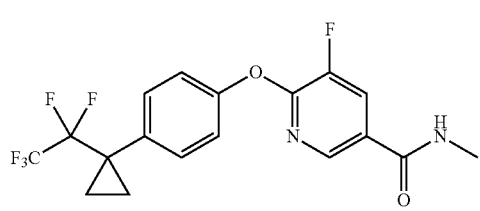

3-fluoro-N-methyl-4-(4-(1-(perfluoroethyl)cyclopropyl)phenoxy)
benzamide

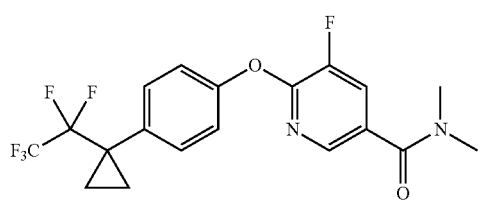

5-fluoro-N,N-dimethyl-6-(4-(1-(perfluoroethyl)cyclopropyl)phenoxy)
nicotinamide

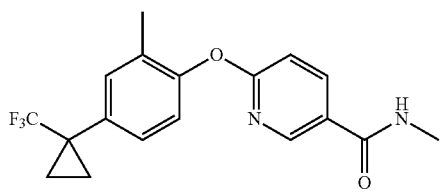

N-methyl-4-(2-methyl-4-(1-(trifluoromethyl)cyclopropyl)phenoxy)
benzamide

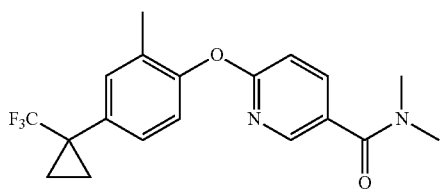

N,N-dimethyl-6-(2-methyl-4-(1-(trifluoromethyl)cyclopropyl)phenoxy)
nicotinamide -continued

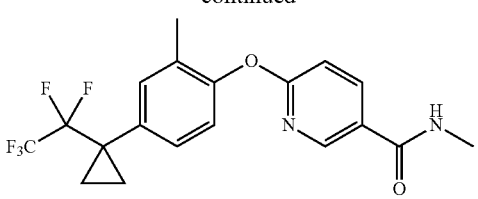

N-methyl-4-(2-methyl-4-(1-(perfluoroethyl)cyclopropyl)phenoxy)
benzamide

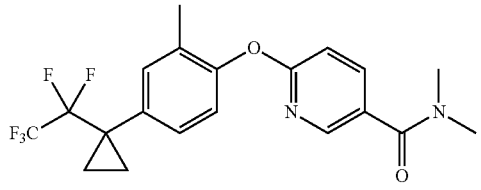

N,N-dimethyl-6-(2-methyl-4-(1-(perfluoroethyl)cyclopropyl)phenoxy)
nicotinamide

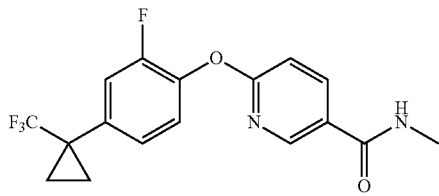

4-(2-fluoro-4-(1-(trifluoromethyl)cyclopropyl)phenoxy)-N-
methylbenzamide

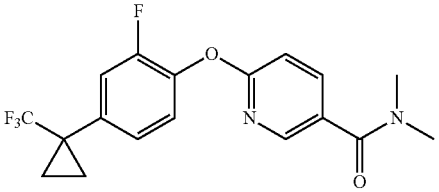

6-(2-fluoro-4-(1-(trifluoromethyl)cyclopropyl)phenoxy)-N,N-
dimethylnicotinamide

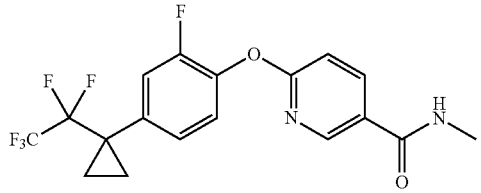

4-(2-fluoro-4-(1-(perfluoroethyl)cyclopropyl)phenoxy)-N-
methylbenzamide

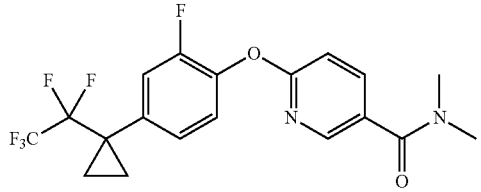

6-(2-fluoro-4-(1-(perfluoroethyl)cyclopropyl)phenoxy)-N,N-
dimethylnicotinamide

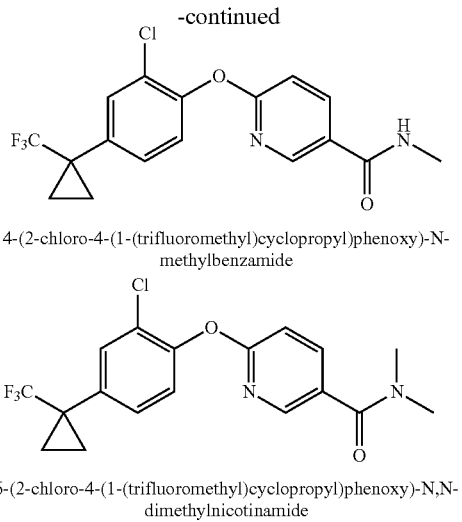

4-(2-chloro-4-(1-(trifluoromethyl)cyclopropyl)phenoxy)-N-methylbenzamide 6-(2-chloro-4-(1-(trifluoromethyl)cyclopropyl)phenoxy)-N,N-dimethylnicotinamide wherein the hyperproliferative disorder is cancer or a precancerous lesion selected from the group consisting of cancer or precancerous lesions of the neuroendocrine system, brain, pancreas, liver, thyroid, genitourinary tract, endothelial tissue, skin, mucosa, skin and mucosal appendages, cornea, epithelial tissues, muscle, hematopoietic system, hematologic system, myeloid lineage, lymphoid lineage, lung, gastrointestinal tract, glands, head and neck, respiratory tract, bladder, epidermis, dermis, submucosa, urothelium, genitals, hair follicles, sebaceous glands, sweat glands, esophagus, tongue, cervix, forebrain, pituitary gland, and adrenal gland, mammary gland, ear, ocular mucosa, oral mucosa, nasal mucosa, anal mucosa, rectal mucosa, cancer related to fingernails and toenails, and cancer associated with, accompanied by and/or caused by viral infections.

24. The method according to claim 1, wherein the hyperproliferative disorder is a hyperproliferative disorder of the hematopoietic system and/or the hematologic system, a hyperproliferative disorder of the myeloid lineage, or a hyperproliferative disorder of the lymphoid lineage.

25. The method according to claim 1, wherein the malignant or precancerous hyperproliferative disorder is a disorder of the hematopoietic system and/or the hematologic system, a cancer of the myeloid lineage, or a cancer of the lymphoid lineage.

26. The method according to claim 1, wherein the malignant or precancerous hyperproliferative disorder is associated with a cancer associated with, accompanied by and/or caused by viral infection.

27. The method according to claim 1, wherein the hyperproliferative disorder is cancer or a precancerous lesion selected from the group consisting of medullary thyroid cancer, non-melanoma skin cancer and precancerous lesions, cutaneous squamous cell carcinoma (SCC), lung SCC, head and neck SCC, oral SCC, esophageal SCC, cervical SCC, periocular SCC, SCC of the thyroid, SCC of the penis, SCC of the vagina, SCC of the prostate, SCC of the bladder, sebaceous gland carcinoma, Merkel cell carcinoma, angiosarcoma, cutaneous B-cell lymphoma, cutaneous T-cell lymphoma, dermatofibrosarcoma, actinic keratosis (AK), Bowen's disease (BD), Kaposi's sarcoma, chronic myelomonocytic leukemia (CMML), acute myeloid leukemia (AML), acute promyelocytic leukemia (APL), B-cell acute lymphoblastic leukemia (B-ALL), pre- B-cell acute lymphoblastic leukemia (pre-B-ALL), T-cell lymphoma, Hodgkin lymphoma or myeloma; or acute lymphoblastic and acute myeloid mixed lineage leukemia with MLL gene translocation, rhabdomyosarcoma, C-cell hyperplasia, anaplastic thyroid cancer (ATC), parathyroid adenoma, intrathyroidal nodules, insular carcinoma, hyalinizing trabecular neoplasm, paraganglioma, small-cell lung cancer (SCLC), lung carcinoid tumors, neuroblastoma, gastrointestinal carcinoid, Goblet-cell carcinoid, pancreatic carcinoid, gastrinoma, glucagenoma, somatostatinoma, VIPoma, insulinoma, non-functional islet cell tumor, multiple endocrine neoplasia type-1, or pulmonary carcinoid, glioma, mixed glioma, glioblastoma multiforme, astrocytoma, anaplastic astrocytoma, glioblastoma, oligodendroglioma, anaplastic oligodendroglioma, anaplastic oligoastrocytoma, ependymoma, anaplastic ependymoma, myxopapillary ependymoma, subependymoma, brain stem glioma, optic nerve glioma, pancreatic acinar cell carcinoma, pancreatic pseudopapillary neoplasm, pancreatic intraductal papillary-mucinous neoplasm, pancreatic mucinous cystadenocarcinoma, pancreatoblastoma and pancreatic intraepithelial neoplasia, hepatocellular carcinoma, fibrolamellar hepatocellular carcinoma, papillary thyroid cancer and follicular thyroid cancer, cervical cancer and angiosarcoma.

28. The method according to claim 21, wherein the hyperproliferative disorder is cancer or a precancerous lesion selected from the group consisting of medullary thyroid cancer, non-melanoma skin cancer and precancerous lesions, cutaneous squamous cell carcinoma (SCC), lung SCC, head and neck SCC, oral SCC, esophageal SCC, cervical SCC, periocular SCC, SCC of the thyroid, SCC of the penis, SCC of the vagina, SCC of the prostate, SCC of the bladder, sebaceous gland carcinoma, Merkel cell carcinoma, angiosarcoma, cutaneous B-cell lymphoma, cutaneous T-cell lymphoma, dermatofibrosarcoma, actinic keratosis (AK), Bowen's disease (BD), Kaposi's sarcoma, chronic myelomonocytic leukemia (CMML), acute myeloid leukemia (AML), acute promyelocytic leukemia (APL), B-cell acute lymphoblastic leukemia (B-ALL), pre- B-cell acute lymphoblastic leukemia (pre-B-ALL), T-cell lymphoma, Hodgkin lymphoma or myeloma; or acute lymphoblastic and acute myeloid mixed lineage leukemia with MLL gene translocation, rhabdomyosarcoma, C-cell hyperplasia, anaplastic thyroid cancer (ATC), parathyroid adenoma, intrathyroidal nodules, insular carcinoma, hyalinizing trabecular neoplasm, paraganglioma, small-cell lung cancer (SCLC), lung carcinoid tumors, neuroblastoma, gastrointestinal carcinoid, Goblet-cell carcinoid, pancreatic carcinoid, gastrinoma, glucagenoma, somatostatinoma, VIPoma, insulinoma, non-functional islet cell tumor, multiple endocrine neoplasia type-1, or pulmonary carcinoid, glioma, mixed glioma, glioblastoma multiforme, astrocytoma, anaplastic astrocytoma, glioblastoma, oligodendroglioma, anaplastic oligodendroglioma, anaplastic oligoastrocytoma, ependymoma, anaplastic ependymoma, myxopapillary ependymoma, subependymoma, brain stem glioma, optic nerve glioma, pancreatic acinar cell carcinoma, pancreatic pseudopapillary neoplasm, pancreatic intraductal papillary-mucinous neoplasm, pancreatic mucinous cystadenocarcinoma, pancreatoblastoma and pancreatic intraepithelial neoplasia, hepatocellular carcinoma, fibrolamellar hepatocellular carcinoma, papillary thyroid cancer and follicular thyroid cancer, cervical cancer and angiosarcoma.

29. The method according to claim 23, wherein the hyperproliferative disorder is cancer or a precancerous lesion selected from the group consisting of medullary thyroid cancer, non-melanoma skin cancer and precancerous lesions, cutaneous squamous cell carcinoma (SCC), lung SCC, head and neck SCC, oral SCC, esophageal SCC, cervical SCC, periocular SCC, SCC of the thyroid, SCC of the penis, SCC of the vagina, SCC of the prostate, SCC of the bladder, sebaceous gland carcinoma, Merkel cell carcinoma, angiosarcoma, cutaneous B-cell lymphoma, cutaneous T-cell lymphoma, dermatofibrosarcoma, actinic keratosis (AK), Bowen's disease (BD), Kaposi's sarcoma, chronic myelomonocytic leukemia (CMML), acute myeloid leukemia (AML), acute promyelocytic leukemia (APL), B-cell acute lymphoblastic leukemia (B-ALL), pre- B-cell acute lymphoblastic leukemia (pre-B-ALL), T-cell lymphoma, Hodgkin lymphoma or myeloma; or acute lymphoblastic and acute myeloid mixed lineage leukemia with MLL gene translocation, rhabdomyosarcoma, C-cell hyperplasia, anaplastic thyroid cancer (ATC), parathyroid adenoma, intrathyroidal nodules, insular carcinoma, hyalinizing trabecular neoplasm, paraganglioma, small-cell lung cancer (SCLC), lung carcinoid tumors, neuroblastoma, gastrointestinal carcinoid, Goblet-cell carcinoid, pancreatic carcinoid, gastrinoma, glucagenoma, somatostatinoma, VlPoma, insulinoma, non-functional islet cell tumor, multiple endocrine neoplasia type-1, or pulmonary carcinoid, glioma, mixed glioma, glioblastoma multiforme, astrocytoma, anaplastic astrocytoma, glioblastoma, oligodendroglioma, anaplastic oligodendroglioma, anaplastic oligoastrocytoma, ependymoma, anaplastic ependymoma, myxopapillary ependymoma, subependymoma, brain stem glioma, optic nerve glioma, pancreatic acinar cell carcinoma, pancreatic pseudopapillary neoplasm, pancreatic intraductal papillary-mucinous neoplasm, pancreatic mucinous cystadenocarcinoma, pancreatoblastoma and pancreatic intraepithelial neoplasia, hepatocellular carcinoma, fibrolamellar hepatocellular carcinoma, papillary thyroid cancer and follicular thyroid cancer, cervical cancer and angiosarcoma.

30. The method of claim 21, wherein the subject is a human subject.

\* \* \* \* \*